(12) United States Patent
Wilks et al.

(10) Patent No.: US 7,593,820 B2
(45) Date of Patent: Sep. 22, 2009

(54) CRYSTAL STRUCTURE OF HUMAN JANUS KINASE 2 (JAK2) AND USES THEREOF

(75) Inventors: Andrew Frederick Wilks, South Yarra (AU); Christopher John Burns, Seddon (AU); Emmanuelle Fantino, Elwood (AU); Isabelle Lucet, Glen Waverley (AU); Jamie Rossjohn, Carnegie (AU); Michelle Leanne Styles, Golden Square (AU)

(73) Assignee: Cytopia Research Pty Ltd, Richmond (AU)

( * ) Notice: Subject to any disclaimer, the term of this patent is extended or adjusted under 35 U.S.C. 154(b) by 0 days.

(21) Appl. No.: 11/248,478

(22) Filed: Oct. 11, 2005

(65) Prior Publication Data

US 2007/0128709 A1   Jun. 7, 2007

(30) Foreign Application Priority Data

May 12, 2005   (AU) .............................. 2005902420

(51) Int. Cl.
G01N 31/00 (2006.01)
C12N 9/12 (2006.01)
G06G 7/58 (2006.01)

(52) U.S. Cl. ............................. 702/27; 435/194; 703/11
(58) Field of Classification Search .................. None
See application file for complete search history.

(56) References Cited

OTHER PUBLICATIONS

Tondel et al. (2002) Journal of Computer-Aided Molecular Design, vol. 16, p. 831-840.*
Thompson et al. (2002) Bioorganic and Medicinal Chemistry Letters, vol. 12, p. 1219-1223.*
Lucet et al. (2006) The structural basis of janus kinase 2 inhibition by a potent and specific pan-Janus kinase inhibitor, Blood, vol. 107, p. 176-183.*
Meydan et al. (1996) Nature, vol. 379, p. 645-648.*
Beddell, Chem. Soc. Rev. (1984) 13:279-314.
Bohm and Stahl, Med. Chem. Res. (1999) 9:445-462.
Booz et al., Mol. Cell Biochem. (2002) 240(1-2):39-46.
Connolly, Science (1983) 221:709-713.
El-Adawi et al., Cardiovasc. Res. (2003) 57(1):129-138.
Ewing et al., J. Comput. Aided Mol. Des. (2001) 15:411-428.
Ferrara et al., J. Med. Chem. (2004) 47:3032-3047.
Flowers et al., J. Immunol. (2004) 172(12):7510-7518.
Gane and Dean, Curr. Opin. Struct. Biol. (2000) 10:401-404.
Giordanetto and Kroemer, Protein Eng. (2002) 15(9):727-737.
Good, Curr. Opin. Drug Discov. Devel. (2001) 4:301-307.
Goodford, J. Med. Chem. (1984) 27:558-564.
Hanks and Hunter, Faseb J. (1995) 9(8):576-596.
Harpur et al., Oncogene (1992) 7:1347-1353.
Hol, Angewandte Chemie (1986) 98:765-777.
Hubbard and Till, Annu. Rev. Biochem. (2000) 69:373-398.
Huse and Kuriyan, Cell (2002) 109:275-282.

(Continued)

*Primary Examiner*—Suzanne M. Noakes
*Assistant Examiner*—Alexander D Kim
(74) *Attorney, Agent, or Firm*—Morrison & Foerster LLP

(57) ABSTRACT

The present invention relates to X-ray crystallography studies of a human Janus Kinase 2 (JAK2) domain. More particularly, it relates to the crystal structure of a JAK2 kinase domain bound to a inhibitor. The invention further relates to the use of the crystal and related structural information to select and screen for compounds that interact with JAK2 and related proteins and to compounds that could be used for the treatment of diseases mediated by inappropriate JAK2 activity.

5 Claims, 7 Drawing Sheets

OTHER PUBLICATIONS

James et al., Nature (2005) 434(7037):1144-1148.
Kisseleva et al., Gene (2002) 285(1-2):1-24.
Kozma et al., EMBO J. (1988) 7(1):147-154.
Kuntz et al., J. Mol. Biol. (1982) 161:269-288.
Langer and Hoffmann, Current Pharmaceutical Design (2001) 7:509-527.
Lattman, Methods Enzymol. (1985) 115:55-77.
Myers et al., J. Biol. Chem. (2001) 276:47771-47774.
Rarey et al., J. Mol. Biol. (1996) 261-470-489.
Rawlings et al., J. Cell Sci. (2004) 117:1281-1283.
Rossmann, Acta Crystallogr. (1990) 46:73-82.
Sadowski et al., Mol. Cell Biol. (1986) 6(12):4396-4408.
Sali and Blundell, J. Mol. Biol. (1993) 234:779-815.
Sheridan and Venkataraghavan, Acc. Chem. Res. (1987) 20:322-329.
Spiotto and Chung, Prostate (2000) 42:88-98.
Takemoto et al., PNAS USA (1997) 94:13897-13902.
Thompson et al., Biorg. Med. Chem. Lett. (2002) 12(8):1219-1223.
Verlinde and Hol, Structure (1994) 2:577-587.
Walters et al., Drug Discovery Today (1998) 3:160-178.
Wang et al., J. Comput. Aided Mol. Des. (2002) 16:11-26.
Wilks and Kurban, Oncogene (1988) 3:289-294.
Wilks et al., Mol. Cell Biol. (1991) 11:2057-2065.
Yoshikawa et al., Nat. Genet. (2001) 28:29-35.
Branden et al., Introduction to Protein Structure, Second Edition, Garland Publishing Inc., New York (1999) pp. 374-375.
Breitenlechner et al., Structure (2003) 11:1595-1607.
Boggon et al., Blood (2005) 106:996-1002.
Drenth, Principles of X-ray Crystallography, Springer, New York (1995) p. 1.
Giege et al., Crystallogenesis of Biological Macromolecules: Facts and Perspectives, Acta Cryst., (1994) D50: 339-350.
Kierzek et al., Biophys. Chem. (2001) 91:1-20.
Koepke et al., J. Mol. Biol. (2000) 298:477-491.
Lopez-Jaramillo et al., Acta Crystallogr. D. Biol. Crystallogr. (2002) 58:209-214.
Molecular Replacement (updated Jun. 7, 2005).
Vihinen et al., Clinical Immunology (2000) 96:108-118.
Wiencek, Ann. Rev. Biomed. Eng. (1999) 1:505-534.

* cited by examiner

SEQUENCE LISTING

```
<160> NUMBER OF SEQ ID NOS: 17

<210> SEQ ID NO 1
<211> LENGTH: 50
<212> TYPE: PRT
<213> ORGANISM: Homo sapiens

<400> SEQUENCE: 1

Val Ala Ser Asp Val Trp Ser Phe Gly Val Val Leu Tyr Glu Leu Phe
1               5                   10                  15

Thr Tyr Ile Glu Lys Ser Lys Ser Pro Pro Ala Glu Phe Met Arg Met
            20                  25                  30

Ile Gly Asn Asp Lys Gln Gly Gln Met Ile Val Phe His Ile Glu Leu
        35                  40                  45

Leu Lys
    50

<210> SEQ ID NO 2
<211> LENGTH: 49
<212> TYPE: PRT
<213> ORGANISM: Homo sapiens

<400> SEQUENCE: 2

Ile Ala Ser Asp Val Trp Ser Phe Gly Thr Leu Tyr Glu Leu Leu Thr
1               5                   10                  15

Tyr Cys Asp Ser Asp Ser Ser Pro Met Ala Leu Phe Leu Lys Met Ile
            20                  25                  30

Gly Pro Thr His Gly Gln Met Thr Val Thr Arg Leu Val Asn Thr Leu
        35                  40                  45

Lys

<210> SEQ ID NO 3
<211> LENGTH: 50
<212> TYPE: PRT
<213> ORGANISM: Homo sapiens

<400> SEQUENCE: 3

Tyr Ala Ser Asp Val Trp Ser Phe Gly Val Thr Leu Leu Glu Leu Leu
1               5                   10                  15

Thr His Cys Asp Ser Ser Gln Ser Pro Pro Thr Lys Phe Leu Glu Leu
            20                  25                  30

Ile Gly Ile Ala Gln Gly Gln Met Thr Val Leu Arg Leu Thr Glu Leu
        35                  40                  45

Leu Glu
    50
```

```
<210> SEQ ID NO 4
<211> LENGTH: 50
<212> TYPE: PRT
<213> ORGANISM: Homo sapiens

<400> SEQUENCE: 4

Arg Gln Ser Asp Val Trp Ser Phe Gly Val Leu Tyr Glu Leu Phe
1               5                   10                  15

Thr Tyr Cys Asp Lys Ser Cys Ser Pro Ser Ala Glu Phe Leu Arg Met
            20                  25                  30

Met Gly Cys Glu Arg Asp Val Pro Ala Leu Cys Arg Leu Leu Glu Leu
        35                  40                  45

Leu Glu
    50

<210> SEQ ID NO 5
<211> LENGTH: 36
<212> TYPE: PRT
<213> ORGANISM: Homo sapiens

<400> SEQUENCE: 5

Ile Lys Ser Asp Val Trp Met Phe Gly Val Cys Met Trp Glu Ile Leu
1               5                   10                  15

Met His Gly Val Lys Pro Phe Gln Gly Val Lys Asn Asn Asp Val Ile
            20                  25                  30

Gly Arg Ile Glu
        35

<210> SEQ ID NO 6
<211> LENGTH: 36
<212> TYPE: PRT
<213> ORGANISM: Homo sapiens

<400> SEQUENCE: 6

Ser Ala Ser Asp Val Trp Ser Phe Gly Ile Leu Leu Thr Glu Ile Val
1               5                   10                  15

Thr His Gly Arg Ile Pro Tyr Pro Gly Met Thr Asn Pro Glu Val Gln
            20                  25                  30

Asn Leu Glu Arg
        35

<210> SEQ ID NO 7
<211> LENGTH: 290
<212> TYPE: PRT
<213> ORGANISM: Human JAK2 kinase domain

<400> SEQUENCE: 7

Gln Phe Glu Glu Arg His Leu Lys Phe Leu Gln Gln Leu Gly Lys Gly
1               5                   10                  15

Asn Phe Gly Ser Val Glu Met Cys Arg Tyr Asp Pro Leu Gln Asp Asn
            20                  25                  30

Thr Gly Glu Val Val Ala Val Lys Lys Leu Gln His Ser Thr Glu Glu
        35                  40                  45

His Leu Arg Asp Phe Glu Arg Glu Ile Glu Ile Leu Lys Ser Leu Gln
    50                  55                  60

His Asp Asn Ile Val Lys Tyr Lys Gly Val Cys Tyr Ser Ala Gly Arg
65                  70                  75                  80

Arg Asn Leu Lys Leu Ile Met Glu Tyr Leu Pro Tyr Gly Ser Leu Arg
                85                  90                  95
```

-continued

Asp Tyr Leu Gln Lys His Lys Glu Arg Ile Asp His Ile Lys Leu Leu
              100                 105                 110

Gln Tyr Thr Ser Gln Ile Cys Lys Gly Met Glu Tyr Leu Gly Thr Lys
              115                 120                 125

Arg Tyr Ile His Arg Asp Leu Ala Thr Arg Asn Ile Leu Val Glu Asn
            130                 135                 140

Glu Asn Arg Val Lys Ile Gly Asp Phe Gly Leu Thr Lys Val Leu Pro
145                 150                 155                 160

Gln Asp Lys Glu Tyr Tyr Lys Val Lys Glu Pro Gly Glu Ser Pro Ile
                165                 170                 175

Phe Trp Tyr Ala Pro Glu Ser Leu Thr Glu Ser Lys Phe Ser Val Ala
              180                 185                 190

Ser Asp Val Trp Ser Phe Gly Val Val Leu Tyr Glu Leu Phe Thr Tyr
              195                 200                 205

Ile Glu Lys Ser Lys Ser Pro Pro Ala Glu Phe Met Arg Met Ile Gly
210                 215                 220

Asn Asp Lys Gln Gly Gln Met Ile Val Phe His Leu Ile Glu Leu Leu
225                 230                 235                 240

Lys Asn Asn Gly Arg Leu Pro Arg Pro Asp Gly Cys Pro Asp Glu Ile
                245                 250                 255

Tyr Met Ile Met Thr Glu Cys Trp Asn Asn Val Asn Gln Arg Pro
              260                 265                 270

Ser Phe Arg Asp Leu Ala Leu Arg Val Asp Gln Ile Arg Asp Gln Met
            275                 280                 285

Ala Gly
    290

<210> SEQ ID NO 8
<211> LENGTH: 293
<212> TYPE: PRT
<213> ORGANISM: Human JAK2 kinase domain

<400> SEQUENCE: 8

Asp Pro Thr Gln Phe Glu Glu Arg His Leu Lys Phe Leu Gln Gln Leu
1               5                   10                  15

Gly Lys Gly Asn Phe Gly Ser Val Glu Met Cys Arg Tyr Asp Pro Leu
              20                  25                  30

Gln Asp Asn Thr Gly Glu Val Val Ala Val Lys Lys Leu Gln His Ser
            35                  40                  45

Thr Glu Glu His Leu Arg Asp Phe Glu Arg Glu Ile Glu Ile Leu Lys
   50                  55                  60

Ser Leu Gln His Asp Asn Ile Val Lys Tyr Lys Gly Val Cys Tyr Ser
65                  70                  75                  80

Ala Gly Arg Arg Asn Leu Lys Leu Ile Met Glu Tyr Leu Pro Tyr Gly
              85                  90                  95

Ser Leu Arg Asp Tyr Leu Gln Lys His Lys Glu Arg Ile Asp His Ile
              100                 105                 110

Lys Leu Leu Gln Tyr Thr Ser Gln Ile Cys Lys Gly Met Glu Tyr Leu
            115                 120                 125

Gly Thr Lys Arg Tyr Ile His Arg Asp Leu Ala Thr Arg Asn Ile Leu
          130                 135                 140

Val Glu Asn Glu Asn Arg Val Lys Ile Gly Asp Phe Gly Leu Thr Lys
145                 150                 155                 160

Val Leu Pro Gln Asp Lys Glu Tyr Tyr Lys Val Lys Glu Pro Gly Glu

```
                      165                 170                 175
Ser Pro Ile Phe Trp Tyr Ala Pro Glu Ser Leu Thr Glu Ser Lys Phe
                180                 185                 190

Ser Val Ala Ser Asp Val Trp Ser Phe Gly Val Val Leu Tyr Glu Leu
            195                 200                 205

Phe Thr Tyr Ile Glu Lys Ser Lys Ser Pro Pro Ala Glu Phe Met Arg
        210                 215                 220

Met Ile Gly Asn Asp Lys Gln Gly Gln Met Ile Val Phe His Leu Ile
225                 230                 235                 240

Glu Leu Leu Lys Asn Asn Gly Arg Leu Pro Arg Pro Asp Gly Cys Pro
                245                 250                 255

Asp Glu Ile Tyr Met Ile Met Thr Glu Cys Trp Asn Asn Asn Val Asn
                260                 265                 270

Gln Arg Pro Ser Phe Arg Asp Leu Ala Leu Arg Val Asp Gln Ile Arg
            275                 280                 285

Asp Gln Met Ala Gly
        290

<210> SEQ ID NO 9
<211> LENGTH: 40
<212> TYPE: PRT
<213> ORGANISM: Homo sapiens

<400> SEQUENCE: 9

Leu Gly Lys Gly Asn Phe Gly Ser Val Val Ala Val Lys Met Glu Tyr
1               5                   10                  15

Leu Pro Tyr Gly Ser Leu Arg Asp Tyr Leu His Arg Asp Leu Ala Thr
            20                  25                  30

Arg Asn Ile Leu Gly Asp Phe Gly
        35                  40

<210> SEQ ID NO 10
<211> LENGTH: 40
<212> TYPE: PRT
<213> ORGANISM: Homo sapiens

<400> SEQUENCE: 10

Leu Gly Glu Gly His Phe Gly Lys Val Ala Val Lys Met Glu Tyr
1               5                   10                  15

Val Pro Leu Gly Ser Leu Arg Asp Tyr Leu His Arg Asp Leu Ala Ala
            20                  25                  30

Arg Asn Val Leu Gly Asp Phe Gly
        35                  40

<210> SEQ ID NO 11
<211> LENGTH: 40
<212> TYPE: PRT
<213> ORGANISM: Homo sapiens

<400> SEQUENCE: 11

Leu Gly Lys Gly Asn Phe Gly Ser Val Val Ala Val Lys Met Glu Tyr
1               5                   10                  15

Leu Pro Ser Gly Cys Leu Arg Asp Phe Leu His Arg Asp Leu Ala Ala
            20                  25                  30

Arg Asn Ile Leu Ala Asp Phe Gly
        35                  40

<210> SEQ ID NO 12
```

```
<211> LENGTH: 40
<212> TYPE: PRT
<213> ORGANISM: Homo sapiens

<400> SEQUENCE: 12

Leu Gly Glu Gly His Phe Gly Lys Val Val Ala Val Lys Met Glu Phe
1               5                   10                  15

Leu Pro Ser Gly Ser Leu Lys Glu Tyr Leu His Arg Asp Leu Ala Ala
            20                  25                  30

Arg Asn Val Leu Gly Asp Phe Gly
        35                  40

<210> SEQ ID NO 13
<211> LENGTH: 40
<212> TYPE: PRT
<213> ORGANISM: Homo sapiens

<400> SEQUENCE: 13

Ile Gly Glu Gly Gln Phe Gly Asp Val Val Ala Ile Lys Met Glu Leu
1               5                   10                  15

Cys Thr Leu Gly Glu Leu Arg Ser Phe Leu His Arg Asp Ile Ala Ala
            20                  25                  30

Arg Asn Val Leu Gly Asp Phe Gly
        35                  40

<210> SEQ ID NO 14
<211> LENGTH: 40
<212> TYPE: PRT
<213> ORGANISM: Homo sapiens

<400> SEQUENCE: 14

Leu Gly Gln Gly Ser Phe Gly Met Val Val Ala Val Lys Met Glu Leu
1               5                   10                  15

Met Ala His Gly Asp Leu Lys Ser Tyr Leu His Arg Asp Leu Ala Ala
            20                  25                  30

Arg Asn Cys Met Gly Asp Phe Gly
        35                  40

<210> SEQ ID NO 15
<211> LENGTH: 40
<212> TYPE: PRT
<213> ORGANISM: Homo sapiens

<400> SEQUENCE: 15

Leu Gly Cys Gly Asn Phe Gly Ser Val Val Ala Ile Lys Met Glu Met
1               5                   10                  15

Ala Gly Gly Gly Pro Leu His Lys Phe Leu His Arg Asp Leu Ala Ala
            20                  25                  30

Arg Asn Val Leu Ser Asp Phe Gly
        35                  40

<210> SEQ ID NO 16
<211> LENGTH: 40
<212> TYPE: PRT
<213> ORGANISM: Homo sapiens

<400> SEQUENCE: 16

Leu Gly Glu Gly Cys Phe Gly Gln Val Val Ala Val Lys Val Glu Tyr
1               5                   10                  15

Ala Ser Lys Gly Asn Leu Arg Glu Tyr Leu His Arg Asp Leu Ala Ala
            20                  25                  30
```

```
Arg Asn Val Leu Ala Asp Phe Gly
        35                  40

<210> SEQ ID NO 17
<211> LENGTH: 40
<212> TYPE: PRT
<213> ORGANISM: Homo sapiens

<400> SEQUENCE: 17

Leu Gly Ala Gly Gln Phe Gly Glu Val Val Ala Val Lys Thr Glu Tyr
 1               5                  10                  15

Met Glu Asn Gly Ser Leu Val Asp Phe Leu His Arg Asp Leu Arg Ala
            20                  25                  30

Ala Asn Ile Leu Ala Asp Phe Gly
        35                  40
```

CRYSTAL STRUCTURE OF HUMAN JANUS KINASE 2 (JAK2) AND USES THEREOF

CROSS-REFERENCE TO RELATED APPLICATIONS

This application claims priority from Australian application 2005902420 filed 12 May 2005. The contents of this document are incorporated herein by reference.

FIELD OF THE INVENTION

The present invention relates to X-ray crystallography studies of a JAK2 kinase domain. More particularly, it relates to the crystal structure of a JAK2 kinase domain bound to an inhibitor. The invention further relates to the use of the crystal and related structural information to select and screen for compounds that interact with JAK2 and related proteins and to compounds that could be used for the treatment of diseases mediated by inappropriate JAK2 activity.

BACKGROUND OF THE INVENTION

Protein kinases are a family of enzymes that catalyse the phosphorylation of specific residues in proteins. In general protein kinases fall into several groups; those which preferentially phosphorylate serine and/or threonine residues, those which preferentially phosphorylate tyrosine residues and those which phosphorylate both tyrosine and Ser/Thr residues. Protein kinases are therefore key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis.

Protein kinases include, for example, but are not limited to, members of the Protein Tyrosine Kinase family (PTKs), which in turn can be divided into the cytoplasmic PTKs and the receptor PTKs (RTKs). The cytoplasmic PTKs include the SRC family (including: BLK; FGR; FYN; HCK; LCK; LYN; SRC; YES and YRK); the BRK Family (including: BRK; FRK, SAD; and SRM); the CSK family (including: CSK and CTK); the BTK family (including BTK; ITK; TEC; MKK2 and TXK), the Janus kinase family (including: JAK1, JAK2, JAK3 and TYK2); the FAK family (including FAK and PYK2); the Fes family (including FES and FER), the ZAP70 family (including ZAP70 and SYK); the ACK family (including ACK1 and ACK2); and the Abl family (including ABL and ARG). The RTK family includes the EGF Receptor family (including, EGFR, HER2, HER3 and HER4); the Insulin Receptor family (including INS R and IGF1 R); the PDGF Receptor family (including PDGFRα, PDGFRβ, CSF1R, KIT, FLK2); the VEGF Receptor family (including; FLT1, FLK1 and FLT4); the FGF Receptor family (including FGFR1, FGFR2, FGFR3 and FGFR4); the CCK4 family (including CCK4); the MET family (including MET and RON); the TRK family (including TRKA, TRKB, and TRKC); the AXL family (including AXL, MER, and SKY); the TIE/TEK family (including TIE1 and TIE2/TEK); the EPH family (including EPHA1, EPHA2, EPHA3, EPHA4, EPHA5, EPHA6, EPHA7, EPHA8, EPHB1, EPHB2, EPHB3, EPHB4, EPHB5, EPHB6); the RYK family (including RYK); the MCK family (including MCK and TYRO10); the ROS family (including ROS); the RET family (including RET); the LTK family (including LTK and ALK); the ROR family (including ROR1 and ROR2); The Musk family (including Musk); the LMR family including LMR1, LMR2 and LMR3); and the SuRTK106 family (including SuRTK106).

Similarly, the serine/threonine specific kinases comprise a number of distinct sub families, including; the extracellular signal regulated kinases (p42/ERK2 and p44/ERKI); c Jun NH2 terminal kinase (JNK); cAMP responsive element binding protein kinases (CREBK); cAMP dependent kinase (CAPK); mitogen activated protein kinase activated protein kinase (MAPK and its relatives); stress activated protein kinase p38/SAPK2; mitogen and stress activated kinase (MSK); protein kinases, PKA, PKB and PKC inter alia.

Additionally, the genomes of a number of pathogenic organisms possess genes encoding protein kinases. For example, the malarial parasite *Plasmodium falciparum* and viruses such as HPV and Hepatitis viruses appear to bear kinase related genes.

Inappropriately high protein kinase activity has been implicated in many diseases resulting from abnormal cellular function. This might arise either directly or indirectly, for example by failure of the proper control mechanisms for the kinase, related for example to mutation, over expression or inappropriate activation of the enzyme; or by over or under production of cytokines or growth factors also participating in the transduction of signals upstream or downstream of the kinase. In all of these instances, selective inhibition of the action of the kinase might be expected to have a beneficial effect.

Diseases where aberrant kinase activity has been implicated include: diabetes; restenosis; atherosclerosis; fibrosis of the liver and kidney; ocular diseases; myelo and lymphoproliferative disorders; cancer such as prostate cancer, colon cancer, breast cancer, head and neck cancer, leukemia and lymphoma; and, auto immune diseases such as Atopic Dermatitis, Asthma, rheumatoid arthritis, Crohn's disease, psoriasis, Crouzon syndrome, achondroplasia, and thanatophoric dysplasia.

The JAK family of protein tyrosine kinases (PTKs) play a central role in the cytokine dependent regulation of the proliferation and end function of several important cell types of the immune system. (reviewed in Kisseleva et al 2002)

The central role played by the JAK family of protein tyrosine kinases in the cytokine dependent regulation of the proliferation and end function of several important cell types means that agents which inhibit JAK are useful in the prevention and chemotherapy of disease states dependent on these enzymes. Potent and specific inhibitors of each of the currently known four JAK family members will provide a means of inhibiting the action of those cytokines that drive immune pathologies, such as asthma (e.g. IL 13; JAK1, TYK2 and JAK2), leukemia/lymphoma (e.g. IL 2: JAK1 and JAK3) and myeloproliferative syndromes such as Polycythemia vera (Takemoto, S et al, 2002; El-Adawi, H. et al. 2003, Booz, G. W., Day, J. N., Speth, R. & Baker, K. M., 2002; James, C. et al., 2005). Furthermore, certain types of cancer such as prostate cancer develop autocrine production of certain cytokines as a selectable mechanism of developing growth and/or metastatic potential. An example of this is cancer of the prostate, where IL 6 is produced by and stimulates the growth of prostate cancer cell lines such as TSU and TC3 (Spiotto M T, and Chung T D, 2000). Interestingly, levels of IL 6 are elevated in sera of patients with metastatic prostate cancer.

A direct comparison of the four currently known mammalian JAK family members reveals the presence of seven highly conserved domains (Harpur et al, 1992). In seeking a nomenclature for the highly conserved domains characteristic of this family of PTKs, the classification used was guided by the approach of Pawson and co workers (Sadowski et al, 1986) in their treatment of the SRC homology (SH) domains. The domains have been enumerated accordingly with most C terminal homology domain designated JAK Homology domain 1 (JH1). The next domain N terminal to JH1 is the kinase related domain, designated here as the JH2 domain. Each domain is then enumerated up to the JH7 located at the N terminus. The high degree of conservation of these JAK homology (JH) domains suggests that they are each likely to play an important role in the cellular processes in which these proteins operate. However, the boundaries of the JAK homology domains are arbitrary, and may or may not define functional domains. Nonetheless, their delineation is a useful device to aid the consideration of the overall structural similarity of this class of proteins The feature most characteristic of the JAK family of PTKs is the possession of two kinase related domains (JH1 and JH2) (Wilks et al, 1991). The putative PTK domain of JAK1 (JH1) contains highly conserved motifs typical of PTK domains, including the presence of a tyrosine residue at position 1022 located 11 residues C terminal to sub domain VII that is considered diagnostic of membership of the tyrosine specific class of protein kinases. Alignment of the human JAK1 PTK domain (255 amino acids), with other members of the PTK class of proteins revealed homology with other functional PTKs (for example, 28% identity with c-fes (Wilks and Kurban, 1988) and 37% homology to TRK (Kozma et al, 1988). The JH1 domains of each of the JAK family members possess an interesting idiosyncrasy within the highly conserved sub domain VIII motif (residues 1015 to 1027 in JAK2) that is believed to lie close to the active site, and define substrate specificity. The phenylalanine and tyrosine residues flanking the conserved tryptophan in this motif are unique to the JAK family of PTKs. Aside from this element, the JH 1 domains of each of the members of the JAK family are typical PTK domains Hanks S K, Hunter T 1995 and contain the conserved structural features: N-terminal lobe, C-terminal lobe glycine-rich/nucleotide binding loop, catalytic loop, activation loop and sets of other amino acids composing the catalytic domain of kinases.

The delineation of a particularly elegant signal transduction pathway downstream of the non-protein tyrosine kinase cytokine receptors has recently been achieved. In this pathway the key components are: (i) A cytokine receptor chain (or chains) such as the Interleukin 4 receptor or the Interferon γ receptor; (ii) a member (or members) of the JAK family of PTKs; (iii) a member(s) of the STAT family of transcription factors, and (iv) a sequence specific DNA element to which the activated STAT will bind. In addition, other effectors and regulators can contribute to JAK/STAT pathway signaling events (reviewed in Rawlings et al, 2004) including, SOCS (suppressors of cytokine signaling), PTPs (protein tyrosine phosphatases), STAMs (signal-transucing adaptor molecules), StIPs (stat-interacting proteins) and adapters of the SH2B/Lnk/APS family.

A review of the JAK/STAT literature offers strong support to the notion that this pathway is important for the recruitment and marshalling of the host immune response to environmental insults, such as viral and bacterial infection. This is well exemplified in Table 1. Information accumulated from gene knock-out experiments have underlined the importance of members of the JAK family to the intracellular signalling triggered by a number of important immune regulatory cytokines. The therapeutic possibilities stemming from inhibiting (or enhancing) the JAK/STAT pathway are thus largely in the sphere of immune modulation, and as such are likely to be promising drugs for the treatment of a range of pathologies in this area. In addition to the diseases listed in Table 1, inhibitors of JAKs could be used as immunosuppressive agents for organ transplants and autoimmune diseases such as lupus, multiple sclerosis, rheumatoid arthritis, Type I diabetes, autoimmune thyroid disorders, Alzheimer's disease and other autoimmune diseases. Additionally, treatment of cancers such as prostate cancer by JAK inhibitors is indicated.

TABLE 1

| Disease Type | Cell Types Involved | Characteristics |
| --- | --- | --- |
| Atopy | | |
| Allergic Asthma | Mast Cells | T-cell activation of |
| Atopic Dermatitis (Eczema) | Eosinophils | B-cells followed by |
| Allergic Rhinitis | T-Cells | IgE mediated |
|  | B-Cells | activation of |
|  |  | resident Mast cells and |
|  |  | Eosinophils |
| Cell Mediated Hypersensitivity | | |
| Allergic Contact Dermatitis | T-cells | T-cell hypersensitivity |
| Hypersensitivity Pneumonitis | B-cells | |
| Rheumatic Diseases | | |
| Systemic Lupus Erythematosus (SLE) | Monocytes | Cytokine Production (e.g. TNF, IL-1, CSF-1, GM-CSF) |
| Rheumatoid Arthritis | Macrophages | T-cell Activation |
| Juvenile Arthritis | Neutrophils | JAK/STAT activation |
| Sjögren's Syndrome | Mast Cells | |
| Scleroderma | Eosinophils | |
| Polymyositis | T-Cells | |
| Ankylosing Spondylitis | B-Cells | |
| Psoriatic Arthritis | | |
| Viral Diseases | | |
| Epstein Barr Virus (EBV) | Lymphocytes | JAK/STAT Activation |
| Hepatitis B | Hepatocytes | JAK/STAT Activation |
| Hepatitis C | Hepatocytes | JAK/STAT Inhibition |
| HIV | Lymphocytes | JAK/STAT Activation |
| HTLV 1 | Lymphocytes | JAK/STAT Activation |
| Varicella-Zoster Virus (VZV) | Fibroblasts | JAK/STAT Inhibition |
| Human Papilloma Virus (HPV) | Epithelial cells | JAK/STAT Inhibition |
| Cancer | | |
| Leukemia | Leucocytes | (Cytokine production |
| Lymphoma | Lymphocytes | (JAK/STAT Activation |
| Neurodegenerative Diseases | | |
| Motor Neuron Disease | Neurons | Mutated SOD1 |
| Cardiovascular Diseases | | |
| Atherosclerosis & Arteriosclerosis | Lymphocytes | JAK/STAT Activation |
|  | Macrophages | JAK/STAT Activation |
|  | Myoepithelial cells | |
| Cardiac Hypertrophy | Cardiac Myocytes | JAK/STAT Activation |
| Ischemia | Cardiac Myocytes | JAK/STAT Activation |
| Pulmonary Hypertension | Lung Epithelium | JAK/STAT Activation |

SUMMARY OF THE INVENTION

The present inventors have determined the crystal structure of the active conformation of JAK2 Kinase domain in complex with a high affinity pan-Janus kinase inhibitor (Thompson et al, 2002) at a resolution of 2.0 Å. The present invention provides for the first time crystals of the JAK2 kinase in complex with a specific Janus kinase inhibitor. The analysis of the three dimensional structure of the JAK2 co-crystals provides previously unknown structural information about the JAK2 kinase and more specifically about the ATP binding domain or site which will contribute to the development of potential drug candidates. The information not only provides a structural basis of high affinity JAK-specific inhibition but will also undoubtedly provide an invaluable tool for the further design of novel, potent and specific therapeutics against the JAK family.

The information presented in this application can be used to predict the structure of other Janus kinase proteins, such as JAK1, JAK3 and TYK2, as well as to select and/or design compounds which interact with JAK2 and other Janus kinase proteins for use as therapeutic agents.

In a first aspect, the present invention provides a crystalline composition comprising JAK2 or a portion thereof, or a crystalline composition comprising JAK2 or a portion thereof co-crystallised with an inhibitor.

In a second aspect, the present invention provides a method of selecting or designing a compound that interacts with JAK2 and thereby modulates an activity mediated by the JAK2, the method comprising the step of assessing the stereochemical complementarity between the compound and a topographic region of JAK2, wherein the topographic region of the JAK2 is characterised by at least a portion of the amino acids and water molecules positioned at atomic coordinates as shown in Appendix 1 or structural coordinates wherein the backbone atoms of the topographic region of JAK2 have a root mean square deviation of not more than 1.5 Å from the backbone atoms of their corresponding partners in the amino acids shown in Appendix 1.

By "stereochemical complementarity" we mean that the compound or a portion thereof makes a sufficient number of energetically favourable contacts with JAK2, or topographic region thereof, as to have a net reduction of free energy on binding to JAK2, or topographic region thereof.

Stereochemical complementarity or how well a given chemical compound structure binds or fits within a specified site or cavity in the protein structure can be measured by using one or more of the scoring functions available for this purpose. (See for example P. Ferrara, H. Gohlke, D. J. Price, G. Klebe, and C. L. Brooks III, Assessing scoring functions for protein-ligand interactions, J. Med. Chem., vol. 47, 3032-3047(2004).) A specific example of such a scoring function is X—SCORE (R. Wang, L. Lai, S. Wang, Further development and validation of empirical scoring functions for structure-based binding affinity prediction, J. Comput.-Aided Mol. Des., vol. 16, 11-26(2002)), which is a scoring function that calculates the dissociation constant of a given protein-ligand complex, and was constructed by calibrating to experimental data on a set of 200 protein-ligand complexes.

By "topographic region" is meant a subset of the molecular surface (Connolly, 1983) of JAK2. This subset may consist of either a single region or multiple disjoint regions. In this context the surface of enclosed cavities within JAK2 are also treated as part of the molecular surface.

In a third aspect, the present invention provides a computer-assisted method for identifying compounds which interact with JAK2 and thereby modulate an activity mediated by JAK2, using a programmed computer comprising a processor, an input device, and an output device, comprising the steps of:

(a) inputting into the computer, through the input device, data comprising the coordinates of the amino acids and water molecules shown in Appendix 1 or structural coordinates wherein the backbone atoms of the topographic region of the JAK2 have a root mean square deviation from the backbone atoms of their corresponding partners as shown in Appendix 1 of not more than 1.5 Å; or one or more subsets of said amino acid and said water molecules;

(b) generating, using computer methods, a set of atomic coordinates of a structure that possesses stereochemical complementarity to the atomic coordinates inputted in step (a), thereby generating a criteria data set;

(c) comparing, using the processor, the criteria data set to a computer database of chemical structures;

(d) selecting from the database, using computer methods, chemical structures which are similar to a portion of said criteria data set; and (e) outputting, to the output device, the selected chemical structures which are complementary to or a similar to a portion of the criteria data set.

In a fourth aspect, the present invention provides a method of screening a putative compound having the ability to modulate the activity of JAK2, comprising the steps of identifying a putative compound by the method of the second or third aspect, and testing the compound for activity.

In a fifth aspect, the present invention provides a computer for generating a three-dimensional representation of a molecule or molecular complex of JAK2, wherein the computer comprises:

(a) a machine-readable data storage medium comprising a date storage material encoded with machine readable data, wherein the machine readable data comprises the coordinates of the amino acids and water molecules shown in Appendix 1 or structural coordinates wherein the backbone atoms of the JAK2 have a root mean square deviation from the backbone atoms of their corresponding partners as shown in Appendix 1 of not more than 1.5 Å, or one or more subsets of said amino acids;

(b) a working memory for storing instructions for processing the machine-readable data;

(c) a central-processing unit coupled to the working memory and to the machine-readable data storage medium, for processing the machine-readable data into the three-dimensional representation; and (d) an output hardware coupled to the central processing unit, for receiving the three-dimensional representation.

In a sixth aspect, there is provided a compound able to modulate the activity of JAK2, the compound being obtained by the method of the second or the third aspect.

In a seventh aspect, there is provided a pharmaceutical composition for the treatment of a JAK2-associated disease state, comprising a compound according to the sixth aspect and a pharmaceutically acceptable carrier or diluent.

In an eighth aspect, there is provided a method of treating a patient suffering or at risk from a disease or condition for which modulation of JAK2 activity provides a therapeutic or prophylactic effect, comprising the administration to the patient of an effective amount of a compound according to the sixth aspect In a ninth aspect, there is provided a method for evaluating the ability of a chemical entity to interact with JAK2, said method comprising the steps of:

(a) creating a computer model of at least one region of JAK2 using structural coordinates comprising at least a portion of the amino acids and water molecules positioned at atomic coordinates as shown in Appendix 1 or structural coordinates wherein the backbone atoms of the topographic region of the JAK2 have a root mean square deviation from the backbone atoms of their corresponding partners as shown in Appendix 1 of not more than 1.5 Å; or (b) employing computational means to perform a fitting operation between the chemical entity and said computer model of said at least one region of the monomers of JAK2; and (c) analysing the results of said fitting operation to quantify the association between the chemical entity and said at least one region of the Janus kinase protein model.

As will be readily understood by persons skilled in this field, the methods of the present invention provide a rational method for designing and selecting compounds which interact with a Janus kinase protein and, specifically, JAK2. In the majority of cases these compounds will require further development in order to increase activity. Such further development is routine in this field and will be assisted by the structural information provided in this application. It is intended that in particular embodiments the methods of the present invention includes such further developmental steps.

In a tenth aspect, there is provided a method of utilising molecular replacement to obtain structural information about a molecule or molecular complex of unknown structure, comprising the steps of:
(i) crystallizing said molecule or molecular complex;
(ii) collecting an X-ray diffraction data set from said crystallised molecule or molecular complex;
(iii) applying at least a portion of the structure coordinates set forth in Appendix 1 to the X-ray diffraction data set to generate a three-dimensional electron density map of at least a portion of the molecule or molecular complex whose structure is unknown.

The term "molecular replacement" refers to a method that involves generating a preliminary model of an crystal of a JAK2 related protein whose structure coordinates are unknown, by orienting and positioning a molecule whose structure coordinates are known (e.g., JAK2 kinase domain coordinates from Appendix I) within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal (Lattman, 1985; Rossmann, 1990).

As would be well understood by those skilled in the art, the structural information of the JAK2 kinase domain contained in Appendix 1 can be used to generate homology models of proteins related to JAK2. Related proteins include a range of different JAK2 variants, including full-length wild type, naturally occurring variants (eg allelic variants and splice variants), truncated variants of wild type or naturally-occurring variants, and mutants of full length or truncated wild-type or naturally occurring variants (that can be mutated at one or more sites) and for other members of the family (eg JAK1, JAK3, TYK2) and their mutants and variants.

Accordingly, in a further aspect, the present invention provides creating a homology model of at least one region of a protein related to JAK2 comprising the step of applying at least a portion of the structural coordinates set forth in Appendix 1 to generate the homology model.

It would be understood by the person skilled in the art that a homology model generated according to this aspect of the invention may be applied in the methods of all other aspects of the invention.

Preferably, the JAK2 related protein is selected from JAK1, JAK3 and TYK2.

In another aspect, the present invention consists in a method of assessing the interaction between a compound and JAK2, the method comprising exposing a crystalline composition comprising JAK2 or portion thereof or variant of these to the compound and measuring the level of binding of the compound to the crystal.

In a yet further aspect, the present invention provides a JAK2 kinase domain in liganded crystalline form or a portion thereof, comprising the amino acid sequence 840-1132 and having the structural coordinates of Appendix 1.

DETAILED DESCRIPTION OF THE INVENTION

Figure 1A:
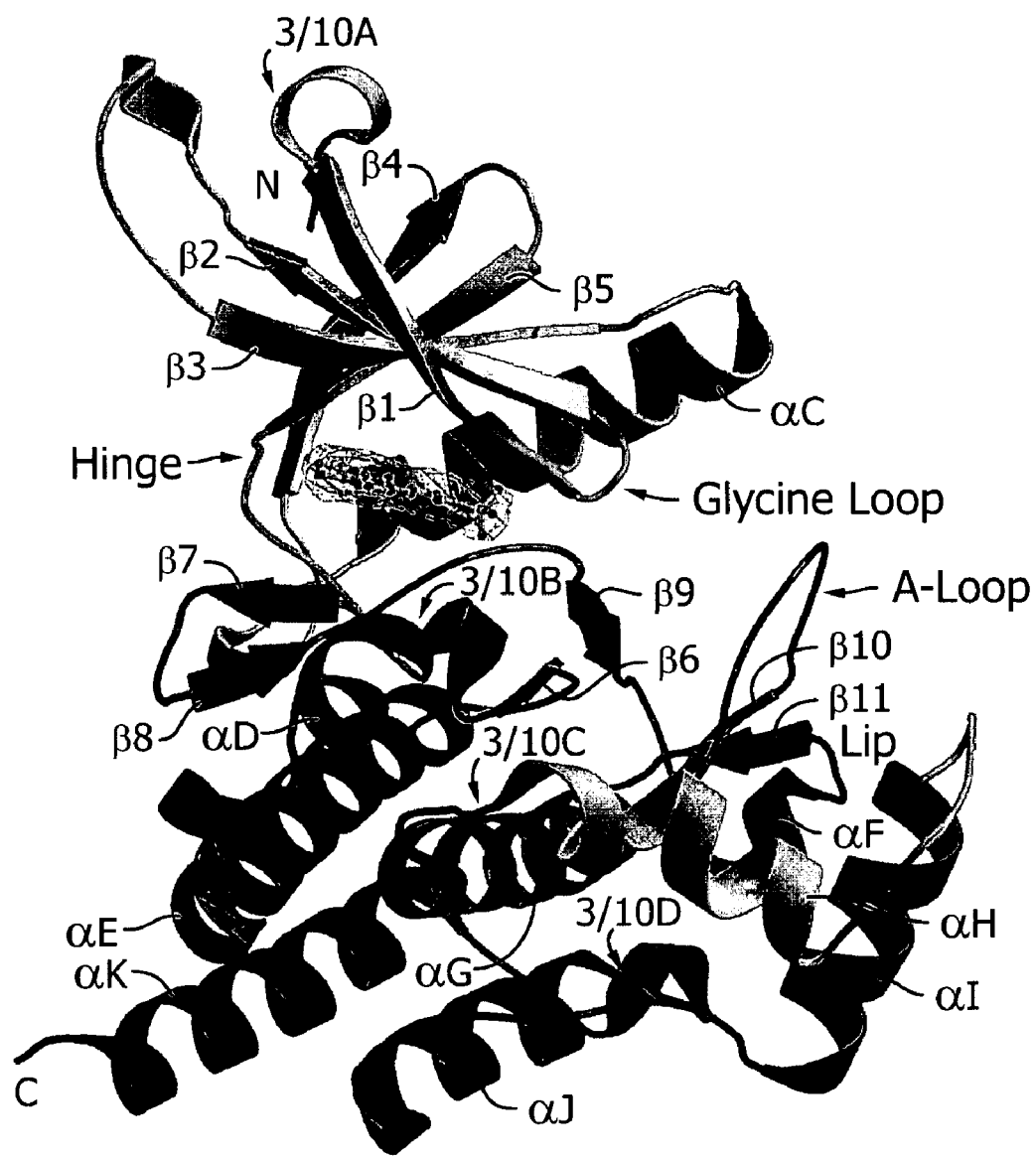
FIG. 1. (a) Ribbon representation of the crystal structure of JAK2 PTK domain in complex with the tetracyclic pyridone. The N-terminal lobe (residues 840/931) shown in light grey comprises a five-stranded anti-parallel β-sheet (β1 to β5) and one α-helix (αC). The COOH-terminal lobe (residues 932/1132) shown in dark grey comprises 8 α-helix (αD-αK) and three 3/10 helices (3/10B, C, D) and three pairs of antiparallel β-strands (β7-β8, β6-β9 and β10-β11). The JAK2 lip coloured in light grey contains one 3/10 helix (3/10C) and one α-helices (αH) connected by a short linker. The bound compound 6 is presented in a ball-and-stick representation and covered with the final 2Fo-Fc electron density map contoured at 1σ. (b) (SEQ ID NO's: 1-6) Amino acid sequence alignment of human JAK2 (SEQ ID NO: 1) PTK domain with the other members of the JAK family TYK2 (SEQ ID NO: 3), JAK3 (SEQ ID NO: 4) and JAK1 (SEQ ID NO: 2) and the kinase domain of FAK (SEQ ID NO: 5) and LCK (SEQ ID NO: 6) around the Lip region. The secondary structure of JAK2 is illustrated directly above the sequence alignment. Cylinders delineate α-helices. Dark grey boxes indict conserved residues. Light grey boxes indict conservatively substituted residues. Genbank accession codes for JAK2, TYK2, JAK3, JAK1 are NP_004963, AAS37680, NP_000206, NP_002218, respectively.

Reference to particular amino acid residues in JAK2 polypeptide residue number is defined by the numbering provided in Swiss Prot O60674 Tyrosine-protein kinase JAK2 (Janus kinase 2) (JAK-2) gi|12643404|sp|O60674|JAK2_HUMAN[12643404].

Clearly the information provided in this application will enable rational design/selection of compounds which will interact with JAK2.

In a first aspect, the present invention provides a crystalline composition comprising JAK2 or a portion thereof, or a crystalline composition comprising JAK2 or a portion thereof co-crystallised with an inhibitor.

Crystals in which JAK2 is co-crystallised with an inhibitor or ligand are known as co-crystals. The present invention provides methods of preparing co-crystals of JAK2 with an inhibitor including:
(i) adding the appropriate inhibitor during expression of the JAK2 or portion thereof in insect cells to form a complex, followed by the purification of the complex and then by crystallisation.
(ii) incubating purified JAK2 or a portion thereof in the presence of an excess of inhibitor to form a complex and then purifying and crystallizing the complex.
(iii) incubating purified JAK2 or a portion thereof with the inhibitor just before crystallisation.
(iv) soaking a crystalline form of JAK2 or portion thereof with a panel of compounds and measuring the level of binding of the compound to the crystal by collecting an X-ray diffraction data set from said crystallised molecule or molecular complex;

In a second aspect, the present invention provides a method of selecting or designing a compound that interacts with JAK2 and thereby modulates an activity mediated by the JAK2, the method comprising the step of assessing the stereochemical complementarity between the compound and a topographic region of JAK2, wherein the topographic region of the Janus kinase protein is characterised by at least a portion of the amino acids and water molecules positioned at atomic coordinates as shown in Appendix 1 or structural coordinates wherein the backbone atoms of the topographic region of JAK2 have a root mean square deviation of not more than 1.5 Å from the backbone atoms of their corresponding partners in the amino acids shown in Appendix 1.

By "stereochemical complementarity" we mean that the compound or a portion thereof makes a sufficient number of energetically favourable contacts with the JAK2, or topographic region thereof, as to have a net reduction of free energy on binding to the JAK2, or topographic region thereof.

Stereochemical complementarity or how well a given chemical compound structure binds or fits to a specified site or cavity in the protein structure can be measured by using one or more of the scoring functions available for this purpose. (See for example P. Ferrara, H. Gohlke, D. J. Price, G. Klebe, and C. L. Brooks III, Assessing scoring functions for protein-ligand interactions, J. Med. Chem., vol. 47, 3032-3047(2004).) A specific example of such a scoring function is X-SCORE (R. Wang, L. Lai, S. Wang, Further development and validation of empirical scoring functions for structure-based binding affinity prediction, J. Comput.-Aided Mol. Des., vol. 16, 11-26(2002)), which is a scoring function that calculates the dissociation constant of a given protein-ligand complex, and was constructed by calibrating to experimental data on a set of 200 protein-ligand complexes.

By "topographic region" is meant a subset of the molecular surface (Connolly, 1983) of JAK2. This subset may consist of either a single region or multiple disjoint regions. In this context the surface of enclosed cavities within JAK2 are also treated as part of the molecular surface.

Preferably, the structural coordinates have a root mean square deviation from the backbone atoms of said amino acids of not more than 1 Å, more preferably not more than 0.7 Å.

In a preferred embodiment, the topographic region of JAK2 is the ATP-binding site defined by amino acids Glu930, Leu932, Asp939, Ser936, Leu855, Arg980, Gly993, Asp994, Ala880, Val911, Leu983, Gly935, Met929 and Tyr 931, Gln853, Gly856, Lys857, Gly858, Asn859, Phe860, Gly861, Ser862, Val863, Met865, Val878, Lys882, Glu898, Leu902, Tyr913, Leu927, Pro933, Tyr934, Asn981, Ile982, Phe995, Gly996. (and include sugar pocket residues Arg938, Ala978, Thr979).

Preferably, the method comprises selecting a compound which has portions that match the amino acid residues positioned in the ATP-binding site.

By "match" we mean that the identified portions interact with the surface residues, for example, via hydrogen bonding or by enthalpy reducing van der Waals interactions which promote desolvation of the biologically active compound with the receptor, in such a way that retention of the compound by the receptor is favoured energetically.

More preferably, the method comprises selecting a compound which forms hydrogen bonds or water-mediated hydrogen bonds with at least one amino acid selected from the group consisting of Glu930, Leu932, Asp939, Ser936, Leu855, Arg980, Gly993 and Asp994.

More preferably, the method comprises selecting a compound which forms hydrophobic contacts with the side chains of at least one amino acid residue selected from the group consisting of Leu855, Ala880, Val911, Leu983, Gly935, Met929, Tyr 931, Pro933, Asn981, Ala993, Asp994, Gly856, Lys857 and Val863.

In another embodiment, crystals of unliganded JAK2 or a portion thereof are exposed to libraries of compounds according to the method of (Nienaber et al., 2000). The most potent ligand will bind to the crystal and can be identified by difference electron density maps.

The present inventors have determined the crystal structure of the active conformation of JAK2 Kinase domain in complex with the tetracyclic pyridone 2-tert-Butyl-9-fluoro-3,6-dihydro-7H-benz[h]imidazo[4,5-f]isoquinolin-7-one (compound 6). Accordingly, in another embodiment of the method of the second aspect, the selection or design of the compound is based on the JAK specific inhibitor 2-tert-Butyl-9-fluoro-3,6-dihydro-7H-benz[h]imidazo[4,5-f]isoquinolin-7-one.

Preferably, the compound is of formula I:

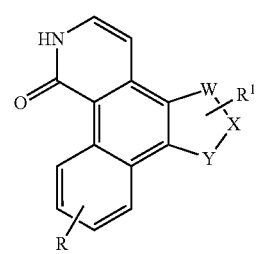

where:
R is one to three groups selected from H, halogen, OH, OR$^2$, NR$^2$R$^3$, CN, NO$_2$, CO$_2$R$^2$, CONR$^2$R$^3$, NR$^4$CONR$^2$R$^3$, OCONR$^2$R$^3$, NR$^2$COOR$^3$, NR$^2$COR$^3$, NR$^2$SO$_2$R$^3$, SO$_2$R$^2$, OC$_{2-6}$alkylOH, OC$_{2-6}$alkylNR$^2$R$^3$, OC$_{1-6}$alkylCN, C$_{1-6}$alkyl OH, C$_{1-6}$alkylNR$^2$R$^3$, C$_{1-6}$alkylCN;

where R$^2$ and R$^3$ are independently H, C$_{1-6}$alkyl, C$_{2-6}$alkenyl, C$_{2-6}$alkynyl, aryl, hetaryl, C$_{1-6}$alkylCN, C$_{2-6}$alkylNR$^5$R$^6$, or may be joined to form a 4-7-membered ring which may contain a heteroatom selected from O, S, SO$_2$ or NR$^7$;

where R$^4$ is H, C$_{1-6}$alkyl;

where R$^5$ and R$^6$ are independently H, C$_{1-6}$alkyl, or may be joined to form a 4-7-membered ring which may contain a heteroatom selected from O, S, SO$_2$ or NR$^7$;

where R$^7$ is H, C$_{1-6}$alkyl, C$_{1-6}$alkyl OH;

W, X, Y form a 5- or 6-membered aromatic ring, selected from furan, pyrrole, imidazole, oxazole, thiazole, pyrazine, pyridazine, pyridine; and R$^1$ is selected from H, halogen, OH, OC$_{1-6}$alkyl, C$_{1-6}$alkyl, C$_{1-6}$alkylCN, NR$^2$R$^3$, C$_{2-6}$ alkyl NR$^2$COR$^3$, aryl, and hetaryl.

In the above description it will be appreciated that:

C$_{1-6}$alkyl means an unsubstituted or optionally substituted straight or branched alkyl chain C$_{2-6}$alkenyl and C$_{2-6}$alkynyl means an unsubstituted or optionally substituted alkenyl or alkynyl chain Aryl means unsubstituted or optionally substituted phenyl In another preferred form, the compound may be selected or modified from a known compound (such as the natural ligand) or identified from a database. It would be expected that such a variant would compete with binding of the natural ligand to JAK2.

In a preferred embodiment of the second aspect, the method further comprises the step of obtaining a compound which possesses stereochemical complementarity to a topographic region of JAK2 and testing the compound for therapeutic activity.

In a third aspect, the present invention provides a computer-assisted method for identifying compounds which interact with JAK2 and thereby modulate an activity mediated by JAK2, using a programmed computer comprising a processor, an input device, and an output device, comprising the steps of:

(a) inputting into the computer, through the input device, data comprising the coordinates of the amino acids and water molecules shown in Appendix 1 or structural coordinates wherein the backbone atoms of the topographic region of the JAK2 protein have a root mean square deviation from the backbone atoms of their corresponding partners as shown in Appendix 1 of not more than 1.5 Å; or one or more subsets of said amino acid and water molecules;

(b) generating, using computer methods, a set of atomic coordinates of a structure that possesses stereochemical complementarity to the atomic coordinates inputted in step (a), thereby generating a criteria data set;

(c) comparing, using the processor, the criteria data set to a computer database of chemical structures;

(d) selecting from the database, using computer methods, chemical structures which are similar to a portion of said criteria data set; and (e) outputting, to the output device, the selected chemical structures which are complementary to or a similar to a portion of the criteria data set.

Preferably, the structural coordinates have a root mean square deviation from the backbone atoms of said amino acids of not more than 1 Å, more preferably not more than 0.7 Å.

Preferably, the method is used to identify potential compounds which are therapeutic agents.

The method according to the third aspect, wherein the method further comprises the step of obtaining a compound with a chemical structure selected in steps (d) and (e) and testing the compound for activity in respect of JAK2.

Preferably, the subset of amino acids is that defining the ATP-binding pocket of JAK2, namely Glu930, Leu932, Asp939, Ser936, Leu855, Arg980, Gly993, Asp994, Ala880, Val911, Leu983, Gly935, Met929 and Tyr 931, Gln853, Gly856, Lys857, Gly858, Asn859, Phe860, Gly861, Ser862, Val863, Met865, Val878, Lys882, Glu898, Leu902, Tyr913, Leu927, Pro933, Tyr934, Asn981, Ile982, Phe995, Gly996. (and includes sugar pocket residues Arg938, Ala978, Thr979).

In a fourth aspect, the present invention provides a method of screening a putative compound having the ability to modulate the activity of JAK2, comprising the steps of identifying a putative compound by the method of the first or second aspect, and testing the compound for activity.

Preferably, the testing of the compound is carried out in vitro. More preferably, the in vitro test is a high throughput assay.

In another embodiment, the testing of the compound is carried out in vivo employing cell-based or whole organism-based screens.

As will be readily understood by those skilled in this field the methods of the present invention provide a rational method for designing and selecting compounds which interact with JAK2. In the majority of cases these compounds will require further development in order to increase activity. Such further development is routine in this field and will be assisted by the structural information provided in this application. It is intended that in particular embodiments the methods of the present invention includes such further developmental steps.

In general, the design of a molecule possessing stereochemical complementarity can be accomplished by means of techniques that optimise, chemically and/or geometrically, the "fit" between a molecule and a target receptor. Known techniques of this sort are reviewed by (Goodford, 1984; Beddell, 1984; Hol, 1986; Sheridan & Venkataraghavan, 1987; Walters et al., 1998; Verlinde & Hol, 1994; Gane & Dean, 2000; Good, 2001; Langer & Hoffmann, 2001); the respective contents of which are hereby incorporated by reference.

There are two preferred approaches to designing a molecule, according to the present invention, that complements the stereochemistry of the ecdysone receptor. The first approach is to dock in silico molecules from a three-dimensional structural database directly to the receptor site, using mostly, but not exclusively, geometric criteria to assess the goodness-of-fit of a particular molecule to the site. In this approach, the number of internal degrees of freedom (and the corresponding local minima in the molecular conformation space) is reduced by considering only the geometric (hardsphere) interactions of two rigid bodies, where one body (the active site) contains "pockets" or "grooves" that form binding sites for the second body (the complementing molecule, as ligand).

This approach is illustrated by (Kuntz et al., 1982), and (Ewing et al., 2001), the contents of which are hereby incorporated by reference, whose algorithm for ligand design is implemented in a commercial software package, DOCK version 4.0, distributed by the Regents of the University of California and further described in a document, provided by the distributor, which is entitled "Overview of the DOCK program suite" the contents of which are hereby incorporated by reference. Pursuant to the Kuntz algorithm, the shape of the cavity represented by the ecdysone receptor site is defined as a series of overlapping spheres of different radii. One or more extant databases of crystallographic data, such as the Cambridge Structural Database System maintained by Cambridge University (University Chemical Laboratory, Lensfield Road, Cambridge CB2 1EW, U.K.), the Protein Data Bank maintained by the Research Collaboratory for Structural Bioinformatics (Rutgers University, N.J., U.S.A.), LeadQuest (Tripos Associates, Inc., St. Louis, Mo.), Available Chemicals Directory (Molecular Design Ltd., San Leandro, Calif.), and the NCI database (National Cancer Institute, U.S.A) is then searched for molecules which approximate the shape thus defined.

Molecules identified in this way, on the basis of geometric parameters, can then be modified to satisfy criteria associated with chemical complementarity, such as hydrogen bonding, ionic interactions and van der Waals interactions. Different scoring functions can be employed to rank and select the best molecule from a database. See for example (Bohm & Stahl, 1999). The software package FlexX, marketed by Tripos Associates, Inc. (St. Louis, Mo.) is another program that can be used in this direct docking approach (Rarey et al., 1996).

The second preferred approach entails an assessment of the interaction of respective chemical groups ("probes") with the active site at sample positions within and around the site, resulting in an array of energy values from which three-dimensional contour surfaces at selected energy levels can be generated. The chemical-probe approach to ligand design is described, for example, by (Goodford, 1984), the contents of which are hereby incorporated by reference, and is implemented in several commercial software packages, such as GRID (product of Molecular Discovery Ltd., West Way House, Elms Parade, Oxford OX2 9LL, U.K.). Pursuant to this approach, the chemical prerequisites for a site-complementing molecule are identified at the outset, by probing the active site with different chemical probes, e.g. water, a methyl group, an amine nitrogen, a carboxyl oxygen, and a hydroxyl. Favoured sites for interaction between the active site and each probe are thus determined, and from the resulting three-dimensional pattern of such sites a putative complementary molecule can be generated. This may be done either by programs that can search three-dimensional databases to identify molecules incorporating desired pharmacophore patterns or by programs which using the favoured sites and probes as input to perform de novo design.

The chemical probe approach also includes the technique known as MCSS (multiple copy simultaneous search).

There are many other approaches to ligand design and development which are known to those skilled in the art. For instance, the methods disclosed in WO 2004/075021 "Molecular Modelling Methods" to Vertex Pharmaceuticals, Inc. The present invention contemplates the use of the structural coordinates disclosed herein in any molecular modelling method or homology modelling method.

Programs suitable for searching three-dimensional databases to identify molecules bearing a desired pharmacophore include MACCS-3D and ISIS/3D (Molecular Design Ltd., San Leandro, Calif.) and Sybyl/3 DB Unity (Tripos Associates, Inc., St. Louis, Mo.).

Programs suitable for pharmacophore selection and design include DISCO (Abbott Laboratories, Abbott Park, Ill.), Catalyst (Accelrys, San Diego, Calif.) and Phase (Schrodinger New York, N.Y.).

Databases of chemical structures are available from a number of sources including Cambridge Crystallographic Data Centre (Cambridge, U.K.), Molecular Design, Ltd., (San Leandro, Calif.), Tripos Associates, Inc. (St. Louis, Mo.) and Chemical Abstracts Service (Columbus, Ohio).

De novo design programs include Ludi (Biosym Technologies Inc., San Diego, Calif.), LeapFrog (Tripos Associates, Inc.), Aladdin (Daylight Chemical Information Systems, Irvine, Calif.) and LigBuilder (Peking University, China).

Those skilled in the art will recognize that the design of a mimetic may require slight structural alteration or adjustment of a chemical structure designed or identified using the methods of the invention.

In the methods of the present invention, it is preferred that a compound selected, designed or identified by the methods possesses one or more of the following characteristics when the compound is modelled interacting with the same topographic region of JAK2 that binds to 2-tert-Butyl-9-fluoro-3,6-dihydro-7H-benz[h]imidazo[4,5-f]isoquinolin-7-one in the crystal structure of the present invention: (i) at least one hydrogen-bond is formed between the compound and at least one portion of the JAK2 with which 2-tert-Butyl-9-fluoro-3,6-dihydro-7H-benz[h]imidazo[4,5-f]isoqiuinolin-7-one forms a hydrogen-bond; (ii) at least three hydrophobic contacts are formed between the compound and at least three of the portions of the JAK2 with which 2-tert-Butyl-9-fluoro-3,6-dihydro-7H-benz[h]imidazo[4,5-f]isoqiuinolin-7-one forms hydrophobic contacts; (iii) there is no steric clash between the topographic region of the JAK2 and the compound wherein steric clash is defined as steric repulsion between non-bonded atoms within one angstrom of each other; and (iv) there is a net reduction of free energy of the compound on binding to the receptor.

In a more preferred form, the compound possesses all of the characteristics.

The invention may be implemented in hardware or software, or a combination of both. However, preferably, the invention is implemented in computer programs executing on programmable computers each comprising at least one processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer or workstation of conventional design or any computational device.

Each program is preferably implemented in a high level procedural or object-oriented programming language to communicate with a computer system. However, the programs can be implemented in assembly or machine language, if desired. In any case, the language may be compiled or interpreted language.

Each such computer program is preferably stored on a storage medium or device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

In another aspect, the present invention consists of a method of designing or selecting a compound which modulates JAK2 activity, the method comprising subjecting a compound obtained by a method according to any one of the previous aspects of the present invention to biological screens and assessing the ability of the compound to modulate JAK2 activity.

Biological assays to measure the activity of JAK2 and other related proteins are well known in this field and are generally based on the measure of tyrosine phosphorylation of a peptide substrate.

In a fifth aspect, the present invention provides a computer for producing a three-dimensional representation of a molecule or molecular complex of JAK2, wherein the computer comprises:

(a) a machine-readable data storage medium comprising a date storage material encoded with machine readable data, wherein the machine readable data comprises the coordinates of the amino acids and water molecules shown in Appendix 1 or structural coordinates wherein the backbone atoms of the topographic region of the JAK2 protein have a root mean square deviation from the backbone atoms of their corresponding partners as shown in Appendix 1 of not more than 1.5 Å, or one or more subsets of said amino acids;

(b) a working memory for storing instructions for processing the machine-readable data;

(c) a central-processing unit coupled to the working memory and to the machine-readable data storage medium, for processing the machine-readable data into the three-dimensional representation; and (d) an output hardware coupled to the central processing unit, for receiving the three-dimensional representation.

Preferably, the representation includes the presence of a compound or ligand associated with the molecule. More preferably, the compound is an inhibitor of the JAK2.

Preferably, the structural coordinates have a root mean square deviation from the backbone atoms of said amino acids of not more than 1.0 angstrom, more preferably not more than 0.7 angstrom.

In a sixth aspect, there is provided a compound able to modulate activity mediated by a Janus kinase protein, preferably JAK2, the compound being obtained by a method according to the present invention.

In a seventh aspect, there is provided a pharmaceutical composition for the treatment of a Janus kinase protein-associated disease state, comprising a compound according to the sixth aspect and a pharmaceutically acceptable carrier or diluent.

In an eighth aspect, there is provided a method of treating a patient suffering or at risk from a disease or condition for which modulation of Janus kinase protein activity, specifically JAK2 activity, provides a therapeutic or prophylactic effect, comprising the administration to the patient of an effective amount of a compound according to the sixth aspect.

Specific diseases or disorders which might be treated or prevented include Allergic Asthma, Atopic Dermatitis (Eczema), Allergic Rhinitis, Allergic Contact Dermatitis, Hypersensitivity Pneumonitis, Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis, Epstein Barr Virus (EBV), Hepatitis B, Hepatitis C, HIV, HTLV 1, Varicella-Zoster Virus (VZV), Human Papilloma Virus (HPV), Leukemia, Lymphoma, Motor Neuron Disease, Atherosclerosis & Arteriosclerosis, Cardiac Hypertrophy, Ischemia, Pulmonary Hypertension.

In addition, JAK kinases can act as a target for therapeutics for treating cell proliferative diseases. Thus, in certain embodiments, the disease or condition is a proliferative disease or neoplasia, such as benign or malignant tumors, psoriasis, leukemias (such as myeloblasticleukemia), myeloproliferative disorders (such as polycythaemia), lymphoma, prostate cancer, liver cancer, breast cancer, sarcoma, neuroblastoma, Wilm's tumor, bladder cancer, thyroid cancer, neoplasias of the epithelial origin such as mammary carcinoma, a cancer of hematopoietic cells, or a chronic inflammatory disease or condition, resulting, for example, from a persistent infection (e.g., tuberculosis, syphilis, fungal infection), from prolonged exposure to endogenous (e.g., elevated plasma lipids) or exogenous (e.g., silica, asbestos, cigarette tar, surgical sutures) toxins, and from autoimmune reactions (e.g., rheumatoid arthritis, systemic lupus erythrymatosis, multiple sclerosis, psoriasis). Thus, chronic inflammatory diseases include many common medical conditions, such as rheumatoid arthritis, restenosis, psoriasis, multiple sclerosis, surgical adhesions, tuberculosis, and chronic inflammatory lung and airway diseases, such as asthma pneumoconiosis, chronic obstructive pulmonary disease, nasal polyps, and pulmonary fibrosis. JAK kinase modulators may also be useful in inhibiting development of hematomous plaque and restenosis, in controlling restenosis, as anti-metastatic agents, in treating diabetic complications, as immunosuppressants, and in control of angiogenesis to the extent a JAK kinase is involved in a particular disease or condition.

In a ninth aspect, there is provided a method for evaluating the ability of a chemical entity to interact with a JAK2, said method comprising the steps of:

(a) creating a computer model of at least one region of JAK2 using structural coordinates comprising at least a portion of the amino acids and water molecules positioned at atomic coordinates as shown in Appendix 1 or structural coordinates wherein the backbone atoms of the topographic region of the JAK2 have a root mean square deviation from the backbone atoms of their corresponding partners as shown in Appendix 1 of not more than 1.5 Å;

(b) employing computational means to perform a fitting operation between the chemical entity and said computer model of said at least one region of the monomers of JAK2; and (c) analysing the results of said fitting operation to quantify the association between the chemical entity and said at least one region of the JAK2 model.

Preferably, the structural coordinates have a root mean square deviation from the backbone atoms of said amino acids of not more than 1.0 angstrom, not more than 0.7 angstrom Preferably, the region is the ATP binding site defined by amino acids defined by amino acids Glu930, Leu932, Asp939, Ser936, Leu855, Arg980, Gly993, Asp994, Ala880, Val911, Leu983, Gly935, Met929 and Tyr 931, Gln853, Gly856, Lys857, Gly858, Asn859, Phe860, Gly861, Ser862, Val863, Met865, Val878, Lys882, Glu898, Leu902, Tyr913, Leu927, Pro933, Tyr934, Asn981, Ile982, Phe995, Gly996. (and include sugar pocket residues Arg938, Ala978, Thr979).

Accordingly, in a further aspect, there is provided a method of utilising molecular replacement to obtain structural information about a molecule or molecular complex of unknown structure, comprising the steps of:

(i) crystallizing said molecule or molecular complex;

(ii) collecting an X-ray diffraction data set from said crystallised molecule or molecular complex;

(iii) applying at least a portion of the structure coordinates set forth in Appendix 1 to the X-ray diffraction data set to generate a three-dimensional electron density map of at least a portion of the molecule or molecular complex whose structure is unknown.

The term "molecular replacement" refers to a method that involves generating a preliminary model of a crystal of a protein related to JAK2 whose structure coordinates are unknown, by orienting and positioning a molecule whose structure coordinates are known (e.g. JAK2.coordinates from Appendix 1) within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal (Lattman, 1985; Rossmann, 1990).

As would be well understood by those skilled in the art, the structural information of the JAK2 kinase domain contained in Appendix 1 can be used to predict, by homology modelling, the three-dimensional structure of proteins related to JAK2. For example, the program Modeler (Sali & Blundell, 1993) builds homology models from the satisfaction of spatial restraints derived from the target (ie, a protein related to JAK2) with the template (which would be the three-dimensional structure of the JAK2 kinase domain in this case). Related proteins include a range of different JAK2 variants, including full-length wild type, naturally occurring variants (eg allelic variants and splice variants), truncated variants of wild type or naturally-occurring variants, and mutants of full length or truncated wild-type or naturally occurring variants (that can be mutated at one or more sites) and for other members of the family (eg JAK1, JAK3, TYK2) and their mutants and variants.

Accordingly, in a further aspect, the present invention provides creating a homology model of at least one region of a protein related to JAK2 comprising the step of applying at least a portion of the structural coordinates set forth in Appendix 1 to generate the homology model.

Preferably, the method comprises the steps of:

(i) selecting at least a portion of the structural coordinates set forth in Appendix 1 that correspond to the region to generate an initial set of structural coordinates;

(ii) replacing the structural coordinates of amino acids not present in the region in the initial set of structural coordinates with standard structural coordinates for the amino acids which are present in the region to generate a further set of structural coordinates;

(iii) refining the further set of structural coordinates by applying spatial restraints so as to generate the homology model.

It would be understood by the person skilled in the art that a homology model generated according to this aspect of the invention may be applied in the methods of all other aspects of the invention.

Preferably, the JAK2 related protein is selected from JAK1, JAK3 and TYK2.

In another aspect, the present invention consists in a method of assessing the interaction between a compound and JAK2, the method comprising exposing a crystalline composition comprising JAK2 or portion thereof or variant of these to the compound and measuring the level of binding of the compound to the crystal.

In a yet further aspect, the present invention provides a JAK2 kinase domain in liganded crystalline form or a portion thereof, comprising the amino acid sequence 840-1132 and having the structural coordinates of Appendix 1.

In order that the nature of the present invention may be more clearly understood, preferred forms thereof will now be described with reference to the following non-limiting examples.

EXAMPLES

Example 1

Cloning of JAK2 Kinase Domain and Assay Protocols

JAK2 kinase domains was produced in the following manner:

The Kinase Domain of Human JAK2 was Amplified from U937 mRNA using the polymerase chain reaction with the following primers:

SALI-jk2 5'-ACG CGT CGA CGG TGC CTT TGA AGA CCG GGA T-3' jk2-NOTI 5'-ATA GTT TAG CGG CCG CTC AGA ATG AAG GTC ATT T-3'

JAK2 PCR products were cloned into the pFastBac HTc expression vector (Gibco) via the Sal I and Not I sites. The JAK2 plasmid was then transformed into competent DH10Bac cells (Gibco), and the recombinant baculovirus produced prepared for transfection into Sf9 insect cells.

Assay Protocols

Kinase assays were performed either in a 96 well capture-based ELISA assay or in 384 well Optiplates (Packard) using an Alphascreen Protein Tyrosine Kinase kit (PerkinElmer BioSignal, Inc. Montreal, Quebec Canada). In either case using approximately 1.5 µg of affinity purified PTK domain in the presence of 50 mM HEPES, pH 7.5, 10 mM $MgCl_2$, 150 mM NaCl and 10 µM-1 mM ATP. The biotinylated substrate biotin-EGPWLEEEEEAYGWMDF-$NH_2$ or biotinylated poly(Glu-Tyr) (final concentration 5 µM) was used as substrate. In the ELISA assay tyrosine phosphorylation was quantitated following transfer to an avidin coated ELISA plate using peroxidase-linked anti-phospho-tyrosine antibody PY20. In the Alphascreen assay, Alphascreen phosphotyrosine acceptor beads followed by streptavidin donor beads were added under subdued light. The ELISA plates were read on a BMG Fluorostar, the Alphascreen plates were read on a Packard Fusion Alpha. Inhibitors were added to the assays fifteen minutes prior to the addition of ATP. Inhibitors were added in aqueous DMSO, with DMSO concentrations never exceeding 1%.

Example 2

Expression and Purification of JAK2 Kinase Domain

The formation of a co-crystal of JAK2 with an inhibitor requires the formation of a complex of JAK2 with an inhibitor. The complex can be formed at various stages during the expression, purification and crystallisation of JAK2. These stages are pointed out below.

The gene encompassing the kinase domain of human Janus kinase 2 (JAK2) (residues 835-1132) was cloned into pFast-Bac, which allows the protein to be expressed fused to a GST cleavable tag. Recombinant Bacmid DNA containing the JAK2 insert was isolated and transfected to *Spodoptera frugiperda* (Sf9) insect cells. Baculovirus obtained from the transfection was then used to infect Sf9 cells grown in suspension to a density of $2 \times 10^6$ cells/ml at a multiplicity of infection>10. In one approach to co-crystallisation, the inhibitor was added at this stage. Cells were grown for 48 h and centrifuged and the pellet stored to −80° C. until use.

Cells were thawed, resuspended into buffer A (20 mM tris pH 8.5, 250 mM NaCl, 0.5% Thesit, 5% Glycerol, 1 mM DTT) containing protease inhibitors (Roche Diagnostics) and lysed by sonication. The resulted suspension was centrifuged at 18000 rpm for 1 h. The supernatant was filtered and recirculated onto a GST resin for 5 h. The GST column was washed extensively then the fusion protein was eluted with 10 mM glutathione. Fractions containing GST-JAK2 were pooled and concentrated to 2 ml and incubated with α-thrombin (Sigma) overnight at 4° C. In another approach to co-crystallisation, the protein was then incubated with 3× molar ratio of inhibitor before being loaded onto Superdex 75 gel filtration column (HiLoad 16/60) equilibrated in 20 mM Tris pH 8.5, 250 mM NaCl, 1 mM DTT. JAK2-inhibitor complex containing fractions were pooled and concentrated to 10 mg/ml for crystallization trials.

In a further approach to co-crystallisation, the purified JAK2 kinase domain was incubated with an excess of compound before crystallisation trials.

Example 3

Crystallization of JAK2 Kinase Domain

Crystallization conditions were initially identified in the Hampton research (Riverside, Calif., USA) screening kit. Optimized crystals were grown by vapor diffusion method in sitting drop plates with equal volume of protein solution of 8 to 12 mg/ml containing 20 mM Tris-HCl pH 8.5, 250 mM NaCl, 1 mM DTT and reservoir solution containing 28% PEG 4000, 0.2M Ammonium acetate, 0.1M citrate buffer pH 6. Single crystals grew overnight at 20° C. and grew to maximal size between 7-14 days.

In a yet further approach to co-crystallisation, the crystals were then soaked in a solution of the inhibitor to prepare a JAK2-inhibitor co-crystal.

Example 4

Chemical Synthesis

Example 4.1
2-(2-Fluoropyridin-4-yl)-1-phenylethanone

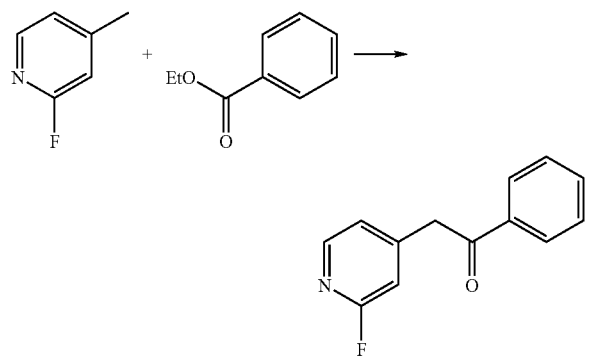

A solution of sodium bis(trimethylsilyl)amide (36 mL, 1M) was diluted with THF (60 mL) and cooled to 0° C. 2-Fluoro-4-methylpyridine (2.0 g, 18 mmol) was then added and after 45 min. at 0° C. ethyl benzoate (3.24 g, 21 mmol) was added dropwise. Stirring was continued for 45 min. and the solution then poured into 2M HCl (100 mL) cooled to 0° C. After thorough mixing, the solution was basified to pH9 with 5M NaOH, and the product extracted into ether (3×30 mL). The ethereal layers were combined and washed with brine (1×30 mL), dried (MgSO4) and concentrated under reduced pressure. The residue was dissolved in a minimum of dichloromethane and precipitated by addition of pet. spirit. The solid was collected and washed with cold pet. spirit to afford the pure product as a pale brown solid (2.8 g, 72%).

$^1$H NMR (CDCl$_3$) δ 4.30 (s, 2H), 6.84 (m, 1H), 7.06-7.08 (m, 1H), 7.45-7.51 (m, 2H), 7.59-7.62 (m, 1H), 7.96 (m, 1H), 7.98 (m, 1H), 8.15 (br d, J=5.1 Hz, 1H).

Example 4.2
2-(2-Fluoropyridin-4-yl)-5,5-dimethyl-1-phenylhexane-1,4-dione

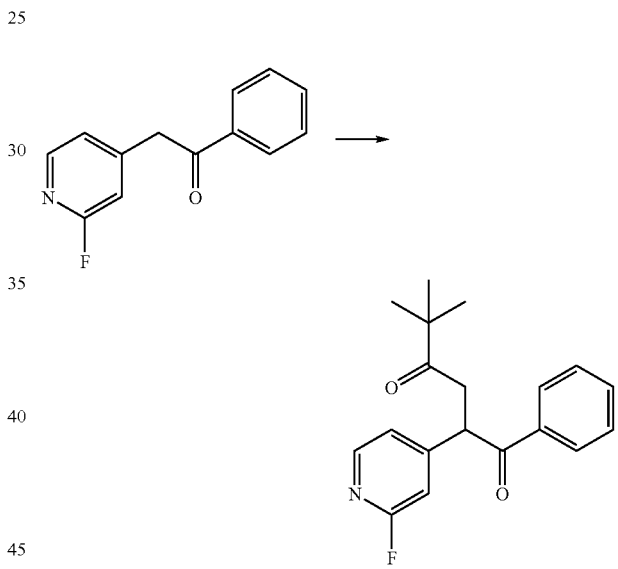

To a solution of 2-(2-fluoropyridin-4-yl)-1-phenylethanone (450 mg, 2.1 mmol) in dry THF (10 mL) at 0° C. was added a solution of sodium bis(trimethylsilyl)amide (2.1 mL, 1M). After 10 min. 1-bromopinacolone (309 μL, 2.3 mmol) was added dropwise and the solution stirred for 2 h. The solution was poured into ethyl acetate (25 mL) and H$_2$O (25 mL) and the layers allowed to separate. The organic layer was collected and the aqueous layer extracted with ethyl acetate (30 mL). The combined organic layers were washed with H2O and brine, dried (MgSO4) and concentrated. The product was purified by flash chromatography using EtOAc-Pet. spirit (20:80) as eluant to give the pure product as a pale yellow oil (574 mg, 87%).

$^1$H NMR (d4-MeOD) δ 1.17 (s, 9H), 2.99 (dd, J=18.3, 3.9 Hz, 1H), 3.72 (dd, J=18.3, 10.2 Hz, 1H), 5.31 (dd, J=10.2, 3.9 Hz, 1H), 7.07 (br s, 1H), 7.27 (ddd, J=5.1, 1.5, 1.5 Hz, 1H), 7.45-7.51 (m, 2H), 7.55-7.61 (m, 1H), 8.00-8.04 (m, 2H), 8.09 (br d, J=5.4 Hz, 1H). m/z (EI) 256 (M−$^t$Bu)$^+$

Example 4.3

4-(5-tert-Butyl-2-phenyl-1H-pyrrol-3-yl)pyridin-2(1H)-one

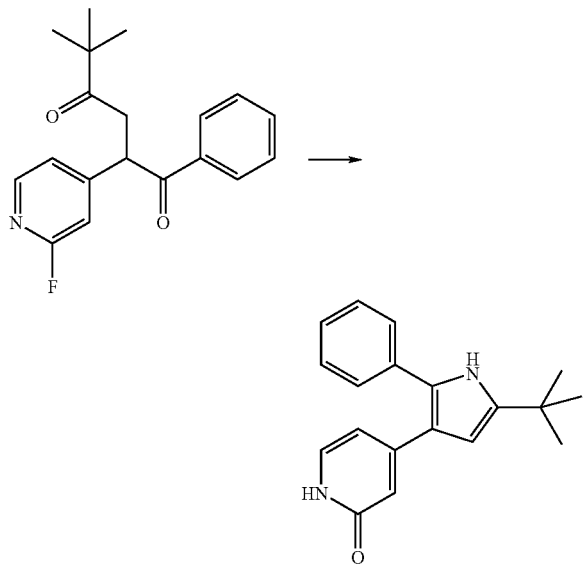

A solution of 2-(2-fluoropyridin-4-yl)-5,5-dimethyl-1-phenylhexane-1,4-dione (200 mg, 0.6 mmol) and ammonium acetate (329 mg, 3.8 mmol) in acetic acid (3 mL) was heated at reflux for 18 h. Upon cooling to RT the solution was slowly added to a mixture of sat'd aqueous NaHCO3 (40 mL) and EtOAc (40 mL). The mixture was stirred for 15 min. and the organic layer was extracted with ethyl acetate (25 mL) and the organic layers combined, washed with sat'd aqueous NaHCO$_3$, H$_2$O and brine, dried (MgSO4) and concentrated. The product was purified by flash chromatography using EtOAc-MeOH (100:0→95:5) as eluant to give the pure product as a cream solid (144 mg, 78%).

$^1$H NMR (d6-DMSO) δ 1.30 (s, 9H), 5.95 (dd, J=6.9, 1.8 Hz, 1H), 6.04 (d, J=2.7 Hz, 1H), 6.12 (d, J=1.2 Hz, 1H), 7.12 (d, J=6.9 Hz, 1H), 7.30-7.42 (m, 5H), 10.89 (m, 1H), 11.10 (br s, 1H). m/z (EI) 292 (M+H)$^+$

Example 4.4

4-(5-tert-Butyl-2-phenyl-3-furyl)pyridin-2(1H)-one

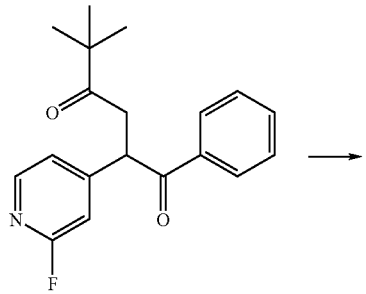

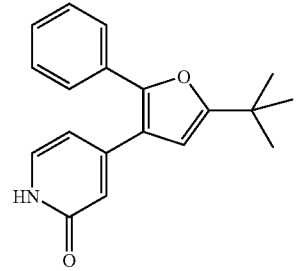

A solution of 2-(2-fluoropyridin-4-yl)-5,5-dimethyl-1-phenylhexane-1,4-dione (200 mg, 0.6 mmol) in acetic acid (3 mL) was heated at reflux for 18 h. Upon cooling to RT the solution was slowly added to a mixture of sat'd aqueous NaHCO3 (40 mL) and EtOAc (40 mL). The mixture was stirred for 15 min. and the organic layer then collected. The aqueous layer was extracted with ethyl acetate (30 mL) and the organic layers combined, washed with sat'd aqueous NaHCO$_3$, H$_2$O and brine, dried (MgSO4) and concentrated. The product was purified by flash chromatography using EtOAc-MeOH (100:0→95:5) as eluant to give the pure product as a cream solid (146 mg, 78%).

$^1$H NMR (d6-DMSO) δ 1.32 (s, 9H), 6.07 (dd, J=6.9, 1.8 Hz, 1H), 6.04 (d, J=2.7 Hz, 1H), 6.34 (d, J=1.2 Hz, 1H), 6.41 (s, 1H), 7.30-7.52 (m, 7H), 11.46 (br s, 1H). m/z (EI) 293 (M+H)$^+$

Example 4.5

2-tert-butyl-1,6-dihydro-7H-benzo[h]pyrrolo[3,2-f]isoquinolin-7-one

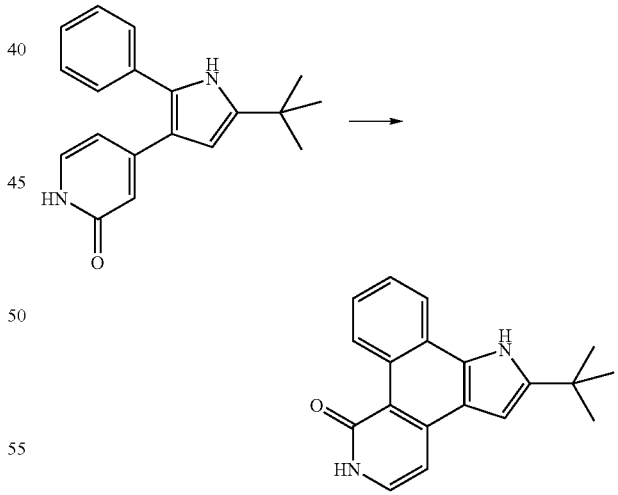

A solution of 4-(5-tert-Butyl-2-phenyl-1H-pyrrol-3-yl)pyridin-2(1H)-one (144 mg, 0.5 mmol) in THF (145 mL) was irradiated with a sun lamp for 5 h. The solution was then concentrated in vacuo and the product purified by flash chromatography using EtOAc-Pet. spirit (80:20) as eluant, to separate the pure product as a cream solid (113 mg, 80%).

$^1$H NMR (d6-DMSO) δ 1.46 (s, 9H), 6.75 (d, J=2.1 Hz, 1H), 7.02 (dd, J=6.6, 0.9 Hz, 1H), 7.42 (dd, J=6.3, 6.3 Hz, 1H), 7.50 (ddd, J=8.4, 6.9, 1.5 Hz, 1H), 7.60 (ddd, J=8.4, 6.9, 1.5Hz, 1H), 8.59 (dd, J=8.1, 1.2 Hz, 1H), 10.22 (dd, J=8.7, 0.9 Hz, 1H), 11.32 (m, 1H), 11.63 (br s, 1H). Acc. Mass: $C_{19}H_{18}N_2O+H^+$ requires 291.1497; found 291.1492.

Example 4.6

2-tert-Buty-1,6-dihydro-7H-benzo[h]furo[3,2-f]isoquinolin-7-one

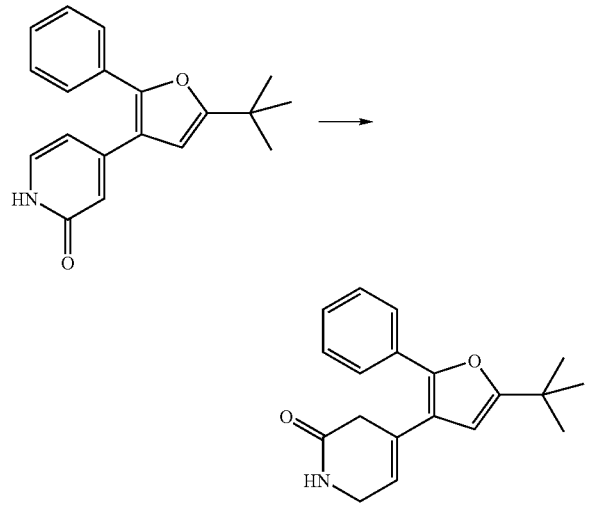

A solution of 4-(5-tert-butyl-2-phenyl-3-furyl)pyridin-2 (1H)-one (50 mg, 0.2 mmol) in THF (50 mL) was irradiated with a sun lamp for 5 h. The solution was then concentrated in vacuo and the product purified by flash chromatography using EtOAc-Pet. Spirit (80:20) as eluant, to separate the pure product as a cream solid (26 mg, 52%).

$^1$H NMR(d6-DMSO) δ 1.47 (s, 9H), 7.07 (dd, J=6.6, 1.5 Hz, 1H), 7.22 (s, 1H), 7.55 (dd, J=6.3, 6.3 Hz, 1H), 7.63-7.73 (m, 2H), 8.28-8.32 (m, 1H), 11.65-11.69 (m, 1H). Acc. Mass: $C_{19}H_{17}NO_2+H^+$ requires 292.1337; found 292.1340.

Example 4.7

2-tert-Butyl-9-fluoro-3,6-dihydro-7H-benz[h]imidazo[4,5-f]isoquinolin-7-one (Compound 6)

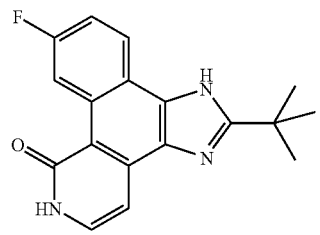

2-tert-Butyl-9-fluoro-3,6-dihydro-7H-benz[h]imidazo[4,5-f]isoquinolin-7-one (Compound 6) was prepared as described by Thompson, et al. (2002) and spectroscopic data are consistent with that reported in the literature.

Example 5

Diffraction Analysis of JAK2

The crystals were flash-cooled to 100K prior to data collection using 5% glycerol, 28% PEG 4000, 0.2M Ammonium acetate, 0.1M citrate buffer pH 6 as a cryoprotectant. X-ray diffraction experiments were performed in the facilities of the Department of Biochemistry and Molecular Biology of the School of Medical Science at Monash University, Clayton, Australia using a Rigaku RU-3HBR rotaing anode generator with helium purged OSMIC focusing mirrors coupled to an R-AXIS IV$^{++}$ detector.

A 2.0 Å data set was merged and processed with a HKL software package (HKL Research, Charlottesville, N.C.). The crystals, with unit cell dimensions a.=b=111.60 Å, and c=70.69 Å belong to space group P4$_1$, with 2 monomers in the asymmetric unit. See Table 2 for a summary of data collection statistics. The structure was determined by molecular replacement method with the program AmoRe in the CCP4 suite. EGFRK was used as a search probe (Protein Data Bank code 1M14). Subsequent refinement by utilizing CNS[59] and O[60] was used. Further refinement was carried out using REF-MAC[61]. The final model, which comprises residues 843-1132, 62 water molecules and two inhibitor molecules, has an $R_{factor}$ of 20.3% and an $R_{free}$ of 25.2% for all reflections between 20 and 2.0 Å. See Table 2 for refinement statistics. The loop between β4 and β5 is poorly ordered and is not included in the final model.

The geometry of the model was performed with PROCHECK which indicated that the structure had excellent geometry.

Data collection and refinement statistics for JAK2 kinase domain/Compound 6 (tetracyclic pyridone) co-crystals are summarized in the following table:

TABLE 2

| Data collection statistics | |
| --- | --- |
| Temperature | 100 K |
| Space Group | P41 |
| Cell dimensions (Å) (a, b, c) | 111.273, 111.273, 70.57 |
| Resolution (Å) | 100-2.00 (2.07-2.00) |
| Total N$^{o.}$ observations | 146053 |
| N$^{o.}$ unique observations | 56521 |
| Multiplicity | 2.58 |
| Data completeness (%) | 96.8 (97.1) |
| No. data > 2σ$_I$ | 73 (39.8) |
| I/σ$_I$ | 15.95 (2.12) |
| R$_{merge}$$^1$ (%) | 6.5 (55.5) |
| Refinement statistics | |
| Non hydrogen atoms | |
| Protein | 4766 |
| Ligand | 46 |
| Water | 395 |
| Resolution (Å) | 100-2.00 |
| R$_{factor}$$^2$ (%) | 20.8 |
| R$_{free}$$^3$ (%) | 24.9 |
| Rms deviations from ideality | |
| Bond lengths (Å) | 0.005 |
| Bond angles (°) | 1.075 |
| Impropers (°) | 0.667 |
| Dihedrals (°) | 21.66 |

TABLE 2-continued

| Ramachandran plot | |
|---|---|
| Most favoured And allowed region (%) | 88 (11.6) |
| B-factors (Å$^2$) | |
| Average main chain | 39.781 |
| Average side chain | 43.095 |
| Average water molecule | 44.138 |
| Ligand | 26.089 |
| r.m.s. deviation bonded Bs | 2.043 |

The value in parentheses are for the highest resolution bin (approximate interval 0.1A)
[1]Rmerge = $\Sigma |I_{hkl} - \langle I_{hkl}\rangle|/\Sigma I_{hkl}$
[2]R factor = $\Sigma I_{hkl} ||Fo| - |Fc||/\Sigma I_{hkl} |Fo|$ for all data exept for 4%, which was used for the $R_{free}$ calculation.

Example 6

Structure Analysis of the JAK2-Compound 6 Complex

The model of JAK2 contains 294 amino acids (spanning the JAK2 sequence 840-1132) and (62) water molecules and the inhibitor molecule. There are two molecules of JAK2 kinase-inhibitor in the asymmetric unit. The r.m.s deviation between the 2 monomers in the asymmetric unit is 0.56 Å, with the largest deviation between residues 857-861, 885-889, 933-935, 942-952, 1010-1014. Unless explicitly stated, structural analysis will be confined to one monomer in the asymmetric unit.

A ribbon diagram of JAK2 kinase domain in complex with compound 6 is shown in FIG. 1(a). Atomic coordinates of JAK2 co-crystallized with compound 6 is provided in Appendix 1 which diagrams coordinates for sequence A (SEQ ID NO: 7) and sequence B (SEQ ID NO: 8) as well as compound 6.

The JAK2 PTK domain exhibits an architecture typical of all previously reported protein kinases, namely a small and large N-terminal and C-terminal lobe respectively. The N-terminal lobe comprises a curled β sheet of five anti-parallel β-strands (β1 to β5) and one α-helix (αC). The COOH-terminal lobe is mainly α-helical with 8 α-helices (αD-αK) and three 3/10 helices (3/10B, C, D) and three pairs of anti-parallel β-strands (β7-β8, β6-β9 and β10-β11).

Figure 1B:
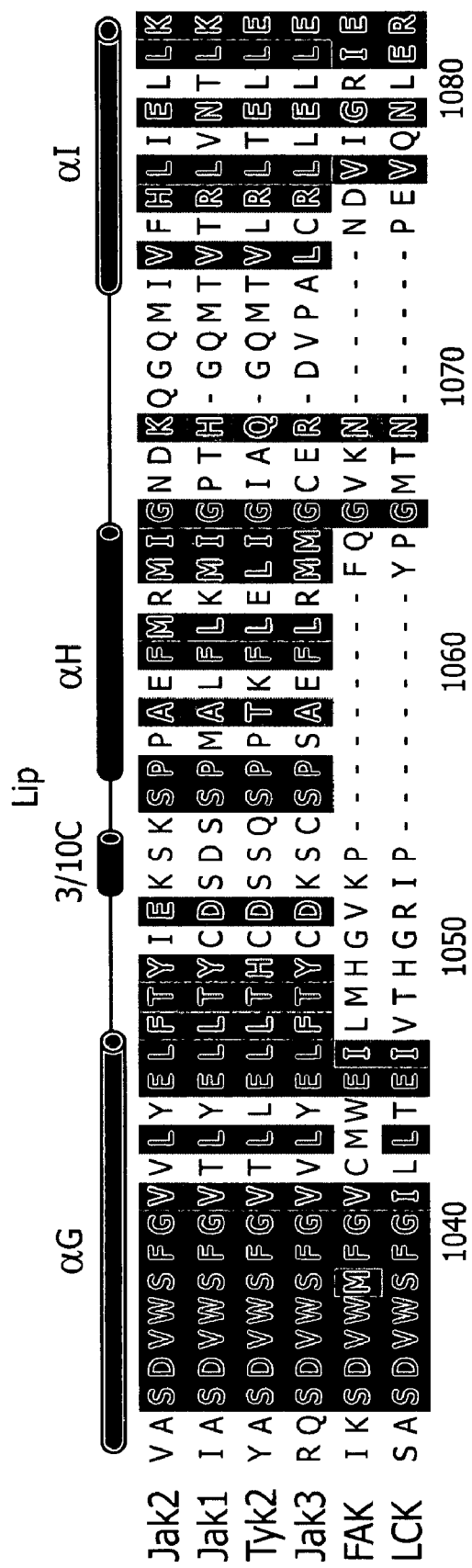

Whilst the JAK2 kinase domain appears to conform in most respects to the structures of other PTKs, the loop structure located between amino acids 1056-1078, termed the JAK2 kinase insertion loop (αH), does not resemble any feature observed in any other kinase. Nonetheless, this loop is a highly conserved feature of the JAK family of PTKs (FIG. 1b) and it most likely plays an important role in the function of the JAK kinase family. The loop structure packs loosely against the base of the C-terminal lobe and is relatively mobile and solvent accessible. In particular, the serine located at residue 1056 in the motif EKSKSPPAEFMR is conserved in all known JAK family kinases, with the exception of the *Drosophila* JAK family member, hopscotch. The exposed nature of this serine, coupled with its presence in a loop within the kinase domain that is not found outside the JAK family, suggests that Ser 1056 may be involved in a phosphorylation event that may have a role in the regulation of JAK function.

6.1 A-loop Conformation

PTKs exist in either a catalytically-inactive state or catalytically active-state (Huse, 2002); these conformational states are governed by the phosphorylation of tandem tyrosine residues within the activation loop that results in the expulsion of the activation loop from the active site. In addition, this conformational switch repositions the highly conserved Asp-Phe-Gly motif (residues 994-996 in JAK2) in the proximity of the active site, allowing a shift in the position of the αC helix. The functional role of these tyrosine residues varies between the Jaks and in JAK2, phosphorylation of the Tyr 1007 is critical for activity (Feng, 1997). The JAK2 PTK domain has been crystallised in an active conformation, in which the activation loop is expelled fully from the ATP-binding pocket, phosphorylated at positions Tyr 1007 and Tyr 1008. The 2 $F_o$-$F_c$ and $F_o$-$F_c$ electron density maps showed clearly that Tyr 1007 and Tyr 1008 were phosphorylated. In addition a salt bridge between Lys882 (β3) and Glu898 (αC helix) in the JAK2 PTK domain structure also represents a characteristic feature of active PTKs.

Figure 2A:
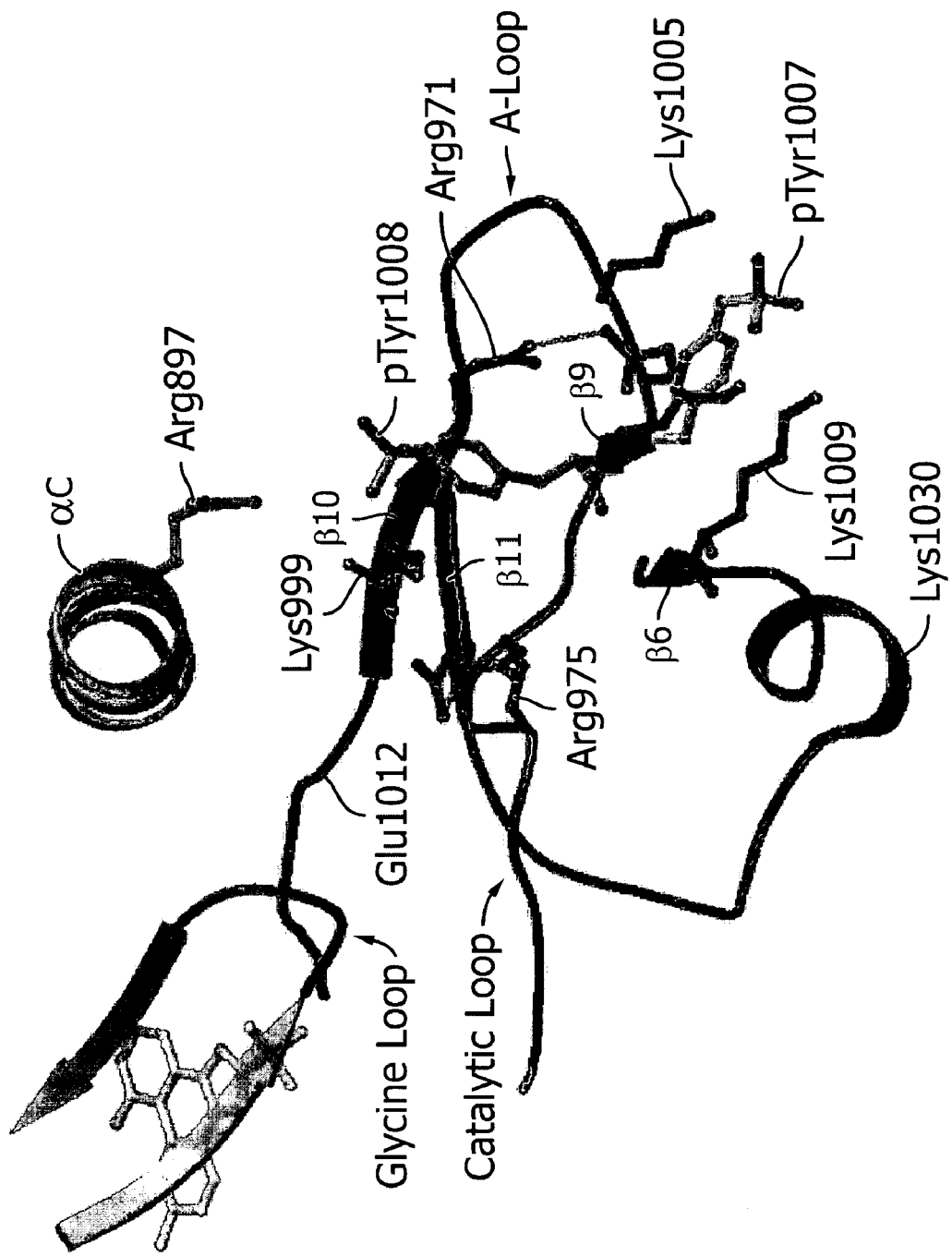
FIG. 2. (a) Ribbon representation of the activation loop of JAK2 PTK domain: Tyr1007 and Tyr 1008 are the sites of phosphorylation within the activation loop. β6 and β11, the two C-terminal strands stabilizing β9 and β10 from the activation loop are shown. (b) Molecular surface representation of JAK2 PTK domain in complex with a tetracyclic pyridone (i) in comparison to the more open LCK active site in complex with staurosporine (ii). GRASP[62] surface, are color coded by electrostatic potential.

The well-ordered conformation of the JAK2 activation loop (residues 994-1023) is stabilized by a large number of interactions including β9 and β10 that formed two two-stranded anti-parallel β-sheets with β6 and β11 respectively; and two arginine residues, Arg 971 and Arg 975 that were observed to stabilize the base and the tip of the activation loop respectively (FIG. 2(a)). In addition, a number of lysine residues stabilized the conformations of the phosphorylation sites pTyr 1007 (Lys 1005, Lys 1009 and Lys 1030) and pTyr 1008 (Lys 999). The conformation of the JAK2 activation loop is similar to that of other PTKs, providing a docking site for protein substrates, ATP analogues and other regulatory proteins such as SOCS-1 and tyrosine phosphatases. The high degree of solvent exposure of pTyr1007 is consistent with this residue being a critical residue for the JAK2 regulatory proteins such as SOCS-1 and PTP1B (Flowers, 2004; Giordanetto, 2003; Yoshikawa, 2001; Myers, 2001). FIG. 2a 6.2 Comparative Analysis In comparison to the active PTK structures previously determined (Hubbard S R and Till J H, 2000), the individual N- and C-terminal lobes superpose well. For example, the sequence similarity and r.m.s.d of the N-terminal lobe of JAK2 PTK domain and other active PTK N-terminal lobes are: IRK (1.45 Å over 63 Cα atoms, 26% identity); EGF (1.38 Å over 69 Cα atoms, 23% identity); LCK (1.19 Å over 65 Cα atoms, 38% identity); FAK (1.46 Å over 69 Cα atoms, 27% identity); ZAP 70 (1.25 Å over 66 Cα atoms, 35% identity). The sequence similarity and r.m.s.d of the C-terminal lobe of JAK2 PTK domain and other active PTK C-terminal lobes are: IRK (1.17 Å over 151 Cα atoms, 39% identity); EGF (0.90 Å over 163 Cα atoms, 43% identity); LCK (1.04 Å over 155 Cα atoms, 39% identity); FAK (0.97 Å over 155 Cα atoms, 40% identity); ZAP 70 (1.19 Å over 166 Cα atoms, 36% identity).

However, in comparison to the other PTKs, the juxtapositioning of the respective lobes are significantly different. For example, after superposing the N-terminal lobe of JAK2 PTK onto the N-terminal lobes of IRK, EGF, LCK and FAK kinases a 13.9°, 13.6°, 10.3° and 18.6° rotation respectively is required to superpose the corresponding C-terminal lobes. As a consequence, the opening angle of the active JAK2 PTK structure is significantly more "closed" than any other active PTK structure determined in presence of nucleotides or analogues. The swing of the N-terminal lobe towards the C-terminal lobe markedly narrows the JAK2 ATP binding site, which is constricted further via the conformations of the activation loop and the glycine loop; the glycine loop (consensus sequence G-xG-x-Φ-G, where Φ is either mainly Phe or Tyr), known to be important in substrate and nucleotide binding, is orientated towards and makes contacts with the activation loop and catalytic loop.

Figure 2B:
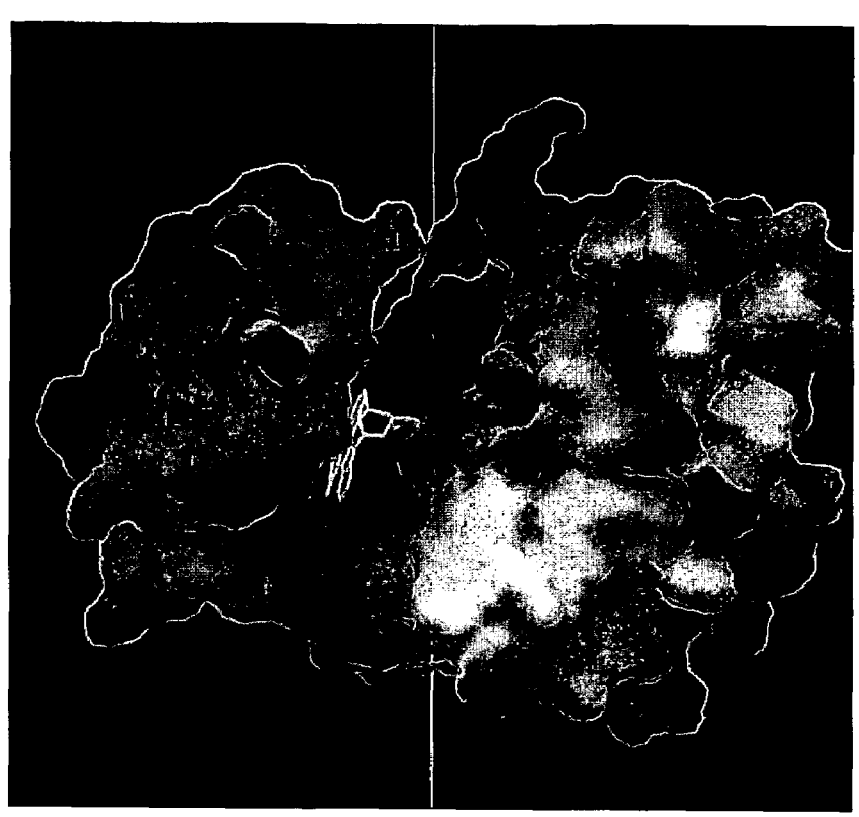
Figure 2B:
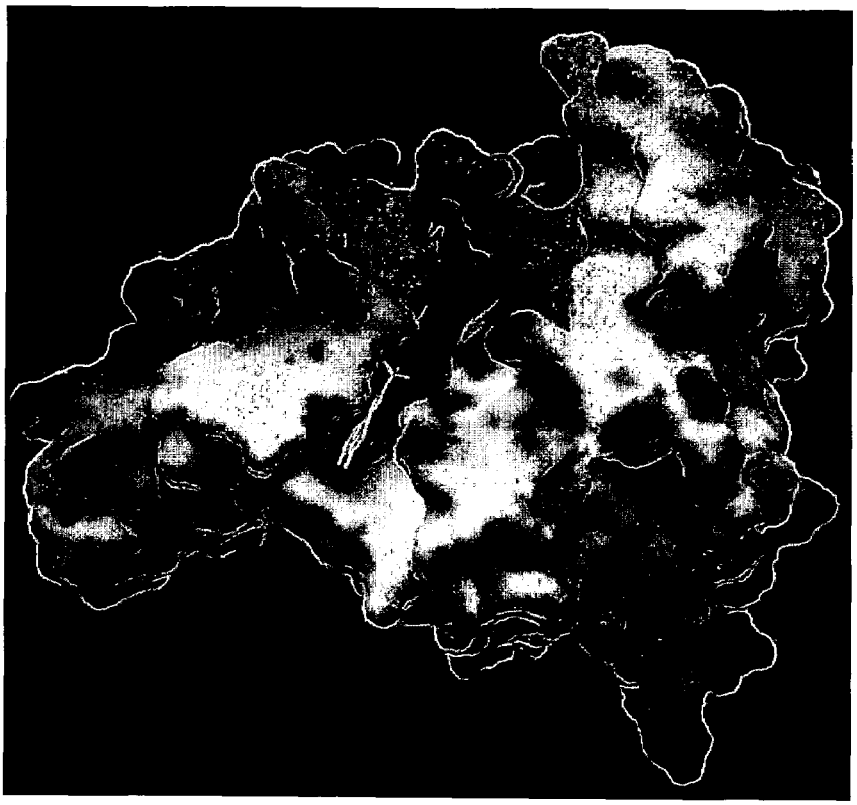
Figure 3A:
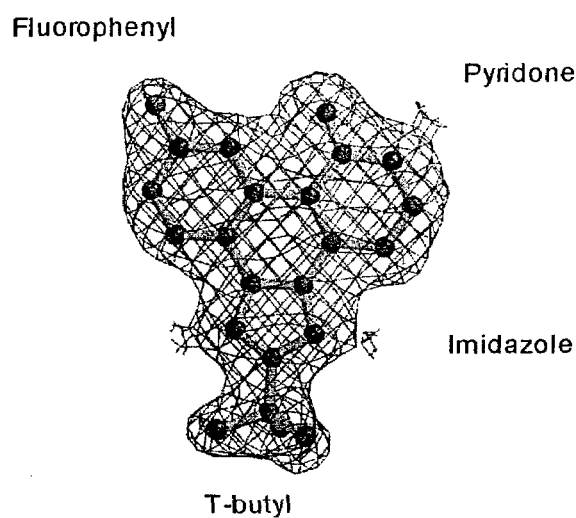
FIG. 3 (a) Structural formula of the tetracyclic pyridone presented in a ball-and-stick representation and covered with the final 2Fo-Fc electron density map contoured at 1σ. (b) Interactions between the tetracyclic pyridone and JAK2 kinase domain.
Figure 3B:
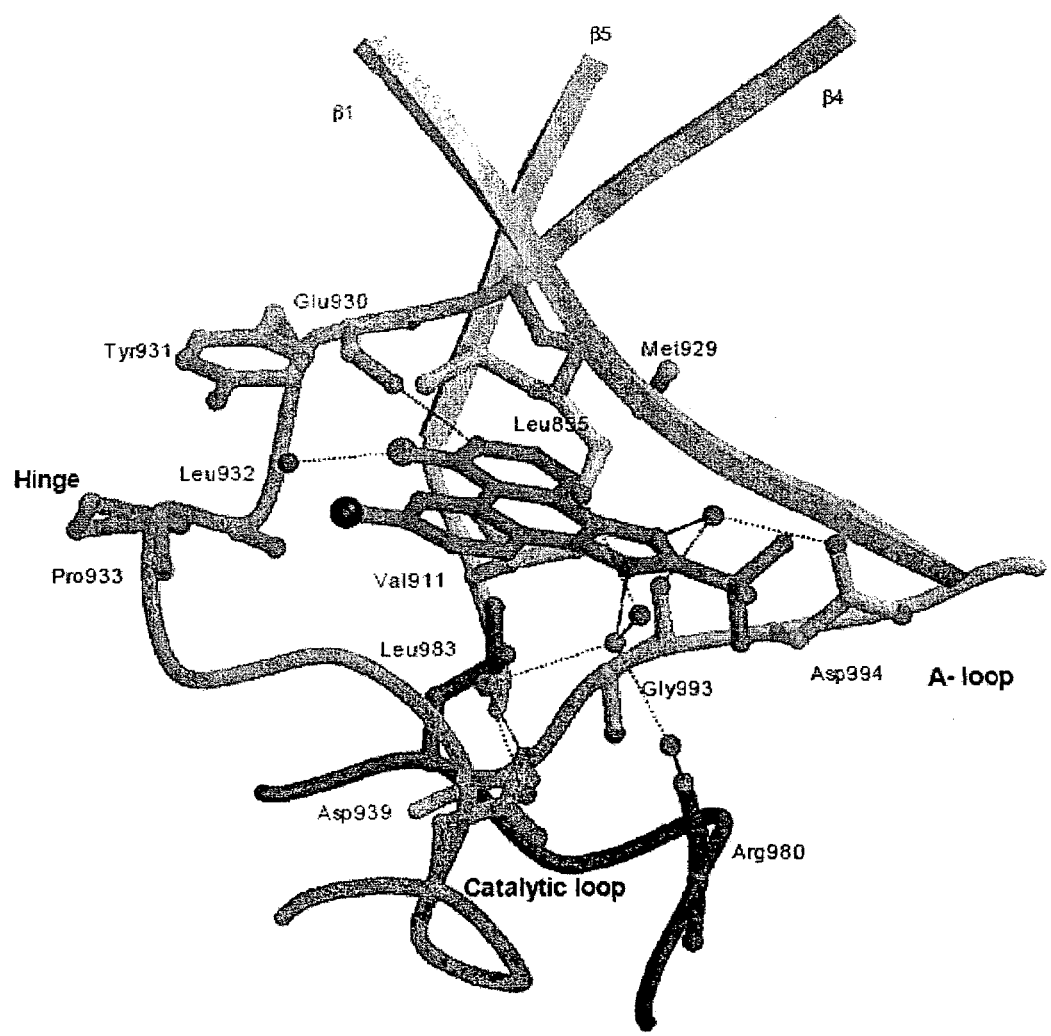

Surface representation of the constricted active site of JAK2 PTK domain in comparison to the more open LCK active site (FIG. 2b).

6.3 Binding Mode

The Jak-specific inhibitor (compound 6) sits snugly within the constricted ATP-binding site that lies deep between the two lobes, occupying a site where the adenine base resides. The inhibitor is well-ordered; moreover the mode of binding of the inhibitor within the JAK2 PTK domain structure is unambiguous—as evidenced by the electron density maps. The inhibitor is orientated such that the fluorophenyl moiety points towards the bulk solvent, the pyridone moiety is orientated towards the gatekeeper residue (Met 929) and the t-butyl group points towards the tip of the glycine loop. There is high shape complementarity between the planar ring system of the inhibitor and the JAK2 PTK, in which the inhibitor buries 225 Å$^3$ of its available 516 Å$^3$ surface area, thereby making numerous contacts with the residues lining the active site.

The tetracyclic pyridone is predominantly hydrophobic, and accordingly forms a large number of van der Waals interactions with JAK2 PTK domain. The planar ring system of the inhibitor is sandwiched between the hydrophobic residues of the N-terminal lobe (Leu 855, Val 863, Ala 880, Val 911, the C-terminal lobe (Leu 983 and Gly 935) and the hinge (Met 929, Tyr 931). In addition, the pyridone ring forms two direct hydrogen bonds with the linker between the N- and C-lobes of JAK2 PTK (The pyridone NH and C=O groups to Glu 930$^O$ and Leu 932$^N$ respectively) that mimic those observed between the adenine group of ATP and other PTKs.

Interestingly, the carbonyl group of Gly 993 points towards the ATP-binding pocket, whereas in all the PTK structures examined, the corresponding carbonyl group points towards the core of the C-terminal lobe. The hydrophobic t-butyl group of the inhibitor is not well-accommodated in the JAK2 active site, being located within and adjacent to a polar pocket that includes Asp 994, Arg 980, Asn 981, Asn 859, Lys 882—a pocket that typically co-ordinates Mg$^{2+}$ ions.

The glycine-loop was observed not to participate in inhibitor contacts in the JAK2 PTK domain, with the Phe 860 residue pointing away from the active site. Instead, the glycine-loop collapses over and restricts the active site, with Asn859 making a water-mediated hydrogen bond to the conserved Asp994 and a hydrogen bond to the conserved catalytic residue Asp976 of the C-terminal lobe.

Table of contacts summarizing interactions between the tetracyclic pyridone and JAK2 kinase domain. (Table 3)

TABLE 3

Contacts between inhibitor and Jak2 PTK domain

| Inhibitor | Jak2 PTK | Nature of interaction |
|---|---|---|
| Imidazole moiety | | |
| C0 | Leu 983CD2 | VDW |
| C1 | Leu 983CD2 | VDW |
| N0 | Val 863CG2 | VDW |
| N0 | Asp 994OD1, Gly 993O | Water mediated H-BOND |
| N1 | Asp 939OD1, Ser 936N, OG, Arg 980O, Leu 855O | Water mediated H-BOND |
| Fluorophenyl moiety | | |
| C3 | Leu 983CD2 | VDW |
| C4 | Leu 855O | VDW |
| C5 | Leu 855CD2, Gly 935CA | VDW |
| C6 | Leu 855CD2, Leu 932CD2, Gly 935CA | VDW |
| C7 | Leu 855CD2, Leu 932O, Tyr 931CE1 | VDW |
| C8 | Leu 855CD1, Leu 883CD2 | VDW |
| F | Leu 855CD2, Leu 932O, Gly 935CA, N, Tyr 931CE1, OH | VDW |
| Pyridone moiety | | |
| C9 | Leu 983CD1, CD2 | VDW |
| C10 | Leu 983CD1, CD2 | VDW |
| C11 | Leu 983CD1, Ala 880CB, Glu 930O, Leu 932N | VDW |
| N2 | Leu 983CD1, Ala 880CB | VDW |
| N2 | Glu 930O | H-BOND |
| C12 | Leu 983CD1, Met 929SD, Ala 880CB, Glu 930O, V 911CG2 | VDW |
| C13 | Gly 993O, Leu 983CD1, Met 929CE | VDW |
| O0 | Leu 932CA, CB, O, Ala 880CB, Glu 930O, Tyr 931CD1, CA, C, | VDW |
| O0 | Leu 932 N | H-BOND |
| t-butyl moiety | | |
| C15 | Asn 981OD1, Arg 980O | VDW |
| C16 | Asp 994OD1, Val 863CG2 | VDW |
| C17 | Lys 857N, C, O Gly 856CA, C | VDW |

6.5 Unique Constricted Nature of JAK2 Active Site: Driver of Tetracyclic Pyridone's Specificity Toward the Jak Kinase Family In JAK2, the unique constricted nature of the active site permits extensive interactions to be made with the inhibitor (the inhibitor is akin to a penny in a slot) whereas other PTK family members have a more accessible active site and consequently will not exhibit a high degree of shape complementarity with the Jak-specific inhibitor. (FIG. 2b)

The planarity of the compound could therefore be an important factor in determining selectivity. The related trisubstituted imidazole, Compound 5, a non-planar precursor of the tetracyclic pyridone (Compound 6) only displays μM affinity towards JAK2 and JAK3 in our hands (data not shown), suggesting that this planarity is a key feature of the preference of Compound 6 for JAK family members.

6.6 Key Residues Conferring Tetracyclic Pyridones Specificity Toward the JAK Kinase Family Secondly, a number of sidechains (Met 929, Tyr 931, Leu 932) within the hinge of JAK2 PTK domain, a hypervariable region across the PTK family, interact with the tetracyclic pyridone. However this hinge region in the JAK family is well conserved and appears to be a key region that determines selectivity towards the tetracyclic pyridone. Moreover, the presence of a conserved Pro (Pro 933 in JAK2) amongst the JAK family, is likely to introduce rigidity into the hinge region, which may represent an important factor in selectivity.

In addition, the presence of the gatekeeper methionine at position 929 appears to be a reasonable indicator of potent binding to the tetracyclic pyridone. For example, PTKs that possess a methionine at an equivalent position (Fak, IRK and ZAP 70) display an IC50 for the tetracyclic pyridone around the 200 nM range (Thompson et al, 2002), whereas other PTKs that possess either a Thr or Val display an IC50 in the uM range. The gatekeeper residue is known to determine the shape and size of the so-called "back pocket" which is also defined by the invariant Glu 898 and Leu 902, Val 911, Leu 927, Gly 993 and Asp 994. In JAK2, Met 929, is orientated towards the centre of the pocket, sterically-hindering the close contact of the tetracyclic pyridone with Leu 902 and Leu 927 of the back pocket. Consequently, Met 929 simultaneously constricts the active site, maximizes its shape complementarity to and sterically constrains the pyridone group. However, Met 929 is not the sole diagnostic for selectivity towards that JAK-specific inhibitor; the combination Met 929, Tyr/Phe 931, and Leu/Val 932 within the JAK family appears to represent a pre-requisite for tetracyclic pyridone specificity and a unique characteristic of the JAK kinases. In addition, water-mediated hydrogen bonds can contribute significantly to the affinity and selectivity of binding. The polar atoms of the imidazole moiety were both involved in water-mediated interactions and the unique orientation of the Gly 993 carbonyl may contribute to this specificity.

Figure 4:
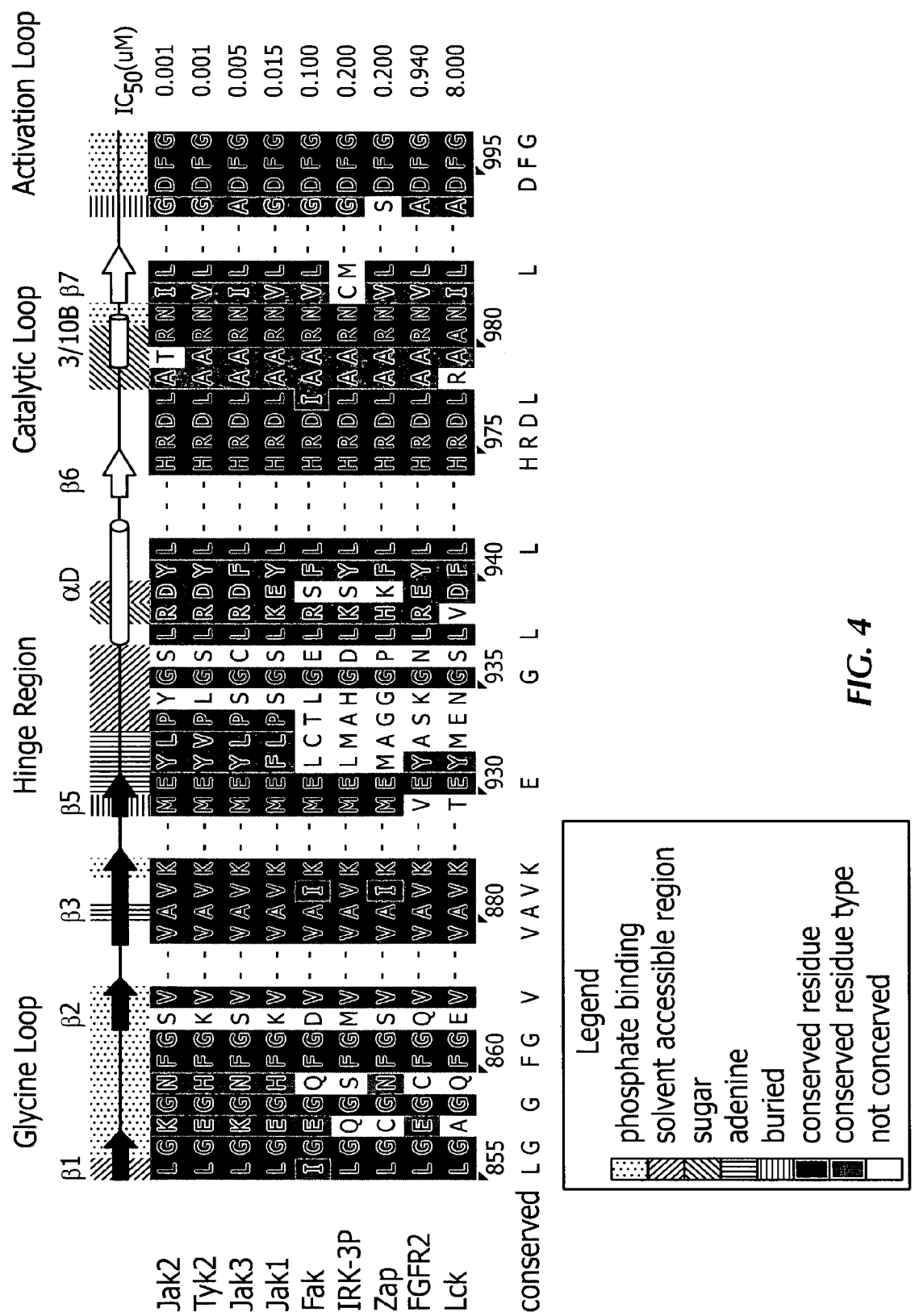
FIG. 4. (SEQ ID NO's: 9-17) Amino acid sequence alignment of the ATP binding site region of human JAK2 (SEQ ID NO: 9) PTK domain with the other members of the JAK family TYK2 (SEQ ID NO: 10), JAK3 (SEQ ID NO: 11) and JAK1 (SEQ ID NO: 12) and the kinase domain of FAK (SEQ ID NO: 13), IRK (SEQ ID NO: 14), ZAP-70 (SEQ ID NO: 15), FGFR2 (SEQ ID NO: 16) and LCK (SEQ ID NO: 17). The secondary structure of JAK2 is illustrated directly above the sequence alignment. Arrows delineate β-strands and cylinders delineate α-helices. Dark grey boxes indict conserved residues. Light grey boxes indict conservatively substituted residues. Residues located in phosphate-binding region, sugar pocket, solvent accessible region, adenine pocket and buried have been highlighted differently. IC50s of tetracyclic pyridone for each kinase are indicated on the right.

However, Met 929 is not the sole diagnostic for selectivity towards that JAK-specific inhibitor; the combination Met 929, Tyr/Phe 931, and Leu/Val 932 within the JAK family appears to represent a pre-requisite for tetracyclic pyridone specificity and a unique characteristic of the JAK kinases (FIG. 4-*alignment*). Although the hinge region is well conserved between the JAK family, subtle but yet significant differences could be exploited for the design of selective JAK inhibitors.

Example 7

In-Silico Screening

Molecular docking of large compound databases to target proteins of known or modelled 3-dimensional structure is now a common approach in the identification of new lead compounds. This "virtual screening" approach relies on fast and accurate estimation of the ligand binding mode and an estimate of ligand affinity. Typically a large database of compounds, either real or virtual is docked to a target structure and a list of the best potential ligands is produced. This ranking should be highly enriched for active compounds which may then be subject to further experimental validation.

The calculation of the ligand binding mode may be carried out by molecular docking programs which are able to dock the ligands in a flexible manner to a protein structure. The estimation of ligand affinity is typically carried out by the use of a separate scoring function. These scoring functions include energy-based approaches which calculate the molecular mechanics force field and rule-based approaches which use empirical rules derived from the analysis of a suitable database of structural information. Consensus scoring involves rescoring each ligand with multiple scoring functions and then using a combination of these rankings to generate a hit list.

The compounds were docked to the JAK2 crystal structure (Appendix 1). We used the program AutoDock (vers. 3.1.0) in this example for the generation of favourable conformations of ligand binding of a library of 50 compounds. The calculations generated an output of 2,370 conformations. A number of scoring functions were applied, including the Autodock scoring function, LUDI-2 and MCSS overlay. Ligand conformations were chosen using a consensus scoring function that included a calculated comparison of how well the conformation overlayed with the tetracyclic pyridine crystal structure. A ranked list of compounds was generated using a consensus of the various individual scores for each ligand.

Figure 5:
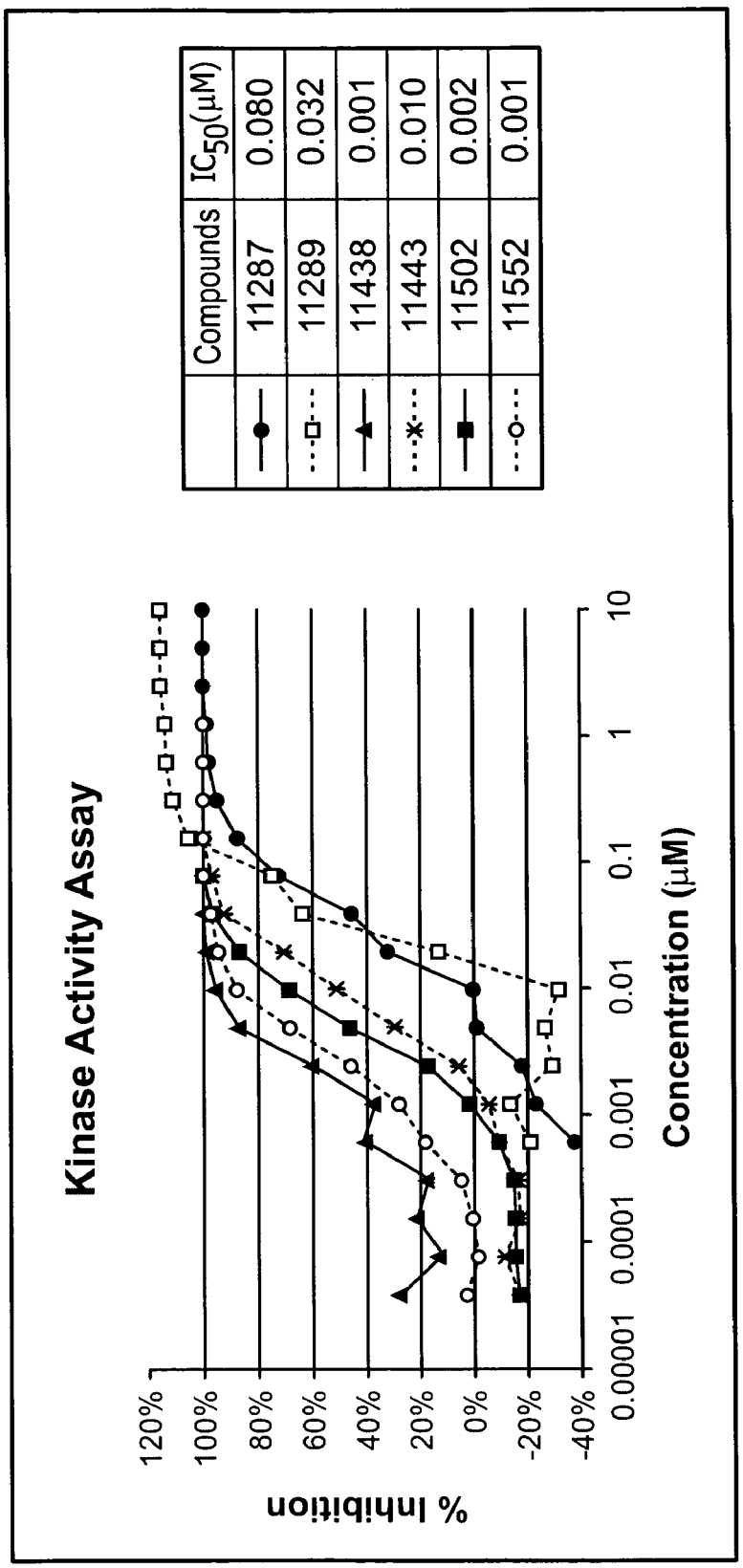
FIG. 5. Effect of selected compounds on JAK2 kinase activity. Titration curves of inhibition and $IC_{50}$ are shown. JAK2 kinase activity is assayed by measurement of the phosphorylation of a peptide substrate in the presence of various concentrations of compound. The results are expressed as percentage inhibition relative to a control without compound.

All compounds in the library were obtained and tested for their ability to modulate JAK2 kinase activity according to the method described above. Of these, eight (or 16%) of the fifty compounds inhibited JAK2 kinase activity at concentrations between $10^{-1}$ and 2 uM. Six of the eight JAK2 hits (compounds CYC11287, CYC11289, CYC11502, CYC11443, CYC11552 and CYC11438) were located in the top 2% of ranked conformations. The results of kinase inhibition assays for these compounds are shown in FIG. 5. All JAK2 hits were located in the top 6% of ranked conformations from the virtual screening calculations.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

APPENDIX 1

```
HEADER    ----                                              XX-XXX-XX   xxxx
COMPND    ---
REMARK  3
REMARK  3  REFINEMENT.
REMARK  3     PROGRAM     : REFMAC 5.2.0005
REMARK  3     AUTHORS     : MURSHUDOV, VAGIN, DODSON
REMARK  3
REMARK  3     REFINEMENT TARGET: MAXIMUM LIKELIHOOD
REMARK  3
REMARK  3  DATA USED IN REFINEMENT.
REMARK  3     RESOLUTION RANGE HIGH       (ANGSTROMS) :   2.00
REMARK  3     RESOLUTION RANGE LOW        (ANGSTROMS) : 111.80
REMARK  3     DATA CUTOFF                    (SIGMA(F)) : NONE
```

APPENDIX 1-continued

```
REMARK  3        COMPLETENESS FOR RANGE                    (%) :  96.86
REMARK  3        NUMBER OF REFLECTIONS                        :  53644
REMARK  3
REMARK  3        FIT TO DATA USED IN REFINEMENT.
REMARK  3          CROSS-VALIDATION METHOD              : THROUGHOUT
REMARK  3          FREE R VALUE TEST SET SELECTION      : RANDOM
REMARK  3          R VALUE          (WORKING + TEST SET) :  .21080
REMARK  3          R VALUE              (WORKING SET) :    .20881
REMARK  3          FREE R VALUE                       :    .24927
REMARK  3          FREE R VALUE TEST SET SIZE     (%) :    5.1
REMARK  3          FREE R VALUE TEST SET COUNT        :    2861
REMARK  3
REMARK  3        FIT IN THE HIGHEST RESOLUTION BIN.
REMARK  3          TOTAL NUMBER OF BINS USED              :    20
REMARK  3          BIN RESOLUTION RANGE HIGH              :    2.001
REMARK  3          BIN RESOLUTION RANGE LOW               :    2.053
REMARK  3          REFLECTION IN BIN         (WORKING SET) :    3980
REMARK  3          BIN COMPLETENESS     (WORKING + TEST) (%) :  96.80
REMARK  3          BIN R VALUE              (WORKING SET) :    .300
REMARK  3          BIN FREE R VALUE SET COUNT             :    201
REMARK  3          BIN FREE R VALUE                       :    .348
REMARK  3
REMARK  3        NUMBER OF NON-HYDROGEN ATOMS USED IN REFINEMENT.
REMARK  3          ALL ATOMS                 :   5203
REMARK  3
REMARK  3        B VALUES.
REMARK  3          FROM WILSON PLOT              (A**2) :  NULL
REMARK  3          MEAN B VALUE            (OVERALL, A**2) :  39.233
REMARK  3          OVERALL ANISOTROPIC B VALUE.
REMARK  3            B11 (A**2) :        .98
REMARK  3            B22 (A**2) :        .98
REMARK  3            B33 (A**2) :      -1.96
REMARK  3            B12 (A**2) :        .00
REMARK  3            B13 (A**2) :        .00
REMARK  3            B23 (A**2) :        .00
REMARK  3
REMARK  3        ESTIMATED OVERALL COORDINATE ERROR.
REMARK  3          ESU BASED ON R VALUE                         (A):   .171
REMARK  3          ESU BASED ON FREE R VALUE                    (A):   .160
REMARK  3          ESU BASED ON MAXIMUM LIKELIHOOD              (A):   .123
REMARK  3          ESU FOR B VALUES BASED ON MAXIMUM LIKELIHOOD (A**2):  8.659
REMARK  3
REMARK  3        CORRELATION COEFFICIENTS.
REMARK  3          CORRELATION COEFFICIENT FO-FC       :    .952
REMARK  3          CORRELATION COEFFICIENT FO-FC FREE  :    .933
REMARK  3
REMARK  3        RMS DEVIATIONS FROM IDEAL VALUES            COUNT    RMS    WEIGHT
REMARK  3          BOND LENGTHS REFINED ATOMS       (A):    4917 ;   .006 ;   .022
REMARK  3          BOND ANGLES REFINED ATOMS   (DEGREES):    6641 ;  1.020 ;  1.985
REMARK  3          TORSION ANGLES, PERIOD 1    (DEGREES):     571 ;  4.730 ;  5.000
REMARK  3          TORSION ANGLES, PERIOD 2    (DEGREES):     251 ; 38.844 ; 24.263
REMARK  3          TORSION ANGLES, PERIOD 3    (DEGREES):     910 ; 13.240 ; 15.000
REMARK  3          TORSION ANGLES, PERIOD 4    (DEGREES):      34 ; 15.598 ; 15.000
REMARK  3          CHIRAL-CENTER RESTRAINTS       (A**3):     690 ;   .060 ;   .200
REMARK  3          GENERAL PLANES REFINED ATOMS     (A):    3730 ;   .002 ;   .020
REMARK  3          NON-BONDED CONTACTS REFINED ATOMS (A):   2336 ;   .161 ;   .200
REMARK  3          NON-BONDED TORSION REFINED ATOMS (A):    3341 ;   .297 ;   .200
REMARK  3          H-BOND (X . . . Y) REFINED ATOMS (A):     450 ;   .089 ;   .200
REMARK  3          SYMMETRY VDW REFINED ATOMS       (A):      70 ;   .118 ;   .200
REMARK  3          SYMMETRY H-BOND REFINED ATOMS    (A):      21 ;   .118 ;   .200
REMARK  3
REMARK  3        ISOTROPIC THERMAL FACTOR RESTRAINTS.         COUNT    RMS    WEIGHT
REMARK  3          MAIN-CHAIN BOND REFINED ATOMS  (A**2):    2987 ;   .850 ;  3.000
REMARK  3          MAIN-CHAIN ANGLE REFINED ATOMS (A**2):    4638 ;  1.434 ;  5.000
REMARK  3          SIDE-CHAIN BOND REFINED ATOMS  (A**2):    2401 ;  1.989 ;  7.000
REMARK  3          SIDE-CHAIN ANGLE REFINED ATOMS (A**2):    2003 ;  3.144 ; 10.000
REMARK  3
REMARK  3        NCS RESTRAINTS STATISTICS
REMARK  3          NUMBER OF NCS GROUPS : NULL
REMARK  3
REMARK  3
REMARK  3        TLS DETAILS
REMARK  3          NUMBER OF TLS GROUPS    : NULL
REMARK  3
REMARK  3
REMARK  3        BULK SOLVENT MODELLING.
REMARK  3          METHOD USED : BABINET MODEL WITH MASK
REMARK  3          PARAMETERS FOR MASK CALCULATION
REMARK  3          VDW PROBE RADIUS        :    1.20
```

APPENDIX 1-continued

| REMARK | 3 | ION PROBE RADIUS | | | : | .80 | | | | | |
|---|---|---|---|---|---|---|---|---|---|---|---|
| REMARK | 3 | SHRINKAGE RADIUS | | | : | .80 | | | | | |
| REMARK | 3 | | | | | | | | | | |
| REMARK | 3 | OTHER REFINEMENT REMARKS: | | | | | | | | | |
| REMARK | 3 | HYDROGENS HAVE BEEN ADDED IN THE RIDING POSITIONS | | | | | | | | | |
| REMARK | 3 | | | | | | | | | | |
| LINK | | SER A 919 | | | | | ASN A 924 | | | gap | |
| LINK | | SER B 919 | | | | | ASN B 924 | | | gap | |
| CRYST1 | 111.273 | 111.273 | | 70.577 | | 90.00 | 90.00 | | 90.00 | P 41 | |
| SCALE1 | | .008987 | .000000 | | .000000 | | | .00000 | | | |
| SCALE2 | | .000000 | .008987 | | .000000 | | | .00000 | | | |
| SCALE3 | | .000000 | .000000 | | .014169 | | | .00000 | | | |
| ATOM | 1 | N | GLN | A | 843 | 134.888 | 59.436 | 5.113 | 1.00 | 57.64 | N |
| ATOM | 2 | CA | GLN | A | 843 | 133.465 | 59.048 | 5.350 | 1.00 | 57.40 | C |
| ATOM | 3 | CB | GLN | A | 843 | 133.156 | 57.698 | 4.689 | 1.00 | 57.55 | C |
| ATOM | 4 | CG | GLN | A | 843 | 133.161 | 57.729 | 3.162 | 1.00 | 58.87 | C |
| ATOM | 5 | CD | GLN | A | 843 | 132.828 | 56.384 | 2.534 | 1.00 | 58.69 | C |
| ATOM | 6 | OE1 | GLN | A | 843 | 133.121 | 55.326 | 3.095 | 1.00 | 61.77 | O |
| ATOM | 7 | NE2 | GLN | A | 843 | 132.218 | 56.421 | 1.354 | 1.00 | 60.07 | N |
| ATOM | 8 | C | GLN | A | 843 | 133.127 | 59.010 | 6.844 | 1.00 | 56.16 | C |
| ATOM | 9 | O | GLN | A | 843 | 133.921 | 59.445 | 7.682 | 1.00 | 56.18 | O |
| ATOM | 10 | N | PHE | A | 844 | 131.939 | 58.500 | 7.163 | 1.00 | 54.83 | N |
| ATOM | 11 | CA | PHE | A | 844 | 131.482 | 58.365 | 8.542 | 1.00 | 53.22 | C |
| ATOM | 12 | CB | PHE | A | 844 | 130.064 | 58.924 | 8.694 | 1.00 | 52.51 | C |
| ATOM | 13 | CG | PHE | A | 844 | 129.997 | 60.427 | 8.695 | 1.00 | 50.28 | C |
| ATOM | 14 | CD1 | PHE | A | 844 | 129.995 | 61.142 | 7.500 | 1.00 | 48.46 | C |
| ATOM | 15 | CE1 | PHE | A | 844 | 129.933 | 62.533 | 7.502 | 1.00 | 47.67 | C |
| ATOM | 16 | CZ | PHE | A | 844 | 129.868 | 63.224 | 8.709 | 1.00 | 47.91 | C |
| ATOM | 17 | CE2 | PHE | A | 844 | 129.866 | 62.521 | 9.907 | 1.00 | 47.41 | C |
| ATOM | 18 | CD2 | PHE | A | 844 | 129.929 | 61.129 | 9.894 | 1.00 | 48.82 | C |
| ATOM | 19 | C | PHE | A | 844 | 131.527 | 56.903 | 8.975 | 1.00 | 53.11 | C |
| ATOM | 20 | O | PHE | A | 844 | 130.963 | 56.031 | 8.310 | 1.00 | 53.20 | O |
| ATOM | 21 | N | GLU | A | 845 | 132.207 | 56.646 | 10.089 | 1.00 | 52.56 | N |
| ATOM | 22 | CA | GLU | A | 845 | 132.359 | 55.291 | 10.612 | 1.00 | 52.42 | C |
| ATOM | 23 | CB | GLU | A | 845 | 133.611 | 55.190 | 11.488 | 1.00 | 52.74 | C |
| ATOM | 24 | CG | GLU | A | 845 | 134.919 | 55.168 | 10.707 | 1.00 | 54.97 | C |
| ATOM | 25 | CD | GLU | A | 845 | 135.260 | 53.789 | 10.167 | 1.00 | 58.02 | C |
| ATOM | 26 | OE1 | GLU | A | 845 | 135.522 | 52.875 | 10.981 | 1.00 | 59.01 | O |
| ATOM | 27 | OE2 | GLU | A | 845 | 135.279 | 53.622 | 8.929 | 1.00 | 58.81 | O |
| ATOM | 28 | C | GLU | A | 845 | 131.127 | 54.842 | 11.392 | 1.00 | 51.78 | C |
| ATOM | 29 | O | GLU | A | 845 | 130.602 | 55.585 | 12.226 | 1.00 | 51.43 | O |
| ATOM | 30 | N | GLU | A | 846 | 130.682 | 53.621 | 11.105 | 1.00 | 51.23 | N |
| ATOM | 31 | CA | GLU | A | 846 | 129.534 | 52.994 | 11.766 | 1.00 | 51.05 | C |
| ATOM | 32 | CB | GLU | A | 846 | 129.368 | 51.558 | 11.246 | 1.00 | 51.66 | C |
| ATOM | 33 | CG | GLU | A | 846 | 128.421 | 50.669 | 12.051 | 1.00 | 55.36 | C |
| ATOM | 34 | CD | GLU | A | 846 | 126.972 | 50.822 | 11.638 | 1.00 | 58.97 | C |
| ATOM | 35 | OE1 | GLU | A | 846 | 126.617 | 50.377 | 10.524 | 1.00 | 60.61 | O |
| ATOM | 36 | OE2 | GLU | A | 846 | 126.184 | 51.378 | 12.435 | 1.00 | 61.11 | O |
| ATOM | 37 | C | GLU | A | 846 | 129.650 | 53.004 | 13.296 | 1.00 | 50.05 | C |
| ATOM | 38 | O | GLU | A | 846 | 128.705 | 53.384 | 13.996 | 1.00 | 49.88 | O |
| ATOM | 39 | N | ARG | A | 847 | 130.817 | 52.604 | 13.798 | 1.00 | 48.70 | N |
| ATOM | 40 | CA | ARG | A | 847 | 131.047 | 52.416 | 15.234 | 1.00 | 47.58 | C |
| ATOM | 41 | CB | ARG | A | 847 | 132.342 | 51.623 | 15.467 | 1.00 | 47.77 | C |
| ATOM | 42 | CG | ARG | A | 847 | 133.618 | 52.322 | 15.004 | 1.00 | 48.87 | C |
| ATOM | 43 | CD | ARG | A | 847 | 134.785 | 51.352 | 14.947 | 1.00 | 51.59 | C |
| ATOM | 44 | NE | ARG | A | 847 | 136.066 | 52.042 | 14.812 | 1.00 | 54.87 | N |
| ATOM | 45 | CZ | ARG | A | 847 | 136.885 | 52.322 | 15.825 | 1.00 | 56.95 | C |
| ATOM | 46 | NH1 | ARG | A | 847 | 136.569 | 51.972 | 17.067 | 1.00 | 57.66 | N |
| ATOM | 47 | NH2 | ARG | A | 847 | 138.028 | 52.955 | 15.595 | 1.00 | 57.91 | N |
| ATOM | 48 | C | ARG | A | 847 | 131.058 | 53.704 | 16.062 | 1.00 | 46.49 | C |
| ATOM | 49 | O | ARG | A | 847 | 130.921 | 53.657 | 17.287 | 1.00 | 46.37 | O |
| ATOM | 50 | N | HIS | A | 848 | 131.226 | 54.844 | 15.393 | 1.00 | 45.10 | N |
| ATOM | 51 | CA | HIS | A | 848 | 131.310 | 56.140 | 16.069 | 1.00 | 43.84 | C |
| ATOM | 52 | CB | HIS | A | 848 | 132.458 | 56.973 | 15.490 | 1.00 | 43.69 | C |
| ATOM | 53 | CG | HIS | A | 848 | 133.817 | 56.401 | 15.755 | 1.00 | 43.82 | C |
| ATOM | 54 | ND1 | HIS | A | 848 | 134.708 | 56.105 | 14.746 | 1.00 | 42.84 | N |
| ATOM | 55 | CE1 | HIS | A | 848 | 135.819 | 55.619 | 15.272 | 1.00 | 42.78 | C |
| ATOM | 56 | NE2 | HIS | A | 848 | 135.679 | 55.587 | 16.585 | 1.00 | 43.06 | N |
| ATOM | 57 | CD2 | HIS | A | 848 | 134.436 | 56.071 | 16.913 | 1.00 | 42.43 | C |
| ATOM | 58 | C | HIS | A | 848 | 129.999 | 56.925 | 16.006 | 1.00 | 43.18 | C |
| ATOM | 59 | O | HIS | A | 848 | 129.897 | 58.028 | 16.551 | 1.00 | 43.38 | O |
| ATOM | 60 | N | LEU | A | 849 | 129.001 | 56.345 | 15.345 | 1.00 | 42.23 | N |
| ATOM | 61 | CA | LEU | A | 849 | 127.690 | 56.963 | 15.199 | 1.00 | 41.45 | C |
| ATOM | 62 | CB | LEU | A | 849 | 127.121 | 56.630 | 13.818 | 1.00 | 41.30 | C |
| ATOM | 63 | CG | LEU | A | 849 | 126.072 | 57.511 | 13.135 | 1.00 | 42.49 | C |
| ATOM | 64 | CD1 | LEU | A | 849 | 126.564 | 58.943 | 12.911 | 1.00 | 39.67 | C |
| ATOM | 65 | CD2 | LEU | A | 849 | 125.685 | 56.871 | 11.808 | 1.00 | 41.95 | C |
| ATOM | 66 | C | LEU | A | 849 | 126.769 | 56.470 | 16.317 | 1.00 | 40.77 | C |
| ATOM | 67 | O | LEU | A | 849 | 126.403 | 55.294 | 16.356 | 1.00 | 41.58 | O |

APPENDIX 1-continued

| | | | | | | | | | | |
|---|---|---|---|---|---|---|---|---|---|---|
| ATOM | 68 | N | LYS | A | 850 | 126.419 | 57.371 | 17.232 | 1.00 | 39.55 | N |
| ATOM | 69 | CA | LYS | A | 850 | 125.627 | 57.027 | 18.417 | 1.00 | 38.67 | C |
| ATOM | 70 | CB | LYS | A | 850 | 126.211 | 57.697 | 19.666 | 1.00 | 38.67 | C |
| ATOM | 71 | CG | LYS | A | 850 | 127.609 | 57.243 | 20.046 | 1.00 | 39.89 | C |
| ATOM | 72 | CD | LYS | A | 850 | 128.095 | 57.984 | 21.283 | 1.00 | 40.35 | C |
| ATOM | 73 | CE | LYS | A | 850 | 129.410 | 57.412 | 21.789 | 1.00 | 44.21 | C |
| ATOM | 74 | NZ | LYS | A | 850 | 129.849 | 58.072 | 23.049 | 1.00 | 45.23 | N |
| ATOM | 75 | C | LYS | A | 850 | 124.164 | 57.436 | 18.260 | 1.00 | 37.20 | C |
| ATOM | 76 | O | LYS | A | 850 | 123.866 | 58.614 | 18.066 | 1.00 | 36.64 | O |
| ATOM | 77 | N | PHE | A | 851 | 123.259 | 56.464 | 18.358 | 1.00 | 35.83 | N |
| ATOM | 78 | CA | PHE | A | 851 | 121.824 | 56.721 | 18.234 | 1.00 | 34.06 | C |
| ATOM | 79 | CB | PHE | A | 851 | 121.042 | 55.407 | 18.106 | 1.00 | 33.67 | C |
| ATOM | 80 | CG | PHE | A | 851 | 119.544 | 55.584 | 18.112 | 1.00 | 32.19 | C |
| ATOM | 81 | CD1 | PHE | A | 851 | 118.855 | 55.850 | 16.930 | 1.00 | 31.41 | C |
| ATOM | 82 | CE1 | PHE | A | 851 | 117.473 | 56.015 | 16.932 | 1.00 | 30.08 | C |
| ATOM | 83 | CZ | PHE | A | 851 | 116.764 | 55.910 | 18.124 | 1.00 | 31.58 | C |
| ATOM | 84 | CE2 | PHE | A | 851 | 117.441 | 55.650 | 19.314 | 1.00 | 30.99 | C |
| ATOM | 85 | CD2 | PHE | A | 851 | 118.823 | 55.486 | 19.300 | 1.00 | 31.48 | C |
| ATOM | 86 | C | PHE | A | 851 | 121.291 | 57.532 | 19.409 | 1.00 | 33.52 | C |
| ATOM | 87 | O | PHE | A | 851 | 121.582 | 57.229 | 20.568 | 1.00 | 33.38 | O |
| ATOM | 88 | N | LEU | A | 852 | 120.497 | 58.553 | 19.100 | 1.00 | 32.33 | N |
| ATOM | 89 | CA | LEU | A | 852 | 119.879 | 59.379 | 20.129 | 1.00 | 31.89 | C |
| ATOM | 90 | CB | LEU | A | 852 | 120.316 | 60.843 | 19.996 | 1.00 | 31.60 | C |
| ATOM | 91 | CG | LEU | A | 852 | 121.803 | 61.150 | 20.201 | 1.00 | 30.44 | C |
| ATOM | 92 | CD1 | LEU | A | 852 | 122.088 | 62.607 | 19.873 | 1.00 | 27.44 | C |
| ATOM | 93 | CD2 | LEU | A | 852 | 122.262 | 60.824 | 21.622 | 1.00 | 29.44 | C |
| ATOM | 94 | C | LEU | A | 852 | 118.358 | 59.252 | 20.119 | 1.00 | 31.92 | C |
| ATOM | 95 | O | LEU | A | 852 | 117.759 | 58.917 | 21.139 | 1.00 | 31.28 | O |
| ATOM | 96 | N | GLN | A | 853 | 117.744 | 59.510 | 18.965 | 1.00 | 31.95 | N |
| ATOM | 97 | CA | GLN | A | 853 | 116.298 | 59.354 | 18.805 | 1.00 | 33.08 | C |
| ATOM | 98 | CB | GLN | A | 853 | 115.537 | 60.501 | 19.485 | 1.00 | 33.08 | C |
| ATOM | 99 | CG | GLN | A | 853 | 115.768 | 61.870 | 18.870 | 1.00 | 33.67 | C |
| ATOM | 100 | CD | GLN | A | 853 | 114.801 | 62.912 | 19.395 | 1.00 | 35.12 | C |
| ATOM | 101 | OE1 | GLN | A | 853 | 115.194 | 63.824 | 20.120 | 1.00 | 38.66 | O |
| ATOM | 102 | NE2 | GLN | A | 853 | 113.527 | 62.778 | 19.037 | 1.00 | 38.83 | N |
| ATOM | 103 | C | GLN | A | 853 | 115.870 | 59.242 | 17.344 | 1.00 | 32.70 | C |
| ATOM | 104 | O | GLN | A | 853 | 116.598 | 59.654 | 16.437 | 1.00 | 31.73 | O |
| ATOM | 105 | N | GLN | A | 854 | 114.685 | 58.671 | 17.137 | 1.00 | 32.72 | N |
| ATOM | 106 | CA | GLN | A | 854 | 114.025 | 58.672 | 15.837 | 1.00 | 33.66 | C |
| ATOM | 107 | CB | GLN | A | 854 | 112.874 | 57.658 | 15.831 | 1.00 | 33.82 | C |
| ATOM | 108 | CG | GLN | A | 854 | 112.060 | 57.594 | 14.535 | 1.00 | 38.48 | C |
| ATOM | 109 | CD | GLN | A | 854 | 112.833 | 57.013 | 13.361 | 1.00 | 42.81 | C |
| ATOM | 110 | OE1 | GLN | A | 854 | 113.713 | 56.166 | 13.532 | 1.00 | 45.81 | O |
| ATOM | 111 | NE2 | GLN | A | 854 | 112.495 | 57.461 | 12.156 | 1.00 | 43.81 | N |
| ATOM | 112 | C | GLN | A | 854 | 113.509 | 60.082 | 15.551 | 1.00 | 33.36 | C |
| ATOM | 113 | O | GLN | A | 854 | 112.875 | 60.703 | 16.411 | 1.00 | 32.92 | O |
| ATOM | 114 | N | LEU | A | 855 | 113.793 | 60.586 | 14.352 | 1.00 | 32.69 | N |
| ATOM | 115 | CA | LEU | A | 855 | 113.381 | 61.938 | 13.971 | 1.00 | 33.23 | C |
| ATOM | 116 | CB | LEU | A | 855 | 114.520 | 62.691 | 13.276 | 1.00 | 32.79 | C |
| ATOM | 117 | CG | LEU | A | 855 | 115.664 | 63.197 | 14.155 | 1.00 | 32.53 | C |
| ATOM | 118 | CD1 | LEU | A | 855 | 116.734 | 63.828 | 13.288 | 1.00 | 32.42 | C |
| ATOM | 119 | CD2 | LEU | A | 855 | 115.169 | 64.181 | 15.213 | 1.00 | 33.58 | C |
| ATOM | 120 | C | LEU | A | 855 | 112.132 | 61.954 | 13.100 | 1.00 | 33.51 | C |
| ATOM | 121 | O | LEU | A | 855 | 111.219 | 62.746 | 13.334 | 1.00 | 34.08 | O |
| ATOM | 122 | N | GLY | A | 856 | 112.100 | 61.085 | 12.096 | 1.00 | 33.68 | N |
| ATOM | 123 | CA | GLY | A | 856 | 110.941 | 60.976 | 11.223 | 1.00 | 34.95 | C |
| ATOM | 124 | C | GLY | A | 856 | 111.035 | 59.844 | 10.222 | 1.00 | 35.71 | C |
| ATOM | 125 | O | GLY | A | 856 | 112.084 | 59.211 | 10.082 | 1.00 | 35.69 | O |
| ATOM | 126 | N | LYS | A | 857 | 109.923 | 59.595 | 9.536 | 1.00 | 36.59 | N |
| ATOM | 127 | CA | LYS | A | 857 | 109.846 | 58.601 | 8.468 | 1.00 | 37.66 | C |
| ATOM | 128 | CB | LYS | A | 857 | 109.069 | 57.366 | 8.931 | 1.00 | 38.29 | C |
| ATOM | 129 | CG | LYS | A | 857 | 109.799 | 56.500 | 9.945 | 1.00 | 39.88 | C |
| ATOM | 130 | CD | LYS | A | 857 | 108.990 | 55.262 | 10.290 | 1.00 | 42.73 | C |
| ATOM | 131 | CE | LYS | A | 857 | 109.735 | 54.374 | 11.272 | 1.00 | 43.61 | C |
| ATOM | 132 | NZ | LYS | A | 857 | 108.955 | 53.146 | 11.590 | 1.00 | 46.22 | N |
| ATOM | 133 | C | LYS | A | 857 | 109.165 | 59.203 | 7.242 | 1.00 | 37.95 | C |
| ATOM | 134 | O | LYS | A | 857 | 108.179 | 59.935 | 7.365 | 1.00 | 37.28 | O |
| ATOM | 135 | N | GLY | A | 858 | 109.690 | 58.885 | 6.063 | 1.00 | 38.53 | N |
| ATOM | 136 | CA | GLY | A | 858 | 109.136 | 59.396 | 4.813 | 1.00 | 39.92 | C |
| ATOM | 137 | C | GLY | A | 858 | 109.345 | 58.451 | 3.649 | 1.00 | 40.66 | C |
| ATOM | 138 | O | GLY | A | 858 | 110.463 | 57.981 | 3.414 | 1.00 | 40.68 | O |
| ATOM | 139 | N | ASN | A | 859 | 108.259 | 58.186 | 2.920 | 1.00 | 41.50 | N |
| ATOM | 140 | CA | ASN | A | 859 | 108.258 | 57.282 | 1.765 | 1.00 | 42.03 | C |
| ATOM | 141 | CB | ASN | A | 859 | 109.017 | 57.901 | .578 | 1.00 | 42.03 | C |
| ATOM | 142 | CG | ASN | A | 859 | 108.346 | 59.160 | .043 | 1.00 | 42.67 | C |
| ATOM | 143 | OD1 | ASN | A | 859 | 107.167 | 59.148 | −.314 | 1.00 | 42.08 | O |
| ATOM | 144 | ND2 | ASN | A | 859 | 109.101 | 60.253 | −.023 | 1.00 | 44.00 | N |
| ATOM | 145 | C | ASN | A | 859 | 108.767 | 55.874 | 2.109 | 1.00 | 42.43 | C |
| ATOM | 146 | O | ASN | A | 859 | 107.990 | 55.026 | 2.558 | 1.00 | 42.99 | O |

APPENDIX 1-continued

| ATOM | 147 | N | PHE | A | 860 | 110.063 | 55.637 | 1.908 | 1.00 | 41.83 | N |
|---|---|---|---|---|---|---|---|---|---|---|---|
| ATOM | 148 | CA | PHE | A | 860 | 110.682 | 54.353 | 2.251 | 1.00 | 41.24 | C |
| ATOM | 149 | CB | PHE | A | 860 | 111.040 | 53.564 | .984 | 1.00 | 41.92 | C |
| ATOM | 150 | CG | PHE | A | 860 | 109.855 | 53.231 | .118 | 1.00 | 43.02 | C |
| ATOM | 151 | CD1 | PHE | A | 860 | 108.965 | 52.222 | .485 | 1.00 | 44.75 | C |
| ATOM | 152 | CE1 | PHE | A | 860 | 107.868 | 51.912 | −.314 | 1.00 | 44.28 | C |
| ATOM | 153 | CZ | PHE | A | 860 | 107.656 | 52.610 | −1.499 | 1.00 | 44.30 | C |
| ATOM | 154 | CE2 | PHE | A | 860 | 108.540 | 53.616 | −1.878 | 1.00 | 43.68 | C |
| ATOM | 155 | CD2 | PHE | A | 860 | 109.633 | 53.921 | −1.070 | 1.00 | 43.80 | C |
| ATOM | 156 | C | PHE | A | 860 | 111.917 | 54.543 | 3.132 | 1.00 | 40.06 | C |
| ATOM | 157 | O | PHE | A | 860 | 112.605 | 53.577 | 3.476 | 1.00 | 39.51 | O |
| ATOM | 158 | N | GLY | A | 861 | 112.183 | 55.795 | 3.498 | 1.00 | 39.19 | N |
| ATOM | 159 | CA | GLY | A | 861 | 113.322 | 56.140 | 4.341 | 1.00 | 38.19 | C |
| ATOM | 160 | C | GLY | A | 861 | 112.947 | 56.471 | 5.774 | 1.00 | 38.05 | C |
| ATOM | 161 | O | GLY | A | 861 | 111.778 | 56.719 | 6.091 | 1.00 | 38.38 | O |
| ATOM | 162 | N | SER | A | 862 | 113.956 | 56.473 | 6.640 | 1.00 | 36.77 | N |
| ATOM | 163 | CA | SER | A | 862 | 113.791 | 56.791 | 8.051 | 1.00 | 35.26 | C |
| ATOM | 164 | CB | SER | A | 862 | 113.683 | 55.506 | 8.874 | 1.00 | 35.48 | C |
| ATOM | 165 | OG | SER | A | 862 | 113.750 | 55.770 | 10.263 | 1.00 | 38.14 | O |
| ATOM | 166 | C | SER | A | 862 | 114.984 | 57.622 | 8.501 | 1.00 | 33.48 | C |
| ATOM | 167 | O | SER | A | 862 | 116.119 | 57.330 | 8.128 | 1.00 | 32.91 | O |
| ATOM | 168 | N | VAL | A | 863 | 114.717 | 58.665 | 9.285 | 1.00 | 32.00 | N |
| ATOM | 169 | CA | VAL | A | 863 | 115.763 | 59.574 | 9.752 | 1.00 | 30.70 | C |
| ATOM | 170 | CB | VAL | A | 863 | 115.506 | 61.045 | 9.320 | 1.00 | 30.47 | C |
| ATOM | 171 | CG1 | VAL | A | 863 | 116.690 | 61.935 | 9.685 | 1.00 | 28.03 | C |
| ATOM | 172 | CG2 | VAL | A | 863 | 115.256 | 61.126 | 7.823 | 1.00 | 31.92 | C |
| ATOM | 173 | C | VAL | A | 863 | 115.924 | 59.483 | 11.267 | 1.00 | 30.51 | C |
| ATOM | 174 | O | VAL | A | 863 | 114.937 | 59.451 | 12.008 | 1.00 | 30.01 | O |
| ATOM | 175 | N | GLU | A | 864 | 117.180 | 59.431 | 11.704 | 1.00 | 30.13 | N |
| ATOM | 176 | CA | GLU | A | 864 | 117.528 | 59.333 | 13.115 | 1.00 | 30.91 | C |
| ATOM | 177 | CB | GLU | A | 864 | 118.213 | 57.994 | 13.407 | 1.00 | 31.64 | C |
| ATOM | 178 | CG | GLU | A | 864 | 117.308 | 56.781 | 13.298 | 1.00 | 31.45 | C |
| ATOM | 179 | CD | GLU | A | 864 | 118.063 | 55.465 | 13.416 | 1.00 | 32.79 | C |
| ATOM | 180 | OE1 | GLU | A | 864 | 119.315 | 55.478 | 13.448 | 1.00 | 34.87 | O |
| ATOM | 181 | OE2 | GLU | A | 864 | 117.395 | 54.412 | 13.473 | 1.00 | 35.54 | O |
| ATOM | 182 | C | GLU | A | 864 | 118.463 | 60.459 | 13.527 | 1.00 | 30.63 | C |
| ATOM | 183 | O | GLU | A | 864 | 119.311 | 60.895 | 12.745 | 1.00 | 31.61 | O |
| ATOM | 184 | N | MET | A | 865 | 118.295 | 60.921 | 14.761 | 1.00 | 30.01 | N |
| ATOM | 185 | CA | MET | A | 865 | 119.228 | 61.841 | 15.391 | 1.00 | 30.29 | C |
| ATOM | 186 | CB | MET | A | 865 | 118.520 | 62.628 | 16.492 | 1.00 | 29.16 | C |
| ATOM | 187 | CG | MET | A | 865 | 119.361 | 63.688 | 17.173 | 1.00 | 29.98 | C |
| ATOM | 188 | SD | MET | A | 865 | 118.472 | 64.395 | 18.571 | 1.00 | 31.43 | S |
| ATOM | 189 | CE | MET | A | 865 | 119.472 | 65.832 | 18.934 | 1.00 | 29.42 | C |
| ATOM | 190 | C | MET | A | 865 | 120.379 | 61.030 | 15.976 | 1.00 | 30.23 | C |
| ATOM | 191 | O | MET | A | 865 | 120.165 | 60.141 | 16.804 | 1.00 | 29.21 | O |
| ATOM | 192 | N | CYS | A | 866 | 121.595 | 61.335 | 15.534 | 1.00 | 30.87 | N |
| ATOM | 193 | CA | CYS | A | 866 | 122.781 | 60.629 | 16.002 | 1.00 | 32.54 | C |
| ATOM | 194 | CB | CYS | A | 866 | 123.278 | 59.643 | 14.941 | 1.00 | 32.56 | C |
| ATOM | 195 | SG | CYS | A | 866 | 122.135 | 58.302 | 14.544 | 1.00 | 35.15 | S |
| ATOM | 196 | C | CYS | A | 866 | 123.898 | 61.596 | 16.370 | 1.00 | 33.40 | C |
| ATOM | 197 | O | CYS | A | 866 | 124.001 | 62.684 | 15.804 | 1.00 | 33.70 | O |
| ATOM | 198 | N | ARG | A | 867 | 124.722 | 61.197 | 17.334 | 1.00 | 34.06 | N |
| ATOM | 199 | CA | ARG | A | 867 | 125.941 | 61.929 | 17.644 | 1.00 | 35.21 | C |
| ATOM | 200 | CB | ARG | A | 867 | 126.128 | 62.060 | 19.158 | 1.00 | 35.33 | C |
| ATOM | 201 | CG | ARG | A | 867 | 127.273 | 62.975 | 19.564 | 1.00 | 37.41 | C |
| ATOM | 202 | CD | ARG | A | 867 | 127.106 | 63.483 | 20.981 | 1.00 | 40.93 | C |
| ATOM | 203 | NE | ARG | A | 867 | 127.781 | 64.767 | 21.158 | 1.00 | 43.43 | N |
| ATOM | 204 | CZ | ARG | A | 867 | 127.513 | 65.638 | 22.125 | 1.00 | 41.48 | C |
| ATOM | 205 | NH1 | ARG | A | 867 | 126.573 | 65.385 | 23.026 | 1.00 | 40.93 | N |
| ATOM | 206 | NH2 | ARG | A | 867 | 128.188 | 66.774 | 22.184 | 1.00 | 45.73 | N |
| ATOM | 207 | C | ARG | A | 867 | 127.118 | 61.195 | 17.012 | 1.00 | 35.91 | C |
| ATOM | 208 | O | ARG | A | 867 | 127.375 | 60.033 | 17.337 | 1.00 | 35.46 | O |
| ATOM | 209 | N | TYR | A | 868 | 127.807 | 61.857 | 16.086 | 1.00 | 36.83 | N |
| ATOM | 210 | CA | TYR | A | 868 | 129.016 | 61.285 | 15.505 | 1.00 | 38.45 | C |
| ATOM | 211 | CB | TYR | A | 868 | 129.239 | 61.735 | 14.057 | 1.00 | 39.30 | C |
| ATOM | 212 | CG | TYR | A | 868 | 130.374 | 60.987 | 13.385 | 1.00 | 40.81 | C |
| ATOM | 213 | CD1 | TYR | A | 868 | 130.280 | 59.614 | 13.143 | 1.00 | 42.54 | C |
| ATOM | 214 | CE1 | TYR | A | 868 | 131.318 | 58.913 | 12.537 | 1.00 | 42.43 | C |
| ATOM | 215 | CZ | TYR | A | 868 | 132.471 | 59.585 | 12.166 | 1.00 | 42.54 | C |
| ATOM | 216 | OH | TYR | A | 868 | 133.493 | 58.886 | 11.564 | 1.00 | 43.21 | O |
| ATOM | 217 | CE2 | TYR | A | 868 | 132.594 | 60.949 | 12.394 | 1.00 | 42.80 | C |
| ATOM | 218 | CD2 | TYR | A | 868 | 131.545 | 61.643 | 13.005 | 1.00 | 41.54 | C |
| ATOM | 219 | C | TYR | A | 868 | 130.204 | 61.647 | 16.380 | 1.00 | 39.17 | C |
| ATOM | 220 | O | TYR | A | 868 | 130.687 | 62.779 | 16.350 | 1.00 | 38.94 | O |
| ATOM | 221 | N | ASP | A | 869 | 130.665 | 60.668 | 17.154 | 1.00 | 40.37 | N |
| ATOM | 222 | CA | ASP | A | 869 | 131.653 | 60.888 | 18.204 | 1.00 | 41.47 | C |
| ATOM | 223 | CB | ASP | A | 869 | 131.006 | 60.580 | 19.562 | 1.00 | 41.42 | C |
| ATOM | 224 | CG | ASP | A | 869 | 131.782 | 61.147 | 20.735 | 1.00 | 41.71 | C |
| ATOM | 225 | OD1 | ASP | A | 869 | 132.436 | 62.201 | 20.587 | 1.00 | 43.12 | O |

APPENDIX 1-continued

| ATOM | 226 | OD2 | ASP | A | 869 | 131.715 | 60.539 | 21.823 | 1.00 | 41.98 | O |
|---|---|---|---|---|---|---|---|---|---|---|---|
| ATOM | 227 | C | ASP | A | 869 | 132.911 | 60.030 | 17.983 | 1.00 | 42.52 | C |
| ATOM | 228 | O | ASP | A | 869 | 133.128 | 59.049 | 18.703 | 1.00 | 42.60 | O |
| ATOM | 229 | N | PRO | A | 870 | 133.751 | 60.402 | 16.991 | 1.00 | 43.57 | N |
| ATOM | 230 | CA | PRO | A | 870 | 134.929 | 59.598 | 16.647 | 1.00 | 44.43 | C |
| ATOM | 231 | CB | PRO | A | 870 | 135.453 | 60.267 | 15.371 | 1.00 | 44.54 | C |
| ATOM | 232 | CG | PRO | A | 870 | 134.974 | 61.660 | 15.451 | 1.00 | 44.17 | C |
| ATOM | 233 | CD | PRO | A | 870 | 133.643 | 61.597 | 16.132 | 1.00 | 43.60 | C |
| ATOM | 234 | C | PRO | A | 870 | 136.016 | 59.573 | 17.723 | 1.00 | 45.21 | C |
| ATOM | 235 | O | PRO | A | 870 | 136.860 | 58.674 | 17.717 | 1.00 | 45.70 | O |
| ATOM | 236 | N | LEU | A | 871 | 135.995 | 60.547 | 18.629 | 1.00 | 45.92 | N |
| ATOM | 237 | CA | LEU | A | 871 | 136.947 | 60.589 | 19.738 | 1.00 | 46.84 | C |
| ATOM | 238 | CB | LEU | A | 871 | 137.346 | 62.035 | 20.062 | 1.00 | 46.98 | C |
| ATOM | 239 | CG | LEU | A | 871 | 138.054 | 62.856 | 18.976 | 1.00 | 47.53 | C |
| ATOM | 240 | CD1 | LEU | A | 871 | 138.160 | 64.313 | 19.402 | 1.00 | 49.15 | C |
| ATOM | 241 | CD2 | LEU | A | 871 | 139.433 | 62.291 | 18.645 | 1.00 | 47.99 | C |
| ATOM | 242 | C | LEU | A | 871 | 136.396 | 59.889 | 20.980 | 1.00 | 47.32 | C |
| ATOM | 243 | O | LEU | A | 871 | 137.109 | 59.718 | 21.974 | 1.00 | 47.23 | O |
| ATOM | 244 | N | GLN | A | 872 | 135.124 | 59.489 | 20.907 | 1.00 | 47.96 | N |
| ATOM | 245 | CA | GLN | A | 872 | 134.432 | 58.757 | 21.979 | 1.00 | 48.49 | C |
| ATOM | 246 | CB | GLN | A | 872 | 134.922 | 57.300 | 22.059 | 1.00 | 48.72 | C |
| ATOM | 247 | CG | GLN | A | 872 | 134.572 | 56.441 | 20.839 | 1.00 | 49.91 | C |
| ATOM | 248 | CD | GLN | A | 872 | 133.095 | 56.074 | 20.764 | 1.00 | 51.98 | C |
| ATOM | 249 | OE1 | GLN | A | 872 | 132.454 | 55.804 | 21.782 | 1.00 | 53.23 | O |
| ATOM | 250 | NE2 | GLN | A | 872 | 132.552 | 56.057 | 19.551 | 1.00 | 51.81 | N |
| ATOM | 251 | C | GLN | A | 872 | 134.521 | 59.451 | 23.344 | 1.00 | 48.62 | C |
| ATOM | 252 | O | GLN | A | 872 | 134.655 | 58.798 | 24.384 | 1.00 | 49.00 | O |
| ATOM | 253 | N | ASP | A | 873 | 134.432 | 60.780 | 23.321 | 1.00 | 48.12 | N |
| ATOM | 254 | CA | ASP | A | 873 | 134.546 | 61.604 | 24.523 | 1.00 | 47.84 | C |
| ATOM | 255 | CB | ASP | A | 873 | 135.869 | 62.386 | 24.507 | 1.00 | 47.95 | C |
| ATOM | 256 | CG | ASP | A | 873 | 135.993 | 63.326 | 23.309 | 1.00 | 48.33 | C |
| ATOM | 257 | OD1 | ASP | A | 873 | 135.159 | 63.254 | 22.380 | 1.00 | 49.23 | O |
| ATOM | 258 | OD2 | ASP | A | 873 | 136.938 | 64.143 | 23.296 | 1.00 | 48.42 | O |
| ATOM | 259 | C | ASP | A | 873 | 133.360 | 62.559 | 24.681 | 1.00 | 47.58 | C |
| ATOM | 260 | O | ASP | A | 873 | 133.397 | 63.473 | 25.510 | 1.00 | 47.56 | O |
| ATOM | 261 | N | ASN | A | 874 | 132.315 | 62.333 | 23.883 | 1.00 | 47.31 | N |
| ATOM | 262 | CA | ASN | A | 874 | 131.115 | 63.178 | 23.854 | 1.00 | 46.79 | C |
| ATOM | 263 | CB | ASN | A | 874 | 130.339 | 63.085 | 25.182 | 1.00 | 47.54 | C |
| ATOM | 264 | CG | ASN | A | 874 | 128.878 | 63.494 | 25.044 | 1.00 | 48.85 | C |
| ATOM | 265 | OD1 | ASN | A | 874 | 128.426 | 64.450 | 25.678 | 1.00 | 50.42 | O |
| ATOM | 266 | ND2 | ASN | A | 874 | 128.133 | 62.769 | 24.216 | 1.00 | 48.62 | N |
| ATOM | 267 | C | ASN | A | 874 | 131.429 | 64.633 | 23.472 | 1.00 | 45.88 | C |
| ATOM | 268 | O | ASN | A | 874 | 131.099 | 65.572 | 24.204 | 1.00 | 46.04 | O |
| ATOM | 269 | N | THR | A | 875 | 132.089 | 64.800 | 22.326 | 1.00 | 44.42 | N |
| ATOM | 270 | CA | THR | A | 875 | 132.406 | 66.124 | 21.777 | 1.00 | 42.93 | C |
| ATOM | 271 | CB | THR | A | 875 | 133.914 | 66.463 | 21.884 | 1.00 | 43.00 | C |
| ATOM | 272 | OG1 | THR | A | 875 | 134.683 | 65.480 | 21.180 | 1.00 | 42.34 | O |
| ATOM | 273 | CG2 | THR | A | 875 | 134.363 | 66.526 | 23.341 | 1.00 | 42.26 | C |
| ATOM | 274 | C | THR | A | 875 | 131.985 | 66.236 | 20.310 | 1.00 | 41.75 | C |
| ATOM | 275 | O | THR | A | 875 | 132.029 | 67.319 | 19.722 | 1.00 | 41.65 | O |
| ATOM | 276 | N | GLY | A | 876 | 131.580 | 65.111 | 19.726 | 1.00 | 40.35 | N |
| ATOM | 277 | CA | GLY | A | 876 | 131.178 | 65.070 | 18.326 | 1.00 | 39.09 | C |
| ATOM | 278 | C | GLY | A | 876 | 129.890 | 65.820 | 18.056 | 1.00 | 38.34 | C |
| ATOM | 279 | O | GLY | A | 876 | 129.085 | 66.041 | 18.963 | 1.00 | 37.98 | O |
| ATOM | 280 | N | GLU | A | 877 | 129.696 | 66.219 | 16.804 | 1.00 | 37.23 | N |
| ATOM | 281 | CA | GLU | A | 877 | 128.490 | 66.941 | 16.422 | 1.00 | 37.01 | C |
| ATOM | 282 | CB | GLU | A | 877 | 128.720 | 67.798 | 15.168 | 1.00 | 36.77 | C |
| ATOM | 283 | CG | GLU | A | 877 | 129.147 | 67.029 | 13.926 | 1.00 | 39.43 | C |
| ATOM | 284 | CD | GLU | A | 877 | 129.230 | 67.901 | 12.684 | 1.00 | 39.39 | C |
| ATOM | 285 | OE1 | GLU | A | 877 | 130.052 | 67.589 | 11.798 | 1.00 | 46.79 | O |
| ATOM | 286 | OE2 | GLU | A | 877 | 128.476 | 68.893 | 12.584 | 1.00 | 44.20 | O |
| ATOM | 287 | C | GLU | A | 877 | 127.297 | 66.004 | 16.242 | 1.00 | 35.31 | C |
| ATOM | 288 | O | GLU | A | 877 | 127.453 | 64.846 | 15.843 | 1.00 | 35.14 | O |
| ATOM | 289 | N | VAL | A | 878 | 126.113 | 66.513 | 16.567 | 1.00 | 33.44 | N |
| ATOM | 290 | CA | VAL | A | 878 | 124.865 | 65.812 | 16.301 | 1.00 | 32.04 | C |
| ATOM | 291 | CB | VAL | A | 878 | 123.699 | 66.361 | 17.160 | 1.00 | 31.85 | C |
| ATOM | 292 | CG1 | VAL | A | 878 | 122.390 | 65.696 | 16.778 | 1.00 | 31.99 | C |
| ATOM | 293 | CG2 | VAL | A | 878 | 123.979 | 66.156 | 18.646 | 1.00 | 30.91 | C |
| ATOM | 294 | C | VAL | A | 878 | 124.540 | 65.951 | 14.816 | 1.00 | 31.79 | C |
| ATOM | 295 | O | VAL | A | 878 | 124.669 | 67.034 | 14.241 | 1.00 | 31.33 | O |
| ATOM | 296 | N | VAL | A | 879 | 124.138 | 64.842 | 14.203 | 1.00 | 31.60 | N |
| ATOM | 297 | CA | VAL | A | 879 | 123.799 | 64.809 | 12.786 | 1.00 | 31.68 | C |
| ATOM | 298 | CB | VAL | A | 879 | 124.926 | 64.153 | 11.937 | 1.00 | 31.88 | C |
| ATOM | 299 | CG1 | VAL | A | 879 | 126.203 | 64.994 | 11.979 | 1.00 | 31.97 | C |
| ATOM | 300 | CG2 | VAL | A | 879 | 125.199 | 62.713 | 12.395 | 1.00 | 30.95 | C |
| ATOM | 301 | C | VAL | A | 879 | 122.489 | 64.055 | 12.568 | 1.00 | 32.04 | C |
| ATOM | 302 | O | VAL | A | 879 | 122.000 | 63.373 | 13.471 | 1.00 | 31.74 | O |
| ATOM | 303 | N | ALA | A | 880 | 121.923 | 64.198 | 11.372 | 1.00 | 31.79 | N |
| ATOM | 304 | CA | ALA | A | 880 | 120.752 | 63.436 | 10.971 | 1.00 | 31.85 | C |

APPENDIX 1-continued

| ATOM | 305 | CB | ALA | A | 880 | 119.742 | 64.332 | 10.293 | 1.00 | 31.81 | C |
| ATOM | 306 | C | ALA | A | 880 | 121.182 | 62.308 | 10.042 | 1.00 | 32.08 | C |
| ATOM | 307 | O | ALA | A | 880 | 121.977 | 62.513 | 9.121 | 1.00 | 32.39 | O |
| ATOM | 308 | N | VAL | A | 881 | 120.665 | 61.112 | 10.299 | 1.00 | 31.97 | N |
| ATOM | 309 | CA | VAL | A | 881 | 121.063 | 59.929 | 9.546 | 1.00 | 31.85 | C |
| ATOM | 310 | CB | VAL | A | 881 | 121.804 | 58.897 | 10.440 | 1.00 | 32.26 | C |
| ATOM | 311 | CG1 | VAL | A | 881 | 122.255 | 57.692 | 9.619 | 1.00 | 31.24 | C |
| ATOM | 312 | CG2 | VAL | A | 881 | 123.001 | 59.544 | 11.133 | 1.00 | 31.15 | C |
| ATOM | 313 | C | VAL | A | 881 | 119.841 | 59.296 | 8.900 | 1.00 | 32.25 | C |
| ATOM | 314 | O | VAL | A | 881 | 118.913 | 58.873 | 9.591 | 1.00 | 31.77 | O |
| ATOM | 315 | N | LYS | A | 882 | 119.843 | 59.255 | 7.571 | 1.00 | 33.02 | N |
| ATOM | 316 | CA | LYS | A | 882 | 118.762 | 58.632 | 6.819 | 1.00 | 34.21 | C |
| ATOM | 317 | CB | LYS | A | 882 | 118.312 | 59.524 | 5.655 | 1.00 | 33.70 | C |
| ATOM | 318 | CG | LYS | A | 882 | 117.098 | 58.992 | 4.897 | 1.00 | 33.99 | C |
| ATOM | 319 | CD | LYS | A | 882 | 116.611 | 59.959 | 3.830 | 1.00 | 34.17 | C |
| ATOM | 320 | CE | LYS | A | 882 | 115.354 | 59.432 | 3.151 | 1.00 | 35.63 | C |
| ATOM | 321 | NZ | LYS | A | 882 | 114.853 | 60.339 | 2.076 | 1.00 | 36.14 | N |
| ATOM | 322 | C | LYS | A | 882 | 119.176 | 57.258 | 6.304 | 1.00 | 35.74 | C |
| ATOM | 323 | O | LYS | A | 882 | 120.257 | 57.097 | 5.735 | 1.00 | 35.35 | O |
| ATOM | 324 | N | LYS | A | 883 | 118.307 | 56.275 | 6.517 | 1.00 | 37.60 | N |
| ATOM | 325 | CA | LYS | A | 883 | 118.477 | 54.948 | 5.936 | 1.00 | 40.13 | C |
| ATOM | 326 | CB | LYS | A | 883 | 119.151 | 53.986 | 6.925 | 1.00 | 39.98 | C |
| ATOM | 327 | CG | LYS | A | 883 | 118.340 | 53.638 | 8.167 | 1.00 | 41.61 | C |
| ATOM | 328 | CD | LYS | A | 883 | 119.076 | 52.597 | 9.003 | 1.00 | 42.12 | C |
| ATOM | 329 | CE | LYS | A | 883 | 118.463 | 52.443 | 10.385 | 1.00 | 46.08 | C |
| ATOM | 330 | NZ | LYS | A | 883 | 119.315 | 51.599 | 11.271 | 1.00 | 46.62 | N |
| ATOM | 331 | C | LYS | A | 883 | 117.138 | 54.394 | 5.458 | 1.00 | 40.95 | C |
| ATOM | 332 | O | LYS | A | 883 | 116.079 | 54.900 | 5.833 | 1.00 | 40.61 | O |
| ATOM | 333 | N | LEU | A | 884 | 117.194 | 53.362 | 4.621 | 1.00 | 42.26 | N |
| ATOM | 334 | CA | LEU | A | 884 | 115.990 | 52.686 | 4.155 | 1.00 | 43.89 | C |
| ATOM | 335 | CB | LEU | A | 884 | 116.290 | 51.830 | 2.919 | 1.00 | 43.81 | C |
| ATOM | 336 | CG | LEU | A | 884 | 116.802 | 52.539 | 1.659 | 1.00 | 44.04 | C |
| ATOM | 337 | CD1 | LEU | A | 884 | 117.362 | 51.526 | .674 | 1.00 | 43.87 | C |
| ATOM | 338 | CD2 | LEU | A | 884 | 115.715 | 53.389 | 1.000 | 1.00 | 44.22 | C |
| ATOM | 339 | C | LEU | A | 884 | 115.415 | 51.826 | 5.275 | 1.00 | 44.99 | C |
| ATOM | 340 | O | LEU | A | 884 | 116.148 | 51.076 | 5.924 | 1.00 | 44.81 | O |
| ATOM | 341 | N | GLN | A | 885 | 114.108 | 51.954 | 5.504 | 1.00 | 46.45 | N |
| ATOM | 342 | CA | GLN | A | 885 | 113.411 | 51.169 | 6.528 | 1.00 | 48.20 | C |
| ATOM | 343 | CB | GLN | A | 885 | 111.957 | 51.638 | 6.679 | 1.00 | 48.29 | C |
| ATOM | 344 | CG | GLN | A | 885 | 111.165 | 50.974 | 7.820 | 1.00 | 49.93 | C |
| ATOM | 345 | CD | GLN | A | 885 | 111.569 | 51.445 | 9.218 | 1.00 | 51.47 | C |
| ATOM | 346 | OE1 | GLN | A | 885 | 112.306 | 52.419 | 9.383 | 1.00 | 51.93 | O |
| ATOM | 347 | NE2 | GLN | A | 885 | 111.073 | 50.748 | 10.234 | 1.00 | 51.87 | N |
| ATOM | 348 | C | GLN | A | 885 | 113.481 | 49.677 | 6.202 | 1.00 | 49.12 | C |
| ATOM | 349 | O | GLN | A | 885 | 113.638 | 48.848 | 7.096 | 1.00 | 49.24 | O |
| ATOM | 350 | N | HIS | A | 886 | 113.368 | 49.350 | 4.918 | 1.00 | 50.46 | N |
| ATOM | 351 | CA | HIS | A | 886 | 113.592 | 47.992 | 4.433 | 1.00 | 51.74 | C |
| ATOM | 352 | CB | HIS | A | 886 | 112.266 | 47.258 | 4.222 | 1.00 | 52.09 | C |
| ATOM | 353 | CG | HIS | A | 886 | 111.599 | 46.848 | 5.497 | 1.00 | 53.85 | C |
| ATOM | 354 | ND1 | HIS | A | 886 | 110.747 | 47.679 | 6.193 | 1.00 | 54.57 | N |
| ATOM | 355 | CE1 | HIS | A | 886 | 110.317 | 47.057 | 7.276 | 1.00 | 55.03 | C |
| ATOM | 356 | NE2 | HIS | A | 886 | 110.862 | 45.854 | 7.311 | 1.00 | 55.27 | N |
| ATOM | 357 | CD2 | HIS | A | 886 | 111.669 | 45.698 | 6.210 | 1.00 | 54.62 | C |
| ATOM | 358 | C | HIS | A | 886 | 114.418 | 48.030 | 3.152 | 1.00 | 52.23 | C |
| ATOM | 359 | O | HIS | A | 886 | 113.964 | 48.531 | 2.120 | 1.00 | 52.00 | O |
| ATOM | 360 | N | SER | A | 887 | 115.637 | 47.504 | 3.235 | 1.00 | 53.14 | N |
| ATOM | 361 | CA | SER | A | 887 | 116.596 | 47.577 | 2.135 | 1.00 | 53.99 | C |
| ATOM | 362 | CB | SER | A | 887 | 118.021 | 47.331 | 2.643 | 1.00 | 54.17 | C |
| ATOM | 363 | OG | SER | A | 887 | 118.978 | 47.671 | 1.655 | 1.00 | 54.73 | O |
| ATOM | 364 | C | SER | A | 887 | 116.256 | 46.624 | .990 | 1.00 | 54.40 | C |
| ATOM | 365 | O | SER | A | 887 | 116.378 | 45.403 | 1.119 | 1.00 | 54.40 | O |
| ATOM | 366 | N | THR | A | 888 | 115.814 | 47.204 | −.122 | 1.00 | 54.85 | N |
| ATOM | 367 | CA | THR | A | 888 | 115.568 | 46.475 | −1.362 | 1.00 | 55.32 | C |
| ATOM | 368 | CB | THR | A | 888 | 114.127 | 46.709 | −1.878 | 1.00 | 55.47 | C |
| ATOM | 369 | OG1 | THR | A | 888 | 113.199 | 46.603 | −.791 | 1.00 | 56.06 | O |
| ATOM | 370 | CG2 | THR | A | 888 | 113.754 | 45.695 | −2.956 | 1.00 | 56.39 | C |
| ATOM | 371 | C | THR | A | 888 | 116.564 | 46.992 | −2.396 | 1.00 | 55.18 | C |
| ATOM | 372 | O | THR | A | 888 | 116.944 | 48.162 | −2.356 | 1.00 | 55.21 | O |
| ATOM | 373 | N | GLU | A | 889 | 116.985 | 46.121 | −3.312 | 1.00 | 55.00 | N |
| ATOM | 374 | CA | GLU | A | 889 | 117.925 | 46.494 | −4.371 | 1.00 | 54.99 | C |
| ATOM | 375 | CB | GLU | A | 889 | 118.306 | 45.270 | −5.214 | 1.00 | 55.28 | C |
| ATOM | 376 | CG | GLU | A | 889 | 119.553 | 45.453 | −6.086 | 1.00 | 56.97 | C |
| ATOM | 377 | CD | GLU | A | 889 | 120.785 | 45.892 | −5.297 | 1.00 | 59.20 | C |
| ATOM | 378 | OE1 | GLU | A | 889 | 121.059 | 45.313 | −4.221 | 1.00 | 59.25 | O |
| ATOM | 379 | OE2 | GLU | A | 889 | 121.483 | 46.818 | −5.763 | 1.00 | 59.70 | O |
| ATOM | 380 | C | GLU | A | 889 | 117.372 | 47.615 | −5.256 | 1.00 | 54.62 | C |
| ATOM | 381 | O | GLU | A | 889 | 118.126 | 48.463 | −5.741 | 1.00 | 54.62 | O |
| ATOM | 382 | N | GLU | A | 890 | 116.054 | 47.607 | −5.452 | 1.00 | 54.09 | N |
| ATOM | 383 | CA | GLU | A | 890 | 115.353 | 48.670 | −6.169 | 1.00 | 53.47 | C |

APPENDIX 1-continued

| ATOM | 384 | CB | GLU | A | 890 | 113.890 | 48.282 | −6.412 | 1.00 | 54.05 | C |
|---|---|---|---|---|---|---|---|---|---|---|---|
| ATOM | 385 | CG | GLU | A | 890 | 113.687 | 47.082 | −7.339 | 1.00 | 56.25 | C |
| ATOM | 386 | CD | GLU | A | 890 | 113.798 | 47.435 | −8.816 | 1.00 | 59.27 | C |
| ATOM | 387 | OE1 | GLU | A | 890 | 113.585 | 48.613 | −9.179 | 1.00 | 60.81 | O |
| ATOM | 388 | OE2 | GLU | A | 890 | 114.094 | 46.525 | −9.620 | 1.00 | 60.37 | O |
| ATOM | 389 | C | GLU | A | 890 | 115.422 | 49.983 | −5.389 | 1.00 | 52.37 | C |
| ATOM | 390 | O | GLU | A | 890 | 115.714 | 51.037 | −5.960 | 1.00 | 52.32 | O |
| ATOM | 391 | N | HIS | A | 891 | 115.158 | 49.907 | −4.084 | 1.00 | 50.81 | N |
| ATOM | 392 | CA | HIS | A | 891 | 115.202 | 51.076 | −3.206 | 1.00 | 49.53 | C |
| ATOM | 393 | CB | HIS | A | 891 | 114.494 | 50.799 | −1.876 | 1.00 | 49.48 | C |
| ATOM | 394 | CG | HIS | A | 891 | 113.005 | 50.688 | −1.995 | 1.00 | 50.83 | C |
| ATOM | 395 | ND1 | HIS | A | 891 | 112.291 | 49.641 | −1.454 | 1.00 | 51.72 | N |
| ATOM | 396 | CE1 | HIS | A | 891 | 111.006 | 49.805 | −1.716 | 1.00 | 52.65 | C |
| ATOM | 397 | NE2 | HIS | A | 891 | 110.862 | 50.919 | −2.412 | 1.00 | 53.10 | N |
| ATOM | 398 | CD2 | HIS | A | 891 | 112.097 | 51.490 | −2.601 | 1.00 | 51.77 | C |
| ATOM | 399 | C | HIS | A | 891 | 116.626 | 51.561 | −2.951 | 1.00 | 48.23 | C |
| ATOM | 400 | O | HIS | A | 891 | 116.845 | 52.756 | −2.759 | 1.00 | 47.93 | O |
| ATOM | 401 | N | LEU | A | 892 | 117.580 | 50.632 | −2.949 | 1.00 | 46.76 | N |
| ATOM | 402 | CA | LEU | A | 892 | 118.996 | 50.960 | −2.779 | 1.00 | 45.74 | C |
| ATOM | 403 | CB | LEU | A | 892 | 119.830 | 49.689 | −2.585 | 1.00 | 45.45 | C |
| ATOM | 404 | CG | LEU | A | 892 | 121.310 | 49.833 | −2.212 | 1.00 | 46.54 | C |
| ATOM | 405 | CD1 | LEU | A | 892 | 121.485 | 50.424 | −.816 | 1.00 | 46.76 | C |
| ATOM | 406 | CD2 | LEU | A | 892 | 122.010 | 48.489 | −2.314 | 1.00 | 46.12 | C |
| ATOM | 407 | C | LEU | A | 892 | 119.517 | 51.765 | −3.968 | 1.00 | 44.72 | C |
| ATOM | 408 | O | LEU | A | 892 | 120.278 | 52.719 | −3.792 | 1.00 | 44.59 | O |
| ATOM | 409 | N | ARG | A | 893 | 119.096 | 51.371 | −5.169 | 1.00 | 43.38 | N |
| ATOM | 410 | CA | ARG | A | 893 | 119.427 | 52.085 | −6.400 | 1.00 | 42.68 | C |
| ATOM | 411 | CB | ARG | A | 893 | 118.959 | 51.279 | −7.619 | 1.00 | 42.63 | C |
| ATOM | 412 | CG | ARG | A | 893 | 119.243 | 51.926 | −8.972 | 1.00 | 44.34 | C |
| ATOM | 413 | CD | ARG | A | 893 | 119.234 | 50.911 | −10.117 | 1.00 | 44.83 | C |
| ATOM | 414 | NE | ARG | A | 893 | 117.958 | 50.206 | −10.263 | 1.00 | 49.60 | N |
| ATOM | 415 | CZ | ARG | A | 893 | 117.756 | 48.929 | −9.941 | 1.00 | 50.08 | C |
| ATOM | 416 | NH1 | ARG | A | 893 | 118.743 | 48.189 | −9.448 | 1.00 | 52.07 | N |
| ATOM | 417 | NH2 | ARG | A | 893 | 116.559 | 48.387 | −10.115 | 1.00 | 50.91 | N |
| ATOM | 418 | C | ARG | A | 893 | 118.821 | 53.494 | −6.396 | 1.00 | 40.86 | C |
| ATOM | 419 | O | ARG | A | 893 | 119.482 | 54.458 | −6.791 | 1.00 | 39.91 | O |
| ATOM | 420 | N | ASP | A | 894 | 117.570 | 53.598 | −5.944 | 1.00 | 39.45 | N |
| ATOM | 421 | CA | ASP | A | 894 | 116.902 | 54.887 | −5.754 | 1.00 | 38.13 | C |
| ATOM | 422 | CB | ASP | A | 894 | 115.449 | 54.687 | −5.310 | 1.00 | 38.17 | C |
| ATOM | 423 | CG | ASP | A | 894 | 114.547 | 54.197 | −6.430 | 1.00 | 40.62 | C |
| ATOM | 424 | OD1 | ASP | A | 894 | 114.932 | 54.290 | −7.615 | 1.00 | 42.30 | O |
| ATOM | 425 | OD2 | ASP | A | 894 | 113.435 | 53.722 | −6.118 | 1.00 | 43.39 | O |
| ATOM | 426 | C | ASP | A | 894 | 117.635 | 55.737 | −4.722 | 1.00 | 36.58 | C |
| ATOM | 427 | O | ASP | A | 894 | 117.874 | 56.923 | −4.946 | 1.00 | 35.90 | O |
| ATOM | 428 | N | PHE | A | 895 | 117.995 | 55.113 | −3.599 | 1.00 | 35.44 | N |
| ATOM | 429 | CA | PHE | A | 895 | 118.684 | 55.791 | −2.502 | 1.00 | 35.13 | C |
| ATOM | 430 | CB | PHE | A | 895 | 118.802 | 54.862 | −1.286 | 1.00 | 34.91 | C |
| ATOM | 431 | CG | PHE | A | 895 | 119.200 | 55.559 | −.008 | 1.00 | 34.98 | C |
| ATOM | 432 | CD1 | PHE | A | 895 | 118.736 | 56.842 | .288 | 1.00 | 35.38 | C |
| ATOM | 433 | CE1 | PHE | A | 895 | 119.102 | 57.479 | 1.476 | 1.00 | 34.72 | C |
| ATOM | 434 | CZ | PHE | A | 895 | 119.923 | 56.828 | 2.386 | 1.00 | 34.21 | C |
| ATOM | 435 | CE2 | PHE | A | 895 | 120.383 | 55.542 | 2.109 | 1.00 | 34.15 | C |
| ATOM | 436 | CD2 | PHE | A | 895 | 120.018 | 54.915 | .918 | 1.00 | 33.71 | C |
| ATOM | 437 | C | PHE | A | 895 | 120.053 | 56.312 | −2.935 | 1.00 | 34.95 | C |
| ATOM | 438 | O | PHE | A | 895 | 120.435 | 57.423 | −2.571 | 1.00 | 35.33 | O |
| ATOM | 439 | N | GLU | A | 896 | 120.773 | 55.514 | −3.724 | 1.00 | 34.38 | N |
| ATOM | 440 | CA | GLU | A | 896 | 122.066 | 55.920 | −4.285 | 1.00 | 34.33 | C |
| ATOM | 441 | CB | GLU | A | 896 | 122.687 | 54.782 | −5.100 | 1.00 | 33.91 | C |
| ATOM | 442 | CG | GLU | A | 896 | 123.350 | 53.692 | −4.268 | 1.00 | 35.92 | C |
| ATOM | 443 | CD | GLU | A | 896 | 123.851 | 52.525 | −5.106 | 1.00 | 36.08 | C |
| ATOM | 444 | OE1 | GLU | A | 896 | 123.804 | 52.603 | −6.354 | 1.00 | 41.38 | O |
| ATOM | 445 | OE2 | GLU | A | 896 | 124.296 | 51.522 | −4.511 | 1.00 | 40.65 | O |
| ATOM | 446 | C | GLU | A | 896 | 121.937 | 57.171 | −5.155 | 1.00 | 33.10 | C |
| ATOM | 447 | O | GLU | A | 896 | 122.761 | 58.079 | −5.065 | 1.00 | 32.74 | O |
| ATOM | 448 | N | ARG | A | 897 | 120.905 | 57.200 | −5.997 | 1.00 | 32.80 | N |
| ATOM | 449 | CA | ARG | A | 897 | 120.602 | 58.367 | −6.822 | 1.00 | 33.11 | C |
| ATOM | 450 | CB | ARG | A | 897 | 119.497 | 58.052 | −7.833 | 1.00 | 33.33 | C |
| ATOM | 451 | CG | ARG | A | 897 | 120.004 | 57.427 | −9.120 | 1.00 | 36.47 | C |
| ATOM | 452 | CD | ARG | A | 897 | 118.856 | 57.003 | −10.019 | 1.00 | 41.94 | C |
| ATOM | 453 | NE | ARG | A | 897 | 118.252 | 55.746 | −9.580 | 1.00 | 46.76 | N |
| ATOM | 454 | CZ | ARG | A | 897 | 117.142 | 55.220 | −10.090 | 1.00 | 49.59 | C |
| ATOM | 455 | NH1 | ARG | A | 897 | 116.485 | 55.840 | −11.065 | 1.00 | 51.02 | N |
| ATOM | 456 | NH2 | ARG | A | 897 | 116.681 | 54.070 | −9.618 | 1.00 | 49.70 | N |
| ATOM | 457 | C | ARG | A | 897 | 120.222 | 59.580 | −5.971 | 1.00 | 32.35 | C |
| ATOM | 458 | O | ARG | A | 897 | 120.674 | 60.688 | −6.241 | 1.00 | 32.28 | O |
| ATOM | 459 | N | GLU | A | 898 | 119.405 | 59.356 | −4.942 | 1.00 | 31.85 | N |
| ATOM | 460 | CA | GLU | A | 898 | 119.020 | 60.409 | −3.997 | 1.00 | 31.35 | C |
| ATOM | 461 | CB | GLU | A | 898 | 118.107 | 59.844 | −2.906 | 1.00 | 31.17 | C |
| ATOM | 462 | CG | GLU | A | 898 | 117.611 | 60.877 | −1.894 | 1.00 | 31.21 | C |

APPENDIX 1-continued

| ATOM | 463 | CD | GLU | A | 898 | 116.898 | 60.249 | −.713 | 1.00 | 31.70 | C |
|---|---|---|---|---|---|---|---|---|---|---|---|
| ATOM | 464 | OE1 | GLU | A | 898 | 116.344 | 59.138 | −.861 | 1.00 | 31.26 | O |
| ATOM | 465 | OE2 | GLU | A | 898 | 116.883 | 60.874 | .368 | 1.00 | 33.40 | O |
| ATOM | 466 | C | GLU | A | 898 | 120.245 | 61.075 | −3.367 | 1.00 | 31.17 | C |
| ATOM | 467 | O | GLU | A | 898 | 120.324 | 62.301 | −3.297 | 1.00 | 30.80 | O |
| ATOM | 468 | N | ILE | A | 899 | 121.192 | 60.256 | −2.915 | 1.00 | 31.75 | N |
| ATOM | 469 | CA | ILE | A | 899 | 122.426 | 60.743 | −2.303 | 1.00 | 32.38 | C |
| ATOM | 470 | CB | ILE | A | 899 | 123.279 | 59.579 | −1.742 | 1.00 | 32.80 | C |
| ATOM | 471 | CG1 | ILE | A | 899 | 122.590 | 58.968 | −.515 | 1.00 | 33.07 | C |
| ATOM | 472 | CD1 | ILE | A | 899 | 123.038 | 57.555 | −.185 | 1.00 | 35.15 | C |
| ATOM | 473 | CG2 | ILE | A | 899 | 124.691 | 60.048 | −1.383 | 1.00 | 33.51 | C |
| ATOM | 474 | C | ILE | A | 899 | 123.227 | 61.600 | −3.286 | 1.00 | 32.28 | C |
| ATOM | 475 | O | ILE | A | 899 | 123.725 | 62.666 | −2.918 | 1.00 | 32.55 | O |
| ATOM | 476 | N | GLU | A | 900 | 123.324 | 61.138 | −4.532 | 1.00 | 32.17 | N |
| ATOM | 477 | CA | GLU | A | 900 | 123.997 | 61.894 | −5.588 | 1.00 | 32.35 | C |
| ATOM | 478 | CB | GLU | A | 900 | 124.142 | 61.058 | −6.864 | 1.00 | 32.78 | C |
| ATOM | 479 | CG | GLU | A | 900 | 125.178 | 59.940 | −6.757 | 1.00 | 37.15 | C |
| ATOM | 480 | CD | GLU | A | 900 | 126.506 | 60.410 | −6.172 | 1.00 | 42.06 | C |
| ATOM | 481 | OE1 | GLU | A | 900 | 126.935 | 59.839 | −5.145 | 1.00 | 44.53 | O |
| ATOM | 482 | OE2 | GLU | A | 900 | 127.113 | 61.353 | −6.730 | 1.00 | 43.50 | O |
| ATOM | 483 | C | GLU | A | 900 | 123.294 | 63.217 | −5.884 | 1.00 | 31.35 | C |
| ATOM | 484 | O | GLU | A | 900 | 123.955 | 64.231 | −6.105 | 1.00 | 30.64 | O |
| ATOM | 485 | N | ILE | A | 901 | 121.961 | 63.194 | −5.880 | 1.00 | 30.95 | N |
| ATOM | 486 | CA | ILE | A | 901 | 121.154 | 64.408 | −6.036 | 1.00 | 31.46 | C |
| ATOM | 487 | CB | ILE | A | 901 | 119.618 | 64.118 | −5.973 | 1.00 | 31.50 | C |
| ATOM | 488 | CG1 | ILE | A | 901 | 119.163 | 63.212 | −7.129 | 1.00 | 32.81 | C |
| ATOM | 489 | CD1 | ILE | A | 901 | 119.232 | 63.830 | −8.503 | 1.00 | 37.97 | C |
| ATOM | 490 | CG2 | ILE | A | 901 | 118.801 | 65.416 | −5.929 | 1.00 | 30.03 | C |
| ATOM | 491 | C | ILE | A | 901 | 121.528 | 65.430 | −4.966 | 1.00 | 31.06 | C |
| ATOM | 492 | O | ILE | A | 901 | 121.906 | 66.554 | −5.289 | 1.00 | 30.72 | O |
| ATOM | 493 | N | LEU | A | 902 | 121.443 | 65.023 | −3.701 | 1.00 | 31.44 | N |
| ATOM | 494 | CA | LEU | A | 902 | 121.672 | 65.934 | −2.575 | 1.00 | 32.11 | C |
| ATOM | 495 | CB | LEU | A | 902 | 121.318 | 65.262 | −1.244 | 1.00 | 32.10 | C |
| ATOM | 496 | CG | LEU | A | 902 | 121.363 | 66.137 | .015 | 1.00 | 33.01 | C |
| ATOM | 497 | CD1 | LEU | A | 902 | 120.541 | 67.411 | −.160 | 1.00 | 29.60 | C |
| ATOM | 498 | CD2 | LEU | A | 902 | 120.896 | 65.358 | 1.231 | 1.00 | 32.28 | C |
| ATOM | 499 | C | LEU | A | 902 | 123.098 | 66.473 | −2.539 | 1.00 | 32.61 | C |
| ATOM | 500 | O | LEU | A | 902 | 123.312 | 67.661 | −2.280 | 1.00 | 32.57 | O |
| ATOM | 501 | N | LYS | A | 903 | 124.061 | 65.593 | −2.807 | 1.00 | 33.09 | N |
| ATOM | 502 | CA | LYS | A | 903 | 125.472 | 65.960 | −2.862 | 1.00 | 34.09 | C |
| ATOM | 503 | CB | LYS | A | 903 | 126.322 | 64.719 | −3.146 | 1.00 | 34.33 | C |
| ATOM | 504 | CG | LYS | A | 903 | 127.801 | 64.883 | −2.851 | 1.00 | 39.43 | C |
| ATOM | 505 | CD | LYS | A | 903 | 128.574 | 63.627 | −3.229 | 1.00 | 43.47 | C |
| ATOM | 506 | CE | LYS | A | 903 | 130.077 | 63.836 | −3.104 | 1.00 | 46.72 | C |
| ATOM | 507 | NZ | LYS | A | 903 | 130.597 | 64.810 | −4.110 | 1.00 | 49.07 | N |
| ATOM | 508 | C | LYS | A | 903 | 125.728 | 67.039 | −3.919 | 1.00 | 33.53 | C |
| ATOM | 509 | O | LYS | A | 903 | 126.579 | 67.911 | −3.728 | 1.00 | 33.72 | O |
| ATOM | 510 | N | SER | A | 904 | 124.976 | 66.979 | −5.018 | 1.00 | 32.28 | N |
| ATOM | 511 | CA | SER | A | 904 | 125.123 | 67.923 | −6.127 | 1.00 | 32.10 | C |
| ATOM | 512 | CB | SER | A | 904 | 124.537 | 67.330 | −7.413 | 1.00 | 31.92 | C |
| ATOM | 513 | OG | SER | A | 904 | 123.119 | 67.405 | −7.417 | 1.00 | 30.53 | O |
| ATOM | 514 | C | SER | A | 904 | 124.479 | 69.283 | −5.841 | 1.00 | 32.04 | C |
| ATOM | 515 | O | SER | A | 904 | 124.635 | 70.226 | −6.619 | 1.00 | 30.97 | O |
| ATOM | 516 | N | LEU | A | 905 | 123.754 | 69.374 | −4.729 | 1.00 | 32.28 | N |
| ATOM | 517 | CA | LEU | A | 905 | 123.036 | 70.592 | −4.369 | 1.00 | 32.75 | C |
| ATOM | 518 | CB | LEU | A | 905 | 121.588 | 70.272 | −3.976 | 1.00 | 32.60 | C |
| ATOM | 519 | CG | LEU | A | 905 | 120.670 | 69.628 | −5.022 | 1.00 | 32.19 | C |
| ATOM | 520 | CD1 | LEU | A | 905 | 119.410 | 69.101 | −4.355 | 1.00 | 30.87 | C |
| ATOM | 521 | CD2 | LEU | A | 905 | 120.329 | 70.597 | −6.154 | 1.00 | 31.42 | C |
| ATOM | 522 | C | LEU | A | 905 | 123.734 | 71.348 | −3.241 | 1.00 | 33.39 | C |
| ATOM | 523 | O | LEU | A | 905 | 123.982 | 70.795 | −2.169 | 1.00 | 34.07 | O |
| ATOM | 524 | N | GLN | A | 906 | 124.056 | 72.611 | −3.502 | 1.00 | 33.91 | N |
| ATOM | 525 | CA | GLN | A | 906 | 124.620 | 73.504 | −2.493 | 1.00 | 34.71 | C |
| ATOM | 526 | CB | GLN | A | 906 | 126.125 | 73.693 | −2.705 | 1.00 | 35.82 | C |
| ATOM | 527 | CG | GLN | A | 906 | 126.965 | 72.466 | −2.365 | 1.00 | 41.28 | C |
| ATOM | 528 | CD | GLN | A | 906 | 128.313 | 72.463 | −3.065 | 1.00 | 47.66 | C |
| ATOM | 529 | OE1 | GLN | A | 906 | 129.357 | 72.337 | −2.423 | 1.00 | 49.69 | O |
| ATOM | 530 | NE2 | GLN | A | 906 | 128.297 | 72.601 | −4.390 | 1.00 | 48.47 | N |
| ATOM | 531 | C | GLN | A | 906 | 123.891 | 74.843 | −2.546 | 1.00 | 33.62 | C |
| ATOM | 532 | O | GLN | A | 906 | 124.109 | 75.653 | −3.455 | 1.00 | 33.25 | O |
| ATOM | 533 | N | HIS | A | 907 | 123.016 | 75.058 | −1.568 | 1.00 | 32.73 | N |
| ATOM | 534 | CA | HIS | A | 907 | 122.147 | 76.230 | −1.535 | 1.00 | 31.49 | C |
| ATOM | 535 | CB | HIS | A | 907 | 120.913 | 75.990 | −2.414 | 1.00 | 30.46 | C |
| ATOM | 536 | CG | HIS | A | 907 | 120.125 | 77.227 | −2.710 | 1.00 | 29.27 | C |
| ATOM | 537 | ND1 | HIS | A | 907 | 119.126 | 77.689 | −1.880 | 1.00 | 28.70 | N |
| ATOM | 538 | CE1 | HIS | A | 907 | 118.609 | 78.794 | −2.389 | 1.00 | 27.37 | C |
| ATOM | 539 | NE2 | HIS | A | 907 | 119.232 | 79.061 | −3.523 | 1.00 | 27.23 | N |
| ATOM | 540 | CD2 | HIS | A | 907 | 120.184 | 78.097 | −3.747 | 1.00 | 27.49 | C |
| ATOM | 541 | C | HIS | A | 907 | 121.727 | 76.491 | −.097 | 1.00 | 31.56 | C |

APPENDIX 1-continued

| ATOM | 542 | O | HIS | A | 907 | 121.562 | 75.550 | .686 | 1.00 | 32.08 | O |
|---|---|---|---|---|---|---|---|---|---|---|---|
| ATOM | 543 | N | ASP | A | 908 | 121.553 | 77.767 | .243 | 1.00 | 31.36 | N |
| ATOM | 544 | CA | ASP | A | 908 | 121.150 | 78.183 | 1.591 | 1.00 | 31.09 | C |
| ATOM | 545 | CB | ASP | A | 908 | 121.014 | 79.711 | 1.662 | 1.00 | 31.88 | C |
| ATOM | 546 | CG | ASP | A | 908 | 122.361 | 80.433 | 1.717 | 1.00 | 33.78 | C |
| ATOM | 547 | OD1 | ASP | A | 908 | 123.419 | 79.770 | 1.798 | 1.00 | 34.53 | O |
| ATOM | 548 | OD2 | ASP | A | 908 | 122.355 | 81.683 | 1.683 | 1.00 | 35.63 | O |
| ATOM | 549 | C | ASP | A | 908 | 119.841 | 77.537 | 2.046 | 1.00 | 30.41 | C |
| ATOM | 550 | O | ASP | A | 908 | 119.622 | 77.335 | 3.245 | 1.00 | 30.39 | O |
| ATOM | 551 | N | ASN | A | 909 | 118.976 | 77.217 | 1.086 | 1.00 | 28.54 | N |
| ATOM | 552 | CA | ASN | A | 909 | 117.653 | 76.681 | 1.390 | 1.00 | 26.74 | C |
| ATOM | 553 | CB | ASN | A | 909 | 116.572 | 77.570 | .773 | 1.00 | 26.43 | C |
| ATOM | 554 | CG | ASN | A | 909 | 116.699 | 79.013 | 1.209 | 1.00 | 25.89 | C |
| ATOM | 555 | OD1 | ASN | A | 909 | 116.561 | 79.336 | 2.392 | 1.00 | 29.38 | O |
| ATOM | 556 | ND2 | ASN | A | 909 | 116.973 | 79.887 | .260 | 1.00 | 19.77 | N |
| ATOM | 557 | C | ASN | A | 909 | 117.482 | 75.223 | .978 | 1.00 | 25.51 | C |
| ATOM | 558 | O | ASN | A | 909 | 116.378 | 74.777 | .660 | 1.00 | 25.38 | O |
| ATOM | 559 | N | ILE | A | 910 | 118.593 | 74.494 | .990 | 1.00 | 25.20 | N |
| ATOM | 560 | CA | ILE | A | 910 | 118.606 | 73.052 | .795 | 1.00 | 25.60 | C |
| ATOM | 561 | CB | ILE | A | 910 | 119.139 | 72.666 | −.610 | 1.00 | 25.36 | C |
| ATOM | 562 | CG1 | ILE | A | 910 | 118.116 | 73.070 | −1.681 | 1.00 | 26.37 | C |
| ATOM | 563 | CD1 | ILE | A | 910 | 118.571 | 72.857 | −3.092 | 1.00 | 32.50 | C |
| ATOM | 564 | CG2 | ILE | A | 910 | 119.457 | 71.161 | −.690 | 1.00 | 24.99 | C |
| ATOM | 565 | C | ILE | A | 910 | 119.459 | 72.435 | 1.901 | 1.00 | 26.11 | C |
| ATOM | 566 | O | ILE | A | 910 | 120.560 | 72.918 | 2.184 | 1.00 | 26.45 | O |
| ATOM | 567 | N | VAL | A | 911 | 118.933 | 71.386 | 2.533 | 1.00 | 26.38 | N |
| ATOM | 568 | CA | VAL | A | 911 | 119.619 | 70.698 | 3.631 | 1.00 | 27.50 | C |
| ATOM | 569 | CB | VAL | A | 911 | 118.763 | 69.516 | 4.200 | 1.00 | 27.59 | C |
| ATOM | 570 | CG1 | VAL | A | 911 | 118.657 | 68.356 | 3.195 | 1.00 | 28.67 | C |
| ATOM | 571 | CG2 | VAL | A | 911 | 119.316 | 69.030 | 5.535 | 1.00 | 25.04 | C |
| ATOM | 572 | C | VAL | A | 911 | 121.016 | 70.231 | 3.205 | 1.00 | 28.18 | C |
| ATOM | 573 | O | VAL | A | 911 | 121.196 | 69.709 | 2.105 | 1.00 | 28.21 | O |
| ATOM | 574 | N | LYS | A | 912 | 121.998 | 70.438 | 4.077 | 1.00 | 29.12 | N |
| ATOM | 575 | CA | LYS | A | 912 | 123.392 | 70.133 | 3.760 | 1.00 | 30.55 | C |
| ATOM | 576 | CB | LYS | A | 912 | 124.343 | 70.914 | 4.677 | 1.00 | 30.43 | C |
| ATOM | 577 | CG | LYS | A | 912 | 124.409 | 72.402 | 4.387 | 1.00 | 31.87 | C |
| ATOM | 578 | CD | LYS | A | 912 | 125.259 | 73.143 | 5.416 | 1.00 | 32.39 | C |
| ATOM | 579 | CE | LYS | A | 912 | 125.381 | 74.620 | 5.060 | 1.00 | 36.79 | C |
| ATOM | 580 | NZ | LYS | A | 912 | 125.822 | 75.460 | 6.216 | 1.00 | 38.91 | N |
| ATOM | 581 | C | LYS | A | 912 | 123.719 | 68.644 | 3.818 | 1.00 | 31.17 | C |
| ATOM | 582 | O | LYS | A | 912 | 123.413 | 67.958 | 4.798 | 1.00 | 30.17 | O |
| ATOM | 583 | N | TYR | A | 913 | 124.331 | 68.157 | 2.743 | 1.00 | 31.69 | N |
| ATOM | 584 | CA | TYR | A | 913 | 124.924 | 66.830 | 2.700 | 1.00 | 32.91 | C |
| ATOM | 585 | CB | TYR | A | 913 | 125.210 | 66.436 | 1.246 | 1.00 | 33.32 | C |
| ATOM | 586 | CG | TYR | A | 913 | 126.094 | 65.216 | 1.074 | 1.00 | 34.17 | C |
| ATOM | 587 | CD1 | TYR | A | 913 | 125.546 | 63.937 | 1.040 | 1.00 | 34.78 | C |
| ATOM | 588 | CE1 | TYR | A | 913 | 126.349 | 62.814 | .878 | 1.00 | 36.03 | C |
| ATOM | 589 | CZ | TYR | A | 913 | 127.718 | 62.969 | .736 | 1.00 | 35.13 | C |
| ATOM | 590 | OH | TYR | A | 913 | 128.513 | 61.861 | .578 | 1.00 | 34.24 | O |
| ATOM | 591 | CE2 | TYR | A | 913 | 128.291 | 64.230 | .765 | 1.00 | 34.83 | C |
| ATOM | 592 | CD2 | TYR | A | 913 | 127.477 | 65.346 | .928 | 1.00 | 35.46 | C |
| ATOM | 593 | C | TYR | A | 913 | 126.216 | 66.844 | 3.511 | 1.00 | 33.16 | C |
| ATOM | 594 | O | TYR | A | 913 | 127.030 | 67.761 | 3.372 | 1.00 | 33.10 | O |
| ATOM | 595 | N | LYS | A | 914 | 126.402 | 65.830 | 4.352 | 1.00 | 33.93 | N |
| ATOM | 596 | CA | LYS | A | 914 | 127.616 | 65.716 | 5.159 | 1.00 | 34.34 | C |
| ATOM | 597 | CB | LYS | A | 914 | 127.275 | 65.643 | 6.649 | 1.00 | 34.84 | C |
| ATOM | 598 | CG | LYS | A | 914 | 126.968 | 66.996 | 7.283 | 1.00 | 35.99 | C |
| ATOM | 599 | CD | LYS | A | 914 | 126.859 | 66.876 | 8.797 | 1.00 | 35.63 | C |
| ATOM | 600 | CE | LYS | A | 914 | 126.977 | 68.230 | 9.484 | 1.00 | 37.72 | C |
| ATOM | 601 | NZ | LYS | A | 914 | 128.377 | 68.747 | 9.496 | 1.00 | 36.31 | N |
| ATOM | 602 | C | LYS | A | 914 | 128.492 | 64.530 | 4.751 | 1.00 | 34.84 | C |
| ATOM | 603 | O | LYS | A | 914 | 129.720 | 64.612 | 4.803 | 1.00 | 33.99 | O |
| ATOM | 604 | N | GLY | A | 915 | 127.856 | 63.436 | 4.346 | 1.00 | 35.23 | N |
| ATOM | 605 | CA | GLY | A | 915 | 128.574 | 62.233 | 3.945 | 1.00 | 36.17 | C |
| ATOM | 606 | C | GLY | A | 915 | 127.706 | 60.991 | 3.900 | 1.00 | 37.23 | C |
| ATOM | 607 | O | GLY | A | 915 | 126.477 | 61.071 | 3.993 | 1.00 | 35.82 | O |
| ATOM | 608 | N | VAL | A | 916 | 128.360 | 59.842 | 3.744 | 1.00 | 38.37 | N |
| ATOM | 609 | CA | VAL | A | 916 | 127.689 | 58.544 | 3.748 | 1.00 | 40.50 | C |
| ATOM | 610 | CB | VAL | A | 916 | 127.669 | 57.877 | 2.342 | 1.00 | 40.26 | C |
| ATOM | 611 | CG1 | VAL | A | 916 | 126.708 | 58.603 | 1.411 | 1.00 | 37.94 | C |
| ATOM | 612 | CG2 | VAL | A | 916 | 129.076 | 57.797 | 1.741 | 1.00 | 38.88 | C |
| ATOM | 613 | C | VAL | A | 916 | 128.333 | 57.589 | 4.751 | 1.00 | 42.90 | C |
| ATOM | 614 | O | VAL | A | 916 | 129.492 | 57.764 | 5.133 | 1.00 | 42.89 | O |
| ATOM | 615 | N | CYS | A | 917 | 127.569 | 56.587 | 5.175 | 1.00 | 45.77 | N |
| ATOM | 616 | CA | CYS | A | 917 | 128.068 | 55.558 | 6.078 | 1.00 | 47.49 | C |
| ATOM | 617 | CB | CYS | A | 917 | 127.351 | 55.633 | 7.429 | 1.00 | 47.41 | C |
| ATOM | 618 | SG | CYS | A | 917 | 127.977 | 54.486 | 8.683 | 1.00 | 48.25 | S |
| ATOM | 619 | C | CYS | A | 917 | 127.891 | 54.182 | 5.447 | 1.00 | 49.12 | C |
| ATOM | 620 | O | CYS | A | 917 | 126.785 | 53.812 | 5.044 | 1.00 | 48.81 | O |

APPENDIX 1-continued

| ATOM | 621 | N | TYR | A | 918 | 128.994 | 53.442 | 5.352 | 1.00 | 51.21 | N |
|---|---|---|---|---|---|---|---|---|---|---|---|
| ATOM | 622 | CA | TYR | A | 918 | 129.003 | 52.091 | 4.789 | 1.00 | 53.16 | C |
| ATOM | 623 | CB | TYR | A | 918 | 130.023 | 51.988 | 3.651 | 1.00 | 53.90 | C |
| ATOM | 624 | CG | TYR | A | 918 | 129.554 | 52.523 | 2.316 | 1.00 | 54.80 | C |
| ATOM | 625 | CD1 | TYR | A | 918 | 129.927 | 53.795 | 1.884 | 1.00 | 55.80 | C |
| ATOM | 626 | CE1 | TYR | A | 918 | 129.504 | 54.290 | .648 | 1.00 | 56.92 | C |
| ATOM | 627 | CZ | TYR | A | 918 | 128.703 | 53.504 | −.168 | 1.00 | 56.30 | C |
| ATOM | 628 | OH | TYR | A | 918 | 128.283 | 53.988 | −1.387 | 1.00 | 55.73 | O |
| ATOM | 629 | CE2 | TYR | A | 918 | 128.325 | 52.233 | .238 | 1.00 | 56.57 | C |
| ATOM | 630 | CD2 | TYR | A | 918 | 128.753 | 51.749 | 1.474 | 1.00 | 56.35 | C |
| ATOM | 631 | C | TYR | A | 918 | 129.336 | 51.048 | 5.852 | 1.00 | 53.89 | C |
| ATOM | 632 | O | TYR | A | 918 | 130.099 | 51.319 | 6.783 | 1.00 | 54.27 | O |
| ATOM | 633 | N | SER | A | 919 | 128.767 | 49.854 | 5.699 | 1.00 | 54.74 | N |
| ATOM | 634 | CA | SER | A | 919 | 129.054 | 48.727 | 6.589 | 1.00 | 55.29 | C |
| ATOM | 635 | CB | SER | A | 919 | 128.036 | 47.603 | 6.379 | 1.00 | 55.20 | C |
| ATOM | 636 | OG | SER | A | 919 | 128.013 | 47.182 | 5.025 | 1.00 | 55.17 | O |
| ATOM | 637 | C | SER | A | 919 | 130.468 | 48.194 | 6.370 | 1.00 | 55.70 | C |
| ATOM | 638 | O | SER | A | 919 | 130.895 | 47.982 | 5.232 | 1.00 | 56.05 | O |
| ATOM | 639 | N | ASN | A | 924 | 124.451 | 48.201 | 4.182 | 1.00 | 45.01 | N |
| ATOM | 640 | CA | ASN | A | 924 | 123.454 | 49.097 | 4.758 | 1.00 | 44.94 | C |
| ATOM | 641 | CB | ASN | A | 924 | 123.138 | 48.706 | 6.211 | 1.00 | 45.73 | C |
| ATOM | 642 | CG | ASN | A | 924 | 124.370 | 48.258 | 6.983 | 1.00 | 48.01 | C |
| ATOM | 643 | OD1 | ASN | A | 924 | 124.546 | 47.069 | 7.253 | 1.00 | 49.18 | O |
| ATOM | 644 | ND2 | ASN | A | 924 | 125.228 | 49.209 | 7.340 | 1.00 | 50.10 | N |
| ATOM | 645 | C | ASN | A | 924 | 123.850 | 50.574 | 4.640 | 1.00 | 43.97 | C |
| ATOM | 646 | O | ASN | A | 924 | 124.466 | 51.148 | 5.545 | 1.00 | 43.97 | O |
| ATOM | 647 | N | LEU | A | 925 | 123.486 | 51.173 | 3.508 | 1.00 | 42.47 | N |
| ATOM | 648 | CA | LEU | A | 925 | 123.870 | 52.542 | 3.181 | 1.00 | 41.19 | C |
| ATOM | 649 | CB | LEU | A | 925 | 123.593 | 52.831 | 1.701 | 1.00 | 41.37 | C |
| ATOM | 650 | CG | LEU | A | 925 | 124.628 | 53.555 | .828 | 1.00 | 41.67 | C |
| ATOM | 651 | CD1 | LEU | A | 925 | 124.018 | 53.863 | −.530 | 1.00 | 40.32 | C |
| ATOM | 652 | CD2 | LEU | A | 925 | 125.185 | 54.827 | 1.459 | 1.00 | 39.09 | C |
| ATOM | 653 | C | LEU | A | 925 | 123.112 | 53.542 | 4.048 | 1.00 | 40.21 | C |
| ATOM | 654 | O | LEU | A | 925 | 121.899 | 53.424 | 4.233 | 1.00 | 39.77 | O |
| ATOM | 655 | N | LYS | A | 926 | 123.839 | 54.519 | 4.580 | 1.00 | 38.89 | N |
| ATOM | 656 | CA | LYS | A | 926 | 123.238 | 55.591 | 5.361 | 1.00 | 38.61 | C |
| ATOM | 657 | CB | LYS | A | 926 | 123.586 | 55.447 | 6.845 | 1.00 | 38.41 | C |
| ATOM | 658 | CG | LYS | A | 926 | 122.857 | 54.300 | 7.545 | 1.00 | 39.75 | C |
| ATOM | 659 | CD | LYS | A | 926 | 123.325 | 54.115 | 8.985 | 1.00 | 40.74 | C |
| ATOM | 660 | CE | LYS | A | 926 | 124.562 | 53.236 | 9.072 | 1.00 | 46.13 | C |
| ATOM | 661 | NZ | LYS | A | 926 | 125.075 | 53.141 | 10.469 | 1.00 | 50.51 | N |
| ATOM | 662 | C | LYS | A | 926 | 123.672 | 56.955 | 4.838 | 1.00 | 37.60 | C |
| ATOM | 663 | O | LYS | A | 926 | 124.845 | 57.164 | 4.525 | 1.00 | 37.37 | O |
| ATOM | 664 | N | LEU | A | 927 | 122.709 | 57.868 | 4.733 | 1.00 | 35.85 | N |
| ATOM | 665 | CA | LEU | A | 927 | 122.970 | 59.245 | 4.322 | 1.00 | 34.69 | C |
| ATOM | 666 | CB | LEU | A | 927 | 121.874 | 59.753 | 3.373 | 1.00 | 34.58 | C |
| ATOM | 667 | CG | LEU | A | 927 | 121.724 | 61.257 | 3.082 | 1.00 | 32.86 | C |
| ATOM | 668 | CD1 | LEU | A | 927 | 122.964 | 61.851 | 2.430 | 1.00 | 34.51 | C |
| ATOM | 669 | CD2 | LEU | A | 927 | 120.504 | 61.498 | 2.208 | 1.00 | 33.96 | C |
| ATOM | 670 | C | LEU | A | 927 | 123.070 | 60.138 | 5.550 | 1.00 | 34.50 | C |
| ATOM | 671 | O | LEU | A | 927 | 122.141 | 60.203 | 6.359 | 1.00 | 34.22 | O |
| ATOM | 672 | N | ILE | A | 928 | 124.204 | 60.820 | 5.676 | 1.00 | 33.86 | N |
| ATOM | 673 | CA | ILE | A | 928 | 124.441 | 61.733 | 6.788 | 1.00 | 33.24 | C |
| ATOM | 674 | CB | ILE | A | 928 | 125.884 | 61.610 | 7.360 | 1.00 | 33.29 | C |
| ATOM | 675 | CG1 | ILE | A | 928 | 126.351 | 60.144 | 7.439 | 1.00 | 34.11 | C |
| ATOM | 676 | CD1 | ILE | A | 928 | 125.537 | 59.228 | 8.354 | 1.00 | 33.83 | C |
| ATOM | 677 | CG2 | ILE | A | 928 | 126.008 | 62.356 | 8.703 | 1.00 | 32.83 | C |
| ATOM | 678 | C | ILE | A | 928 | 124.191 | 63.167 | 6.331 | 1.00 | 32.78 | C |
| ATOM | 679 | O | ILE | A | 928 | 124.838 | 63.659 | 5.401 | 1.00 | 32.38 | O |
| ATOM | 680 | N | MET | A | 929 | 123.237 | 63.819 | 6.988 | 1.00 | 31.82 | N |
| ATOM | 681 | CA | MET | A | 929 | 122.895 | 65.207 | 6.707 | 1.00 | 31.03 | C |
| ATOM | 682 | CB | MET | A | 929 | 121.419 | 65.328 | 6.315 | 1.00 | 30.55 | C |
| ATOM | 683 | CG | MET | A | 929 | 121.067 | 64.755 | 4.946 | 1.00 | 29.98 | C |
| ATOM | 684 | SD | MET | A | 929 | 119.288 | 64.715 | 4.650 | 1.00 | 31.46 | S |
| ATOM | 685 | CE | MET | A | 929 | 118.827 | 63.242 | 5.568 | 1.00 | 28.39 | C |
| ATOM | 686 | C | MET | A | 929 | 123.155 | 66.055 | 7.941 | 1.00 | 30.82 | C |
| ATOM | 687 | O | MET | A | 929 | 123.335 | 65.522 | 9.043 | 1.00 | 30.42 | O |
| ATOM | 688 | N | GLU | A | 930 | 123.171 | 67.374 | 7.758 | 1.00 | 30.53 | N |
| ATOM | 689 | CA | GLU | A | 930 | 123.190 | 68.294 | 8.894 | 1.00 | 29.84 | C |
| ATOM | 690 | CB | GLU | A | 930 | 123.325 | 69.750 | 8.433 | 1.00 | 29.85 | C |
| ATOM | 691 | CG | GLU | A | 930 | 122.160 | 70.260 | 7.584 | 1.00 | 29.67 | C |
| ATOM | 692 | CD | GLU | A | 930 | 122.185 | 71.762 | 7.360 | 1.00 | 30.15 | C |
| ATOM | 693 | OE1 | GLU | A | 930 | 121.596 | 72.218 | 6.359 | 1.00 | 28.08 | O |
| ATOM | 694 | OE2 | GLU | A | 930 | 122.781 | 72.493 | 8.179 | 1.00 | 32.34 | O |
| ATOM | 695 | C | GLU | A | 930 | 121.916 | 68.114 | 9.722 | 1.00 | 29.45 | C |
| ATOM | 696 | O | GLU | A | 930 | 120.848 | 67.805 | 9.179 | 1.00 | 28.61 | O |
| ATOM | 697 | N | TYR | A | 931 | 122.041 | 68.292 | 11.032 | 1.00 | 28.71 | N |
| ATOM | 698 | CA | TYR | A | 931 | 120.885 | 68.256 | 11.918 | 1.00 | 28.30 | C |
| ATOM | 699 | CB | TYR | A | 931 | 121.264 | 67.700 | 13.294 | 1.00 | 27.95 | C |

APPENDIX 1-continued

| | | | | | | | | | | |
|---|---|---|---|---|---|---|---|---|---|---|
| ATOM | 700 | CG | TYR | A | 931 | 120.166 | 67.790 | 14.336 | 1.00 | 27.73 | C |
| ATOM | 701 | CD1 | TYR | A | 931 | 118.991 | 67.047 | 14.213 | 1.00 | 26.74 | C |
| ATOM | 702 | CE1 | TYR | A | 931 | 117.980 | 67.127 | 15.177 | 1.00 | 25.89 | C |
| ATOM | 703 | CZ | TYR | A | 931 | 118.149 | 67.949 | 16.279 | 1.00 | 28.28 | C |
| ATOM | 704 | OH | TYR | A | 931 | 117.157 | 68.033 | 17.232 | 1.00 | 29.90 | O |
| ATOM | 705 | CE2 | TYR | A | 931 | 119.307 | 68.693 | 16.426 | 1.00 | 28.43 | C |
| ATOM | 706 | CD2 | TYR | A | 931 | 120.310 | 68.609 | 15.455 | 1.00 | 29.30 | C |
| ATOM | 707 | C | TYR | A | 931 | 120.301 | 69.654 | 12.044 | 1.00 | 27.95 | C |
| ATOM | 708 | O | TYR | A | 931 | 120.990 | 70.595 | 12.451 | 1.00 | 27.88 | O |
| ATOM | 709 | N | LEU | A | 932 | 119.030 | 69.780 | 11.676 | 1.00 | 27.44 | N |
| ATOM | 710 | CA | LEU | A | 932 | 118.318 | 71.047 | 11.770 | 1.00 | 26.02 | C |
| ATOM | 711 | CB | LEU | A | 932 | 117.601 | 71.370 | 10.456 | 1.00 | 26.33 | C |
| ATOM | 712 | CG | LEU | A | 932 | 118.543 | 71.583 | 9.257 | 1.00 | 27.14 | C |
| ATOM | 713 | CD1 | LEU | A | 932 | 117.774 | 71.812 | 7.971 | 1.00 | 28.70 | C |
| ATOM | 714 | CD2 | LEU | A | 932 | 119.515 | 72.734 | 9.503 | 1.00 | 29.23 | C |
| ATOM | 715 | C | LEU | A | 932 | 117.375 | 71.013 | 12.971 | 1.00 | 25.40 | C |
| ATOM | 716 | O | LEU | A | 932 | 116.326 | 70.365 | 12.929 | 1.00 | 23.88 | O |
| ATOM | 717 | N | PRO | A | 933 | 117.755 | 71.724 | 14.049 | 1.00 | 25.72 | N |
| ATOM | 718 | CA | PRO | A | 933 | 117.218 | 71.507 | 15.396 | 1.00 | 25.54 | C |
| ATOM | 719 | CB | PRO | A | 933 | 118.093 | 72.413 | 16.271 | 1.00 | 25.61 | C |
| ATOM | 720 | CG | PRO | A | 933 | 118.554 | 73.488 | 15.355 | 1.00 | 26.58 | C |
| ATOM | 721 | CD | PRO | A | 933 | 118.744 | 72.820 | 14.023 | 1.00 | 26.53 | C |
| ATOM | 722 | C | PRO | A | 933 | 115.734 | 71.839 | 15.586 | 1.00 | 25.50 | C |
| ATOM | 723 | O | PRO | A | 933 | 115.131 | 71.380 | 16.555 | 1.00 | 25.50 | O |
| ATOM | 724 | N | TYR | A | 934 | 115.153 | 72.614 | 14.675 | 1.00 | 25.38 | N |
| ATOM | 725 | CA | TYR | A | 934 | 113.747 | 72.994 | 14.799 | 1.00 | 25.56 | C |
| ATOM | 726 | CB | TYR | A | 934 | 113.534 | 74.455 | 14.380 | 1.00 | 25.45 | C |
| ATOM | 727 | CG | TYR | A | 934 | 114.106 | 75.449 | 15.371 | 1.00 | 28.03 | C |
| ATOM | 728 | CD1 | TYR | A | 934 | 115.429 | 75.884 | 15.274 | 1.00 | 25.72 | C |
| ATOM | 729 | CE1 | TYR | A | 934 | 115.962 | 76.788 | 16.197 | 1.00 | 28.01 | C |
| ATOM | 730 | CZ | TYR | A | 934 | 115.163 | 77.263 | 17.225 | 1.00 | 28.25 | C |
| ATOM | 731 | OH | TYR | A | 934 | 115.673 | 78.156 | 18.141 | 1.00 | 28.79 | O |
| ATOM | 732 | CE2 | TYR | A | 934 | 113.847 | 76.842 | 17.342 | 1.00 | 28.73 | C |
| ATOM | 733 | CD2 | TYR | A | 934 | 113.328 | 75.938 | 16.421 | 1.00 | 28.16 | C |
| ATOM | 734 | C | TYR | A | 934 | 112.779 | 72.047 | 14.082 | 1.00 | 25.81 | C |
| ATOM | 735 | O | TYR | A | 934 | 111.561 | 72.213 | 14.176 | 1.00 | 26.83 | O |
| ATOM | 736 | N | GLY | A | 935 | 113.322 | 71.051 | 13.382 | 1.00 | 25.05 | N |
| ATOM | 737 | CA | GLY | A | 935 | 112.514 | 70.007 | 12.749 | 1.00 | 24.83 | C |
| ATOM | 738 | C | GLY | A | 935 | 111.764 | 70.452 | 11.510 | 1.00 | 24.95 | C |
| ATOM | 739 | O | GLY | A | 935 | 112.117 | 71.455 | 10.892 | 1.00 | 24.16 | O |
| ATOM | 740 | N | SER | A | 936 | 110.727 | 69.700 | 11.142 | 1.00 | 25.76 | N |
| ATOM | 741 | CA | SER | A | 936 | 109.936 | 70.025 | 9.952 | 1.00 | 27.36 | C |
| ATOM | 742 | CB | SER | A | 936 | 109.044 | 68.852 | 9.532 | 1.00 | 28.09 | C |
| ATOM | 743 | OG | SER | A | 936 | 108.010 | 68.616 | 10.475 | 1.00 | 31.82 | O |
| ATOM | 744 | C | SER | A | 936 | 109.092 | 71.279 | 10.165 | 1.00 | 27.85 | C |
| ATOM | 745 | O | SER | A | 936 | 108.658 | 71.559 | 11.284 | 1.00 | 27.50 | O |
| ATOM | 746 | N | LEU | A | 937 | 108.876 | 72.025 | 9.083 | 1.00 | 29.07 | N |
| ATOM | 747 | CA | LEU | A | 937 | 108.048 | 73.232 | 9.100 | 1.00 | 30.91 | C |
| ATOM | 748 | CB | LEU | A | 937 | 108.047 | 73.900 | 7.718 | 1.00 | 30.72 | C |
| ATOM | 749 | CG | LEU | A | 937 | 108.216 | 75.419 | 7.578 | 1.00 | 33.80 | C |
| ATOM | 750 | CD1 | LEU | A | 937 | 107.896 | 75.838 | 6.142 | 1.00 | 31.43 | C |
| ATOM | 751 | CD2 | LEU | A | 937 | 107.387 | 76.231 | 8.574 | 1.00 | 28.57 | C |
| ATOM | 752 | C | LEU | A | 937 | 106.616 | 72.900 | 9.507 | 1.00 | 31.68 | C |
| ATOM | 753 | O | LEU | A | 937 | 105.964 | 73.688 | 10.194 | 1.00 | 32.19 | O |
| ATOM | 754 | N | ARG | A | 938 | 106.141 | 71.734 | 9.072 | 1.00 | 32.69 | N |
| ATOM | 755 | CA | ARG | A | 938 | 104.807 | 71.238 | 9.405 | 1.00 | 34.55 | C |
| ATOM | 756 | CB | ARG | A | 938 | 104.610 | 69.843 | 8.809 | 1.00 | 35.21 | C |
| ATOM | 757 | CG | ARG | A | 938 | 103.171 | 69.503 | 8.466 | 1.00 | 40.23 | C |
| ATOM | 758 | CD | ARG | A | 938 | 102.576 | 68.474 | 9.397 | 1.00 | 49.74 | C |
| ATOM | 759 | NE | ARG | A | 938 | 101.214 | 68.126 | 8.991 | 1.00 | 57.01 | N |
| ATOM | 760 | CZ | ARG | A | 938 | 100.903 | 67.186 | 8.102 | 1.00 | 60.49 | C |
| ATOM | 761 | NH1 | ARG | A | 938 | 101.855 | 66.475 | 7.508 | 1.00 | 62.24 | N |
| ATOM | 762 | NH2 | ARG | A | 938 | 99.631 | 66.955 | 7.804 | 1.00 | 62.16 | N |
| ATOM | 763 | C | ARG | A | 938 | 104.581 | 71.208 | 10.919 | 1.00 | 35.11 | C |
| ATOM | 764 | O | ARG | A | 938 | 103.601 | 71.773 | 11.419 | 1.00 | 34.41 | O |
| ATOM | 765 | N | ASP | A | 939 | 105.500 | 70.560 | 11.634 | 1.00 | 35.11 | N |
| ATOM | 766 | CA | ASP | A | 939 | 105.423 | 70.442 | 13.090 | 1.00 | 35.54 | C |
| ATOM | 767 | CB | ASP | A | 939 | 106.358 | 69.337 | 13.594 | 1.00 | 36.45 | C |
| ATOM | 768 | CG | ASP | A | 939 | 105.955 | 67.955 | 13.108 | 1.00 | 39.22 | C |
| ATOM | 769 | OD1 | ASP | A | 939 | 106.861 | 67.133 | 12.855 | 1.00 | 45.13 | O |
| ATOM | 770 | OD2 | ASP | A | 939 | 104.741 | 67.682 | 12.979 | 1.00 | 43.88 | O |
| ATOM | 771 | C | ASP | A | 939 | 105.745 | 71.754 | 13.797 | 1.00 | 35.24 | C |
| ATOM | 772 | O | ASP | A | 939 | 105.114 | 72.088 | 14.796 | 1.00 | 35.10 | O |
| ATOM | 773 | N | TYR | A | 940 | 106.729 | 72.485 | 13.276 | 1.00 | 35.14 | N |
| ATOM | 774 | CA | TYR | A | 940 | 107.149 | 73.765 | 13.851 | 1.00 | 35.95 | C |
| ATOM | 775 | CB | TYR | A | 940 | 108.398 | 74.287 | 13.132 | 1.00 | 36.35 | C |
| ATOM | 776 | CG | TYR | A | 940 | 108.880 | 75.652 | 13.582 | 1.00 | 37.79 | C |
| ATOM | 777 | CD1 | TYR | A | 940 | 109.479 | 75.829 | 14.832 | 1.00 | 37.90 | C |
| ATOM | 778 | CE1 | TYR | A | 940 | 109.930 | 77.083 | 15.243 | 1.00 | 39.27 | C |

APPENDIX 1-continued

| ATOM | 779 | CZ | TYR | A | 940 | 109.788 | 78.170 | 14.392 | 1.00 | 38.66 | C |
| ATOM | 780 | OH | TYR | A | 940 | 110.232 | 79.410 | 14.784 | 1.00 | 39.87 | O |
| ATOM | 781 | CE2 | TYR | A | 940 | 109.205 | 78.018 | 13.144 | 1.00 | 38.04 | C |
| ATOM | 782 | CD2 | TYR | A | 940 | 108.758 | 76.762 | 12.746 | 1.00 | 37.83 | C |
| ATOM | 783 | C | TYR | A | 940 | 106.029 | 74.807 | 13.815 | 1.00 | 36.51 | C |
| ATOM | 784 | O | TYR | A | 940 | 105.791 | 75.502 | 14.806 | 1.00 | 35.35 | O |
| ATOM | 785 | N | LEU | A | 941 | 105.347 | 74.899 | 12.675 | 1.00 | 37.38 | N |
| ATOM | 786 | CA | LEU | A | 941 | 104.258 | 75.858 | 12.485 | 1.00 | 39.11 | C |
| ATOM | 787 | CB | LEU | A | 941 | 103.857 | 75.925 | 11.005 | 1.00 | 38.67 | C |
| ATOM | 788 | CG | LEU | A | 941 | 102.808 | 76.950 | 10.561 | 1.00 | 39.97 | C |
| ATOM | 789 | CD1 | LEU | A | 941 | 103.278 | 78.370 | 10.824 | 1.00 | 40.52 | C |
| ATOM | 790 | CD2 | LEU | A | 941 | 102.483 | 76.762 | 9.088 | 1.00 | 39.37 | C |
| ATOM | 791 | C | LEU | A | 941 | 103.042 | 75.533 | 13.353 | 1.00 | 40.05 | C |
| ATOM | 792 | O | LEU | A | 941 | 102.443 | 76.428 | 13.948 | 1.00 | 40.33 | O |
| ATOM | 793 | N | GLN | A | 942 | 102.692 | 74.251 | 13.414 | 1.00 | 41.88 | N |
| ATOM | 794 | CA | GLN | A | 942 | 101.548 | 73.775 | 14.188 | 1.00 | 44.30 | C |
| ATOM | 795 | CB | GLN | A | 942 | 101.314 | 72.286 | 13.911 | 1.00 | 44.15 | C |
| ATOM | 796 | CG | GLN | A | 942 | 99.960 | 71.754 | 14.365 | 1.00 | 46.64 | C |
| ATOM | 797 | CD | GLN | A | 942 | 99.728 | 70.310 | 13.950 | 1.00 | 46.74 | C |
| ATOM | 798 | OE1 | GLN | A | 942 | 100.578 | 69.443 | 14.167 | 1.00 | 51.58 | O |
| ATOM | 799 | NE2 | GLN | A | 942 | 98.567 | 70.044 | 13.356 | 1.00 | 49.88 | N |
| ATOM | 800 | C | GLN | A | 942 | 101.726 | 74.016 | 15.688 | 1.00 | 45.20 | C |
| ATOM | 801 | O | GLN | A | 942 | 100.785 | 74.425 | 16.372 | 1.00 | 45.49 | O |
| ATOM | 802 | N | LYS | A | 943 | 102.938 | 73.772 | 16.186 | 1.00 | 45.96 | N |
| ATOM | 803 | CA | LYS | A | 943 | 103.239 | 73.891 | 17.613 | 1.00 | 46.53 | C |
| ATOM | 804 | CB | LYS | A | 943 | 104.451 | 73.030 | 17.985 | 1.00 | 47.01 | C |
| ATOM | 805 | CG | LYS | A | 943 | 104.215 | 71.528 | 17.920 | 1.00 | 49.44 | C |
| ATOM | 806 | CD | LYS | A | 943 | 105.525 | 70.773 | 18.110 | 1.00 | 52.34 | C |
| ATOM | 807 | CE | LYS | A | 943 | 105.373 | 69.292 | 17.802 | 1.00 | 53.33 | C |
| ATOM | 808 | NZ | LYS | A | 943 | 106.681 | 68.581 | 17.888 | 1.00 | 54.18 | N |
| ATOM | 809 | C | LYS | A | 943 | 103.478 | 75.327 | 18.073 | 1.00 | 46.45 | C |
| ATOM | 810 | O | LYS | A | 943 | 103.295 | 75.639 | 19.252 | 1.00 | 46.80 | O |
| ATOM | 811 | N | HIS | A | 944 | 103.885 | 76.198 | 17.151 | 1.00 | 46.11 | N |
| ATOM | 812 | CA | HIS | A | 944 | 104.277 | 77.565 | 17.512 | 1.00 | 46.14 | C |
| ATOM | 813 | CB | HIS | A | 944 | 105.803 | 77.699 | 17.470 | 1.00 | 46.79 | C |
| ATOM | 814 | CG | HIS | A | 944 | 106.515 | 76.665 | 18.285 | 1.00 | 48.39 | C |
| ATOM | 815 | ND1 | HIS | A | 944 | 106.958 | 75.474 | 17.752 | 1.00 | 49.08 | N |
| ATOM | 816 | CE1 | HIS | A | 944 | 107.533 | 74.755 | 18.700 | 1.00 | 49.95 | C |
| ATOM | 817 | NE2 | HIS | A | 944 | 107.469 | 75.433 | 19.832 | 1.00 | 50.89 | N |
| ATOM | 818 | CD2 | HIS | A | 944 | 106.834 | 76.629 | 19.601 | 1.00 | 49.68 | C |
| ATOM | 819 | C | HIS | A | 944 | 103.597 | 78.644 | 16.665 | 1.00 | 45.64 | C |
| ATOM | 820 | O | HIS | A | 944 | 104.197 | 79.676 | 16.348 | 1.00 | 45.42 | O |
| ATOM | 821 | N | LYS | A | 945 | 102.329 | 78.405 | 16.337 | 1.00 | 45.50 | N |
| ATOM | 822 | CA | LYS | A | 945 | 101.527 | 79.296 | 15.487 | 1.00 | 45.39 | C |
| ATOM | 823 | CB | LYS | A | 945 | 100.156 | 78.667 | 15.205 | 1.00 | 44.96 | C |
| ATOM | 824 | CG | LYS | A | 945 | 99.360 | 78.295 | 16.448 | 1.00 | 45.34 | C |
| ATOM | 825 | CD | LYS | A | 945 | 98.147 | 77.450 | 16.106 | 1.00 | 46.37 | C |
| ATOM | 826 | CE | LYS | A | 945 | 97.463 | 76.949 | 17.372 | 1.00 | 48.34 | C |
| ATOM | 827 | NZ | LYS | A | 945 | 96.286 | 76.087 | 17.071 | 1.00 | 50.68 | N |
| ATOM | 828 | C | LYS | A | 945 | 101.359 | 80.730 | 16.011 | 1.00 | 45.64 | C |
| ATOM | 829 | O | LYS | A | 945 | 101.103 | 81.648 | 15.228 | 1.00 | 45.43 | O |
| ATOM | 830 | N | GLU | A | 946 | 101.503 | 80.918 | 17.324 | 1.00 | 45.94 | N |
| ATOM | 831 | CA | GLU | A | 946 | 101.391 | 82.248 | 17.938 | 1.00 | 46.43 | C |
| ATOM | 832 | CB | GLU | A | 946 | 101.220 | 82.156 | 19.464 | 1.00 | 46.76 | C |
| ATOM | 833 | CG | GLU | A | 946 | 100.462 | 80.936 | 19.980 | 1.00 | 48.88 | C |
| ATOM | 834 | CD | GLU | A | 946 | 101.387 | 79.815 | 20.433 | 1.00 | 51.94 | C |
| ATOM | 835 | OE1 | GLU | A | 946 | 102.192 | 79.325 | 19.610 | 1.00 | 51.20 | O |
| ATOM | 836 | OE2 | GLU | A | 946 | 101.305 | 79.424 | 21.619 | 1.00 | 53.63 | O |
| ATOM | 837 | C | GLU | A | 946 | 102.601 | 83.127 | 17.619 | 1.00 | 46.31 | C |
| ATOM | 838 | O | GLU | A | 946 | 102.491 | 84.354 | 17.573 | 1.00 | 46.54 | O |
| ATOM | 839 | N | ARG | A | 947 | 103.750 | 82.487 | 17.410 | 1.00 | 46.10 | N |
| ATOM | 840 | CA | ARG | A | 947 | 105.012 | 83.175 | 17.142 | 1.00 | 46.55 | C |
| ATOM | 841 | CB | ARG | A | 947 | 106.187 | 82.281 | 17.564 | 1.00 | 46.75 | C |
| ATOM | 842 | CG | ARG | A | 947 | 107.578 | 82.889 | 17.367 | 1.00 | 49.10 | C |
| ATOM | 843 | CD | ARG | A | 947 | 108.682 | 81.982 | 17.908 | 1.00 | 48.21 | C |
| ATOM | 844 | NE | ARG | A | 947 | 108.858 | 82.123 | 19.354 | 1.00 | 51.41 | N |
| ATOM | 845 | CZ | ARG | A | 947 | 108.343 | 81.303 | 20.266 | 1.00 | 52.39 | C |
| ATOM | 846 | NH1 | ARG | A | 947 | 107.614 | 80.256 | 19.898 | 1.00 | 53.12 | N |
| ATOM | 847 | NH2 | ARG | A | 947 | 108.564 | 81.527 | 21.555 | 1.00 | 52.03 | N |
| ATOM | 848 | C | ARG | A | 947 | 105.157 | 83.579 | 15.672 | 1.00 | 45.38 | C |
| ATOM | 849 | O | ARG | A | 947 | 105.828 | 84.565 | 15.354 | 1.00 | 45.90 | O |
| ATOM | 850 | N | ILE | A | 948 | 104.519 | 82.820 | 14.785 | 1.00 | 43.70 | N |
| ATOM | 851 | CA | ILE | A | 948 | 104.714 | 82.974 | 13.345 | 1.00 | 41.81 | C |
| ATOM | 852 | CB | ILE | A | 948 | 104.891 | 81.593 | 12.661 | 1.00 | 41.78 | C |
| ATOM | 853 | CG1 | ILE | A | 948 | 105.976 | 80.781 | 13.381 | 1.00 | 41.26 | C |
| ATOM | 854 | CD1 | ILE | A | 948 | 105.766 | 79.284 | 13.347 | 1.00 | 39.98 | C |
| ATOM | 855 | CG2 | ILE | A | 948 | 105.234 | 81.760 | 11.182 | 1.00 | 40.72 | C |
| ATOM | 856 | C | ILE | A | 948 | 103.573 | 83.763 | 12.693 | 1.00 | 40.88 | C |
| ATOM | 857 | O | ILE | A | 948 | 102.435 | 83.295 | 12.631 | 1.00 | 40.95 | O |

APPENDIX 1-continued

| | | | | | | | | | | | |
|---|---|---|---|---|---|---|---|---|---|---|---|
| ATOM | 858 | N | ASP | A | 949 | 103.887 | 84.964 | 12.214 | 1.00 | 39.80 | N |
| ATOM | 859 | CA | ASP | A | 949 | 102.899 | 85.794 | 11.523 | 1.00 | 39.66 | C |
| ATOM | 860 | CB | ASP | A | 949 | 103.034 | 87.277 | 11.919 | 1.00 | 39.99 | C |
| ATOM | 861 | CG | ASP | A | 949 | 104.386 | 87.880 | 11.551 | 1.00 | 42.04 | C |
| ATOM | 862 | OD1 | ASP | A | 949 | 104.531 | 89.112 | 11.698 | 1.00 | 44.44 | O |
| ATOM | 863 | OD2 | ASP | A | 949 | 105.302 | 87.145 | 11.126 | 1.00 | 44.68 | O |
| ATOM | 864 | C | ASP | A | 949 | 102.957 | 85.607 | 10.004 | 1.00 | 38.77 | C |
| ATOM | 865 | O | ASP | A | 949 | 103.789 | 84.854 | 9.494 | 1.00 | 37.40 | O |
| ATOM | 866 | N | HIS | A | 950 | 102.067 | 86.297 | 9.294 | 1.00 | 38.90 | N |
| ATOM | 867 | CA | HIS | A | 950 | 101.977 | 86.203 | 7.836 | 1.00 | 38.95 | C |
| ATOM | 868 | CB | HIS | A | 950 | 100.765 | 86.985 | 7.331 | 1.00 | 39.18 | C |
| ATOM | 869 | CG | HIS | A | 950 | 99.474 | 86.237 | 7.450 | 1.00 | 38.66 | C |
| ATOM | 870 | ND1 | HIS | A | 950 | 98.299 | 86.689 | 6.894 | 1.00 | 39.10 | N |
| ATOM | 871 | CE1 | HIS | A | 950 | 97.331 | 85.829 | 7.154 | 1.00 | 39.42 | C |
| ATOM | 872 | NE2 | HIS | A | 950 | 97.840 | 84.826 | 7.847 | 1.00 | 40.22 | N |
| ATOM | 873 | CD2 | HIS | A | 950 | 99.179 | 85.056 | 8.045 | 1.00 | 39.34 | C |
| ATOM | 874 | C | HIS | A | 950 | 103.249 | 86.653 | 7.123 | 1.00 | 39.05 | C |
| ATOM | 875 | O | HIS | A | 950 | 103.614 | 86.091 | 6.087 | 1.00 | 39.16 | O |
| ATOM | 876 | N | ILE | A | 951 | 103.916 | 87.660 | 7.687 | 1.00 | 38.58 | N |
| ATOM | 877 | CA | ILE | A | 951 | 105.191 | 88.154 | 7.160 | 1.00 | 38.85 | C |
| ATOM | 878 | CB | ILE | A | 951 | 105.679 | 89.417 | 7.927 | 1.00 | 39.05 | C |
| ATOM | 879 | CG1 | ILE | A | 951 | 104.609 | 90.518 | 7.884 | 1.00 | 40.45 | C |
| ATOM | 880 | CD1 | ILE | A | 951 | 104.848 | 91.677 | 8.846 | 1.00 | 40.35 | C |
| ATOM | 881 | CG2 | ILE | A | 951 | 106.997 | 89.936 | 7.347 | 1.00 | 39.09 | C |
| ATOM | 882 | C | ILE | A | 951 | 106.257 | 87.050 | 7.184 | 1.00 | 37.74 | C |
| ATOM | 883 | O | ILE | A | 951 | 107.008 | 86.882 | 6.219 | 1.00 | 37.23 | O |
| ATOM | 884 | N | LYS | A | 952 | 106.306 | 86.295 | 8.281 | 1.00 | 36.79 | N |
| ATOM | 885 | CA | LYS | A | 952 | 107.221 | 85.158 | 8.407 | 1.00 | 36.23 | C |
| ATOM | 886 | CB | LYS | A | 952 | 107.251 | 84.648 | 9.848 | 1.00 | 36.84 | C |
| ATOM | 887 | CG | LYS | A | 952 | 108.202 | 85.401 | 10.758 | 1.00 | 40.89 | C |
| ATOM | 888 | CD | LYS | A | 952 | 109.598 | 84.786 | 10.735 | 1.00 | 44.84 | C |
| ATOM | 889 | CE | LYS | A | 952 | 110.474 | 85.363 | 11.841 | 1.00 | 48.83 | C |
| ATOM | 890 | NZ | LYS | A | 952 | 109.927 | 85.124 | 13.214 | 1.00 | 50.72 | N |
| ATOM | 891 | C | LYS | A | 952 | 106.868 | 84.015 | 7.453 | 1.00 | 34.83 | C |
| ATOM | 892 | O | LYS | A | 952 | 107.761 | 83.362 | 6.904 | 1.00 | 33.70 | O |
| ATOM | 893 | N | LEU | A | 953 | 105.569 | 83.780 | 7.262 | 1.00 | 33.71 | N |
| ATOM | 894 | CA | LEU | A | 953 | 105.098 | 82.758 | 6.323 | 1.00 | 32.83 | C |
| ATOM | 895 | CB | LEU | A | 953 | 103.571 | 82.625 | 6.361 | 1.00 | 32.70 | C |
| ATOM | 896 | CG | LEU | A | 953 | 102.882 | 82.056 | 7.608 | 1.00 | 32.62 | C |
| ATOM | 897 | CD1 | LEU | A | 953 | 101.389 | 81.929 | 7.354 | 1.00 | 33.40 | C |
| ATOM | 898 | CD2 | LEU | A | 953 | 103.461 | 80.709 | 8.017 | 1.00 | 33.22 | C |
| ATOM | 899 | C | LEU | A | 953 | 105.559 | 83.055 | 4.900 | 1.00 | 32.52 | C |
| ATOM | 900 | O | LEU | A | 953 | 105.892 | 82.141 | 4.144 | 1.00 | 31.63 | O |
| ATOM | 901 | N | LEU | A | 954 | 105.584 | 84.337 | 4.545 | 1.00 | 32.22 | N |
| ATOM | 902 | CA | LEU | A | 954 | 106.011 | 84.749 | 3.211 | 1.00 | 32.11 | C |
| ATOM | 903 | CB | LEU | A | 954 | 105.449 | 86.130 | 2.858 | 1.00 | 32.58 | C |
| ATOM | 904 | CG | LEU | A | 954 | 103.926 | 86.234 | 2.717 | 1.00 | 32.68 | C |
| ATOM | 905 | CD1 | LEU | A | 954 | 103.524 | 87.660 | 2.379 | 1.00 | 33.85 | C |
| ATOM | 906 | CD2 | LEU | A | 954 | 103.381 | 85.257 | 1.679 | 1.00 | 31.73 | C |
| ATOM | 907 | C | LEU | A | 954 | 107.531 | 84.709 | 3.065 | 1.00 | 31.77 | C |
| ATOM | 908 | O | LEU | A | 954 | 108.046 | 84.479 | 1.967 | 1.00 | 31.30 | O |
| ATOM | 909 | N | GLN | A | 955 | 108.240 | 84.933 | 4.171 | 1.00 | 31.70 | N |
| ATOM | 910 | CA | GLN | A | 955 | 109.690 | 84.755 | 4.195 | 1.00 | 32.66 | C |
| ATOM | 911 | CB | GLN | A | 955 | 110.293 | 85.205 | 5.529 | 1.00 | 32.84 | C |
| ATOM | 912 | CG | GLN | A | 955 | 111.826 | 85.211 | 5.529 | 1.00 | 34.20 | C |
| ATOM | 913 | CD | GLN | A | 955 | 112.447 | 85.543 | 6.879 | 1.00 | 34.89 | C |
| ATOM | 914 | OE1 | GLN | A | 955 | 113.652 | 85.789 | 6.967 | 1.00 | 37.99 | O |
| ATOM | 915 | NE2 | GLN | A | 955 | 111.636 | 85.547 | 7.933 | 1.00 | 37.94 | N |
| ATOM | 916 | C | GLN | A | 955 | 110.052 | 83.294 | 3.900 | 1.00 | 31.30 | C |
| ATOM | 917 | O | GLN | A | 955 | 110.925 | 83.027 | 3.072 | 1.00 | 30.94 | O |
| ATOM | 918 | N | TYR | A | 956 | 109.367 | 82.363 | 4.567 | 1.00 | 30.32 | N |
| ATOM | 919 | CA | TYR | A | 956 | 109.557 | 80.932 | 4.319 | 1.00 | 29.76 | C |
| ATOM | 920 | CB | TYR | A | 956 | 108.727 | 80.071 | 5.283 | 1.00 | 29.80 | C |
| ATOM | 921 | CG | TYR | A | 956 | 108.993 | 80.273 | 6.767 | 1.00 | 29.06 | C |
| ATOM | 922 | CD1 | TYR | A | 956 | 108.008 | 79.973 | 7.706 | 1.00 | 30.03 | C |
| ATOM | 923 | CE1 | TYR | A | 956 | 108.231 | 80.145 | 9.072 | 1.00 | 32.24 | C |
| ATOM | 924 | CZ | TYR | A | 956 | 109.452 | 80.628 | 9.512 | 1.00 | 30.99 | C |
| ATOM | 925 | OH | TYR | A | 956 | 109.665 | 80.802 | 10.863 | 1.00 | 31.56 | O |
| ATOM | 926 | CE2 | TYR | A | 956 | 110.451 | 80.938 | 8.601 | 1.00 | 31.36 | C |
| ATOM | 927 | CD2 | TYR | A | 956 | 110.217 | 80.759 | 7.233 | 1.00 | 28.69 | C |
| ATOM | 928 | C | TYR | A | 956 | 109.188 | 80.580 | 2.882 | 1.00 | 29.79 | C |
| ATOM | 929 | O | TYR | A | 956 | 109.895 | 79.814 | 2.224 | 1.00 | 28.98 | O |
| ATOM | 930 | N | THR | A | 957 | 108.082 | 81.151 | 2.408 | 1.00 | 29.32 | N |
| ATOM | 931 | CA | THR | A | 957 | 107.579 | 80.917 | 1.051 | 1.00 | 29.91 | C |
| ATOM | 932 | CB | THR | A | 957 | 106.254 | 81.676 | .819 | 1.00 | 29.44 | C |
| ATOM | 933 | OG1 | THR | A | 957 | 105.271 | 81.201 | 1.746 | 1.00 | 30.16 | O |
| ATOM | 934 | CG2 | THR | A | 957 | 105.734 | 81.473 | -.604 | 1.00 | 30.09 | C |
| ATOM | 935 | C | THR | A | 957 | 108.616 | 81.311 | .001 | 1.00 | 29.63 | C |
| ATOM | 936 | O | THR | A | 957 | 108.867 | 80.564 | -.949 | 1.00 | 30.57 | O |

APPENDIX 1-continued

| ATOM | 937 | N | SER | A | 958 | 109.224 | 82.478 | .196 | 1.00 | 29.10 | N |
|---|---|---|---|---|---|---|---|---|---|---|---|
| ATOM | 938 | CA | SER | A | 958 | 110.272 | 82.986 | −.688 | 1.00 | 29.58 | C |
| ATOM | 939 | CB | SER | A | 958 | 110.695 | 84.387 | −.242 | 1.00 | 29.90 | C |
| ATOM | 940 | OG | SER | A | 958 | 111.628 | 84.952 | −1.143 | 1.00 | 33.53 | O |
| ATOM | 941 | C | SER | A | 958 | 111.482 | 82.051 | −.721 | 1.00 | 28.94 | C |
| ATOM | 942 | O | SER | A | 958 | 112.016 | 81.754 | −1.792 | 1.00 | 28.50 | O |
| ATOM | 943 | N | GLN | A | 959 | 111.899 | 81.588 | .456 | 1.00 | 28.08 | N |
| ATOM | 944 | CA | GLN | A | 959 | 113.033 | 80.670 | .586 | 1.00 | 27.62 | C |
| ATOM | 945 | CB | GLN | A | 959 | 113.377 | 80.460 | 2.064 | 1.00 | 27.67 | C |
| ATOM | 946 | CG | GLN | A | 959 | 114.004 | 81.697 | 2.716 | 1.00 | 25.86 | C |
| ATOM | 947 | CD | GLN | A | 959 | 114.034 | 81.632 | 4.230 | 1.00 | 27.78 | C |
| ATOM | 948 | OE1 | GLN | A | 959 | 113.602 | 80.650 | 4.836 | 1.00 | 28.80 | O |
| ATOM | 949 | NE2 | GLN | A | 959 | 114.540 | 82.690 | 4.852 | 1.00 | 23.55 | N |
| ATOM | 950 | C | GLN | A | 959 | 112.786 | 79.330 | −.110 | 1.00 | 28.09 | C |
| ATOM | 951 | O | GLN | A | 959 | 113.692 | 78.771 | −.731 | 1.00 | 28.11 | O |
| ATOM | 952 | N | ILE | A | 960 | 111.557 | 78.828 | −.001 | 1.00 | 28.07 | N |
| ATOM | 953 | CA | ILE | A | 960 | 111.143 | 77.599 | −.682 | 1.00 | 28.36 | C |
| ATOM | 954 | CB | ILE | A | 960 | 109.733 | 77.136 | −.216 | 1.00 | 27.62 | C |
| ATOM | 955 | CG1 | ILE | A | 960 | 109.781 | 76.711 | 1.257 | 1.00 | 27.77 | C |
| ATOM | 956 | CD1 | ILE | A | 960 | 108.442 | 76.776 | 1.990 | 1.00 | 25.50 | C |
| ATOM | 957 | CG2 | ILE | A | 960 | 109.211 | 75.983 | −1.089 | 1.00 | 29.20 | C |
| ATOM | 958 | C | ILE | A | 960 | 111.211 | 77.768 | −2.208 | 1.00 | 28.53 | C |
| ATOM | 959 | O | ILE | A | 960 | 111.724 | 76.891 | −2.910 | 1.00 | 27.98 | O |
| ATOM | 960 | N | CYS | A | 961 | 110.715 | 78.903 | −2.704 | 1.00 | 28.99 | N |
| ATOM | 961 | CA | CYS | A | 961 | 110.765 | 79.223 | −4.135 | 1.00 | 29.85 | C |
| ATOM | 962 | CB | CYS | A | 961 | 110.054 | 80.546 | −4.425 | 1.00 | 30.74 | C |
| ATOM | 963 | SG | CYS | A | 961 | 108.270 | 80.453 | −4.336 | 1.00 | 36.71 | S |
| ATOM | 964 | C | CYS | A | 961 | 112.189 | 79.301 | −4.666 | 1.00 | 29.47 | C |
| ATOM | 965 | O | CYS | A | 961 | 112.468 | 78.835 | −5.770 | 1.00 | 29.66 | O |
| ATOM | 966 | N | LYS | A | 962 | 113.080 | 79.903 | −3.883 | 1.00 | 29.70 | N |
| ATOM | 967 | CA | LYS | A | 962 | 114.473 | 80.064 | −4.293 | 1.00 | 30.04 | C |
| ATOM | 968 | CB | LYS | A | 962 | 115.187 | 81.099 | −3.420 | 1.00 | 30.28 | C |
| ATOM | 969 | CG | LYS | A | 962 | 114.705 | 82.520 | −3.690 | 1.00 | 33.95 | C |
| ATOM | 970 | CD | LYS | A | 962 | 115.313 | 83.537 | −2.747 | 1.00 | 38.42 | C |
| ATOM | 971 | CE | LYS | A | 962 | 114.655 | 84.897 | −2.946 | 1.00 | 41.54 | C |
| ATOM | 972 | NZ | LYS | A | 962 | 115.162 | 85.918 | −1.988 | 1.00 | 44.66 | N |
| ATOM | 973 | C | LYS | A | 962 | 115.205 | 78.726 | −4.309 | 1.00 | 29.60 | C |
| ATOM | 974 | O | LYS | A | 962 | 116.016 | 78.471 | −5.199 | 1.00 | 29.70 | O |
| ATOM | 975 | N | GLY | A | 963 | 114.895 | 77.869 | −3.337 | 1.00 | 29.07 | N |
| ATOM | 976 | CA | GLY | A | 963 | 115.408 | 76.500 | −3.322 | 1.00 | 28.26 | C |
| ATOM | 977 | C | GLY | A | 963 | 114.923 | 75.701 | −4.521 | 1.00 | 28.26 | C |
| ATOM | 978 | O | GLY | A | 963 | 115.693 | 74.954 | −5.129 | 1.00 | 27.78 | O |
| ATOM | 979 | N | MET | A | 964 | 113.647 | 75.872 | −4.863 | 1.00 | 27.99 | N |
| ATOM | 980 | CA | MET | A | 964 | 113.042 | 75.182 | −6.006 | 1.00 | 28.69 | C |
| ATOM | 981 | CB | MET | A | 964 | 111.513 | 75.278 | −5.956 | 1.00 | 28.85 | C |
| ATOM | 982 | CG | MET | A | 964 | 110.865 | 74.354 | −4.924 | 1.00 | 30.69 | C |
| ATOM | 983 | SD | MET | A | 964 | 111.433 | 72.641 | −5.031 | 1.00 | 30.35 | S |
| ATOM | 984 | CE | MET | A | 964 | 110.903 | 72.183 | −6.680 | 1.00 | 32.31 | C |
| ATOM | 985 | C | MET | A | 964 | 113.552 | 75.675 | −7.360 | 1.00 | 28.97 | C |
| ATOM | 986 | O | MET | A | 964 | 113.713 | 74.886 | −8.296 | 1.00 | 28.66 | O |
| ATOM | 987 | N | GLU | A | 965 | 113.786 | 76.981 | −7.471 | 1.00 | 29.53 | N |
| ATOM | 988 | CA | GLU | A | 965 | 114.376 | 77.535 | −8.687 | 1.00 | 30.79 | C |
| ATOM | 989 | CB | GLU | A | 965 | 114.417 | 79.069 | −8.642 | 1.00 | 31.06 | C |
| ATOM | 990 | CG | GLU | A | 965 | 115.163 | 79.753 | −9.806 | 1.00 | 36.42 | C |
| ATOM | 991 | CD | GLU | A | 965 | 114.684 | 79.335 | −11.203 | 1.00 | 42.33 | C |
| ATOM | 992 | OE1 | GLU | A | 965 | 113.629 | 78.676 | −11.326 | 1.00 | 44.45 | O |
| ATOM | 993 | OE2 | GLU | A | 965 | 115.377 | 79.671 | −12.189 | 1.00 | 44.57 | O |
| ATOM | 994 | C | GLU | A | 965 | 115.763 | 76.931 | −8.904 | 1.00 | 30.59 | C |
| ATOM | 995 | O | GLU | A | 965 | 116.128 | 76.585 | −10.028 | 1.00 | 30.28 | O |
| ATOM | 996 | N | TYR | A | 966 | 116.512 | 76.782 | −7.814 | 1.00 | 30.75 | N |
| ATOM | 997 | CA | TYR | A | 966 | 117.821 | 76.144 | −7.853 | 1.00 | 31.41 | C |
| ATOM | 998 | CB | TYR | A | 966 | 118.517 | 76.260 | −6.492 | 1.00 | 31.99 | C |
| ATOM | 999 | CG | TYR | A | 966 | 119.889 | 75.623 | −6.420 | 1.00 | 32.12 | C |
| ATOM | 1000 | CD1 | TYR | A | 966 | 120.960 | 76.115 | −7.171 | 1.00 | 32.52 | C |
| ATOM | 1001 | CE1 | TYR | A | 966 | 122.221 | 75.527 | −7.095 | 1.00 | 31.53 | C |
| ATOM | 1002 | CZ | TYR | A | 966 | 122.415 | 74.443 | −6.252 | 1.00 | 32.36 | C |
| ATOM | 1003 | OH | TYR | A | 966 | 123.647 | 73.842 | −6.155 | 1.00 | 33.86 | O |
| ATOM | 1004 | CE2 | TYR | A | 966 | 121.370 | 73.948 | −5.496 | 1.00 | 34.56 | C |
| ATOM | 1005 | CD2 | TYR | A | 966 | 120.120 | 74.538 | −5.583 | 1.00 | 32.55 | C |
| ATOM | 1006 | C | TYR | A | 966 | 117.732 | 74.688 | −8.316 | 1.00 | 31.68 | C |
| ATOM | 1007 | O | TYR | A | 966 | 118.561 | 74.247 | −9.110 | 1.00 | 31.64 | O |
| ATOM | 1008 | N | LEU | A | 967 | 116.726 | 73.954 | −7.836 | 1.00 | 31.36 | N |
| ATOM | 1009 | CA | LEU | A | 967 | 116.472 | 72.588 | −8.310 | 1.00 | 32.06 | C |
| ATOM | 1010 | CB | LEU | A | 967 | 115.255 | 71.966 | −7.616 | 1.00 | 32.22 | C |
| ATOM | 1011 | CG | LEU | A | 967 | 115.295 | 71.466 | −6.173 | 1.00 | 34.85 | C |
| ATOM | 1012 | CD1 | LEU | A | 967 | 114.326 | 70.295 | −6.049 | 1.00 | 33.72 | C |
| ATOM | 1013 | CD2 | LEU | A | 967 | 116.682 | 71.037 | −5.756 | 1.00 | 36.30 | C |
| ATOM | 1014 | C | LEU | A | 967 | 116.240 | 72.544 | −9.815 | 1.00 | 31.46 | C |
| ATOM | 1015 | O | LEU | A | 967 | 116.772 | 71.673 | −10.505 | 1.00 | 30.64 | O |

APPENDIX 1-continued

| ATOM | 1016 | N | GLY | A | 968 | 115.430 | 73.483 | −10.303 | 1.00 | 31.30 | N |
|---|---|---|---|---|---|---|---|---|---|---|---|
| ATOM | 1017 | CA | GLY | A | 968 | 115.074 | 73.569 | −11.717 | 1.00 | 31.73 | C |
| ATOM | 1018 | C | GLY | A | 968 | 116.254 | 73.843 | −12.625 | 1.00 | 32.18 | C |
| ATOM | 1019 | O | GLY | A | 968 | 116.276 | 73.396 | −13.773 | 1.00 | 32.73 | O |
| ATOM | 1020 | N | THR | A | 969 | 117.237 | 74.574 | −12.103 | 1.00 | 32.50 | N |
| ATOM | 1021 | CA | THR | A | 969 | 118.447 | 74.907 | −12.848 | 1.00 | 33.05 | C |
| ATOM | 1022 | CB | THR | A | 969 | 119.280 | 76.003 | −12.115 | 1.00 | 32.74 | C |
| ATOM | 1023 | OG1 | THR | A | 969 | 120.005 | 76.785 | −13.071 | 1.00 | 40.04 | O |
| ATOM | 1024 | CG2 | THR | A | 969 | 120.254 | 75.406 | −11.113 | 1.00 | 29.95 | C |
| ATOM | 1025 | C | THR | A | 969 | 119.278 | 73.648 | −13.140 | 1.00 | 33.06 | C |
| ATOM | 1026 | O | THR | A | 969 | 120.088 | 73.629 | −14.067 | 1.00 | 33.20 | O |
| ATOM | 1027 | N | LYS | A | 970 | 119.052 | 72.597 | −12.354 | 1.00 | 32.77 | N |
| ATOM | 1028 | CA | LYS | A | 970 | 119.732 | 71.316 | −12.553 | 1.00 | 32.66 | C |
| ATOM | 1029 | CB | LYS | A | 970 | 120.312 | 70.799 | −11.233 | 1.00 | 32.90 | C |
| ATOM | 1030 | CG | LYS | A | 970 | 121.206 | 71.814 | −10.532 | 1.00 | 35.09 | C |
| ATOM | 1031 | CD | LYS | A | 970 | 122.339 | 71.169 | −9.766 | 1.00 | 38.07 | C |
| ATOM | 1032 | CE | LYS | A | 970 | 123.293 | 72.238 | −9.256 | 1.00 | 41.10 | C |
| ATOM | 1033 | NZ | LYS | A | 970 | 124.627 | 71.675 | −8.911 | 1.00 | 45.93 | N |
| ATOM | 1034 | C | LYS | A | 970 | 118.787 | 70.293 | −13.179 | 1.00 | 32.12 | C |
| ATOM | 1035 | O | LYS | A | 970 | 119.127 | 69.116 | −13.310 | 1.00 | 31.66 | O |
| ATOM | 1036 | N | ARG | A | 971 | 117.605 | 70.769 | −13.573 | 1.00 | 31.60 | N |
| ATOM | 1037 | CA | ARG | A | 971 | 116.549 | 69.947 | −14.179 | 1.00 | 31.45 | C |
| ATOM | 1038 | CB | ARG | A | 971 | 116.975 | 69.421 | −15.563 | 1.00 | 31.46 | C |
| ATOM | 1039 | CG | ARG | A | 971 | 117.106 | 70.534 | −16.611 | 1.00 | 33.19 | C |
| ATOM | 1040 | CD | ARG | A | 971 | 117.600 | 70.038 | −17.972 | 1.00 | 32.46 | C |
| ATOM | 1041 | NE | ARG | A | 971 | 116.664 | 69.126 | −18.635 | 1.00 | 33.54 | N |
| ATOM | 1042 | CZ | ARG | A | 971 | 115.600 | 69.505 | −19.342 | 1.00 | 34.82 | C |
| ATOM | 1043 | NH1 | ARG | A | 971 | 115.303 | 70.792 | −19.483 | 1.00 | 36.08 | N |
| ATOM | 1044 | NH2 | ARG | A | 971 | 114.823 | 68.592 | −19.907 | 1.00 | 31.01 | N |
| ATOM | 1045 | C | ARG | A | 971 | 116.052 | 68.832 | −13.248 | 1.00 | 31.49 | C |
| ATOM | 1046 | O | ARG | A | 971 | 115.624 | 67.767 | −13.700 | 1.00 | 30.46 | O |
| ATOM | 1047 | N | TYR | A | 972 | 116.113 | 69.101 | −11.944 | 1.00 | 30.63 | N |
| ATOM | 1048 | CA | TYR | A | 972 | 115.582 | 68.197 | −10.931 | 1.00 | 30.18 | C |
| ATOM | 1049 | CB | TYR | A | 972 | 116.351 | 68.329 | −9.611 | 1.00 | 30.22 | C |
| ATOM | 1050 | CG | TYR | A | 972 | 117.802 | 67.889 | −9.628 | 1.00 | 32.31 | C |
| ATOM | 1051 | CD1 | TYR | A | 972 | 118.666 | 68.265 | −8.598 | 1.00 | 33.24 | C |
| ATOM | 1052 | CE1 | TYR | A | 972 | 119.997 | 67.866 | −8.593 | 1.00 | 33.94 | C |
| ATOM | 1053 | CZ | TYR | A | 972 | 120.482 | 67.089 | −9.628 | 1.00 | 32.39 | C |
| ATOM | 1054 | OH | TYR | A | 972 | 121.799 | 66.697 | −9.622 | 1.00 | 30.95 | O |
| ATOM | 1055 | CE2 | TYR | A | 972 | 119.650 | 66.704 | −10.668 | 1.00 | 35.09 | C |
| ATOM | 1056 | CD2 | TYR | A | 972 | 118.316 | 67.100 | −10.661 | 1.00 | 32.53 | C |
| ATOM | 1057 | C | TYR | A | 972 | 114.112 | 68.509 | −10.675 | 1.00 | 30.09 | C |
| ATOM | 1058 | O | TYR | A | 972 | 113.731 | 69.676 | −10.548 | 1.00 | 29.43 | O |
| ATOM | 1059 | N | ILE | A | 973 | 113.297 | 67.459 | −10.606 | 1.00 | 29.39 | N |
| ATOM | 1060 | CA | ILE | A | 973 | 111.889 | 67.581 | −10.236 | 1.00 | 29.45 | C |
| ATOM | 1061 | CB | ILE | A | 973 | 110.945 | 66.883 | −11.260 | 1.00 | 29.46 | C |
| ATOM | 1062 | CG1 | ILE | A | 973 | 111.346 | 67.212 | −12.708 | 1.00 | 28.31 | C |
| ATOM | 1063 | CD1 | ILE | A | 973 | 111.337 | 68.706 | −13.067 | 1.00 | 27.71 | C |
| ATOM | 1064 | CG2 | ILE | A | 973 | 109.479 | 67.243 | −10.988 | 1.00 | 29.83 | C |
| ATOM | 1065 | C | ILE | A | 973 | 111.719 | 66.949 | −8.862 | 1.00 | 28.93 | C |
| ATOM | 1066 | O | ILE | A | 973 | 112.007 | 65.766 | −8.682 | 1.00 | 29.23 | O |
| ATOM | 1067 | N | HIS | A | 974 | 111.263 | 67.742 | −7.896 | 1.00 | 28.78 | N |
| ATOM | 1068 | CA | HIS | A | 974 | 111.178 | 67.287 | −6.507 | 1.00 | 28.14 | C |
| ATOM | 1069 | CB | HIS | A | 974 | 110.919 | 68.460 | −5.559 | 1.00 | 28.27 | C |
| ATOM | 1070 | CG | HIS | A | 974 | 111.031 | 68.082 | −4.120 | 1.00 | 28.13 | C |
| ATOM | 1071 | ND1 | HIS | A | 974 | 112.205 | 68.205 | −3.410 | 1.00 | 26.97 | N |
| ATOM | 1072 | CE1 | HIS | A | 974 | 112.017 | 67.769 | −2.178 | 1.00 | 24.11 | C |
| ATOM | 1073 | NE2 | HIS | A | 974 | 110.770 | 67.350 | −2.069 | 1.00 | 27.95 | N |
| ATOM | 1074 | CD2 | HIS | A | 974 | 110.134 | 67.526 | −3.273 | 1.00 | 25.69 | C |
| ATOM | 1075 | C | HIS | A | 974 | 110.146 | 66.177 | −6.285 | 1.00 | 28.20 | C |
| ATOM | 1076 | O | HIS | A | 974 | 110.448 | 65.167 | −5.638 | 1.00 | 28.37 | O |
| ATOM | 1077 | N | ARG | A | 975 | 108.937 | 66.379 | −6.809 | 1.00 | 27.76 | N |
| ATOM | 1078 | CA | ARG | A | 975 | 107.857 | 65.375 | −6.794 | 1.00 | 29.26 | C |
| ATOM | 1079 | CB | ARG | A | 975 | 108.331 | 64.041 | −7.399 | 1.00 | 29.14 | C |
| ATOM | 1080 | CG | ARG | A | 975 | 108.646 | 64.095 | −8.881 | 1.00 | 30.67 | C |
| ATOM | 1081 | CD | ARG | A | 975 | 108.903 | 62.708 | −9.437 | 1.00 | 31.36 | C |
| ATOM | 1082 | NE | ARG | A | 975 | 107.750 | 61.830 | −9.255 | 1.00 | 34.51 | N |
| ATOM | 1083 | CZ | ARG | A | 975 | 107.748 | 60.715 | −8.528 | 1.00 | 36.35 | C |
| ATOM | 1084 | NH1 | ARG | A | 975 | 108.849 | 60.302 | −7.912 | 1.00 | 35.10 | N |
| ATOM | 1085 | NH2 | ARG | A | 975 | 106.637 | 59.998 | −8.436 | 1.00 | 37.15 | N |
| ATOM | 1086 | C | ARG | A | 975 | 107.192 | 65.109 | −5.437 | 1.00 | 29.75 | C |
| ATOM | 1087 | O | ARG | A | 975 | 106.308 | 64.250 | −5.343 | 1.00 | 30.84 | O |
| ATOM | 1088 | N | ASP | A | 976 | 107.601 | 65.835 | −4.396 | 1.00 | 29.53 | N |
| ATOM | 1089 | CA | ASP | A | 976 | 107.086 | 65.597 | −3.042 | 1.00 | 29.48 | C |
| ATOM | 1090 | CB | ASP | A | 976 | 107.880 | 64.465 | −2.368 | 1.00 | 29.33 | C |
| ATOM | 1091 | CG | ASP | A | 976 | 107.117 | 63.787 | −1.228 | 1.00 | 31.32 | C |
| ATOM | 1092 | OD1 | ASP | A | 976 | 105.866 | 63.817 | −1.215 | 1.00 | 29.07 | O |
| ATOM | 1093 | OD2 | ASP | A | 976 | 107.782 | 63.206 | −.340 | 1.00 | 30.67 | O |
| ATOM | 1094 | C | ASP | A | 976 | 107.118 | 66.874 | −2.186 | 1.00 | 30.05 | C |

APPENDIX 1-continued

| ATOM | 1095 | O | ASP | A | 976 | 107.367 | 66.822 | −.975 | 1.00 | 29.45 | O |
|---|---|---|---|---|---|---|---|---|---|---|---|
| ATOM | 1096 | N | LEU | A | 977 | 106.874 | 68.020 | −2.820 | 1.00 | 29.54 | N |
| ATOM | 1097 | CA | LEU | A | 977 | 106.813 | 69.287 | −2.096 | 1.00 | 29.90 | C |
| ATOM | 1098 | CB | LEU | A | 977 | 106.749 | 70.479 | −3.052 | 1.00 | 30.34 | C |
| ATOM | 1099 | CG | LEU | A | 977 | 108.069 | 71.059 | −3.557 | 1.00 | 33.44 | C |
| ATOM | 1100 | CD1 | LEU | A | 977 | 107.774 | 72.248 | −4.472 | 1.00 | 33.31 | C |
| ATOM | 1101 | CD2 | LEU | A | 977 | 108.977 | 71.470 | −2.389 | 1.00 | 34.68 | C |
| ATOM | 1102 | C | LEU | A | 977 | 105.629 | 69.324 | −1.144 | 1.00 | 29.43 | C |
| ATOM | 1103 | O | LEU | A | 977 | 104.476 | 69.206 | −1.563 | 1.00 | 29.88 | O |
| ATOM | 1104 | N | ALA | A | 978 | 105.945 | 69.475 | .138 | 1.00 | 28.33 | N |
| ATOM | 1105 | CA | ALA | A | 978 | 104.971 | 69.516 | 1.222 | 1.00 | 28.06 | C |
| ATOM | 1106 | CB | ALA | A | 978 | 104.399 | 68.123 | 1.485 | 1.00 | 27.98 | C |
| ATOM | 1107 | C | ALA | A | 978 | 105.702 | 70.033 | 2.454 | 1.00 | 27.32 | C |
| ATOM | 1108 | O | ALA | A | 978 | 106.903 | 69.796 | 2.597 | 1.00 | 25.77 | O |
| ATOM | 1109 | N | THR | A | 979 | 104.991 | 70.723 | 3.346 | 1.00 | 26.95 | N |
| ATOM | 1110 | CA | THR | A | 979 | 105.618 | 71.276 | 4.557 | 1.00 | 26.80 | C |
| ATOM | 1111 | CB | THR | A | 979 | 104.637 | 72.113 | 5.425 | 1.00 | 26.65 | C |
| ATOM | 1112 | OG1 | THR | A | 979 | 103.582 | 71.277 | 5.915 | 1.00 | 26.23 | O |
| ATOM | 1113 | CG2 | THR | A | 979 | 104.055 | 73.278 | 4.627 | 1.00 | 23.99 | C |
| ATOM | 1114 | C | THR | A | 979 | 106.303 | 70.221 | 5.438 | 1.00 | 27.00 | C |
| ATOM | 1115 | O | THR | A | 979 | 107.231 | 70.542 | 6.180 | 1.00 | 27.86 | O |
| ATOM | 1116 | N | ARG | A | 980 | 105.852 | 68.971 | 5.349 | 1.00 | 27.12 | N |
| ATOM | 1117 | CA | ARG | A | 980 | 106.491 | 67.856 | 6.072 | 1.00 | 28.96 | C |
| ATOM | 1118 | CB | ARG | A | 980 | 105.655 | 66.572 | 5.960 | 1.00 | 29.20 | C |
| ATOM | 1119 | CG | ARG | A | 980 | 105.576 | 65.996 | 4.552 | 1.00 | 30.12 | C |
| ATOM | 1120 | CD | ARG | A | 980 | 104.691 | 64.761 | 4.471 | 1.00 | 32.18 | C |
| ATOM | 1121 | NE | ARG | A | 980 | 104.522 | 64.355 | 3.074 | 1.00 | 40.42 | N |
| ATOM | 1122 | CZ | ARG | A | 980 | 103.518 | 64.740 | 2.287 | 1.00 | 43.13 | C |
| ATOM | 1123 | NH1 | ARG | A | 980 | 102.555 | 65.532 | 2.751 | 1.00 | 45.32 | N |
| ATOM | 1124 | NH2 | ARG | A | 980 | 103.472 | 64.323 | 1.030 | 1.00 | 44.35 | N |
| ATOM | 1125 | C | ARG | A | 980 | 107.924 | 67.598 | 5.589 | 1.00 | 28.42 | C |
| ATOM | 1126 | O | ARG | A | 980 | 108.734 | 67.013 | 6.314 | 1.00 | 27.89 | O |
| ATOM | 1127 | N | ASN | A | 981 | 108.217 | 68.037 | 4.366 | 1.00 | 28.14 | N |
| ATOM | 1128 | CA | ASN | A | 981 | 109.536 | 67.871 | 3.754 | 1.00 | 28.81 | C |
| ATOM | 1129 | CB | ASN | A | 981 | 109.386 | 67.348 | 2.323 | 1.00 | 28.66 | C |
| ATOM | 1130 | CG | ASN | A | 981 | 108.919 | 65.906 | 2.282 | 1.00 | 31.08 | C |
| ATOM | 1131 | OD1 | ASN | A | 981 | 109.322 | 65.092 | 3.109 | 1.00 | 30.44 | O |
| ATOM | 1132 | ND2 | ASN | A | 981 | 108.064 | 65.584 | 1.319 | 1.00 | 31.55 | N |
| ATOM | 1133 | C | ASN | A | 981 | 110.396 | 69.136 | 3.780 | 1.00 | 28.38 | C |
| ATOM | 1134 | O | ASN | A | 981 | 111.479 | 69.176 | 3.192 | 1.00 | 27.77 | O |
| ATOM | 1135 | N | ILE | A | 982 | 109.897 | 70.164 | 4.459 | 1.00 | 28.53 | N |
| ATOM | 1136 | CA | ILE | A | 982 | 110.649 | 71.390 | 4.686 | 1.00 | 27.96 | C |
| ATOM | 1137 | CB | ILE | A | 982 | 109.791 | 72.664 | 4.419 | 1.00 | 28.73 | C |
| ATOM | 1138 | CG1 | ILE | A | 982 | 109.077 | 72.591 | 3.058 | 1.00 | 29.29 | C |
| ATOM | 1139 | CD1 | ILE | A | 982 | 109.994 | 72.552 | 1.839 | 1.00 | 31.85 | C |
| ATOM | 1140 | CG2 | ILE | A | 982 | 110.640 | 73.930 | 4.539 | 1.00 | 27.48 | C |
| ATOM | 1141 | C | ILE | A | 982 | 111.125 | 71.377 | 6.133 | 1.00 | 27.32 | C |
| ATOM | 1142 | O | ILE | A | 982 | 110.371 | 71.010 | 7.038 | 1.00 | 27.24 | O |
| ATOM | 1143 | N | LEU | A | 983 | 112.377 | 71.771 | 6.341 | 1.00 | 26.56 | N |
| ATOM | 1144 | CA | LEU | A | 983 | 112.973 | 71.794 | 7.671 | 1.00 | 26.34 | C |
| ATOM | 1145 | CB | LEU | A | 983 | 114.238 | 70.936 | 7.716 | 1.00 | 25.64 | C |
| ATOM | 1146 | CG | LEU | A | 983 | 114.151 | 69.460 | 7.327 | 1.00 | 27.21 | C |
| ATOM | 1147 | CD1 | LEU | A | 983 | 115.552 | 68.912 | 7.190 | 1.00 | 26.77 | C |
| ATOM | 1148 | CD2 | LEU | A | 983 | 113.350 | 68.646 | 8.340 | 1.00 | 28.15 | C |
| ATOM | 1149 | C | LEU | A | 983 | 113.308 | 73.213 | 8.093 | 1.00 | 26.65 | C |
| ATOM | 1150 | O | LEU | A | 983 | 113.522 | 74.087 | 7.253 | 1.00 | 27.06 | O |
| ATOM | 1151 | N | VAL | A | 984 | 113.361 | 73.428 | 9.402 | 1.00 | 26.78 | N |
| ATOM | 1152 | CA | VAL | A | 984 | 113.591 | 74.753 | 9.960 | 1.00 | 27.48 | C |
| ATOM | 1153 | CB | VAL | A | 984 | 112.483 | 75.126 | 10.986 | 1.00 | 27.02 | C |
| ATOM | 1154 | CG1 | VAL | A | 984 | 112.677 | 76.537 | 11.516 | 1.00 | 26.89 | C |
| ATOM | 1155 | CG2 | VAL | A | 984 | 111.098 | 74.979 | 10.369 | 1.00 | 27.86 | C |
| ATOM | 1156 | C | VAL | A | 984 | 114.973 | 74.794 | 10.612 | 1.00 | 27.93 | C |
| ATOM | 1157 | O | VAL | A | 984 | 115.223 | 74.093 | 11.592 | 1.00 | 28.18 | O |
| ATOM | 1158 | N | GLU | A | 985 | 115.874 | 75.599 | 10.053 | 1.00 | 29.15 | N |
| ATOM | 1159 | CA | GLU | A | 985 | 117.193 | 75.798 | 10.657 | 1.00 | 31.28 | C |
| ATOM | 1160 | CB | GLU | A | 985 | 118.207 | 76.336 | 9.638 | 1.00 | 31.09 | C |
| ATOM | 1161 | CG | GLU | A | 985 | 119.618 | 76.481 | 10.216 | 1.00 | 32.78 | C |
| ATOM | 1162 | CD | GLU | A | 985 | 120.642 | 77.010 | 9.225 | 1.00 | 32.83 | C |
| ATOM | 1163 | OE1 | GLU | A | 985 | 120.253 | 77.629 | 8.212 | 1.00 | 33.46 | O |
| ATOM | 1164 | OE2 | GLU | A | 985 | 121.850 | 76.809 | 9.471 | 1.00 | 38.55 | O |
| ATOM | 1165 | C | GLU | A | 985 | 117.087 | 76.743 | 11.852 | 1.00 | 31.80 | C |
| ATOM | 1166 | O | GLU | A | 985 | 117.649 | 76.481 | 12.915 | 1.00 | 32.45 | O |
| ATOM | 1167 | N | ASN | A | 986 | 116.373 | 77.846 | 11.653 | 1.00 | 33.75 | N |
| ATOM | 1168 | CA | ASN | A | 986 | 116.072 | 78.804 | 12.714 | 1.00 | 35.18 | C |
| ATOM | 1169 | CB | ASN | A | 986 | 117.251 | 79.766 | 12.959 | 1.00 | 35.11 | C |
| ATOM | 1170 | CG | ASN | A | 986 | 117.637 | 80.565 | 11.720 | 1.00 | 35.82 | C |
| ATOM | 1171 | OD1 | ASN | A | 986 | 116.865 | 81.387 | 11.227 | 1.00 | 35.02 | O |
| ATOM | 1172 | ND2 | ASN | A | 986 | 118.851 | 80.340 | 11.229 | 1.00 | 35.61 | N |
| ATOM | 1173 | C | ASN | A | 986 | 114.778 | 79.553 | 12.403 | 1.00 | 36.29 | C |

APPENDIX 1-continued

| | | | | | | | | | | | |
|---|---|---|---|---|---|---|---|---|---|---|---|
| ATOM | 1174 | O | ASN | A | 986 | 114.127 | 79.278 | 11.392 | 1.00 | 36.61 | O |
| ATOM | 1175 | N | GLU | A | 987 | 114.419 | 80.498 | 13.270 | 1.00 | 37.60 | N |
| ATOM | 1176 | CA | GLU | A | 987 | 113.184 | 81.278 | 13.152 | 1.00 | 39.32 | C |
| ATOM | 1177 | CB | GLU | A | 987 | 113.115 | 82.302 | 14.291 | 1.00 | 39.45 | C |
| ATOM | 1178 | CG | GLU | A | 987 | 111.711 | 82.753 | 14.671 | 1.00 | 42.78 | C |
| ATOM | 1179 | CD | GLU | A | 987 | 111.699 | 83.831 | 15.756 | 1.00 | 42.80 | C |
| ATOM | 1180 | OE1 | GLU | A | 987 | 112.775 | 84.153 | 16.312 | 1.00 | 47.57 | O |
| ATOM | 1181 | OE2 | GLU | A | 987 | 110.603 | 84.357 | 16.054 | 1.00 | 47.86 | O |
| ATOM | 1182 | C | GLU | A | 987 | 113.055 | 81.994 | 11.805 | 1.00 | 38.39 | C |
| ATOM | 1183 | O | GLU | A | 987 | 111.945 | 82.266 | 11.342 | 1.00 | 38.36 | O |
| ATOM | 1184 | N | ASN | A | 988 | 114.195 | 82.280 | 11.181 | 1.00 | 38.02 | N |
| ATOM | 1185 | CA | ASN | A | 988 | 114.240 | 83.057 | 9.944 | 1.00 | 38.37 | C |
| ATOM | 1186 | CB | ASN | A | 988 | 115.221 | 84.226 | 10.097 | 1.00 | 38.78 | C |
| ATOM | 1187 | CG | ASN | A | 988 | 114.839 | 85.171 | 11.225 | 1.00 | 40.23 | C |
| ATOM | 1188 | OD1 | ASN | A | 988 | 113.693 | 85.614 | 11.322 | 1.00 | 41.93 | O |
| ATOM | 1189 | ND2 | ASN | A | 988 | 115.804 | 85.489 | 12.081 | 1.00 | 41.91 | N |
| ATOM | 1190 | C | ASN | A | 988 | 114.572 | 82.269 | 8.668 | 1.00 | 37.62 | C |
| ATOM | 1191 | O | ASN | A | 988 | 114.447 | 82.809 | 7.565 | 1.00 | 38.01 | O |
| ATOM | 1192 | N | ARG | A | 989 | 114.993 | 81.010 | 8.809 | 1.00 | 36.18 | N |
| ATOM | 1193 | CA | ARG | A | 989 | 115.422 | 80.217 | 7.649 | 1.00 | 34.98 | C |
| ATOM | 1194 | CB | ARG | A | 989 | 116.956 | 80.171 | 7.554 | 1.00 | 35.01 | C |
| ATOM | 1195 | CG | ARG | A | 989 | 117.480 | 79.545 | 6.255 | 1.00 | 36.49 | C |
| ATOM | 1196 | CD | ARG | A | 989 | 118.973 | 79.770 | 6.056 | 1.00 | 37.08 | C |
| ATOM | 1197 | NE | ARG | A | 989 | 119.291 | 81.168 | 5.764 | 1.00 | 43.99 | N |
| ATOM | 1198 | CZ | ARG | A | 989 | 120.493 | 81.615 | 5.406 | 1.00 | 45.75 | C |
| ATOM | 1199 | NH1 | ARG | A | 989 | 121.520 | 80.781 | 5.283 | 1.00 | 46.57 | N |
| ATOM | 1200 | NH2 | ARG | A | 989 | 120.670 | 82.908 | 5.166 | 1.00 | 48.22 | N |
| ATOM | 1201 | C | ARG | A | 989 | 114.847 | 78.801 | 7.597 | 1.00 | 32.82 | C |
| ATOM | 1202 | O | ARG | A | 989 | 114.968 | 78.036 | 8.556 | 1.00 | 31.15 | O |
| ATOM | 1203 | N | VAL | A | 990 | 114.229 | 78.469 | 6.463 | 1.00 | 30.87 | N |
| ATOM | 1204 | CA | VAL | A | 990 | 113.797 | 77.099 | 6.176 | 1.00 | 29.83 | C |
| ATOM | 1205 | CB | VAL | A | 990 | 112.263 | 76.979 | 5.914 | 1.00 | 30.03 | C |
| ATOM | 1206 | CG1 | VAL | A | 990 | 111.463 | 77.437 | 7.133 | 1.00 | 29.08 | C |
| ATOM | 1207 | CG2 | VAL | A | 990 | 111.841 | 77.736 | 4.655 | 1.00 | 29.21 | C |
| ATOM | 1208 | C | VAL | A | 990 | 114.593 | 76.495 | 5.010 | 1.00 | 29.28 | C |
| ATOM | 1209 | O | VAL | A | 990 | 115.205 | 77.221 | 4.219 | 1.00 | 28.51 | O |
| ATOM | 1210 | N | LYS | A | 991 | 114.590 | 75.167 | 4.925 | 1.00 | 27.41 | N |
| ATOM | 1211 | CA | LYS | A | 991 | 115.309 | 74.446 | 3.876 | 1.00 | 27.10 | C |
| ATOM | 1212 | CB | LYS | A | 991 | 116.649 | 73.905 | 4.394 | 1.00 | 26.36 | C |
| ATOM | 1213 | CG | LYS | A | 991 | 117.629 | 74.959 | 4.896 | 1.00 | 27.87 | C |
| ATOM | 1214 | CD | LYS | A | 991 | 119.023 | 74.376 | 5.071 | 1.00 | 26.83 | C |
| ATOM | 1215 | CE | LYS | A | 991 | 119.933 | 75.342 | 5.808 | 1.00 | 27.50 | C |
| ATOM | 1216 | NZ | LYS | A | 991 | 121.334 | 74.845 | 5.851 | 1.00 | 24.01 | N |
| ATOM | 1217 | C | LYS | A | 991 | 114.473 | 73.283 | 3.367 | 1.00 | 26.71 | C |
| ATOM | 1218 | O | LYS | A | 991 | 113.777 | 72.625 | 4.141 | 1.00 | 27.54 | O |
| ATOM | 1219 | N | ILE | A | 992 | 114.536 | 73.037 | 2.063 | 1.00 | 26.85 | N |
| ATOM | 1220 | CA | ILE | A | 992 | 113.975 | 71.811 | 1.502 | 1.00 | 26.94 | C |
| ATOM | 1221 | CB | ILE | A | 992 | 113.980 | 71.828 | −.040 | 1.00 | 27.14 | C |
| ATOM | 1222 | CG1 | ILE | A | 992 | 113.291 | 73.103 | −.554 | 1.00 | 29.11 | C |
| ATOM | 1223 | CD1 | ILE | A | 992 | 113.511 | 73.393 | −2.024 | 1.00 | 31.29 | C |
| ATOM | 1224 | CG2 | ILE | A | 992 | 113.311 | 70.565 | −.591 | 1.00 | 27.13 | C |
| ATOM | 1225 | C | ILE | A | 992 | 114.828 | 70.675 | 2.065 | 1.00 | 26.61 | C |
| ATOM | 1226 | O | ILE | A | 992 | 116.048 | 70.677 | 1.906 | 1.00 | 26.48 | O |
| ATOM | 1227 | N | GLY | A | 993 | 114.183 | 69.733 | 2.751 | 1.00 | 26.57 | N |
| ATOM | 1228 | CA | GLY | A | 993 | 114.894 | 68.799 | 3.625 | 1.00 | 27.11 | C |
| ATOM | 1229 | C | GLY | A | 993 | 114.909 | 67.325 | 3.268 | 1.00 | 27.51 | C |
| ATOM | 1230 | O | GLY | A | 993 | 115.530 | 66.525 | 3.969 | 1.00 | 27.63 | O |
| ATOM | 1231 | N | ASP | A | 994 | 114.227 | 66.957 | 2.187 | 1.00 | 27.98 | N |
| ATOM | 1232 | CA | ASP | A | 994 | 114.203 | 65.568 | 1.737 | 1.00 | 27.55 | C |
| ATOM | 1233 | CB | ASP | A | 994 | 113.044 | 64.803 | 2.377 | 1.00 | 27.85 | C |
| ATOM | 1234 | CG | ASP | A | 994 | 113.170 | 63.306 | 2.187 | 1.00 | 27.97 | C |
| ATOM | 1235 | OD1 | ASP | A | 994 | 113.906 | 62.674 | 2.971 | 1.00 | 26.72 | O |
| ATOM | 1236 | OD2 | ASP | A | 994 | 112.544 | 62.764 | 1.248 | 1.00 | 29.93 | O |
| ATOM | 1237 | C | ASP | A | 994 | 114.085 | 65.498 | .226 | 1.00 | 27.84 | C |
| ATOM | 1238 | O | ASP | A | 994 | 113.435 | 66.346 | −.386 | 1.00 | 28.21 | O |
| ATOM | 1239 | N | PHE | A | 995 | 114.714 | 64.485 | −.368 | 1.00 | 27.53 | N |
| ATOM | 1240 | CA | PHE | A | 995 | 114.728 | 64.330 | −1.824 | 1.00 | 27.66 | C |
| ATOM | 1241 | CB | PHE | A | 995 | 116.032 | 64.896 | −2.407 | 1.00 | 28.01 | C |
| ATOM | 1242 | CG | PHE | A | 995 | 116.222 | 66.363 | −2.140 | 1.00 | 28.20 | C |
| ATOM | 1243 | CD1 | PHE | A | 995 | 115.728 | 67.313 | −3.027 | 1.00 | 28.72 | C |
| ATOM | 1244 | CE1 | PHE | A | 995 | 115.890 | 68.669 | −2.776 | 1.00 | 28.48 | C |
| ATOM | 1245 | CZ | PHE | A | 995 | 116.548 | 69.089 | −1.630 | 1.00 | 27.49 | C |
| ATOM | 1246 | CE2 | PHE | A | 995 | 117.039 | 68.154 | −.733 | 1.00 | 29.19 | C |
| ATOM | 1247 | CD2 | PHE | A | 995 | 116.876 | 66.796 | −.991 | 1.00 | 28.93 | C |
| ATOM | 1248 | C | PHE | A | 995 | 114.497 | 62.882 | −2.266 | 1.00 | 27.86 | C |
| ATOM | 1249 | O | PHE | A | 995 | 114.979 | 62.457 | −3.319 | 1.00 | 27.69 | O |
| ATOM | 1250 | N | GLY | A | 996 | 113.729 | 62.144 | −1.464 | 1.00 | 28.26 | N |
| ATOM | 1251 | CA | GLY | A | 996 | 113.458 | 60.726 | −1.705 | 1.00 | 27.42 | C |
| ATOM | 1252 | C | GLY | A | 996 | 112.774 | 60.392 | −3.019 | 1.00 | 27.92 | C |

APPENDIX 1-continued

| ATOM | 1253 | O | GLY | A | 996 | 112.978 | 59.307 | −3.564 | 1.00 | 28.17 | O |
|---|---|---|---|---|---|---|---|---|---|---|---|
| ATOM | 1254 | N | LEU | A | 997 | 111.974 | 61.324 | −3.535 | 1.00 | 28.25 | N |
| ATOM | 1255 | CA | LEU | A | 997 | 111.222 | 61.108 | −4.775 | 1.00 | 28.28 | C |
| ATOM | 1256 | CB | LEU | A | 997 | 109.723 | 61.368 | −4.543 | 1.00 | 28.96 | C |
| ATOM | 1257 | CG | LEU | A | 997 | 108.975 | 60.467 | −3.549 | 1.00 | 29.04 | C |
| ATOM | 1258 | CD1 | LEU | A | 997 | 107.503 | 60.848 | −3.494 | 1.00 | 29.63 | C |
| ATOM | 1259 | CD2 | LEU | A | 997 | 109.128 | 58.982 | −3.890 | 1.00 | 29.27 | C |
| ATOM | 1260 | C | LEU | A | 997 | 111.731 | 61.945 | −5.953 | 1.00 | 27.84 | C |
| ATOM | 1261 | O | LEU | A | 997 | 111.130 | 61.940 | −7.036 | 1.00 | 27.31 | O |
| ATOM | 1262 | N | THR | A | 998 | 112.844 | 62.644 | −5.740 | 1.00 | 27.08 | N |
| ATOM | 1263 | CA | THR | A | 998 | 113.390 | 63.581 | −6.722 | 1.00 | 27.01 | C |
| ATOM | 1264 | CB | THR | A | 998 | 114.433 | 64.530 | −6.072 | 1.00 | 27.79 | C |
| ATOM | 1265 | OG1 | THR | A | 998 | 113.800 | 65.290 | −5.037 | 1.00 | 27.41 | O |
| ATOM | 1266 | CG2 | THR | A | 998 | 115.032 | 65.494 | −7.102 | 1.00 | 27.60 | C |
| ATOM | 1267 | C | THR | A | 998 | 113.987 | 62.865 | −7.937 | 1.00 | 27.55 | C |
| ATOM | 1268 | O | THR | A | 998 | 114.784 | 61.937 | −7.791 | 1.00 | 26.24 | O |
| ATOM | 1269 | N | LYS | A | 999 | 113.578 | 63.303 | −9.127 | 1.00 | 27.64 | N |
| ATOM | 1270 | CA | LYS | A | 999 | 114.048 | 62.726 | −10.387 | 1.00 | 28.34 | C |
| ATOM | 1271 | CB | LYS | A | 999 | 112.882 | 62.097 | −11.159 | 1.00 | 28.46 | C |
| ATOM | 1272 | CG | LYS | A | 999 | 112.141 | 60.979 | −10.420 | 1.00 | 30.04 | C |
| ATOM | 1273 | CD | LYS | A | 999 | 112.949 | 59.684 | −10.383 | 1.00 | 32.11 | C |
| ATOM | 1274 | CE | LYS | A | 999 | 112.198 | 58.588 | −9.643 | 1.00 | 32.75 | C |
| ATOM | 1275 | NZ | LYS | A | 999 | 112.979 | 57.320 | −9.597 | 1.00 | 35.86 | N |
| ATOM | 1276 | C | LYS | A | 999 | 114.730 | 63.781 | −11.256 | 1.00 | 29.09 | C |
| ATOM | 1277 | O | LYS | A | 999 | 114.477 | 64.979 | −11.109 | 1.00 | 28.41 | O |
| ATOM | 1278 | N | VAL | A | 1000 | 115.600 | 63.332 | −12.156 | 1.00 | 29.90 | N |
| ATOM | 1279 | CA | VAL | A | 1000 | 116.224 | 64.219 | −13.134 | 1.00 | 31.53 | C |
| ATOM | 1280 | CB | VAL | A | 1000 | 117.712 | 63.863 | −13.390 | 1.00 | 32.08 | C |
| ATOM | 1281 | CG1 | VAL | A | 1000 | 118.411 | 64.990 | −14.151 | 1.00 | 31.19 | C |
| ATOM | 1282 | CG2 | VAL | A | 1000 | 118.435 | 63.580 | −12.086 | 1.00 | 32.97 | C |
| ATOM | 1283 | C | VAL | A | 1000 | 115.462 | 64.089 | −14.444 | 1.00 | 32.33 | C |
| ATOM | 1284 | O | VAL | A | 1000 | 115.183 | 62.975 | −14.894 | 1.00 | 32.64 | O |
| ATOM | 1285 | N | LEU | A | 1001 | 115.121 | 65.226 | −15.048 | 1.00 | 32.53 | N |
| ATOM | 1286 | CA | LEU | A | 1001 | 114.492 | 65.234 | −16.366 | 1.00 | 33.40 | C |
| ATOM | 1287 | CB | LEU | A | 1001 | 114.132 | 66.660 | −16.800 | 1.00 | 33.52 | C |
| ATOM | 1288 | CG | LEU | A | 1001 | 112.980 | 67.411 | −16.122 | 1.00 | 32.68 | C |
| ATOM | 1289 | CD1 | LEU | A | 1001 | 112.943 | 68.848 | −16.622 | 1.00 | 33.14 | C |
| ATOM | 1290 | CD2 | LEU | A | 1001 | 111.638 | 66.734 | −16.360 | 1.00 | 31.64 | C |
| ATOM | 1291 | C | LEU | A | 1001 | 115.422 | 64.610 | −17.407 | 1.00 | 34.06 | C |
| ATOM | 1292 | O | LEU | A | 1001 | 116.642 | 64.762 | −17.318 | 1.00 | 33.88 | O |
| ATOM | 1293 | N | PRO | A | 1002 | 114.850 | 63.885 | −18.386 | 1.00 | 34.81 | N |
| ATOM | 1294 | CA | PRO | A | 1002 | 115.657 | 63.478 | −19.539 | 1.00 | 35.89 | C |
| ATOM | 1295 | CB | PRO | A | 1002 | 114.723 | 62.549 | −20.316 | 1.00 | 35.10 | C |
| ATOM | 1296 | CG | PRO | A | 1002 | 113.353 | 62.940 | −19.901 | 1.00 | 35.42 | C |
| ATOM | 1297 | CD | PRO | A | 1002 | 113.463 | 63.398 | −18.477 | 1.00 | 34.76 | C |
| ATOM | 1298 | C | PRO | A | 1002 | 116.017 | 64.705 | −20.374 | 1.00 | 37.02 | C |
| ATOM | 1299 | O | PRO | A | 1002 | 115.294 | 65.705 | −20.335 | 1.00 | 37.13 | O |
| ATOM | 1300 | N | GLN | A | 1003 | 117.125 | 64.630 | −21.109 | 1.00 | 39.04 | N |
| ATOM | 1301 | CA | GLN | A | 1003 | 117.607 | 65.759 | −21.912 | 1.00 | 41.12 | C |
| ATOM | 1302 | CB | GLN | A | 1003 | 118.907 | 65.393 | −22.642 | 1.00 | 41.28 | C |
| ATOM | 1303 | CG | GLN | A | 1003 | 120.165 | 65.476 | −21.780 | 1.00 | 43.96 | C |
| ATOM | 1304 | CD | GLN | A | 1003 | 121.447 | 65.270 | −22.579 | 1.00 | 43.89 | C |
| ATOM | 1305 | OE1 | GLN | A | 1003 | 121.520 | 64.409 | −23.459 | 1.00 | 48.12 | O |
| ATOM | 1306 | NE2 | GLN | A | 1003 | 122.469 | 66.062 | −22.267 | 1.00 | 46.70 | N |
| ATOM | 1307 | C | GLN | A | 1003 | 116.577 | 66.268 | −22.922 | 1.00 | 40.86 | C |
| ATOM | 1308 | O | GLN | A | 1003 | 116.474 | 67.474 | −23.155 | 1.00 | 41.64 | O |
| ATOM | 1309 | N | ASP | A | 1004 | 115.811 | 65.344 | −23.499 | 1.00 | 40.51 | N |
| ATOM | 1310 | CA | ASP | A | 1004 | 114.933 | 65.642 | −24.633 | 1.00 | 40.57 | C |
| ATOM | 1311 | CB | ASP | A | 1004 | 114.986 | 64.491 | −25.651 | 1.00 | 40.80 | C |
| ATOM | 1312 | CG | ASP | A | 1004 | 114.377 | 63.195 | −25.115 | 1.00 | 42.55 | C |
| ATOM | 1313 | OD1 | ASP | A | 1004 | 114.500 | 62.918 | −23.900 | 1.00 | 44.13 | O |
| ATOM | 1314 | OD2 | ASP | A | 1004 | 113.779 | 62.446 | −25.918 | 1.00 | 42.40 | O |
| ATOM | 1315 | C | ASP | A | 1004 | 113.477 | 65.954 | −24.262 | 1.00 | 39.88 | C |
| ATOM | 1316 | O | ASP | A | 1004 | 112.664 | 66.242 | −25.142 | 1.00 | 39.82 | O |
| ATOM | 1317 | N | LYS | A | 1005 | 113.150 | 65.892 | −22.972 | 1.00 | 39.39 | N |
| ATOM | 1318 | CA | LYS | A | 1005 | 111.770 | 66.093 | −22.516 | 1.00 | 38.72 | C |
| ATOM | 1319 | CB | LYS | A | 1005 | 111.107 | 64.747 | −22.196 | 1.00 | 38.91 | C |
| ATOM | 1320 | CG | LYS | A | 1005 | 110.845 | 63.839 | −23.394 | 1.00 | 39.90 | C |
| ATOM | 1321 | CD | LYS | A | 1005 | 109.569 | 64.226 | −24.123 | 1.00 | 42.79 | C |
| ATOM | 1322 | CE | LYS | A | 1005 | 109.132 | 63.128 | −25.072 | 1.00 | 44.18 | C |
| ATOM | 1323 | NZ | LYS | A | 1005 | 107.990 | 63.557 | −25.924 | 1.00 | 45.38 | N |
| ATOM | 1324 | C | LYS | A | 1005 | 111.667 | 67.016 | −21.301 | 1.00 | 38.07 | C |
| ATOM | 1325 | O | LYS | A | 1005 | 112.583 | 67.086 | −20.482 | 1.00 | 37.21 | O |
| ATOM | 1326 | N | GLU | A | 1006 | 110.537 | 67.710 | −21.189 | 1.00 | 38.05 | N |
| ATOM | 1327 | CA | GLU | A | 1006 | 110.297 | 68.639 | −20.083 | 1.00 | 37.97 | C |
| ATOM | 1328 | CB | GLU | A | 1006 | 109.696 | 69.950 | −20.603 | 1.00 | 38.63 | C |
| ATOM | 1329 | CG | GLU | A | 1006 | 110.655 | 70.761 | −21.467 | 1.00 | 39.09 | C |
| ATOM | 1330 | CD | GLU | A | 1006 | 111.955 | 71.087 | −20.750 | 1.00 | 41.12 | C |
| ATOM | 1331 | OE1 | GLU | A | 1006 | 112.998 | 70.505 | −21.111 | 1.00 | 41.85 | O |

APPENDIX 1-continued

| ATOM | 1332 | OE2 | GLU | A | 1006 | 111.928 | 71.913 | −19.814 | 1.00 | 44.52 | O |
|---|---|---|---|---|---|---|---|---|---|---|---|
| ATOM | 1333 | C | GLU | A | 1006 | 109.427 | 68.039 | −18.978 | 1.00 | 37.87 | C |
| ATOM | 1334 | O | GLU | A | 1006 | 109.092 | 68.714 | −18.003 | 1.00 | 36.88 | O |
| ATOM | 1335 | O1P | PTR | A | 1007 | 104.689 | 62.149 | −25.165 | 1.00 | 48.27 | O |
| ATOM | 1336 | P | PTR | A | 1007 | 104.915 | 63.346 | −24.323 | 1.00 | 48.86 | P |
| ATOM | 1337 | O2P | PTR | A | 1007 | 105.466 | 64.485 | −25.205 | 1.00 | 49.05 | O |
| ATOM | 1338 | O3P | PTR | A | 1007 | 103.580 | 63.781 | −23.691 | 1.00 | 47.83 | O |
| ATOM | 1339 | OH | PTR | A | 1007 | 105.990 | 62.970 | −23.179 | 1.00 | 43.86 | O |
| ATOM | 1340 | CZ | PTR | A | 1007 | 106.173 | 63.634 | −22.149 | 1.00 | 41.67 | C |
| ATOM | 1341 | CE2 | PTR | A | 1007 | 106.368 | 62.958 | −20.956 | 1.00 | 39.11 | C |
| ATOM | 1342 | CD2 | PTR | A | 1007 | 106.582 | 63.673 | −19.786 | 1.00 | 39.74 | C |
| ATOM | 1343 | CE1 | PTR | A | 1007 | 106.205 | 65.022 | −22.176 | 1.00 | 41.08 | C |
| ATOM | 1344 | CD1 | PTR | A | 1007 | 106.418 | 65.728 | −20.998 | 1.00 | 40.85 | C |
| ATOM | 1345 | CG | PTR | A | 1007 | 106.624 | 65.066 | −19.789 | 1.00 | 39.56 | C |
| ATOM | 1346 | CB | PTR | A | 1007 | 106.855 | 65.843 | −18.509 | 1.00 | 39.29 | C |
| ATOM | 1347 | CA | PTR | A | 1007 | 108.334 | 66.021 | −18.125 | 1.00 | 38.79 | C |
| ATOM | 1348 | N | PTR | A | 1007 | 109.074 | 66.766 | −19.141 | 1.00 | 38.11 | N |
| ATOM | 1349 | C | PTR | A | 1007 | 109.035 | 64.691 | −17.854 | 1.00 | 39.17 | C |
| ATOM | 1350 | O | PTR | A | 1007 | 109.925 | 64.281 | −18.606 | 1.00 | 38.93 | O |
| ATOM | 1351 | O1P | PTR | A | 1008 | 114.975 | 57.587 | −14.829 | 1.00 | 63.45 | O |
| ATOM | 1352 | P | PTR | A | 1008 | 113.538 | 57.322 | −14.587 | 1.00 | 63.76 | P |
| ATOM | 1353 | O2P | PTR | A | 1008 | 112.772 | 57.344 | −15.926 | 1.00 | 64.26 | O |
| ATOM | 1354 | O3P | PTR | A | 1008 | 113.368 | 55.947 | −13.914 | 1.00 | 63.84 | O |
| ATOM | 1355 | OH | PTR | A | 1008 | 112.975 | 58.461 | −13.598 | 1.00 | 53.96 | O |
| ATOM | 1356 | CZ | PTR | A | 1008 | 112.377 | 59.463 | −13.997 | 1.00 | 50.87 | C |
| ATOM | 1357 | CE2 | PTR | A | 1008 | 113.036 | 60.438 | −14.730 | 1.00 | 50.96 | C |
| ATOM | 1358 | CD2 | PTR | A | 1008 | 112.341 | 61.562 | −15.154 | 1.00 | 48.44 | C |
| ATOM | 1359 | CE1 | PTR | A | 1008 | 111.042 | 59.615 | −13.678 | 1.00 | 49.29 | C |
| ATOM | 1360 | CD1 | PTR | A | 1008 | 110.358 | 60.741 | −14.105 | 1.00 | 48.14 | C |
| ATOM | 1361 | CG | PTR | A | 1008 | 110.992 | 61.732 | −14.851 | 1.00 | 46.34 | C |
| ATOM | 1362 | CB | PTR | A | 1008 | 110.247 | 62.966 | −15.311 | 1.00 | 42.48 | C |
| ATOM | 1363 | CA | PTR | A | 1008 | 109.180 | 62.739 | −16.388 | 1.00 | 40.32 | C |
| ATOM | 1364 | N | PTR | A | 1008 | 108.633 | 64.034 | −16.770 | 1.00 | 39.66 | N |
| ATOM | 1365 | C | PTR | A | 1008 | 108.027 | 61.854 | −15.927 | 1.00 | 39.13 | C |
| ATOM | 1366 | O | PTR | A | 1008 | 107.262 | 62.230 | −15.036 | 1.00 | 38.23 | O |
| ATOM | 1367 | N | LYS | A | 1009 | 107.901 | 60.688 | −16.554 | 1.00 | 38.26 | N |
| ATOM | 1368 | CA | LYS | A | 1009 | 106.842 | 59.740 | −16.228 | 1.00 | 38.07 | C |
| ATOM | 1369 | CB | LYS | A | 1009 | 106.291 | 59.081 | −17.494 | 1.00 | 38.39 | C |
| ATOM | 1370 | CG | LYS | A | 1009 | 105.320 | 59.938 | −18.286 | 1.00 | 39.17 | C |
| ATOM | 1371 | CD | LYS | A | 1009 | 104.634 | 59.097 | −19.345 | 1.00 | 41.93 | C |
| ATOM | 1372 | CE | LYS | A | 1009 | 103.565 | 59.873 | −20.080 | 1.00 | 44.03 | C |
| ATOM | 1373 | NZ | LYS | A | 1009 | 102.761 | 58.969 | −20.950 | 1.00 | 46.00 | N |
| ATOM | 1374 | C | LYS | A | 1009 | 107.335 | 58.671 | −15.260 | 1.00 | 38.26 | C |
| ATOM | 1375 | O | LYS | A | 1009 | 108.307 | 57.967 | −15.537 | 1.00 | 37.32 | O |
| ATOM | 1376 | N | VAL | A | 1010 | 106.656 | 58.564 | −14.122 | 1.00 | 38.64 | N |
| ATOM | 1377 | CA | VAL | A | 1010 | 106.994 | 57.576 | −13.100 | 1.00 | 40.12 | C |
| ATOM | 1378 | CB | VAL | A | 1010 | 108.169 | 58.059 | −12.184 | 1.00 | 40.49 | C |
| ATOM | 1379 | CG1 | VAL | A | 1010 | 107.916 | 59.463 | −11.651 | 1.00 | 39.25 | C |
| ATOM | 1380 | CG2 | VAL | A | 1010 | 108.449 | 57.073 | −11.046 | 1.00 | 41.61 | C |
| ATOM | 1381 | C | VAL | A | 1010 | 105.758 | 57.193 | −12.286 | 1.00 | 40.92 | C |
| ATOM | 1382 | O | VAL | A | 1010 | 104.980 | 58.055 | −11.868 | 1.00 | 40.65 | O |
| ATOM | 1383 | N | LYS | A | 1011 | 105.581 | 55.889 | −12.092 | 1.00 | 42.42 | N |
| ATOM | 1384 | CA | LYS | A | 1011 | 104.505 | 55.357 | −11.266 | 1.00 | 44.78 | C |
| ATOM | 1385 | CB | LYS | A | 1011 | 103.415 | 54.720 | −12.141 | 1.00 | 45.06 | C |
| ATOM | 1386 | CG | LYS | A | 1011 | 102.259 | 54.063 | −11.382 | 1.00 | 46.83 | C |
| ATOM | 1387 | CD | LYS | A | 1011 | 101.354 | 55.077 | −10.703 | 1.00 | 48.61 | C |
| ATOM | 1388 | CE | LYS | A | 1011 | 100.277 | 54.375 | −9.891 | 1.00 | 50.28 | C |
| ATOM | 1389 | NZ | LYS | A | 1011 | 99.457 | 55.335 | −9.105 | 1.00 | 51.98 | N |
| ATOM | 1390 | C | LYS | A | 1011 | 105.094 | 54.355 | −10.276 | 1.00 | 46.28 | C |
| ATOM | 1391 | O | LYS | A | 1011 | 105.367 | 53.202 | −10.621 | 1.00 | 46.10 | O |
| ATOM | 1392 | N | GLU | A | 1012 | 105.299 | 54.818 | −9.048 | 1.00 | 48.17 | N |
| ATOM | 1393 | CA | GLU | A | 1012 | 105.932 | 54.017 | −8.005 | 1.00 | 50.32 | C |
| ATOM | 1394 | CB | GLU | A | 1012 | 106.697 | 54.924 | −7.035 | 1.00 | 50.78 | C |
| ATOM | 1395 | CG | GLU | A | 1012 | 108.028 | 55.423 | −7.591 | 1.00 | 53.99 | C |
| ATOM | 1396 | CD | GLU | A | 1012 | 108.342 | 56.856 | −7.196 | 1.00 | 57.54 | C |
| ATOM | 1397 | OE1 | GLU | A | 1012 | 107.415 | 57.696 | −7.195 | 1.00 | 58.06 | O |
| ATOM | 1398 | OE2 | GLU | A | 1012 | 109.522 | 57.147 | −6.902 | 1.00 | 59.10 | O |
| ATOM | 1399 | C | GLU | A | 1012 | 104.919 | 53.152 | −7.255 | 1.00 | 50.85 | C |
| ATOM | 1400 | O | GLU | A | 1012 | 103.774 | 53.568 | −7.061 | 1.00 | 50.82 | O |
| ATOM | 1401 | N | PRO | A | 1013 | 105.333 | 51.934 | −6.849 | 1.00 | 51.76 | N |
| ATOM | 1402 | CA | PRO | A | 1013 | 104.477 | 51.067 | −6.034 | 1.00 | 52.28 | C |
| ATOM | 1403 | CB | PRO | A | 1013 | 105.295 | 49.777 | −5.908 | 1.00 | 52.23 | C |
| ATOM | 1404 | CG | PRO | A | 1013 | 106.704 | 50.190 | −6.146 | 1.00 | 52.85 | C |
| ATOM | 1405 | CD | PRO | A | 1013 | 106.627 | 51.293 | −7.152 | 1.00 | 51.86 | C |
| ATOM | 1406 | C | PRO | A | 1013 | 104.204 | 51.661 | −4.653 | 1.00 | 52.56 | C |
| ATOM | 1407 | O | PRO | A | 1013 | 105.041 | 52.392 | −4.113 | 1.00 | 52.70 | O |
| ATOM | 1408 | N | GLY | A | 1014 | 103.034 | 51.349 | −4.101 | 1.00 | 52.73 | N |
| ATOM | 1409 | CA | GLY | A | 1014 | 102.642 | 51.843 | −2.785 | 1.00 | 52.70 | C |
| ATOM | 1410 | C | GLY | A | 1014 | 101.742 | 53.061 | −2.853 | 1.00 | 52.50 | C |

APPENDIX 1-continued

| ATOM | 1411 | O | GLY | A | 1014 | 100.935 | 53.200 | -3.777 | 1.00 | 53.14 | O |
|---|---|---|---|---|---|---|---|---|---|---|---|
| ATOM | 1412 | N | GLU | A | 1015 | 101.891 | 53.949 | -1.872 | 1.00 | 51.67 | N |
| ATOM | 1413 | CA | GLU | A | 1015 | 101.014 | 55.111 | -1.736 | 1.00 | 50.43 | C |
| ATOM | 1414 | CB | GLU | A | 1015 | 100.490 | 55.232 | -.299 | 1.00 | 51.15 | C |
| ATOM | 1415 | CG | GLU | A | 1015 | 99.783 | 53.982 | .242 | 1.00 | 53.54 | C |
| ATOM | 1416 | CD | GLU | A | 1015 | 98.528 | 53.603 | -.537 | 1.00 | 56.64 | C |
| ATOM | 1417 | OE1 | GLU | A | 1015 | 97.802 | 54.510 | -1.002 | 1.00 | 57.52 | O |
| ATOM | 1418 | OE2 | GLU | A | 1015 | 98.262 | 52.389 | -.675 | 1.00 | 58.18 | O |
| ATOM | 1419 | C | GLU | A | 1015 | 101.694 | 56.411 | -2.158 | 1.00 | 48.69 | C |
| ATOM | 1420 | O | GLU | A | 1015 | 102.850 | 56.666 | -1.810 | 1.00 | 49.37 | O |
| ATOM | 1421 | N | SER | A | 1016 | 100.958 | 57.226 | -2.910 | 1.00 | 45.82 | N |
| ATOM | 1422 | CA | SER | A | 1016 | 101.433 | 58.529 | -3.358 | 1.00 | 42.96 | C |
| ATOM | 1423 | CB | SER | A | 1016 | 101.254 | 58.666 | -4.873 | 1.00 | 42.89 | C |
| ATOM | 1424 | OG | SER | A | 1016 | 102.191 | 57.864 | -5.569 | 1.00 | 44.42 | O |
| ATOM | 1425 | C | SER | A | 1016 | 100.697 | 59.658 | -2.633 | 1.00 | 40.53 | C |
| ATOM | 1426 | O | SER | A | 1016 | 99.547 | 59.482 | -2.225 | 1.00 | 39.36 | O |
| ATOM | 1427 | N | PRO | A | 1017 | 101.360 | 60.821 | -2.464 | 1.00 | 38.93 | N |
| ATOM | 1428 | CA | PRO | A | 1017 | 100.697 | 61.990 | -1.886 | 1.00 | 37.36 | C |
| ATOM | 1429 | CB | PRO | A | 1017 | 101.865 | 62.913 | -1.534 | 1.00 | 37.20 | C |
| ATOM | 1430 | CG | PRO | A | 1017 | 102.928 | 62.563 | -2.517 | 1.00 | 38.72 | C |
| ATOM | 1431 | CD | PRO | A | 1017 | 102.773 | 61.095 | -2.796 | 1.00 | 38.46 | C |
| ATOM | 1432 | C | PRO | A | 1017 | 99.753 | 62.653 | -2.897 | 1.00 | 36.46 | C |
| ATOM | 1433 | O | PRO | A | 1017 | 99.998 | 63.779 | -3.340 | 1.00 | 35.53 | O |
| ATOM | 1434 | N | ILE | A | 1018 | 98.676 | 61.945 | -3.234 | 1.00 | 35.35 | N |
| ATOM | 1435 | CA | ILE | A | 1018 | 97.741 | 62.352 | -4.292 | 1.00 | 35.25 | C |
| ATOM | 1436 | CB | ILE | A | 1018 | 96.634 | 61.280 | -4.530 | 1.00 | 35.45 | C |
| ATOM | 1437 | CG1 | ILE | A | 1018 | 95.882 | 60.965 | -3.228 | 1.00 | 36.89 | C |
| ATOM | 1438 | CD1 | ILE | A | 1018 | 94.488 | 60.384 | -3.427 | 1.00 | 37.23 | C |
| ATOM | 1439 | CG2 | ILE | A | 1018 | 97.238 | 60.018 | -5.154 | 1.00 | 35.09 | C |
| ATOM | 1440 | C | ILE | A | 1018 | 97.094 | 63.732 | -4.102 | 1.00 | 34.61 | C |
| ATOM | 1441 | O | ILE | A | 1018 | 96.729 | 64.386 | -5.080 | 1.00 | 35.43 | O |
| ATOM | 1442 | N | PHE | A | 1019 | 96.966 | 64.178 | -2.855 | 1.00 | 34.31 | N |
| ATOM | 1443 | CA | PHE | A | 1019 | 96.332 | 65.467 | -2.571 | 1.00 | 33.59 | C |
| ATOM | 1444 | CB | PHE | A | 1019 | 95.668 | 65.454 | -1.191 | 1.00 | 34.35 | C |
| ATOM | 1445 | CG | PHE | A | 1019 | 94.621 | 64.381 | -1.036 | 1.00 | 35.51 | C |
| ATOM | 1446 | CD1 | PHE | A | 1019 | 94.809 | 63.331 | -.142 | 1.00 | 36.69 | C |
| ATOM | 1447 | CE1 | PHE | A | 1019 | 93.845 | 62.333 | .000 | 1.00 | 37.31 | C |
| ATOM | 1448 | CZ | PHE | A | 1019 | 92.687 | 62.375 | -.769 | 1.00 | 36.90 | C |
| ATOM | 1449 | CE2 | PHE | A | 1019 | 92.494 | 63.414 | -1.674 | 1.00 | 36.82 | C |
| ATOM | 1450 | CD2 | PHE | A | 1019 | 93.460 | 64.407 | -1.804 | 1.00 | 36.03 | C |
| ATOM | 1451 | C | PHE | A | 1019 | 97.275 | 66.666 | -2.739 | 1.00 | 33.02 | C |
| ATOM | 1452 | O | PHE | A | 1019 | 96.871 | 67.814 | -2.551 | 1.00 | 32.45 | O |
| ATOM | 1453 | N | TRP | A | 1020 | 98.524 | 66.383 | -3.107 | 1.00 | 32.05 | N |
| ATOM | 1454 | CA | TRP | A | 1020 | 99.500 | 67.410 | -3.469 | 1.00 | 31.45 | C |
| ATOM | 1455 | CB | TRP | A | 1020 | 100.797 | 67.216 | -2.681 | 1.00 | 30.81 | C |
| ATOM | 1456 | CG | TRP | A | 1020 | 100.802 | 67.844 | -1.312 | 1.00 | 30.49 | C |
| ATOM | 1457 | CD1 | TRP | A | 1020 | 101.441 | 68.993 | -.943 | 1.00 | 29.47 | C |
| ATOM | 1458 | NE1 | TRP | A | 1020 | 101.224 | 69.251 | .391 | 1.00 | 30.97 | N |
| ATOM | 1459 | CE2 | TRP | A | 1020 | 100.436 | 68.259 | .913 | 1.00 | 30.77 | C |
| ATOM | 1460 | CD2 | TRP | A | 1020 | 100.149 | 67.351 | -.132 | 1.00 | 31.06 | C |
| ATOM | 1461 | CE3 | TRP | A | 1020 | 99.349 | 66.233 | .143 | 1.00 | 31.15 | C |
| ATOM | 1462 | CZ3 | TRP | A | 1020 | 98.867 | 66.059 | 1.438 | 1.00 | 31.36 | C |
| ATOM | 1463 | CH2 | TRP | A | 1020 | 99.168 | 66.983 | 2.454 | 1.00 | 30.99 | C |
| ATOM | 1464 | CZ2 | TRP | A | 1020 | 99.949 | 68.086 | 2.212 | 1.00 | 30.84 | C |
| ATOM | 1465 | C | TRP | A | 1020 | 99.797 | 67.361 | -4.969 | 1.00 | 31.75 | C |
| ATOM | 1466 | O | TRP | A | 1020 | 100.491 | 68.230 | -5.502 | 1.00 | 31.94 | O |
| ATOM | 1467 | N | TYR | A | 1021 | 99.258 | 66.343 | -5.637 | 1.00 | 32.25 | N |
| ATOM | 1468 | CA | TYR | A | 1021 | 99.537 | 66.066 | -7.049 | 1.00 | 33.22 | C |
| ATOM | 1469 | CB | TYR | A | 1021 | 99.209 | 64.604 | -7.367 | 1.00 | 33.90 | C |
| ATOM | 1470 | CG | TYR | A | 1021 | 100.350 | 63.617 | -7.208 | 1.00 | 35.88 | C |
| ATOM | 1471 | CD1 | TYR | A | 1021 | 101.403 | 63.855 | -6.323 | 1.00 | 35.90 | C |
| ATOM | 1472 | CE1 | TYR | A | 1021 | 102.442 | 62.939 | -6.179 | 1.00 | 36.24 | C |
| ATOM | 1473 | CZ | TYR | A | 1021 | 102.426 | 61.769 | -6.915 | 1.00 | 36.01 | C |
| ATOM | 1474 | OH | TYR | A | 1021 | 103.446 | 60.857 | -6.776 | 1.00 | 39.91 | O |
| ATOM | 1475 | CE2 | TYR | A | 1021 | 101.386 | 61.504 | -7.789 | 1.00 | 38.04 | C |
| ATOM | 1476 | CD2 | TYR | A | 1021 | 100.357 | 62.425 | -7.930 | 1.00 | 36.09 | C |
| ATOM | 1477 | C | TYR | A | 1021 | 98.768 | 66.964 | -8.012 | 1.00 | 32.81 | C |
| ATOM | 1478 | O | TYR | A | 1021 | 97.584 | 67.244 | -7.810 | 1.00 | 33.07 | O |
| ATOM | 1479 | N | ALA | A | 1022 | 99.456 | 67.403 | -9.062 | 1.00 | 32.27 | N |
| ATOM | 1480 | CA | ALA | A | 1022 | 98.825 | 68.075 | -10.195 | 1.00 | 32.15 | C |
| ATOM | 1481 | CB | ALA | A | 1022 | 99.891 | 68.660 | -11.114 | 1.00 | 31.15 | C |
| ATOM | 1482 | C | ALA | A | 1022 | 97.953 | 67.063 | -10.950 | 1.00 | 31.87 | C |
| ATOM | 1483 | O | ALA | A | 1022 | 98.216 | 65.862 | -10.879 | 1.00 | 31.24 | O |
| ATOM | 1484 | N | PRO | A | 1023 | 96.915 | 67.538 | -11.673 | 1.00 | 32.08 | N |
| ATOM | 1485 | CA | PRO | A | 1023 | 96.000 | 66.625 | -12.373 | 1.00 | 32.22 | C |
| ATOM | 1486 | CB | PRO | A | 1023 | 95.044 | 67.572 | -13.108 | 1.00 | 32.54 | C |
| ATOM | 1487 | CG | PRO | A | 1023 | 95.124 | 68.854 | -12.362 | 1.00 | 32.55 | C |
| ATOM | 1488 | CD | PRO | A | 1023 | 96.537 | 68.947 | -11.885 | 1.00 | 32.48 | C |
| ATOM | 1489 | C | PRO | A | 1023 | 96.704 | 65.701 | -13.371 | 1.00 | 32.30 | C |

APPENDIX 1-continued

| ATOM | 1490 | O | PRO | A | 1023 | 96.339 | 64.524 | −13.477 | 1.00 | 32.57 | O |
|---|---|---|---|---|---|---|---|---|---|---|---|
| ATOM | 1491 | N | GLU | A | 1024 | 97.701 | 66.227 | −14.083 | 1.00 | 31.93 | N |
| ATOM | 1492 | CA | GLU | A | 1024 | 98.444 | 65.440 | −15.071 | 1.00 | 32.27 | C |
| ATOM | 1493 | CB | GLU | A | 1024 | 99.195 | 66.342 | −16.067 | 1.00 | 32.33 | C |
| ATOM | 1494 | CG | GLU | A | 1024 | 100.480 | 66.997 | −15.539 | 1.00 | 32.86 | C |
| ATOM | 1495 | CD | GLU | A | 1024 | 100.243 | 68.252 | −14.706 | 1.00 | 33.57 | C |
| ATOM | 1496 | OE1 | GLU | A | 1024 | 99.073 | 68.616 | −14.464 | 1.00 | 33.98 | O |
| ATOM | 1497 | OE2 | GLU | A | 1024 | 101.242 | 68.891 | −14.306 | 1.00 | 33.06 | O |
| ATOM | 1498 | C | GLU | A | 1024 | 99.382 | 64.418 | −14.421 | 1.00 | 32.34 | C |
| ATOM | 1499 | O | GLU | A | 1024 | 99.793 | 63.452 | −15.065 | 1.00 | 32.80 | O |
| ATOM | 1500 | N | SER | A | 1025 | 99.711 | 64.633 | −13.148 | 1.00 | 32.21 | N |
| ATOM | 1501 | CA | SER | A | 1025 | 100.458 | 63.645 | −12.368 | 1.00 | 32.31 | C |
| ATOM | 1502 | CB | SER | A | 1025 | 101.122 | 64.295 | −11.153 | 1.00 | 31.50 | C |
| ATOM | 1503 | OG | SER | A | 1025 | 102.008 | 65.324 | −11.550 | 1.00 | 31.15 | O |
| ATOM | 1504 | C | SER | A | 1025 | 99.546 | 62.504 | −11.922 | 1.00 | 33.06 | C |
| ATOM | 1505 | O | SER | A | 1025 | 99.996 | 61.369 | −11.749 | 1.00 | 32.78 | O |
| ATOM | 1506 | N | LEU | A | 1026 | 98.266 | 62.815 | −11.736 | 1.00 | 33.64 | N |
| ATOM | 1507 | CA | LEU | A | 1026 | 97.265 | 61.822 | −11.343 | 1.00 | 34.21 | C |
| ATOM | 1508 | CB | LEU | A | 1026 | 96.053 | 62.504 | −10.701 | 1.00 | 34.06 | C |
| ATOM | 1509 | CG | LEU | A | 1026 | 96.230 | 63.217 | −9.360 | 1.00 | 34.81 | C |
| ATOM | 1510 | CD1 | LEU | A | 1026 | 95.020 | 64.091 | −9.076 | 1.00 | 35.54 | C |
| ATOM | 1511 | CD2 | LEU | A | 1026 | 96.449 | 62.215 | −8.234 | 1.00 | 37.39 | C |
| ATOM | 1512 | C | LEU | A | 1026 | 96.801 | 60.984 | −12.529 | 1.00 | 34.35 | C |
| ATOM | 1513 | O | LEU | A | 1026 | 96.628 | 59.770 | −12.410 | 1.00 | 34.81 | O |
| ATOM | 1514 | N | THR | A | 1027 | 96.601 | 61.643 | −13.668 | 1.00 | 34.79 | N |
| ATOM | 1515 | CA | THR | A | 1027 | 96.025 | 61.011 | −14.855 | 1.00 | 35.42 | C |
| ATOM | 1516 | CB | THR | A | 1027 | 95.208 | 62.017 | −15.695 | 1.00 | 35.54 | C |
| ATOM | 1517 | OG1 | THR | A | 1027 | 95.994 | 63.191 | −15.936 | 1.00 | 35.79 | O |
| ATOM | 1518 | CG2 | THR | A | 1027 | 93.930 | 62.405 | −14.978 | 1.00 | 36.35 | C |
| ATOM | 1519 | C | THR | A | 1027 | 97.061 | 60.372 | −15.773 | 1.00 | 35.48 | C |
| ATOM | 1520 | O | THR | A | 1027 | 96.795 | 59.332 | −16.377 | 1.00 | 35.57 | O |
| ATOM | 1521 | N | GLU | A | 1028 | 98.228 | 61.004 | −15.882 | 1.00 | 35.80 | N |
| ATOM | 1522 | CA | GLU | A | 1028 | 99.247 | 60.603 | −16.854 | 1.00 | 36.47 | C |
| ATOM | 1523 | CB | GLU | A | 1028 | 99.473 | 61.719 | −17.883 | 1.00 | 36.35 | C |
| ATOM | 1524 | CG | GLU | A | 1028 | 98.239 | 62.118 | −18.686 | 1.00 | 39.09 | C |
| ATOM | 1525 | CD | GLU | A | 1028 | 98.503 | 63.288 | −19.616 | 1.00 | 39.02 | C |
| ATOM | 1526 | OE1 | GLU | A | 1028 | 97.996 | 64.396 | −19.336 | 1.00 | 45.52 | O |
| ATOM | 1527 | OE2 | GLU | A | 1028 | 99.226 | 63.106 | −20.619 | 1.00 | 43.74 | O |
| ATOM | 1528 | C | GLU | A | 1028 | 100.584 | 60.222 | −16.212 | 1.00 | 34.85 | C |
| ATOM | 1529 | O | GLU | A | 1028 | 101.500 | 59.774 | −16.907 | 1.00 | 34.44 | O |
| ATOM | 1530 | N | SER | A | 1029 | 100.686 | 60.402 | −14.893 | 1.00 | 33.41 | N |
| ATOM | 1531 | CA | SER | A | 1029 | 101.934 | 60.179 | −14.146 | 1.00 | 32.57 | C |
| ATOM | 1532 | CB | SER | A | 1029 | 102.361 | 58.702 | −14.189 | 1.00 | 32.34 | C |
| ATOM | 1533 | OG | SER | A | 1029 | 101.383 | 57.860 | −13.606 | 1.00 | 34.62 | O |
| ATOM | 1534 | C | SER | A | 1029 | 103.074 | 61.082 | −14.632 | 1.00 | 31.35 | C |
| ATOM | 1535 | O | SER | A | 1029 | 104.248 | 60.711 | −14.559 | 1.00 | 30.40 | O |
| ATOM | 1536 | N | LYS | A | 1030 | 102.709 | 62.266 | −15.120 | 1.00 | 31.01 | N |
| ATOM | 1537 | CA | LYS | A | 1030 | 103.663 | 63.238 | −15.648 | 1.00 | 31.06 | C |
| ATOM | 1538 | CB | LYS | A | 1030 | 103.028 | 64.049 | −16.775 | 1.00 | 31.18 | C |
| ATOM | 1539 | CG | LYS | A | 1030 | 103.155 | 63.460 | −18.163 | 1.00 | 34.65 | C |
| ATOM | 1540 | CD | LYS | A | 1030 | 102.499 | 64.408 | −19.157 | 1.00 | 38.16 | C |
| ATOM | 1541 | CE | LYS | A | 1030 | 102.932 | 64.143 | −20.578 | 1.00 | 39.89 | C |
| ATOM | 1542 | NZ | LYS | A | 1030 | 102.511 | 65.258 | −21.478 | 1.00 | 39.00 | N |
| ATOM | 1543 | C | LYS | A | 1030 | 104.133 | 64.191 | −14.557 | 1.00 | 30.60 | C |
| ATOM | 1544 | O | LYS | A | 1030 | 103.319 | 64.822 | −13.879 | 1.00 | 30.78 | O |
| ATOM | 1545 | N | PHE | A | 1031 | 105.450 | 64.295 | −14.403 | 1.00 | 29.97 | N |
| ATOM | 1546 | CA | PHE | A | 1031 | 106.048 | 65.181 | −13.411 | 1.00 | 29.33 | C |
| ATOM | 1547 | CB | PHE | A | 1031 | 106.736 | 64.374 | −12.306 | 1.00 | 28.90 | C |
| ATOM | 1548 | CG | PHE | A | 1031 | 105.787 | 63.537 | −11.496 | 1.00 | 30.18 | C |
| ATOM | 1549 | CD1 | PHE | A | 1031 | 105.458 | 62.246 | −11.900 | 1.00 | 28.61 | C |
| ATOM | 1550 | CE1 | PHE | A | 1031 | 104.572 | 61.470 | −11.163 | 1.00 | 26.05 | C |
| ATOM | 1551 | CZ | PHE | A | 1031 | 104.004 | 61.982 | −10.011 | 1.00 | 28.86 | C |
| ATOM | 1552 | CE2 | PHE | A | 1031 | 104.322 | 63.272 | −9.592 | 1.00 | 30.52 | C |
| ATOM | 1553 | CD2 | PHE | A | 1031 | 105.208 | 64.044 | −10.338 | 1.00 | 28.62 | C |
| ATOM | 1554 | C | PHE | A | 1031 | 107.019 | 66.145 | −14.077 | 1.00 | 28.97 | C |
| ATOM | 1555 | O | PHE | A | 1031 | 107.803 | 65.757 | −14.943 | 1.00 | 28.52 | O |
| ATOM | 1556 | N | SER | A | 1032 | 106.946 | 67.406 | −13.663 | 1.00 | 28.76 | N |
| ATOM | 1557 | CA | SER | A | 1032 | 107.683 | 68.492 | −14.294 | 1.00 | 28.03 | C |
| ATOM | 1558 | CB | SER | A | 1032 | 106.911 | 68.991 | −15.516 | 1.00 | 28.06 | C |
| ATOM | 1559 | OG | SER | A | 1032 | 105.623 | 69.448 | −15.134 | 1.00 | 28.68 | O |
| ATOM | 1560 | C | SER | A | 1032 | 107.841 | 69.635 | −13.301 | 1.00 | 28.11 | C |
| ATOM | 1561 | O | SER | A | 1032 | 107.267 | 69.598 | −12.209 | 1.00 | 26.90 | O |
| ATOM | 1562 | N | VAL | A | 1033 | 108.610 | 70.652 | −13.687 | 1.00 | 28.34 | N |
| ATOM | 1563 | CA | VAL | A | 1033 | 108.706 | 71.881 | −12.902 | 1.00 | 28.54 | C |
| ATOM | 1564 | CB | VAL | A | 1033 | 109.586 | 72.950 | −13.595 | 1.00 | 28.84 | C |
| ATOM | 1565 | CG1 | VAL | A | 1033 | 109.582 | 74.263 | −12.798 | 1.00 | 25.97 | C |
| ATOM | 1566 | CG2 | VAL | A | 1033 | 111.010 | 72.444 | −13.767 | 1.00 | 28.01 | C |
| ATOM | 1567 | C | VAL | A | 1033 | 107.300 | 72.431 | −12.633 | 1.00 | 28.53 | C |
| ATOM | 1568 | O | VAL | A | 1033 | 107.001 | 72.859 | −11.522 | 1.00 | 28.39 | O |

APPENDIX 1-continued

| ATOM | 1569 | N | ALA | A | 1034 | 106.439 | 72.383 | −13.650 | 1.00 | 28.91 | N |
| --- | --- | --- | --- | --- | --- | --- | --- | --- | --- | --- | --- |
| ATOM | 1570 | CA | ALA | A | 1034 | 105.058 | 72.851 | −13.530 | 1.00 | 28.36 | C |
| ATOM | 1571 | CB | ALA | A | 1034 | 104.373 | 72.847 | −14.888 | 1.00 | 28.43 | C |
| ATOM | 1572 | C | ALA | A | 1034 | 104.235 | 72.061 | −12.506 | 1.00 | 28.76 | C |
| ATOM | 1573 | O | ALA | A | 1034 | 103.373 | 72.631 | −11.836 | 1.00 | 28.92 | O |
| ATOM | 1574 | N | SER | A | 1035 | 104.497 | 70.760 | −12.384 | 1.00 | 28.37 | N |
| ATOM | 1575 | CA | SER | A | 1035 | 103.834 | 69.957 | −11.356 | 1.00 | 28.47 | C |
| ATOM | 1576 | CB | SER | A | 1035 | 103.885 | 68.456 | −11.673 | 1.00 | 28.86 | C |
| ATOM | 1577 | OG | SER | A | 1035 | 105.190 | 67.922 | −11.559 | 1.00 | 27.92 | O |
| ATOM | 1578 | C | SER | A | 1035 | 104.381 | 70.269 | −9.956 | 1.00 | 28.16 | C |
| ATOM | 1579 | O | SER | A | 1035 | 103.624 | 70.260 | −8.982 | 1.00 | 28.59 | O |
| ATOM | 1580 | N | ASP | A | 1036 | 105.680 | 70.568 | −9.868 | 1.00 | 26.57 | N |
| ATOM | 1581 | CA | ASP | A | 1036 | 106.276 | 71.086 | −8.629 | 1.00 | 26.36 | C |
| ATOM | 1582 | CB | ASP | A | 1036 | 107.793 | 71.280 | −8.770 | 1.00 | 26.01 | C |
| ATOM | 1583 | CG | ASP | A | 1036 | 108.591 | 70.006 | −8.501 | 1.00 | 26.39 | C |
| ATOM | 1584 | OD1 | ASP | A | 1036 | 108.020 | 68.994 | −8.033 | 1.00 | 24.85 | O |
| ATOM | 1585 | OD2 | ASP | A | 1036 | 109.814 | 70.028 | −8.757 | 1.00 | 25.54 | O |
| ATOM | 1586 | C | ASP | A | 1036 | 105.622 | 72.413 | −8.222 | 1.00 | 26.26 | C |
| ATOM | 1587 | O | ASP | A | 1036 | 105.364 | 72.641 | −7.040 | 1.00 | 26.34 | O |
| ATOM | 1588 | N | VAL | A | 1037 | 105.359 | 73.277 | −9.204 | 1.00 | 26.41 | N |
| ATOM | 1589 | CA | VAL | A | 1037 | 104.658 | 74.551 | −8.965 | 1.00 | 27.03 | C |
| ATOM | 1590 | CB | VAL | A | 1037 | 104.613 | 75.447 | −10.236 | 1.00 | 27.39 | C |
| ATOM | 1591 | CG1 | VAL | A | 1037 | 103.656 | 76.635 | −10.052 | 1.00 | 27.37 | C |
| ATOM | 1592 | CG2 | VAL | A | 1037 | 106.007 | 75.959 | −10.577 | 1.00 | 28.27 | C |
| ATOM | 1593 | C | VAL | A | 1037 | 103.248 | 74.326 | −8.405 | 1.00 | 26.90 | C |
| ATOM | 1594 | O | VAL | A | 1037 | 102.847 | 74.999 | −7.453 | 1.00 | 27.00 | O |
| ATOM | 1595 | N | TRP | A | 1038 | 102.506 | 73.382 | −8.989 | 1.00 | 27.10 | N |
| ATOM | 1596 | CA | TRP | A | 1038 | 101.193 | 73.003 | −8.459 | 1.00 | 27.11 | C |
| ATOM | 1597 | CB | TRP | A | 1038 | 100.575 | 71.843 | −9.255 | 1.00 | 27.26 | C |
| ATOM | 1598 | CG | TRP | A | 1038 | 99.267 | 71.333 | −8.679 | 1.00 | 27.41 | C |
| ATOM | 1599 | CD1 | TRP | A | 1038 | 99.102 | 70.611 | −7.529 | 1.00 | 27.10 | C |
| ATOM | 1600 | NE1 | TRP | A | 1038 | 97.771 | 70.330 | −7.329 | 1.00 | 29.42 | N |
| ATOM | 1601 | CE2 | TRP | A | 1038 | 97.044 | 70.865 | −8.360 | 1.00 | 27.70 | C |
| ATOM | 1602 | CD2 | TRP | A | 1038 | 97.954 | 71.504 | −9.234 | 1.00 | 27.76 | C |
| ATOM | 1603 | CE3 | TRP | A | 1038 | 97.459 | 72.132 | −10.385 | 1.00 | 28.25 | C |
| ATOM | 1604 | CZ3 | TRP | A | 1038 | 96.083 | 72.106 | −10.623 | 1.00 | 27.50 | C |
| ATOM | 1605 | CH2 | TRP | A | 1038 | 95.203 | 71.463 | −9.731 | 1.00 | 27.37 | C |
| ATOM | 1606 | CZ2 | TRP | A | 1038 | 95.664 | 70.838 | −8.600 | 1.00 | 27.12 | C |
| ATOM | 1607 | C | TRP | A | 1038 | 101.300 | 72.643 | −6.977 | 1.00 | 27.33 | C |
| ATOM | 1608 | O | TRP | A | 1038 | 100.582 | 73.202 | −6.146 | 1.00 | 27.38 | O |
| ATOM | 1609 | N | SER | A | 1039 | 102.204 | 71.716 | −6.658 | 1.00 | 27.53 | N |
| ATOM | 1610 | CA | SER | A | 1039 | 102.433 | 71.282 | −5.279 | 1.00 | 27.06 | C |
| ATOM | 1611 | CB | SER | A | 1039 | 103.453 | 70.140 | −5.233 | 1.00 | 26.75 | C |
| ATOM | 1612 | OG | SER | A | 1039 | 102.969 | 69.002 | −5.928 | 1.00 | 27.57 | O |
| ATOM | 1613 | C | SER | A | 1039 | 102.885 | 72.433 | −4.382 | 1.00 | 27.30 | C |
| ATOM | 1614 | O | SER | A | 1039 | 102.520 | 72.485 | −3.205 | 1.00 | 27.51 | O |
| ATOM | 1615 | N | PHE | A | 1040 | 103.678 | 73.349 | −4.935 | 1.00 | 27.63 | N |
| ATOM | 1616 | CA | PHE | A | 1040 | 104.051 | 74.560 | −4.202 | 1.00 | 28.56 | C |
| ATOM | 1617 | CB | PHE | A | 1040 | 105.029 | 75.440 | −4.990 | 1.00 | 28.05 | C |
| ATOM | 1618 | CG | PHE | A | 1040 | 105.159 | 76.822 | −4.426 | 1.00 | 30.38 | C |
| ATOM | 1619 | CD1 | PHE | A | 1040 | 106.016 | 77.073 | −3.359 | 1.00 | 32.21 | C |
| ATOM | 1620 | CE1 | PHE | A | 1040 | 106.109 | 78.345 | −2.811 | 1.00 | 33.61 | C |
| ATOM | 1621 | CZ | PHE | A | 1040 | 105.331 | 79.377 | −3.324 | 1.00 | 32.04 | C |
| ATOM | 1622 | CE2 | PHE | A | 1040 | 104.464 | 79.135 | −4.378 | 1.00 | 33.11 | C |
| ATOM | 1623 | CD2 | PHE | A | 1040 | 104.378 | 77.863 | −4.920 | 1.00 | 29.37 | C |
| ATOM | 1624 | C | PHE | A | 1040 | 102.818 | 75.377 | −3.790 | 1.00 | 28.61 | C |
| ATOM | 1625 | O | PHE | A | 1040 | 102.793 | 75.961 | −2.708 | 1.00 | 29.53 | O |
| ATOM | 1626 | N | GLY | A | 1041 | 101.809 | 75.422 | −4.659 | 1.00 | 28.09 | N |
| ATOM | 1627 | CA | GLY | A | 1041 | 100.525 | 76.046 | −4.323 | 1.00 | 28.70 | C |
| ATOM | 1628 | C | GLY | A | 1041 | 99.881 | 75.412 | −3.100 | 1.00 | 28.31 | C |
| ATOM | 1629 | O | GLY | A | 1041 | 99.328 | 76.111 | −2.246 | 1.00 | 27.91 | O |
| ATOM | 1630 | N | VAL | A | 1042 | 99.964 | 74.085 | −3.017 | 1.00 | 28.99 | N |
| ATOM | 1631 | CA | VAL | A | 1042 | 99.440 | 73.337 | −1.869 | 1.00 | 29.48 | C |
| ATOM | 1632 | CB | VAL | A | 1042 | 99.399 | 71.811 | −2.131 | 1.00 | 29.46 | C |
| ATOM | 1633 | CG1 | VAL | A | 1042 | 98.679 | 71.089 | −.998 | 1.00 | 29.26 | C |
| ATOM | 1634 | CG2 | VAL | A | 1042 | 98.714 | 71.509 | −3.458 | 1.00 | 28.62 | C |
| ATOM | 1635 | C | VAL | A | 1042 | 100.257 | 73.642 | −.609 | 1.00 | 30.13 | C |
| ATOM | 1636 | O | VAL | A | 1042 | 99.688 | 73.808 | .475 | 1.00 | 31.20 | O |
| ATOM | 1637 | N | VAL | A | 1043 | 101.580 | 73.732 | −.760 | 1.00 | 29.03 | N |
| ATOM | 1638 | CA | VAL | A | 1043 | 102.465 | 74.143 | .337 | 1.00 | 28.30 | C |
| ATOM | 1639 | CB | VAL | A | 1043 | 103.966 | 74.148 | −.083 | 1.00 | 28.06 | C |
| ATOM | 1640 | CG1 | VAL | A | 1043 | 104.844 | 74.748 | 1.014 | 1.00 | 28.64 | C |
| ATOM | 1641 | CG2 | VAL | A | 1043 | 104.438 | 72.740 | −.407 | 1.00 | 27.90 | C |
| ATOM | 1642 | C | VAL | A | 1043 | 102.061 | 75.516 | .884 | 1.00 | 28.18 | C |
| ATOM | 1643 | O | VAL | A | 1043 | 101.958 | 75.697 | 2.102 | 1.00 | 28.56 | O |
| ATOM | 1644 | N | LEU | A | 1044 | 101.825 | 76.471 | −.016 | 1.00 | 26.63 | N |
| ATOM | 1645 | CA | LEU | A | 1044 | 101.370 | 77.808 | .374 | 1.00 | 27.06 | C |
| ATOM | 1646 | CB | LEU | A | 1044 | 101.269 | 78.731 | −.852 | 1.00 | 26.72 | C |
| ATOM | 1647 | CG | LEU | A | 1044 | 101.052 | 80.239 | −.652 | 1.00 | 27.02 | C |

APPENDIX 1-continued

| ATOM | 1648 | CD1 | LEU | A | 1044 | 102.078 | 80.861 | .296 | 1.00 | 26.10 | C |
|---|---|---|---|---|---|---|---|---|---|---|---|
| ATOM | 1649 | CD2 | LEU | A | 1044 | 101.089 | 80.942 | −1.995 | 1.00 | 26.79 | C |
| ATOM | 1650 | C | LEU | A | 1044 | 100.040 | 77.746 | 1.124 | 1.00 | 26.91 | C |
| ATOM | 1651 | O | LEU | A | 1044 | 99.865 | 78.421 | 2.143 | 1.00 | 27.65 | O |
| ATOM | 1652 | N | TYR | A | 1045 | 99.109 | 76.941 | .612 | 1.00 | 27.51 | N |
| ATOM | 1653 | CA | TYR | A | 1045 | 97.854 | 76.657 | 1.305 | 1.00 | 27.86 | C |
| ATOM | 1654 | CB | TYR | A | 1045 | 96.991 | 75.670 | .508 | 1.00 | 28.37 | C |
| ATOM | 1655 | CG | TYR | A | 1045 | 95.775 | 75.176 | 1.269 | 1.00 | 28.94 | C |
| ATOM | 1656 | CD1 | TYR | A | 1045 | 94.582 | 75.905 | 1.276 | 1.00 | 28.81 | C |
| ATOM | 1657 | CE1 | TYR | A | 1045 | 93.472 | 75.456 | 1.981 | 1.00 | 28.88 | C |
| ATOM | 1658 | CZ | TYR | A | 1045 | 93.550 | 74.268 | 2.686 | 1.00 | 30.65 | C |
| ATOM | 1659 | OH | TYR | A | 1045 | 92.460 | 73.814 | 3.385 | 1.00 | 31.78 | O |
| ATOM | 1660 | CE2 | TYR | A | 1045 | 94.722 | 73.528 | 2.693 | 1.00 | 29.71 | C |
| ATOM | 1661 | CD2 | TYR | A | 1045 | 95.823 | 73.985 | 1.991 | 1.00 | 29.50 | C |
| ATOM | 1662 | C | TYR | A | 1045 | 98.109 | 76.124 | 2.716 | 1.00 | 27.50 | C |
| ATOM | 1663 | O | TYR | A | 1045 | 97.561 | 76.650 | 3.682 | 1.00 | 26.55 | O |
| ATOM | 1664 | N | GLU | A | 1046 | 98.941 | 75.085 | 2.822 | 1.00 | 27.70 | N |
| ATOM | 1665 | CA | GLU | A | 1046 | 99.296 | 74.487 | 4.116 | 1.00 | 27.96 | C |
| ATOM | 1666 | CB | GLU | A | 1046 | 100.437 | 73.479 | 3.964 | 1.00 | 27.76 | C |
| ATOM | 1667 | CG | GLU | A | 1046 | 100.110 | 72.187 | 3.263 | 1.00 | 28.14 | C |
| ATOM | 1668 | CD | GLU | A | 1046 | 101.276 | 71.215 | 3.333 | 1.00 | 28.32 | C |
| ATOM | 1669 | OE1 | GLU | A | 1046 | 101.445 | 70.566 | 4.387 | 1.00 | 23.96 | O |
| ATOM | 1670 | OE2 | GLU | A | 1046 | 102.030 | 71.112 | 2.341 | 1.00 | 29.51 | O |
| ATOM | 1671 | C | GLU | A | 1046 | 99.727 | 75.548 | 5.124 | 1.00 | 27.58 | C |
| ATOM | 1672 | O | GLU | A | 1046 | 99.211 | 75.599 | 6.244 | 1.00 | 27.43 | O |
| ATOM | 1673 | N | LEU | A | 1047 | 100.675 | 76.386 | 4.713 | 1.00 | 27.84 | N |
| ATOM | 1674 | CA | LEU | A | 1047 | 101.260 | 77.403 | 5.586 | 1.00 | 28.76 | C |
| ATOM | 1675 | CB | LEU | A | 1047 | 102.357 | 78.188 | 4.856 | 1.00 | 28.14 | C |
| ATOM | 1676 | CG | LEU | A | 1047 | 103.662 | 77.458 | 4.501 | 1.00 | 29.79 | C |
| ATOM | 1677 | CD1 | LEU | A | 1047 | 104.561 | 78.356 | 3.664 | 1.00 | 29.26 | C |
| ATOM | 1678 | CD2 | LEU | A | 1047 | 104.393 | 76.983 | 5.746 | 1.00 | 27.60 | C |
| ATOM | 1679 | C | LEU | A | 1047 | 100.218 | 78.363 | 6.148 | 1.00 | 28.98 | C |
| ATOM | 1680 | O | LEU | A | 1047 | 100.236 | 78.681 | 7.337 | 1.00 | 28.93 | O |
| ATOM | 1681 | N | PHE | A | 1048 | 99.309 | 78.816 | 5.290 | 1.00 | 29.40 | N |
| ATOM | 1682 | CA | PHE | A | 1048 | 98.295 | 79.779 | 5.706 | 1.00 | 29.37 | C |
| ATOM | 1683 | CB | PHE | A | 1048 | 97.854 | 80.655 | 4.526 | 1.00 | 29.12 | C |
| ATOM | 1684 | CG | PHE | A | 1048 | 98.804 | 81.793 | 4.248 | 1.00 | 29.83 | C |
| ATOM | 1685 | CD1 | PHE | A | 1048 | 99.979 | 81.582 | 3.524 | 1.00 | 28.48 | C |
| ATOM | 1686 | CE1 | PHE | A | 1048 | 100.872 | 82.627 | 3.288 | 1.00 | 29.32 | C |
| ATOM | 1687 | CZ | PHE | A | 1048 | 100.593 | 83.900 | 3.780 | 1.00 | 29.46 | C |
| ATOM | 1688 | CE2 | PHE | A | 1048 | 99.427 | 84.120 | 4.509 | 1.00 | 29.99 | C |
| ATOM | 1689 | CD2 | PHE | A | 1048 | 98.544 | 83.065 | 4.744 | 1.00 | 27.87 | C |
| ATOM | 1690 | C | PHE | A | 1048 | 97.126 | 79.161 | 6.482 | 1.00 | 29.14 | C |
| ATOM | 1691 | O | PHE | A | 1048 | 96.357 | 79.880 | 7.119 | 1.00 | 29.87 | O |
| ATOM | 1692 | N | THR | A | 1049 | 97.018 | 77.832 | 6.457 | 1.00 | 29.19 | N |
| ATOM | 1693 | CA | THR | A | 1049 | 96.093 | 77.127 | 7.353 | 1.00 | 29.30 | C |
| ATOM | 1694 | CB | THR | A | 1049 | 95.652 | 75.739 | 6.810 | 1.00 | 29.27 | C |
| ATOM | 1695 | OG1 | THR | A | 1049 | 96.762 | 74.831 | 6.811 | 1.00 | 28.87 | O |
| ATOM | 1696 | CG2 | THR | A | 1049 | 95.072 | 75.849 | 5.410 | 1.00 | 28.21 | C |
| ATOM | 1697 | C | THR | A | 1049 | 96.695 | 76.931 | 8.746 | 1.00 | 29.83 | C |
| ATOM | 1698 | O | THR | A | 1049 | 96.001 | 76.496 | 9.668 | 1.00 | 29.63 | O |
| ATOM | 1699 | N | TYR | A | 1050 | 97.984 | 77.249 | 8.888 | 1.00 | 30.41 | N |
| ATOM | 1700 | CA | TYR | A | 1050 | 98.745 | 76.994 | 10.125 | 1.00 | 31.65 | C |
| ATOM | 1701 | CB | TYR | A | 1050 | 98.339 | 77.973 | 11.235 | 1.00 | 30.70 | C |
| ATOM | 1702 | CG | TYR | A | 1050 | 98.938 | 79.352 | 11.070 | 1.00 | 29.78 | C |
| ATOM | 1703 | CD1 | TYR | A | 1050 | 98.325 | 80.312 | 10.265 | 1.00 | 27.38 | C |
| ATOM | 1704 | CE1 | TYR | A | 1050 | 98.878 | 81.580 | 10.110 | 1.00 | 26.98 | C |
| ATOM | 1705 | CZ | TYR | A | 1050 | 100.055 | 81.892 | 10.769 | 1.00 | 28.87 | C |
| ATOM | 1706 | OH | TYR | A | 1050 | 100.616 | 83.140 | 10.627 | 1.00 | 30.06 | O |
| ATOM | 1707 | CE2 | TYR | A | 1050 | 100.679 | 80.952 | 11.569 | 1.00 | 27.74 | C |
| ATOM | 1708 | CD2 | TYR | A | 1050 | 100.121 | 79.695 | 11.715 | 1.00 | 27.08 | C |
| ATOM | 1709 | C | TYR | A | 1050 | 98.653 | 75.534 | 10.594 | 1.00 | 32.60 | C |
| ATOM | 1710 | O | TYR | A | 1050 | 98.699 | 75.245 | 11.795 | 1.00 | 33.38 | O |
| ATOM | 1711 | N | ILE | A | 1051 | 98.541 | 74.630 | 9.619 | 1.00 | 33.56 | N |
| ATOM | 1712 | CA | ILE | A | 1051 | 98.409 | 73.179 | 9.829 | 1.00 | 34.36 | C |
| ATOM | 1713 | CB | ILE | A | 1051 | 99.761 | 72.492 | 10.250 | 1.00 | 34.47 | C |
| ATOM | 1714 | CG1 | ILE | A | 1051 | 100.988 | 73.181 | 9.619 | 1.00 | 33.68 | C |
| ATOM | 1715 | CD1 | ILE | A | 1051 | 101.113 | 73.061 | 8.100 | 1.00 | 35.02 | C |
| ATOM | 1716 | CG2 | ILE | A | 1051 | 99.734 | 70.993 | 9.931 | 1.00 | 34.71 | C |
| ATOM | 1717 | C | ILE | A | 1051 | 97.269 | 72.800 | 10.793 | 1.00 | 35.90 | C |
| ATOM | 1718 | O | ILE | A | 1051 | 97.416 | 71.902 | 11.629 | 1.00 | 36.07 | O |
| ATOM | 1719 | N | GLU | A | 1052 | 96.135 | 73.488 | 10.671 | 1.00 | 36.27 | N |
| ATOM | 1720 | CA | GLU | A | 1052 | 94.936 | 73.118 | 11.419 | 1.00 | 37.33 | C |
| ATOM | 1721 | CB | GLU | A | 1052 | 93.857 | 74.196 | 11.300 | 1.00 | 37.18 | C |
| ATOM | 1722 | CG | GLU | A | 1052 | 92.646 | 73.974 | 12.203 | 1.00 | 37.01 | C |
| ATOM | 1723 | CD | GLU | A | 1052 | 91.622 | 75.090 | 12.109 | 1.00 | 37.56 | C |
| ATOM | 1724 | OE1 | GLU | A | 1052 | 91.949 | 76.167 | 11.565 | 1.00 | 38.71 | O |
| ATOM | 1725 | OE2 | GLU | A | 1052 | 90.485 | 74.892 | 12.588 | 1.00 | 37.91 | O |
| ATOM | 1726 | C | GLU | A | 1052 | 94.433 | 71.778 | 10.886 | 1.00 | 38.27 | C |

APPENDIX 1-continued

| ATOM | 1727 | O | GLU | A | 1052 | 94.189 | 71.634 | 9.686 | 1.00 | 38.19 | O |
|---|---|---|---|---|---|---|---|---|---|---|---|
| ATOM | 1728 | N | LYS | A | 1053 | 94.288 | 70.811 | 11.789 | 1.00 | 39.70 | N |
| ATOM | 1729 | CA | LYS | A | 1053 | 94.047 | 69.408 | 11.431 | 1.00 | 41.14 | C |
| ATOM | 1730 | CB | LYS | A | 1053 | 93.835 | 68.566 | 12.692 | 1.00 | 41.74 | C |
| ATOM | 1731 | CG | LYS | A | 1053 | 94.301 | 67.125 | 12.567 | 1.00 | 44.77 | C |
| ATOM | 1732 | CD | LYS | A | 1053 | 94.419 | 66.469 | 13.940 | 1.00 | 48.72 | C |
| ATOM | 1733 | CE | LYS | A | 1053 | 95.148 | 65.131 | 13.867 | 1.00 | 52.32 | C |
| ATOM | 1734 | NZ | LYS | A | 1053 | 96.593 | 65.280 | 13.516 | 1.00 | 53.25 | N |
| ATOM | 1735 | C | LYS | A | 1053 | 92.891 | 69.208 | 10.450 | 1.00 | 41.08 | C |
| ATOM | 1736 | O | LYS | A | 1053 | 93.026 | 68.466 | 9.471 | 1.00 | 41.72 | O |
| ATOM | 1737 | N | SER | A | 1054 | 91.771 | 69.883 | 10.706 | 1.00 | 40.14 | N |
| ATOM | 1738 | CA | SER | A | 1054 | 90.583 | 69.777 | 9.856 | 1.00 | 39.74 | C |
| ATOM | 1739 | CB | SER | A | 1054 | 89.347 | 70.316 | 10.586 | 1.00 | 39.83 | C |
| ATOM | 1740 | OG | SER | A | 1054 | 89.422 | 71.721 | 10.767 | 1.00 | 40.64 | O |
| ATOM | 1741 | C | SER | A | 1054 | 90.740 | 70.471 | 8.498 | 1.00 | 39.16 | C |
| ATOM | 1742 | O | SER | A | 1054 | 89.940 | 70.243 | 7.590 | 1.00 | 39.11 | O |
| ATOM | 1743 | N | LYS | A | 1055 | 91.770 | 71.306 | 8.367 | 1.00 | 38.58 | N |
| ATOM | 1744 | CA | LYS | A | 1055 | 91.982 | 72.104 | 7.156 | 1.00 | 37.99 | C |
| ATOM | 1745 | CB | LYS | A | 1055 | 92.367 | 73.547 | 7.518 | 1.00 | 38.05 | C |
| ATOM | 1746 | CG | LYS | A | 1055 | 91.433 | 74.245 | 8.501 | 1.00 | 38.00 | C |
| ATOM | 1747 | CD | LYS | A | 1055 | 90.076 | 74.569 | 7.895 | 1.00 | 37.24 | C |
| ATOM | 1748 | CE | LYS | A | 1055 | 89.216 | 75.328 | 8.892 | 1.00 | 36.53 | C |
| ATOM | 1749 | NZ | LYS | A | 1055 | 87.844 | 75.563 | 8.372 | 1.00 | 38.28 | N |
| ATOM | 1750 | C | LYS | A | 1055 | 93.022 | 71.518 | 6.197 | 1.00 | 37.78 | C |
| ATOM | 1751 | O | LYS | A | 1055 | 93.299 | 72.110 | 5.152 | 1.00 | 37.75 | O |
| ATOM | 1752 | N | SER | A | 1056 | 93.591 | 70.364 | 6.543 | 1.00 | 37.36 | N |
| ATOM | 1753 | CA | SER | A | 1056 | 94.605 | 69.718 | 5.701 | 1.00 | 37.30 | C |
| ATOM | 1754 | CB | SER | A | 1056 | 95.137 | 68.444 | 6.367 | 1.00 | 37.13 | C |
| ATOM | 1755 | OG | SER | A | 1056 | 94.226 | 67.367 | 6.222 | 1.00 | 38.25 | O |
| ATOM | 1756 | C | SER | A | 1056 | 94.059 | 69.397 | 4.306 | 1.00 | 36.87 | C |
| ATOM | 1757 | O | SER | A | 1056 | 92.868 | 69.122 | 4.159 | 1.00 | 37.37 | O |
| ATOM | 1758 | N | PRO | A | 1057 | 94.925 | 69.451 | 3.274 | 1.00 | 36.95 | N |
| ATOM | 1759 | CA | PRO | A | 1057 | 94.520 | 69.035 | 1.929 | 1.00 | 36.51 | C |
| ATOM | 1760 | CB | PRO | A | 1057 | 95.846 | 68.984 | 1.163 | 1.00 | 36.09 | C |
| ATOM | 1761 | CG | PRO | A | 1057 | 96.679 | 70.022 | 1.832 | 1.00 | 36.63 | C |
| ATOM | 1762 | CD | PRO | A | 1057 | 96.317 | 69.946 | 3.294 | 1.00 | 36.51 | C |
| ATOM | 1763 | C | PRO | A | 1057 | 93.768 | 67.692 | 1.865 | 1.00 | 36.50 | C |
| ATOM | 1764 | O | PRO | A | 1057 | 92.718 | 67.636 | 1.221 | 1.00 | 36.07 | O |
| ATOM | 1765 | N | PRO | A | 1058 | 94.283 | 66.619 | 2.518 | 1.00 | 36.42 | N |
| ATOM | 1766 | CA | PRO | A | 1058 | 93.497 | 65.383 | 2.505 | 1.00 | 36.63 | C |
| ATOM | 1767 | CB | PRO | A | 1058 | 94.333 | 64.423 | 3.362 | 1.00 | 36.50 | C |
| ATOM | 1768 | CG | PRO | A | 1058 | 95.710 | 64.943 | 3.267 | 1.00 | 36.32 | C |
| ATOM | 1769 | CD | PRO | A | 1058 | 95.549 | 66.430 | 3.251 | 1.00 | 36.28 | C |
| ATOM | 1770 | C | PRO | A | 1058 | 92.096 | 65.549 | 3.095 | 1.00 | 36.85 | C |
| ATOM | 1771 | O | PRO | A | 1058 | 91.127 | 65.106 | 2.482 | 1.00 | 36.21 | O |
| ATOM | 1772 | N | ALA | A | 1059 | 91.993 | 66.196 | 4.257 | 1.00 | 37.48 | N |
| ATOM | 1773 | CA | ALA | A | 1059 | 90.702 | 66.399 | 4.921 | 1.00 | 38.30 | C |
| ATOM | 1774 | CB | ALA | A | 1059 | 90.895 | 67.014 | 6.303 | 1.00 | 38.21 | C |
| ATOM | 1775 | C | ALA | A | 1059 | 89.728 | 67.238 | 4.087 | 1.00 | 39.01 | C |
| ATOM | 1776 | O | ALA | A | 1059 | 88.537 | 66.922 | 4.014 | 1.00 | 38.99 | O |
| ATOM | 1777 | N | GLU | A | 1060 | 90.242 | 68.293 | 3.455 | 1.00 | 39.12 | N |
| ATOM | 1778 | CA | GLU | A | 1060 | 89.426 | 69.189 | 2.631 | 1.00 | 39.77 | C |
| ATOM | 1779 | CB | GLU | A | 1060 | 90.198 | 70.464 | 2.279 | 1.00 | 39.94 | C |
| ATOM | 1780 | CG | GLU | A | 1060 | 90.333 | 71.458 | 3.426 | 1.00 | 42.71 | C |
| ATOM | 1781 | CD | GLU | A | 1060 | 89.085 | 72.296 | 3.646 | 1.00 | 45.55 | C |
| ATOM | 1782 | OE1 | GLU | A | 1060 | 88.210 | 72.333 | 2.753 | 1.00 | 47.70 | O |
| ATOM | 1783 | OE2 | GLU | A | 1060 | 88.981 | 72.925 | 4.721 | 1.00 | 47.46 | O |
| ATOM | 1784 | C | GLU | A | 1060 | 88.918 | 68.518 | 1.356 | 1.00 | 39.66 | C |
| ATOM | 1785 | O | GLU | A | 1060 | 87.725 | 68.593 | 1.050 | 1.00 | 39.43 | O |
| ATOM | 1786 | N | PHE | A | 1061 | 89.822 | 67.874 | .618 | 1.00 | 39.38 | N |
| ATOM | 1787 | CA | PHE | A | 1061 | 89.454 | 67.161 | −.605 | 1.00 | 39.48 | C |
| ATOM | 1788 | CB | PHE | A | 1061 | 90.694 | 66.654 | −1.352 | 1.00 | 39.09 | C |
| ATOM | 1789 | CG | PHE | A | 1061 | 91.391 | 67.707 | −2.179 | 1.00 | 37.49 | C |
| ATOM | 1790 | CD1 | PHE | A | 1061 | 92.742 | 67.983 | −1.981 | 1.00 | 37.32 | C |
| ATOM | 1791 | CE1 | PHE | A | 1061 | 93.396 | 68.947 | −2.749 | 1.00 | 35.67 | C |
| ATOM | 1792 | CZ | PHE | A | 1061 | 92.694 | 69.650 | −3.727 | 1.00 | 36.27 | C |
| ATOM | 1793 | CE2 | PHE | A | 1061 | 91.345 | 69.383 | −3.933 | 1.00 | 36.54 | C |
| ATOM | 1794 | CD2 | PHE | A | 1061 | 90.702 | 68.415 | −3.163 | 1.00 | 36.40 | C |
| ATOM | 1795 | C | PHE | A | 1061 | 88.489 | 66.004 | −.330 | 1.00 | 40.73 | C |
| ATOM | 1796 | O | PHE | A | 1061 | 87.543 | 65.793 | −1.089 | 1.00 | 40.34 | O |
| ATOM | 1797 | N | MET | A | 1062 | 88.727 | 65.270 | .758 | 1.00 | 41.93 | N |
| ATOM | 1798 | CA | MET | A | 1062 | 87.859 | 64.152 | 1.147 | 1.00 | 43.68 | C |
| ATOM | 1799 | CB | MET | A | 1062 | 88.455 | 63.357 | 2.314 | 1.00 | 43.68 | C |
| ATOM | 1800 | CG | MET | A | 1062 | 89.620 | 62.443 | 1.930 | 1.00 | 44.50 | C |
| ATOM | 1801 | SD | MET | A | 1062 | 89.226 | 61.227 | .654 | 1.00 | 47.16 | S |
| ATOM | 1802 | CE | MET | A | 1062 | 88.147 | 60.115 | 1.557 | 1.00 | 47.59 | C |
| ATOM | 1803 | C | MET | A | 1062 | 86.436 | 64.597 | 1.483 | 1.00 | 44.95 | C |
| ATOM | 1804 | O | MET | A | 1062 | 85.486 | 63.856 | 1.244 | 1.00 | 45.09 | O |
| ATOM | 1805 | N | ARG | A | 1063 | 86.298 | 65.802 | 2.032 | 1.00 | 46.66 | N |

APPENDIX 1-continued

| ATOM | 1806 | CA | ARG | A | 1063 | 84.982 | 66.386 | 2.291 | 1.00 | 48.63 | C |
|------|------|------|------|---|------|--------|--------|--------|------|-------|---|
| ATOM | 1807 | CB | ARG | A | 1063 | 85.083 | 67.579 | 3.243 | 1.00 | 48.88 | C |
| ATOM | 1808 | CG | ARG | A | 1063 | 85.219 | 67.190 | 4.708 | 1.00 | 50.61 | C |
| ATOM | 1809 | CD | ARG | A | 1063 | 84.889 | 68.352 | 5.634 | 1.00 | 52.47 | C |
| ATOM | 1810 | NE | ARG | A | 1063 | 85.855 | 69.444 | 5.520 | 1.00 | 53.65 | N |
| ATOM | 1811 | CZ | ARG | A | 1063 | 86.962 | 69.555 | 6.249 | 1.00 | 53.34 | C |
| ATOM | 1812 | NH1 | ARG | A | 1063 | 87.266 | 68.639 | 7.162 | 1.00 | 53.32 | N |
| ATOM | 1813 | NH2 | ARG | A | 1063 | 87.769 | 70.589 | 6.064 | 1.00 | 53.05 | N |
| ATOM | 1814 | C | ARG | A | 1063 | 84.279 | 66.796 | 1.000 | 1.00 | 49.71 | C |
| ATOM | 1815 | O | ARG | A | 1063 | 83.073 | 66.583 | .850 | 1.00 | 49.89 | O |
| ATOM | 1816 | N | MET | A | 1064 | 85.039 | 67.382 | .075 | 1.00 | 50.90 | N |
| ATOM | 1817 | CA | MET | A | 1064 | 84.516 | 67.790 | −1.229 | 1.00 | 52.52 | C |
| ATOM | 1818 | CB | MET | A | 1064 | 85.527 | 68.674 | −1.964 | 1.00 | 52.43 | C |
| ATOM | 1819 | CG | MET | A | 1064 | 85.588 | 70.108 | −1.452 | 1.00 | 52.74 | C |
| ATOM | 1820 | SD | MET | A | 1064 | 86.738 | 71.153 | −2.370 | 1.00 | 53.19 | S |
| ATOM | 1821 | CE | MET | A | 1064 | 88.288 | 70.759 | −1.566 | 1.00 | 53.28 | C |
| ATOM | 1822 | C | MET | A | 1064 | 84.128 | 66.584 | −2.085 | 1.00 | 53.47 | C |
| ATOM | 1823 | O | MET | A | 1064 | 83.106 | 66.605 | −2.773 | 1.00 | 53.15 | O |
| ATOM | 1824 | N | ILE | A | 1065 | 84.952 | 65.539 | −2.028 | 1.00 | 55.02 | N |
| ATOM | 1825 | CA | ILE | A | 1065 | 84.677 | 64.266 | −2.698 | 1.00 | 56.57 | C |
| ATOM | 1826 | CB | ILE | A | 1065 | 85.951 | 63.374 | −2.744 | 1.00 | 56.51 | C |
| ATOM | 1827 | CG1 | ILE | A | 1065 | 86.958 | 63.935 | −3.755 | 1.00 | 57.09 | C |
| ATOM | 1828 | CD1 | ILE | A | 1065 | 88.391 | 63.485 | −3.523 | 1.00 | 58.05 | C |
| ATOM | 1829 | CG2 | ILE | A | 1065 | 85.611 | 61.923 | −3.083 | 1.00 | 56.94 | C |
| ATOM | 1830 | C | ILE | A | 1065 | 83.531 | 63.535 | −1.994 | 1.00 | 57.81 | C |
| ATOM | 1831 | O | ILE | A | 1065 | 82.690 | 62.905 | −2.641 | 1.00 | 57.83 | O |
| ATOM | 1832 | N | GLY | A | 1066 | 83.499 | 63.647 | −.668 | 1.00 | 59.26 | N |
| ATOM | 1833 | CA | GLY | A | 1066 | 82.523 | 62.948 | .158 | 1.00 | 61.08 | C |
| ATOM | 1834 | C | GLY | A | 1066 | 83.219 | 61.857 | .942 | 1.00 | 62.56 | C |
| ATOM | 1835 | O | GLY | A | 1066 | 83.771 | 60.926 | .354 | 1.00 | 62.52 | O |
| ATOM | 1836 | N | ASN | A | 1067 | 83.201 | 61.981 | 2.269 | 1.00 | 64.30 | N |
| ATOM | 1837 | CA | ASN | A | 1067 | 83.852 | 61.014 | 3.164 | 1.00 | 65.94 | C |
| ATOM | 1838 | CB | ASN | A | 1067 | 83.793 | 61.492 | 4.620 | 1.00 | 66.00 | C |
| ATOM | 1839 | CG | ASN | A | 1067 | 84.645 | 62.727 | 4.866 | 1.00 | 66.63 | C |
| ATOM | 1840 | OD1 | ASN | A | 1067 | 85.786 | 62.629 | 5.318 | 1.00 | 66.79 | O |
| ATOM | 1841 | ND2 | ASN | A | 1067 | 84.094 | 63.897 | 4.561 | 1.00 | 66.71 | N |
| ATOM | 1842 | C | ASN | A | 1067 | 83.297 | 59.592 | 3.037 | 1.00 | 66.96 | C |
| ATOM | 1843 | O | ASN | A | 1067 | 83.924 | 58.628 | 3.484 | 1.00 | 67.07 | O |
| ATOM | 1844 | N | ASP | A | 1068 | 82.123 | 59.478 | 2.416 | 1.00 | 68.14 | N |
| ATOM | 1845 | CA | ASP | A | 1068 | 81.539 | 58.189 | 2.046 | 1.00 | 69.36 | C |
| ATOM | 1846 | CB | ASP | A | 1068 | 80.029 | 58.340 | 1.809 | 1.00 | 69.67 | C |
| ATOM | 1847 | CG | ASP | A | 1068 | 79.698 | 59.420 | .786 | 1.00 | 70.79 | C |
| ATOM | 1848 | OD1 | ASP | A | 1068 | 79.121 | 59.082 | −.269 | 1.00 | 72.05 | O |
| ATOM | 1849 | OD2 | ASP | A | 1068 | 80.017 | 60.603 | 1.033 | 1.00 | 71.49 | O |
| ATOM | 1850 | C | ASP | A | 1068 | 82.227 | 57.609 | .802 | 1.00 | 69.87 | C |
| ATOM | 1851 | O | ASP | A | 1068 | 81.603 | 56.905 | .001 | 1.00 | 69.84 | O |
| ATOM | 1852 | N | ALA | A | 1069 | 83.518 | 57.909 | .659 | 1.00 | 70.48 | N |
| ATOM | 1853 | CA | ALA | A | 1069 | 84.314 | 57.482 | −.489 | 1.00 | 70.94 | C |
| ATOM | 1854 | CB | ALA | A | 1069 | 85.551 | 58.362 | −.631 | 1.00 | 70.95 | C |
| ATOM | 1855 | C | ALA | A | 1069 | 84.715 | 56.013 | −.398 | 1.00 | 71.24 | C |
| ATOM | 1856 | O | ALA | A | 1069 | 84.600 | 55.387 | .661 | 1.00 | 71.29 | O |
| ATOM | 1857 | N | GLN | A | 1070 | 85.188 | 55.475 | −1.519 | 1.00 | 71.36 | N |
| ATOM | 1858 | CA | GLN | A | 1070 | 85.618 | 54.083 | −1.600 | 1.00 | 71.44 | C |
| ATOM | 1859 | CB | GLN | A | 1070 | 85.304 | 53.510 | −2.988 | 1.00 | 71.45 | C |
| ATOM | 1860 | CG | GLN | A | 1070 | 83.822 | 53.558 | −3.353 | 1.00 | 71.84 | C |
| ATOM | 1861 | CD | GLN | A | 1070 | 83.568 | 53.337 | −4.832 | 1.00 | 71.97 | C |
| ATOM | 1862 | OE1 | GLN | A | 1070 | 83.774 | 52.242 | −5.356 | 1.00 | 72.90 | O |
| ATOM | 1863 | NE2 | GLN | A | 1070 | 83.104 | 54.380 | −5.513 | 1.00 | 72.52 | N |
| ATOM | 1864 | C | GLN | A | 1070 | 87.107 | 53.968 | −1.256 | 1.00 | 71.04 | C |
| ATOM | 1865 | O | GLN | A | 1070 | 87.530 | 54.401 | −.181 | 1.00 | 71.07 | O |
| ATOM | 1866 | N | GLY | A | 1071 | 87.892 | 53.392 | −2.163 | 1.00 | 70.65 | N |
| ATOM | 1867 | CA | GLY | A | 1071 | 89.330 | 53.233 | −1.959 | 1.00 | 70.08 | C |
| ATOM | 1868 | C | GLY | A | 1071 | 90.111 | 53.514 | −3.227 | 1.00 | 69.59 | C |
| ATOM | 1869 | O | GLY | A | 1071 | 90.876 | 54.479 | −3.294 | 1.00 | 69.62 | O |
| ATOM | 1870 | N | GLN | A | 1072 | 89.911 | 52.665 | −4.231 | 1.00 | 69.02 | N |
| ATOM | 1871 | CA | GLN | A | 1072 | 90.553 | 52.822 | −5.536 | 1.00 | 68.44 | C |
| ATOM | 1872 | CB | GLN | A | 1072 | 90.510 | 51.503 | −6.317 | 1.00 | 68.61 | C |
| ATOM | 1873 | CG | GLN | A | 1072 | 91.275 | 50.351 | −5.664 | 1.00 | 69.11 | C |
| ATOM | 1874 | CD | GLN | A | 1072 | 90.950 | 48.992 | −6.274 | 1.00 | 69.10 | C |
| ATOM | 1875 | OE1 | GLN | A | 1072 | 90.063 | 48.868 | −7.121 | 1.00 | 69.82 | O |
| ATOM | 1876 | NE2 | GLN | A | 1072 | 91.669 | 47.964 | −5.837 | 1.00 | 69.97 | N |
| ATOM | 1877 | C | GLN | A | 1072 | 89.891 | 53.934 | −6.351 | 1.00 | 67.47 | C |
| ATOM | 1878 | O | GLN | A | 1072 | 90.487 | 54.464 | −7.293 | 1.00 | 67.49 | O |
| ATOM | 1879 | N | MET | A | 1073 | 88.660 | 54.280 | −5.976 | 1.00 | 66.08 | N |
| ATOM | 1880 | CA | MET | A | 1073 | 87.882 | 55.309 | −6.667 | 1.00 | 64.55 | C |
| ATOM | 1881 | CB | MET | A | 1073 | 86.383 | 55.002 | −6.566 | 1.00 | 64.82 | C |
| ATOM | 1882 | CG | MET | A | 1073 | 85.916 | 53.855 | −7.460 | 1.00 | 65.95 | C |
| ATOM | 1883 | SD | MET | A | 1073 | 85.654 | 54.325 | −9.185 | 1.00 | 67.45 | S |
| ATOM | 1884 | CE | MET | A | 1073 | 84.081 | 55.179 | −9.081 | 1.00 | 67.43 | C |

APPENDIX 1-continued

| ATOM | 1885 | C | MET | A | 1073 | 88.172 | 56.726 | −6.165 | 1.00 | 62.83 | C |
|---|---|---|---|---|---|---|---|---|---|---|---|
| ATOM | 1886 | O | MET | A | 1073 | 87.748 | 57.702 | −6.787 | 1.00 | 62.61 | O |
| ATOM | 1887 | N | ILE | A | 1074 | 88.895 | 56.831 | −5.049 | 1.00 | 60.92 | N |
| ATOM | 1888 | CA | ILE | A | 1074 | 89.264 | 58.127 | −4.460 | 1.00 | 59.10 | C |
| ATOM | 1889 | CB | ILE | A | 1074 | 90.049 | 57.958 | −3.123 | 1.00 | 59.16 | C |
| ATOM | 1890 | CG1 | ILE | A | 1074 | 89.132 | 57.381 | −2.036 | 1.00 | 59.59 | C |
| ATOM | 1891 | CD1 | ILE | A | 1074 | 89.857 | 56.884 | −.787 | 1.00 | 59.35 | C |
| ATOM | 1892 | CG2 | ILE | A | 1074 | 90.651 | 59.290 | −2.663 | 1.00 | 58.39 | C |
| ATOM | 1893 | C | ILE | A | 1074 | 90.050 | 58.990 | −5.451 | 1.00 | 57.36 | C |
| ATOM | 1894 | O | ILE | A | 1074 | 89.751 | 60.175 | −5.623 | 1.00 | 57.17 | O |
| ATOM | 1895 | N | VAL | A | 1075 | 91.038 | 58.383 | −6.106 | 1.00 | 55.55 | N |
| ATOM | 1896 | CA | VAL | A | 1075 | 91.840 | 59.061 | −7.127 | 1.00 | 54.01 | C |
| ATOM | 1897 | CB | VAL | A | 1075 | 93.016 | 58.173 | −7.620 | 1.00 | 54.21 | C |
| ATOM | 1898 | CG1 | VAL | A | 1075 | 93.919 | 58.945 | −8.575 | 1.00 | 54.35 | C |
| ATOM | 1899 | CG2 | VAL | A | 1075 | 93.828 | 57.649 | −6.441 | 1.00 | 54.49 | C |
| ATOM | 1900 | C | VAL | A | 1075 | 90.963 | 59.492 | −8.309 | 1.00 | 52.53 | C |
| ATOM | 1901 | O | VAL | A | 1075 | 91.107 | 60.604 | −8.821 | 1.00 | 52.18 | O |
| ATOM | 1902 | N | PHE | A | 1076 | 90.047 | 58.614 | −8.716 | 1.00 | 51.04 | N |
| ATOM | 1903 | CA | PHE | A | 1076 | 89.126 | 58.885 | −9.822 | 1.00 | 49.56 | C |
| ATOM | 1904 | CB | PHE | A | 1076 | 88.286 | 57.640 | −10.141 | 1.00 | 49.76 | C |
| ATOM | 1905 | CG | PHE | A | 1076 | 87.258 | 57.855 | −11.223 | 1.00 | 50.08 | C |
| ATOM | 1906 | CD1 | PHE | A | 1076 | 87.644 | 57.998 | −12.554 | 1.00 | 50.41 | C |
| ATOM | 1907 | CE1 | PHE | A | 1076 | 86.695 | 58.196 | −13.557 | 1.00 | 50.47 | C |
| ATOM | 1908 | CZ | PHE | A | 1076 | 85.343 | 58.246 | −13.231 | 1.00 | 50.03 | C |
| ATOM | 1909 | CE2 | PHE | A | 1076 | 84.945 | 58.101 | −11.905 | 1.00 | 50.29 | C |
| ATOM | 1910 | CD2 | PHE | A | 1076 | 85.902 | 57.905 | −10.910 | 1.00 | 50.69 | C |
| ATOM | 1911 | C | PHE | A | 1076 | 88.224 | 60.091 | −9.550 | 1.00 | 48.19 | C |
| ATOM | 1912 | O | PHE | A | 1076 | 87.997 | 60.913 | −10.440 | 1.00 | 47.69 | O |
| ATOM | 1913 | N | HIS | A | 1077 | 87.717 | 60.189 | −8.323 | 1.00 | 46.92 | N |
| ATOM | 1914 | CA | HIS | A | 1077 | 86.860 | 61.306 | −7.929 | 1.00 | 46.14 | C |
| ATOM | 1915 | CB | HIS | A | 1077 | 86.063 | 60.965 | −6.670 | 1.00 | 46.52 | C |
| ATOM | 1916 | CG | HIS | A | 1077 | 84.945 | 59.998 | −6.908 | 1.00 | 48.28 | C |
| ATOM | 1917 | ND1 | HIS | A | 1077 | 83.767 | 60.360 | −7.524 | 1.00 | 49.57 | N |
| ATOM | 1918 | CE1 | HIS | A | 1077 | 82.971 | 59.308 | −7.601 | 1.00 | 50.38 | C |
| ATOM | 1919 | NE2 | HIS | A | 1077 | 83.590 | 58.277 | −7.055 | 1.00 | 50.44 | N |
| ATOM | 1920 | CD2 | HIS | A | 1077 | 84.826 | 58.682 | −6.613 | 1.00 | 49.54 | C |
| ATOM | 1921 | C | HIS | A | 1077 | 87.656 | 62.594 | −7.731 | 1.00 | 44.85 | C |
| ATOM | 1922 | O | HIS | A | 1077 | 87.151 | 63.687 | −7.999 | 1.00 | 44.79 | O |
| ATOM | 1923 | N | LEU | A | 1078 | 88.896 | 62.458 | −7.263 | 1.00 | 43.47 | N |
| ATOM | 1924 | CA | LEU | A | 1078 | 89.800 | 63.598 | −7.116 | 1.00 | 42.00 | C |
| ATOM | 1925 | CB | LEU | A | 1078 | 91.086 | 63.187 | −6.385 | 1.00 | 41.56 | C |
| ATOM | 1926 | CG | LEU | A | 1078 | 92.213 | 64.216 | −6.224 | 1.00 | 41.11 | C |
| ATOM | 1927 | CD1 | LEU | A | 1078 | 91.782 | 65.419 | −5.389 | 1.00 | 39.25 | C |
| ATOM | 1928 | CD2 | LEU | A | 1078 | 93.442 | 63.558 | −5.619 | 1.00 | 41.47 | C |
| ATOM | 1929 | C | LEU | A | 1078 | 90.118 | 64.214 | −8.477 | 1.00 | 41.22 | C |
| ATOM | 1930 | O | LEU | A | 1078 | 90.094 | 65.435 | −8.632 | 1.00 | 41.49 | O |
| ATOM | 1931 | N | ILE | A | 1079 | 90.401 | 63.358 | −9.457 | 1.00 | 40.73 | N |
| ATOM | 1932 | CA | ILE | A | 1079 | 90.656 | 63.789 | −10.832 | 1.00 | 40.22 | C |
| ATOM | 1933 | CB | ILE | A | 1079 | 90.971 | 62.580 | −11.757 | 1.00 | 40.39 | C |
| ATOM | 1934 | CG1 | ILE | A | 1079 | 92.383 | 62.052 | −11.474 | 1.00 | 39.94 | C |
| ATOM | 1935 | CD1 | ILE | A | 1079 | 92.620 | 60.615 | −11.920 | 1.00 | 40.64 | C |
| ATOM | 1936 | CG2 | ILE | A | 1079 | 90.823 | 62.961 | −13.233 | 1.00 | 39.77 | C |
| ATOM | 1937 | C | ILE | A | 1079 | 89.479 | 64.599 | −11.380 | 1.00 | 40.12 | C |
| ATOM | 1938 | O | ILE | A | 1079 | 89.676 | 65.671 | −11.956 | 1.00 | 39.65 | O |
| ATOM | 1939 | N | GLU | A | 1080 | 88.265 | 64.089 | −11.176 | 1.00 | 40.31 | N |
| ATOM | 1940 | CA | GLU | A | 1080 | 87.048 | 64.742 | −11.665 | 1.00 | 40.74 | C |
| ATOM | 1941 | CB | GLU | A | 1080 | 85.828 | 63.827 | −11.504 | 1.00 | 41.01 | C |
| ATOM | 1942 | CG | GLU | A | 1080 | 85.849 | 62.587 | −12.396 | 1.00 | 44.71 | C |
| ATOM | 1943 | CD | GLU | A | 1080 | 85.902 | 62.920 | −13.879 | 1.00 | 48.26 | C |
| ATOM | 1944 | OE1 | GLU | A | 1080 | 84.894 | 63.428 | −14.418 | 1.00 | 50.74 | O |
| ATOM | 1945 | OE2 | GLU | A | 1080 | 86.954 | 62.665 | −14.506 | 1.00 | 49.39 | O |
| ATOM | 1946 | C | GLU | A | 1080 | 86.799 | 66.089 | −10.990 | 1.00 | 39.92 | C |
| ATOM | 1947 | O | GLU | A | 1080 | 86.413 | 67.054 | −11.651 | 1.00 | 39.63 | O |
| ATOM | 1948 | N | LEU | A | 1081 | 87.030 | 66.145 | −9.678 | 1.00 | 39.72 | N |
| ATOM | 1949 | CA | LEU | A | 1081 | 86.880 | 67.382 | −8.911 | 1.00 | 39.40 | C |
| ATOM | 1950 | CB | LEU | A | 1081 | 87.150 | 67.133 | −7.422 | 1.00 | 39.27 | C |
| ATOM | 1951 | CG | LEU | A | 1081 | 86.998 | 68.306 | −6.443 | 1.00 | 40.33 | C |
| ATOM | 1952 | CD1 | LEU | A | 1081 | 85.542 | 68.744 | −6.297 | 1.00 | 41.37 | C |
| ATOM | 1953 | CD2 | LEU | A | 1081 | 87.576 | 67.943 | −5.085 | 1.00 | 39.90 | C |
| ATOM | 1954 | C | LEU | A | 1081 | 87.788 | 68.490 | −9.450 | 1.00 | 39.01 | C |
| ATOM | 1955 | O | LEU | A | 1081 | 87.341 | 69.622 | −9.656 | 1.00 | 39.46 | O |
| ATOM | 1956 | N | LEU | A | 1082 | 89.054 | 68.151 | −9.691 | 1.00 | 38.13 | N |
| ATOM | 1957 | CA | LEU | A | 1082 | 90.034 | 69.108 | −10.210 | 1.00 | 37.85 | C |
| ATOM | 1958 | CB | LEU | A | 1082 | 91.458 | 68.554 | −10.080 | 1.00 | 37.30 | C |
| ATOM | 1959 | CG | LEU | A | 1082 | 91.970 | 68.257 | −8.663 | 1.00 | 35.69 | C |
| ATOM | 1960 | CD1 | LEU | A | 1082 | 93.259 | 67.443 | −8.705 | 1.00 | 33.62 | C |
| ATOM | 1961 | CD2 | LEU | A | 1082 | 92.159 | 69.530 | −7.841 | 1.00 | 33.46 | C |
| ATOM | 1962 | C | LEU | A | 1082 | 89.740 | 69.519 | −11.655 | 1.00 | 38.24 | C |
| ATOM | 1963 | O | LEU | A | 1082 | 89.980 | 70.667 | −12.041 | 1.00 | 37.99 | O |

APPENDIX 1-continued

| ATOM | 1964 | N | LYS | A | 1083 | 89.214 | 68.578 | −12.438 | 1.00 | 39.04 | N |
|---|---|---|---|---|---|---|---|---|---|---|---|
| ATOM | 1965 | CA | LYS | A | 1083 | 88.805 | 68.833 | −13.820 | 1.00 | 40.21 | C |
| ATOM | 1966 | CB | LYS | A | 1083 | 88.356 | 67.530 | −14.493 | 1.00 | 40.86 | C |
| ATOM | 1967 | CG | LYS | A | 1083 | 88.164 | 67.629 | −16.002 | 1.00 | 43.73 | C |
| ATOM | 1968 | CD | LYS | A | 1083 | 87.385 | 66.439 | −16.544 | 1.00 | 46.64 | C |
| ATOM | 1969 | CE | LYS | A | 1083 | 87.059 | 66.621 | −18.020 | 1.00 | 48.87 | C |
| ATOM | 1970 | NZ | LYS | A | 1083 | 86.179 | 65.532 | −18.538 | 1.00 | 51.48 | N |
| ATOM | 1971 | C | LYS | A | 1083 | 87.689 | 69.881 | −13.887 | 1.00 | 40.36 | C |
| ATOM | 1972 | O | LYS | A | 1083 | 87.672 | 70.721 | −14.788 | 1.00 | 40.28 | O |
| ATOM | 1973 | N | ASN | A | 1084 | 86.775 | 69.830 | −12.921 | 1.00 | 40.75 | N |
| ATOM | 1974 | CA | ASN | A | 1084 | 85.664 | 70.778 | −12.836 | 1.00 | 41.57 | C |
| ATOM | 1975 | CB | ASN | A | 1084 | 84.408 | 70.077 | −12.305 | 1.00 | 42.23 | C |
| ATOM | 1976 | CG | ASN | A | 1084 | 83.839 | 69.067 | −13.288 | 1.00 | 44.20 | C |
| ATOM | 1977 | OD1 | ASN | A | 1084 | 83.772 | 69.320 | −14.492 | 1.00 | 46.97 | O |
| ATOM | 1978 | ND2 | ASN | A | 1084 | 83.418 | 67.916 | −12.774 | 1.00 | 45.42 | N |
| ATOM | 1979 | C | ASN | A | 1084 | 85.989 | 72.018 | −11.997 | 1.00 | 41.36 | C |
| ATOM | 1980 | O | ASN | A | 1084 | 85.088 | 72.680 | −11.474 | 1.00 | 41.56 | O |
| ATOM | 1981 | N | ASN | A | 1085 | 87.284 | 72.320 | −11.886 | 1.00 | 41.04 | N |
| ATOM | 1982 | CA | ASN | A | 1085 | 87.801 | 73.483 | −11.152 | 1.00 | 40.91 | C |
| ATOM | 1983 | CB | ASN | A | 1085 | 87.462 | 74.798 | −11.876 | 1.00 | 41.68 | C |
| ATOM | 1984 | CG | ASN | A | 1085 | 88.206 | 74.947 | −13.198 | 1.00 | 44.78 | C |
| ATOM | 1985 | OD1 | ASN | A | 1085 | 89.400 | 74.648 | −13.298 | 1.00 | 45.83 | O |
| ATOM | 1986 | ND2 | ASN | A | 1085 | 87.501 | 75.422 | −14.219 | 1.00 | 48.05 | N |
| ATOM | 1987 | C | ASN | A | 1085 | 87.432 | 73.547 | −9.663 | 1.00 | 39.86 | C |
| ATOM | 1988 | O | ASN | A | 1085 | 87.314 | 74.630 | −9.082 | 1.00 | 39.90 | O |
| ATOM | 1989 | N | GLY | A | 1086 | 87.259 | 72.375 | −9.056 | 1.00 | 38.36 | N |
| ATOM | 1990 | CA | GLY | A | 1086 | 87.129 | 72.267 | −7.607 | 1.00 | 37.27 | C |
| ATOM | 1991 | C | GLY | A | 1086 | 88.511 | 72.388 | −6.997 | 1.00 | 36.59 | C |
| ATOM | 1992 | O | GLY | A | 1086 | 89.462 | 71.763 | −7.473 | 1.00 | 35.74 | O |
| ATOM | 1993 | N | ARG | A | 1087 | 88.628 | 73.205 | −5.954 | 1.00 | 35.98 | N |
| ATOM | 1994 | CA | ARG | A | 1087 | 89.926 | 73.489 | −5.348 | 1.00 | 36.06 | C |
| ATOM | 1995 | CB | ARG | A | 1087 | 90.592 | 74.674 | −6.055 | 1.00 | 36.85 | C |
| ATOM | 1996 | CG | ARG | A | 1087 | 91.544 | 74.260 | −7.172 | 1.00 | 38.82 | C |
| ATOM | 1997 | CD | ARG | A | 1087 | 91.220 | 74.987 | −8.453 | 1.00 | 42.19 | C |
| ATOM | 1998 | NE | ARG | A | 1087 | 92.087 | 74.598 | −9.567 | 1.00 | 40.18 | N |
| ATOM | 1999 | CZ | ARG | A | 1087 | 91.930 | 73.503 | −10.309 | 1.00 | 39.01 | C |
| ATOM | 2000 | NH1 | ARG | A | 1087 | 90.951 | 72.643 | −10.058 | 1.00 | 39.65 | N |
| ATOM | 2001 | NH2 | ARG | A | 1087 | 92.767 | 73.261 | −11.306 | 1.00 | 39.58 | N |
| ATOM | 2002 | C | ARG | A | 1087 | 89.847 | 73.744 | −3.849 | 1.00 | 35.47 | C |
| ATOM | 2003 | O | ARG | A | 1087 | 88.777 | 74.037 | −3.310 | 1.00 | 34.88 | O |
| ATOM | 2004 | N | LEU | A | 1088 | 90.997 | 73.619 | −3.189 | 1.00 | 34.52 | N |
| ATOM | 2005 | CA | LEU | A | 1088 | 91.144 | 73.955 | −1.779 | 1.00 | 33.33 | C |
| ATOM | 2006 | CB | LEU | A | 1088 | 92.607 | 73.810 | −1.344 | 1.00 | 33.05 | C |
| ATOM | 2007 | CG | LEU | A | 1088 | 93.217 | 72.403 | −1.375 | 1.00 | 31.62 | C |
| ATOM | 2008 | CD1 | LEU | A | 1088 | 94.726 | 72.455 | −1.195 | 1.00 | 30.99 | C |
| ATOM | 2009 | CD2 | LEU | A | 1088 | 92.574 | 71.498 | −.323 | 1.00 | 31.31 | C |
| ATOM | 2010 | C | LEU | A | 1088 | 90.659 | 75.381 | −1.531 | 1.00 | 33.16 | C |
| ATOM | 2011 | O | LEU | A | 1088 | 90.949 | 76.281 | −2.326 | 1.00 | 32.62 | O |
| ATOM | 2012 | N | PRO | A | 1089 | 89.905 | 75.588 | −.436 | 1.00 | 33.02 | N |
| ATOM | 2013 | CA | PRO | A | 1089 | 89.369 | 76.913 | −.146 | 1.00 | 32.83 | C |
| ATOM | 2014 | CB | PRO | A | 1089 | 88.388 | 76.648 | 1.000 | 1.00 | 33.06 | C |
| ATOM | 2015 | CG | PRO | A | 1089 | 88.934 | 75.453 | 1.683 | 1.00 | 32.60 | C |
| ATOM | 2016 | CD | PRO | A | 1089 | 89.519 | 74.602 | .593 | 1.00 | 32.89 | C |
| ATOM | 2017 | C | PRO | A | 1089 | 90.458 | 77.875 | .309 | 1.00 | 32.83 | C |
| ATOM | 2018 | O | PRO | A | 1089 | 91.568 | 77.449 | .643 | 1.00 | 32.84 | O |
| ATOM | 2019 | N | ARG | A | 1090 | 90.138 | 79.164 | .304 | 1.00 | 32.17 | N |
| ATOM | 2020 | CA | ARG | A | 1090 | 91.003 | 80.178 | .881 | 1.00 | 32.27 | C |
| ATOM | 2021 | CB | ARG | A | 1090 | 90.440 | 81.568 | .578 | 1.00 | 32.64 | C |
| ATOM | 2022 | CG | ARG | A | 1090 | 91.248 | 82.727 | 1.120 | 1.00 | 33.64 | C |
| ATOM | 2023 | CD | ARG | A | 1090 | 90.438 | 84.015 | 1.037 | 1.00 | 40.32 | C |
| ATOM | 2024 | NE | ARG | A | 1090 | 90.767 | 84.917 | 2.137 | 1.00 | 45.38 | N |
| ATOM | 2025 | CZ | ARG | A | 1090 | 90.217 | 84.865 | 3.349 | 1.00 | 45.23 | C |
| ATOM | 2026 | NH1 | ARG | A | 1090 | 89.292 | 83.955 | 3.634 | 1.00 | 46.17 | N |
| ATOM | 2027 | NH2 | ARG | A | 1090 | 90.594 | 85.731 | 4.279 | 1.00 | 47.82 | N |
| ATOM | 2028 | C | ARG | A | 1090 | 91.103 | 79.938 | 2.391 | 1.00 | 32.31 | C |
| ATOM | 2029 | O | ARG | A | 1090 | 90.076 | 79.887 | 3.074 | 1.00 | 32.50 | O |
| ATOM | 2030 | N | PRO | A | 1091 | 92.334 | 79.753 | 2.912 | 1.00 | 32.38 | N |
| ATOM | 2031 | CA | PRO | A | 1091 | 92.526 | 79.583 | 4.359 | 1.00 | 32.26 | C |
| ATOM | 2032 | CB | PRO | A | 1091 | 94.049 | 79.510 | 4.503 | 1.00 | 32.41 | C |
| ATOM | 2033 | CG | PRO | A | 1091 | 94.527 | 79.024 | 3.171 | 1.00 | 31.29 | C |
| ATOM | 2034 | CD | PRO | A | 1091 | 93.612 | 79.670 | 2.181 | 1.00 | 32.28 | C |
| ATOM | 2035 | C | PRO | A | 1091 | 91.985 | 80.762 | 5.168 | 1.00 | 32.37 | C |
| ATOM | 2036 | O | PRO | A | 1091 | 91.956 | 81.891 | 4.673 | 1.00 | 32.23 | O |
| ATOM | 2037 | N | ASP | A | 1092 | 91.559 | 80.492 | 6.400 | 1.00 | 32.41 | N |
| ATOM | 2038 | CA | ASP | A | 1092 | 91.068 | 81.537 | 7.297 | 1.00 | 32.23 | C |
| ATOM | 2039 | CB | ASP | A | 1092 | 90.666 | 80.945 | 8.655 | 1.00 | 32.80 | C |
| ATOM | 2040 | CG | ASP | A | 1092 | 89.471 | 80.002 | 8.565 | 1.00 | 35.50 | C |
| ATOM | 2041 | OD1 | ASP | A | 1092 | 88.891 | 79.838 | 7.468 | 1.00 | 38.29 | O |
| ATOM | 2042 | OD2 | ASP | A | 1092 | 89.105 | 79.420 | 9.607 | 1.00 | 37.43 | O |

APPENDIX 1-continued

| ATOM | 2043 | C | ASP | A | 1092 | 92.138 | 82.610 | 7.482 | 1.00 | 31.41 | C |
|---|---|---|---|---|---|---|---|---|---|---|---|
| ATOM | 2044 | O | ASP | A | 1092 | 93.277 | 82.304 | 7.837 | 1.00 | 31.26 | O |
| ATOM | 2045 | N | GLY | A | 1093 | 91.772 | 83.858 | 7.200 | 1.00 | 30.50 | N |
| ATOM | 2046 | CA | GLY | A | 1093 | 92.677 | 84.994 | 7.363 | 1.00 | 30.67 | C |
| ATOM | 2047 | C | GLY | A | 1093 | 93.689 | 85.233 | 6.254 | 1.00 | 31.29 | C |
| ATOM | 2048 | O | GLY | A | 1093 | 94.472 | 86.181 | 6.327 | 1.00 | 30.60 | O |
| ATOM | 2049 | N | CYS | A | 1094 | 93.676 | 84.386 | 5.226 | 1.00 | 31.84 | N |
| ATOM | 2050 | CA | CYS | A | 1094 | 94.613 | 84.514 | 4.109 | 1.00 | 32.12 | C |
| ATOM | 2051 | CB | CYS | A | 1094 | 94.635 | 83.228 | 3.277 | 1.00 | 31.74 | C |
| ATOM | 2052 | SG | CYS | A | 1094 | 95.697 | 83.296 | 1.822 | 1.00 | 32.89 | S |
| ATOM | 2053 | C | CYS | A | 1094 | 94.272 | 85.715 | 3.223 | 1.00 | 32.49 | C |
| ATOM | 2054 | O | CYS | A | 1094 | 93.136 | 85.838 | 2.767 | 1.00 | 31.57 | O |
| ATOM | 2055 | N | PRO | A | 1095 | 95.257 | 86.606 | 2.980 | 1.00 | 33.97 | N |
| ATOM | 2056 | CA | PRO | A | 1095 | 95.037 | 87.757 | 2.100 | 1.00 | 35.04 | C |
| ATOM | 2057 | CB | PRO | A | 1095 | 96.399 | 88.459 | 2.082 | 1.00 | 35.29 | C |
| ATOM | 2058 | CG | PRO | A | 1095 | 97.095 | 87.987 | 3.303 | 1.00 | 35.25 | C |
| ATOM | 2059 | CD | PRO | A | 1095 | 96.629 | 86.585 | 3.516 | 1.00 | 34.20 | C |
| ATOM | 2060 | C | PRO | A | 1095 | 94.660 | 87.311 | .691 | 1.00 | 36.48 | C |
| ATOM | 2061 | O | PRO | A | 1095 | 95.173 | 86.297 | .198 | 1.00 | 36.20 | O |
| ATOM | 2062 | N | ASP | A | 1096 | 93.767 | 88.065 | .057 | 1.00 | 37.02 | N |
| ATOM | 2063 | CA | ASP | A | 1096 | 93.240 | 87.707 | −1.254 | 1.00 | 38.45 | C |
| ATOM | 2064 | CB | ASP | A | 1096 | 92.203 | 88.732 | −1.715 | 1.00 | 39.69 | C |
| ATOM | 2065 | CG | ASP | A | 1096 | 91.042 | 88.092 | −2.444 | 1.00 | 43.48 | C |
| ATOM | 2066 | OD1 | ASP | A | 1096 | 89.907 | 88.165 | −1.924 | 1.00 | 48.55 | O |
| ATOM | 2067 | OD2 | ASP | A | 1096 | 91.261 | 87.505 | −3.525 | 1.00 | 47.49 | O |
| ATOM | 2068 | C | ASP | A | 1096 | 94.348 | 87.551 | −2.296 | 1.00 | 38.10 | C |
| ATOM | 2069 | O | ASP | A | 1096 | 94.295 | 86.642 | −3.126 | 1.00 | 37.91 | O |
| ATOM | 2070 | N | GLU | A | 1097 | 95.354 | 88.423 | −2.223 | 1.00 | 37.79 | N |
| ATOM | 2071 | CA | GLU | A | 1097 | 96.507 | 88.379 | −3.128 | 1.00 | 38.23 | C |
| ATOM | 2072 | CB | GLU | A | 1097 | 97.358 | 89.650 | −3.005 | 1.00 | 38.00 | C |
| ATOM | 2073 | CG | GLU | A | 1097 | 97.954 | 89.904 | −1.620 | 1.00 | 40.71 | C |
| ATOM | 2074 | CD | GLU | A | 1097 | 98.619 | 91.268 | −1.500 | 1.00 | 41.25 | C |
| ATOM | 2075 | OE1 | GLU | A | 1097 | 98.827 | 91.940 | −2.536 | 1.00 | 45.21 | O |
| ATOM | 2076 | OE2 | GLU | A | 1097 | 98.935 | 91.670 | −.359 | 1.00 | 47.57 | O |
| ATOM | 2077 | C | GLU | A | 1097 | 97.376 | 87.128 | −2.961 | 1.00 | 36.85 | C |
| ATOM | 2078 | O | GLU | A | 1097 | 98.026 | 86.691 | −3.916 | 1.00 | 36.92 | O |
| ATOM | 2079 | N | ILE | A | 1098 | 97.389 | 86.562 | −1.755 | 1.00 | 34.80 | N |
| ATOM | 2080 | CA | ILE | A | 1098 | 98.115 | 85.319 | −1.497 | 1.00 | 33.27 | C |
| ATOM | 2081 | CB | ILE | A | 1098 | 98.443 | 85.118 | .015 | 1.00 | 32.91 | C |
| ATOM | 2082 | CG1 | ILE | A | 1098 | 99.255 | 86.297 | .572 | 1.00 | 33.03 | C |
| ATOM | 2083 | CD1 | ILE | A | 1098 | 100.539 | 86.621 | −.189 | 1.00 | 34.43 | C |
| ATOM | 2084 | CG2 | ILE | A | 1098 | 99.165 | 83.783 | .259 | 1.00 | 34.12 | C |
| ATOM | 2085 | C | ILE | A | 1098 | 97.329 | 84.133 | −2.052 | 1.00 | 32.64 | C |
| ATOM | 2086 | O | ILE | A | 1098 | 97.914 | 83.231 | −2.656 | 1.00 | 31.65 | O |
| ATOM | 2087 | N | TYR | A | 1099 | 96.010 | 84.147 | −1.857 | 1.00 | 31.78 | N |
| ATOM | 2088 | CA | TYR | A | 1099 | 95.140 | 83.114 | −2.421 | 1.00 | 32.51 | C |
| ATOM | 2089 | CB | TYR | A | 1099 | 93.687 | 83.272 | −1.956 | 1.00 | 32.07 | C |
| ATOM | 2090 | CG | TYR | A | 1099 | 92.809 | 82.092 | −2.334 | 1.00 | 32.58 | C |
| ATOM | 2091 | CD1 | TYR | A | 1099 | 91.653 | 82.262 | −3.097 | 1.00 | 33.65 | C |
| ATOM | 2092 | CE1 | TYR | A | 1099 | 90.854 | 81.168 | −3.446 | 1.00 | 33.56 | C |
| ATOM | 2093 | CZ | TYR | A | 1099 | 91.228 | 79.892 | −3.038 | 1.00 | 32.21 | C |
| ATOM | 2094 | OH | TYR | A | 1099 | 90.471 | 78.790 | −3.365 | 1.00 | 31.91 | O |
| ATOM | 2095 | CE2 | TYR | A | 1099 | 92.370 | 79.707 | −2.293 | 1.00 | 32.41 | C |
| ATOM | 2096 | CD2 | TYR | A | 1099 | 93.154 | 80.799 | −1.948 | 1.00 | 32.52 | C |
| ATOM | 2097 | C | TYR | A | 1099 | 95.204 | 83.078 | −3.948 | 1.00 | 33.68 | C |
| ATOM | 2098 | O | TYR | A | 1099 | 95.126 | 82.002 | −4.549 | 1.00 | 33.84 | O |
| ATOM | 2099 | N | MET | A | 1100 | 95.353 | 84.253 | −4.563 | 1.00 | 34.08 | N |
| ATOM | 2100 | CA | MET | A | 1100 | 95.495 | 84.361 | −6.018 | 1.00 | 35.82 | C |
| ATOM | 2101 | CB | MET | A | 1100 | 95.541 | 85.825 | −6.476 | 1.00 | 35.01 | C |
| ATOM | 2102 | CG | MET | A | 1100 | 94.246 | 86.602 | −6.227 | 1.00 | 38.71 | C |
| ATOM | 2103 | SD | MET | A | 1100 | 94.067 | 88.165 | −7.127 | 1.00 | 41.75 | S |
| ATOM | 2104 | CE | MET | A | 1100 | 95.434 | 89.136 | −6.492 | 1.00 | 43.08 | C |
| ATOM | 2105 | C | MET | A | 1100 | 96.724 | 83.598 | −6.518 | 1.00 | 33.70 | C |
| ATOM | 2106 | O | MET | A | 1100 | 96.660 | 82.939 | −7.552 | 1.00 | 32.83 | O |
| ATOM | 2107 | N | ILE | A | 1101 | 97.826 | 83.684 | −5.771 | 1.00 | 33.01 | N |
| ATOM | 2108 | CA | ILE | A | 1101 | 99.052 | 82.949 | −6.090 | 1.00 | 32.64 | C |
| ATOM | 2109 | CB | ILE | A | 1101 | 100.230 | 83.336 | −5.148 | 1.00 | 32.91 | C |
| ATOM | 2110 | CG1 | ILE | A | 1101 | 100.665 | 84.785 | −5.405 | 1.00 | 32.67 | C |
| ATOM | 2111 | CD1 | ILE | A | 1101 | 101.666 | 85.341 | −4.395 | 1.00 | 33.37 | C |
| ATOM | 2112 | CG2 | ILE | A | 1101 | 101.414 | 82.384 | −5.327 | 1.00 | 31.82 | C |
| ATOM | 2113 | C | ILE | A | 1101 | 98.793 | 81.441 | −6.067 | 1.00 | 32.44 | C |
| ATOM | 2114 | O | ILE | A | 1101 | 99.186 | 80.728 | −6.996 | 1.00 | 31.74 | O |
| ATOM | 2115 | N | MET | A | 1102 | 98.120 | 80.978 | −5.012 | 1.00 | 31.74 | N |
| ATOM | 2116 | CA | MET | A | 1102 | 97.688 | 79.584 | −4.889 | 1.00 | 32.50 | C |
| ATOM | 2117 | CB | MET | A | 1102 | 96.865 | 79.383 | −3.612 | 1.00 | 32.02 | C |
| ATOM | 2118 | CG | MET | A | 1102 | 97.680 | 79.297 | −2.332 | 1.00 | 33.83 | C |
| ATOM | 2119 | SD | MET | A | 1102 | 96.707 | 79.555 | −.831 | 1.00 | 34.64 | S |
| ATOM | 2120 | CE | MET | A | 1102 | 95.367 | 78.407 | −1.028 | 1.00 | 34.47 | C |
| ATOM | 2121 | C | MET | A | 1102 | 96.865 | 79.135 | −6.094 | 1.00 | 32.11 | C |

APPENDIX 1-continued

| ATOM | 2122 | O | MET | A | 1102 | 97.169 | 78.115 | −6.710 | 1.00 | 31.98 | O |
|---|---|---|---|---|---|---|---|---|---|---|---|
| ATOM | 2123 | N | THR | A | 1103 | 95.830 | 79.906 | −6.430 | 1.00 | 31.73 | N |
| ATOM | 2124 | CA | THR | A | 1103 | 94.918 | 79.536 | −7.516 | 1.00 | 31.60 | C |
| ATOM | 2125 | CB | THR | A | 1103 | 93.653 | 80.424 | −7.557 | 1.00 | 31.92 | C |
| ATOM | 2126 | OG1 | THR | A | 1103 | 94.030 | 81.800 | −7.658 | 1.00 | 34.69 | O |
| ATOM | 2127 | CG2 | THR | A | 1103 | 92.809 | 80.217 | −6.307 | 1.00 | 31.47 | C |
| ATOM | 2128 | C | THR | A | 1103 | 95.601 | 79.527 | −8.884 | 1.00 | 31.09 | C |
| ATOM | 2129 | O | THR | A | 1103 | 95.251 | 78.722 | −9.746 | 1.00 | 30.78 | O |
| ATOM | 2130 | N | GLU | A | 1104 | 96.572 | 80.420 | −9.068 | 1.00 | 30.19 | N |
| ATOM | 2131 | CA | GLU | A | 1104 | 97.359 | 80.472 | −10.299 | 1.00 | 31.54 | C |
| ATOM | 2132 | CB | GLU | A | 1104 | 98.115 | 81.796 | −10.406 | 1.00 | 31.48 | C |
| ATOM | 2133 | CG | GLU | A | 1104 | 97.220 | 82.986 | −10.740 | 1.00 | 34.29 | C |
| ATOM | 2134 | CD | GLU | A | 1104 | 97.994 | 84.279 | −10.894 | 1.00 | 34.64 | C |
| ATOM | 2135 | OE1 | GLU | A | 1104 | 99.087 | 84.250 | −11.496 | 1.00 | 41.18 | O |
| ATOM | 2136 | OE2 | GLU | A | 1104 | 97.504 | 85.327 | −10.421 | 1.00 | 38.29 | O |
| ATOM | 2137 | C | GLU | A | 1104 | 98.322 | 79.285 | −10.423 | 1.00 | 30.14 | C |
| ATOM | 2138 | O | GLU | A | 1104 | 98.598 | 78.816 | −11.531 | 1.00 | 29.66 | O |
| ATOM | 2139 | N | CYS | A | 1105 | 98.825 | 78.806 | −9.287 | 1.00 | 28.74 | N |
| ATOM | 2140 | CA | CYS | A | 1105 | 99.621 | 77.577 | −9.254 | 1.00 | 28.29 | C |
| ATOM | 2141 | CB | CYS | A | 1105 | 100.284 | 77.391 | −7.887 | 1.00 | 27.43 | C |
| ATOM | 2142 | SG | CYS | A | 1105 | 101.593 | 78.579 | −7.528 | 1.00 | 29.05 | S |
| ATOM | 2143 | C | CYS | A | 1105 | 98.755 | 76.363 | −9.585 | 1.00 | 28.19 | C |
| ATOM | 2144 | O | CYS | A | 1105 | 99.229 | 75.401 | −10.196 | 1.00 | 28.80 | O |
| ATOM | 2145 | N | TRP | A | 1106 | 97.484 | 76.419 | −9.187 | 1.00 | 27.83 | N |
| ATOM | 2146 | CA | TRP | A | 1106 | 96.544 | 75.334 | −9.444 | 1.00 | 28.64 | C |
| ATOM | 2147 | CB | TRP | A | 1106 | 95.543 | 75.185 | −8.295 | 1.00 | 28.80 | C |
| ATOM | 2148 | CG | TRP | A | 1106 | 96.164 | 75.003 | −6.947 | 1.00 | 29.94 | C |
| ATOM | 2149 | CD1 | TRP | A | 1106 | 97.325 | 74.340 | −6.653 | 1.00 | 28.70 | C |
| ATOM | 2150 | NE1 | TRP | A | 1106 | 97.563 | 74.379 | −5.300 | 1.00 | 29.85 | N |
| ATOM | 2151 | CE2 | TRP | A | 1106 | 96.544 | 75.064 | −4.690 | 1.00 | 30.41 | C |
| ATOM | 2152 | CD2 | TRP | A | 1106 | 95.641 | 75.470 | −5.700 | 1.00 | 30.35 | C |
| ATOM | 2153 | CE3 | TRP | A | 1106 | 94.500 | 76.199 | −5.338 | 1.00 | 28.41 | C |
| ATOM | 2154 | CZ3 | TRP | A | 1106 | 94.296 | 76.492 | −3.997 | 1.00 | 29.85 | C |
| ATOM | 2155 | CH2 | TRP | A | 1106 | 95.212 | 76.068 | −3.013 | 1.00 | 30.12 | C |
| ATOM | 2156 | CZ2 | TRP | A | 1106 | 96.339 | 75.358 | −3.340 | 1.00 | 30.54 | C |
| ATOM | 2157 | C | TRP | A | 1106 | 95.797 | 75.482 | −10.773 | 1.00 | 29.04 | C |
| ATOM | 2158 | O | TRP | A | 1106 | 94.587 | 75.263 | −10.843 | 1.00 | 29.04 | O |
| ATOM | 2159 | N | ASN | A | 1107 | 96.522 | 75.846 | −11.825 | 1.00 | 29.42 | N |
| ATOM | 2160 | CA | ASN | A | 1107 | 95.944 | 75.898 | −13.162 | 1.00 | 30.19 | C |
| ATOM | 2161 | CB | ASN | A | 1107 | 96.698 | 76.904 | −14.040 | 1.00 | 29.71 | C |
| ATOM | 2162 | CG | ASN | A | 1107 | 95.860 | 77.418 | −15.202 | 1.00 | 30.76 | C |
| ATOM | 2163 | OD1 | ASN | A | 1107 | 95.170 | 76.654 | −15.878 | 1.00 | 33.65 | O |
| ATOM | 2164 | ND2 | ASN | A | 1107 | 95.924 | 78.723 | −15.443 | 1.00 | 29.53 | N |
| ATOM | 2165 | C | ASN | A | 1107 | 95.984 | 74.509 | −13.782 | 1.00 | 30.68 | C |
| ATOM | 2166 | O | ASN | A | 1107 | 97.018 | 73.842 | −13.743 | 1.00 | 30.97 | O |
| ATOM | 2167 | N | ASN | A | 1108 | 94.851 | 74.070 | −14.327 | 1.00 | 31.69 | N |
| ATOM | 2168 | CA | ASN | A | 1108 | 94.778 | 72.815 | −15.072 | 1.00 | 32.26 | C |
| ATOM | 2169 | CB | ASN | A | 1108 | 93.340 | 72.529 | −15.521 | 1.00 | 32.31 | C |
| ATOM | 2170 | CG | ASN | A | 1108 | 92.450 | 72.045 | −14.385 | 1.00 | 33.78 | C |
| ATOM | 2171 | OD1 | ASN | A | 1108 | 92.929 | 71.523 | −13.378 | 1.00 | 32.08 | O |
| ATOM | 2172 | ND2 | ASN | A | 1108 | 91.139 | 72.209 | −14.553 | 1.00 | 32.61 | N |
| ATOM | 2173 | C | ASN | A | 1108 | 95.706 | 72.831 | −16.286 | 1.00 | 32.79 | C |
| ATOM | 2174 | O | ASN | A | 1108 | 96.264 | 71.800 | −16.665 | 1.00 | 33.90 | O |
| ATOM | 2175 | N | ASN | A | 1109 | 95.861 | 74.006 | −16.889 | 1.00 | 32.55 | N |
| ATOM | 2176 | CA | ASN | A | 1109 | 96.768 | 74.185 | −18.016 | 1.00 | 32.43 | C |
| ATOM | 2177 | CB | ASN | A | 1109 | 96.378 | 75.417 | −18.836 | 1.00 | 32.53 | C |
| ATOM | 2178 | CG | ASN | A | 1109 | 94.913 | 75.409 | −19.241 | 1.00 | 34.58 | C |
| ATOM | 2179 | OD1 | ASN | A | 1109 | 94.454 | 74.505 | −19.939 | 1.00 | 34.82 | O |
| ATOM | 2180 | ND2 | ASN | A | 1109 | 94.172 | 76.421 | −18.801 | 1.00 | 35.62 | N |
| ATOM | 2181 | C | ASN | A | 1109 | 98.205 | 74.287 | −17.522 | 1.00 | 32.32 | C |
| ATOM | 2182 | O | ASN | A | 1109 | 98.613 | 75.305 | −16.962 | 1.00 | 31.54 | O |
| ATOM | 2183 | N | VAL | A | 1110 | 98.954 | 73.208 | −17.731 | 1.00 | 33.03 | N |
| ATOM | 2184 | CA | VAL | A | 1110 | 100.330 | 73.064 | −17.254 | 1.00 | 34.03 | C |
| ATOM | 2185 | CB | VAL | A | 1110 | 100.957 | 71.753 | −17.808 | 1.00 | 34.36 | C |
| ATOM | 2186 | CG1 | VAL | A | 1110 | 102.447 | 71.668 | −17.518 | 1.00 | 36.37 | C |
| ATOM | 2187 | CG2 | VAL | A | 1110 | 100.238 | 70.543 | −17.234 | 1.00 | 35.01 | C |
| ATOM | 2188 | C | VAL | A | 1110 | 101.203 | 74.279 | −17.590 | 1.00 | 33.85 | C |
| ATOM | 2189 | O | VAL | A | 1110 | 101.935 | 74.777 | −16.734 | 1.00 | 34.10 | O |
| ATOM | 2190 | N | ASN | A | 1111 | 101.089 | 74.760 | −18.826 | 1.00 | 33.80 | N |
| ATOM | 2191 | CA | ASN | A | 1111 | 101.910 | 75.858 | −19.332 | 1.00 | 33.69 | C |
| ATOM | 2192 | CB | ASN | A | 1111 | 101.838 | 75.896 | −20.863 | 1.00 | 34.56 | C |
| ATOM | 2193 | CG | ASN | A | 1111 | 100.475 | 76.337 | −21.378 | 1.00 | 36.20 | C |
| ATOM | 2194 | OD1 | ASN | A | 1111 | 99.438 | 75.832 | −20.945 | 1.00 | 38.85 | O |
| ATOM | 2195 | ND2 | ASN | A | 1111 | 100.476 | 77.280 | −22.314 | 1.00 | 36.11 | N |
| ATOM | 2196 | C | ASN | A | 1111 | 101.560 | 77.240 | −18.772 | 1.00 | 33.61 | C |
| ATOM | 2197 | O | ASN | A | 1111 | 102.329 | 78.191 | −18.937 | 1.00 | 33.04 | O |
| ATOM | 2198 | N | GLN | A | 1112 | 100.401 | 77.348 | −18.125 | 1.00 | 32.82 | N |
| ATOM | 2199 | CA | GLN | A | 1112 | 99.919 | 78.630 | −17.609 | 1.00 | 33.29 | C |
| ATOM | 2200 | CB | GLN | A | 1112 | 98.404 | 78.747 | −17.788 | 1.00 | 33.11 | C |

APPENDIX 1-continued

| ATOM | 2201 | CG | GLN | A | 1112 | 97.966 | 79.024 | −19.224 | 1.00 | 35.33 | C |
|---|---|---|---|---|---|---|---|---|---|---|---|
| ATOM | 2202 | CD | GLN | A | 1112 | 96.458 | 78.965 | −19.413 | 1.00 | 35.84 | C |
| ATOM | 2203 | OE1 | GLN | A | 1112 | 95.690 | 79.031 | −18.452 | 1.00 | 41.62 | O |
| ATOM | 2204 | NE2 | GLN | A | 1112 | 96.029 | 78.841 | −20.664 | 1.00 | 41.33 | N |
| ATOM | 2205 | C | GLN | A | 1112 | 100.310 | 78.889 | −16.153 | 1.00 | 32.19 | C |
| ATOM | 2206 | O | GLN | A | 1112 | 100.055 | 79.969 | −15.617 | 1.00 | 32.54 | O |
| ATOM | 2207 | N | ARG | A | 1113 | 100.927 | 77.898 | −15.518 | 1.00 | 32.01 | N |
| ATOM | 2208 | CA | ARG | A | 1113 | 101.399 | 78.047 | −14.143 | 1.00 | 30.96 | C |
| ATOM | 2209 | CB | ARG | A | 1113 | 101.690 | 76.678 | −13.523 | 1.00 | 30.99 | C |
| ATOM | 2210 | CG | ARG | A | 1113 | 100.450 | 75.804 | −13.388 | 1.00 | 31.27 | C |
| ATOM | 2211 | CD | ARG | A | 1113 | 100.790 | 74.369 | −13.027 | 1.00 | 29.37 | C |
| ATOM | 2212 | NE | ARG | A | 1113 | 99.663 | 73.483 | −13.306 | 1.00 | 30.45 | N |
| ATOM | 2213 | CZ | ARG | A | 1113 | 99.745 | 72.158 | −13.415 | 1.00 | 30.20 | C |
| ATOM | 2214 | NH1 | ARG | A | 1113 | 100.907 | 71.536 | −13.259 | 1.00 | 27.30 | N |
| ATOM | 2215 | NH2 | ARG | A | 1113 | 98.653 | 71.450 | −13.682 | 1.00 | 30.23 | N |
| ATOM | 2216 | C | ARG | A | 1113 | 102.634 | 78.944 | −14.112 | 1.00 | 30.70 | C |
| ATOM | 2217 | O | ARG | A | 1113 | 103.483 | 78.855 | −15.000 | 1.00 | 30.19 | O |
| ATOM | 2218 | N | PRO | A | 1114 | 102.727 | 79.836 | −13.105 | 1.00 | 30.82 | N |
| ATOM | 2219 | CA | PRO | A | 1114 | 103.891 | 80.721 | −12.986 | 1.00 | 30.15 | C |
| ATOM | 2220 | CB | PRO | A | 1114 | 103.565 | 81.574 | −11.753 | 1.00 | 30.07 | C |
| ATOM | 2221 | CG | PRO | A | 1114 | 102.523 | 80.819 | −11.011 | 1.00 | 31.07 | C |
| ATOM | 2222 | CD | PRO | A | 1114 | 101.737 | 80.080 | −12.038 | 1.00 | 30.60 | C |
| ATOM | 2223 | C | PRO | A | 1114 | 105.208 | 79.967 | −12.778 | 1.00 | 30.21 | C |
| ATOM | 2224 | O | PRO | A | 1114 | 105.206 | 78.818 | −12.338 | 1.00 | 30.29 | O |
| ATOM | 2225 | N | SER | A | 1115 | 106.320 | 80.614 | −13.112 | 1.00 | 29.56 | N |
| ATOM | 2226 | CA | SER | A | 1115 | 107.637 | 80.063 | −12.831 | 1.00 | 30.42 | C |
| ATOM | 2227 | CB | SER | A | 1115 | 108.686 | 80.718 | −13.726 | 1.00 | 30.29 | C |
| ATOM | 2228 | OG | SER | A | 1115 | 108.746 | 82.113 | −13.486 | 1.00 | 30.62 | O |
| ATOM | 2229 | C | SER | A | 1115 | 107.979 | 80.301 | −11.361 | 1.00 | 30.64 | C |
| ATOM | 2230 | O | SER | A | 1115 | 107.392 | 81.178 | −10.721 | 1.00 | 30.82 | O |
| ATOM | 2231 | N | PHE | A | 1116 | 108.923 | 79.526 | −10.828 | 1.00 | 30.34 | N |
| ATOM | 2232 | CA | PHE | A | 1116 | 109.390 | 79.739 | −9.457 | 1.00 | 30.69 | C |
| ATOM | 2233 | CB | PHE | A | 1116 | 110.322 | 78.612 | −9.006 | 1.00 | 30.07 | C |
| ATOM | 2234 | CG | PHE | A | 1116 | 109.594 | 77.382 | −8.536 | 1.00 | 29.82 | C |
| ATOM | 2235 | CD1 | PHE | A | 1116 | 108.793 | 77.426 | −7.397 | 1.00 | 30.04 | C |
| ATOM | 2236 | CE1 | PHE | A | 1116 | 108.110 | 76.291 | −6.958 | 1.00 | 28.50 | C |
| ATOM | 2237 | CZ | PHE | A | 1116 | 108.230 | 75.093 | −7.660 | 1.00 | 27.78 | C |
| ATOM | 2238 | CE2 | PHE | A | 1116 | 109.030 | 75.036 | −8.797 | 1.00 | 28.28 | C |
| ATOM | 2239 | CD2 | PHE | A | 1116 | 109.707 | 76.181 | −9.230 | 1.00 | 28.16 | C |
| ATOM | 2240 | C | PHE | A | 1116 | 110.059 | 81.100 | −9.281 | 1.00 | 31.26 | C |
| ATOM | 2241 | O | PHE | A | 1116 | 109.931 | 81.732 | −8.232 | 1.00 | 31.17 | O |
| ATOM | 2242 | N | ARG | A | 1117 | 110.753 | 81.553 | −10.321 | 1.00 | 31.27 | N |
| ATOM | 2243 | CA | ARG | A | 1117 | 111.368 | 82.876 | −10.325 | 1.00 | 33.07 | C |
| ATOM | 2244 | CB | ARG | A | 1117 | 112.182 | 83.075 | −11.603 | 1.00 | 33.79 | C |
| ATOM | 2245 | CG | ARG | A | 1117 | 113.301 | 84.091 | −11.473 | 1.00 | 40.81 | C |
| ATOM | 2246 | CD | ARG | A | 1117 | 114.630 | 83.458 | −11.077 | 1.00 | 49.26 | C |
| ATOM | 2247 | NE | ARG | A | 1117 | 115.730 | 84.417 | −11.189 | 1.00 | 53.85 | N |
| ATOM | 2248 | CZ | ARG | A | 1117 | 117.023 | 84.097 | −11.184 | 1.00 | 56.75 | C |
| ATOM | 2249 | NH1 | ARG | A | 1117 | 117.408 | 82.830 | −11.073 | 1.00 | 58.87 | N |
| ATOM | 2250 | NH2 | ARG | A | 1117 | 117.939 | 85.051 | −11.293 | 1.00 | 58.89 | N |
| ATOM | 2251 | C | ARG | A | 1117 | 110.326 | 83.993 | −10.168 | 1.00 | 32.65 | C |
| ATOM | 2252 | O | ARG | A | 1117 | 110.512 | 84.913 | −9.365 | 1.00 | 32.15 | O |
| ATOM | 2253 | N | ASP | A | 1118 | 109.230 | 83.897 | −10.922 | 1.00 | 32.27 | N |
| ATOM | 2254 | CA | ASP | A | 1118 | 108.153 | 84.890 | −10.862 | 1.00 | 32.36 | C |
| ATOM | 2255 | CB | ASP | A | 1118 | 107.207 | 84.755 | −12.059 | 1.00 | 31.98 | C |
| ATOM | 2256 | CG | ASP | A | 1118 | 107.823 | 85.262 | −13.357 | 1.00 | 34.86 | C |
| ATOM | 2257 | OD1 | ASP | A | 1118 | 108.958 | 85.785 | −13.330 | 1.00 | 36.85 | O |
| ATOM | 2258 | OD2 | ASP | A | 1118 | 107.166 | 85.139 | −14.412 | 1.00 | 36.53 | O |
| ATOM | 2259 | C | ASP | A | 1118 | 107.368 | 84.807 | −9.558 | 1.00 | 32.08 | C |
| ATOM | 2260 | O | ASP | A | 1118 | 106.901 | 85.826 | −9.046 | 1.00 | 31.77 | O |
| ATOM | 2261 | N | LEU | A | 1119 | 107.222 | 83.592 | −9.033 | 1.00 | 32.51 | N |
| ATOM | 2262 | CA | LEU | A | 1119 | 106.595 | 83.382 | −7.730 | 1.00 | 32.59 | C |
| ATOM | 2263 | CB | LEU | A | 1119 | 106.457 | 81.887 | −7.415 | 1.00 | 32.57 | C |
| ATOM | 2264 | CG | LEU | A | 1119 | 105.362 | 81.125 | −8.170 | 1.00 | 32.41 | C |
| ATOM | 2265 | CD1 | LEU | A | 1119 | 105.551 | 79.615 | −8.047 | 1.00 | 31.76 | C |
| ATOM | 2266 | CD2 | LEU | A | 1119 | 103.972 | 81.547 | −7.706 | 1.00 | 31.24 | C |
| ATOM | 2267 | C | LEU | A | 1119 | 107.376 | 84.094 | −6.633 | 1.00 | 32.79 | C |
| ATOM | 2268 | O | LEU | A | 1119 | 106.790 | 84.796 | −5.813 | 1.00 | 32.74 | O |
| ATOM | 2269 | N | ALA | A | 1120 | 108.698 | 83.920 | −6.637 | 1.00 | 33.24 | N |
| ATOM | 2270 | CA | ALA | A | 1120 | 109.584 | 84.605 | −5.693 | 1.00 | 33.92 | C |
| ATOM | 2271 | CB | ALA | A | 1120 | 111.029 | 84.190 | −5.922 | 1.00 | 33.55 | C |
| ATOM | 2272 | C | ALA | A | 1120 | 109.441 | 86.124 | −5.797 | 1.00 | 34.63 | C |
| ATOM | 2273 | O | ALA | A | 1120 | 109.371 | 86.816 | −4.780 | 1.00 | 34.60 | O |
| ATOM | 2274 | N | LEU | A | 1121 | 109.386 | 86.626 | −7.031 | 1.00 | 35.42 | N |
| ATOM | 2275 | CA | LEU | A | 1121 | 109.231 | 88.056 | −7.298 | 1.00 | 36.30 | C |
| ATOM | 2276 | CB | LEU | A | 1121 | 109.306 | 88.339 | −8.804 | 1.00 | 36.89 | C |
| ATOM | 2277 | CG | LEU | A | 1121 | 110.668 | 88.257 | −9.502 | 1.00 | 39.48 | C |
| ATOM | 2278 | CD1 | LEU | A | 1121 | 110.486 | 88.237 | −11.015 | 1.00 | 41.35 | C |
| ATOM | 2279 | CD2 | LEU | A | 1121 | 111.588 | 89.404 | −9.086 | 1.00 | 41.70 | C |

APPENDIX 1-continued

| ATOM | 2280 | C | LEU | A | 1121 | 107.924 | 88.601 | −6.732 | 1.00 | 36.02 | C |
|---|---|---|---|---|---|---|---|---|---|---|---|
| ATOM | 2281 | O | LEU | A | 1121 | 107.914 | 89.640 | −6.070 | 1.00 | 35.64 | O |
| ATOM | 2282 | N | ARG | A | 1122 | 106.830 | 87.890 | −6.999 | 1.00 | 35.93 | N |
| ATOM | 2283 | CA | ARG | A | 1122 | 105.505 | 88.279 | −6.524 | 1.00 | 36.38 | C |
| ATOM | 2284 | CB | ARG | A | 1122 | 104.426 | 87.397 | −7.154 | 1.00 | 36.25 | C |
| ATOM | 2285 | CG | ARG | A | 1122 | 104.147 | 87.726 | −8.613 | 1.00 | 38.82 | C |
| ATOM | 2286 | CD | ARG | A | 1122 | 103.252 | 86.683 | −9.261 | 1.00 | 42.25 | C |
| ATOM | 2287 | NE | ARG | A | 1122 | 101.884 | 86.736 | −8.750 | 1.00 | 44.51 | N |
| ATOM | 2288 | CZ | ARG | A | 1122 | 100.892 | 85.955 | −9.168 | 1.00 | 46.42 | C |
| ATOM | 2289 | NH1 | ARG | A | 1122 | 101.105 | 85.048 | −10.114 | 1.00 | 47.14 | N |
| ATOM | 2290 | NH2 | ARG | A | 1122 | 99.683 | 86.083 | −8.636 | 1.00 | 44.46 | N |
| ATOM | 2291 | C | ARG | A | 1122 | 105.409 | 88.241 | −5.000 | 1.00 | 36.10 | C |
| ATOM | 2292 | O | ARG | A | 1122 | 104.871 | 89.166 | −4.386 | 1.00 | 35.98 | O |
| ATOM | 2293 | N | VAL | A | 1123 | 105.941 | 87.177 | −4.402 | 1.00 | 35.56 | N |
| ATOM | 2294 | CA | VAL | A | 1123 | 105.963 | 87.023 | −2.946 | 1.00 | 35.81 | C |
| ATOM | 2295 | CB | VAL | A | 1123 | 106.436 | 85.595 | −2.526 | 1.00 | 35.57 | C |
| ATOM | 2296 | CG1 | VAL | A | 1123 | 106.793 | 85.534 | −1.042 | 1.00 | 35.15 | C |
| ATOM | 2297 | CG2 | VAL | A | 1123 | 105.360 | 84.566 | −2.850 | 1.00 | 33.47 | C |
| ATOM | 2298 | C | VAL | A | 1123 | 106.803 | 88.115 | −2.274 | 1.00 | 36.71 | C |
| ATOM | 2299 | O | VAL | A | 1123 | 106.347 | 88.743 | −1.318 | 1.00 | 36.95 | O |
| ATOM | 2300 | N | ASP | A | 1124 | 108.012 | 88.348 | −2.787 | 1.00 | 37.81 | N |
| ATOM | 2301 | CA | ASP | A | 1124 | 108.909 | 89.379 | −2.246 | 1.00 | 39.47 | C |
| ATOM | 2302 | CB | ASP | A | 1124 | 110.288 | 89.324 | −2.915 | 1.00 | 39.39 | C |
| ATOM | 2303 | CG | ASP | A | 1124 | 111.129 | 88.145 | −2.442 | 1.00 | 40.65 | C |
| ATOM | 2304 | OD1 | ASP | A | 1124 | 110.646 | 87.349 | −1.605 | 1.00 | 40.10 | O |
| ATOM | 2305 | OD2 | ASP | A | 1124 | 112.282 | 88.015 | −2.908 | 1.00 | 38.77 | O |
| ATOM | 2306 | C | ASP | A | 1124 | 108.328 | 90.785 | −2.368 | 1.00 | 40.92 | C |
| ATOM | 2307 | O | ASP | A | 1124 | 108.585 | 91.641 | −1.518 | 1.00 | 40.74 | O |
| ATOM | 2308 | N | GLN | A | 1125 | 107.548 | 91.012 | −3.424 | 1.00 | 42.29 | N |
| ATOM | 2309 | CA | GLN | A | 1125 | 106.852 | 92.283 | −3.622 | 1.00 | 44.31 | C |
| ATOM | 2310 | CB | GLN | A | 1125 | 106.258 | 92.359 | −5.033 | 1.00 | 44.01 | C |
| ATOM | 2311 | CG | GLN | A | 1125 | 105.676 | 93.719 | −5.400 | 1.00 | 45.90 | C |
| ATOM | 2312 | CD | GLN | A | 1125 | 105.278 | 93.828 | −6.865 | 1.00 | 46.21 | C |
| ATOM | 2313 | OE1 | GLN | A | 1125 | 105.360 | 92.858 | −7.625 | 1.00 | 49.68 | O |
| ATOM | 2314 | NE2 | GLN | A | 1125 | 104.843 | 95.019 | −7.268 | 1.00 | 48.06 | N |
| ATOM | 2315 | C | GLN | A | 1125 | 105.762 | 92.481 | −2.566 | 1.00 | 44.55 | C |
| ATOM | 2316 | O | GLN | A | 1125 | 105.623 | 93.574 | −2.015 | 1.00 | 44.44 | O |
| ATOM | 2317 | N | ILE | A | 1126 | 105.005 | 91.420 | −2.286 | 1.00 | 45.00 | N |
| ATOM | 2318 | CA | ILE | A | 1126 | 103.960 | 91.450 | −1.259 | 1.00 | 46.01 | C |
| ATOM | 2319 | CB | ILE | A | 1126 | 103.031 | 90.211 | −1.347 | 1.00 | 46.08 | C |
| ATOM | 2320 | CG1 | ILE | A | 1126 | 102.236 | 90.245 | −2.657 | 1.00 | 45.28 | C |
| ATOM | 2321 | CD1 | ILE | A | 1126 | 101.596 | 88.927 | −3.043 | 1.00 | 46.07 | C |
| ATOM | 2322 | CG2 | ILE | A | 1126 | 102.076 | 90.146 | −.148 | 1.00 | 46.26 | C |
| ATOM | 2323 | C | ILE | A | 1126 | 104.572 | 91.604 | .139 | 1.00 | 46.96 | C |
| ATOM | 2324 | O | ILE | A | 1126 | 104.030 | 92.324 | .983 | 1.00 | 46.93 | O |
| ATOM | 2325 | N | ARG | A | 1127 | 105.709 | 90.943 | .361 | 1.00 | 48.18 | N |
| ATOM | 2326 | CA | ARG | A | 1127 | 106.487 | 91.089 | 1.595 | 1.00 | 49.46 | C |
| ATOM | 2327 | CB | ARG | A | 1127 | 107.766 | 90.249 | 1.530 | 1.00 | 49.20 | C |
| ATOM | 2328 | CG | ARG | A | 1127 | 107.560 | 88.758 | 1.740 | 1.00 | 48.87 | C |
| ATOM | 2329 | CD | ARG | A | 1127 | 108.847 | 87.979 | 1.496 | 1.00 | 48.89 | C |
| ATOM | 2330 | NE | ARG | A | 1127 | 109.834 | 88.207 | 2.550 | 1.00 | 47.73 | N |
| ATOM | 2331 | CZ | ARG | A | 1127 | 111.144 | 88.015 | 2.418 | 1.00 | 47.64 | C |
| ATOM | 2332 | NH1 | ARG | A | 1127 | 111.655 | 87.593 | 1.268 | 1.00 | 46.27 | N |
| ATOM | 2333 | NH2 | ARG | A | 1127 | 111.950 | 88.255 | 3.443 | 1.00 | 48.07 | N |
| ATOM | 2334 | C | ARG | A | 1127 | 106.850 | 92.547 | 1.878 | 1.00 | 50.95 | C |
| ATOM | 2335 | O | ARG | A | 1127 | 106.677 | 93.028 | 3.000 | 1.00 | 50.92 | O |
| ATOM | 2336 | N | ASP | A | 1128 | 107.348 | 93.238 | .852 | 1.00 | 52.72 | N |
| ATOM | 2337 | CA | ASP | A | 1128 | 107.763 | 94.640 | .966 | 1.00 | 54.65 | C |
| ATOM | 2338 | CB | ASP | A | 1128 | 108.545 | 95.077 | −.278 | 1.00 | 54.70 | C |
| ATOM | 2339 | CG | ASP | A | 1128 | 109.857 | 94.325 | −.448 | 1.00 | 55.18 | C |
| ATOM | 2340 | OD1 | ASP | A | 1128 | 110.334 | 93.700 | .525 | 1.00 | 55.99 | O |
| ATOM | 2341 | OD2 | ASP | A | 1128 | 110.416 | 94.365 | −1.565 | 1.00 | 54.79 | O |
| ATOM | 2342 | C | ASP | A | 1128 | 106.588 | 95.589 | 1.196 | 1.00 | 55.80 | C |
| ATOM | 2343 | O | ASP | A | 1128 | 106.722 | 96.586 | 1.909 | 1.00 | 56.38 | O |
| ATOM | 2344 | N | GLN | A | 1129 | 105.446 | 95.274 | .588 | 1.00 | 56.99 | N |
| ATOM | 2345 | CA | GLN | A | 1129 | 104.230 | 96.075 | .738 | 1.00 | 58.38 | C |
| ATOM | 2346 | CB | GLN | A | 1129 | 103.237 | 95.768 | −.387 | 1.00 | 58.18 | C |
| ATOM | 2347 | CG | GLN | A | 1129 | 103.683 | 96.269 | −1.760 | 1.00 | 58.82 | C |
| ATOM | 2348 | CD | GLN | A | 1129 | 102.751 | 95.852 | −2.888 | 1.00 | 58.65 | C |
| ATOM | 2349 | OE1 | GLN | A | 1129 | 102.171 | 94.764 | −2.868 | 1.00 | 59.49 | O |
| ATOM | 2350 | NE2 | GLN | A | 1129 | 102.612 | 96.718 | −3.886 | 1.00 | 57.97 | N |
| ATOM | 2351 | C | GLN | A | 1129 | 103.576 | 95.874 | 2.107 | 1.00 | 59.39 | C |
| ATOM | 2352 | O | GLN | A | 1129 | 102.812 | 96.726 | 2.569 | 1.00 | 59.35 | O |
| ATOM | 2353 | N | MET | A | 1130 | 103.880 | 94.745 | 2.745 | 1.00 | 60.62 | N |
| ATOM | 2354 | CA | MET | A | 1130 | 103.419 | 94.464 | 4.104 | 1.00 | 61.92 | C |
| ATOM | 2355 | CB | MET | A | 1130 | 103.248 | 92.957 | 4.316 | 1.00 | 61.97 | C |
| ATOM | 2356 | CG | MET | A | 1130 | 102.003 | 92.366 | 3.668 | 1.00 | 62.00 | C |
| ATOM | 2357 | SD | MET | A | 1130 | 101.854 | 90.584 | 3.920 | 1.00 | 62.12 | S |
| ATOM | 2358 | CE | MET | A | 1130 | 101.363 | 90.508 | 5.642 | 1.00 | 62.59 | C |

APPENDIX 1-continued

| ATOM | 2359 | C | MET | A | 1130 | 104.375 | 95.035 | 5.154 | 1.00 | 62.79 | C |
|---|---|---|---|---|---|---|---|---|---|---|---|
| ATOM | 2360 | O | MET | A | 1130 | 103.997 | 95.211 | 6.315 | 1.00 | 62.94 | O |
| ATOM | 2361 | N | ALA | A | 1131 | 105.607 | 95.321 | 4.735 | 1.00 | 63.75 | N |
| ATOM | 2362 | CA | ALA | A | 1131 | 106.647 | 95.826 | 5.630 | 1.00 | 64.58 | C |
| ATOM | 2363 | CB | ALA | A | 1131 | 108.034 | 95.515 | 5.068 | 1.00 | 64.53 | C |
| ATOM | 2364 | C | ALA | A | 1131 | 106.500 | 97.322 | 5.910 | 1.00 | 65.38 | C |
| ATOM | 2365 | O | ALA | A | 1131 | 106.303 | 97.726 | 7.059 | 1.00 | 65.76 | O |
| ATOM | 2366 | N | GLY | A | 1132 | 106.592 | 98.133 | 4.857 | 1.00 | 65.91 | N |
| ATOM | 2367 | CA | GLY | A | 1132 | 106.525 | 99.588 | 4.983 | 1.00 | 66.66 | C |
| ATOM | 2368 | C | GLY | A | 1132 | 105.108 | 100.123 | 5.076 | 1.00 | 67.04 | C |
| ATOM | 2369 | O | GLY | A | 1132 | 104.740 | 101.063 | 4.369 | 1.00 | 67.25 | O |
| ATOM | 2370 | OXT | GLY | A | 1132 | 104.292 | 99.637 | 5.860 | 1.00 | 67.22 | O |
| ATOM | 2371 | N | ASP | B | 840 | 92.260 | 131.810 | 18.779 | 1.00 | 54.02 | N |
| ATOM | 2372 | CA | ASP | B | 840 | 92.393 | 130.355 | 18.484 | 1.00 | 53.72 | C |
| ATOM | 2373 | CB | ASP | B | 840 | 93.339 | 129.690 | 19.493 | 1.00 | 54.02 | C |
| ATOM | 2374 | CG | ASP | B | 840 | 93.798 | 128.305 | 19.055 | 1.00 | 55.68 | C |
| ATOM | 2375 | OD1 | ASP | B | 840 | 93.429 | 127.853 | 17.947 | 1.00 | 57.40 | O |
| ATOM | 2376 | OD2 | ASP | B | 840 | 94.540 | 127.662 | 19.828 | 1.00 | 56.97 | O |
| ATOM | 2377 | C | ASP | B | 840 | 91.020 | 129.675 | 18.492 | 1.00 | 53.17 | C |
| ATOM | 2378 | O | ASP | B | 840 | 90.423 | 129.493 | 19.558 | 1.00 | 53.04 | O |
| ATOM | 2379 | N | PRO | B | 841 | 90.516 | 129.300 | 17.297 | 1.00 | 52.67 | N |
| ATOM | 2380 | CA | PRO | B | 841 | 89.203 | 128.665 | 17.132 | 1.00 | 51.94 | C |
| ATOM | 2381 | CB | PRO | B | 841 | 89.078 | 128.504 | 15.611 | 1.00 | 51.72 | C |
| ATOM | 2382 | CG | PRO | B | 841 | 90.061 | 129.455 | 15.033 | 1.00 | 52.19 | C |
| ATOM | 2383 | CD | PRO | B | 841 | 91.194 | 129.477 | 16.001 | 1.00 | 52.60 | C |
| ATOM | 2384 | C | PRO | B | 841 | 89.096 | 127.297 | 17.809 | 1.00 | 51.30 | C |
| ATOM | 2385 | O | PRO | B | 841 | 87.986 | 126.827 | 18.067 | 1.00 | 51.07 | O |
| ATOM | 2386 | N | THR | B | 842 | 90.239 | 126.674 | 18.088 | 1.00 | 50.83 | N |
| ATOM | 2387 | CA | THR | B | 842 | 90.283 | 125.375 | 18.762 | 1.00 | 50.24 | C |
| ATOM | 2388 | CB | THR | B | 842 | 91.537 | 124.557 | 18.335 | 1.00 | 50.47 | C |
| ATOM | 2389 | OG1 | THR | B | 842 | 91.285 | 123.158 | 18.502 | 1.00 | 52.85 | O |
| ATOM | 2390 | CG2 | THR | B | 842 | 92.765 | 124.949 | 19.142 | 1.00 | 50.50 | C |
| ATOM | 2391 | C | THR | B | 842 | 90.194 | 125.509 | 20.294 | 1.00 | 49.63 | C |
| ATOM | 2392 | O | THR | B | 842 | 90.090 | 124.509 | 21.009 | 1.00 | 48.86 | O |
| ATOM | 2393 | N | GLN | B | 843 | 90.238 | 126.746 | 20.785 | 1.00 | 48.82 | N |
| ATOM | 2394 | CA | GLN | B | 843 | 90.070 | 127.022 | 22.211 | 1.00 | 48.57 | C |
| ATOM | 2395 | CB | GLN | B | 843 | 91.111 | 128.033 | 22.712 | 1.00 | 48.76 | C |
| ATOM | 2396 | CG | GLN | B | 843 | 92.571 | 127.613 | 22.519 | 1.00 | 50.77 | C |
| ATOM | 2397 | CD | GLN | B | 843 | 92.949 | 126.359 | 23.294 | 1.00 | 53.43 | C |
| ATOM | 2398 | OE1 | GLN | B | 843 | 92.814 | 126.302 | 24.518 | 1.00 | 54.47 | O |
| ATOM | 2399 | NE2 | GLN | B | 843 | 93.437 | 125.350 | 22.580 | 1.00 | 53.71 | N |
| ATOM | 2400 | C | GLN | B | 843 | 88.655 | 127.532 | 22.472 | 1.00 | 48.02 | C |
| ATOM | 2401 | O | GLN | B | 843 | 88.274 | 128.610 | 22.008 | 1.00 | 48.07 | O |
| ATOM | 2402 | N | PHE | B | 844 | 87.880 | 126.743 | 23.210 | 1.00 | 46.97 | N |
| ATOM | 2403 | CA | PHE | B | 844 | 86.487 | 127.072 | 23.489 | 1.00 | 46.40 | C |
| ATOM | 2404 | CB | PHE | B | 844 | 85.592 | 125.848 | 23.263 | 1.00 | 45.81 | C |
| ATOM | 2405 | CG | PHE | B | 844 | 85.384 | 125.506 | 21.811 | 1.00 | 44.37 | C |
| ATOM | 2406 | CD1 | PHE | B | 844 | 86.378 | 124.861 | 21.079 | 1.00 | 43.17 | C |
| ATOM | 2407 | CE1 | PHE | B | 844 | 86.184 | 124.547 | 19.735 | 1.00 | 42.75 | C |
| ATOM | 2408 | CZ | PHE | B | 844 | 84.987 | 124.875 | 19.113 | 1.00 | 42.28 | C |
| ATOM | 2409 | CE2 | PHE | B | 844 | 83.987 | 125.516 | 19.833 | 1.00 | 42.97 | C |
| ATOM | 2410 | CD2 | PHE | B | 844 | 84.189 | 125.827 | 21.175 | 1.00 | 43.28 | C |
| ATOM | 2411 | C | PHE | B | 844 | 86.316 | 127.619 | 24.902 | 1.00 | 46.70 | C |
| ATOM | 2412 | O | PHE | B | 844 | 86.756 | 127.004 | 25.876 | 1.00 | 46.82 | O |
| ATOM | 2413 | N | GLU | B | 845 | 85.686 | 128.788 | 24.997 | 1.00 | 47.25 | N |
| ATOM | 2414 | CA | GLU | B | 845 | 85.435 | 129.444 | 26.278 | 1.00 | 47.88 | C |
| ATOM | 2415 | CB | GLU | B | 845 | 85.237 | 130.951 | 26.085 | 1.00 | 48.17 | C |
| ATOM | 2416 | CG | GLU | B | 845 | 86.450 | 131.687 | 25.527 | 1.00 | 50.56 | C |
| ATOM | 2417 | CD | GLU | B | 845 | 87.485 | 132.008 | 26.590 | 1.00 | 53.74 | C |
| ATOM | 2418 | OE1 | GLU | B | 845 | 87.237 | 132.917 | 27.413 | 1.00 | 54.07 | O |
| ATOM | 2419 | OE2 | GLU | B | 845 | 88.553 | 131.357 | 26.592 | 1.00 | 55.29 | O |
| ATOM | 2420 | C | GLU | B | 845 | 84.212 | 128.838 | 26.957 | 1.00 | 47.74 | C |
| ATOM | 2421 | O | GLU | B | 845 | 83.151 | 128.707 | 26.341 | 1.00 | 47.56 | O |
| ATOM | 2422 | N | GLU | B | 846 | 84.375 | 128.472 | 28.226 | 1.00 | 47.88 | N |
| ATOM | 2423 | CA | GLU | B | 846 | 83.297 | 127.901 | 29.037 | 1.00 | 48.40 | C |
| ATOM | 2424 | CB | GLU | B | 846 | 83.825 | 127.543 | 30.434 | 1.00 | 48.84 | C |
| ATOM | 2425 | CG | GLU | B | 846 | 82.779 | 127.062 | 31.440 | 1.00 | 51.74 | C |
| ATOM | 2426 | CD | GLU | B | 846 | 82.424 | 125.595 | 31.280 | 1.00 | 54.97 | C |
| ATOM | 2427 | OE1 | GLU | B | 846 | 82.815 | 124.796 | 32.157 | 1.00 | 55.85 | O |
| ATOM | 2428 | OE2 | GLU | B | 846 | 81.757 | 125.238 | 30.284 | 1.00 | 55.54 | O |
| ATOM | 2429 | C | GLU | B | 846 | 82.091 | 128.844 | 29.132 | 1.00 | 48.08 | C |
| ATOM | 2430 | O | GLU | B | 846 | 80.943 | 128.401 | 29.049 | 1.00 | 47.92 | O |
| ATOM | 2431 | N | ARG | B | 847 | 82.368 | 130.138 | 29.287 | 1.00 | 47.93 | N |
| ATOM | 2432 | CA | ARG | B | 847 | 81.334 | 131.171 | 29.429 | 1.00 | 48.18 | C |
| ATOM | 2433 | CB | ARG | B | 847 | 81.975 | 132.543 | 29.685 | 1.00 | 48.36 | C |
| ATOM | 2434 | CG | ARG | B | 847 | 82.945 | 133.005 | 28.596 | 1.00 | 49.48 | C |
| ATOM | 2435 | CD | ARG | B | 847 | 83.640 | 134.305 | 28.966 | 1.00 | 49.62 | C |
| ATOM | 2436 | NE | ARG | B | 847 | 84.640 | 134.678 | 27.965 | 1.00 | 53.50 | N |
| ATOM | 2437 | CZ | ARG | B | 847 | 85.367 | 135.793 | 27.996 | 1.00 | 55.22 | C |

APPENDIX 1-continued

| ATOM | 2438 | NH1 | ARG | B | 847 | 85.219 | 136.670 | 28.982 | 1.00 | 56.18 | N |
|---|---|---|---|---|---|---|---|---|---|---|---|
| ATOM | 2439 | NH2 | ARG | B | 847 | 86.248 | 136.031 | 27.033 | 1.00 | 55.59 | N |
| ATOM | 2440 | C | ARG | B | 847 | 80.366 | 131.258 | 28.244 | 1.00 | 47.45 | C |
| ATOM | 2441 | O | ARG | B | 847 | 79.219 | 131.677 | 28.408 | 1.00 | 47.85 | O |
| ATOM | 2442 | N | HIS | B | 848 | 80.834 | 130.862 | 27.061 | 1.00 | 46.47 | N |
| ATOM | 2443 | CA | HIS | B | 848 | 80.039 | 130.954 | 25.834 | 1.00 | 45.76 | C |
| ATOM | 2444 | CB | HIS | B | 848 | 80.894 | 131.489 | 24.680 | 1.00 | 45.70 | C |
| ATOM | 2445 | CG | HIS | B | 848 | 81.526 | 132.818 | 24.957 | 1.00 | 46.86 | C |
| ATOM | 2446 | ND1 | HIS | B | 848 | 82.851 | 133.083 | 24.685 | 1.00 | 47.66 | N |
| ATOM | 2447 | CE1 | HIS | B | 848 | 83.129 | 134.327 | 25.030 | 1.00 | 47.69 | C |
| ATOM | 2448 | NE2 | HIS | B | 848 | 82.034 | 134.879 | 25.519 | 1.00 | 47.94 | N |
| ATOM | 2449 | CD2 | HIS | B | 848 | 81.017 | 133.956 | 25.487 | 1.00 | 46.96 | C |
| ATOM | 2450 | C | HIS | B | 848 | 79.399 | 129.623 | 25.441 | 1.00 | 45.05 | C |
| ATOM | 2451 | O | HIS | B | 848 | 78.522 | 129.578 | 24.575 | 1.00 | 44.89 | O |
| ATOM | 2452 | N | LEU | B | 849 | 79.840 | 128.547 | 26.088 | 1.00 | 44.18 | N |
| ATOM | 2453 | CA | LEU | B | 849 | 79.345 | 127.206 | 25.809 | 1.00 | 43.56 | C |
| ATOM | 2454 | CB | LEU | B | 849 | 80.395 | 126.173 | 26.236 | 1.00 | 43.39 | C |
| ATOM | 2455 | CG | LEU | B | 849 | 80.549 | 124.838 | 25.497 | 1.00 | 44.60 | C |
| ATOM | 2456 | CD1 | LEU | B | 849 | 80.738 | 125.014 | 23.990 | 1.00 | 43.63 | C |
| ATOM | 2457 | CD2 | LEU | B | 849 | 81.722 | 124.066 | 26.091 | 1.00 | 43.92 | C |
| ATOM | 2458 | C | LEU | B | 849 | 78.016 | 126.980 | 26.533 | 1.00 | 43.40 | C |
| ATOM | 2459 | O | LEU | B | 849 | 77.990 | 126.721 | 27.740 | 1.00 | 43.37 | O |
| ATOM | 2460 | N | LYS | B | 850 | 76.915 | 127.097 | 25.792 | 1.00 | 42.72 | N |
| ATOM | 2461 | CA | LYS | B | 850 | 75.576 | 126.994 | 26.378 | 1.00 | 42.46 | C |
| ATOM | 2462 | CB | LYS | B | 850 | 74.628 | 128.047 | 25.790 | 1.00 | 42.65 | C |
| ATOM | 2463 | CG | LYS | B | 850 | 74.878 | 129.462 | 26.318 | 1.00 | 43.79 | C |
| ATOM | 2464 | CD | LYS | B | 850 | 73.699 | 130.400 | 26.059 | 1.00 | 44.35 | C |
| ATOM | 2465 | CE | LYS | B | 850 | 73.717 | 130.963 | 24.643 | 1.00 | 48.03 | C |
| ATOM | 2466 | NZ | LYS | B | 850 | 72.655 | 131.984 | 24.423 | 1.00 | 48.71 | N |
| ATOM | 2467 | C | LYS | B | 850 | 74.981 | 125.594 | 26.260 | 1.00 | 41.47 | C |
| ATOM | 2468 | O | LYS | B | 850 | 74.784 | 125.078 | 25.159 | 1.00 | 40.87 | O |
| ATOM | 2469 | N | PHE | B | 851 | 74.696 | 124.998 | 27.415 | 1.00 | 40.87 | N |
| ATOM | 2470 | CA | PHE | B | 851 | 74.176 | 123.635 | 27.509 | 1.00 | 40.50 | C |
| ATOM | 2471 | CB | PHE | B | 851 | 74.190 | 123.185 | 28.974 | 1.00 | 40.11 | C |
| ATOM | 2472 | CG | PHE | B | 851 | 73.674 | 121.790 | 29.197 | 1.00 | 38.76 | C |
| ATOM | 2473 | CD1 | PHE | B | 851 | 74.400 | 120.684 | 28.767 | 1.00 | 37.57 | C |
| ATOM | 2474 | CE1 | PHE | B | 851 | 73.926 | 119.392 | 28.982 | 1.00 | 38.89 | C |
| ATOM | 2475 | CZ | PHE | B | 851 | 72.717 | 119.198 | 29.645 | 1.00 | 38.42 | C |
| ATOM | 2476 | CE2 | PHE | B | 851 | 71.987 | 120.296 | 30.086 | 1.00 | 38.86 | C |
| ATOM | 2477 | CD2 | PHE | B | 851 | 72.470 | 121.583 | 29.864 | 1.00 | 39.00 | C |
| ATOM | 2478 | C | PHE | B | 851 | 72.772 | 123.508 | 26.923 | 1.00 | 40.83 | C |
| ATOM | 2479 | O | PHE | B | 851 | 71.926 | 124.382 | 27.122 | 1.00 | 40.70 | O |
| ATOM | 2480 | N | LEU | B | 852 | 72.540 | 122.418 | 26.194 | 1.00 | 41.30 | N |
| ATOM | 2481 | CA | LEU | B | 852 | 71.230 | 122.135 | 25.603 | 1.00 | 41.68 | C |
| ATOM | 2482 | CB | LEU | B | 852 | 71.302 | 122.137 | 24.068 | 1.00 | 41.32 | C |
| ATOM | 2483 | CG | LEU | B | 852 | 71.784 | 123.417 | 23.368 | 1.00 | 41.01 | C |
| ATOM | 2484 | CD1 | LEU | B | 852 | 71.997 | 123.175 | 21.880 | 1.00 | 41.24 | C |
| ATOM | 2485 | CD2 | LEU | B | 852 | 70.829 | 124.588 | 23.586 | 1.00 | 40.50 | C |
| ATOM | 2486 | C | LEU | B | 852 | 70.645 | 120.819 | 26.127 | 1.00 | 42.17 | C |
| ATOM | 2487 | O | LEU | B | 852 | 69.520 | 120.797 | 26.627 | 1.00 | 42.19 | O |
| ATOM | 2488 | N | GLN | B | 853 | 71.416 | 119.734 | 26.017 | 1.00 | 42.55 | N |
| ATOM | 2489 | CA | GLN | B | 853 | 71.016 | 118.418 | 26.538 | 1.00 | 42.88 | C |
| ATOM | 2490 | CB | GLN | B | 853 | 69.893 | 117.800 | 25.689 | 1.00 | 43.03 | C |
| ATOM | 2491 | CG | GLN | B | 853 | 70.264 | 117.539 | 24.231 | 1.00 | 43.89 | C |
| ATOM | 2492 | CD | GLN | B | 853 | 69.316 | 116.567 | 23.549 | 1.00 | 44.62 | C |
| ATOM | 2493 | OE1 | GLN | B | 853 | 68.605 | 116.934 | 22.612 | 1.00 | 48.86 | O |
| ATOM | 2494 | NE2 | GLN | B | 853 | 69.300 | 115.321 | 24.017 | 1.00 | 46.57 | N |
| ATOM | 2495 | C | GLN | B | 853 | 72.195 | 117.447 | 26.622 | 1.00 | 42.50 | C |
| ATOM | 2496 | O | GLN | B | 853 | 73.258 | 117.697 | 26.047 | 1.00 | 42.24 | O |
| ATOM | 2497 | N | GLN | B | 854 | 72.001 | 116.346 | 27.346 | 1.00 | 42.12 | N |
| ATOM | 2498 | CA | GLN | B | 854 | 72.961 | 115.247 | 27.342 | 1.00 | 42.33 | C |
| ATOM | 2499 | CB | GLN | B | 854 | 72.852 | 114.407 | 28.617 | 1.00 | 42.91 | C |
| ATOM | 2500 | CG | GLN | B | 854 | 74.054 | 113.491 | 28.847 | 1.00 | 46.02 | C |
| ATOM | 2501 | CD | GLN | B | 854 | 73.667 | 112.120 | 29.376 | 1.00 | 51.24 | C |
| ATOM | 2502 | OE1 | GLN | B | 854 | 73.981 | 111.774 | 30.516 | 1.00 | 54.40 | O |
| ATOM | 2503 | NE2 | GLN | B | 854 | 72.986 | 111.329 | 28.547 | 1.00 | 50.15 | N |
| ATOM | 2504 | C | GLN | B | 854 | 72.715 | 114.367 | 26.120 | 1.00 | 41.36 | C |
| ATOM | 2505 | O | GLN | B | 854 | 71.566 | 114.110 | 25.753 | 1.00 | 40.99 | O |
| ATOM | 2506 | N | LEU | B | 855 | 73.799 | 113.911 | 25.498 | 1.00 | 40.25 | N |
| ATOM | 2507 | CA | LEU | B | 855 | 73.722 | 113.081 | 24.299 | 1.00 | 39.46 | C |
| ATOM | 2508 | CB | LEU | B | 855 | 74.682 | 113.598 | 23.220 | 1.00 | 39.26 | C |
| ATOM | 2509 | CG | LEU | B | 855 | 74.384 | 114.965 | 22.597 | 1.00 | 39.53 | C |
| ATOM | 2510 | CD1 | LEU | B | 855 | 75.540 | 115.412 | 21.713 | 1.00 | 38.81 | C |
| ATOM | 2511 | CD2 | LEU | B | 855 | 73.068 | 114.960 | 21.814 | 1.00 | 39.48 | C |
| ATOM | 2512 | C | LEU | B | 855 | 74.009 | 111.615 | 24.602 | 1.00 | 38.96 | C |
| ATOM | 2513 | O | LEU | B | 855 | 73.297 | 110.727 | 24.134 | 1.00 | 38.66 | O |
| ATOM | 2514 | N | GLY | B | 856 | 75.052 | 111.369 | 25.389 | 1.00 | 38.95 | N |
| ATOM | 2515 | CA | GLY | B | 856 | 75.436 | 110.015 | 25.757 | 1.00 | 39.16 | C |
| ATOM | 2516 | C | GLY | B | 856 | 76.316 | 109.963 | 26.988 | 1.00 | 39.87 | C |

APPENDIX 1-continued

| ATOM | 2517 | O | GLY | B | 856 | 76.760 | 110.994 | 27.492 | 1.00 | 39.00 | O |
|---|---|---|---|---|---|---|---|---|---|---|---|
| ATOM | 2518 | N | LYS | B | 857 | 76.564 | 108.751 | 27.468 | 1.00 | 40.97 | N |
| ATOM | 2519 | CA | LYS | B | 857 | 77.404 | 108.535 | 28.640 | 1.00 | 43.43 | C |
| ATOM | 2520 | CB | LYS | B | 857 | 76.560 | 108.519 | 29.922 | 1.00 | 43.49 | C |
| ATOM | 2521 | CG | LYS | B | 857 | 75.363 | 107.572 | 29.890 | 1.00 | 44.69 | C |
| ATOM | 2522 | CD | LYS | B | 857 | 74.448 | 107.789 | 31.089 | 1.00 | 44.94 | C |
| ATOM | 2523 | CE | LYS | B | 857 | 73.087 | 107.127 | 30.886 | 1.00 | 47.92 | C |
| ATOM | 2524 | NZ | LYS | B | 857 | 73.161 | 105.637 | 30.845 | 1.00 | 48.33 | N |
| ATOM | 2525 | C | LYS | B | 857 | 78.227 | 107.256 | 28.522 | 1.00 | 44.73 | C |
| ATOM | 2526 | O | LYS | B | 857 | 77.859 | 106.324 | 27.803 | 1.00 | 44.43 | O |
| ATOM | 2527 | N | GLY | B | 858 | 79.356 | 107.240 | 29.223 | 1.00 | 46.77 | N |
| ATOM | 2528 | CA | GLY | B | 858 | 80.180 | 106.048 | 29.377 | 1.00 | 48.63 | C |
| ATOM | 2529 | C | GLY | B | 858 | 80.605 | 105.925 | 30.827 | 1.00 | 50.31 | C |
| ATOM | 2530 | O | GLY | B | 858 | 80.075 | 106.624 | 31.702 | 1.00 | 50.26 | O |
| ATOM | 2531 | N | ASN | B | 859 | 81.555 | 105.032 | 31.087 | 1.00 | 51.48 | N |
| ATOM | 2532 | CA | ASN | B | 859 | 82.142 | 104.903 | 32.417 | 1.00 | 52.40 | C |
| ATOM | 2533 | CB | ASN | B | 859 | 82.936 | 103.598 | 32.540 | 1.00 | 52.83 | C |
| ATOM | 2534 | CG | ASN | B | 859 | 82.041 | 102.370 | 32.612 | 1.00 | 54.15 | C |
| ATOM | 2535 | OD1 | ASN | B | 859 | 81.195 | 102.250 | 33.503 | 1.00 | 55.68 | O |
| ATOM | 2536 | ND2 | ASN | B | 859 | 82.234 | 101.442 | 31.680 | 1.00 | 55.04 | N |
| ATOM | 2537 | C | ASN | B | 859 | 83.020 | 106.110 | 32.749 | 1.00 | 52.48 | C |
| ATOM | 2538 | O | ASN | B | 859 | 83.030 | 106.581 | 33.889 | 1.00 | 52.67 | O |
| ATOM | 2539 | N | PHE | B | 860 | 83.742 | 106.602 | 31.739 | 1.00 | 52.55 | N |
| ATOM | 2540 | CA | PHE | B | 860 | 84.582 | 107.798 | 31.854 | 1.00 | 52.84 | C |
| ATOM | 2541 | CB | PHE | B | 860 | 85.214 | 108.159 | 30.502 | 1.00 | 54.12 | C |
| ATOM | 2542 | CG | PHE | B | 860 | 86.016 | 107.057 | 29.879 | 1.00 | 57.38 | C |
| ATOM | 2543 | CD1 | PHE | B | 860 | 85.425 | 106.177 | 28.977 | 1.00 | 59.57 | C |
| ATOM | 2544 | CE1 | PHE | B | 860 | 86.165 | 105.162 | 28.386 | 1.00 | 60.24 | C |
| ATOM | 2545 | CZ | PHE | B | 860 | 87.515 | 105.029 | 28.686 | 1.00 | 59.89 | C |
| ATOM | 2546 | CE2 | PHE | B | 860 | 88.121 | 105.907 | 29.576 | 1.00 | 60.92 | C |
| ATOM | 2547 | CD2 | PHE | B | 860 | 87.372 | 106.920 | 30.163 | 1.00 | 60.06 | C |
| ATOM | 2548 | C | PHE | B | 860 | 83.758 | 108.994 | 32.309 | 1.00 | 51.03 | C |
| ATOM | 2549 | O | PHE | B | 860 | 83.953 | 109.533 | 33.401 | 1.00 | 50.94 | O |
| ATOM | 2550 | N | GLY | B | 861 | 82.840 | 109.399 | 31.440 | 1.00 | 49.04 | N |
| ATOM | 2551 | CA | GLY | B | 861 | 82.015 | 110.567 | 31.660 | 1.00 | 46.75 | C |
| ATOM | 2552 | C | GLY | B | 861 | 80.869 | 110.600 | 30.676 | 1.00 | 44.62 | C |
| ATOM | 2553 | O | GLY | B | 861 | 80.309 | 109.559 | 30.330 | 1.00 | 44.88 | O |
| ATOM | 2554 | N | SER | B | 862 | 80.529 | 111.801 | 30.218 | 1.00 | 41.93 | N |
| ATOM | 2555 | CA | SER | B | 862 | 79.370 | 111.989 | 29.360 | 1.00 | 39.05 | C |
| ATOM | 2556 | CB | SER | B | 862 | 78.176 | 112.488 | 30.183 | 1.00 | 39.02 | C |
| ATOM | 2557 | OG | SER | B | 862 | 78.457 | 113.744 | 30.769 | 1.00 | 40.74 | O |
| ATOM | 2558 | C | SER | B | 862 | 79.650 | 112.942 | 28.205 | 1.00 | 36.43 | C |
| ATOM | 2559 | O | SER | B | 862 | 80.655 | 113.658 | 28.198 | 1.00 | 35.12 | O |
| ATOM | 2560 | N | VAL | B | 863 | 78.750 | 112.931 | 27.227 | 1.00 | 34.46 | N |
| ATOM | 2561 | CA | VAL | B | 863 | 78.809 | 113.843 | 26.095 | 1.00 | 33.58 | C |
| ATOM | 2562 | CB | VAL | B | 863 | 78.972 | 113.082 | 24.751 | 1.00 | 33.42 | C |
| ATOM | 2563 | CG1 | VAL | B | 863 | 78.980 | 114.049 | 23.567 | 1.00 | 32.69 | C |
| ATOM | 2564 | CG2 | VAL | B | 863 | 80.251 | 112.253 | 24.764 | 1.00 | 32.40 | C |
| ATOM | 2565 | C | VAL | B | 863 | 77.553 | 114.711 | 26.100 | 1.00 | 33.23 | C |
| ATOM | 2566 | O | VAL | B | 863 | 76.436 | 114.210 | 26.253 | 1.00 | 32.15 | O |
| ATOM | 2567 | N | GLU | B | 864 | 77.757 | 116.016 | 25.954 | 1.00 | 33.55 | N |
| ATOM | 2568 | CA | GLU | B | 864 | 76.676 | 116.992 | 26.010 | 1.00 | 35.25 | C |
| ATOM | 2569 | CB | GLU | B | 864 | 76.905 | 117.980 | 27.160 | 1.00 | 34.48 | C |
| ATOM | 2570 | CG | GLU | B | 864 | 77.134 | 117.332 | 28.523 | 1.00 | 38.07 | C |
| ATOM | 2571 | CD | GLU | B | 864 | 77.404 | 118.339 | 29.637 | 1.00 | 37.68 | C |
| ATOM | 2572 | OE1 | GLU | B | 864 | 77.879 | 119.462 | 29.350 | 1.00 | 41.91 | O |
| ATOM | 2573 | OE2 | GLU | B | 864 | 77.144 | 117.996 | 30.810 | 1.00 | 41.23 | O |
| ATOM | 2574 | C | GLU | B | 864 | 76.568 | 117.765 | 24.702 | 1.00 | 35.43 | C |
| ATOM | 2575 | O | GLU | B | 864 | 77.579 | 118.073 | 24.061 | 1.00 | 35.80 | O |
| ATOM | 2576 | N | MET | B | 865 | 75.333 | 118.073 | 24.320 | 1.00 | 35.69 | N |
| ATOM | 2577 | CA | MET | B | 865 | 75.052 | 118.953 | 23.197 | 1.00 | 36.90 | C |
| ATOM | 2578 | CB | MET | B | 865 | 73.677 | 118.625 | 22.615 | 1.00 | 36.54 | C |
| ATOM | 2579 | CG | MET | B | 865 | 73.320 | 119.361 | 21.342 | 1.00 | 37.92 | C |
| ATOM | 2580 | SD | MET | B | 865 | 71.568 | 119.152 | 20.984 | 1.00 | 40.02 | S |
| ATOM | 2581 | CE | MET | B | 865 | 71.372 | 120.176 | 19.528 | 1.00 | 39.28 | C |
| ATOM | 2582 | C | MET | B | 865 | 75.088 | 120.398 | 23.691 | 1.00 | 36.66 | C |
| ATOM | 2583 | O | MET | B | 865 | 74.343 | 120.767 | 24.605 | 1.00 | 35.99 | O |
| ATOM | 2584 | N | CYS | B | 866 | 75.964 | 121.204 | 23.095 | 1.00 | 36.86 | N |
| ATOM | 2585 | CA | CYS | B | 866 | 76.116 | 122.609 | 23.477 | 1.00 | 37.59 | C |
| ATOM | 2586 | CB | CYS | B | 866 | 77.366 | 122.801 | 24.338 | 1.00 | 38.22 | C |
| ATOM | 2587 | SG | CYS | B | 866 | 77.354 | 121.937 | 25.915 | 1.00 | 37.73 | S |
| ATOM | 2588 | C | CYS | B | 866 | 76.215 | 123.527 | 22.267 | 1.00 | 37.79 | C |
| ATOM | 2589 | O | CYS | B | 866 | 76.805 | 123.163 | 21.252 | 1.00 | 37.64 | O |
| ATOM | 2590 | N | ARG | B | 867 | 75.636 | 124.718 | 22.384 | 1.00 | 37.94 | N |
| ATOM | 2591 | CA | ARG | B | 867 | 75.862 | 125.773 | 21.405 | 1.00 | 38.63 | C |
| ATOM | 2592 | CB | ARG | B | 867 | 74.583 | 126.580 | 21.153 | 1.00 | 38.48 | C |
| ATOM | 2593 | CG | ARG | B | 867 | 74.776 | 127.757 | 20.193 | 1.00 | 38.95 | C |
| ATOM | 2594 | CD | ARG | B | 867 | 73.476 | 128.489 | 19.900 | 1.00 | 39.91 | C |
| ATOM | 2595 | NE | ARG | B | 867 | 72.700 | 127.817 | 18.860 | 1.00 | 44.78 | N |

APPENDIX 1-continued

| ATOM | 2596 | CZ | ARG | B | 867 | 71.603 | 127.097 | 19.078 | 1.00 | 46.17 | C |
| --- | --- | --- | --- | --- | --- | --- | --- | --- | --- | --- | --- |
| ATOM | 2597 | NH1 | ARG | B | 867 | 71.123 | 126.951 | 20.307 | 1.00 | 47.99 | N |
| ATOM | 2598 | NH2 | ARG | B | 867 | 70.979 | 126.527 | 18.058 | 1.00 | 46.26 | N |
| ATOM | 2599 | C | ARG | B | 867 | 76.979 | 126.686 | 21.902 | 1.00 | 38.71 | C |
| ATOM | 2600 | O | ARG | B | 867 | 76.896 | 127.231 | 23.006 | 1.00 | 38.17 | O |
| ATOM | 2601 | N | TYR | B | 868 | 78.031 | 126.831 | 21.099 | 1.00 | 38.89 | N |
| ATOM | 2602 | CA | TYR | B | 868 | 79.066 | 127.814 | 21.386 | 1.00 | 39.46 | C |
| ATOM | 2603 | CB | TYR | B | 868 | 80.411 | 127.415 | 20.771 | 1.00 | 39.90 | C |
| ATOM | 2604 | CG | TYR | B | 868 | 81.576 | 128.248 | 21.269 | 1.00 | 40.23 | C |
| ATOM | 2605 | CD1 | TYR | B | 868 | 81.966 | 128.202 | 22.609 | 1.00 | 41.23 | C |
| ATOM | 2606 | CE1 | TYR | B | 868 | 83.032 | 128.960 | 23.076 | 1.00 | 40.23 | C |
| ATOM | 2607 | CZ | TYR | B | 868 | 83.726 | 129.779 | 22.200 | 1.00 | 41.63 | C |
| ATOM | 2608 | OH | TYR | B | 868 | 84.783 | 130.527 | 22.671 | 1.00 | 41.58 | O |
| ATOM | 2609 | CE2 | TYR | B | 868 | 83.361 | 129.844 | 20.862 | 1.00 | 39.19 | C |
| ATOM | 2610 | CD2 | TYR | B | 868 | 82.288 | 129.079 | 20.404 | 1.00 | 39.79 | C |
| ATOM | 2611 | C | TYR | B | 868 | 78.588 | 129.155 | 20.847 | 1.00 | 39.74 | C |
| ATOM | 2612 | O | TYR | B | 868 | 78.653 | 129.406 | 19.643 | 1.00 | 40.09 | O |
| ATOM | 2613 | N | ASP | B | 869 | 78.107 | 130.008 | 21.748 | 1.00 | 39.47 | N |
| ATOM | 2614 | CA | ASP | B | 869 | 77.362 | 131.205 | 21.361 | 1.00 | 39.24 | C |
| ATOM | 2615 | CB | ASP | B | 869 | 75.882 | 131.001 | 21.706 | 1.00 | 39.35 | C |
| ATOM | 2616 | CG | ASP | B | 869 | 74.960 | 131.957 | 20.973 | 1.00 | 39.86 | C |
| ATOM | 2617 | OD1 | ASP | B | 869 | 75.203 | 132.258 | 19.783 | 1.00 | 41.30 | O |
| ATOM | 2618 | OD2 | ASP | B | 869 | 73.965 | 132.388 | 21.591 | 1.00 | 38.55 | O |
| ATOM | 2619 | C | ASP | B | 869 | 77.908 | 132.480 | 22.019 | 1.00 | 39.27 | C |
| ATOM | 2620 | O | ASP | B | 869 | 77.243 | 133.072 | 22.875 | 1.00 | 38.72 | O |
| ATOM | 2621 | N | PRO | B | 870 | 79.121 | 132.916 | 21.612 | 1.00 | 39.51 | N |
| ATOM | 2622 | CA | PRO | B | 870 | 79.735 | 134.114 | 22.199 | 1.00 | 39.48 | C |
| ATOM | 2623 | CB | PRO | B | 870 | 81.111 | 134.171 | 21.526 | 1.00 | 39.70 | C |
| ATOM | 2624 | CG | PRO | B | 870 | 80.950 | 133.406 | 20.266 | 1.00 | 39.38 | C |
| ATOM | 2625 | CD | PRO | B | 870 | 79.987 | 132.313 | 20.582 | 1.00 | 39.31 | C |
| ATOM | 2626 | C | PRO | B | 870 | 78.958 | 135.403 | 21.931 | 1.00 | 39.87 | C |
| ATOM | 2627 | O | PRO | B | 870 | 79.066 | 136.354 | 22.709 | 1.00 | 39.88 | O |
| ATOM | 2628 | N | LEU | B | 871 | 78.179 | 135.424 | 20.850 | 1.00 | 40.08 | N |
| ATOM | 2629 | CA | LEU | B | 871 | 77.369 | 136.590 | 20.495 | 1.00 | 40.44 | C |
| ATOM | 2630 | CB | LEU | B | 871 | 77.092 | 136.626 | 18.986 | 1.00 | 40.19 | C |
| ATOM | 2631 | CG | LEU | B | 871 | 78.263 | 136.664 | 17.998 | 1.00 | 39.98 | C |
| ATOM | 2632 | CD1 | LEU | B | 871 | 77.739 | 136.656 | 16.573 | 1.00 | 39.24 | C |
| ATOM | 2633 | CD2 | LEU | B | 871 | 79.157 | 137.872 | 18.229 | 1.00 | 39.27 | C |
| ATOM | 2634 | C | LEU | B | 871 | 76.052 | 136.651 | 21.273 | 1.00 | 41.09 | C |
| ATOM | 2635 | O | LEU | B | 871 | 75.385 | 137.686 | 21.282 | 1.00 | 40.54 | O |
| ATOM | 2636 | N | GLN | B | 872 | 75.692 | 135.537 | 21.915 | 1.00 | 42.04 | N |
| ATOM | 2637 | CA | GLN | B | 872 | 74.471 | 135.418 | 22.732 | 1.00 | 43.22 | C |
| ATOM | 2638 | CB | GLN | B | 872 | 74.507 | 136.369 | 23.940 | 1.00 | 43.13 | C |
| ATOM | 2639 | CG | GLN | B | 872 | 75.720 | 136.227 | 24.851 | 1.00 | 44.55 | C |
| ATOM | 2640 | CD | GLN | B | 872 | 75.664 | 137.176 | 26.038 | 1.00 | 45.18 | C |
| ATOM | 2641 | OE1 | GLN | B | 872 | 74.838 | 137.017 | 26.938 | 1.00 | 48.05 | O |
| ATOM | 2642 | NE2 | GLN | B | 872 | 76.547 | 138.170 | 26.044 | 1.00 | 48.10 | N |
| ATOM | 2643 | C | GLN | B | 872 | 73.177 | 135.624 | 21.930 | 1.00 | 43.26 | C |
| ATOM | 2644 | O | GLN | B | 872 | 72.152 | 136.028 | 22.485 | 1.00 | 43.36 | O |
| ATOM | 2645 | N | ASP | B | 873 | 73.228 | 135.333 | 20.631 | 1.00 | 43.51 | N |
| ATOM | 2646 | CA | ASP | B | 873 | 72.082 | 135.527 | 19.740 | 1.00 | 43.80 | C |
| ATOM | 2647 | CB | ASP | B | 873 | 72.389 | 136.614 | 18.697 | 1.00 | 43.69 | C |
| ATOM | 2648 | CG | ASP | B | 873 | 73.621 | 136.299 | 17.852 | 1.00 | 43.26 | C |
| ATOM | 2649 | OD1 | ASP | B | 873 | 74.205 | 135.203 | 17.996 | 1.00 | 42.81 | O |
| ATOM | 2650 | OD2 | ASP | B | 873 | 74.008 | 137.162 | 17.036 | 1.00 | 42.70 | O |
| ATOM | 2651 | C | ASP | B | 873 | 71.643 | 134.228 | 19.056 | 1.00 | 44.29 | C |
| ATOM | 2652 | O | ASP | B | 873 | 70.862 | 134.252 | 18.098 | 1.00 | 44.26 | O |
| ATOM | 2653 | N | ASN | B | 874 | 72.164 | 133.106 | 19.555 | 1.00 | 44.68 | N |
| ATOM | 2654 | CA | ASN | B | 874 | 71.834 | 131.755 | 19.069 | 1.00 | 45.20 | C |
| ATOM | 2655 | CB | ASN | B | 874 | 70.338 | 131.443 | 19.256 | 1.00 | 45.63 | C |
| ATOM | 2656 | CG | ASN | B | 874 | 69.872 | 131.643 | 20.689 | 1.00 | 46.80 | C |
| ATOM | 2657 | OD1 | ASN | B | 874 | 70.423 | 131.060 | 21.624 | 1.00 | 48.15 | O |
| ATOM | 2658 | ND2 | ASN | B | 874 | 68.848 | 132.471 | 20.867 | 1.00 | 48.30 | N |
| ATOM | 2659 | C | ASN | B | 874 | 72.294 | 131.443 | 17.637 | 1.00 | 45.08 | C |
| ATOM | 2660 | O | ASN | B | 874 | 71.834 | 130.474 | 17.026 | 1.00 | 45.64 | O |
| ATOM | 2661 | N | THR | B | 875 | 73.211 | 132.258 | 17.117 | 1.00 | 44.57 | N |
| ATOM | 2662 | CA | THR | B | 875 | 73.792 | 132.031 | 15.791 | 1.00 | 43.72 | C |
| ATOM | 2663 | CB | THR | B | 875 | 74.195 | 133.357 | 15.099 | 1.00 | 43.81 | C |
| ATOM | 2664 | OG1 | THR | B | 875 | 75.177 | 134.037 | 15.891 | 1.00 | 43.37 | O |
| ATOM | 2665 | CG2 | THR | B | 875 | 72.981 | 134.263 | 14.896 | 1.00 | 43.74 | C |
| ATOM | 2666 | C | THR | B | 875 | 75.014 | 131.111 | 15.860 | 1.00 | 43.18 | C |
| ATOM | 2667 | O | THR | B | 875 | 75.511 | 130.647 | 14.831 | 1.00 | 43.22 | O |
| ATOM | 2668 | N | GLY | B | 876 | 75.487 | 130.853 | 17.078 | 1.00 | 42.53 | N |
| ATOM | 2669 | CA | GLY | B | 876 | 76.661 | 130.012 | 17.307 | 1.00 | 42.17 | C |
| ATOM | 2670 | C | GLY | B | 876 | 76.490 | 128.560 | 16.896 | 1.00 | 41.94 | C |
| ATOM | 2671 | O | GLY | B | 876 | 75.366 | 128.053 | 16.810 | 1.00 | 41.40 | O |
| ATOM | 2672 | N | GLU | B | 877 | 77.614 | 127.894 | 16.642 | 1.00 | 41.83 | N |
| ATOM | 2673 | CA | GLU | B | 877 | 77.609 | 126.507 | 16.181 | 1.00 | 42.13 | C |
| ATOM | 2674 | CB | GLU | B | 877 | 78.950 | 126.142 | 15.533 | 1.00 | 42.04 | C |

APPENDIX 1-continued

| ATOM | 2675 | CG | GLU | B | 877 | 78.899 | 124.878 | 14.669 | 1.00 | 43.86 | C |
| --- | --- | --- | --- | --- | --- | --- | --- | --- | --- | --- | --- |
| ATOM | 2676 | CD | GLU | B | 877 | 80.254 | 124.475 | 14.104 | 1.00 | 44.17 | C |
| ATOM | 2677 | OE1 | GLU | B | 877 | 81.256 | 124.502 | 14.853 | 1.00 | 45.47 | O |
| ATOM | 2678 | OE2 | GLU | B | 877 | 80.312 | 124.119 | 12.906 | 1.00 | 48.64 | O |
| ATOM | 2679 | C | GLU | B | 877 | 77.292 | 125.531 | 17.310 | 1.00 | 40.75 | C |
| ATOM | 2680 | O | GLU | B | 877 | 77.735 | 125.711 | 18.447 | 1.00 | 41.19 | O |
| ATOM | 2681 | N | VAL | B | 878 | 76.517 | 124.502 | 16.978 | 1.00 | 38.96 | N |
| ATOM | 2682 | CA | VAL | B | 878 | 76.212 | 123.423 | 17.906 | 1.00 | 37.71 | C |
| ATOM | 2683 | CB | VAL | B | 878 | 74.847 | 122.768 | 17.594 | 1.00 | 37.74 | C |
| ATOM | 2684 | CG1 | VAL | B | 878 | 74.589 | 121.590 | 18.518 | 1.00 | 37.80 | C |
| ATOM | 2685 | CG2 | VAL | B | 878 | 73.726 | 123.792 | 17.720 | 1.00 | 38.82 | C |
| ATOM | 2686 | C | VAL | B | 878 | 77.332 | 122.385 | 17.852 | 1.00 | 36.45 | C |
| ATOM | 2687 | O | VAL | B | 878 | 77.703 | 121.906 | 16.777 | 1.00 | 35.73 | O |
| ATOM | 2688 | N | VAL | B | 879 | 77.875 | 122.066 | 19.024 | 1.00 | 34.61 | N |
| ATOM | 2689 | CA | VAL | B | 879 | 78.986 | 121.124 | 19.150 | 1.00 | 33.48 | C |
| ATOM | 2690 | CB | VAL | B | 879 | 80.312 | 121.846 | 19.536 | 1.00 | 33.91 | C |
| ATOM | 2691 | CG1 | VAL | B | 879 | 80.781 | 122.769 | 18.411 | 1.00 | 31.89 | C |
| ATOM | 2692 | CG2 | VAL | B | 879 | 80.165 | 122.619 | 20.853 | 1.00 | 32.12 | C |
| ATOM | 2693 | C | VAL | B | 879 | 78.672 | 120.032 | 20.176 | 1.00 | 32.80 | C |
| ATOM | 2694 | O | VAL | B | 879 | 77.760 | 120.179 | 20.995 | 1.00 | 32.50 | O |
| ATOM | 2695 | N | ALA | B | 880 | 79.422 | 118.935 | 20.114 | 1.00 | 31.65 | N |
| ATOM | 2696 | CA | ALA | B | 880 | 79.358 | 117.896 | 21.137 | 1.00 | 31.11 | C |
| ATOM | 2697 | CB | ALA | B | 880 | 79.360 | 116.521 | 20.504 | 1.00 | 30.91 | C |
| ATOM | 2698 | C | ALA | B | 880 | 80.533 | 118.049 | 22.098 | 1.00 | 30.35 | C |
| ATOM | 2699 | O | ALA | B | 880 | 81.683 | 118.173 | 21.672 | 1.00 | 30.33 | O |
| ATOM | 2700 | N | VAL | B | 881 | 80.233 | 118.047 | 23.393 | 1.00 | 29.73 | N |
| ATOM | 2701 | CA | VAL | B | 881 | 81.238 | 118.288 | 24.423 | 1.00 | 29.15 | C |
| ATOM | 2702 | CB | VAL | B | 881 | 80.897 | 119.545 | 25.268 | 1.00 | 29.07 | C |
| ATOM | 2703 | CG1 | VAL | B | 881 | 82.008 | 119.840 | 26.274 | 1.00 | 30.30 | C |
| ATOM | 2704 | CG2 | VAL | B | 881 | 80.664 | 120.752 | 24.374 | 1.00 | 27.54 | C |
| ATOM | 2705 | C | VAL | B | 881 | 81.377 | 117.070 | 25.333 | 1.00 | 29.68 | C |
| ATOM | 2706 | O | VAL | B | 881 | 80.423 | 116.674 | 26.007 | 1.00 | 29.85 | O |
| ATOM | 2707 | N | LYS | B | 882 | 82.570 | 116.482 | 25.350 | 1.00 | 29.74 | N |
| ATOM | 2708 | CA | LYS | B | 882 | 82.855 | 115.350 | 26.228 | 1.00 | 30.30 | C |
| ATOM | 2709 | CB | LYS | B | 882 | 83.664 | 114.280 | 25.492 | 1.00 | 29.96 | C |
| ATOM | 2710 | CG | LYS | B | 882 | 83.774 | 112.964 | 26.248 | 1.00 | 30.50 | C |
| ATOM | 2711 | CD | LYS | B | 882 | 84.659 | 111.973 | 25.512 | 1.00 | 30.16 | C |
| ATOM | 2712 | CE | LYS | B | 882 | 84.665 | 110.624 | 26.214 | 1.00 | 31.45 | C |
| ATOM | 2713 | NZ | LYS | B | 882 | 85.512 | 109.623 | 25.498 | 1.00 | 29.73 | N |
| ATOM | 2714 | C | LYS | B | 882 | 83.590 | 115.796 | 27.491 | 1.00 | 30.85 | C |
| ATOM | 2715 | O | LYS | B | 882 | 84.600 | 116.496 | 27.415 | 1.00 | 29.68 | O |
| ATOM | 2716 | N | LYS | B | 883 | 83.072 | 115.376 | 28.643 | 1.00 | 32.05 | N |
| ATOM | 2717 | CA | LYS | B | 883 | 83.670 | 115.684 | 29.943 | 1.00 | 33.57 | C |
| ATOM | 2718 | CB | LYS | B | 883 | 82.814 | 116.709 | 30.701 | 1.00 | 33.22 | C |
| ATOM | 2719 | CG | LYS | B | 883 | 81.469 | 116.172 | 31.192 | 1.00 | 34.67 | C |
| ATOM | 2720 | CD | LYS | B | 883 | 80.657 | 117.236 | 31.909 | 1.00 | 35.17 | C |
| ATOM | 2721 | CE | LYS | B | 883 | 79.460 | 116.614 | 32.613 | 1.00 | 39.03 | C |
| ATOM | 2722 | NZ | LYS | B | 883 | 78.520 | 117.638 | 33.157 | 1.00 | 38.05 | N |
| ATOM | 2723 | C | LYS | B | 883 | 83.841 | 114.414 | 30.778 | 1.00 | 34.06 | C |
| ATOM | 2724 | O | LYS | B | 883 | 83.156 | 113.414 | 30.545 | 1.00 | 34.08 | O |
| ATOM | 2725 | N | LEU | B | 884 | 84.755 | 114.459 | 31.746 | 1.00 | 35.01 | N |
| ATOM | 2726 | CA | LEU | B | 884 | 84.953 | 113.350 | 32.681 | 1.00 | 35.96 | C |
| ATOM | 2727 | CB | LEU | B | 884 | 86.418 | 113.256 | 33.123 | 1.00 | 36.30 | C |
| ATOM | 2728 | CG | LEU | B | 884 | 87.530 | 112.912 | 32.130 | 1.00 | 37.46 | C |
| ATOM | 2729 | CD1 | LEU | B | 884 | 88.861 | 112.853 | 32.863 | 1.00 | 37.93 | C |
| ATOM | 2730 | CD2 | LEU | B | 884 | 87.260 | 111.599 | 31.406 | 1.00 | 38.90 | C |
| ATOM | 2731 | C | LEU | B | 884 | 84.070 | 113.509 | 33.915 | 1.00 | 36.27 | C |
| ATOM | 2732 | O | LEU | B | 884 | 83.859 | 114.623 | 34.394 | 1.00 | 36.04 | O |
| ATOM | 2733 | N | GLN | B | 885 | 83.561 | 112.389 | 34.424 | 1.00 | 37.29 | N |
| ATOM | 2734 | CA | GLN | B | 885 | 82.795 | 112.382 | 35.671 | 1.00 | 38.37 | C |
| ATOM | 2735 | CB | GLN | B | 885 | 81.567 | 111.465 | 35.568 | 1.00 | 39.13 | C |
| ATOM | 2736 | CG | GLN | B | 885 | 80.582 | 111.800 | 34.441 | 1.00 | 43.33 | C |
| ATOM | 2737 | CD | GLN | B | 885 | 79.631 | 112.946 | 34.762 | 1.00 | 47.24 | C |
| ATOM | 2738 | OE1 | GLN | B | 885 | 79.544 | 113.410 | 35.901 | 1.00 | 49.98 | O |
| ATOM | 2739 | NE2 | GLN | B | 885 | 78.903 | 113.400 | 33.748 | 1.00 | 47.06 | N |
| ATOM | 2740 | C | GLN | B | 885 | 83.673 | 111.944 | 36.846 | 1.00 | 37.92 | C |
| ATOM | 2741 | O | GLN | B | 885 | 83.343 | 112.198 | 38.003 | 1.00 | 37.39 | O |
| ATOM | 2742 | N | HIS | B | 886 | 84.787 | 111.282 | 36.539 | 1.00 | 37.77 | N |
| ATOM | 2743 | CA | HIS | B | 886 | 85.708 | 110.784 | 37.561 | 1.00 | 37.58 | C |
| ATOM | 2744 | CB | HIS | B | 886 | 85.641 | 109.253 | 37.631 | 1.00 | 37.97 | C |
| ATOM | 2745 | CG | HIS | B | 886 | 86.415 | 108.653 | 38.766 | 1.00 | 39.88 | C |
| ATOM | 2746 | ND1 | HIS | B | 886 | 86.668 | 109.328 | 39.942 | 1.00 | 41.27 | N |
| ATOM | 2747 | CE1 | HIS | B | 886 | 87.349 | 108.546 | 40.759 | 1.00 | 41.29 | C |
| ATOM | 2748 | NE2 | HIS | B | 886 | 87.545 | 107.386 | 40.159 | 1.00 | 42.71 | N |
| ATOM | 2749 | CD2 | HIS | B | 886 | 86.965 | 107.424 | 38.914 | 1.00 | 41.76 | C |
| ATOM | 2750 | C | HIS | B | 886 | 87.124 | 111.273 | 37.266 | 1.00 | 37.30 | C |
| ATOM | 2751 | O | HIS | B | 886 | 87.911 | 110.586 | 36.614 | 1.00 | 36.75 | O |
| ATOM | 2752 | N | SER | B | 887 | 87.435 | 112.469 | 37.760 | 1.00 | 37.01 | N |
| ATOM | 2753 | CA | SER | B | 887 | 88.661 | 113.179 | 37.396 | 1.00 | 37.08 | C |

APPENDIX 1-continued

| ATOM | 2754 | CB | SER | B | 887 | 88.406 | 114.691 | 37.377 | 1.00 | 37.09 | C |
|---|---|---|---|---|---|---|---|---|---|---|---|
| ATOM | 2755 | OG | SER | B | 887 | 87.266 | 115.009 | 36.595 | 1.00 | 38.57 | O |
| ATOM | 2756 | C | SER | B | 887 | 89.865 | 112.852 | 38.290 | 1.00 | 36.70 | C |
| ATOM | 2757 | O | SER | B | 887 | 90.433 | 113.742 | 38.931 | 1.00 | 36.65 | O |
| ATOM | 2758 | N | THR | B | 888 | 90.252 | 111.578 | 38.326 | 1.00 | 36.36 | N |
| ATOM | 2759 | CA | THR | B | 888 | 91.495 | 111.173 | 38.989 | 1.00 | 36.67 | C |
| ATOM | 2760 | CB | THR | B | 888 | 91.579 | 109.648 | 39.213 | 1.00 | 36.43 | C |
| ATOM | 2761 | OG1 | THR | B | 888 | 91.390 | 108.963 | 37.968 | 1.00 | 36.00 | O |
| ATOM | 2762 | CG2 | THR | B | 888 | 90.540 | 109.188 | 40.214 | 1.00 | 36.09 | C |
| ATOM | 2763 | C | THR | B | 888 | 92.688 | 111.598 | 38.139 | 1.00 | 37.16 | C |
| ATOM | 2764 | O | THR | B | 888 | 92.528 | 111.922 | 36.960 | 1.00 | 36.81 | O |
| ATOM | 2765 | N | GLU | B | 889 | 93.877 | 111.585 | 38.737 | 1.00 | 37.74 | N |
| ATOM | 2766 | CA | GLU | B | 889 | 95.112 | 111.901 | 38.019 | 1.00 | 39.09 | C |
| ATOM | 2767 | CB | GLU | B | 889 | 96.324 | 111.811 | 38.952 | 1.00 | 39.21 | C |
| ATOM | 2768 | CG | GLU | B | 889 | 96.417 | 112.945 | 39.967 | 1.00 | 40.85 | C |
| ATOM | 2769 | CD | GLU | B | 889 | 97.614 | 112.819 | 40.898 | 1.00 | 41.54 | C |
| ATOM | 2770 | OE1 | GLU | B | 889 | 98.650 | 112.248 | 40.485 | 1.00 | 46.01 | O |
| ATOM | 2771 | OE2 | GLU | B | 889 | 97.520 | 113.301 | 42.049 | 1.00 | 45.80 | O |
| ATOM | 2772 | C | GLU | B | 889 | 95.306 | 110.995 | 36.803 | 1.00 | 38.59 | C |
| ATOM | 2773 | O | GLU | B | 889 | 95.716 | 111.462 | 35.738 | 1.00 | 37.87 | O |
| ATOM | 2774 | N | GLU | B | 890 | 94.990 | 109.711 | 36.969 | 1.00 | 38.74 | N |
| ATOM | 2775 | CA | GLU | B | 890 | 95.117 | 108.721 | 35.897 | 1.00 | 39.80 | C |
| ATOM | 2776 | CB | GLU | B | 890 | 95.041 | 107.294 | 36.456 | 1.00 | 39.97 | C |
| ATOM | 2777 | CG | GLU | B | 890 | 96.303 | 106.859 | 37.212 | 1.00 | 42.83 | C |
| ATOM | 2778 | CD | GLU | B | 890 | 96.223 | 105.445 | 37.774 | 1.00 | 42.37 | C |
| ATOM | 2779 | OE1 | GLU | B | 890 | 95.578 | 104.574 | 37.147 | 1.00 | 48.14 | O |
| ATOM | 2780 | OE2 | GLU | B | 890 | 96.822 | 105.202 | 38.846 | 1.00 | 45.28 | O |
| ATOM | 2781 | C | GLU | B | 890 | 94.095 | 108.924 | 34.774 | 1.00 | 38.85 | C |
| ATOM | 2782 | O | GLU | B | 890 | 94.444 | 108.819 | 33.596 | 1.00 | 38.58 | O |
| ATOM | 2783 | N | HIS | B | 891 | 92.845 | 109.216 | 35.137 | 1.00 | 37.99 | N |
| ATOM | 2784 | CA | HIS | B | 891 | 91.799 | 109.483 | 34.147 | 1.00 | 37.41 | C |
| ATOM | 2785 | CB | HIS | B | 891 | 90.407 | 109.526 | 34.788 | 1.00 | 37.54 | C |
| ATOM | 2786 | CG | HIS | B | 891 | 89.875 | 108.183 | 35.191 | 1.00 | 38.51 | C |
| ATOM | 2787 | ND1 | HIS | B | 891 | 90.100 | 107.038 | 34.457 | 1.00 | 40.67 | N |
| ATOM | 2788 | CE1 | HIS | B | 891 | 89.508 | 106.015 | 35.047 | 1.00 | 40.62 | C |
| ATOM | 2789 | NE2 | HIS | B | 891 | 88.894 | 106.457 | 36.129 | 1.00 | 39.89 | N |
| ATOM | 2790 | CD2 | HIS | B | 891 | 89.103 | 107.810 | 36.239 | 1.00 | 39.57 | C |
| ATOM | 2791 | C | HIS | B | 891 | 92.063 | 110.775 | 33.382 | 1.00 | 36.78 | C |
| ATOM | 2792 | O | HIS | B | 891 | 91.780 | 110.859 | 32.186 | 1.00 | 36.41 | O |
| ATOM | 2793 | N | LEU | B | 892 | 92.606 | 111.774 | 34.076 | 1.00 | 36.59 | N |
| ATOM | 2794 | CA | LEU | B | 892 | 92.961 | 113.049 | 33.450 | 1.00 | 36.72 | C |
| ATOM | 2795 | CB | LEU | B | 892 | 93.338 | 114.096 | 34.504 | 1.00 | 36.82 | C |
| ATOM | 2796 | CG | LEU | B | 892 | 92.206 | 114.746 | 35.308 | 1.00 | 37.10 | C |
| ATOM | 2797 | CD1 | LEU | B | 892 | 92.746 | 115.359 | 36.593 | 1.00 | 37.78 | C |
| ATOM | 2798 | CD2 | LEU | B | 892 | 91.460 | 115.791 | 34.482 | 1.00 | 38.54 | C |
| ATOM | 2799 | C | LEU | B | 892 | 94.090 | 112.870 | 32.436 | 1.00 | 36.41 | C |
| ATOM | 2800 | O | LEU | B | 892 | 94.039 | 113.436 | 31.343 | 1.00 | 35.68 | O |
| ATOM | 2801 | N | ARG | B | 893 | 95.092 | 112.072 | 32.803 | 1.00 | 36.62 | N |
| ATOM | 2802 | CA | ARG | B | 893 | 96.197 | 111.734 | 31.904 | 1.00 | 37.56 | C |
| ATOM | 2803 | CB | ARG | B | 893 | 97.246 | 110.880 | 32.630 | 1.00 | 37.34 | C |
| ATOM | 2804 | CG | ARG | B | 893 | 98.416 | 110.430 | 31.751 | 1.00 | 39.54 | C |
| ATOM | 2805 | CD | ARG | B | 893 | 99.556 | 109.814 | 32.562 | 1.00 | 40.53 | C |
| ATOM | 2806 | NE | ARG | B | 893 | 99.208 | 108.518 | 33.148 | 1.00 | 46.66 | N |
| ATOM | 2807 | CZ | ARG | B | 893 | 98.982 | 108.306 | 34.444 | 1.00 | 48.49 | C |
| ATOM | 2808 | NH1 | ARG | B | 893 | 99.065 | 109.302 | 35.320 | 1.00 | 48.73 | N |
| ATOM | 2809 | NH2 | ARG | B | 893 | 98.674 | 107.087 | 34.866 | 1.00 | 50.19 | N |
| ATOM | 2810 | C | ARG | B | 893 | 95.698 | 111.025 | 30.640 | 1.00 | 36.31 | C |
| ATOM | 2811 | O | ARG | B | 893 | 96.123 | 111.356 | 29.530 | 1.00 | 36.38 | O |
| ATOM | 2812 | N | ASP | B | 894 | 94.798 | 110.060 | 30.817 | 1.00 | 35.51 | N |
| ATOM | 2813 | CA | ASP | B | 894 | 94.207 | 109.328 | 29.696 | 1.00 | 35.25 | C |
| ATOM | 2814 | CB | ASP | B | 894 | 93.337 | 108.169 | 30.195 | 1.00 | 34.99 | C |
| ATOM | 2815 | CG | ASP | B | 894 | 94.151 | 107.043 | 30.820 | 1.00 | 37.02 | C |
| ATOM | 2816 | OD1 | ASP | B | 894 | 95.400 | 107.121 | 30.825 | 1.00 | 38.53 | O |
| ATOM | 2817 | OD2 | ASP | B | 894 | 93.535 | 106.071 | 31.310 | 1.00 | 36.36 | O |
| ATOM | 2818 | C | ASP | B | 894 | 93.399 | 110.239 | 28.775 | 1.00 | 35.08 | C |
| ATOM | 2819 | O | ASP | B | 894 | 93.476 | 110.113 | 27.552 | 1.00 | 35.90 | O |
| ATOM | 2820 | N | PHE | B | 895 | 92.637 | 111.158 | 29.370 | 1.00 | 34.24 | N |
| ATOM | 2821 | CA | PHE | B | 895 | 91.806 | 112.100 | 28.617 | 1.00 | 33.82 | C |
| ATOM | 2822 | CB | PHE | B | 895 | 90.860 | 112.861 | 29.555 | 1.00 | 33.18 | C |
| ATOM | 2823 | CG | PHE | B | 895 | 89.711 | 113.550 | 28.852 | 1.00 | 33.95 | C |
| ATOM | 2824 | CD1 | PHE | B | 895 | 89.017 | 112.917 | 27.822 | 1.00 | 34.82 | C |
| ATOM | 2825 | CE1 | PHE | B | 895 | 87.955 | 113.551 | 27.181 | 1.00 | 34.61 | C |
| ATOM | 2826 | CZ | PHE | B | 895 | 87.562 | 114.821 | 27.584 | 1.00 | 33.15 | C |
| ATOM | 2827 | CE2 | PHE | B | 895 | 88.239 | 115.460 | 28.615 | 1.00 | 34.66 | C |
| ATOM | 2828 | CD2 | PHE | B | 895 | 89.304 | 114.821 | 29.247 | 1.00 | 34.22 | C |
| ATOM | 2829 | C | PHE | B | 895 | 92.649 | 113.065 | 27.778 | 1.00 | 33.91 | C |
| ATOM | 2830 | O | PHE | B | 895 | 92.308 | 113.347 | 26.628 | 1.00 | 33.32 | O |
| ATOM | 2831 | N | GLU | B | 896 | 93.747 | 113.557 | 28.355 | 1.00 | 34.25 | N |
| ATOM | 2832 | CA | GLU | B | 896 | 94.719 | 114.374 | 27.621 | 1.00 | 35.32 | C |

APPENDIX 1-continued

| | | | | | | | | | | |
|---|---|---|---|---|---|---|---|---|---|---|
| ATOM | 2833 | CB | GLU | B | 896 | 95.879 | 114.800 | 28.532 | 1.00 | 35.66 | C |
| ATOM | 2834 | CG | GLU | B | 896 | 95.521 | 115.813 | 29.622 | 1.00 | 40.67 | C |
| ATOM | 2835 | CD | GLU | B | 896 | 95.697 | 117.266 | 29.191 | 1.00 | 46.63 | C |
| ATOM | 2836 | OE1 | GLU | B | 896 | 95.418 | 117.597 | 28.016 | 1.00 | 49.80 | O |
| ATOM | 2837 | OE2 | GLU | B | 896 | 96.107 | 118.088 | 30.040 | 1.00 | 48.16 | O |
| ATOM | 2838 | C | GLU | B | 896 | 95.259 | 113.620 | 26.400 | 1.00 | 34.55 | C |
| ATOM | 2839 | O | GLU | B | 896 | 95.364 | 114.184 | 25.309 | 1.00 | 34.65 | O |
| ATOM | 2840 | N | ARG | B | 897 | 95.585 | 112.342 | 26.593 | 1.00 | 33.63 | N |
| ATOM | 2841 | CA | ARG | B | 897 | 96.074 | 111.487 | 25.513 | 1.00 | 34.03 | C |
| ATOM | 2842 | CB | ARG | B | 897 | 96.641 | 110.179 | 26.071 | 1.00 | 34.59 | C |
| ATOM | 2843 | CG | ARG | B | 897 | 98.019 | 110.327 | 26.709 | 1.00 | 38.65 | C |
| ATOM | 2844 | CD | ARG | B | 897 | 98.651 | 108.974 | 27.015 | 1.00 | 43.78 | C |
| ATOM | 2845 | NE | ARG | B | 897 | 98.140 | 108.387 | 28.254 | 1.00 | 49.16 | N |
| ATOM | 2846 | CZ | ARG | B | 897 | 98.505 | 107.201 | 28.737 | 1.00 | 52.77 | C |
| ATOM | 2847 | NH1 | ARG | B | 897 | 99.388 | 106.447 | 28.090 | 1.00 | 53.43 | N |
| ATOM | 2848 | NH2 | ARG | B | 897 | 97.979 | 106.763 | 29.874 | 1.00 | 54.14 | N |
| ATOM | 2849 | C | ARG | B | 897 | 94.993 | 111.204 | 24.468 | 1.00 | 33.02 | C |
| ATOM | 2850 | O | ARG | B | 897 | 95.285 | 111.134 | 23.272 | 1.00 | 31.72 | O |
| ATOM | 2851 | N | GLU | B | 898 | 93.751 | 111.053 | 24.928 | 1.00 | 32.04 | N |
| ATOM | 2852 | CA | GLU | B | 898 | 92.607 | 110.821 | 24.048 | 1.00 | 31.89 | C |
| ATOM | 2853 | CB | GLU | B | 898 | 91.340 | 110.558 | 24.869 | 1.00 | 31.59 | C |
| ATOM | 2854 | CG | GLU | B | 898 | 90.083 | 110.321 | 24.030 | 1.00 | 31.71 | C |
| ATOM | 2855 | CD | GLU | B | 898 | 88.806 | 110.323 | 24.856 | 1.00 | 31.88 | C |
| ATOM | 2856 | OE1 | GLU | B | 898 | 88.875 | 110.090 | 26.083 | 1.00 | 28.31 | O |
| ATOM | 2857 | OE2 | GLU | B | 898 | 87.729 | 110.549 | 24.269 | 1.00 | 34.28 | O |
| ATOM | 2858 | C | GLU | B | 898 | 92.388 | 112.008 | 23.111 | 1.00 | 32.22 | C |
| ATOM | 2859 | O | GLU | B | 898 | 92.129 | 111.826 | 21.919 | 1.00 | 32.13 | O |
| ATOM | 2860 | N | ILE | B | 899 | 92.497 | 113.216 | 23.662 | 1.00 | 32.34 | N |
| ATOM | 2861 | CA | ILE | B | 899 | 92.361 | 114.448 | 22.884 | 1.00 | 33.28 | C |
| ATOM | 2862 | CB | ILE | B | 899 | 92.393 | 115.702 | 23.794 | 1.00 | 33.02 | C |
| ATOM | 2863 | CG1 | ILE | B | 899 | 91.132 | 115.744 | 24.667 | 1.00 | 33.85 | C |
| ATOM | 2864 | CD1 | ILE | B | 899 | 91.232 | 116.659 | 25.874 | 1.00 | 32.27 | C |
| ATOM | 2865 | CG2 | ILE | B | 899 | 92.504 | 116.981 | 22.967 | 1.00 | 32.81 | C |
| ATOM | 2866 | C | ILE | B | 899 | 93.427 | 114.522 | 21.785 | 1.00 | 33.79 | C |
| ATOM | 2867 | O | ILE | B | 899 | 93.107 | 114.816 | 20.631 | 1.00 | 33.74 | O |
| ATOM | 2868 | N | GLU | B | 900 | 94.677 | 114.229 | 22.147 | 1.00 | 34.41 | N |
| ATOM | 2869 | CA | GLU | B | 900 | 95.792 | 114.239 | 21.194 | 1.00 | 35.59 | C |
| ATOM | 2870 | CB | GLU | B | 900 | 97.133 | 114.010 | 21.903 | 1.00 | 35.70 | C |
| ATOM | 2871 | CG | GLU | B | 900 | 97.557 | 115.135 | 22.843 | 1.00 | 39.54 | C |
| ATOM | 2872 | CD | GLU | B | 900 | 97.607 | 116.501 | 22.168 | 1.00 | 44.28 | C |
| ATOM | 2873 | OE1 | GLU | B | 900 | 96.970 | 117.441 | 22.691 | 1.00 | 45.25 | O |
| ATOM | 2874 | OE2 | GLU | B | 900 | 98.272 | 116.635 | 21.115 | 1.00 | 45.60 | O |
| ATOM | 2875 | C | GLU | B | 900 | 95.600 | 113.208 | 20.087 | 1.00 | 35.21 | C |
| ATOM | 2876 | O | GLU | B | 900 | 95.879 | 113.487 | 18.918 | 1.00 | 35.42 | O |
| ATOM | 2877 | N | ILE | B | 901 | 95.117 | 112.024 | 20.465 | 1.00 | 34.92 | N |
| ATOM | 2878 | CA | ILE | B | 901 | 94.803 | 110.962 | 19.508 | 1.00 | 34.20 | C |
| ATOM | 2879 | CB | ILE | B | 901 | 94.337 | 109.661 | 20.226 | 1.00 | 34.14 | C |
| ATOM | 2880 | CG1 | ILE | B | 901 | 95.549 | 108.908 | 20.784 | 1.00 | 34.60 | C |
| ATOM | 2881 | CD1 | ILE | B | 901 | 95.226 | 107.954 | 21.919 | 1.00 | 33.90 | C |
| ATOM | 2882 | CG2 | ILE | B | 901 | 93.545 | 108.748 | 19.282 | 1.00 | 33.19 | C |
| ATOM | 2883 | C | ILE | B | 901 | 93.774 | 111.439 | 18.483 | 1.00 | 34.31 | C |
| ATOM | 2884 | O | ILE | B | 901 | 94.006 | 111.332 | 17.278 | 1.00 | 34.14 | O |
| ATOM | 2885 | N | LEU | B | 902 | 92.659 | 111.988 | 18.966 | 1.00 | 33.95 | N |
| ATOM | 2886 | CA | LEU | B | 902 | 91.576 | 112.434 | 18.090 | 1.00 | 34.43 | C |
| ATOM | 2887 | CB | LEU | B | 902 | 90.325 | 112.794 | 18.901 | 1.00 | 34.71 | C |
| ATOM | 2888 | CG | LEU | B | 902 | 89.042 | 113.102 | 18.116 | 1.00 | 36.02 | C |
| ATOM | 2889 | CD1 | LEU | B | 902 | 88.585 | 111.913 | 17.268 | 1.00 | 34.17 | C |
| ATOM | 2890 | CD2 | LEU | B | 902 | 87.941 | 113.541 | 19.061 | 1.00 | 34.78 | C |
| ATOM | 2891 | C | LEU | B | 902 | 91.994 | 113.601 | 17.198 | 1.00 | 34.10 | C |
| ATOM | 2892 | O | LEU | B | 902 | 91.665 | 113.623 | 16.011 | 1.00 | 33.85 | O |
| ATOM | 2893 | N | LYS | B | 903 | 92.717 | 114.557 | 17.779 | 1.00 | 34.23 | N |
| ATOM | 2894 | CA | LYS | B | 903 | 93.268 | 115.696 | 17.043 | 1.00 | 34.85 | C |
| ATOM | 2895 | CB | LYS | B | 903 | 94.020 | 116.632 | 17.998 | 1.00 | 34.78 | C |
| ATOM | 2896 | CG | LYS | B | 903 | 94.619 | 117.869 | 17.337 | 1.00 | 36.57 | C |
| ATOM | 2897 | CD | LYS | B | 903 | 95.364 | 118.735 | 18.337 | 1.00 | 37.00 | C |
| ATOM | 2898 | CE | LYS | B | 903 | 96.022 | 119.918 | 17.641 | 1.00 | 42.64 | C |
| ATOM | 2899 | NZ | LYS | B | 903 | 96.646 | 120.863 | 18.613 | 1.00 | 45.90 | N |
| ATOM | 2900 | C | LYS | B | 903 | 94.181 | 115.258 | 15.887 | 1.00 | 34.28 | C |
| ATOM | 2901 | O | LYS | B | 903 | 94.214 | 115.905 | 14.837 | 1.00 | 33.58 | O |
| ATOM | 2902 | N | SER | B | 904 | 94.907 | 114.158 | 16.088 | 1.00 | 34.22 | N |
| ATOM | 2903 | CA | SER | B | 904 | 95.828 | 113.634 | 15.078 | 1.00 | 34.83 | C |
| ATOM | 2904 | CB | SER | B | 904 | 96.892 | 112.739 | 15.727 | 1.00 | 35.15 | C |
| ATOM | 2905 | OG | SER | B | 904 | 96.351 | 111.479 | 16.087 | 1.00 | 34.47 | O |
| ATOM | 2906 | C | SER | B | 904 | 95.113 | 112.874 | 13.960 | 1.00 | 35.17 | C |
| ATOM | 2907 | O | SER | B | 904 | 95.711 | 112.582 | 12.923 | 1.00 | 35.13 | O |
| ATOM | 2908 | N | LEU | B | 905 | 93.838 | 112.551 | 14.177 | 1.00 | 35.71 | N |
| ATOM | 2909 | CA | LEU | B | 905 | 93.060 | 111.792 | 13.199 | 1.00 | 36.13 | C |
| ATOM | 2910 | CB | LEU | B | 905 | 92.140 | 110.778 | 13.892 | 1.00 | 35.70 | C |
| ATOM | 2911 | CG | LEU | B | 905 | 92.783 | 109.656 | 14.713 | 1.00 | 34.56 | C |

APPENDIX 1-continued

| ATOM | 2912 | CD1 | LEU | B | 905 | 91.734 | 108.943 | 15.553 | 1.00 | 33.36 | C |
|---|---|---|---|---|---|---|---|---|---|---|---|
| ATOM | 2913 | CD2 | LEU | B | 905 | 93.542 | 108.673 | 13.831 | 1.00 | 32.35 | C |
| ATOM | 2914 | C | LEU | B | 905 | 92.246 | 112.710 | 12.299 | 1.00 | 36.80 | C |
| ATOM | 2915 | O | LEU | B | 905 | 91.500 | 113.566 | 12.777 | 1.00 | 37.43 | O |
| ATOM | 2916 | N | GLN | B | 906 | 92.415 | 112.528 | 10.992 | 1.00 | 37.52 | N |
| ATOM | 2917 | CA | GLN | B | 906 | 91.650 | 113.256 | 9.987 | 1.00 | 38.25 | C |
| ATOM | 2918 | CB | GLN | B | 906 | 92.473 | 114.410 | 9.396 | 1.00 | 38.23 | C |
| ATOM | 2919 | CG | GLN | B | 906 | 92.653 | 115.598 | 10.350 | 1.00 | 41.13 | C |
| ATOM | 2920 | CD | GLN | B | 906 | 93.521 | 116.718 | 9.784 | 1.00 | 41.03 | C |
| ATOM | 2921 | OE1 | GLN | B | 906 | 94.222 | 116.545 | 8.783 | 1.00 | 44.94 | O |
| ATOM | 2922 | NE2 | GLN | B | 906 | 93.480 | 117.878 | 10.436 | 1.00 | 45.96 | N |
| ATOM | 2923 | C | GLN | B | 906 | 91.208 | 112.273 | 8.909 | 1.00 | 37.14 | C |
| ATOM | 2924 | O | GLN | B | 906 | 91.995 | 111.880 | 8.044 | 1.00 | 37.39 | O |
| ATOM | 2925 | N | HIS | B | 907 | 89.946 | 111.861 | 8.990 | 1.00 | 35.98 | N |
| ATOM | 2926 | CA | HIS | B | 907 | 89.392 | 110.839 | 8.107 | 1.00 | 35.38 | C |
| ATOM | 2927 | CB | HIS | B | 907 | 89.702 | 109.443 | 8.659 | 1.00 | 34.83 | C |
| ATOM | 2928 | CG | HIS | B | 907 | 89.477 | 108.336 | 7.677 | 1.00 | 34.43 | C |
| ATOM | 2929 | ND1 | HIS | B | 907 | 88.286 | 107.649 | 7.590 | 1.00 | 32.89 | N |
| ATOM | 2930 | CE1 | HIS | B | 907 | 88.377 | 106.730 | 6.646 | 1.00 | 32.37 | C |
| ATOM | 2931 | NE2 | HIS | B | 907 | 89.588 | 106.792 | 6.121 | 1.00 | 33.95 | N |
| ATOM | 2932 | CD2 | HIS | B | 907 | 90.296 | 107.787 | 6.750 | 1.00 | 32.26 | C |
| ATOM | 2933 | C | HIS | B | 907 | 87.887 | 111.026 | 7.989 | 1.00 | 34.87 | C |
| ATOM | 2934 | O | HIS | B | 907 | 87.243 | 111.491 | 8.932 | 1.00 | 35.28 | O |
| ATOM | 2935 | N | ASP | B | 908 | 87.335 | 110.656 | 6.836 | 1.00 | 33.87 | N |
| ATOM | 2936 | CA | ASP | B | 908 | 85.897 | 110.775 | 6.573 | 1.00 | 33.54 | C |
| ATOM | 2937 | CB | ASP | B | 908 | 85.580 | 110.358 | 5.132 | 1.00 | 34.10 | C |
| ATOM | 2938 | CG | ASP | B | 908 | 85.944 | 111.425 | 4.116 | 1.00 | 37.40 | C |
| ATOM | 2939 | OD1 | ASP | B | 908 | 86.309 | 112.550 | 4.519 | 1.00 | 40.64 | O |
| ATOM | 2940 | OD2 | ASP | B | 908 | 85.860 | 111.135 | 2.903 | 1.00 | 41.27 | O |
| ATOM | 2941 | C | ASP | B | 908 | 85.037 | 109.960 | 7.538 | 1.00 | 32.27 | C |
| ATOM | 2942 | O | ASP | B | 908 | 83.900 | 110.335 | 7.834 | 1.00 | 31.84 | O |
| ATOM | 2943 | N | ASN | B | 909 | 85.587 | 108.849 | 8.022 | 1.00 | 31.12 | N |
| ATOM | 2944 | CA | ASN | B | 909 | 84.849 | 107.924 | 8.876 | 1.00 | 30.57 | C |
| ATOM | 2945 | CB | ASN | B | 909 | 84.915 | 106.511 | 8.298 | 1.00 | 30.12 | C |
| ATOM | 2946 | CG | ASN | B | 909 | 84.394 | 106.443 | 6.875 | 1.00 | 30.97 | C |
| ATOM | 2947 | OD1 | ASN | B | 909 | 83.260 | 106.836 | 6.596 | 1.00 | 34.51 | O |
| ATOM | 2948 | ND2 | ASN | B | 909 | 85.223 | 105.953 | 5.968 | 1.00 | 27.62 | N |
| ATOM | 2949 | C | ASN | B | 909 | 85.316 | 107.946 | 10.329 | 1.00 | 30.18 | C |
| ATOM | 2950 | O | ASN | B | 909 | 85.210 | 106.948 | 11.044 | 1.00 | 30.32 | O |
| ATOM | 2951 | N | ILE | B | 910 | 85.843 | 109.095 | 10.744 | 1.00 | 29.69 | N |
| ATOM | 2952 | CA | ILE | B | 910 | 86.232 | 109.342 | 12.129 | 1.00 | 30.54 | C |
| ATOM | 2953 | CB | ILE | B | 910 | 87.775 | 109.275 | 12.316 | 1.00 | 30.32 | C |
| ATOM | 2954 | CG1 | ILE | B | 910 | 88.275 | 107.840 | 12.101 | 1.00 | 29.90 | C |
| ATOM | 2955 | CD1 | ILE | B | 910 | 89.774 | 107.685 | 12.112 | 1.00 | 31.73 | C |
| ATOM | 2956 | CG2 | ILE | B | 910 | 88.185 | 109.799 | 13.700 | 1.00 | 29.69 | C |
| ATOM | 2957 | C | ILE | B | 910 | 85.687 | 110.706 | 12.556 | 1.00 | 30.56 | C |
| ATOM | 2958 | O | ILE | B | 910 | 85.902 | 111.713 | 11.870 | 1.00 | 30.27 | O |
| ATOM | 2959 | N | VAL | B | 911 | 84.975 | 110.723 | 13.684 | 1.00 | 30.65 | N |
| ATOM | 2960 | CA | VAL | B | 911 | 84.375 | 111.944 | 14.235 | 1.00 | 30.27 | C |
| ATOM | 2961 | CB | VAL | B | 911 | 83.682 | 111.671 | 15.607 | 1.00 | 30.51 | C |
| ATOM | 2962 | CG1 | VAL | B | 911 | 84.705 | 111.326 | 16.698 | 1.00 | 30.51 | C |
| ATOM | 2963 | CG2 | VAL | B | 911 | 82.801 | 112.847 | 16.027 | 1.00 | 28.53 | C |
| ATOM | 2964 | C | VAL | B | 911 | 85.402 | 113.085 | 14.322 | 1.00 | 31.18 | C |
| ATOM | 2965 | O | VAL | B | 911 | 86.557 | 112.869 | 14.700 | 1.00 | 31.18 | O |
| ATOM | 2966 | N | LYS | B | 912 | 84.978 | 114.287 | 13.948 | 1.00 | 31.46 | N |
| ATOM | 2967 | CA | LYS | B | 912 | 85.887 | 115.424 | 13.840 | 1.00 | 33.53 | C |
| ATOM | 2968 | CB | LYS | B | 912 | 85.335 | 116.478 | 12.873 | 1.00 | 33.15 | C |
| ATOM | 2969 | CG | LYS | B | 912 | 85.458 | 116.088 | 11.408 | 1.00 | 35.15 | C |
| ATOM | 2970 | CD | LYS | B | 912 | 84.764 | 117.090 | 10.492 | 1.00 | 35.80 | C |
| ATOM | 2971 | CE | LYS | B | 912 | 84.931 | 116.694 | 9.031 | 1.00 | 40.83 | C |
| ATOM | 2972 | NZ | LYS | B | 912 | 84.240 | 117.639 | 8.106 | 1.00 | 45.20 | N |
| ATOM | 2973 | C | LYS | B | 912 | 86.211 | 116.063 | 15.184 | 1.00 | 33.31 | C |
| ATOM | 2974 | O | LYS | B | 912 | 85.320 | 116.342 | 15.986 | 1.00 | 32.71 | O |
| ATOM | 2975 | N | TYR | B | 913 | 87.504 | 116.273 | 15.413 | 1.00 | 34.07 | N |
| ATOM | 2976 | CA | TYR | B | 913 | 87.995 | 117.064 | 16.532 | 1.00 | 33.89 | C |
| ATOM | 2977 | CB | TYR | B | 913 | 89.489 | 116.790 | 16.746 | 1.00 | 34.62 | C |
| ATOM | 2978 | CG | TYR | B | 913 | 90.177 | 117.734 | 17.712 | 1.00 | 35.19 | C |
| ATOM | 2979 | CD1 | TYR | B | 913 | 90.110 | 117.521 | 19.088 | 1.00 | 37.39 | C |
| ATOM | 2980 | CE1 | TYR | B | 913 | 90.736 | 118.383 | 19.982 | 1.00 | 35.54 | C |
| ATOM | 2981 | CZ | TYR | B | 913 | 91.445 | 119.467 | 19.500 | 1.00 | 36.41 | C |
| ATOM | 2982 | OH | TYR | B | 913 | 92.062 | 120.318 | 20.387 | 1.00 | 36.73 | O |
| ATOM | 2983 | CE2 | TYR | B | 913 | 91.531 | 119.703 | 18.135 | 1.00 | 35.84 | C |
| ATOM | 2984 | CD2 | TYR | B | 913 | 90.900 | 118.834 | 17.249 | 1.00 | 34.78 | C |
| ATOM | 2985 | C | TYR | B | 913 | 87.757 | 118.542 | 16.230 | 1.00 | 34.19 | C |
| ATOM | 2986 | O | TYR | B | 913 | 88.075 | 119.017 | 15.136 | 1.00 | 33.20 | O |
| ATOM | 2987 | N | LYS | B | 914 | 87.190 | 119.262 | 17.194 | 1.00 | 34.27 | N |
| ATOM | 2988 | CA | LYS | B | 914 | 86.977 | 120.701 | 17.041 | 1.00 | 35.15 | C |
| ATOM | 2989 | CB | LYS | B | 914 | 85.502 | 121.070 | 17.219 | 1.00 | 35.55 | C |
| ATOM | 2990 | CG | LYS | B | 914 | 84.644 | 120.709 | 16.017 | 1.00 | 39.06 | C |

APPENDIX 1-continued

| ATOM | 2991 | CD | LYS | B | 914 | 83.332 | 121.472 | 16.010 | 1.00 | 43.31 | C |
|---|---|---|---|---|---|---|---|---|---|---|---|
| ATOM | 2992 | CE | LYS | B | 914 | 82.638 | 121.366 | 14.657 | 1.00 | 45.62 | C |
| ATOM | 2993 | NZ | LYS | B | 914 | 83.350 | 122.131 | 13.587 | 1.00 | 47.31 | N |
| ATOM | 2994 | C | LYS | B | 914 | 87.866 | 121.527 | 17.968 | 1.00 | 35.27 | C |
| ATOM | 2995 | O | LYS | B | 914 | 88.358 | 122.588 | 17.576 | 1.00 | 34.84 | O |
| ATOM | 2996 | N | GLY | B | 915 | 88.075 | 121.041 | 19.189 | 1.00 | 34.72 | N |
| ATOM | 2997 | CA | GLY | B | 915 | 88.930 | 121.740 | 20.136 | 1.00 | 35.27 | C |
| ATOM | 2998 | C | GLY | B | 915 | 88.844 | 121.276 | 21.574 | 1.00 | 36.12 | C |
| ATOM | 2999 | O | GLY | B | 915 | 88.399 | 120.160 | 21.856 | 1.00 | 34.68 | O |
| ATOM | 3000 | N | VAL | B | 916 | 89.287 | 122.148 | 22.478 | 1.00 | 37.80 | N |
| ATOM | 3001 | CA | VAL | B | 916 | 89.291 | 121.880 | 23.916 | 1.00 | 39.48 | C |
| ATOM | 3002 | CB | VAL | B | 916 | 90.716 | 121.580 | 24.458 | 1.00 | 39.51 | C |
| ATOM | 3003 | CG1 | VAL | B | 916 | 91.155 | 120.176 | 24.075 | 1.00 | 38.97 | C |
| ATOM | 3004 | CG2 | VAL | B | 916 | 91.728 | 122.628 | 23.978 | 1.00 | 38.56 | C |
| ATOM | 3005 | C | VAL | B | 916 | 88.696 | 123.038 | 24.712 | 1.00 | 41.30 | C |
| ATOM | 3006 | O | VAL | B | 916 | 88.664 | 124.178 | 24.240 | 1.00 | 41.02 | O |
| ATOM | 3007 | N | CYS | B | 917 | 88.227 | 122.729 | 25.920 | 1.00 | 43.77 | N |
| ATOM | 3008 | CA | CYS | B | 917 | 87.741 | 123.734 | 26.859 | 1.00 | 45.47 | C |
| ATOM | 3009 | CB | CYS | B | 917 | 86.222 | 123.632 | 27.024 | 1.00 | 45.46 | C |
| ATOM | 3010 | SG | CYS | B | 917 | 85.507 | 124.848 | 28.165 | 1.00 | 45.29 | S |
| ATOM | 3011 | C | CYS | B | 917 | 88.441 | 123.570 | 28.207 | 1.00 | 47.33 | C |
| ATOM | 3012 | O | CYS | B | 917 | 88.378 | 122.502 | 28.822 | 1.00 | 47.05 | O |
| ATOM | 3013 | N | TYR | B | 918 | 89.114 | 124.632 | 28.647 | 1.00 | 49.91 | N |
| ATOM | 3014 | CA | TYR | B | 918 | 89.834 | 124.654 | 29.923 | 1.00 | 52.30 | C |
| ATOM | 3015 | CB | TYR | B | 918 | 91.276 | 125.124 | 29.716 | 1.00 | 53.08 | C |
| ATOM | 3016 | CG | TYR | B | 918 | 92.207 | 124.106 | 29.091 | 1.00 | 54.48 | C |
| ATOM | 3017 | CD1 | TYR | B | 918 | 92.489 | 124.136 | 27.725 | 1.00 | 54.91 | C |
| ATOM | 3018 | CE1 | TYR | B | 918 | 93.354 | 123.207 | 27.147 | 1.00 | 55.41 | C |
| ATOM | 3019 | CZ | TYR | B | 918 | 93.952 | 122.239 | 27.940 | 1.00 | 55.64 | C |
| ATOM | 3020 | OH | TYR | B | 918 | 94.808 | 121.319 | 27.373 | 1.00 | 55.93 | O |
| ATOM | 3021 | CE2 | TYR | B | 918 | 93.695 | 122.194 | 29.303 | 1.00 | 55.74 | C |
| ATOM | 3022 | CD2 | TYR | B | 918 | 92.826 | 123.127 | 29.871 | 1.00 | 55.69 | C |
| ATOM | 3023 | C | TYR | B | 918 | 89.156 | 125.578 | 30.935 | 1.00 | 53.48 | C |
| ATOM | 3024 | O | TYR | B | 918 | 88.484 | 126.540 | 30.555 | 1.00 | 53.53 | O |
| ATOM | 3025 | N | SER | B | 919 | 89.341 | 125.283 | 32.220 | 1.00 | 54.77 | N |
| ATOM | 3026 | CA | SER | B | 919 | 88.854 | 126.150 | 33.294 | 1.00 | 55.75 | C |
| ATOM | 3027 | CB | SER | B | 919 | 88.067 | 125.350 | 34.339 | 1.00 | 56.03 | C |
| ATOM | 3028 | OG | SER | B | 919 | 88.931 | 124.633 | 35.208 | 1.00 | 56.92 | O |
| ATOM | 3029 | C | SER | B | 919 | 90.017 | 126.886 | 33.955 | 1.00 | 56.05 | C |
| ATOM | 3030 | O | SER | B | 919 | 91.110 | 126.334 | 34.105 | 1.00 | 56.41 | O |
| ATOM | 3031 | N | ASN | B | 924 | 88.886 | 121.902 | 34.615 | 1.00 | 45.62 | N |
| ATOM | 3032 | CA | ASN | B | 924 | 87.990 | 120.860 | 34.126 | 1.00 | 45.44 | C |
| ATOM | 3033 | CB | ASN | B | 924 | 86.563 | 121.088 | 34.637 | 1.00 | 46.19 | C |
| ATOM | 3034 | CG | ASN | B | 924 | 86.434 | 120.860 | 36.136 | 1.00 | 48.25 | C |
| ATOM | 3035 | OD1 | ASN | B | 924 | 85.903 | 121.705 | 36.858 | 1.00 | 50.65 | O |
| ATOM | 3036 | ND2 | ASN | B | 924 | 86.923 | 119.716 | 36.611 | 1.00 | 49.95 | N |
| ATOM | 3037 | C | ASN | B | 924 | 88.021 | 120.744 | 32.602 | 1.00 | 44.58 | C |
| ATOM | 3038 | O | ASN | B | 924 | 87.204 | 121.347 | 31.898 | 1.00 | 44.76 | O |
| ATOM | 3039 | N | LEU | B | 925 | 88.979 | 119.957 | 32.115 | 1.00 | 43.17 | N |
| ATOM | 3040 | CA | LEU | B | 925 | 89.232 | 119.776 | 30.687 | 1.00 | 41.84 | C |
| ATOM | 3041 | CB | LEU | B | 925 | 90.483 | 118.917 | 30.493 | 1.00 | 42.11 | C |
| ATOM | 3042 | CG | LEU | B | 925 | 91.514 | 119.207 | 29.396 | 1.00 | 43.96 | C |
| ATOM | 3043 | CD1 | LEU | B | 925 | 92.260 | 117.923 | 29.085 | 1.00 | 43.29 | C |
| ATOM | 3044 | CD2 | LEU | B | 925 | 90.925 | 119.799 | 28.118 | 1.00 | 44.18 | C |
| ATOM | 3045 | C | LEU | B | 925 | 88.056 | 119.108 | 29.979 | 1.00 | 40.25 | C |
| ATOM | 3046 | O | LEU | B | 925 | 87.531 | 118.096 | 30.444 | 1.00 | 39.63 | O |
| ATOM | 3047 | N | LYS | B | 926 | 87.653 | 119.686 | 28.851 | 1.00 | 39.07 | N |
| ATOM | 3048 | CA | LYS | B | 926 | 86.584 | 119.126 | 28.029 | 1.00 | 38.21 | C |
| ATOM | 3049 | CB | LYS | B | 926 | 85.295 | 119.935 | 28.192 | 1.00 | 38.11 | C |
| ATOM | 3050 | CG | LYS | B | 926 | 84.668 | 119.808 | 29.582 | 1.00 | 39.89 | C |
| ATOM | 3051 | CD | LYS | B | 926 | 83.306 | 120.477 | 29.679 | 1.00 | 40.63 | C |
| ATOM | 3052 | CE | LYS | B | 926 | 83.424 | 121.974 | 29.904 | 1.00 | 45.99 | C |
| ATOM | 3053 | NZ | LYS | B | 926 | 82.125 | 122.547 | 30.357 | 1.00 | 49.69 | N |
| ATOM | 3054 | C | LYS | B | 926 | 86.993 | 119.035 | 26.560 | 1.00 | 36.41 | C |
| ATOM | 3055 | O | LYS | B | 926 | 87.713 | 119.894 | 26.051 | 1.00 | 36.09 | O |
| ATOM | 3056 | N | LEU | B | 927 | 86.537 | 117.978 | 25.896 | 1.00 | 34.54 | N |
| ATOM | 3057 | CA | LEU | B | 927 | 86.845 | 117.745 | 24.487 | 1.00 | 33.02 | C |
| ATOM | 3058 | CB | LEU | B | 927 | 87.204 | 116.270 | 24.257 | 1.00 | 32.26 | C |
| ATOM | 3059 | CG | LEU | B | 927 | 87.157 | 115.678 | 22.841 | 1.00 | 31.98 | C |
| ATOM | 3060 | CD1 | LEU | B | 927 | 88.189 | 116.318 | 21.911 | 1.00 | 28.55 | C |
| ATOM | 3061 | CD2 | LEU | B | 927 | 87.347 | 114.168 | 22.898 | 1.00 | 32.41 | C |
| ATOM | 3062 | C | LEU | B | 927 | 85.670 | 118.164 | 23.608 | 1.00 | 32.58 | C |
| ATOM | 3063 | O | LEU | B | 927 | 84.537 | 117.724 | 23.815 | 1.00 | 32.34 | O |
| ATOM | 3064 | N | ILE | B | 928 | 85.955 | 119.017 | 22.628 | 1.00 | 32.20 | N |
| ATOM | 3065 | CA | ILE | B | 928 | 84.928 | 119.548 | 21.733 | 1.00 | 31.91 | C |
| ATOM | 3066 | CB | ILE | B | 928 | 85.092 | 121.079 | 21.501 | 1.00 | 31.90 | C |
| ATOM | 3067 | CG1 | ILE | B | 928 | 85.393 | 121.826 | 22.814 | 1.00 | 32.77 | C |
| ATOM | 3068 | CD1 | ILE | B | 928 | 84.302 | 121.756 | 23.875 | 1.00 | 32.26 | C |
| ATOM | 3069 | CG2 | ILE | B | 928 | 83.872 | 121.657 | 20.779 | 1.00 | 31.74 | C |

APPENDIX 1-continued

| | | | | | | | | | | | |
|---|---|---|---|---|---|---|---|---|---|---|---|
| ATOM | 3070 | C | ILE | B | 928 | 84.967 | 118.812 | 20.395 | 1.00 | 31.68 | C |
| ATOM | 3071 | O | ILE | B | 928 | 85.995 | 118.792 | 19.713 | 1.00 | 31.13 | O |
| ATOM | 3072 | N | MET | B | 929 | 83.841 | 118.204 | 20.036 | 1.00 | 30.93 | N |
| ATOM | 3073 | CA | MET | B | 929 | 83.726 | 117.453 | 18.792 | 1.00 | 31.15 | C |
| ATOM | 3074 | CB | MET | B | 929 | 83.487 | 115.968 | 19.086 | 1.00 | 31.12 | C |
| ATOM | 3075 | CG | MET | B | 929 | 84.673 | 115.242 | 19.705 | 1.00 | 31.13 | C |
| ATOM | 3076 | SD | MET | B | 929 | 84.275 | 113.549 | 20.180 | 1.00 | 32.29 | S |
| ATOM | 3077 | CE | MET | B | 929 | 83.337 | 113.824 | 21.685 | 1.00 | 29.39 | C |
| ATOM | 3078 | C | MET | B | 929 | 82.586 | 117.998 | 17.944 | 1.00 | 30.66 | C |
| ATOM | 3079 | O | MET | B | 929 | 81.768 | 118.784 | 18.425 | 1.00 | 30.37 | O |
| ATOM | 3080 | N | GLU | B | 930 | 82.543 | 117.588 | 16.678 | 1.00 | 30.74 | N |
| ATOM | 3081 | CA | GLU | B | 930 | 81.407 | 117.892 | 15.812 | 1.00 | 30.99 | C |
| ATOM | 3082 | CB | GLU | B | 930 | 81.675 | 117.444 | 14.368 | 1.00 | 30.73 | C |
| ATOM | 3083 | CG | GLU | B | 930 | 81.780 | 115.929 | 14.177 | 1.00 | 29.52 | C |
| ATOM | 3084 | CD | GLU | B | 930 | 81.823 | 115.506 | 12.721 | 1.00 | 31.29 | C |
| ATOM | 3085 | OE1 | GLU | B | 930 | 82.479 | 114.485 | 12.427 | 1.00 | 29.83 | O |
| ATOM | 3086 | OE2 | GLU | B | 930 | 81.203 | 116.184 | 11.872 | 1.00 | 28.95 | O |
| ATOM | 3087 | C | GLU | B | 930 | 80.147 | 117.218 | 16.358 | 1.00 | 31.37 | C |
| ATOM | 3088 | O | GLU | B | 930 | 80.222 | 116.154 | 16.980 | 1.00 | 30.89 | O |
| ATOM | 3089 | N | TYR | B | 931 | 79.000 | 117.852 | 16.139 | 1.00 | 31.64 | N |
| ATOM | 3090 | CA | TYR | B | 931 | 77.726 | 117.294 | 16.568 | 1.00 | 31.88 | C |
| ATOM | 3091 | CB | TYR | B | 931 | 76.777 | 118.406 | 17.036 | 1.00 | 32.46 | C |
| ATOM | 3092 | CG | TYR | B | 931 | 75.358 | 117.954 | 17.318 | 1.00 | 32.14 | C |
| ATOM | 3093 | CD1 | TYR | B | 931 | 75.090 | 116.951 | 18.253 | 1.00 | 31.34 | C |
| ATOM | 3094 | CE1 | TYR | B | 931 | 73.785 | 116.539 | 18.512 | 1.00 | 30.12 | C |
| ATOM | 3095 | CZ | TYR | B | 931 | 72.732 | 117.146 | 17.840 | 1.00 | 32.62 | C |
| ATOM | 3096 | OH | TYR | B | 931 | 71.438 | 116.753 | 18.087 | 1.00 | 32.89 | O |
| ATOM | 3097 | CE2 | TYR | B | 931 | 72.974 | 118.145 | 16.913 | 1.00 | 30.95 | C |
| ATOM | 3098 | CD2 | TYR | B | 931 | 74.280 | 118.545 | 16.658 | 1.00 | 32.50 | C |
| ATOM | 3099 | C | TYR | B | 931 | 77.103 | 116.478 | 15.445 | 1.00 | 31.93 | C |
| ATOM | 3100 | O | TYR | B | 931 | 76.932 | 116.971 | 14.328 | 1.00 | 31.95 | O |
| ATOM | 3101 | N | LEU | B | 932 | 76.784 | 115.224 | 15.755 | 1.00 | 31.68 | N |
| ATOM | 3102 | CA | LEU | B | 932 | 76.143 | 114.314 | 14.812 | 1.00 | 31.31 | C |
| ATOM | 3103 | CB | LEU | B | 932 | 77.056 | 113.113 | 14.518 | 1.00 | 30.97 | C |
| ATOM | 3104 | CG | LEU | B | 932 | 78.384 | 113.402 | 13.799 | 1.00 | 32.93 | C |
| ATOM | 3105 | CD1 | LEU | B | 932 | 79.332 | 112.214 | 13.894 | 1.00 | 33.23 | C |
| ATOM | 3106 | CD2 | LEU | B | 932 | 78.162 | 113.794 | 12.338 | 1.00 | 31.08 | C |
| ATOM | 3107 | C | LEU | B | 932 | 74.778 | 113.869 | 15.357 | 1.00 | 31.38 | C |
| ATOM | 3108 | O | LEU | B | 932 | 74.689 | 112.869 | 16.074 | 1.00 | 30.56 | O |
| ATOM | 3109 | N | PRO | B | 933 | 73.708 | 114.619 | 15.012 | 1.00 | 32.19 | N |
| ATOM | 3110 | CA | PRO | B | 933 | 72.366 | 114.463 | 15.588 | 1.00 | 32.51 | C |
| ATOM | 3111 | CB | PRO | B | 933 | 71.518 | 115.482 | 14.806 | 1.00 | 33.14 | C |
| ATOM | 3112 | CG | PRO | B | 933 | 72.311 | 115.803 | 13.591 | 1.00 | 32.87 | C |
| ATOM | 3113 | CD | PRO | B | 933 | 73.738 | 115.701 | 14.012 | 1.00 | 32.43 | C |
| ATOM | 3114 | C | PRO | B | 933 | 71.749 | 113.070 | 15.479 | 1.00 | 32.89 | C |
| ATOM | 3115 | O | PRO | B | 933 | 70.938 | 112.703 | 16.331 | 1.00 | 32.80 | O |
| ATOM | 3116 | N | TYR | B | 934 | 72.128 | 112.303 | 14.458 | 1.00 | 33.06 | N |
| ATOM | 3117 | CA | TYR | B | 934 | 71.574 | 110.960 | 14.266 | 1.00 | 34.00 | C |
| ATOM | 3118 | CB | TYR | B | 934 | 71.858 | 110.433 | 12.853 | 1.00 | 35.44 | C |
| ATOM | 3119 | CG | TYR | B | 934 | 71.031 | 111.113 | 11.783 | 1.00 | 38.05 | C |
| ATOM | 3120 | CD1 | TYR | B | 934 | 71.632 | 111.920 | 10.818 | 1.00 | 38.48 | C |
| ATOM | 3121 | CE1 | TYR | B | 934 | 70.876 | 112.553 | 9.837 | 1.00 | 39.61 | C |
| ATOM | 3122 | CZ | TYR | B | 934 | 69.499 | 112.385 | 9.820 | 1.00 | 41.12 | C |
| ATOM | 3123 | OH | TYR | B | 934 | 68.744 | 113.009 | 8.851 | 1.00 | 41.70 | O |
| ATOM | 3124 | CE2 | TYR | B | 934 | 68.877 | 111.592 | 10.770 | 1.00 | 41.79 | C |
| ATOM | 3125 | CD2 | TYR | B | 934 | 69.644 | 110.961 | 11.744 | 1.00 | 40.46 | C |
| ATOM | 3126 | C | TYR | B | 934 | 72.009 | 109.956 | 15.337 | 1.00 | 33.36 | C |
| ATOM | 3127 | O | TYR | B | 934 | 71.412 | 108.885 | 15.469 | 1.00 | 32.97 | O |
| ATOM | 3128 | N | GLY | B | 935 | 73.036 | 110.312 | 16.106 | 1.00 | 32.78 | N |
| ATOM | 3129 | CA | GLY | B | 935 | 73.460 | 109.507 | 17.249 | 1.00 | 32.21 | C |
| ATOM | 3130 | C | GLY | B | 935 | 74.197 | 108.239 | 16.869 | 1.00 | 32.46 | C |
| ATOM | 3131 | O | GLY | B | 935 | 74.742 | 108.133 | 15.766 | 1.00 | 32.02 | O |
| ATOM | 3132 | N | SER | B | 936 | 74.207 | 107.276 | 17.787 | 1.00 | 32.57 | N |
| ATOM | 3133 | CA | SER | B | 936 | 74.956 | 106.037 | 17.599 | 1.00 | 33.74 | C |
| ATOM | 3134 | CB | SER | B | 936 | 75.159 | 105.310 | 18.932 | 1.00 | 33.98 | C |
| ATOM | 3135 | OG | SER | B | 936 | 73.938 | 104.779 | 19.416 | 1.00 | 38.27 | O |
| ATOM | 3136 | C | SER | B | 936 | 74.290 | 105.103 | 16.598 | 1.00 | 33.64 | C |
| ATOM | 3137 | O | SER | B | 936 | 73.063 | 105.078 | 16.477 | 1.00 | 33.46 | O |
| ATOM | 3138 | N | LEU | B | 937 | 75.116 | 104.333 | 15.894 | 1.00 | 33.45 | N |
| ATOM | 3139 | CA | LEU | B | 937 | 74.639 | 103.334 | 14.943 | 1.00 | 33.69 | C |
| ATOM | 3140 | CB | LEU | B | 937 | 75.817 | 102.710 | 14.183 | 1.00 | 33.05 | C |
| ATOM | 3141 | CG | LEU | B | 937 | 75.573 | 101.663 | 13.087 | 1.00 | 33.80 | C |
| ATOM | 3142 | CD1 | LEU | B | 937 | 74.550 | 102.129 | 12.050 | 1.00 | 33.50 | C |
| ATOM | 3143 | CD2 | LEU | B | 937 | 76.888 | 101.312 | 12.413 | 1.00 | 33.15 | C |
| ATOM | 3144 | C | LEU | B | 937 | 73.802 | 102.260 | 15.634 | 1.00 | 33.92 | C |
| ATOM | 3145 | O | LEU | B | 937 | 72.864 | 101.730 | 15.043 | 1.00 | 33.65 | O |
| ATOM | 3146 | N | ARG | B | 938 | 74.143 | 101.952 | 16.885 | 1.00 | 34.83 | N |
| ATOM | 3147 | CA | ARG | B | 938 | 73.382 | 100.995 | 17.683 | 1.00 | 36.45 | C |
| ATOM | 3148 | CB | ARG | B | 938 | 73.988 | 100.867 | 19.083 | 1.00 | 36.64 | C |

APPENDIX 1-continued

| | | | | | | | | | | | |
|---|---|---|---|---|---|---|---|---|---|---|---|
| ATOM | 3149 | CG | ARG | B | 938 | 73.335 | 99.811 | 19.958 | 1.00 | 40.47 | C |
| ATOM | 3150 | CD | ARG | B | 938 | 74.253 | 99.406 | 21.095 | 1.00 | 46.50 | C |
| ATOM | 3151 | NE | ARG | B | 938 | 73.505 | 98.907 | 22.245 | 1.00 | 53.02 | N |
| ATOM | 3152 | CZ | ARG | B | 938 | 73.287 | 99.600 | 23.360 | 1.00 | 56.41 | C |
| ATOM | 3153 | NH1 | ARG | B | 938 | 73.769 | 100.830 | 23.496 | 1.00 | 57.90 | N |
| ATOM | 3154 | NH2 | ARG | B | 938 | 72.590 | 99.057 | 24.350 | 1.00 | 58.32 | N |
| ATOM | 3155 | C | ARG | B | 938 | 71.905 | 101.392 | 17.765 | 1.00 | 36.92 | C |
| ATOM | 3156 | O | ARG | B | 938 | 71.021 | 100.566 | 17.538 | 1.00 | 37.43 | O |
| ATOM | 3157 | N | ASP | B | 939 | 71.650 | 102.663 | 18.066 | 1.00 | 37.08 | N |
| ATOM | 3158 | CA | ASP | B | 939 | 70.286 | 103.181 | 18.169 | 1.00 | 37.35 | C |
| ATOM | 3159 | CB | ASP | B | 939 | 70.266 | 104.465 | 19.003 | 1.00 | 37.79 | C |
| ATOM | 3160 | CG | ASP | B | 939 | 70.735 | 104.242 | 20.429 | 1.00 | 40.55 | C |
| ATOM | 3161 | OD1 | ASP | B | 939 | 71.557 | 105.046 | 20.919 | 1.00 | 43.96 | O |
| ATOM | 3162 | OD2 | ASP | B | 939 | 70.294 | 103.255 | 21.059 | 1.00 | 42.92 | O |
| ATOM | 3163 | C | ASP | B | 939 | 69.642 | 103.416 | 16.804 | 1.00 | 37.24 | C |
| ATOM | 3164 | O | ASP | B | 939 | 68.455 | 103.146 | 16.621 | 1.00 | 37.24 | O |
| ATOM | 3165 | N | TYR | B | 940 | 70.433 | 103.909 | 15.854 | 1.00 | 37.06 | N |
| ATOM | 3166 | CA | TYR | B | 940 | 69.949 | 104.223 | 14.508 | 1.00 | 37.06 | C |
| ATOM | 3167 | CB | TYR | B | 940 | 71.049 | 104.936 | 13.714 | 1.00 | 36.78 | C |
| ATOM | 3168 | CG | TYR | B | 940 | 70.647 | 105.397 | 12.329 | 1.00 | 35.49 | C |
| ATOM | 3169 | CD1 | TYR | B | 940 | 69.944 | 106.590 | 12.146 | 1.00 | 35.13 | C |
| ATOM | 3170 | CE1 | TYR | B | 940 | 69.581 | 107.021 | 10.876 | 1.00 | 35.13 | C |
| ATOM | 3171 | CZ | TYR | B | 940 | 69.925 | 106.257 | 9.771 | 1.00 | 35.51 | C |
| ATOM | 3172 | OH | TYR | B | 940 | 69.569 | 106.678 | 8.514 | 1.00 | 35.61 | O |
| ATOM | 3173 | CE2 | TYR | B | 940 | 70.627 | 105.073 | 9.924 | 1.00 | 33.97 | C |
| ATOM | 3174 | CD2 | TYR | B | 940 | 70.985 | 104.651 | 11.200 | 1.00 | 36.09 | C |
| ATOM | 3175 | C | TYR | B | 940 | 69.459 | 102.982 | 13.758 | 1.00 | 37.91 | C |
| ATOM | 3176 | O | TYR | B | 940 | 68.422 | 103.023 | 13.090 | 1.00 | 37.37 | O |
| ATOM | 3177 | N | LEU | B | 941 | 70.205 | 101.886 | 13.884 | 1.00 | 38.35 | N |
| ATOM | 3178 | CA | LEU | B | 941 | 69.904 | 100.640 | 13.180 | 1.00 | 39.56 | C |
| ATOM | 3179 | CB | LEU | B | 941 | 71.035 | 99.628 | 13.397 | 1.00 | 39.62 | C |
| ATOM | 3180 | CG | LEU | B | 941 | 71.084 | 98.363 | 12.541 | 1.00 | 41.00 | C |
| ATOM | 3181 | CD1 | LEU | B | 941 | 71.045 | 98.695 | 11.052 | 1.00 | 42.05 | C |
| ATOM | 3182 | CD2 | LEU | B | 941 | 72.331 | 97.571 | 12.882 | 1.00 | 40.06 | C |
| ATOM | 3183 | C | LEU | B | 941 | 68.560 | 100.037 | 13.588 | 1.00 | 40.08 | C |
| ATOM | 3184 | O | LEU | B | 941 | 67.797 | 99.570 | 12.733 | 1.00 | 39.29 | O |
| ATOM | 3185 | N | GLN | B | 942 | 68.282 | 100.059 | 14.891 | 1.00 | 41.18 | N |
| ATOM | 3186 | CA | GLN | B | 942 | 67.036 | 99.532 | 15.456 | 1.00 | 42.78 | C |
| ATOM | 3187 | CB | GLN | B | 942 | 67.000 | 99.749 | 16.974 | 1.00 | 43.09 | C |
| ATOM | 3188 | CG | GLN | B | 942 | 68.099 | 99.050 | 17.745 | 1.00 | 43.73 | C |
| ATOM | 3189 | CD | GLN | B | 942 | 67.939 | 99.187 | 19.248 | 1.00 | 44.38 | C |
| ATOM | 3190 | OE1 | GLN | B | 942 | 67.046 | 98.585 | 19.846 | 1.00 | 46.50 | O |
| ATOM | 3191 | NE2 | GLN | B | 942 | 68.815 | 99.973 | 19.868 | 1.00 | 47.52 | N |
| ATOM | 3192 | C | GLN | B | 942 | 65.785 | 100.153 | 14.832 | 1.00 | 42.86 | C |
| ATOM | 3193 | O | GLN | B | 942 | 64.880 | 99.437 | 14.396 | 1.00 | 42.78 | O |
| ATOM | 3194 | N | LYS | B | 943 | 65.744 | 101.483 | 14.789 | 1.00 | 43.20 | N |
| ATOM | 3195 | CA | LYS | B | 943 | 64.550 | 102.202 | 14.336 | 1.00 | 44.09 | C |
| ATOM | 3196 | CB | LYS | B | 943 | 64.480 | 103.606 | 14.953 | 1.00 | 44.07 | C |
| ATOM | 3197 | CG | LYS | B | 943 | 65.757 | 104.432 | 14.847 | 1.00 | 45.22 | C |
| ATOM | 3198 | CD | LYS | B | 943 | 65.715 | 105.641 | 15.780 | 1.00 | 45.76 | C |
| ATOM | 3199 | CE | LYS | B | 943 | 65.856 | 105.230 | 17.246 | 1.00 | 47.72 | C |
| ATOM | 3200 | NZ | LYS | B | 943 | 65.684 | 106.376 | 18.181 | 1.00 | 49.48 | N |
| ATOM | 3201 | C | LYS | B | 943 | 64.389 | 102.262 | 12.815 | 1.00 | 43.34 | C |
| ATOM | 3202 | O | LYS | B | 943 | 63.295 | 102.543 | 12.320 | 1.00 | 43.54 | O |
| ATOM | 3203 | N | HIS | B | 944 | 65.468 | 101.989 | 12.084 | 1.00 | 42.73 | N |
| ATOM | 3204 | CA | HIS | B | 944 | 65.442 | 102.053 | 10.622 | 1.00 | 42.02 | C |
| ATOM | 3205 | CB | HIS | B | 944 | 66.465 | 103.077 | 10.119 | 1.00 | 42.11 | C |
| ATOM | 3206 | CG | HIS | B | 944 | 66.182 | 104.479 | 10.556 | 1.00 | 43.38 | C |
| ATOM | 3207 | ND1 | HIS | B | 944 | 65.234 | 105.272 | 9.947 | 1.00 | 44.76 | N |
| ATOM | 3208 | CE1 | HIS | B | 944 | 65.203 | 106.452 | 10.539 | 1.00 | 45.02 | C |
| ATOM | 3209 | NE2 | HIS | B | 944 | 66.098 | 106.454 | 11.510 | 1.00 | 44.72 | N |
| ATOM | 3210 | CD2 | HIS | B | 944 | 66.724 | 105.232 | 11.542 | 1.00 | 44.24 | C |
| ATOM | 3211 | C | HIS | B | 944 | 65.660 | 100.694 | 9.945 | 1.00 | 41.62 | C |
| ATOM | 3212 | O | HIS | B | 944 | 65.965 | 100.635 | 8.751 | 1.00 | 40.92 | O |
| ATOM | 3213 | N | LYS | B | 945 | 65.472 | 99.614 | 10.706 | 1.00 | 41.53 | N |
| ATOM | 3214 | CA | LYS | B | 945 | 65.741 | 98.244 | 10.241 | 1.00 | 41.50 | C |
| ATOM | 3215 | CB | LYS | B | 945 | 65.471 | 97.221 | 11.356 | 1.00 | 41.24 | C |
| ATOM | 3216 | CG | LYS | B | 945 | 64.021 | 97.120 | 11.820 | 1.00 | 41.96 | C |
| ATOM | 3217 | CD | LYS | B | 945 | 63.836 | 95.962 | 12.792 | 1.00 | 42.96 | C |
| ATOM | 3218 | CE | LYS | B | 945 | 62.362 | 95.728 | 13.100 | 1.00 | 44.43 | C |
| ATOM | 3219 | NZ | LYS | B | 945 | 62.153 | 94.482 | 13.887 | 1.00 | 46.15 | N |
| ATOM | 3220 | C | LYS | B | 945 | 65.014 | 97.844 | 8.948 | 1.00 | 41.30 | C |
| ATOM | 3221 | O | LYS | B | 945 | 65.598 | 97.186 | 8.085 | 1.00 | 41.06 | O |
| ATOM | 3222 | N | GLU | B | 946 | 63.751 | 98.248 | 8.820 | 1.00 | 40.70 | N |
| ATOM | 3223 | CA | GLU | B | 946 | 62.944 | 97.940 | 7.635 | 1.00 | 40.80 | C |
| ATOM | 3224 | CB | GLU | B | 946 | 61.482 | 98.337 | 7.863 | 1.00 | 40.59 | C |
| ATOM | 3225 | CG | GLU | B | 946 | 60.730 | 97.425 | 8.827 | 1.00 | 42.66 | C |
| ATOM | 3226 | CD | GLU | B | 946 | 59.340 | 97.939 | 9.162 | 1.00 | 42.77 | C |
| ATOM | 3227 | OE1 | GLU | B | 946 | 59.230 | 98.879 | 9.980 | 1.00 | 45.47 | O |

APPENDIX 1-continued

| ATOM | 3228 | OE2 | GLU | B | 946 | 58.356 | 97.396 | 8.617 | 1.00 | 44.68 | O |
|---|---|---|---|---|---|---|---|---|---|---|---|
| ATOM | 3229 | C | GLU | B | 946 | 63.487 | 98.636 | 6.388 | 1.00 | 39.80 | C |
| ATOM | 3230 | O | GLU | B | 946 | 63.285 | 98.170 | 5.267 | 1.00 | 39.97 | O |
| ATOM | 3231 | N | ARG | B | 947 | 64.188 | 99.744 | 6.608 | 1.00 | 38.66 | N |
| ATOM | 3232 | CA | ARG | B | 947 | 64.714 | 100.590 | 5.546 | 1.00 | 38.63 | C |
| ATOM | 3233 | CB | ARG | B | 947 | 64.647 | 102.052 | 6.004 | 1.00 | 39.14 | C |
| ATOM | 3234 | CG | ARG | B | 947 | 64.771 | 103.099 | 4.918 | 1.00 | 43.28 | C |
| ATOM | 3235 | CD | ARG | B | 947 | 64.871 | 104.483 | 5.542 | 1.00 | 47.51 | C |
| ATOM | 3236 | NE | ARG | B | 947 | 65.292 | 105.503 | 4.583 | 1.00 | 52.68 | N |
| ATOM | 3237 | CZ | ARG | B | 947 | 65.718 | 106.720 | 4.915 | 1.00 | 55.59 | C |
| ATOM | 3238 | NH1 | ARG | B | 947 | 65.787 | 107.091 | 6.191 | 1.00 | 54.83 | N |
| ATOM | 3239 | NH2 | ARG | B | 947 | 66.080 | 107.573 | 3.965 | 1.00 | 57.05 | N |
| ATOM | 3240 | C | ARG | B | 947 | 66.154 | 100.211 | 5.176 | 1.00 | 37.19 | C |
| ATOM | 3241 | O | ARG | B | 947 | 66.612 | 100.499 | 4.067 | 1.00 | 37.11 | O |
| ATOM | 3242 | N | ILE | B | 948 | 66.856 | 99.556 | 6.099 | 1.00 | 35.71 | N |
| ATOM | 3243 | CA | ILE | B | 948 | 68.284 | 99.274 | 5.921 | 1.00 | 34.81 | C |
| ATOM | 3244 | CB | ILE | B | 948 | 69.113 | 99.593 | 7.196 | 1.00 | 34.96 | C |
| ATOM | 3245 | CG1 | ILE | B | 948 | 68.961 | 101.077 | 7.555 | 1.00 | 34.50 | C |
| ATOM | 3246 | CD1 | ILE | B | 948 | 69.583 | 101.481 | 8.880 | 1.00 | 34.30 | C |
| ATOM | 3247 | CG2 | ILE | B | 948 | 70.590 | 99.251 | 6.985 | 1.00 | 35.54 | C |
| ATOM | 3248 | C | ILE | B | 948 | 68.562 | 97.865 | 5.392 | 1.00 | 34.31 | C |
| ATOM | 3249 | O | ILE | B | 948 | 68.254 | 96.856 | 6.033 | 1.00 | 33.97 | O |
| ATOM | 3250 | N | ASP | B | 949 | 69.169 | 97.846 | 4.211 | 1.00 | 33.88 | N |
| ATOM | 3251 | CA | ASP | B | 949 | 69.445 | 96.655 | 3.423 | 1.00 | 33.99 | C |
| ATOM | 3252 | CB | ASP | B | 949 | 69.618 | 97.097 | 1.968 | 1.00 | 34.02 | C |
| ATOM | 3253 | CG | ASP | B | 949 | 68.977 | 96.156 | .999 | 1.00 | 37.49 | C |
| ATOM | 3254 | OD1 | ASP | B | 949 | 68.457 | 95.109 | 1.443 | 1.00 | 44.39 | O |
| ATOM | 3255 | OD2 | ASP | B | 949 | 68.993 | 96.461 | −.210 | 1.00 | 35.56 | O |
| ATOM | 3256 | C | ASP | B | 949 | 70.727 | 95.959 | 3.869 | 1.00 | 32.91 | C |
| ATOM | 3257 | O | ASP | B | 949 | 71.534 | 96.556 | 4.580 | 1.00 | 33.07 | O |
| ATOM | 3258 | N | HIS | B | 950 | 70.927 | 94.712 | 3.434 | 1.00 | 32.34 | N |
| ATOM | 3259 | CA | HIS | B | 950 | 72.208 | 94.024 | 3.648 | 1.00 | 31.68 | C |
| ATOM | 3260 | CB | HIS | B | 950 | 72.176 | 92.568 | 3.168 | 1.00 | 32.19 | C |
| ATOM | 3261 | CG | HIS | B | 950 | 71.439 | 91.637 | 4.081 | 1.00 | 33.66 | C |
| ATOM | 3262 | ND1 | HIS | B | 950 | 70.932 | 90.428 | 3.654 | 1.00 | 34.86 | N |
| ATOM | 3263 | CE1 | HIS | B | 950 | 70.332 | 89.823 | 4.663 | 1.00 | 36.16 | C |
| ATOM | 3264 | NE2 | HIS | B | 950 | 70.424 | 90.600 | 5.728 | 1.00 | 35.95 | N |
| ATOM | 3265 | CD2 | HIS | B | 950 | 71.109 | 91.741 | 5.390 | 1.00 | 33.26 | C |
| ATOM | 3266 | C | HIS | B | 950 | 73.346 | 94.770 | 2.955 | 1.00 | 31.10 | C |
| ATOM | 3267 | O | HIS | B | 950 | 74.433 | 94.911 | 3.518 | 1.00 | 30.52 | O |
| ATOM | 3268 | N | ILE | B | 951 | 73.083 | 95.257 | 1.742 | 1.00 | 30.46 | N |
| ATOM | 3269 | CA | ILE | B | 951 | 74.072 | 96.032 | .991 | 1.00 | 30.57 | C |
| ATOM | 3270 | CB | ILE | B | 951 | 73.660 | 96.235 | −.503 | 1.00 | 31.06 | C |
| ATOM | 3271 | CG1 | ILE | B | 951 | 74.879 | 96.628 | −1.351 | 1.00 | 32.96 | C |
| ATOM | 3272 | CD1 | ILE | B | 951 | 74.757 | 96.286 | −2.831 | 1.00 | 35.71 | C |
| ATOM | 3273 | CG2 | ILE | B | 951 | 72.505 | 97.235 | −.642 | 1.00 | 30.48 | C |
| ATOM | 3274 | C | ILE | B | 951 | 74.401 | 97.359 | 1.687 | 1.00 | 29.50 | C |
| ATOM | 3275 | O | ILE | B | 951 | 75.541 | 97.819 | 1.640 | 1.00 | 30.12 | O |
| ATOM | 3276 | N | LYS | B | 952 | 73.405 | 97.953 | 2.346 | 1.00 | 28.89 | N |
| ATOM | 3277 | CA | LYS | B | 952 | 73.616 | 99.174 | 3.123 | 1.00 | 28.72 | C |
| ATOM | 3278 | CB | LYS | B | 952 | 72.281 | 99.851 | 3.471 | 1.00 | 28.24 | C |
| ATOM | 3279 | CG | LYS | B | 952 | 72.400 | 101.200 | 4.208 | 1.00 | 28.78 | C |
| ATOM | 3280 | CD | LYS | B | 952 | 73.337 | 102.189 | 3.508 | 1.00 | 28.20 | C |
| ATOM | 3281 | CE | LYS | B | 952 | 72.696 | 102.837 | 2.288 | 1.00 | 29.08 | C |
| ATOM | 3282 | NZ | LYS | B | 952 | 71.724 | 103.889 | 2.685 | 1.00 | 31.92 | N |
| ATOM | 3283 | C | LYS | B | 952 | 74.437 | 98.881 | 4.377 | 1.00 | 28.00 | C |
| ATOM | 3284 | O | LYS | B | 952 | 75.314 | 99.667 | 4.744 | 1.00 | 28.59 | O |
| ATOM | 3285 | N | LEU | B | 953 | 74.159 | 97.749 | 5.022 | 1.00 | 27.82 | N |
| ATOM | 3286 | CA | LEU | B | 953 | 74.967 | 97.289 | 6.162 | 1.00 | 28.76 | C |
| ATOM | 3287 | CB | LEU | B | 953 | 74.416 | 95.980 | 6.743 | 1.00 | 28.11 | C |
| ATOM | 3288 | CG | LEU | B | 953 | 73.079 | 95.987 | 7.493 | 1.00 | 27.92 | C |
| ATOM | 3289 | CD1 | LEU | B | 953 | 72.723 | 94.577 | 7.935 | 1.00 | 25.88 | C |
| ATOM | 3290 | CD2 | LEU | B | 953 | 73.104 | 96.925 | 8.689 | 1.00 | 29.56 | C |
| ATOM | 3291 | C | LEU | B | 953 | 76.439 | 97.112 | 5.781 | 1.00 | 28.88 | C |
| ATOM | 3292 | O | LEU | B | 953 | 77.332 | 97.464 | 6.553 | 1.00 | 29.62 | O |
| ATOM | 3293 | N | LEU | B | 954 | 76.681 | 96.576 | 4.586 | 1.00 | 28.96 | N |
| ATOM | 3294 | CA | LEU | B | 954 | 78.043 | 96.382 | 4.090 | 1.00 | 29.35 | C |
| ATOM | 3295 | CB | LEU | B | 954 | 78.073 | 95.406 | 2.911 | 1.00 | 28.40 | C |
| ATOM | 3296 | CG | LEU | B | 954 | 77.743 | 93.933 | 3.173 | 1.00 | 30.67 | C |
| ATOM | 3297 | CD1 | LEU | B | 954 | 77.952 | 93.126 | 1.900 | 1.00 | 29.86 | C |
| ATOM | 3298 | CD2 | LEU | B | 954 | 78.573 | 93.352 | 4.321 | 1.00 | 31.85 | C |
| ATOM | 3299 | C | LEU | B | 954 | 78.714 | 97.697 | 3.710 | 1.00 | 29.38 | C |
| ATOM | 3300 | O | LEU | B | 954 | 79.938 | 97.803 | 3.762 | 1.00 | 29.68 | O |
| ATOM | 3301 | N | GLN | B | 955 | 77.909 | 98.688 | 3.328 | 1.00 | 29.53 | N |
| ATOM | 3302 | CA | GLN | B | 955 | 78.400 | 100.043 | 3.086 | 1.00 | 30.41 | C |
| ATOM | 3303 | CB | GLN | B | 955 | 77.293 | 100.923 | 2.489 | 1.00 | 30.29 | C |
| ATOM | 3304 | CG | GLN | B | 955 | 77.696 | 102.378 | 2.227 | 1.00 | 31.53 | C |
| ATOM | 3305 | CD | GLN | B | 955 | 76.630 | 103.170 | 1.480 | 1.00 | 32.27 | C |
| ATOM | 3306 | OE1 | GLN | B | 955 | 76.307 | 104.298 | 1.851 | 1.00 | 37.26 | O |

APPENDIX 1-continued

| ATOM | 3307 | NE2 | GLN | B | 955 | 76.082 | 102.584 | .420 | 1.00 | 35.79 | N |
|---|---|---|---|---|---|---|---|---|---|---|---|
| ATOM | 3308 | C | GLN | B | 955 | 78.950 | 100.650 | 4.380 | 1.00 | 30.22 | C |
| ATOM | 3309 | O | GLN | B | 955 | 80.040 | 101.227 | 4.384 | 1.00 | 29.40 | O |
| ATOM | 3310 | N | TYR | B | 956 | 78.194 | 100.505 | 5.470 | 1.00 | 30.00 | N |
| ATOM | 3311 | CA | TYR | B | 956 | 78.645 | 100.940 | 6.793 | 1.00 | 30.15 | C |
| ATOM | 3312 | CB | TYR | B | 956 | 77.543 | 100.756 | 7.844 | 1.00 | 29.95 | C |
| ATOM | 3313 | CG | TYR | B | 956 | 76.247 | 101.509 | 7.599 | 1.00 | 30.71 | C |
| ATOM | 3314 | CD1 | TYR | B | 956 | 75.030 | 100.981 | 8.034 | 1.00 | 30.82 | C |
| ATOM | 3315 | CE1 | TYR | B | 956 | 73.832 | 101.663 | 7.828 | 1.00 | 30.62 | C |
| ATOM | 3316 | CZ | TYR | B | 956 | 73.843 | 102.889 | 7.178 | 1.00 | 30.69 | C |
| ATOM | 3317 | OH | TYR | B | 956 | 72.657 | 103.562 | 6.972 | 1.00 | 31.04 | O |
| ATOM | 3318 | CE2 | TYR | B | 956 | 75.037 | 103.437 | 6.735 | 1.00 | 30.42 | C |
| ATOM | 3319 | CD2 | TYR | B | 956 | 76.233 | 102.747 | 6.948 | 1.00 | 29.36 | C |
| ATOM | 3320 | C | TYR | B | 956 | 79.882 | 100.156 | 7.224 | 1.00 | 30.52 | C |
| ATOM | 3321 | O | TYR | B | 956 | 80.839 | 100.731 | 7.746 | 1.00 | 30.82 | O |
| ATOM | 3322 | N | THR | B | 957 | 79.847 | 98.844 | 6.996 | 1.00 | 30.52 | N |
| ATOM | 3323 | CA | THR | B | 957 | 80.950 | 97.939 | 7.333 | 1.00 | 31.03 | C |
| ATOM | 3324 | CB | THR | B | 957 | 80.606 | 96.487 | 6.950 | 1.00 | 30.67 | C |
| ATOM | 3325 | OG1 | THR | B | 957 | 79.397 | 96.096 | 7.610 | 1.00 | 30.36 | O |
| ATOM | 3326 | CG2 | THR | B | 957 | 81.721 | 95.526 | 7.350 | 1.00 | 30.15 | C |
| ATOM | 3327 | C | THR | B | 957 | 82.257 | 98.371 | 6.666 | 1.00 | 31.50 | C |
| ATOM | 3328 | O | THR | B | 957 | 83.298 | 98.451 | 7.324 | 1.00 | 31.28 | O |
| ATOM | 3329 | N | SER | B | 958 | 82.182 | 98.660 | 5.367 | 1.00 | 32.00 | N |
| ATOM | 3330 | CA | SER | B | 958 | 83.324 | 99.135 | 4.588 | 1.00 | 31.80 | C |
| ATOM | 3331 | CB | SER | B | 958 | 82.918 | 99.342 | 3.127 | 1.00 | 32.15 | C |
| ATOM | 3332 | OG | SER | B | 958 | 84.047 | 99.658 | 2.329 | 1.00 | 33.47 | O |
| ATOM | 3333 | C | SER | B | 958 | 83.917 | 100.427 | 5.156 | 1.00 | 31.65 | C |
| ATOM | 3334 | O | SER | B | 958 | 85.137 | 100.566 | 5.261 | 1.00 | 31.74 | O |
| ATOM | 3335 | N | GLN | B | 959 | 83.047 | 101.364 | 5.523 | 1.00 | 30.74 | N |
| ATOM | 3336 | CA | GLN | B | 959 | 83.466 | 102.622 | 6.131 | 1.00 | 30.94 | C |
| ATOM | 3337 | CB | GLN | B | 959 | 82.271 | 103.560 | 6.291 | 1.00 | 30.81 | C |
| ATOM | 3338 | CG | GLN | B | 959 | 81.749 | 104.089 | 4.962 | 1.00 | 33.55 | C |
| ATOM | 3339 | CD | GLN | B | 959 | 80.396 | 104.752 | 5.073 | 1.00 | 33.99 | C |
| ATOM | 3340 | OE1 | GLN | B | 959 | 79.863 | 104.928 | 6.169 | 1.00 | 35.78 | O |
| ATOM | 3341 | NE2 | GLN | B | 959 | 79.828 | 105.125 | 3.931 | 1.00 | 32.27 | N |
| ATOM | 3342 | C | GLN | B | 959 | 84.183 | 102.418 | 7.468 | 1.00 | 30.63 | C |
| ATOM | 3343 | O | GLN | B | 959 | 85.186 | 103.083 | 7.741 | 1.00 | 30.40 | O |
| ATOM | 3344 | N | ILE | B | 960 | 83.671 | 101.494 | 8.283 | 1.00 | 30.32 | N |
| ATOM | 3345 | CA | ILE | B | 960 | 84.305 | 101.119 | 9.552 | 1.00 | 31.44 | C |
| ATOM | 3346 | CB | ILE | B | 960 | 83.431 | 100.115 | 10.374 | 1.00 | 31.51 | C |
| ATOM | 3347 | CG1 | ILE | B | 960 | 82.053 | 100.709 | 10.719 | 1.00 | 32.52 | C |
| ATOM | 3348 | CD1 | ILE | B | 960 | 82.093 | 102.043 | 11.443 | 1.00 | 39.33 | C |
| ATOM | 3349 | CG2 | ILE | B | 960 | 84.162 | 99.641 | 11.642 | 1.00 | 28.67 | C |
| ATOM | 3350 | C | ILE | B | 960 | 85.696 | 100.523 | 9.305 | 1.00 | 31.86 | C |
| ATOM | 3351 | O | ILE | B | 960 | 86.670 | 100.912 | 9.956 | 1.00 | 31.47 | O |
| ATOM | 3352 | N | CYS | B | 961 | 85.782 | 99.586 | 8.362 | 1.00 | 32.41 | N |
| ATOM | 3353 | CA | CYS | B | 961 | 87.063 | 98.988 | 7.976 | 1.00 | 33.96 | C |
| ATOM | 3354 | CB | CYS | B | 961 | 86.880 | 97.999 | 6.827 | 1.00 | 34.63 | C |
| ATOM | 3355 | SG | CYS | B | 961 | 86.221 | 96.424 | 7.338 | 1.00 | 41.29 | S |
| ATOM | 3356 | C | CYS | B | 961 | 88.096 | 100.035 | 7.577 | 1.00 | 33.24 | C |
| ATOM | 3357 | O | CYS | B | 961 | 89.249 | 99.969 | 8.009 | 1.00 | 33.54 | O |
| ATOM | 3358 | N | LYS | B | 962 | 87.672 | 100.994 | 6.758 | 1.00 | 32.86 | N |
| ATOM | 3359 | CA | LYS | B | 962 | 88.562 | 102.033 | 6.242 | 1.00 | 33.32 | C |
| ATOM | 3360 | CB | LYS | B | 962 | 87.905 | 102.774 | 5.073 | 1.00 | 33.82 | C |
| ATOM | 3361 | CG | LYS | B | 962 | 87.890 | 101.944 | 3.794 | 1.00 | 38.06 | C |
| ATOM | 3362 | CD | LYS | B | 962 | 86.944 | 102.501 | 2.744 | 1.00 | 43.69 | C |
| ATOM | 3363 | CE | LYS | B | 962 | 86.814 | 101.525 | 1.575 | 1.00 | 46.04 | C |
| ATOM | 3364 | NZ | LYS | B | 962 | 85.853 | 101.989 | .539 | 1.00 | 47.92 | N |
| ATOM | 3365 | C | LYS | B | 962 | 89.028 | 102.997 | 7.328 | 1.00 | 32.09 | C |
| ATOM | 3366 | O | LYS | B | 962 | 90.172 | 103.452 | 7.308 | 1.00 | 31.85 | O |
| ATOM | 3367 | N | GLY | B | 963 | 88.140 | 103.297 | 8.274 | 1.00 | 31.13 | N |
| ATOM | 3368 | CA | GLY | B | 963 | 88.500 | 104.091 | 9.449 | 1.00 | 30.17 | C |
| ATOM | 3369 | C | GLY | B | 963 | 89.527 | 103.364 | 10.298 | 1.00 | 29.29 | C |
| ATOM | 3370 | O | GLY | B | 963 | 90.491 | 103.966 | 10.771 | 1.00 | 29.24 | O |
| ATOM | 3371 | N | MET | B | 964 | 89.316 | 102.061 | 10.474 | 1.00 | 29.17 | N |
| ATOM | 3372 | CA | MET | B | 964 | 90.212 | 101.207 | 11.255 | 1.00 | 29.44 | C |
| ATOM | 3373 | CB | MET | B | 964 | 89.539 | 99.873 | 11.576 | 1.00 | 28.99 | C |
| ATOM | 3374 | CG | MET | B | 964 | 88.466 | 99.953 | 12.662 | 1.00 | 29.20 | C |
| ATOM | 3375 | SD | MET | B | 964 | 89.030 | 100.779 | 14.168 | 1.00 | 30.35 | S |
| ATOM | 3376 | CE | MET | B | 964 | 90.292 | 99.650 | 14.755 | 1.00 | 31.85 | C |
| ATOM | 3377 | C | MET | B | 964 | 91.559 | 100.970 | 10.572 | 1.00 | 30.17 | C |
| ATOM | 3378 | O | MET | B | 964 | 92.587 | 100.855 | 11.239 | 1.00 | 30.50 | O |
| ATOM | 3379 | N | GLU | B | 965 | 91.540 | 100.895 | 9.244 | 1.00 | 31.13 | N |
| ATOM | 3380 | CA | GLU | B | 965 | 92.758 | 100.785 | 8.449 | 1.00 | 32.20 | C |
| ATOM | 3381 | CB | GLU | B | 965 | 92.401 | 100.634 | 6.969 | 1.00 | 32.20 | C |
| ATOM | 3382 | CG | GLU | B | 965 | 93.476 | 99.961 | 6.126 | 1.00 | 36.13 | C |
| ATOM | 3383 | CD | GLU | B | 965 | 93.126 | 99.908 | 4.645 | 1.00 | 34.81 | C |
| ATOM | 3384 | OE1 | GLU | B | 965 | 91.921 | 99.883 | 4.303 | 1.00 | 39.59 | O |
| ATOM | 3385 | OE2 | GLU | B | 965 | 94.064 | 99.885 | 3.820 | 1.00 | 41.04 | O |

APPENDIX 1-continued

| | | | | | | | | | | | |
|---|---|---|---|---|---|---|---|---|---|---|---|
| ATOM | 3386 | C | GLU | B | 965 | 93.624 | 102.026 | 8.674 | 1.00 | 31.35 | C |
| ATOM | 3387 | O | GLU | B | 965 | 94.842 | 101.927 | 8.834 | 1.00 | 31.14 | O |
| ATOM | 3388 | N | TYR | B | 966 | 92.970 | 103.186 | 8.708 | 1.00 | 30.89 | N |
| ATOM | 3389 | CA | TYR | B | 966 | 93.619 | 104.471 | 8.959 | 1.00 | 30.78 | C |
| ATOM | 3390 | CB | TYR | B | 966 | 92.628 | 105.610 | 8.700 | 1.00 | 31.05 | C |
| ATOM | 3391 | CG | TYR | B | 966 | 93.152 | 106.998 | 8.991 | 1.00 | 32.37 | C |
| ATOM | 3392 | CD1 | TYR | B | 966 | 94.146 | 107.577 | 8.198 | 1.00 | 32.94 | C |
| ATOM | 3393 | CE1 | TYR | B | 966 | 94.622 | 108.855 | 8.464 | 1.00 | 34.12 | C |
| ATOM | 3394 | CZ | TYR | B | 966 | 94.094 | 109.571 | 9.530 | 1.00 | 34.30 | C |
| ATOM | 3395 | OH | TYR | B | 966 | 94.549 | 110.839 | 9.808 | 1.00 | 33.28 | O |
| ATOM | 3396 | CE2 | TYR | B | 966 | 93.104 | 109.018 | 10.320 | 1.00 | 33.66 | C |
| ATOM | 3397 | CD2 | TYR | B | 966 | 92.641 | 107.741 | 10.049 | 1.00 | 32.59 | C |
| ATOM | 3398 | C | TYR | B | 966 | 94.222 | 104.569 | 10.368 | 1.00 | 30.95 | C |
| ATOM | 3399 | O | TYR | B | 966 | 95.313 | 105.115 | 10.536 | 1.00 | 30.01 | O |
| ATOM | 3400 | N | LEU | B | 967 | 93.512 | 104.042 | 11.369 | 1.00 | 31.29 | N |
| ATOM | 3401 | CA | LEU | B | 967 | 94.039 | 103.947 | 12.735 | 1.00 | 32.32 | C |
| ATOM | 3402 | CB | LEU | B | 967 | 93.017 | 103.299 | 13.683 | 1.00 | 32.60 | C |
| ATOM | 3403 | CG | LEU | B | 967 | 91.949 | 104.133 | 14.399 | 1.00 | 34.00 | C |
| ATOM | 3404 | CD1 | LEU | B | 967 | 91.353 | 103.329 | 15.540 | 1.00 | 33.60 | C |
| ATOM | 3405 | CD2 | LEU | B | 967 | 92.516 | 105.423 | 14.944 | 1.00 | 36.16 | C |
| ATOM | 3406 | C | LEU | B | 967 | 95.344 | 103.149 | 12.783 | 1.00 | 32.49 | C |
| ATOM | 3407 | O | LEU | B | 967 | 96.286 | 103.527 | 13.478 | 1.00 | 31.31 | O |
| ATOM | 3408 | N | GLY | B | 968 | 95.380 | 102.045 | 12.038 | 1.00 | 33.59 | N |
| ATOM | 3409 | CA | GLY | B | 968 | 96.550 | 101.173 | 11.961 | 1.00 | 34.30 | C |
| ATOM | 3410 | C | GLY | B | 968 | 97.809 | 101.844 | 11.441 | 1.00 | 35.25 | C |
| ATOM | 3411 | O | GLY | B | 968 | 98.912 | 101.507 | 11.874 | 1.00 | 36.00 | O |
| ATOM | 3412 | N | THR | B | 969 | 97.646 | 102.791 | 10.515 | 1.00 | 35.49 | N |
| ATOM | 3413 | CA | THR | B | 969 | 98.778 | 103.550 | 9.967 | 1.00 | 35.98 | C |
| ATOM | 3414 | CB | THR | B | 969 | 98.389 | 104.375 | 8.711 | 1.00 | 36.12 | C |
| ATOM | 3415 | OG1 | THR | B | 969 | 97.463 | 105.409 | 9.069 | 1.00 | 35.56 | O |
| ATOM | 3416 | CG2 | THR | B | 969 | 97.774 | 103.487 | 7.636 | 1.00 | 36.35 | C |
| ATOM | 3417 | C | THR | B | 969 | 99.388 | 104.482 | 11.018 | 1.00 | 36.30 | C |
| ATOM | 3418 | O | THR | B | 969 | 100.553 | 104.874 | 10.913 | 1.00 | 36.64 | O |
| ATOM | 3419 | N | LYS | B | 970 | 98.586 | 104.826 | 12.025 | 1.00 | 35.92 | N |
| ATOM | 3420 | CA | LYS | B | 970 | 99.030 | 105.640 | 13.154 | 1.00 | 35.97 | C |
| ATOM | 3421 | CB | LYS | B | 970 | 97.896 | 106.556 | 13.629 | 1.00 | 36.26 | C |
| ATOM | 3422 | CG | LYS | B | 970 | 97.272 | 107.440 | 12.554 | 1.00 | 39.31 | C |
| ATOM | 3423 | CD | LYS | B | 970 | 97.939 | 108.801 | 12.477 | 1.00 | 44.16 | C |
| ATOM | 3424 | CE | LYS | B | 970 | 97.229 | 109.696 | 11.474 | 1.00 | 45.78 | C |
| ATOM | 3425 | NZ | LYS | B | 970 | 97.825 | 111.059 | 11.412 | 1.00 | 48.93 | N |
| ATOM | 3426 | C | LYS | B | 970 | 99.486 | 104.750 | 14.314 | 1.00 | 35.16 | C |
| ATOM | 3427 | O | LYS | B | 970 | 99.939 | 105.250 | 15.347 | 1.00 | 35.24 | O |
| ATOM | 3428 | N | ARG | B | 971 | 99.361 | 103.436 | 14.127 | 1.00 | 34.49 | N |
| ATOM | 3429 | CA | ARG | B | 971 | 99.644 | 102.429 | 15.160 | 1.00 | 34.18 | C |
| ATOM | 3430 | CB | ARG | B | 971 | 101.144 | 102.369 | 15.508 | 1.00 | 34.67 | C |
| ATOM | 3431 | CG | ARG | B | 971 | 102.060 | 102.265 | 14.287 | 1.00 | 35.05 | C |
| ATOM | 3432 | CD | ARG | B | 971 | 103.472 | 101.827 | 14.647 | 1.00 | 36.00 | C |
| ATOM | 3433 | NE | ARG | B | 971 | 103.595 | 100.370 | 14.695 | 1.00 | 41.05 | N |
| ATOM | 3434 | CZ | ARG | B | 971 | 103.978 | 99.673 | 15.760 | 1.00 | 42.09 | C |
| ATOM | 3435 | NH1 | ARG | B | 971 | 104.301 | 100.289 | 16.891 | 1.00 | 43.11 | N |
| ATOM | 3436 | NH2 | ARG | B | 971 | 104.050 | 98.352 | 15.689 | 1.00 | 44.43 | N |
| ATOM | 3437 | C | ARG | B | 971 | 98.768 | 102.605 | 16.412 | 1.00 | 33.56 | C |
| ATOM | 3438 | O | ARG | B | 971 | 99.210 | 102.354 | 17.537 | 1.00 | 32.82 | O |
| ATOM | 3439 | N | TYR | B | 972 | 97.526 | 103.042 | 16.195 | 1.00 | 32.33 | N |
| ATOM | 3440 | CA | TYR | B | 972 | 96.535 | 103.165 | 17.262 | 1.00 | 31.84 | C |
| ATOM | 3441 | CB | TYR | B | 972 | 95.579 | 104.341 | 17.020 | 1.00 | 31.56 | C |
| ATOM | 3442 | CG | TYR | B | 972 | 96.197 | 105.725 | 17.041 | 1.00 | 33.31 | C |
| ATOM | 3443 | CD1 | TYR | B | 972 | 95.569 | 106.791 | 16.395 | 1.00 | 33.20 | C |
| ATOM | 3444 | CE1 | TYR | B | 972 | 96.117 | 108.066 | 16.409 | 1.00 | 32.92 | C |
| ATOM | 3445 | CZ | TYR | B | 972 | 97.310 | 108.287 | 17.072 | 1.00 | 33.16 | C |
| ATOM | 3446 | OH | TYR | B | 972 | 97.860 | 109.545 | 17.088 | 1.00 | 32.99 | O |
| ATOM | 3447 | CE2 | TYR | B | 972 | 97.954 | 107.251 | 17.721 | 1.00 | 33.82 | C |
| ATOM | 3448 | CD2 | TYR | B | 972 | 97.397 | 105.978 | 17.706 | 1.00 | 32.81 | C |
| ATOM | 3449 | C | TYR | B | 972 | 95.713 | 101.889 | 17.375 | 1.00 | 31.22 | C |
| ATOM | 3450 | O | TYR | B | 972 | 95.314 | 101.302 | 16.365 | 1.00 | 31.10 | O |
| ATOM | 3451 | N | ILE | B | 973 | 95.460 | 101.472 | 18.611 | 1.00 | 30.19 | N |
| ATOM | 3452 | CA | ILE | B | 973 | 94.583 | 100.342 | 18.891 | 1.00 | 30.08 | C |
| ATOM | 3453 | CB | ILE | B | 973 | 95.262 | 99.302 | 19.821 | 1.00 | 30.27 | C |
| ATOM | 3454 | CG1 | ILE | B | 973 | 96.670 | 98.942 | 19.324 | 1.00 | 32.49 | C |
| ATOM | 3455 | CD1 | ILE | B | 973 | 96.750 | 98.420 | 17.893 | 1.00 | 31.88 | C |
| ATOM | 3456 | CG2 | ILE | B | 973 | 94.382 | 98.064 | 19.997 | 1.00 | 31.98 | C |
| ATOM | 3457 | C | ILE | B | 973 | 93.332 | 100.893 | 19.565 | 1.00 | 29.64 | C |
| ATOM | 3458 | O | ILE | B | 973 | 93.418 | 101.495 | 20.638 | 1.00 | 29.10 | O |
| ATOM | 3459 | N | HIS | B | 974 | 92.177 | 100.693 | 18.933 | 1.00 | 29.62 | N |
| ATOM | 3460 | CA | HIS | B | 974 | 90.925 | 101.273 | 19.424 | 1.00 | 29.69 | C |
| ATOM | 3461 | CB | HIS | B | 974 | 89.809 | 101.151 | 18.386 | 1.00 | 29.31 | C |
| ATOM | 3462 | CG | HIS | B | 974 | 88.613 | 101.995 | 18.698 | 1.00 | 29.91 | C |
| ATOM | 3463 | ND1 | HIS | B | 974 | 87.598 | 101.570 | 19.527 | 1.00 | 28.60 | N |
| ATOM | 3464 | CE1 | HIS | B | 974 | 86.688 | 102.523 | 19.628 | 1.00 | 32.65 | C |

APPENDIX 1-continued

| ATOM | 3465 | NE2 | HIS | B | 974 | 87.079 | 103.552 | 18.898 | 1.00 | 31.27 | N |
|------|------|-----|-----|---|-----|--------|---------|--------|------|-------|---|
| ATOM | 3466 | CD2 | HIS | B | 974 | 88.283 | 103.249 | 18.309 | 1.00 | 30.37 | C |
| ATOM | 3467 | C | HIS | B | 974 | 90.477 | 100.684 | 20.760 | 1.00 | 30.10 | C |
| ATOM | 3468 | O | HIS | B | 974 | 90.075 | 101.425 | 21.662 | 1.00 | 30.69 | O |
| ATOM | 3469 | N | ARG | B | 975 | 90.537 | 99.356 | 20.869 | 1.00 | 30.30 | N |
| ATOM | 3470 | CA | ARG | B | 975 | 90.237 | 98.630 | 22.113 | 1.00 | 31.90 | C |
| ATOM | 3471 | CB | ARG | B | 975 | 91.090 | 99.158 | 23.277 | 1.00 | 31.59 | C |
| ATOM | 3472 | CG | ARG | B | 975 | 92.586 | 98.911 | 23.142 | 1.00 | 32.97 | C |
| ATOM | 3473 | CD | ARG | B | 975 | 93.332 | 99.220 | 24.435 | 1.00 | 33.10 | C |
| ATOM | 3474 | NE | ARG | B | 975 | 92.706 | 98.585 | 25.593 | 1.00 | 41.88 | N |
| ATOM | 3475 | CZ | ARG | B | 975 | 92.171 | 99.237 | 26.622 | 1.00 | 42.04 | C |
| ATOM | 3476 | NH1 | ARG | B | 975 | 92.194 | 100.562 | 26.670 | 1.00 | 44.32 | N |
| ATOM | 3477 | NH2 | ARG | B | 975 | 91.621 | 98.557 | 27.615 | 1.00 | 45.03 | N |
| ATOM | 3478 | C | ARG | B | 975 | 88.760 | 98.606 | 22.535 | 1.00 | 32.22 | C |
| ATOM | 3479 | O | ARG | B | 975 | 88.413 | 97.946 | 23.518 | 1.00 | 33.60 | O |
| ATOM | 3480 | N | ASP | B | 976 | 87.896 | 99.311 | 21.806 | 1.00 | 31.22 | N |
| ATOM | 3481 | CA | ASP | B | 976 | 86.495 | 99.463 | 22.216 | 1.00 | 31.15 | C |
| ATOM | 3482 | CB | ASP | B | 976 | 86.345 | 100.691 | 23.130 | 1.00 | 30.65 | C |
| ATOM | 3483 | CG | ASP | B | 976 | 85.071 | 100.659 | 23.974 | 1.00 | 33.97 | C |
| ATOM | 3484 | OD1 | ASP | B | 976 | 84.509 | 99.565 | 24.205 | 1.00 | 37.14 | O |
| ATOM | 3485 | OD2 | ASP | B | 976 | 84.632 | 101.740 | 24.415 | 1.00 | 35.29 | O |
| ATOM | 3486 | C | ASP | B | 976 | 85.542 | 99.568 | 21.020 | 1.00 | 31.12 | C |
| ATOM | 3487 | O | ASP | B | 976 | 84.616 | 100.389 | 21.023 | 1.00 | 30.34 | O |
| ATOM | 3488 | N | LEU | B | 977 | 85.777 | 98.745 | 20.000 | 1.00 | 30.23 | N |
| ATOM | 3489 | CA | LEU | B | 977 | 84.904 | 98.712 | 18.828 | 1.00 | 30.81 | C |
| ATOM | 3490 | CB | LEU | B | 977 | 85.574 | 98.011 | 17.640 | 1.00 | 31.62 | C |
| ATOM | 3491 | CG | LEU | B | 977 | 86.459 | 98.814 | 16.682 | 1.00 | 33.65 | C |
| ATOM | 3492 | CD1 | LEU | B | 977 | 86.973 | 97.891 | 15.585 | 1.00 | 32.02 | C |
| ATOM | 3493 | CD2 | LEU | B | 977 | 85.713 | 99.997 | 16.069 | 1.00 | 34.51 | C |
| ATOM | 3494 | C | LEU | B | 977 | 83.581 | 98.034 | 19.156 | 1.00 | 30.44 | C |
| ATOM | 3495 | O | LEU | B | 977 | 83.551 | 96.889 | 19.610 | 1.00 | 30.65 | O |
| ATOM | 3496 | N | ALA | B | 978 | 82.500 | 98.775 | 18.933 | 1.00 | 29.25 | N |
| ATOM | 3497 | CA | ALA | B | 978 | 81.126 | 98.328 | 19.157 | 1.00 | 28.96 | C |
| ATOM | 3498 | CB | ALA | B | 978 | 80.812 | 98.255 | 20.651 | 1.00 | 28.80 | C |
| ATOM | 3499 | C | ALA | B | 978 | 80.235 | 99.350 | 18.470 | 1.00 | 27.78 | C |
| ATOM | 3500 | O | ALA | B | 978 | 80.657 | 100.489 | 18.259 | 1.00 | 27.47 | O |
| ATOM | 3501 | N | THR | B | 979 | 79.014 | 98.956 | 18.115 | 1.00 | 28.15 | N |
| ATOM | 3502 | CA | THR | B | 979 | 78.093 | 99.859 | 17.412 | 1.00 | 28.37 | C |
| ATOM | 3503 | CB | THR | B | 979 | 76.822 | 99.144 | 16.883 | 1.00 | 28.79 | C |
| ATOM | 3504 | OG1 | THR | B | 979 | 76.081 | 98.583 | 17.977 | 1.00 | 28.46 | O |
| ATOM | 3505 | CG2 | THR | B | 979 | 77.187 | 98.053 | 15.883 | 1.00 | 28.40 | C |
| ATOM | 3506 | C | THR | B | 979 | 77.686 | 101.062 | 18.263 | 1.00 | 28.60 | C |
| ATOM | 3507 | O | THR | B | 979 | 77.326 | 102.109 | 17.724 | 1.00 | 29.33 | O |
| ATOM | 3508 | N | ARG | B | 980 | 77.761 | 100.919 | 19.586 | 1.00 | 28.59 | N |
| ATOM | 3509 | CA | ARG | B | 980 | 77.471 | 102.036 | 20.488 | 1.00 | 29.31 | C |
| ATOM | 3510 | CB | ARG | B | 980 | 77.293 | 101.557 | 21.935 | 1.00 | 30.63 | C |
| ATOM | 3511 | CG | ARG | B | 980 | 78.549 | 101.043 | 22.633 | 1.00 | 33.73 | C |
| ATOM | 3512 | CD | ARG | B | 980 | 78.351 | 101.042 | 24.150 | 1.00 | 42.09 | C |
| ATOM | 3513 | NE | ARG | B | 980 | 77.236 | 100.185 | 24.558 | 1.00 | 48.81 | N |
| ATOM | 3514 | CZ | ARG | B | 980 | 76.431 | 100.420 | 25.594 | 1.00 | 52.44 | C |
| ATOM | 3515 | NH1 | ARG | B | 980 | 76.593 | 101.500 | 26.350 | 1.00 | 52.36 | N |
| ATOM | 3516 | NH2 | ARG | B | 980 | 75.450 | 99.570 | 25.871 | 1.00 | 52.80 | N |
| ATOM | 3517 | C | ARG | B | 980 | 78.520 | 103.151 | 20.402 | 1.00 | 28.63 | C |
| ATOM | 3518 | O | ARG | B | 980 | 78.258 | 104.285 | 20.795 | 1.00 | 28.22 | O |
| ATOM | 3519 | N | ASN | B | 981 | 79.698 | 102.822 | 19.875 | 1.00 | 28.75 | N |
| ATOM | 3520 | CA | ASN | B | 981 | 80.787 | 103.790 | 19.727 | 1.00 | 28.33 | C |
| ATOM | 3521 | CB | ASN | B | 981 | 82.102 | 103.188 | 20.232 | 1.00 | 28.70 | C |
| ATOM | 3522 | CG | ASN | B | 981 | 82.105 | 102.992 | 21.730 | 1.00 | 30.50 | C |
| ATOM | 3523 | OD1 | ASN | B | 981 | 81.583 | 103.824 | 22.475 | 1.00 | 30.46 | O |
| ATOM | 3524 | ND2 | ASN | B | 981 | 82.679 | 101.887 | 22.184 | 1.00 | 30.47 | N |
| ATOM | 3525 | C | ASN | B | 981 | 80.935 | 104.294 | 18.299 | 1.00 | 28.41 | C |
| ATOM | 3526 | O | ASN | B | 981 | 81.839 | 105.076 | 17.990 | 1.00 | 28.77 | O |
| ATOM | 3527 | N | ILE | B | 982 | 80.034 | 103.838 | 17.435 | 1.00 | 28.42 | N |
| ATOM | 3528 | CA | ILE | B | 982 | 79.985 | 104.279 | 16.049 | 1.00 | 28.94 | C |
| ATOM | 3529 | CB | ILE | B | 982 | 79.837 | 103.081 | 15.078 | 1.00 | 28.89 | C |
| ATOM | 3530 | CG1 | ILE | B | 982 | 81.078 | 102.180 | 15.152 | 1.00 | 29.07 | C |
| ATOM | 3531 | CD1 | ILE | B | 982 | 80.825 | 100.738 | 14.748 | 1.00 | 35.33 | C |
| ATOM | 3532 | CG2 | ILE | B | 982 | 79.612 | 103.568 | 13.647 | 1.00 | 28.60 | C |
| ATOM | 3533 | C | ILE | B | 982 | 78.822 | 105.252 | 15.892 | 1.00 | 29.04 | C |
| ATOM | 3534 | O | ILE | B | 982 | 77.712 | 104.976 | 16.345 | 1.00 | 29.35 | O |
| ATOM | 3535 | N | LEU | B | 983 | 79.088 | 106.391 | 15.258 | 1.00 | 28.51 | N |
| ATOM | 3536 | CA | LEU | B | 983 | 78.082 | 107.431 | 15.073 | 1.00 | 28.47 | C |
| ATOM | 3537 | CB | LEU | B | 983 | 78.626 | 108.789 | 15.522 | 1.00 | 28.05 | C |
| ATOM | 3538 | CG | LEU | B | 983 | 79.073 | 108.943 | 16.982 | 1.00 | 28.53 | C |
| ATOM | 3539 | CD1 | LEU | B | 983 | 79.804 | 110.265 | 17.165 | 1.00 | 27.00 | C |
| ATOM | 3540 | CD2 | LEU | B | 983 | 77.895 | 108.833 | 17.948 | 1.00 | 29.26 | C |
| ATOM | 3541 | C | LEU | B | 983 | 77.611 | 107.505 | 13.623 | 1.00 | 29.11 | C |
| ATOM | 3542 | O | LEU | B | 983 | 78.321 | 107.087 | 12.708 | 1.00 | 28.96 | O |
| ATOM | 3543 | N | VAL | B | 984 | 76.414 | 108.049 | 13.429 | 1.00 | 29.27 | N |

APPENDIX 1-continued

| ATOM | 3544 | CA | VAL | B | 984 | 75.807 | 108.156 | 12.107 | 1.00 | 29.79 | C |
| ATOM | 3545 | CB | VAL | B | 984 | 74.363 | 107.585 | 12.111 | 1.00 | 29.65 | C |
| ATOM | 3546 | CG1 | VAL | B | 984 | 73.723 | 107.714 | 10.739 | 1.00 | 29.83 | C |
| ATOM | 3547 | CG2 | VAL | B | 984 | 74.361 | 106.131 | 12.561 | 1.00 | 29.26 | C |
| ATOM | 3548 | C | VAL | B | 984 | 75.782 | 109.618 | 11.660 | 1.00 | 31.00 | C |
| ATOM | 3549 | O | VAL | B | 984 | 75.150 | 110.453 | 12.310 | 1.00 | 31.26 | O |
| ATOM | 3550 | N | GLU | B | 985 | 76.475 | 109.928 | 10.564 | 1.00 | 31.24 | N |
| ATOM | 3551 | CA | GLU | B | 985 | 76.400 | 111.272 | 9.983 | 1.00 | 33.33 | C |
| ATOM | 3552 | CB | GLU | B | 985 | 77.646 | 111.620 | 9.163 | 1.00 | 33.19 | C |
| ATOM | 3553 | CG | GLU | B | 985 | 77.624 | 113.058 | 8.626 | 1.00 | 34.19 | C |
| ATOM | 3554 | CD | GLU | B | 985 | 78.926 | 113.495 | 7.984 | 1.00 | 36.81 | C |
| ATOM | 3555 | OE1 | GLU | B | 985 | 79.644 | 112.644 | 7.420 | 1.00 | 43.53 | O |
| ATOM | 3556 | OE2 | GLU | B | 985 | 79.229 | 114.707 | 8.035 | 1.00 | 42.79 | O |
| ATOM | 3557 | C | GLU | B | 985 | 75.136 | 111.422 | 9.138 | 1.00 | 33.29 | C |
| ATOM | 3558 | O | GLU | B | 985 | 74.469 | 112.458 | 9.181 | 1.00 | 33.43 | O |
| ATOM | 3559 | N | ASN | B | 986 | 74.830 | 110.382 | 8.365 | 1.00 | 33.33 | N |
| ATOM | 3560 | CA | ASN | B | 986 | 73.567 | 110.267 | 7.637 | 1.00 | 33.90 | C |
| ATOM | 3561 | CB | ASN | B | 986 | 73.515 | 111.230 | 6.437 | 1.00 | 33.38 | C |
| ATOM | 3562 | CG | ASN | B | 986 | 74.676 | 111.042 | 5.473 | 1.00 | 36.04 | C |
| ATOM | 3563 | OD1 | ASN | B | 986 | 74.940 | 109.936 | 5.000 | 1.00 | 35.94 | O |
| ATOM | 3564 | ND2 | ASN | B | 986 | 75.370 | 112.134 | 5.165 | 1.00 | 36.24 | N |
| ATOM | 3565 | C | ASN | B | 986 | 73.323 | 108.817 | 7.212 | 1.00 | 33.95 | C |
| ATOM | 3566 | O | ASN | B | 986 | 74.120 | 107.929 | 7.533 | 1.00 | 33.40 | O |
| ATOM | 3567 | N | GLU | B | 987 | 72.231 | 108.588 | 6.484 | 1.00 | 34.13 | N |
| ATOM | 3568 | CA | GLU | B | 987 | 71.852 | 107.250 | 6.023 | 1.00 | 34.77 | C |
| ATOM | 3569 | CB | GLU | B | 987 | 70.543 | 107.307 | 5.219 | 1.00 | 34.29 | C |
| ATOM | 3570 | CG | GLU | B | 987 | 70.643 | 108.053 | 3.892 | 1.00 | 36.75 | C |
| ATOM | 3571 | CD | GLU | B | 987 | 69.291 | 108.279 | 3.240 | 1.00 | 37.39 | C |
| ATOM | 3572 | OE1 | GLU | B | 987 | 68.633 | 107.285 | 2.863 | 1.00 | 41.05 | O |
| ATOM | 3573 | OE2 | GLU | B | 987 | 68.891 | 109.455 | 3.099 | 1.00 | 43.66 | O |
| ATOM | 3574 | C | GLU | B | 987 | 72.945 | 106.555 | 5.207 | 1.00 | 33.65 | C |
| ATOM | 3575 | O | GLU | B | 987 | 72.921 | 105.336 | 5.047 | 1.00 | 34.40 | O |
| ATOM | 3576 | N | ASN | B | 988 | 73.898 | 107.335 | 4.702 | 1.00 | 33.10 | N |
| ATOM | 3577 | CA | ASN | B | 988 | 74.965 | 106.807 | 3.858 | 1.00 | 33.07 | C |
| ATOM | 3578 | CB | ASN | B | 988 | 75.014 | 107.578 | 2.535 | 1.00 | 32.71 | C |
| ATOM | 3579 | CG | ASN | B | 988 | 73.866 | 107.228 | 1.611 | 1.00 | 30.97 | C |
| ATOM | 3580 | OD1 | ASN | B | 988 | 73.568 | 106.055 | 1.391 | 1.00 | 32.34 | O |
| ATOM | 3581 | ND2 | ASN | B | 988 | 73.217 | 108.247 | 1.057 | 1.00 | 29.98 | N |
| ATOM | 3582 | C | ASN | B | 988 | 76.359 | 106.786 | 4.491 | 1.00 | 33.30 | C |
| ATOM | 3583 | O | ASN | B | 988 | 77.282 | 106.201 | 3.921 | 1.00 | 34.04 | O |
| ATOM | 3584 | N | ARG | B | 989 | 76.516 | 107.420 | 5.654 | 1.00 | 32.63 | N |
| ATOM | 3585 | CA | ARG | B | 989 | 77.840 | 107.565 | 6.264 | 1.00 | 33.03 | C |
| ATOM | 3586 | CB | ARG | B | 989 | 78.467 | 108.912 | 5.888 | 1.00 | 32.50 | C |
| ATOM | 3587 | CG | ARG | B | 989 | 79.958 | 109.009 | 6.211 | 1.00 | 35.41 | C |
| ATOM | 3588 | CD | ARG | B | 989 | 80.596 | 110.292 | 5.686 | 1.00 | 36.47 | C |
| ATOM | 3589 | NE | ARG | B | 989 | 80.380 | 110.480 | 4.252 | 1.00 | 46.69 | N |
| ATOM | 3590 | CZ | ARG | B | 989 | 79.567 | 111.391 | 3.718 | 1.00 | 49.87 | C |
| ATOM | 3591 | NH1 | ARG | B | 989 | 78.883 | 112.230 | 4.491 | 1.00 | 51.00 | N |
| ATOM | 3592 | NH2 | ARG | B | 989 | 79.443 | 111.467 | 2.400 | 1.00 | 52.33 | N |
| ATOM | 3593 | C | ARG | B | 989 | 77.866 | 107.388 | 7.781 | 1.00 | 31.63 | C |
| ATOM | 3594 | O | ARG | B | 989 | 77.124 | 108.047 | 8.515 | 1.00 | 30.43 | O |
| ATOM | 3595 | N | VAL | B | 990 | 78.746 | 106.498 | 8.233 | 1.00 | 31.29 | N |
| ATOM | 3596 | CA | VAL | B | 990 | 79.012 | 106.314 | 9.660 | 1.00 | 30.36 | C |
| ATOM | 3597 | CB | VAL | B | 990 | 78.780 | 104.844 | 10.119 | 1.00 | 30.35 | C |
| ATOM | 3598 | CG1 | VAL | B | 990 | 77.318 | 104.450 | 9.956 | 1.00 | 29.27 | C |
| ATOM | 3599 | CG2 | VAL | B | 990 | 79.691 | 103.873 | 9.366 | 1.00 | 30.78 | C |
| ATOM | 3600 | C | VAL | B | 990 | 80.433 | 106.774 | 10.012 | 1.00 | 29.84 | C |
| ATOM | 3601 | O | VAL | B | 990 | 81.292 | 106.891 | 9.135 | 1.00 | 29.44 | O |
| ATOM | 3602 | N | LYS | B | 991 | 80.667 | 107.050 | 11.293 | 1.00 | 29.13 | N |
| ATOM | 3603 | CA | LYS | B | 991 | 81.991 | 107.439 | 11.774 | 1.00 | 29.33 | C |
| ATOM | 3604 | CB | LYS | B | 991 | 82.078 | 108.954 | 11.989 | 1.00 | 29.54 | C |
| ATOM | 3605 | CG | LYS | B | 991 | 81.946 | 109.806 | 10.745 | 1.00 | 30.61 | C |
| ATOM | 3606 | CD | LYS | B | 991 | 82.197 | 111.264 | 11.074 | 1.00 | 33.14 | C |
| ATOM | 3607 | CE | LYS | B | 991 | 81.930 | 112.148 | 9.879 | 1.00 | 34.80 | C |
| ATOM | 3608 | NZ | LYS | B | 991 | 82.439 | 113.528 | 10.094 | 1.00 | 34.87 | N |
| ATOM | 3609 | C | LYS | B | 991 | 82.310 | 106.746 | 13.090 | 1.00 | 29.17 | C |
| ATOM | 3610 | O | LYS | B | 991 | 81.445 | 106.626 | 13.957 | 1.00 | 29.84 | O |
| ATOM | 3611 | N | ILE | B | 992 | 83.554 | 106.303 | 13.247 | 1.00 | 28.69 | N |
| ATOM | 3612 | CA | ILE | B | 992 | 84.027 | 105.864 | 14.557 | 1.00 | 28.63 | C |
| ATOM | 3613 | CB | ILE | B | 992 | 85.419 | 105.199 | 14.484 | 1.00 | 28.91 | C |
| ATOM | 3614 | CG1 | ILE | B | 992 | 85.419 | 104.097 | 13.411 | 1.00 | 29.19 | C |
| ATOM | 3615 | CD1 | ILE | B | 992 | 86.790 | 103.541 | 13.069 | 1.00 | 28.85 | C |
| ATOM | 3616 | CG2 | ILE | B | 992 | 85.819 | 104.633 | 15.856 | 1.00 | 28.55 | C |
| ATOM | 3617 | C | ILE | B | 992 | 84.012 | 107.110 | 15.449 | 1.00 | 27.97 | C |
| ATOM | 3618 | O | ILE | B | 992 | 84.614 | 108.131 | 15.111 | 1.00 | 27.00 | O |
| ATOM | 3619 | N | GLY | B | 993 | 83.288 | 107.031 | 16.563 | 1.00 | 28.73 | N |
| ATOM | 3620 | CA | GLY | B | 993 | 82.879 | 108.235 | 17.291 | 1.00 | 28.70 | C |
| ATOM | 3621 | C | GLY | B | 993 | 83.345 | 108.412 | 18.721 | 1.00 | 29.13 | C |
| ATOM | 3622 | O | GLY | B | 993 | 82.942 | 109.369 | 19.388 | 1.00 | 28.71 | O |

APPENDIX 1-continued

| ATOM | 3623 | N | ASP | B | 994 | 84.178 | 107.492 | 19.200 | 1.00 | 28.90 | N |
|---|---|---|---|---|---|---|---|---|---|---|---|
| ATOM | 3624 | CA | ASP | B | 994 | 84.782 | 107.614 | 20.529 | 1.00 | 29.07 | C |
| ATOM | 3625 | CB | ASP | B | 994 | 83.878 | 107.028 | 21.611 | 1.00 | 28.73 | C |
| ATOM | 3626 | CG | ASP | B | 994 | 84.331 | 107.410 | 23.007 | 1.00 | 29.92 | C |
| ATOM | 3627 | OD1 | ASP | B | 994 | 84.066 | 108.559 | 23.423 | 1.00 | 30.35 | O |
| ATOM | 3628 | OD2 | ASP | B | 994 | 84.961 | 106.569 | 23.682 | 1.00 | 30.32 | O |
| ATOM | 3629 | C | ASP | B | 994 | 86.133 | 106.918 | 20.570 | 1.00 | 29.66 | C |
| ATOM | 3630 | O | ASP | B | 994 | 86.313 | 105.871 | 19.948 | 1.00 | 30.16 | O |
| ATOM | 3631 | N | PHE | B | 995 | 87.076 | 107.509 | 21.302 | 1.00 | 29.72 | N |
| ATOM | 3632 | CA | PHE | B | 995 | 88.436 | 106.976 | 21.396 | 1.00 | 29.97 | C |
| ATOM | 3633 | CB | PHE | B | 995 | 89.375 | 107.760 | 20.469 | 1.00 | 30.10 | C |
| ATOM | 3634 | CG | PHE | B | 995 | 89.060 | 107.579 | 19.009 | 1.00 | 31.55 | C |
| ATOM | 3635 | CD1 | PHE | B | 995 | 89.688 | 106.581 | 18.267 | 1.00 | 31.25 | C |
| ATOM | 3636 | CE1 | PHE | B | 995 | 89.387 | 106.397 | 16.922 | 1.00 | 32.33 | C |
| ATOM | 3637 | CZ | PHE | B | 995 | 88.445 | 107.212 | 16.307 | 1.00 | 29.62 | C |
| ATOM | 3638 | CE2 | PHE | B | 995 | 87.807 | 108.207 | 17.036 | 1.00 | 33.04 | C |
| ATOM | 3639 | CD2 | PHE | B | 995 | 88.115 | 108.385 | 18.381 | 1.00 | 31.66 | C |
| ATOM | 3640 | C | PHE | B | 995 | 88.948 | 106.959 | 22.838 | 1.00 | 29.99 | C |
| ATOM | 3641 | O | PHE | B | 995 | 90.151 | 107.068 | 23.084 | 1.00 | 30.46 | O |
| ATOM | 3642 | N | GLY | B | 996 | 88.020 | 106.790 | 23.780 | 1.00 | 30.00 | N |
| ATOM | 3643 | CA | GLY | B | 996 | 88.323 | 106.815 | 25.211 | 1.00 | 30.36 | C |
| ATOM | 3644 | C | GLY | B | 996 | 89.287 | 105.748 | 25.697 | 1.00 | 30.77 | C |
| ATOM | 3645 | O | GLY | B | 996 | 89.985 | 105.949 | 26.693 | 1.00 | 30.93 | O |
| ATOM | 3646 | N | LEU | B | 997 | 89.326 | 104.615 | 24.998 | 1.00 | 30.78 | N |
| ATOM | 3647 | CA | LEU | B | 997 | 90.197 | 103.501 | 25.377 | 1.00 | 31.41 | C |
| ATOM | 3648 | CB | LEU | B | 997 | 89.384 | 102.207 | 25.530 | 1.00 | 32.10 | C |
| ATOM | 3649 | CG | LEU | B | 997 | 88.421 | 102.084 | 26.719 | 1.00 | 33.08 | C |
| ATOM | 3650 | CD1 | LEU | B | 997 | 87.619 | 100.797 | 26.625 | 1.00 | 35.70 | C |
| ATOM | 3651 | CD2 | LEU | B | 997 | 89.169 | 102.135 | 28.044 | 1.00 | 36.89 | C |
| ATOM | 3652 | C | LEU | B | 997 | 91.352 | 103.293 | 24.397 | 1.00 | 31.12 | C |
| ATOM | 3653 | O | LEU | B | 997 | 92.142 | 102.356 | 24.551 | 1.00 | 31.51 | O |
| ATOM | 3654 | N | THR | B | 998 | 91.451 | 104.175 | 23.405 | 1.00 | 30.67 | N |
| ATOM | 3655 | CA | THR | B | 998 | 92.452 | 104.049 | 22.344 | 1.00 | 30.55 | C |
| ATOM | 3656 | CB | THR | B | 998 | 92.156 | 105.007 | 21.164 | 1.00 | 30.00 | C |
| ATOM | 3657 | OG1 | THR | B | 998 | 90.888 | 104.669 | 20.594 | 1.00 | 29.21 | O |
| ATOM | 3658 | CG2 | THR | B | 998 | 93.223 | 104.900 | 20.075 | 1.00 | 29.17 | C |
| ATOM | 3659 | C | THR | B | 998 | 93.877 | 104.232 | 22.875 | 1.00 | 31.46 | C |
| ATOM | 3660 | O | THR | B | 998 | 94.158 | 105.170 | 23.629 | 1.00 | 31.18 | O |
| ATOM | 3661 | N | LYS | B | 999 | 94.756 | 103.310 | 22.484 | 1.00 | 31.86 | N |
| ATOM | 3662 | CA | LYS | B | 999 | 96.158 | 103.333 | 22.891 | 1.00 | 32.80 | C |
| ATOM | 3663 | CB | LYS | B | 999 | 96.491 | 102.109 | 23.749 | 1.00 | 32.32 | C |
| ATOM | 3664 | CG | LYS | B | 999 | 95.741 | 102.027 | 25.074 | 1.00 | 33.71 | C |
| ATOM | 3665 | CD | LYS | B | 999 | 96.283 | 103.015 | 26.091 | 1.00 | 35.43 | C |
| ATOM | 3666 | CE | LYS | B | 999 | 95.611 | 102.838 | 27.441 | 1.00 | 36.64 | C |
| ATOM | 3667 | NZ | LYS | B | 999 | 95.982 | 103.935 | 28.376 | 1.00 | 36.51 | N |
| ATOM | 3668 | C | LYS | B | 999 | 97.084 | 103.371 | 21.680 | 1.00 | 34.11 | C |
| ATOM | 3669 | O | LYS | B | 999 | 96.731 | 102.890 | 20.599 | 1.00 | 33.13 | O |
| ATOM | 3670 | N | VAL | B | 1000 | 98.265 | 103.956 | 21.872 | 1.00 | 35.36 | N |
| ATOM | 3671 | CA | VAL | B | 1000 | 99.311 | 103.961 | 20.859 | 1.00 | 36.71 | C |
| ATOM | 3672 | CB | VAL | B | 1000 | 100.121 | 105.282 | 20.864 | 1.00 | 36.81 | C |
| ATOM | 3673 | CG1 | VAL | B | 1000 | 101.032 | 105.363 | 19.640 | 1.00 | 36.24 | C |
| ATOM | 3674 | CG2 | VAL | B | 1000 | 99.194 | 106.488 | 20.920 | 1.00 | 37.90 | C |
| ATOM | 3675 | C | VAL | B | 1000 | 100.251 | 102.801 | 21.150 | 1.00 | 37.88 | C |
| ATOM | 3676 | O | VAL | B | 1000 | 100.732 | 102.653 | 22.276 | 1.00 | 38.13 | O |
| ATOM | 3677 | N | LEU | B | 1001 | 100.494 | 101.973 | 20.139 | 1.00 | 39.33 | N |
| ATOM | 3678 | CA | LEU | B | 1001 | 101.455 | 100.881 | 20.242 | 1.00 | 41.60 | C |
| ATOM | 3679 | CB | LEU | B | 1001 | 101.503 | 100.092 | 18.929 | 1.00 | 41.76 | C |
| ATOM | 3680 | CG | LEU | B | 1001 | 101.065 | 98.623 | 18.868 | 1.00 | 42.06 | C |
| ATOM | 3681 | CD1 | LEU | B | 1001 | 100.023 | 98.255 | 19.916 | 1.00 | 43.43 | C |
| ATOM | 3682 | CD2 | LEU | B | 1001 | 100.575 | 98.283 | 17.467 | 1.00 | 42.02 | C |
| ATOM | 3683 | C | LEU | B | 1001 | 102.851 | 101.400 | 20.583 | 1.00 | 43.08 | C |
| ATOM | 3684 | O | LEU | B | 1001 | 103.273 | 102.428 | 20.048 | 1.00 | 43.35 | O |
| ATOM | 3685 | N | PRO | B | 1002 | 103.564 | 100.705 | 21.491 | 1.00 | 44.66 | N |
| ATOM | 3686 | CA | PRO | B | 1002 | 104.972 | 101.024 | 21.719 | 1.00 | 45.96 | C |
| ATOM | 3687 | CB | PRO | B | 1002 | 105.386 | 100.035 | 22.814 | 1.00 | 45.85 | C |
| ATOM | 3688 | CG | PRO | B | 1002 | 104.109 | 99.621 | 23.465 | 1.00 | 45.28 | C |
| ATOM | 3689 | CD | PRO | B | 1002 | 103.106 | 99.606 | 22.360 | 1.00 | 44.78 | C |
| ATOM | 3690 | C | PRO | B | 1002 | 105.777 | 100.771 | 20.448 | 1.00 | 47.45 | C |
| ATOM | 3691 | O | PRO | B | 1002 | 105.372 | 99.954 | 19.615 | 1.00 | 47.32 | O |
| ATOM | 3692 | N | GLN | B | 1003 | 106.898 | 101.471 | 20.301 | 1.00 | 49.53 | N |
| ATOM | 3693 | CA | GLN | B | 1003 | 107.731 | 101.363 | 19.099 | 1.00 | 51.55 | C |
| ATOM | 3694 | CB | GLN | B | 1003 | 108.912 | 102.338 | 19.171 | 1.00 | 51.67 | C |
| ATOM | 3695 | CG | GLN | B | 1003 | 108.518 | 103.810 | 19.061 | 1.00 | 52.83 | C |
| ATOM | 3696 | CD | GLN | B | 1003 | 109.713 | 104.740 | 18.914 | 1.00 | 52.81 | C |
| ATOM | 3697 | OE1 | GLN | B | 1003 | 110.732 | 104.381 | 18.318 | 1.00 | 54.84 | O |
| ATOM | 3698 | NE2 | GLN | B | 1003 | 109.588 | 105.949 | 19.453 | 1.00 | 54.15 | N |
| ATOM | 3699 | C | GLN | B | 1003 | 108.231 | 99.938 | 18.846 | 1.00 | 52.29 | C |
| ATOM | 3700 | O | GLN | B | 1003 | 108.247 | 99.472 | 17.705 | 1.00 | 52.23 | O |
| ATOM | 3701 | N | ASP | B | 1004 | 108.612 | 99.251 | 19.921 | 1.00 | 53.61 | N |

APPENDIX 1-continued

| ATOM | 3702 | CA | ASP | B | 1004 | 109.225 | 97.924 | 19.837 | 1.00 | 54.85 | C |
|---|---|---|---|---|---|---|---|---|---|---|---|
| ATOM | 3703 | CB | ASP | B | 1004 | 110.244 | 97.742 | 20.975 | 1.00 | 55.25 | C |
| ATOM | 3704 | CG | ASP | B | 1004 | 109.608 | 97.814 | 22.364 | 1.00 | 56.68 | C |
| ATOM | 3705 | OD1 | ASP | B | 1004 | 108.714 | 98.663 | 22.582 | 1.00 | 56.97 | O |
| ATOM | 3706 | OD2 | ASP | B | 1004 | 110.013 | 97.024 | 23.244 | 1.00 | 57.56 | O |
| ATOM | 3707 | C | ASP | B | 1004 | 108.229 | 96.757 | 19.834 | 1.00 | 55.18 | C |
| ATOM | 3708 | O | ASP | B | 1004 | 108.624 | 95.605 | 19.630 | 1.00 | 55.50 | O |
| ATOM | 3709 | N | LYS | B | 1005 | 106.947 | 97.051 | 20.050 | 1.00 | 55.26 | N |
| ATOM | 3710 | CA | LYS | B | 1005 | 105.945 | 95.997 | 20.243 | 1.00 | 55.10 | C |
| ATOM | 3711 | CB | LYS | B | 1005 | 105.439 | 95.993 | 21.695 | 1.00 | 55.34 | C |
| ATOM | 3712 | CG | LYS | B | 1005 | 106.476 | 95.566 | 22.735 | 1.00 | 56.85 | C |
| ATOM | 3713 | CD | LYS | B | 1005 | 106.873 | 94.101 | 22.578 | 1.00 | 58.98 | C |
| ATOM | 3714 | CE | LYS | B | 1005 | 108.070 | 93.756 | 23.447 | 1.00 | 60.17 | C |
| ATOM | 3715 | NZ | LYS | B | 1005 | 108.530 | 92.357 | 23.219 | 1.00 | 61.36 | N |
| ATOM | 3716 | C | LYS | B | 1005 | 104.763 | 96.050 | 19.275 | 1.00 | 54.65 | C |
| ATOM | 3717 | O | LYS | B | 1005 | 104.386 | 97.118 | 18.788 | 1.00 | 54.32 | O |
| ATOM | 3718 | N | GLU | B | 1006 | 104.192 | 94.877 | 19.010 | 1.00 | 54.28 | N |
| ATOM | 3719 | CA | GLU | B | 1006 | 103.000 | 94.741 | 18.176 | 1.00 | 54.21 | C |
| ATOM | 3720 | CB | GLU | B | 1006 | 103.152 | 93.560 | 17.209 | 1.00 | 54.20 | C |
| ATOM | 3721 | CG | GLU | B | 1006 | 104.182 | 93.775 | 16.103 | 1.00 | 54.50 | C |
| ATOM | 3722 | CD | GLU | B | 1006 | 103.827 | 94.930 | 15.183 | 1.00 | 55.57 | C |
| ATOM | 3723 | OE1 | GLU | B | 1006 | 104.691 | 95.806 | 14.974 | 1.00 | 56.38 | O |
| ATOM | 3724 | OE2 | GLU | B | 1006 | 102.686 | 94.967 | 14.677 | 1.00 | 55.58 | O |
| ATOM | 3725 | C | GLU | B | 1006 | 101.736 | 94.572 | 19.025 | 1.00 | 54.06 | C |
| ATOM | 3726 | O | GLU | B | 1006 | 100.643 | 94.358 | 18.495 | 1.00 | 53.52 | O |
| ATOM | 3727 | O1P | PTR | B | 1007 | 105.471 | 89.098 | 26.309 | 1.00 | 61.42 | O |
| ATOM | 3728 | P | PTR | B | 1007 | 104.686 | 89.273 | 25.065 | 1.00 | 60.85 | P |
| ATOM | 3729 | O2P | PTR | B | 1007 | 105.346 | 88.501 | 23.906 | 1.00 | 60.01 | O |
| ATOM | 3730 | O3P | PTR | B | 1007 | 103.256 | 88.743 | 25.282 | 1.00 | 61.35 | O |
| ATOM | 3731 | OH | PTR | B | 1007 | 104.653 | 90.847 | 24.708 | 1.00 | 58.83 | O |
| ATOM | 3732 | CZ | PTR | B | 1007 | 103.744 | 91.341 | 24.035 | 1.00 | 57.22 | C |
| ATOM | 3733 | CE2 | PTR | B | 1007 | 102.813 | 92.160 | 24.647 | 1.00 | 56.56 | C |
| ATOM | 3734 | CD2 | PTR | B | 1007 | 101.792 | 92.718 | 23.894 | 1.00 | 55.67 | C |
| ATOM | 3735 | CE1 | PTR | B | 1007 | 103.663 | 91.084 | 22.675 | 1.00 | 56.96 | C |
| ATOM | 3736 | CD1 | PTR | B | 1007 | 102.636 | 91.645 | 21.931 | 1.00 | 56.38 | C |
| ATOM | 3737 | CG | PTR | B | 1007 | 101.693 | 92.483 | 22.522 | 1.00 | 55.79 | C |
| ATOM | 3738 | CB | PTR | B | 1007 | 100.570 | 93.087 | 21.703 | 1.00 | 55.36 | C |
| ATOM | 3739 | CA | PTR | B | 1007 | 100.787 | 94.552 | 21.283 | 1.00 | 55.10 | C |
| ATOM | 3740 | N | PTR | B | 1007 | 101.900 | 94.669 | 20.342 | 1.00 | 54.39 | N |
| ATOM | 3741 | C | PTR | B | 1007 | 100.973 | 95.492 | 22.476 | 1.00 | 55.47 | C |
| ATOM | 3742 | O | PTR | B | 1007 | 102.055 | 96.048 | 22.680 | 1.00 | 55.07 | O |
| ATOM | 3743 | O1P | PTR | B | 1008 | 101.258 | 103.594 | 28.836 | 1.00 | 69.98 | O |
| ATOM | 3744 | P | PTR | B | 1008 | 100.515 | 102.325 | 28.646 | 1.00 | 70.01 | P |
| ATOM | 3745 | O2P | PTR | B | 1008 | 101.486 | 101.137 | 28.804 | 1.00 | 70.34 | O |
| ATOM | 3746 | O3P | PTR | B | 1008 | 99.387 | 102.227 | 29.693 | 1.00 | 68.98 | O |
| ATOM | 3747 | OH | PTR | B | 1008 | 99.868 | 102.336 | 27.167 | 1.00 | 64.19 | O |
| ATOM | 3748 | CZ | PTR | B | 1008 | 99.726 | 101.325 | 26.471 | 1.00 | 61.71 | C |
| ATOM | 3749 | CE2 | PTR | B | 1008 | 100.226 | 101.335 | 25.182 | 1.00 | 61.14 | C |
| ATOM | 3750 | CD2 | PTR | B | 1008 | 100.070 | 100.218 | 24.375 | 1.00 | 60.36 | C |
| ATOM | 3751 | CE1 | PTR | B | 1008 | 99.060 | 100.209 | 26.950 | 1.00 | 60.49 | C |
| ATOM | 3752 | CD1 | PTR | B | 1008 | 98.912 | 99.095 | 26.136 | 1.00 | 59.68 | C |
| ATOM | 3753 | CG | PTR | B | 1008 | 99.416 | 99.079 | 24.836 | 1.00 | 59.25 | C |
| ATOM | 3754 | CB | PTR | B | 1008 | 99.244 | 97.871 | 23.933 | 1.00 | 58.19 | C |
| ATOM | 3755 | CA | PTR | B | 1008 | 99.898 | 96.564 | 24.398 | 1.00 | 57.00 | C |
| ATOM | 3756 | N | PTR | B | 1008 | 99.908 | 95.659 | 23.256 | 1.00 | 56.07 | N |
| ATOM | 3757 | C | PTR | B | 1008 | 99.130 | 95.903 | 25.538 | 1.00 | 57.25 | C |
| ATOM | 3758 | O | PTR | B | 1008 | 98.004 | 95.437 | 25.351 | 1.00 | 56.44 | O |
| ATOM | 3759 | N | LYS | B | 1009 | 99.752 | 95.854 | 26.713 | 1.00 | 58.08 | N |
| ATOM | 3760 | CA | LYS | B | 1009 | 99.101 | 95.337 | 27.915 | 1.00 | 59.63 | C |
| ATOM | 3761 | CB | LYS | B | 1009 | 100.037 | 94.404 | 28.689 | 1.00 | 59.49 | C |
| ATOM | 3762 | CG | LYS | B | 1009 | 100.275 | 93.063 | 28.007 | 1.00 | 59.86 | C |
| ATOM | 3763 | CD | LYS | B | 1009 | 101.151 | 92.156 | 28.855 | 1.00 | 59.77 | C |
| ATOM | 3764 | CE | LYS | B | 1009 | 101.410 | 90.833 | 28.156 | 1.00 | 59.38 | C |
| ATOM | 3765 | NZ | LYS | B | 1009 | 102.345 | 89.969 | 28.923 | 1.00 | 59.74 | N |
| ATOM | 3766 | C | LYS | B | 1009 | 98.622 | 96.485 | 28.800 | 1.00 | 60.79 | C |
| ATOM | 3767 | O | LYS | B | 1009 | 99.418 | 97.324 | 29.226 | 1.00 | 60.52 | O |
| ATOM | 3768 | N | VAL | B | 1010 | 97.318 | 96.519 | 29.065 | 1.00 | 62.61 | N |
| ATOM | 3769 | CA | VAL | B | 1010 | 96.709 | 97.623 | 29.811 | 1.00 | 64.66 | C |
| ATOM | 3770 | CB | VAL | B | 1010 | 95.461 | 98.210 | 29.084 | 1.00 | 64.61 | C |
| ATOM | 3771 | CG1 | VAL | B | 1010 | 95.798 | 98.604 | 27.652 | 1.00 | 64.63 | C |
| ATOM | 3772 | CG2 | VAL | B | 1010 | 94.292 | 97.233 | 29.111 | 1.00 | 64.71 | C |
| ATOM | 3773 | C | VAL | B | 1010 | 96.321 | 97.243 | 31.240 | 1.00 | 66.26 | C |
| ATOM | 3774 | O | VAL | B | 1010 | 95.964 | 96.093 | 31.515 | 1.00 | 66.38 | O |
| ATOM | 3775 | N | LYS | B | 1011 | 96.404 | 98.219 | 32.143 | 1.00 | 68.20 | N |
| ATOM | 3776 | CA | LYS | B | 1011 | 95.867 | 98.079 | 33.493 | 1.00 | 69.95 | C |
| ATOM | 3777 | CB | LYS | B | 1011 | 96.370 | 99.200 | 34.410 | 1.00 | 70.17 | C |
| ATOM | 3778 | CG | LYS | B | 1011 | 97.861 | 99.162 | 34.747 | 1.00 | 71.73 | C |
| ATOM | 3779 | CD | LYS | B | 1011 | 98.685 | 100.025 | 33.793 | 1.00 | 73.06 | C |
| ATOM | 3780 | CE | LYS | B | 1011 | 100.044 | 100.384 | 34.387 | 1.00 | 73.68 | C |

APPENDIX 1-continued

| ATOM | 3781 | NZ | LYS | B | 1011 | 100.945 | 99.204 | 34.539 | 1.00 | 74.05 | N |
|---|---|---|---|---|---|---|---|---|---|---|---|
| ATOM | 3782 | C | LYS | B | 1011 | 94.344 | 98.127 | 33.414 | 1.00 | 70.97 | C |
| ATOM | 3783 | O | LYS | B | 1011 | 93.786 | 98.878 | 32.608 | 1.00 | 71.00 | O |
| ATOM | 3784 | N | GLU | B | 1012 | 93.675 | 97.330 | 34.243 | 1.00 | 72.11 | N |
| ATOM | 3785 | CA | GLU | B | 1012 | 92.211 | 97.295 | 34.249 | 1.00 | 73.09 | C |
| ATOM | 3786 | CB | GLU | B | 1012 | 91.689 | 95.937 | 33.750 | 1.00 | 73.05 | C |
| ATOM | 3787 | CG | GLU | B | 1012 | 91.989 | 95.655 | 32.275 | 1.00 | 74.21 | C |
| ATOM | 3788 | CD | GLU | B | 1012 | 91.170 | 94.507 | 31.693 | 1.00 | 74.35 | C |
| ATOM | 3789 | OE1 | GLU | B | 1012 | 91.648 | 93.871 | 30.726 | 1.00 | 74.91 | O |
| ATOM | 3790 | OE2 | GLU | B | 1012 | 90.051 | 94.242 | 32.188 | 1.00 | 76.34 | O |
| ATOM | 3791 | C | GLU | B | 1012 | 91.610 | 97.659 | 35.617 | 1.00 | 72.85 | C |
| ATOM | 3792 | O | GLU | B | 1012 | 91.313 | 96.772 | 36.424 | 1.00 | 73.08 | O |
| ATOM | 3793 | N | PRO | B | 1013 | 91.455 | 98.973 | 35.888 | 1.00 | 72.58 | N |
| ATOM | 3794 | CA | PRO | B | 1013 | 90.746 | 99.451 | 37.074 | 1.00 | 71.98 | C |
| ATOM | 3795 | CB | PRO | B | 1013 | 91.523 | 100.721 | 37.445 | 1.00 | 72.10 | C |
| ATOM | 3796 | CG | PRO | B | 1013 | 92.216 | 101.163 | 36.155 | 1.00 | 72.66 | C |
| ATOM | 3797 | CD | PRO | B | 1013 | 91.987 | 100.103 | 35.106 | 1.00 | 72.55 | C |
| ATOM | 3798 | C | PRO | B | 1013 | 89.274 | 99.790 | 36.795 | 1.00 | 71.01 | C |
| ATOM | 3799 | O | PRO | B | 1013 | 88.572 | 100.284 | 37.683 | 1.00 | 71.17 | O |
| ATOM | 3800 | N | GLY | B | 1014 | 88.822 | 99.521 | 35.571 | 1.00 | 69.75 | N |
| ATOM | 3801 | CA | GLY | B | 1014 | 87.446 | 99.794 | 35.161 | 1.00 | 68.07 | C |
| ATOM | 3802 | C | GLY | B | 1014 | 86.808 | 98.620 | 34.442 | 1.00 | 66.62 | C |
| ATOM | 3803 | O | GLY | B | 1014 | 87.502 | 97.696 | 34.001 | 1.00 | 66.57 | O |
| ATOM | 3804 | N | GLU | B | 1015 | 85.482 | 98.660 | 34.323 | 1.00 | 64.84 | N |
| ATOM | 3805 | CA | GLU | B | 1015 | 84.724 | 97.591 | 33.676 | 1.00 | 62.85 | C |
| ATOM | 3806 | CB | GLU | B | 1015 | 83.218 | 97.757 | 33.929 | 1.00 | 63.46 | C |
| ATOM | 3807 | CG | GLU | B | 1015 | 82.346 | 96.574 | 33.475 | 1.00 | 65.96 | C |
| ATOM | 3808 | CD | GLU | B | 1015 | 82.699 | 95.253 | 34.155 | 1.00 | 68.56 | C |
| ATOM | 3809 | OE1 | GLU | B | 1015 | 83.000 | 95.255 | 35.370 | 1.00 | 69.96 | O |
| ATOM | 3810 | OE2 | GLU | B | 1015 | 82.665 | 94.207 | 33.471 | 1.00 | 68.74 | O |
| ATOM | 3811 | C | GLU | B | 1015 | 85.025 | 97.519 | 32.180 | 1.00 | 60.39 | C |
| ATOM | 3812 | O | GLU | B | 1015 | 85.052 | 98.539 | 31.486 | 1.00 | 60.60 | O |
| ATOM | 3813 | N | SER | B | 1016 | 85.260 | 96.301 | 31.702 | 1.00 | 57.01 | N |
| ATOM | 3814 | CA | SER | B | 1016 | 85.615 | 96.061 | 30.310 | 1.00 | 53.45 | C |
| ATOM | 3815 | CB | SER | B | 1016 | 86.847 | 95.160 | 30.242 | 1.00 | 53.75 | C |
| ATOM | 3816 | OG | SER | B | 1016 | 87.906 | 95.683 | 31.027 | 1.00 | 54.90 | O |
| ATOM | 3817 | C | SER | B | 1016 | 84.453 | 95.419 | 29.551 | 1.00 | 50.29 | C |
| ATOM | 3818 | O | SER | B | 1016 | 83.714 | 94.612 | 30.121 | 1.00 | 49.77 | O |
| ATOM | 3819 | N | PRO | B | 1017 | 84.278 | 95.786 | 28.264 | 1.00 | 47.18 | N |
| ATOM | 3820 | CA | PRO | B | 1017 | 83.268 | 95.135 | 27.426 | 1.00 | 45.19 | C |
| ATOM | 3821 | CB | PRO | B | 1017 | 83.163 | 96.066 | 26.214 | 1.00 | 45.05 | C |
| ATOM | 3822 | CG | PRO | B | 1017 | 84.482 | 96.736 | 26.134 | 1.00 | 46.00 | C |
| ATOM | 3823 | CD | PRO | B | 1017 | 85.000 | 96.848 | 27.538 | 1.00 | 46.89 | C |
| ATOM | 3824 | C | PRO | B | 1017 | 83.706 | 93.724 | 27.019 | 1.00 | 42.88 | C |
| ATOM | 3825 | O | PRO | B | 1017 | 84.071 | 93.486 | 25.863 | 1.00 | 42.53 | O |
| ATOM | 3826 | N | ILE | B | 1018 | 83.645 | 92.800 | 27.976 | 1.00 | 40.52 | N |
| ATOM | 3827 | CA | ILE | B | 1018 | 84.216 | 91.453 | 27.833 | 1.00 | 38.64 | C |
| ATOM | 3828 | CB | ILE | B | 1018 | 84.142 | 90.645 | 29.162 | 1.00 | 38.23 | C |
| ATOM | 3829 | CG1 | ILE | B | 1018 | 82.694 | 90.533 | 29.661 | 1.00 | 38.65 | C |
| ATOM | 3830 | CD1 | ILE | B | 1018 | 82.434 | 89.359 | 30.593 | 1.00 | 37.60 | C |
| ATOM | 3831 | CG2 | ILE | B | 1018 | 85.049 | 91.277 | 30.223 | 1.00 | 37.69 | C |
| ATOM | 3832 | C | ILE | B | 1018 | 83.640 | 90.621 | 26.682 | 1.00 | 37.18 | C |
| ATOM | 3833 | O | ILE | B | 1018 | 84.318 | 89.738 | 26.155 | 1.00 | 37.49 | O |
| ATOM | 3834 | N | PHE | B | 1019 | 82.402 | 90.910 | 26.290 | 1.00 | 36.10 | N |
| ATOM | 3835 | CA | PHE | B | 1019 | 81.741 | 90.154 | 25.225 | 1.00 | 34.79 | C |
| ATOM | 3836 | CB | PHE | B | 1019 | 80.221 | 90.138 | 25.429 | 1.00 | 34.85 | C |
| ATOM | 3837 | CG | PHE | B | 1019 | 79.793 | 89.480 | 26.715 | 1.00 | 35.05 | C |
| ATOM | 3838 | CD1 | PHE | B | 1019 | 79.234 | 90.232 | 27.744 | 1.00 | 34.89 | C |
| ATOM | 3839 | CE1 | PHE | B | 1019 | 78.841 | 89.626 | 28.940 | 1.00 | 35.66 | C |
| ATOM | 3840 | CZ | PHE | B | 1019 | 79.021 | 88.256 | 29.118 | 1.00 | 35.38 | C |
| ATOM | 3841 | CE2 | PHE | B | 1019 | 79.589 | 87.496 | 28.100 | 1.00 | 33.38 | C |
| ATOM | 3842 | CD2 | PHE | B | 1019 | 79.974 | 88.111 | 26.908 | 1.00 | 33.91 | C |
| ATOM | 3843 | C | PHE | B | 1019 | 82.124 | 90.634 | 23.821 | 1.00 | 33.80 | C |
| ATOM | 3844 | O | PHE | B | 1019 | 81.687 | 90.060 | 22.819 | 1.00 | 33.37 | O |
| ATOM | 3845 | N | TRP | B | 1020 | 82.951 | 91.677 | 23.767 | 1.00 | 32.88 | N |
| ATOM | 3846 | CA | TRP | B | 1020 | 83.541 | 92.164 | 22.519 | 1.00 | 32.85 | C |
| ATOM | 3847 | CB | TRP | B | 1020 | 83.309 | 93.672 | 22.367 | 1.00 | 33.05 | C |
| ATOM | 3848 | CG | TRP | B | 1020 | 81.984 | 94.036 | 21.761 | 1.00 | 33.39 | C |
| ATOM | 3849 | CD1 | TRP | B | 1020 | 81.758 | 94.451 | 20.478 | 1.00 | 32.54 | C |
| ATOM | 3850 | NE1 | TRP | B | 1020 | 80.419 | 94.695 | 20.287 | 1.00 | 32.71 | N |
| ATOM | 3851 | CE2 | TRP | B | 1020 | 79.748 | 94.444 | 21.455 | 1.00 | 32.73 | C |
| ATOM | 3852 | CD2 | TRP | B | 1020 | 80.703 | 94.027 | 22.410 | 1.00 | 33.50 | C |
| ATOM | 3853 | CE3 | TRP | B | 1020 | 80.270 | 93.705 | 23.705 | 1.00 | 33.52 | C |
| ATOM | 3854 | CZ3 | TRP | B | 1020 | 78.910 | 93.810 | 24.001 | 1.00 | 33.84 | C |
| ATOM | 3855 | CH2 | TRP | B | 1020 | 77.984 | 94.230 | 23.026 | 1.00 | 32.83 | C |
| ATOM | 3856 | CZ2 | TRP | B | 1020 | 78.382 | 94.551 | 21.753 | 1.00 | 33.29 | C |
| ATOM | 3857 | C | TRP | B | 1020 | 85.041 | 91.858 | 22.451 | 1.00 | 32.55 | C |
| ATOM | 3858 | O | TRP | B | 1020 | 85.684 | 92.098 | 21.426 | 1.00 | 31.71 | O |
| ATOM | 3859 | N | TYR | B | 1021 | 85.577 | 91.315 | 23.546 | 1.00 | 32.48 | N |

APPENDIX 1-continued

| ATOM | 3860 | CA  | TYR | B | 1021 | 87.014  | 91.104 | 23.726 | 1.00 | 31.99 | C |
|------|------|-----|-----|---|------|---------|--------|--------|------|-------|---|
| ATOM | 3861 | CB  | TYR | B | 1021 | 87.357  | 91.115 | 25.221 | 1.00 | 32.88 | C |
| ATOM | 3862 | CG  | TYR | B | 1021 | 87.717  | 92.468 | 25.807 | 1.00 | 34.16 | C |
| ATOM | 3863 | CD1 | TYR | B | 1021 | 87.328  | 93.657 | 25.188 | 1.00 | 36.26 | C |
| ATOM | 3864 | CE1 | TYR | B | 1021 | 87.657  | 94.897 | 25.733 | 1.00 | 36.59 | C |
| ATOM | 3865 | CZ  | TYR | B | 1021 | 88.365  | 94.955 | 26.919 | 1.00 | 37.03 | C |
| ATOM | 3866 | OH  | TYR | B | 1021 | 88.686  | 96.181 | 27.463 | 1.00 | 38.71 | O |
| ATOM | 3867 | CE2 | TYR | B | 1021 | 88.754  | 93.789 | 27.561 | 1.00 | 37.02 | C |
| ATOM | 3868 | CD2 | TYR | B | 1021 | 88.424  | 92.555 | 27.005 | 1.00 | 35.04 | C |
| ATOM | 3869 | C   | TYR | B | 1021 | 87.541  | 89.810 | 23.111 | 1.00 | 31.29 | C |
| ATOM | 3870 | O   | TYR | B | 1021 | 86.906  | 88.755 | 23.202 | 1.00 | 30.84 | O |
| ATOM | 3871 | N   | ALA | B | 1022 | 88.719  | 89.907 | 22.497 | 1.00 | 30.52 | N |
| ATOM | 3872 | CA  | ALA | B | 1022 | 89.463  | 88.743 | 22.023 | 1.00 | 30.01 | C |
| ATOM | 3873 | CB  | ALA | B | 1022 | 90.641  | 89.186 | 21.173 | 1.00 | 29.20 | C |
| ATOM | 3874 | C   | ALA | B | 1022 | 89.944  | 87.914 | 23.219 | 1.00 | 30.05 | C |
| ATOM | 3875 | O   | ALA | B | 1022 | 90.149  | 88.463 | 24.307 | 1.00 | 29.66 | O |
| ATOM | 3876 | N   | PRO | B | 1023 | 90.115  | 86.590 | 23.032 | 1.00 | 30.06 | N |
| ATOM | 3877 | CA  | PRO | B | 1023 | 90.547  | 85.717 | 24.124 | 1.00 | 29.71 | C |
| ATOM | 3878 | CB  | PRO | B | 1023 | 90.821  | 84.389 | 23.417 | 1.00 | 30.28 | C |
| ATOM | 3879 | CG  | PRO | B | 1023 | 89.910  | 84.405 | 22.248 | 1.00 | 30.58 | C |
| ATOM | 3880 | CD  | PRO | B | 1023 | 89.896  | 85.830 | 21.788 | 1.00 | 29.80 | C |
| ATOM | 3881 | C   | PRO | B | 1023 | 91.801  | 86.204 | 24.849 | 1.00 | 29.80 | C |
| ATOM | 3882 | O   | PRO | B | 1023 | 91.849  | 86.145 | 26.076 | 1.00 | 30.04 | O |
| ATOM | 3883 | N   | GLU | B | 1024 | 92.791  | 86.695 | 24.100 | 1.00 | 29.59 | N |
| ATOM | 3884 | CA  | GLU | B | 1024 | 94.055  | 87.160 | 24.687 | 1.00 | 30.06 | C |
| ATOM | 3885 | CB  | GLU | B | 1024 | 95.169  | 87.244 | 23.629 | 1.00 | 29.64 | C |
| ATOM | 3886 | CG  | GLU | B | 1024 | 95.046  | 88.392 | 22.628 | 1.00 | 30.87 | C |
| ATOM | 3887 | CD  | GLU | B | 1024 | 94.116  | 88.100 | 21.454 | 1.00 | 31.83 | C |
| ATOM | 3888 | OE1 | GLU | B | 1024 | 93.459  | 87.034 | 21.430 | 1.00 | 30.77 | O |
| ATOM | 3889 | OE2 | GLU | B | 1024 | 94.048  | 88.953 | 20.542 | 1.00 | 31.48 | O |
| ATOM | 3890 | C   | GLU | B | 1024 | 93.920  | 88.474 | 25.467 | 1.00 | 29.85 | C |
| ATOM | 3891 | O   | GLU | B | 1024 | 94.735  | 88.764 | 26.342 | 1.00 | 29.75 | O |
| ATOM | 3892 | N   | SER | B | 1025 | 92.897  | 89.264 | 25.142 | 1.00 | 29.85 | N |
| ATOM | 3893 | CA  | SER | B | 1025 | 92.565  | 90.457 | 25.922 | 1.00 | 29.27 | C |
| ATOM | 3894 | CB  | SER | B | 1025 | 91.622  | 91.372 | 25.139 | 1.00 | 28.63 | C |
| ATOM | 3895 | OG  | SER | B | 1025 | 92.186  | 91.733 | 23.891 | 1.00 | 26.83 | O |
| ATOM | 3896 | C   | SER | B | 1025 | 91.926  | 90.047 | 27.247 | 1.00 | 29.70 | C |
| ATOM | 3897 | O   | SER | B | 1025 | 92.178  | 90.656 | 28.286 | 1.00 | 29.46 | O |
| ATOM | 3898 | N   | LEU | B | 1026 | 91.100  | 89.006 | 27.194 | 1.00 | 30.60 | N |
| ATOM | 3899 | CA  | LEU | B | 1026 | 90.470  | 88.436 | 28.383 | 1.00 | 32.54 | C |
| ATOM | 3900 | CB  | LEU | B | 1026 | 89.426  | 87.389 | 27.975 | 1.00 | 32.05 | C |
| ATOM | 3901 | CG  | LEU | B | 1026 | 87.915  | 87.661 | 28.031 | 1.00 | 34.30 | C |
| ATOM | 3902 | CD1 | LEU | B | 1026 | 87.542  | 89.143 | 28.103 | 1.00 | 31.03 | C |
| ATOM | 3903 | CD2 | LEU | B | 1026 | 87.221  | 86.970 | 26.863 | 1.00 | 31.61 | C |
| ATOM | 3904 | C   | LEU | B | 1026 | 91.480  | 87.806 | 29.343 | 1.00 | 33.28 | C |
| ATOM | 3905 | O   | LEU | B | 1026 | 91.367  | 87.964 | 30.559 | 1.00 | 33.45 | O |
| ATOM | 3906 | N   | THR | B | 1027 | 92.464  | 87.099 | 28.790 | 1.00 | 34.60 | N |
| ATOM | 3907 | CA  | THR | B | 1027 | 93.390  | 86.293 | 29.592 | 1.00 | 35.56 | C |
| ATOM | 3908 | CB  | THR | B | 1027 | 93.824  | 85.013 | 28.847 | 1.00 | 35.94 | C |
| ATOM | 3909 | OG1 | THR | B | 1027 | 94.443  | 85.371 | 27.604 | 1.00 | 35.87 | O |
| ATOM | 3910 | CG2 | THR | B | 1027 | 92.628  | 84.101 | 28.586 | 1.00 | 35.52 | C |
| ATOM | 3911 | C   | THR | B | 1027 | 94.649  | 87.036 | 30.027 | 1.00 | 36.21 | C |
| ATOM | 3912 | O   | THR | B | 1027 | 95.111  | 86.863 | 31.155 | 1.00 | 36.27 | O |
| ATOM | 3913 | N   | GLU | B | 1028 | 95.201  | 87.852 | 29.132 | 1.00 | 36.77 | N |
| ATOM | 3914 | CA  | GLU | B | 1028 | 96.491  | 88.504 | 29.369 | 1.00 | 37.77 | C |
| ATOM | 3915 | CB  | GLU | B | 1028 | 97.538  | 87.994 | 28.369 | 1.00 | 37.90 | C |
| ATOM | 3916 | CG  | GLU | B | 1028 | 97.717  | 86.480 | 28.311 | 1.00 | 40.18 | C |
| ATOM | 3917 | CD  | GLU | B | 1028 | 98.709  | 86.057 | 27.242 | 1.00 | 40.08 | C |
| ATOM | 3918 | OE1 | GLU | B | 1028 | 98.318  | 85.300 | 26.328 | 1.00 | 43.68 | O |
| ATOM | 3919 | OE2 | GLU | B | 1028 | 99.880  | 86.494 | 27.307 | 1.00 | 44.58 | O |
| ATOM | 3920 | C   | GLU | B | 1028 | 96.424  | 90.031 | 29.281 | 1.00 | 37.10 | C |
| ATOM | 3921 | O   | GLU | B | 1028 | 97.441  | 90.706 | 29.454 | 1.00 | 37.62 | O |
| ATOM | 3922 | N   | SER | B | 1029 | 95.234  | 90.568 | 29.007 | 1.00 | 36.43 | N |
| ATOM | 3923 | CA  | SER | B | 1029 | 95.041  | 92.004 | 28.755 | 1.00 | 35.84 | C |
| ATOM | 3924 | CB  | SER | B | 1029 | 95.325  | 92.841 | 30.011 | 1.00 | 36.01 | C |
| ATOM | 3925 | OG  | SER | B | 1029 | 94.245  | 92.776 | 30.922 | 1.00 | 39.67 | O |
| ATOM | 3926 | C   | SER | B | 1029 | 95.863  | 92.507 | 27.565 | 1.00 | 34.80 | C |
| ATOM | 3927 | O   | SER | B | 1029 | 96.308  | 93.655 | 27.546 | 1.00 | 34.41 | O |
| ATOM | 3928 | N   | LYS | B | 1030 | 96.051  | 91.636 | 26.577 | 1.00 | 34.66 | N |
| ATOM | 3929 | CA  | LYS | B | 1030 | 96.818  | 91.959 | 25.378 | 1.00 | 34.55 | C |
| ATOM | 3930 | CB  | LYS | B | 1030 | 97.532  | 90.717 | 24.835 | 1.00 | 34.42 | C |
| ATOM | 3931 | CG  | LYS | B | 1030 | 98.738  | 90.281 | 25.652 | 1.00 | 37.34 | C |
| ATOM | 3932 | CD  | LYS | B | 1030 | 99.310  | 88.950 | 25.168 | 1.00 | 36.15 | C |
| ATOM | 3933 | CE  | LYS | B | 1030 | 100.190 | 89.105 | 23.934 | 1.00 | 39.37 | C |
| ATOM | 3934 | NZ  | LYS | B | 1030 | 100.858 | 87.818 | 23.577 | 1.00 | 39.49 | N |
| ATOM | 3935 | C   | LYS | B | 1030 | 95.922  | 92.555 | 24.303 | 1.00 | 33.31 | C |
| ATOM | 3936 | O   | LYS | B | 1030 | 94.948  | 91.931 | 23.873 | 1.00 | 33.18 | O |
| ATOM | 3937 | N   | PHE | B | 1031 | 96.266  | 93.764 | 23.874 | 1.00 | 32.40 | N |
| ATOM | 3938 | CA  | PHE | B | 1031 | 95.510  | 94.476 | 22.851 | 1.00 | 32.12 | C |

APPENDIX 1-continued

| | | | | | | | | | | |
|---|---|---|---|---|---|---|---|---|---|---|
| ATOM | 3939 | CB | PHE | B | 1031 | 94.862 | 95.733 | 23.435 | 1.00 | 31.54 | C |
| ATOM | 3940 | CG | PHE | B | 1031 | 93.796 | 95.444 | 24.448 | 1.00 | 31.00 | C |
| ATOM | 3941 | CD1 | PHE | B | 1031 | 94.115 | 95.316 | 25.799 | 1.00 | 32.43 | C |
| ATOM | 3942 | CE1 | PHE | B | 1031 | 93.125 | 95.038 | 26.740 | 1.00 | 30.28 | C |
| ATOM | 3943 | CZ | PHE | B | 1031 | 91.807 | 94.887 | 26.333 | 1.00 | 31.13 | C |
| ATOM | 3944 | CE2 | PHE | B | 1031 | 91.477 | 95.008 | 24.985 | 1.00 | 28.35 | C |
| ATOM | 3945 | CD2 | PHE | B | 1031 | 92.471 | 95.285 | 24.053 | 1.00 | 29.16 | C |
| ATOM | 3946 | C | PHE | B | 1031 | 96.396 | 94.825 | 21.663 | 1.00 | 32.07 | C |
| ATOM | 3947 | O | PHE | B | 1031 | 97.534 | 95.266 | 21.830 | 1.00 | 32.15 | O |
| ATOM | 3948 | N | SER | B | 1032 | 95.851 | 94.626 | 20.467 | 1.00 | 32.10 | N |
| ATOM | 3949 | CA | SER | B | 1032 | 96.593 | 94.770 | 19.221 | 1.00 | 31.41 | C |
| ATOM | 3950 | CB | SER | B | 1032 | 97.352 | 93.473 | 18.922 | 1.00 | 31.74 | C |
| ATOM | 3951 | OG | SER | B | 1032 | 96.450 | 92.384 | 18.785 | 1.00 | 30.88 | O |
| ATOM | 3952 | C | SER | B | 1032 | 95.626 | 95.063 | 18.085 | 1.00 | 31.25 | C |
| ATOM | 3953 | O | SER | B | 1032 | 94.419 | 95.176 | 18.306 | 1.00 | 30.95 | O |
| ATOM | 3954 | N | VAL | B | 1033 | 96.159 | 95.188 | 16.871 | 1.00 | 30.59 | N |
| ATOM | 3955 | CA | VAL | B | 1033 | 95.333 | 95.333 | 15.675 | 1.00 | 30.98 | C |
| ATOM | 3956 | CB | VAL | B | 1033 | 96.196 | 95.535 | 14.401 | 1.00 | 30.84 | C |
| ATOM | 3957 | CG1 | VAL | B | 1033 | 95.344 | 95.447 | 13.141 | 1.00 | 31.08 | C |
| ATOM | 3958 | CG2 | VAL | B | 1033 | 96.923 | 96.873 | 14.453 | 1.00 | 30.35 | C |
| ATOM | 3959 | C | VAL | B | 1033 | 94.427 | 94.110 | 15.523 | 1.00 | 31.22 | C |
| ATOM | 3960 | O | VAL | B | 1033 | 93.248 | 94.237 | 15.185 | 1.00 | 31.22 | O |
| ATOM | 3961 | N | ALA | B | 1034 | 94.986 | 92.932 | 15.797 | 1.00 | 30.82 | N |
| ATOM | 3962 | CA | ALA | B | 1034 | 94.252 | 91.674 | 15.700 | 1.00 | 30.25 | C |
| ATOM | 3963 | CB | ALA | B | 1034 | 95.204 | 90.497 | 15.778 | 1.00 | 30.15 | C |
| ATOM | 3964 | C | ALA | B | 1034 | 93.136 | 91.539 | 16.741 | 1.00 | 29.85 | C |
| ATOM | 3965 | O | ALA | B | 1034 | 92.142 | 90.860 | 16.488 | 1.00 | 30.02 | O |
| ATOM | 3966 | N | SER | B | 1035 | 93.293 | 92.169 | 17.906 | 1.00 | 28.62 | N |
| ATOM | 3967 | CA | SER | B | 1035 | 92.192 | 92.203 | 18.873 | 1.00 | 28.78 | C |
| ATOM | 3968 | CB | SER | B | 1035 | 92.677 | 92.457 | 20.308 | 1.00 | 28.03 | C |
| ATOM | 3969 | OG | SER | B | 1035 | 93.274 | 93.731 | 20.451 | 1.00 | 28.75 | O |
| ATOM | 3970 | C | SER | B | 1035 | 91.104 | 93.193 | 18.438 | 1.00 | 28.01 | C |
| ATOM | 3971 | O | SER | B | 1035 | 89.925 | 92.981 | 18.718 | 1.00 | 27.99 | O |
| ATOM | 3972 | N | ASP | B | 1036 | 91.500 | 94.258 | 17.739 | 1.00 | 27.82 | N |
| ATOM | 3973 | CA | ASP | B | 1036 | 90.536 | 95.160 | 17.098 | 1.00 | 27.95 | C |
| ATOM | 3974 | CB | ASP | B | 1036 | 91.221 | 96.409 | 16.532 | 1.00 | 27.58 | C |
| ATOM | 3975 | CG | ASP | B | 1036 | 91.436 | 97.495 | 17.578 | 1.00 | 29.28 | C |
| ATOM | 3976 | OD1 | ASP | B | 1036 | 90.926 | 97.367 | 18.713 | 1.00 | 30.50 | O |
| ATOM | 3977 | OD2 | ASP | B | 1036 | 92.117 | 98.490 | 17.255 | 1.00 | 30.50 | O |
| ATOM | 3978 | C | ASP | B | 1036 | 89.756 | 94.449 | 15.993 | 1.00 | 27.26 | C |
| ATOM | 3979 | O | ASP | B | 1036 | 88.570 | 94.712 | 15.803 | 1.00 | 27.24 | O |
| ATOM | 3980 | N | VAL | B | 1037 | 90.433 | 93.557 | 15.268 | 1.00 | 27.69 | N |
| ATOM | 3981 | CA | VAL | B | 1037 | 89.798 | 92.742 | 14.229 | 1.00 | 26.74 | C |
| ATOM | 3982 | CB | VAL | B | 1037 | 90.850 | 91.969 | 13.386 | 1.00 | 27.00 | C |
| ATOM | 3983 | CG1 | VAL | B | 1037 | 90.187 | 90.920 | 12.502 | 1.00 | 25.89 | C |
| ATOM | 3984 | CG2 | VAL | B | 1037 | 91.659 | 92.940 | 12.531 | 1.00 | 25.33 | C |
| ATOM | 3985 | C | VAL | B | 1037 | 88.753 | 91.783 | 14.822 | 1.00 | 26.70 | C |
| ATOM | 3986 | O | VAL | B | 1037 | 87.679 | 91.606 | 14.249 | 1.00 | 26.59 | O |
| ATOM | 3987 | N | TRP | B | 1038 | 89.078 | 91.174 | 15.962 | 1.00 | 26.80 | N |
| ATOM | 3988 | CA | TRP | B | 1038 | 88.131 | 90.325 | 16.682 | 1.00 | 27.82 | C |
| ATOM | 3989 | CB | TRP | B | 1038 | 88.762 | 89.748 | 17.959 | 1.00 | 28.11 | C |
| ATOM | 3990 | CG | TRP | B | 1038 | 87.800 | 88.935 | 18.804 | 1.00 | 29.39 | C |
| ATOM | 3991 | CD1 | TRP | B | 1038 | 86.763 | 89.414 | 19.566 | 1.00 | 28.54 | C |
| ATOM | 3992 | NE1 | TRP | B | 1038 | 86.110 | 88.374 | 20.184 | 1.00 | 29.41 | N |
| ATOM | 3993 | CE2 | TRP | B | 1038 | 86.720 | 87.197 | 19.839 | 1.00 | 29.24 | C |
| ATOM | 3994 | CD2 | TRP | B | 1038 | 87.789 | 87.510 | 18.967 | 1.00 | 28.61 | C |
| ATOM | 3995 | CE3 | TRP | B | 1038 | 88.581 | 86.467 | 18.464 | 1.00 | 27.57 | C |
| ATOM | 3996 | CZ3 | TRP | B | 1038 | 88.282 | 85.160 | 18.842 | 1.00 | 26.92 | C |
| ATOM | 3997 | CH2 | TRP | B | 1038 | 87.208 | 84.882 | 19.707 | 1.00 | 28.92 | C |
| ATOM | 3998 | CZ2 | TRP | B | 1038 | 86.421 | 85.883 | 20.217 | 1.00 | 29.54 | C |
| ATOM | 3999 | C | TRP | B | 1038 | 86.873 | 91.130 | 17.023 | 1.00 | 28.48 | C |
| ATOM | 4000 | O | TRP | B | 1038 | 85.757 | 90.705 | 16.718 | 1.00 | 28.50 | O |
| ATOM | 4001 | N | SER | B | 1039 | 87.068 | 92.294 | 17.643 | 1.00 | 28.36 | N |
| ATOM | 4002 | CA | SER | B | 1039 | 85.957 | 93.160 | 18.036 | 1.00 | 29.27 | C |
| ATOM | 4003 | CB | SER | B | 1039 | 86.458 | 94.350 | 18.856 | 1.00 | 29.08 | C |
| ATOM | 4004 | OG | SER | B | 1039 | 87.076 | 93.913 | 20.055 | 1.00 | 32.42 | O |
| ATOM | 4005 | C | SER | B | 1039 | 85.156 | 93.630 | 16.821 | 1.00 | 29.10 | C |
| ATOM | 4006 | O | SER | B | 1039 | 83.930 | 93.712 | 16.881 | 1.00 | 29.65 | O |
| ATOM | 4007 | N | PHE | B | 1040 | 85.851 | 93.914 | 15.718 | 1.00 | 29.24 | N |
| ATOM | 4008 | CA | PHE | B | 1040 | 85.192 | 94.260 | 14.456 | 1.00 | 29.30 | C |
| ATOM | 4009 | CB | PHE | B | 1040 | 86.214 | 94.561 | 13.355 | 1.00 | 30.00 | C |
| ATOM | 4010 | CG | PHE | B | 1040 | 85.607 | 94.630 | 11.982 | 1.00 | 31.39 | C |
| ATOM | 4011 | CD1 | PHE | B | 1040 | 84.955 | 95.781 | 11.555 | 1.00 | 33.07 | C |
| ATOM | 4012 | CE1 | PHE | B | 1040 | 84.376 | 95.840 | 10.292 | 1.00 | 34.82 | C |
| ATOM | 4013 | CZ | PHE | B | 1040 | 84.439 | 94.733 | 9.450 | 1.00 | 33.72 | C |
| ATOM | 4014 | CE2 | PHE | B | 1040 | 85.078 | 93.577 | 9.869 | 1.00 | 32.51 | C |
| ATOM | 4015 | CD2 | PHE | B | 1040 | 85.656 | 93.528 | 11.131 | 1.00 | 32.13 | C |
| ATOM | 4016 | C | PHE | B | 1040 | 84.215 | 93.176 | 13.978 | 1.00 | 28.87 | C |
| ATOM | 4017 | O | PHE | B | 1040 | 83.142 | 93.488 | 13.454 | 1.00 | 28.08 | O |

APPENDIX 1-continued

| | | | | | | | | | | | |
|---|---|---|---|---|---|---|---|---|---|---|---|
| ATOM | 4018 | N   | GLY | B | 1041 | 84.602 | 91.912 | 14.145 | 1.00 | 28.61 | N |
| ATOM | 4019 | CA  | GLY | B | 1041 | 83.745 | 90.783 | 13.800 | 1.00 | 28.04 | C |
| ATOM | 4020 | C   | GLY | B | 1041 | 82.472 | 90.778 | 14.629 | 1.00 | 27.99 | C |
| ATOM | 4021 | O   | GLY | B | 1041 | 81.397 | 90.434 | 14.131 | 1.00 | 27.73 | O |
| ATOM | 4022 | N   | VAL | B | 1042 | 82.600 | 91.159 | 15.900 | 1.00 | 27.24 | N |
| ATOM | 4023 | CA  | VAL | B | 1042 | 81.445 | 91.302 | 16.786 | 1.00 | 27.13 | C |
| ATOM | 4024 | CB  | VAL | B | 1042 | 81.865 | 91.489 | 18.267 | 1.00 | 27.15 | C |
| ATOM | 4025 | CG1 | VAL | B | 1042 | 80.645 | 91.472 | 19.186 | 1.00 | 26.17 | C |
| ATOM | 4026 | CG2 | VAL | B | 1042 | 82.840 | 90.397 | 18.682 | 1.00 | 27.13 | C |
| ATOM | 4027 | C   | VAL | B | 1042 | 80.565 | 92.463 | 16.312 | 1.00 | 26.92 | C |
| ATOM | 4028 | O   | VAL | B | 1042 | 79.342 | 92.350 | 16.318 | 1.00 | 28.31 | O |
| ATOM | 4029 | N   | VAL | B | 1043 | 81.192 | 93.561 | 15.883 | 1.00 | 26.22 | N |
| ATOM | 4030 | CA  | VAL | B | 1043 | 80.470 | 94.709 | 15.309 | 1.00 | 26.29 | C |
| ATOM | 4031 | CB  | VAL | B | 1043 | 81.430 | 95.872 | 14.915 | 1.00 | 25.67 | C |
| ATOM | 4032 | CG1 | VAL | B | 1043 | 80.704 | 96.950 | 14.104 | 1.00 | 25.74 | C |
| ATOM | 4033 | CG2 | VAL | B | 1043 | 82.076 | 96.481 | 16.150 | 1.00 | 24.81 | C |
| ATOM | 4034 | C   | VAL | B | 1043 | 79.643 | 94.272 | 14.096 | 1.00 | 27.00 | C |
| ATOM | 4035 | O   | VAL | B | 1043 | 78.475 | 94.646 | 13.970 | 1.00 | 26.99 | O |
| ATOM | 4036 | N   | LEU | B | 1044 | 80.259 | 93.475 | 13.221 | 1.00 | 26.26 | N |
| ATOM | 4037 | CA  | LEU | B | 1044 | 79.593 | 92.944 | 12.036 | 1.00 | 26.93 | C |
| ATOM | 4038 | CB  | LEU | B | 1044 | 80.594 | 92.196 | 11.146 | 1.00 | 27.41 | C |
| ATOM | 4039 | CG  | LEU | B | 1044 | 80.137 | 91.666 |  9.781 | 1.00 | 27.44 | C |
| ATOM | 4040 | CD1 | LEU | B | 1044 | 79.504 | 92.754 |  8.920 | 1.00 | 26.45 | C |
| ATOM | 4041 | CD2 | LEU | B | 1044 | 81.317 | 91.040 |  9.065 | 1.00 | 26.31 | C |
| ATOM | 4042 | C   | LEU | B | 1044 | 78.418 | 92.042 | 12.406 | 1.00 | 26.93 | C |
| ATOM | 4043 | O   | LEU | B | 1044 | 77.375 | 92.088 | 11.754 | 1.00 | 27.01 | O |
| ATOM | 4044 | N   | TYR | B | 1045 | 78.601 | 91.222 | 13.442 | 1.00 | 26.84 | N |
| ATOM | 4045 | CA  | TYR | B | 1045 | 77.508 | 90.450 | 14.038 | 1.00 | 27.56 | C |
| ATOM | 4046 | CB  | TYR | B | 1045 | 78.010 | 89.601 | 15.219 | 1.00 | 27.40 | C |
| ATOM | 4047 | CG  | TYR | B | 1045 | 76.897 | 88.947 | 16.013 | 1.00 | 28.16 | C |
| ATOM | 4048 | CD1 | TYR | B | 1045 | 76.383 | 87.707 | 15.639 | 1.00 | 27.10 | C |
| ATOM | 4049 | CE1 | TYR | B | 1045 | 75.357 | 87.106 | 16.357 | 1.00 | 29.57 | C |
| ATOM | 4050 | CZ  | TYR | B | 1045 | 74.832 | 87.749 | 17.463 | 1.00 | 28.81 | C |
| ATOM | 4051 | OH  | TYR | B | 1045 | 73.817 | 87.154 | 18.169 | 1.00 | 29.55 | O |
| ATOM | 4052 | CE2 | TYR | B | 1045 | 75.323 | 88.981 | 17.859 | 1.00 | 27.89 | C |
| ATOM | 4053 | CD2 | TYR | B | 1045 | 76.350 | 89.574 | 17.133 | 1.00 | 26.63 | C |
| ATOM | 4054 | C   | TYR | B | 1045 | 76.365 | 91.365 | 14.496 | 1.00 | 27.64 | C |
| ATOM | 4055 | O   | TYR | B | 1045 | 75.208 | 91.135 | 14.146 | 1.00 | 27.69 | O |
| ATOM | 4056 | N   | GLU | B | 1046 | 76.701 | 92.385 | 15.285 | 1.00 | 27.19 | N |
| ATOM | 4057 | CA  | GLU | B | 1046 | 75.726 | 93.362 | 15.774 | 1.00 | 28.22 | C |
| ATOM | 4058 | CB  | GLU | B | 1046 | 76.425 | 94.535 | 16.460 | 1.00 | 28.39 | C |
| ATOM | 4059 | CG  | GLU | B | 1046 | 77.053 | 94.247 | 17.805 | 1.00 | 29.16 | C |
| ATOM | 4060 | CD  | GLU | B | 1046 | 77.580 | 95.512 | 18.439 | 1.00 | 29.81 | C |
| ATOM | 4061 | OE1 | GLU | B | 1046 | 76.771 | 96.263 | 19.031 | 1.00 | 29.13 | O |
| ATOM | 4062 | OE2 | GLU | B | 1046 | 78.798 | 95.767 | 18.324 | 1.00 | 26.50 | O |
| ATOM | 4063 | C   | GLU | B | 1046 | 74.890 | 93.911 | 14.629 | 1.00 | 28.32 | C |
| ATOM | 4064 | O   | GLU | B | 1046 | 73.660 | 93.926 | 14.702 | 1.00 | 28.68 | O |
| ATOM | 4065 | N   | LEU | B | 1047 | 75.573 | 94.350 | 13.573 | 1.00 | 27.56 | N |
| ATOM | 4066 | CA  | LEU | B | 1047 | 74.920 | 94.944 | 12.409 | 1.00 | 28.20 | C |
| ATOM | 4067 | CB  | LEU | B | 1047 | 75.952 | 95.336 | 11.342 | 1.00 | 27.51 | C |
| ATOM | 4068 | CG  | LEU | B | 1047 | 76.925 | 96.472 | 11.674 | 1.00 | 28.94 | C |
| ATOM | 4069 | CD1 | LEU | B | 1047 | 77.880 | 96.713 | 10.511 | 1.00 | 29.99 | C |
| ATOM | 4070 | CD2 | LEU | B | 1047 | 76.188 | 97.759 | 12.040 | 1.00 | 29.86 | C |
| ATOM | 4071 | C   | LEU | B | 1047 | 73.862 | 94.024 | 11.815 | 1.00 | 27.54 | C |
| ATOM | 4072 | O   | LEU | B | 1047 | 72.738 | 94.449 | 11.555 | 1.00 | 27.51 | O |
| ATOM | 4073 | N   | PHE | B | 1048 | 74.220 | 92.757 | 11.632 | 1.00 | 28.08 | N |
| ATOM | 4074 | CA  | PHE | B | 1048 | 73.329 | 91.795 | 10.988 | 1.00 | 29.28 | C |
| ATOM | 4075 | CB  | PHE | B | 1048 | 74.135 | 90.720 | 10.243 | 1.00 | 28.69 | C |
| ATOM | 4076 | CG  | PHE | B | 1048 | 74.609 | 91.174 |  8.890 | 1.00 | 29.66 | C |
| ATOM | 4077 | CD1 | PHE | B | 1048 | 75.680 | 92.058 |  8.770 | 1.00 | 28.53 | C |
| ATOM | 4078 | CE1 | PHE | B | 1048 | 76.103 | 92.501 |  7.519 | 1.00 | 30.50 | C |
| ATOM | 4079 | CZ  | PHE | B | 1048 | 75.451 | 92.063 |  6.373 | 1.00 | 29.31 | C |
| ATOM | 4080 | CE2 | PHE | B | 1048 | 74.376 | 91.185 |  6.482 | 1.00 | 30.20 | C |
| ATOM | 4081 | CD2 | PHE | B | 1048 | 73.958 | 90.750 |  7.735 | 1.00 | 28.51 | C |
| ATOM | 4082 | C   | PHE | B | 1048 | 72.240 | 91.215 | 11.894 | 1.00 | 29.75 | C |
| ATOM | 4083 | O   | PHE | B | 1048 | 71.347 | 90.514 | 11.418 | 1.00 | 30.41 | O |
| ATOM | 4084 | N   | THR | B | 1049 | 72.304 | 91.525 | 13.187 | 1.00 | 30.72 | N |
| ATOM | 4085 | CA  | THR | B | 1049 | 71.198 | 91.233 | 14.105 | 1.00 | 31.32 | C |
| ATOM | 4086 | CB  | THR | B | 1049 | 71.679 | 90.959 | 15.549 | 1.00 | 31.40 | C |
| ATOM | 4087 | OG1 | THR | B | 1049 | 72.339 | 92.122 | 16.068 | 1.00 | 31.61 | O |
| ATOM | 4088 | CG2 | THR | B | 1049 | 72.610 | 89.764 | 15.600 | 1.00 | 32.20 | C |
| ATOM | 4089 | C   | THR | B | 1049 | 70.215 | 92.399 | 14.163 | 1.00 | 31.98 | C |
| ATOM | 4090 | O   | THR | B | 1049 | 69.133 | 92.275 | 14.743 | 1.00 | 32.11 | O |
| ATOM | 4091 | N   | TYR | B | 1050 | 70.606 | 93.530 | 13.574 | 1.00 | 32.64 | N |
| ATOM | 4092 | CA  | TYR | B | 1050 | 69.825 | 94.775 | 13.625 | 1.00 | 33.44 | C |
| ATOM | 4093 | CB  | TYR | B | 1050 | 68.526 | 94.650 | 12.812 | 1.00 | 32.90 | C |
| ATOM | 4094 | CG  | TYR | B | 1050 | 68.732 | 94.646 | 11.315 | 1.00 | 32.02 | C |
| ATOM | 4095 | CD1 | TYR | B | 1050 | 68.969 | 93.457 | 10.625 | 1.00 | 33.01 | C |
| ATOM | 4096 | CE1 | TYR | B | 1050 | 69.159 | 93.453 |  9.243 | 1.00 | 33.31 | C |

APPENDIX 1-continued

| ATOM | 4097 | CZ | TYR | B | 1050 | 69.107 | 94.651 | 8.542 | 1.00 | 32.34 | C |
|---|---|---|---|---|---|---|---|---|---|---|---|
| ATOM | 4098 | OH | TYR | B | 1050 | 69.291 | 94.659 | 7.177 | 1.00 | 32.00 | O |
| ATOM | 4099 | CE2 | TYR | B | 1050 | 68.875 | 95.841 | 9.208 | 1.00 | 30.08 | C |
| ATOM | 4100 | CD2 | TYR | B | 1050 | 68.688 | 95.833 | 10.585 | 1.00 | 32.23 | C |
| ATOM | 4101 | C | TYR | B | 1050 | 69.540 | 95.218 | 15.066 | 1.00 | 34.48 | C |
| ATOM | 4102 | O | TYR | B | 1050 | 68.544 | 95.895 | 15.339 | 1.00 | 34.29 | O |
| ATOM | 4103 | N | ILE | B | 1051 | 70.440 | 94.831 | 15.971 | 1.00 | 35.78 | N |
| ATOM | 4104 | CA | ILE | B | 1051 | 70.354 | 95.136 | 17.407 | 1.00 | 37.43 | C |
| ATOM | 4105 | CB | ILE | B | 1051 | 70.669 | 96.645 | 17.727 | 1.00 | 37.10 | C |
| ATOM | 4106 | CG1 | ILE | B | 1051 | 71.702 | 97.243 | 16.748 | 1.00 | 35.99 | C |
| ATOM | 4107 | CD1 | ILE | B | 1051 | 73.126 | 96.678 | 16.843 | 1.00 | 37.25 | C |
| ATOM | 4108 | CG2 | ILE | B | 1051 | 71.093 | 96.826 | 19.193 | 1.00 | 36.79 | C |
| ATOM | 4109 | C | ILE | B | 1051 | 69.022 | 94.677 | 18.030 | 1.00 | 39.23 | C |
| ATOM | 4110 | O | ILE | B | 1051 | 68.407 | 95.388 | 18.830 | 1.00 | 39.34 | O |
| ATOM | 4111 | N | GLU | B | 1052 | 68.585 | 93.481 | 17.637 | 1.00 | 41.27 | N |
| ATOM | 4112 | CA | GLU | B | 1052 | 67.469 | 92.802 | 18.287 | 1.00 | 43.94 | C |
| ATOM | 4113 | CB | GLU | B | 1052 | 67.077 | 91.553 | 17.492 | 1.00 | 43.70 | C |
| ATOM | 4114 | CG | GLU | B | 1052 | 65.692 | 90.999 | 17.809 | 1.00 | 46.25 | C |
| ATOM | 4115 | CD | GLU | B | 1052 | 65.419 | 89.649 | 17.153 | 1.00 | 46.32 | C |
| ATOM | 4116 | OE1 | GLU | B | 1052 | 64.494 | 88.945 | 17.614 | 1.00 | 50.70 | O |
| ATOM | 4117 | OE2 | GLU | B | 1052 | 66.123 | 89.285 | 16.183 | 1.00 | 48.91 | O |
| ATOM | 4118 | C | GLU | B | 1052 | 67.931 | 92.432 | 19.695 | 1.00 | 44.41 | C |
| ATOM | 4119 | O | GLU | B | 1052 | 68.927 | 91.723 | 19.856 | 1.00 | 44.10 | O |
| ATOM | 4120 | N | LYS | B | 1053 | 67.217 | 92.929 | 20.706 | 1.00 | 45.76 | N |
| ATOM | 4121 | CA | LYS | B | 1053 | 67.664 | 92.862 | 22.110 | 1.00 | 46.63 | C |
| ATOM | 4122 | CB | LYS | B | 1053 | 66.602 | 93.448 | 23.049 | 1.00 | 46.99 | C |
| ATOM | 4123 | CG | LYS | B | 1053 | 66.690 | 94.959 | 23.219 | 1.00 | 48.55 | C |
| ATOM | 4124 | CD | LYS | B | 1053 | 65.461 | 95.516 | 23.936 | 1.00 | 48.22 | C |
| ATOM | 4125 | CE | LYS | B | 1053 | 65.720 | 96.910 | 24.503 | 1.00 | 51.20 | C |
| ATOM | 4126 | NZ | LYS | B | 1053 | 66.066 | 97.915 | 23.455 | 1.00 | 52.27 | N |
| ATOM | 4127 | C | LYS | B | 1053 | 68.100 | 91.481 | 22.599 | 1.00 | 46.05 | C |
| ATOM | 4128 | O | LYS | B | 1053 | 69.127 | 91.352 | 23.275 | 1.00 | 46.74 | O |
| ATOM | 4129 | N | SER | B | 1054 | 67.326 | 90.457 | 22.249 | 1.00 | 44.93 | N |
| ATOM | 4130 | CA | SER | B | 1054 | 67.616 | 89.086 | 22.665 | 1.00 | 44.19 | C |
| ATOM | 4131 | CB | SER | B | 1054 | 66.384 | 88.202 | 22.457 | 1.00 | 44.34 | C |
| ATOM | 4132 | OG | SER | B | 1054 | 66.028 | 88.151 | 21.086 | 1.00 | 45.80 | O |
| ATOM | 4133 | C | SER | B | 1054 | 68.818 | 88.483 | 21.932 | 1.00 | 43.33 | C |
| ATOM | 4134 | O | SER | B | 1054 | 69.323 | 87.427 | 22.320 | 1.00 | 43.09 | O |
| ATOM | 4135 | N | LYS | B | 1055 | 69.273 | 89.161 | 20.881 | 1.00 | 42.41 | N |
| ATOM | 4136 | CA | LYS | B | 1055 | 70.322 | 88.632 | 20.010 | 1.00 | 41.24 | C |
| ATOM | 4137 | CB | LYS | B | 1055 | 69.901 | 88.749 | 18.536 | 1.00 | 41.48 | C |
| ATOM | 4138 | CG | LYS | B | 1055 | 68.615 | 88.008 | 18.169 | 1.00 | 41.99 | C |
| ATOM | 4139 | CD | LYS | B | 1055 | 68.830 | 86.501 | 18.067 | 1.00 | 44.92 | C |
| ATOM | 4140 | CE | LYS | B | 1055 | 67.613 | 85.793 | 17.484 | 1.00 | 47.00 | C |
| ATOM | 4141 | NZ | LYS | B | 1055 | 66.471 | 85.747 | 18.436 | 1.00 | 47.75 | N |
| ATOM | 4142 | C | LYS | B | 1055 | 71.690 | 89.287 | 20.226 | 1.00 | 40.14 | C |
| ATOM | 4143 | O | LYS | B | 1055 | 72.648 | 88.960 | 19.525 | 1.00 | 39.71 | O |
| ATOM | 4144 | N | SER | B | 1056 | 71.776 | 90.198 | 21.196 | 1.00 | 39.07 | N |
| ATOM | 4145 | CA | SER | B | 1056 | 73.025 | 90.902 | 21.513 | 1.00 | 37.84 | C |
| ATOM | 4146 | CB | SER | B | 1056 | 72.782 | 91.964 | 22.593 | 1.00 | 38.24 | C |
| ATOM | 4147 | OG | SER | B | 1056 | 72.630 | 91.375 | 23.874 | 1.00 | 37.23 | O |
| ATOM | 4148 | C | SER | B | 1056 | 74.134 | 89.942 | 21.966 | 1.00 | 36.93 | C |
| ATOM | 4149 | O | SER | B | 1056 | 73.838 | 88.864 | 22.483 | 1.00 | 36.82 | O |
| ATOM | 4150 | N | PRO | B | 1057 | 75.414 | 90.322 | 21.756 | 1.00 | 36.00 | N |
| ATOM | 4151 | CA | PRO | B | 1057 | 76.533 | 89.509 | 22.253 | 1.00 | 35.70 | C |
| ATOM | 4152 | CB | PRO | B | 1057 | 77.760 | 90.387 | 21.973 | 1.00 | 35.68 | C |
| ATOM | 4153 | CG | PRO | B | 1057 | 77.352 | 91.204 | 20.790 | 1.00 | 35.23 | C |
| ATOM | 4154 | CD | PRO | B | 1057 | 75.892 | 91.501 | 21.005 | 1.00 | 35.69 | C |
| ATOM | 4155 | C | PRO | B | 1057 | 76.440 | 89.108 | 23.743 | 1.00 | 35.70 | C |
| ATOM | 4156 | O | PRO | B | 1057 | 76.595 | 87.922 | 24.043 | 1.00 | 34.96 | O |
| ATOM | 4157 | N | PRO | B | 1058 | 76.174 | 90.066 | 24.668 | 1.00 | 35.94 | N |
| ATOM | 4158 | CA | PRO | B | 1058 | 76.066 | 89.632 | 26.065 | 1.00 | 36.41 | C |
| ATOM | 4159 | CB | PRO | B | 1058 | 75.763 | 90.933 | 26.821 | 1.00 | 36.50 | C |
| ATOM | 4160 | CG | PRO | B | 1058 | 76.269 | 92.010 | 25.936 | 1.00 | 37.17 | C |
| ATOM | 4161 | CD | PRO | B | 1058 | 75.971 | 91.522 | 24.553 | 1.00 | 36.21 | C |
| ATOM | 4162 | C | PRO | B | 1058 | 74.946 | 88.616 | 26.281 | 1.00 | 36.51 | C |
| ATOM | 4163 | O | PRO | B | 1058 | 75.164 | 87.607 | 26.950 | 1.00 | 36.19 | O |
| ATOM | 4164 | N | ALA | B | 1059 | 73.776 | 88.871 | 25.698 | 1.00 | 36.74 | N |
| ATOM | 4165 | CA | ALA | B | 1059 | 72.629 | 87.967 | 25.816 | 1.00 | 37.09 | C |
| ATOM | 4166 | CB | ALA | B | 1059 | 71.386 | 88.590 | 25.183 | 1.00 | 37.28 | C |
| ATOM | 4167 | C | ALA | B | 1059 | 72.888 | 86.577 | 25.228 | 1.00 | 37.21 | C |
| ATOM | 4168 | O | ALA | B | 1059 | 72.478 | 85.572 | 25.809 | 1.00 | 37.17 | O |
| ATOM | 4169 | N | GLU | B | 1060 | 73.565 | 86.528 | 24.082 | 1.00 | 37.34 | N |
| ATOM | 4170 | CA | GLU | B | 1060 | 73.839 | 85.263 | 23.395 | 1.00 | 37.99 | C |
| ATOM | 4171 | CB | GLU | B | 1060 | 74.177 | 85.501 | 21.919 | 1.00 | 38.32 | C |
| ATOM | 4172 | CG | GLU | B | 1060 | 72.981 | 85.884 | 21.051 | 1.00 | 39.50 | C |
| ATOM | 4173 | CD | GLU | B | 1060 | 72.133 | 84.694 | 20.618 | 1.00 | 42.72 | C |
| ATOM | 4174 | OE1 | GLU | B | 1060 | 72.511 | 83.530 | 20.884 | 1.00 | 44.62 | O |
| ATOM | 4175 | OE2 | GLU | B | 1060 | 71.078 | 84.928 | 19.997 | 1.00 | 45.69 | O |

APPENDIX 1-continued

| ATOM | 4176 | C | GLU | B | 1060 | 74.942 | 84.443 | 24.065 | 1.00 | 38.32 | C |
|---|---|---|---|---|---|---|---|---|---|---|---|
| ATOM | 4177 | O | GLU | B | 1060 | 74.846 | 83.216 | 24.138 | 1.00 | 38.29 | O |
| ATOM | 4178 | N | PHE | B | 1061 | 75.987 | 85.117 | 24.542 | 1.00 | 38.58 | N |
| ATOM | 4179 | CA | PHE | B | 1061 | 77.051 | 84.442 | 25.281 | 1.00 | 39.14 | C |
| ATOM | 4180 | CB | PHE | B | 1061 | 78.261 | 85.358 | 25.487 | 1.00 | 38.44 | C |
| ATOM | 4181 | CG | PHE | B | 1061 | 79.221 | 85.390 | 24.320 | 1.00 | 36.41 | C |
| ATOM | 4182 | CD1 | PHE | B | 1061 | 79.606 | 86.602 | 23.755 | 1.00 | 36.28 | C |
| ATOM | 4183 | CE1 | PHE | B | 1061 | 80.504 | 86.644 | 22.685 | 1.00 | 35.58 | C |
| ATOM | 4184 | CZ | PHE | B | 1061 | 81.021 | 85.462 | 22.171 | 1.00 | 33.96 | C |
| ATOM | 4185 | CE2 | PHE | B | 1061 | 80.645 | 84.244 | 22.726 | 1.00 | 35.47 | C |
| ATOM | 4186 | CD2 | PHE | B | 1061 | 79.754 | 84.213 | 23.800 | 1.00 | 34.65 | C |
| ATOM | 4187 | C | PHE | B | 1061 | 76.550 | 83.912 | 26.626 | 1.00 | 40.81 | C |
| ATOM | 4188 | O | PHE | B | 1061 | 76.857 | 82.779 | 26.998 | 1.00 | 40.73 | O |
| ATOM | 4189 | N | MET | B | 1062 | 75.774 | 84.729 | 27.341 | 1.00 | 42.43 | N |
| ATOM | 4190 | CA | MET | B | 1062 | 75.202 | 84.334 | 28.634 | 1.00 | 44.75 | C |
| ATOM | 4191 | CB | MET | B | 1062 | 74.522 | 85.520 | 29.328 | 1.00 | 44.54 | C |
| ATOM | 4192 | CG | MET | B | 1062 | 75.476 | 86.570 | 29.899 | 1.00 | 45.47 | C |
| ATOM | 4193 | SD | MET | B | 1062 | 76.672 | 85.934 | 31.097 | 1.00 | 49.13 | S |
| ATOM | 4194 | CE | MET | B | 1062 | 75.614 | 85.577 | 32.502 | 1.00 | 46.89 | C |
| ATOM | 4195 | C | MET | B | 1062 | 74.218 | 83.170 | 28.508 | 1.00 | 46.45 | C |
| ATOM | 4196 | O | MET | B | 1062 | 74.021 | 82.413 | 29.459 | 1.00 | 46.47 | O |
| ATOM | 4197 | N | ARG | B | 1063 | 73.609 | 83.035 | 27.332 | 1.00 | 48.76 | N |
| ATOM | 4198 | CA | ARG | B | 1063 | 72.679 | 81.945 | 27.053 | 1.00 | 51.08 | C |
| ATOM | 4199 | CB | ARG | B | 1063 | 71.874 | 82.239 | 25.783 | 1.00 | 51.55 | C |
| ATOM | 4200 | CG | ARG | B | 1063 | 70.639 | 81.370 | 25.601 | 1.00 | 54.02 | C |
| ATOM | 4201 | CD | ARG | B | 1063 | 69.861 | 81.780 | 24.361 | 1.00 | 57.16 | C |
| ATOM | 4202 | NE | ARG | B | 1063 | 68.639 | 80.994 | 24.195 | 1.00 | 61.30 | N |
| ATOM | 4203 | CZ | ARG | B | 1063 | 67.781 | 81.130 | 23.185 | 1.00 | 62.41 | C |
| ATOM | 4204 | NH1 | ARG | B | 1063 | 67.998 | 82.026 | 22.228 | 1.00 | 62.48 | N |
| ATOM | 4205 | NH2 | ARG | B | 1063 | 66.700 | 80.363 | 23.132 | 1.00 | 62.41 | N |
| ATOM | 4206 | C | ARG | B | 1063 | 73.405 | 80.603 | 26.932 | 1.00 | 52.24 | C |
| ATOM | 4207 | O | ARG | B | 1063 | 73.012 | 79.625 | 27.570 | 1.00 | 52.58 | O |
| ATOM | 4208 | N | MET | B | 1064 | 74.465 | 80.564 | 26.125 | 1.00 | 53.33 | N |
| ATOM | 4209 | CA | MET | B | 1064 | 75.213 | 79.321 | 25.898 | 1.00 | 54.54 | C |
| ATOM | 4210 | CB | MET | B | 1064 | 75.902 | 79.316 | 24.524 | 1.00 | 54.57 | C |
| ATOM | 4211 | CG | MET | B | 1064 | 76.825 | 80.492 | 24.245 | 1.00 | 55.18 | C |
| ATOM | 4212 | SD | MET | B | 1064 | 77.156 | 80.714 | 22.483 | 1.00 | 54.18 | S |
| ATOM | 4213 | CE | MET | B | 1064 | 78.109 | 79.244 | 22.100 | 1.00 | 54.27 | C |
| ATOM | 4214 | C | MET | B | 1064 | 76.189 | 78.978 | 27.030 | 1.00 | 55.52 | C |
| ATOM | 4215 | O | MET | B | 1064 | 76.655 | 77.841 | 27.130 | 1.00 | 55.15 | O |
| ATOM | 4216 | N | ILE | B | 1065 | 76.491 | 79.961 | 27.875 | 1.00 | 56.91 | N |
| ATOM | 4217 | CA | ILE | B | 1065 | 77.203 | 79.705 | 29.125 | 1.00 | 58.48 | C |
| ATOM | 4218 | CB | ILE | B | 1065 | 77.946 | 80.964 | 29.649 | 1.00 | 58.22 | C |
| ATOM | 4219 | CG1 | ILE | B | 1065 | 79.168 | 81.270 | 28.777 | 1.00 | 58.01 | C |
| ATOM | 4220 | CD1 | ILE | B | 1065 | 79.712 | 82.683 | 28.934 | 1.00 | 57.25 | C |
| ATOM | 4221 | CG2 | ILE | B | 1065 | 78.380 | 80.769 | 31.099 | 1.00 | 58.45 | C |
| ATOM | 4222 | C | ILE | B | 1065 | 76.202 | 79.209 | 30.168 | 1.00 | 59.93 | C |
| ATOM | 4223 | O | ILE | B | 1065 | 76.451 | 78.219 | 30.861 | 1.00 | 60.15 | O |
| ATOM | 4224 | N | GLY | B | 1066 | 75.066 | 79.899 | 30.255 | 1.00 | 61.42 | N |
| ATOM | 4225 | CA | GLY | B | 1066 | 74.030 | 79.598 | 31.236 | 1.00 | 63.00 | C |
| ATOM | 4226 | C | GLY | B | 1066 | 73.819 | 80.779 | 32.161 | 1.00 | 64.46 | C |
| ATOM | 4227 | O | GLY | B | 1066 | 74.760 | 81.239 | 32.811 | 1.00 | 64.57 | O |
| ATOM | 4228 | N | ASN | B | 1067 | 72.585 | 81.276 | 32.210 | 1.00 | 65.89 | N |
| ATOM | 4229 | CA | ASN | B | 1067 | 72.223 | 82.392 | 33.090 | 1.00 | 67.25 | C |
| ATOM | 4230 | CB | ASN | B | 1067 | 70.837 | 82.937 | 32.725 | 1.00 | 67.42 | C |
| ATOM | 4231 | CG | ASN | B | 1067 | 70.841 | 83.730 | 31.428 | 1.00 | 67.84 | C |
| ATOM | 4232 | OD1 | ASN | B | 1067 | 71.583 | 84.702 | 31.279 | 1.00 | 68.54 | O |
| ATOM | 4233 | ND2 | ASN | B | 1067 | 69.998 | 83.323 | 30.485 | 1.00 | 68.08 | N |
| ATOM | 4234 | C | ASN | B | 1067 | 72.280 | 82.027 | 34.576 | 1.00 | 68.04 | C |
| ATOM | 4235 | O | ASN | B | 1067 | 72.264 | 82.906 | 35.443 | 1.00 | 68.22 | O |
| ATOM | 4236 | N | ASP | B | 1068 | 72.363 | 80.727 | 34.854 | 1.00 | 68.90 | N |
| ATOM | 4237 | CA | ASP | B | 1068 | 72.438 | 80.201 | 36.217 | 1.00 | 69.70 | C |
| ATOM | 4238 | CB | ASP | B | 1068 | 72.036 | 78.719 | 36.236 | 1.00 | 69.95 | C |
| ATOM | 4239 | CG | ASP | B | 1068 | 70.666 | 78.470 | 35.617 | 1.00 | 70.89 | C |
| ATOM | 4240 | OD1 | ASP | B | 1068 | 70.470 | 78.801 | 34.426 | 1.00 | 70.65 | O |
| ATOM | 4241 | OD2 | ASP | B | 1068 | 69.787 | 77.930 | 36.322 | 1.00 | 71.83 | O |
| ATOM | 4242 | C | ASP | B | 1068 | 73.827 | 80.383 | 36.841 | 1.00 | 70.02 | C |
| ATOM | 4243 | O | ASP | B | 1068 | 74.046 | 80.019 | 38.001 | 1.00 | 70.24 | O |
| ATOM | 4244 | N | ALA | B | 1069 | 74.754 | 80.948 | 36.068 | 1.00 | 70.20 | N |
| ATOM | 4245 | CA | ALA | B | 1069 | 76.121 | 81.206 | 36.527 | 1.00 | 70.18 | C |
| ATOM | 4246 | CB | ALA | B | 1069 | 77.047 | 81.423 | 35.332 | 1.00 | 70.23 | C |
| ATOM | 4247 | C | ALA | B | 1069 | 76.193 | 82.396 | 37.486 | 1.00 | 70.08 | C |
| ATOM | 4248 | O | ALA | B | 1069 | 75.229 | 83.155 | 37.624 | 1.00 | 70.02 | O |
| ATOM | 4249 | N | GLN | B | 1070 | 77.344 | 82.553 | 38.140 | 1.00 | 69.82 | N |
| ATOM | 4250 | CA | GLN | B | 1070 | 77.570 | 83.645 | 39.091 | 1.00 | 69.38 | C |
| ATOM | 4251 | CB | GLN | B | 1070 | 78.675 | 83.272 | 40.090 | 1.00 | 69.34 | C |
| ATOM | 4252 | CG | GLN | B | 1070 | 78.261 | 82.221 | 41.119 | 1.00 | 70.15 | C |
| ATOM | 4253 | CD | GLN | B | 1070 | 79.256 | 82.071 | 42.262 | 1.00 | 69.98 | C |
| ATOM | 4254 | OE1 | GLN | B | 1070 | 80.426 | 82.443 | 42.145 | 1.00 | 70.68 | O |

APPENDIX 1-continued

| ATOM | 4255 | NE2 | GLN | B | 1070 | 78.790 | 81.517 | 43.377 | 1.00 | 70.41 | N |
|---|---|---|---|---|---|---|---|---|---|---|---|
| ATOM | 4256 | C | GLN | B | 1070 | 77.881 | 84.977 | 38.394 | 1.00 | 68.40 | C |
| ATOM | 4257 | O | GLN | B | 1070 | 77.381 | 85.245 | 37.299 | 1.00 | 68.37 | O |
| ATOM | 4258 | N | GLY | B | 1071 | 78.697 | 85.809 | 39.040 | 1.00 | 67.29 | N |
| ATOM | 4259 | CA | GLY | B | 1071 | 79.034 | 87.133 | 38.524 | 1.00 | 65.90 | C |
| ATOM | 4260 | C | GLY | B | 1071 | 80.490 | 87.268 | 38.124 | 1.00 | 64.90 | C |
| ATOM | 4261 | O | GLY | B | 1071 | 80.796 | 87.642 | 36.991 | 1.00 | 65.08 | O |
| ATOM | 4262 | N | GLN | B | 1072 | 81.388 | 86.967 | 39.060 | 1.00 | 63.51 | N |
| ATOM | 4263 | CA | GLN | B | 1072 | 82.831 | 87.035 | 38.809 | 1.00 | 62.30 | C |
| ATOM | 4264 | CB | GLN | B | 1072 | 83.608 | 87.137 | 40.128 | 1.00 | 62.39 | C |
| ATOM | 4265 | CG | GLN | B | 1072 | 83.376 | 88.439 | 40.895 | 1.00 | 63.12 | C |
| ATOM | 4266 | CD | GLN | B | 1072 | 84.322 | 88.612 | 42.073 | 1.00 | 63.32 | C |
| ATOM | 4267 | OE1 | GLN | B | 1072 | 85.543 | 88.521 | 41.927 | 1.00 | 65.49 | O |
| ATOM | 4268 | NE2 | GLN | B | 1072 | 83.759 | 88.875 | 43.248 | 1.00 | 64.66 | N |
| ATOM | 4269 | C | GLN | B | 1072 | 83.322 | 85.838 | 37.991 | 1.00 | 60.41 | C |
| ATOM | 4270 | O | GLN | B | 1072 | 84.422 | 85.864 | 37.431 | 1.00 | 60.43 | O |
| ATOM | 4271 | N | MET | B | 1073 | 82.490 | 84.802 | 37.922 | 1.00 | 58.17 | N |
| ATOM | 4272 | CA | MET | B | 1073 | 82.800 | 83.571 | 37.197 | 1.00 | 56.11 | C |
| ATOM | 4273 | CB | MET | B | 1073 | 81.997 | 82.405 | 37.781 | 1.00 | 56.47 | C |
| ATOM | 4274 | CG | MET | B | 1073 | 82.241 | 82.161 | 39.262 | 1.00 | 57.88 | C |
| ATOM | 4275 | SD | MET | B | 1073 | 83.732 | 81.203 | 39.574 | 1.00 | 60.40 | S |
| ATOM | 4276 | CE | MET | B | 1073 | 83.092 | 79.543 | 39.356 | 1.00 | 60.72 | C |
| ATOM | 4277 | C | MET | B | 1073 | 82.519 | 83.689 | 35.698 | 1.00 | 54.10 | C |
| ATOM | 4278 | O | MET | B | 1073 | 82.992 | 82.866 | 34.909 | 1.00 | 53.74 | O |
| ATOM | 4279 | N | ILE | B | 1074 | 81.753 | 84.712 | 35.318 | 1.00 | 51.62 | N |
| ATOM | 4280 | CA | ILE | B | 1074 | 81.326 | 84.923 | 33.929 | 1.00 | 49.50 | C |
| ATOM | 4281 | CB | ILE | B | 1074 | 80.471 | 86.220 | 33.778 | 1.00 | 49.46 | C |
| ATOM | 4282 | CG1 | ILE | B | 1074 | 79.140 | 86.071 | 34.529 | 1.00 | 50.27 | C |
| ATOM | 4283 | CD1 | ILE | B | 1074 | 78.380 | 87.376 | 34.751 | 1.00 | 49.95 | C |
| ATOM | 4284 | CG2 | ILE | B | 1074 | 80.227 | 86.555 | 32.302 | 1.00 | 49.62 | C |
| ATOM | 4285 | C | ILE | B | 1074 | 82.503 | 84.913 | 32.945 | 1.00 | 47.20 | C |
| ATOM | 4286 | O | ILE | B | 1074 | 82.480 | 84.174 | 31.958 | 1.00 | 46.48 | O |
| ATOM | 4287 | N | VAL | B | 1075 | 83.524 | 85.720 | 33.231 | 1.00 | 45.29 | N |
| ATOM | 4288 | CA | VAL | B | 1075 | 84.699 | 85.848 | 32.363 | 1.00 | 43.88 | C |
| ATOM | 4289 | CB | VAL | B | 1075 | 85.716 | 86.900 | 32.902 | 1.00 | 43.90 | C |
| ATOM | 4290 | CG1 | VAL | B | 1075 | 86.901 | 87.050 | 31.955 | 1.00 | 44.88 | C |
| ATOM | 4291 | CG2 | VAL | B | 1075 | 85.048 | 88.250 | 33.101 | 1.00 | 45.46 | C |
| ATOM | 4292 | C | VAL | B | 1075 | 85.398 | 84.499 | 32.150 | 1.00 | 42.41 | C |
| ATOM | 4293 | O | VAL | B | 1075 | 85.773 | 84.160 | 31.027 | 1.00 | 41.64 | O |
| ATOM | 4294 | N | PHE | B | 1076 | 85.551 | 83.732 | 33.228 | 1.00 | 40.95 | N |
| ATOM | 4295 | CA | PHE | B | 1076 | 86.253 | 82.450 | 33.169 | 1.00 | 39.97 | C |
| ATOM | 4296 | CB | PHE | B | 1076 | 86.596 | 81.950 | 34.575 | 1.00 | 40.20 | C |
| ATOM | 4297 | CG | PHE | B | 1076 | 87.573 | 82.829 | 35.304 | 1.00 | 41.27 | C |
| ATOM | 4298 | CD1 | PHE | B | 1076 | 87.161 | 83.593 | 36.391 | 1.00 | 42.11 | C |
| ATOM | 4299 | CE1 | PHE | B | 1076 | 88.063 | 84.411 | 37.069 | 1.00 | 42.54 | C |
| ATOM | 4300 | CZ | PHE | B | 1076 | 89.391 | 84.475 | 36.652 | 1.00 | 42.89 | C |
| ATOM | 4301 | CE2 | PHE | B | 1076 | 89.812 | 83.720 | 35.562 | 1.00 | 42.81 | C |
| ATOM | 4302 | CD2 | PHE | B | 1076 | 88.904 | 82.903 | 34.895 | 1.00 | 41.46 | C |
| ATOM | 4303 | C | PHE | B | 1076 | 85.496 | 81.389 | 32.373 | 1.00 | 38.72 | C |
| ATOM | 4304 | O | PHE | B | 1076 | 86.109 | 80.585 | 31.666 | 1.00 | 38.34 | O |
| ATOM | 4305 | N | HIS | B | 1077 | 84.169 | 81.395 | 32.486 | 1.00 | 37.62 | N |
| ATOM | 4306 | CA | HIS | B | 1077 | 83.323 | 80.549 | 31.646 | 1.00 | 36.38 | C |
| ATOM | 4307 | CB | HIS | B | 1077 | 81.875 | 80.565 | 32.138 | 1.00 | 36.49 | C |
| ATOM | 4308 | CG | HIS | B | 1077 | 81.652 | 79.780 | 33.394 | 1.00 | 35.37 | C |
| ATOM | 4309 | ND1 | HIS | B | 1077 | 81.710 | 78.404 | 33.432 | 1.00 | 35.33 | N |
| ATOM | 4310 | CE1 | HIS | B | 1077 | 81.471 | 77.989 | 34.664 | 1.00 | 35.02 | C |
| ATOM | 4311 | NE2 | HIS | B | 1077 | 81.252 | 79.046 | 35.425 | 1.00 | 33.46 | N |
| ATOM | 4312 | CD2 | HIS | B | 1077 | 81.358 | 80.179 | 34.654 | 1.00 | 35.75 | C |
| ATOM | 4313 | C | HIS | B | 1077 | 83.393 | 80.995 | 30.184 | 1.00 | 35.82 | C |
| ATOM | 4314 | O | HIS | B | 1077 | 83.422 | 80.161 | 29.276 | 1.00 | 35.43 | O |
| ATOM | 4315 | N | LEU | B | 1078 | 83.423 | 82.312 | 29.971 | 1.00 | 34.76 | N |
| ATOM | 4316 | CA | LEU | B | 1078 | 83.556 | 82.891 | 28.633 | 1.00 | 34.12 | C |
| ATOM | 4317 | CB | LEU | B | 1078 | 83.412 | 84.420 | 28.681 | 1.00 | 33.95 | C |
| ATOM | 4318 | CG | LEU | B | 1078 | 83.582 | 85.232 | 27.386 | 1.00 | 34.48 | C |
| ATOM | 4319 | CD1 | LEU | B | 1078 | 82.554 | 84.846 | 26.326 | 1.00 | 33.35 | C |
| ATOM | 4320 | CD2 | LEU | B | 1078 | 83.512 | 86.722 | 27.680 | 1.00 | 33.90 | C |
| ATOM | 4321 | C | LEU | B | 1078 | 84.880 | 82.488 | 27.983 | 1.00 | 33.79 | C |
| ATOM | 4322 | O | LEU | B | 1078 | 84.906 | 82.101 | 26.813 | 1.00 | 33.60 | O |
| ATOM | 4323 | N | ILE | B | 1079 | 85.967 | 82.574 | 28.751 | 1.00 | 33.63 | N |
| ATOM | 4324 | CA | ILE | B | 1079 | 87.299 | 82.171 | 28.287 | 1.00 | 33.72 | C |
| ATOM | 4325 | CB | ILE | B | 1079 | 88.388 | 82.433 | 29.370 | 1.00 | 33.67 | C |
| ATOM | 4326 | CG1 | ILE | B | 1079 | 88.659 | 83.936 | 29.491 | 1.00 | 32.84 | C |
| ATOM | 4327 | CD1 | ILE | B | 1079 | 89.401 | 84.342 | 30.758 | 1.00 | 33.78 | C |
| ATOM | 4328 | CG2 | ILE | B | 1079 | 89.688 | 81.685 | 29.051 | 1.00 | 31.75 | C |
| ATOM | 4329 | C | ILE | B | 1079 | 87.306 | 80.709 | 27.832 | 1.00 | 34.06 | C |
| ATOM | 4330 | O | ILE | B | 1079 | 87.792 | 80.398 | 26.744 | 1.00 | 34.56 | O |
| ATOM | 4331 | N | GLU | B | 1080 | 86.748 | 79.825 | 28.659 | 1.00 | 34.49 | N |
| ATOM | 4332 | CA | GLU | B | 1080 | 86.659 | 78.400 | 28.328 | 1.00 | 35.23 | C |
| ATOM | 4333 | CB | GLU | B | 1080 | 86.151 | 77.583 | 29.523 | 1.00 | 35.16 | C |

APPENDIX 1-continued

| ATOM | 4334 | CG | GLU | B | 1080 | 87.178 | 77.399 | 30.631 | 1.00 | 37.88 | C |
|---|---|---|---|---|---|---|---|---|---|---|---|
| ATOM | 4335 | CD | GLU | B | 1080 | 88.499 | 76.838 | 30.124 | 1.00 | 40.95 | C |
| ATOM | 4336 | OE1 | GLU | B | 1080 | 88.507 | 75.714 | 29.574 | 1.00 | 40.35 | O |
| ATOM | 4337 | OE2 | GLU | B | 1080 | 89.529 | 77.528 | 30.278 | 1.00 | 42.97 | O |
| ATOM | 4338 | C | GLU | B | 1080 | 85.789 | 78.144 | 27.100 | 1.00 | 34.72 | C |
| ATOM | 4339 | O | GLU | B | 1080 | 86.149 | 77.337 | 26.240 | 1.00 | 35.34 | O |
| ATOM | 4340 | N | LEU | B | 1081 | 84.654 | 78.835 | 27.027 | 1.00 | 34.28 | N |
| ATOM | 4341 | CA | LEU | B | 1081 | 83.753 | 78.743 | 25.878 | 1.00 | 34.42 | C |
| ATOM | 4342 | CB | LEU | B | 1081 | 82.532 | 79.651 | 26.078 | 1.00 | 34.50 | C |
| ATOM | 4343 | CG | LEU | B | 1081 | 81.487 | 79.732 | 24.959 | 1.00 | 35.63 | C |
| ATOM | 4344 | CD1 | LEU | B | 1081 | 80.752 | 78.409 | 24.776 | 1.00 | 37.55 | C |
| ATOM | 4345 | CD2 | LEU | B | 1081 | 80.499 | 80.851 | 25.245 | 1.00 | 35.58 | C |
| ATOM | 4346 | C | LEU | B | 1081 | 84.467 | 79.094 | 24.571 | 1.00 | 33.63 | C |
| ATOM | 4347 | O | LEU | B | 1081 | 84.376 | 78.353 | 23.591 | 1.00 | 32.74 | O |
| ATOM | 4348 | N | LEU | B | 1082 | 85.179 | 80.219 | 24.573 | 1.00 | 33.80 | N |
| ATOM | 4349 | CA | LEU | B | 1082 | 85.910 | 80.685 | 23.392 | 1.00 | 34.60 | C |
| ATOM | 4350 | CB | LEU | B | 1082 | 86.418 | 82.119 | 23.594 | 1.00 | 34.52 | C |
| ATOM | 4351 | CG | LEU | B | 1082 | 85.384 | 83.247 | 23.709 | 1.00 | 34.49 | C |
| ATOM | 4352 | CD1 | LEU | B | 1082 | 86.055 | 84.541 | 24.136 | 1.00 | 32.87 | C |
| ATOM | 4353 | CD2 | LEU | B | 1082 | 84.610 | 83.442 | 22.407 | 1.00 | 35.33 | C |
| ATOM | 4354 | C | LEU | B | 1082 | 87.066 | 79.753 | 23.033 | 1.00 | 35.47 | C |
| ATOM | 4355 | O | LEU | B | 1082 | 87.350 | 79.534 | 21.852 | 1.00 | 35.49 | O |
| ATOM | 4356 | N | LYS | B | 1083 | 87.715 | 79.208 | 24.063 | 1.00 | 36.36 | N |
| ATOM | 4357 | CA | LYS | B | 1083 | 88.802 | 78.241 | 23.912 | 1.00 | 37.60 | C |
| ATOM | 4358 | CB | LYS | B | 1083 | 89.404 | 77.917 | 25.284 | 1.00 | 37.37 | C |
| ATOM | 4359 | CG | LYS | B | 1083 | 90.741 | 77.197 | 25.250 | 1.00 | 38.70 | C |
| ATOM | 4360 | CD | LYS | B | 1083 | 91.227 | 76.895 | 26.663 | 1.00 | 39.14 | C |
| ATOM | 4361 | CE | LYS | B | 1083 | 92.509 | 76.076 | 26.647 | 1.00 | 43.16 | C |
| ATOM | 4362 | NZ | LYS | B | 1083 | 93.022 | 75.806 | 28.024 | 1.00 | 43.69 | N |
| ATOM | 4363 | C | LYS | B | 1083 | 88.318 | 76.961 | 23.227 | 1.00 | 37.62 | C |
| ATOM | 4364 | O | LYS | B | 1083 | 89.035 | 76.374 | 22.413 | 1.00 | 37.79 | O |
| ATOM | 4365 | N | ASN | B | 1084 | 87.098 | 76.543 | 23.560 | 1.00 | 38.19 | N |
| ATOM | 4366 | CA | ASN | B | 1084 | 86.478 | 75.361 | 22.962 | 1.00 | 38.70 | C |
| ATOM | 4367 | CB | ASN | B | 1084 | 85.533 | 74.695 | 23.969 | 1.00 | 38.70 | C |
| ATOM | 4368 | CG | ASN | B | 1084 | 86.263 | 74.166 | 25.194 | 1.00 | 39.41 | C |
| ATOM | 4369 | OD1 | ASN | B | 1084 | 87.315 | 73.537 | 25.083 | 1.00 | 40.95 | O |
| ATOM | 4370 | ND2 | ASN | B | 1084 | 85.703 | 74.418 | 26.371 | 1.00 | 39.14 | N |
| ATOM | 4371 | C | ASN | B | 1084 | 85.753 | 75.676 | 21.648 | 1.00 | 39.10 | C |
| ATOM | 4372 | O | ASN | B | 1084 | 84.862 | 74.937 | 21.220 | 1.00 | 39.36 | O |
| ATOM | 4373 | N | ASN | B | 1085 | 86.164 | 76.779 | 21.020 | 1.00 | 39.47 | N |
| ATOM | 4374 | CA | ASN | B | 1085 | 85.600 | 77.284 | 19.760 | 1.00 | 39.53 | C |
| ATOM | 4375 | CB | ASN | B | 1085 | 86.039 | 76.424 | 18.564 | 1.00 | 40.23 | C |
| ATOM | 4376 | CG | ASN | B | 1085 | 87.449 | 76.758 | 18.096 | 1.00 | 41.80 | C |
| ATOM | 4377 | OD1 | ASN | B | 1085 | 87.779 | 77.922 | 17.855 | 1.00 | 41.00 | O |
| ATOM | 4378 | ND2 | ASN | B | 1085 | 88.286 | 75.735 | 17.965 | 1.00 | 43.87 | N |
| ATOM | 4379 | C | ASN | B | 1085 | 84.092 | 77.579 | 19.750 | 1.00 | 38.90 | C |
| ATOM | 4380 | O | ASN | B | 1085 | 83.435 | 77.497 | 18.709 | 1.00 | 39.13 | O |
| ATOM | 4381 | N | GLY | B | 1086 | 83.557 | 77.922 | 20.918 | 1.00 | 37.91 | N |
| ATOM | 4382 | CA | GLY | B | 1086 | 82.191 | 78.416 | 21.023 | 1.00 | 37.18 | C |
| ATOM | 4383 | C | GLY | B | 1086 | 82.150 | 79.843 | 20.517 | 1.00 | 36.89 | C |
| ATOM | 4384 | O | GLY | B | 1086 | 83.022 | 80.648 | 20.847 | 1.00 | 36.66 | O |
| ATOM | 4385 | N | ARG | B | 1087 | 81.147 | 80.151 | 19.700 | 1.00 | 36.98 | N |
| ATOM | 4386 | CA | ARG | B | 1087 | 81.032 | 81.474 | 19.088 | 1.00 | 37.09 | C |
| ATOM | 4387 | CB | ARG | B | 1087 | 81.782 | 81.507 | 17.750 | 1.00 | 37.27 | C |
| ATOM | 4388 | CG | ARG | B | 1087 | 83.216 | 82.002 | 17.877 | 1.00 | 38.91 | C |
| ATOM | 4389 | CD | ARG | B | 1087 | 84.189 | 80.970 | 17.360 | 1.00 | 42.23 | C |
| ATOM | 4390 | NE | ARG | B | 1087 | 85.586 | 81.383 | 17.505 | 1.00 | 42.13 | N |
| ATOM | 4391 | CZ | ARG | B | 1087 | 86.315 | 81.231 | 18.609 | 1.00 | 41.76 | C |
| ATOM | 4392 | NH1 | ARG | B | 1087 | 85.788 | 80.695 | 19.704 | 1.00 | 40.13 | N |
| ATOM | 4393 | NH2 | ARG | B | 1087 | 87.578 | 81.632 | 18.621 | 1.00 | 41.04 | N |
| ATOM | 4394 | C | ARG | B | 1087 | 79.587 | 81.923 | 18.907 | 1.00 | 36.54 | C |
| ATOM | 4395 | O | ARG | B | 1087 | 78.657 | 81.151 | 18.995 | 1.00 | 36.29 | O |
| ATOM | 4396 | N | LEU | B | 1088 | 79.415 | 83.223 | 18.670 | 1.00 | 36.15 | N |
| ATOM | 4397 | CA | LEU | B | 1088 | 78.111 | 83.802 | 18.366 | 1.00 | 36.33 | C |
| ATOM | 4398 | CB | LEU | B | 1088 | 78.221 | 85.320 | 18.186 | 1.00 | 35.89 | C |
| ATOM | 4399 | CG | LEU | B | 1088 | 78.653 | 86.149 | 19.400 | 1.00 | 35.56 | C |
| ATOM | 4400 | CD1 | LEU | B | 1088 | 79.089 | 87.546 | 18.974 | 1.00 | 36.88 | C |
| ATOM | 4401 | CD2 | LEU | B | 1088 | 77.549 | 86.222 | 20.449 | 1.00 | 36.31 | C |
| ATOM | 4402 | C | LEU | B | 1088 | 77.532 | 83.157 | 17.108 | 1.00 | 36.46 | C |
| ATOM | 4403 | O | LEU | B | 1088 | 78.269 | 82.895 | 16.153 | 1.00 | 36.64 | O |
| ATOM | 4404 | N | PRO | B | 1089 | 76.212 | 82.888 | 17.106 | 1.00 | 36.66 | N |
| ATOM | 4405 | CA | PRO | B | 1089 | 75.598 | 82.191 | 15.979 | 1.00 | 36.84 | C |
| ATOM | 4406 | CB | PRO | B | 1089 | 74.224 | 81.802 | 16.525 | 1.00 | 36.93 | C |
| ATOM | 4407 | CG | PRO | B | 1089 | 73.905 | 82.880 | 17.502 | 1.00 | 37.24 | C |
| ATOM | 4408 | CD | PRO | B | 1089 | 75.222 | 83.226 | 18.147 | 1.00 | 36.53 | C |
| ATOM | 4409 | C | PRO | B | 1089 | 75.437 | 83.102 | 14.767 | 1.00 | 37.06 | C |
| ATOM | 4410 | O | PRO | B | 1089 | 75.589 | 84.319 | 14.885 | 1.00 | 36.87 | O |
| ATOM | 4411 | N | ARG | B | 1090 | 75.142 | 82.509 | 13.614 | 1.00 | 37.55 | N |
| ATOM | 4412 | CA | ARG | B | 1090 | 74.790 | 83.279 | 12.429 | 1.00 | 37.88 | C |

APPENDIX 1-continued

| ATOM | 4413 | CB | ARG | B | 1090 | 74.684 | 82.367 | 11.203 | 1.00 | 38.36 | C |
|---|---|---|---|---|---|---|---|---|---|---|---|
| ATOM | 4414 | CG | ARG | B | 1090 | 74.417 | 83.104 | 9.891 | 1.00 | 37.11 | C |
| ATOM | 4415 | CD | ARG | B | 1090 | 74.385 | 82.150 | 8.699 | 1.00 | 38.80 | C |
| ATOM | 4416 | NE | ARG | B | 1090 | 73.357 | 81.117 | 8.835 | 1.00 | 42.67 | N |
| ATOM | 4417 | CZ | ARG | B | 1090 | 72.073 | 81.274 | 8.522 | 1.00 | 44.72 | C |
| ATOM | 4418 | NH1 | ARG | B | 1090 | 71.626 | 82.432 | 8.047 | 1.00 | 45.14 | N |
| ATOM | 4419 | NH2 | ARG | B | 1090 | 71.228 | 80.266 | 8.687 | 1.00 | 46.31 | N |
| ATOM | 4420 | C | ARG | B | 1090 | 73.468 | 83.992 | 12.690 | 1.00 | 37.79 | C |
| ATOM | 4421 | O | ARG | B | 1090 | 72.470 | 83.340 | 13.009 | 1.00 | 37.95 | O |
| ATOM | 4422 | N | PRO | B | 1091 | 73.461 | 85.335 | 12.574 | 1.00 | 37.94 | N |
| ATOM | 4423 | CA | PRO | B | 1091 | 72.238 | 86.109 | 12.787 | 1.00 | 37.91 | C |
| ATOM | 4424 | CB | PRO | B | 1091 | 72.672 | 87.546 | 12.482 | 1.00 | 37.36 | C |
| ATOM | 4425 | CG | PRO | B | 1091 | 74.148 | 87.552 | 12.676 | 1.00 | 38.03 | C |
| ATOM | 4426 | CD | PRO | B | 1091 | 74.607 | 86.202 | 12.238 | 1.00 | 37.70 | C |
| ATOM | 4427 | C | PRO | B | 1091 | 71.141 | 85.677 | 11.819 | 1.00 | 37.93 | C |
| ATOM | 4428 | O | PRO | B | 1091 | 71.445 | 85.186 | 10.728 | 1.00 | 37.94 | O |
| ATOM | 4429 | N | ASP | B | 1092 | 69.884 | 85.843 | 12.224 | 1.00 | 38.11 | N |
| ATOM | 4430 | CA | ASP | B | 1092 | 68.749 | 85.489 | 11.373 | 1.00 | 38.34 | C |
| ATOM | 4431 | CB | ASP | B | 1092 | 67.423 | 85.840 | 12.055 | 1.00 | 39.11 | C |
| ATOM | 4432 | CG | ASP | B | 1092 | 67.111 | 84.939 | 13.240 | 1.00 | 41.36 | C |
| ATOM | 4433 | OD1 | ASP | B | 1092 | 67.616 | 83.796 | 13.291 | 1.00 | 44.24 | O |
| ATOM | 4434 | OD2 | ASP | B | 1092 | 66.343 | 85.376 | 14.124 | 1.00 | 45.53 | O |
| ATOM | 4435 | C | ASP | B | 1092 | 68.851 | 86.185 | 10.018 | 1.00 | 37.65 | C |
| ATOM | 4436 | O | ASP | B | 1092 | 69.008 | 87.408 | 9.946 | 1.00 | 37.39 | O |
| ATOM | 4437 | N | GLY | B | 1093 | 68.799 | 85.391 | 8.953 | 1.00 | 37.16 | N |
| ATOM | 4438 | CA | GLY | B | 1093 | 68.832 | 85.909 | 7.587 | 1.00 | 37.38 | C |
| ATOM | 4439 | C | GLY | B | 1093 | 70.183 | 86.393 | 7.082 | 1.00 | 37.38 | C |
| ATOM | 4440 | O | GLY | B | 1093 | 70.269 | 86.943 | 5.985 | 1.00 | 37.34 | O |
| ATOM | 4441 | N | CYS | B | 1094 | 71.238 | 86.193 | 7.869 | 1.00 | 37.42 | N |
| ATOM | 4442 | CA | CYS | B | 1094 | 72.586 | 86.582 | 7.453 | 1.00 | 37.91 | C |
| ATOM | 4443 | CB | CYS | B | 1094 | 73.535 | 86.650 | 8.653 | 1.00 | 37.85 | C |
| ATOM | 4444 | SG | CYS | B | 1094 | 75.228 | 87.156 | 8.245 | 1.00 | 36.03 | S |
| ATOM | 4445 | C | CYS | B | 1094 | 73.135 | 85.615 | 6.405 | 1.00 | 38.78 | C |
| ATOM | 4446 | O | CYS | B | 1094 | 73.079 | 84.398 | 6.602 | 1.00 | 39.16 | O |
| ATOM | 4447 | N | PRO | B | 1095 | 73.647 | 86.152 | 5.278 | 1.00 | 39.45 | N |
| ATOM | 4448 | CA | PRO | B | 1095 | 74.312 | 85.333 | 4.262 | 1.00 | 39.76 | C |
| ATOM | 4449 | CB | PRO | B | 1095 | 74.686 | 86.351 | 3.177 | 1.00 | 39.95 | C |
| ATOM | 4450 | CG | PRO | B | 1095 | 73.767 | 87.507 | 3.399 | 1.00 | 39.51 | C |
| ATOM | 4451 | CD | PRO | B | 1095 | 73.603 | 87.572 | 4.884 | 1.00 | 39.33 | C |
| ATOM | 4452 | C | PRO | B | 1095 | 75.569 | 84.665 | 4.813 | 1.00 | 40.38 | C |
| ATOM | 4453 | O | PRO | B | 1095 | 76.309 | 85.282 | 5.584 | 1.00 | 39.88 | O |
| ATOM | 4454 | N | ASP | B | 1096 | 75.793 | 83.412 | 4.417 | 1.00 | 40.93 | N |
| ATOM | 4455 | CA | ASP | B | 1096 | 76.938 | 82.624 | 4.884 | 1.00 | 41.50 | C |
| ATOM | 4456 | CB | ASP | B | 1096 | 76.931 | 81.229 | 4.249 | 1.00 | 42.31 | C |
| ATOM | 4457 | CG | ASP | B | 1096 | 76.138 | 80.218 | 5.062 | 1.00 | 46.23 | C |
| ATOM | 4458 | OD1 | ASP | B | 1096 | 75.286 | 79.521 | 4.471 | 1.00 | 49.95 | O |
| ATOM | 4459 | OD2 | ASP | B | 1096 | 76.369 | 80.116 | 6.289 | 1.00 | 49.36 | O |
| ATOM | 4460 | C | ASP | B | 1096 | 78.283 | 83.305 | 4.634 | 1.00 | 40.80 | C |
| ATOM | 4461 | O | ASP | B | 1096 | 79.173 | 83.258 | 5.486 | 1.00 | 40.49 | O |
| ATOM | 4462 | N | GLU | B | 1097 | 78.414 | 83.939 | 3.471 | 1.00 | 40.08 | N |
| ATOM | 4463 | CA | GLU | B | 1097 | 79.633 | 84.655 | 3.096 | 1.00 | 40.09 | C |
| ATOM | 4464 | CB | GLU | B | 1097 | 79.516 | 85.195 | 1.668 | 1.00 | 40.22 | C |
| ATOM | 4465 | CG | GLU | B | 1097 | 80.847 | 85.610 | 1.048 | 1.00 | 42.39 | C |
| ATOM | 4466 | CD | GLU | B | 1097 | 80.758 | 85.879 | −.447 | 1.00 | 42.35 | C |
| ATOM | 4467 | OE1 | GLU | B | 1097 | 79.679 | 86.287 | −.933 | 1.00 | 45.83 | O |
| ATOM | 4468 | OE2 | GLU | B | 1097 | 81.781 | 85.687 | −1.138 | 1.00 | 45.62 | O |
| ATOM | 4469 | C | GLU | B | 1097 | 79.955 | 85.783 | 4.079 | 1.00 | 38.64 | C |
| ATOM | 4470 | O | GLU | B | 1097 | 81.124 | 86.043 | 4.371 | 1.00 | 38.53 | O |
| ATOM | 4471 | N | ILE | B | 1098 | 78.915 | 86.438 | 4.590 | 1.00 | 37.52 | N |
| ATOM | 4472 | CA | ILE | B | 1098 | 79.080 | 87.486 | 5.596 | 1.00 | 36.41 | C |
| ATOM | 4473 | CB | ILE | B | 1098 | 77.822 | 88.398 | 5.714 | 1.00 | 36.24 | C |
| ATOM | 4474 | CG1 | ILE | B | 1098 | 77.381 | 88.931 | 4.339 | 1.00 | 37.12 | C |
| ATOM | 4475 | CD1 | ILE | B | 1098 | 78.444 | 89.700 | 3.562 | 1.00 | 37.78 | C |
| ATOM | 4476 | CG2 | ILE | B | 1098 | 78.063 | 89.539 | 6.709 | 1.00 | 35.24 | C |
| ATOM | 4477 | C | ILE | B | 1098 | 79.432 | 86.876 | 6.956 | 1.00 | 35.22 | C |
| ATOM | 4478 | O | ILE | B | 1098 | 80.312 | 87.381 | 7.652 | 1.00 | 34.46 | O |
| ATOM | 4479 | N | TYR | B | 1099 | 78.748 | 85.790 | 7.320 | 1.00 | 34.62 | N |
| ATOM | 4480 | CA | TYR | B | 1099 | 79.034 | 85.079 | 8.569 | 1.00 | 34.76 | C |
| ATOM | 4481 | CB | TYR | B | 1099 | 78.002 | 83.972 | 8.839 | 1.00 | 34.86 | C |
| ATOM | 4482 | CG | TYR | B | 1099 | 78.194 | 83.266 | 10.172 | 1.00 | 34.50 | C |
| ATOM | 4483 | CD1 | TYR | B | 1099 | 78.481 | 81.901 | 10.234 | 1.00 | 35.85 | C |
| ATOM | 4484 | CE1 | TYR | B | 1099 | 78.662 | 81.256 | 11.465 | 1.00 | 35.54 | C |
| ATOM | 4485 | CZ | TYR | B | 1099 | 78.565 | 81.990 | 12.641 | 1.00 | 34.87 | C |
| ATOM | 4486 | OH | TYR | B | 1099 | 78.739 | 81.388 | 13.866 | 1.00 | 35.13 | O |
| ATOM | 4487 | CE2 | TYR | B | 1099 | 78.288 | 83.341 | 12.599 | 1.00 | 34.73 | C |
| ATOM | 4488 | CD2 | TYR | B | 1099 | 78.106 | 83.971 | 11.370 | 1.00 | 33.86 | C |
| ATOM | 4489 | C | TYR | B | 1099 | 80.452 | 84.502 | 8.586 | 1.00 | 35.16 | C |
| ATOM | 4490 | O | TYR | B | 1099 | 81.081 | 84.427 | 9.644 | 1.00 | 34.30 | O |
| ATOM | 4491 | N | MET | B | 1100 | 80.947 | 84.104 | 7.414 | 1.00 | 35.39 | N |

APPENDIX 1-continued

| | | | | | | | | | | |
|---|---|---|---|---|---|---|---|---|---|---|
| ATOM | 4492 | CA | MET | B | 1100 | 82.316 | 83.601 | 7.281 | 1.00 | 36.90 | C |
| ATOM | 4493 | CB | MET | B | 1100 | 82.547 | 82.981 | 5.899 | 1.00 | 36.89 | C |
| ATOM | 4494 | CG | MET | B | 1100 | 82.093 | 81.527 | 5.804 | 1.00 | 38.66 | C |
| ATOM | 4495 | SD | MET | B | 1100 | 82.450 | 80.747 | 4.215 | 1.00 | 42.19 | S |
| ATOM | 4496 | CE | MET | B | 1100 | 81.050 | 81.283 | 3.237 | 1.00 | 40.79 | C |
| ATOM | 4497 | C | MET | B | 1100 | 83.366 | 84.672 | 7.587 | 1.00 | 35.05 | C |
| ATOM | 4498 | O | MET | B | 1100 | 84.433 | 84.359 | 8.113 | 1.00 | 34.63 | O |
| ATOM | 4499 | N | ILE | B | 1101 | 83.053 | 85.927 | 7.266 | 1.00 | 34.29 | N |
| ATOM | 4500 | CA | ILE | B | 1101 | 83.911 | 87.059 | 7.630 | 1.00 | 33.92 | C |
| ATOM | 4501 | CB | ILE | B | 1101 | 83.441 | 88.386 | 6.976 | 1.00 | 34.10 | C |
| ATOM | 4502 | CG1 | ILE | B | 1101 | 83.508 | 88.287 | 5.445 | 1.00 | 33.92 | C |
| ATOM | 4503 | CD1 | ILE | B | 1101 | 82.967 | 89.507 | 4.714 | 1.00 | 34.19 | C |
| ATOM | 4504 | CG2 | ILE | B | 1101 | 84.281 | 89.565 | 7.477 | 1.00 | 33.40 | C |
| ATOM | 4505 | C | ILE | B | 1101 | 83.980 | 87.203 | 9.154 | 1.00 | 33.37 | C |
| ATOM | 4506 | O | ILE | B | 1101 | 85.057 | 87.409 | 9.713 | 1.00 | 33.05 | O |
| ATOM | 4507 | N | MET | B | 1102 | 82.826 | 87.083 | 9.812 | 1.00 | 33.60 | N |
| ATOM | 4508 | CA | MET | B | 1102 | 82.740 | 87.112 | 11.275 | 1.00 | 34.17 | C |
| ATOM | 4509 | CB | MET | B | 1102 | 81.286 | 86.958 | 11.731 | 1.00 | 34.19 | C |
| ATOM | 4510 | CG | MET | B | 1102 | 80.443 | 88.216 | 11.639 | 1.00 | 34.57 | C |
| ATOM | 4511 | SD | MET | B | 1102 | 78.664 | 87.886 | 11.645 | 1.00 | 35.71 | S |
| ATOM | 4512 | CE | MET | B | 1102 | 78.452 | 86.857 | 13.075 | 1.00 | 39.08 | C |
| ATOM | 4513 | C | MET | B | 1102 | 83.597 | 86.023 | 11.926 | 1.00 | 33.68 | C |
| ATOM | 4514 | O | MET | B | 1102 | 84.404 | 86.313 | 12.809 | 1.00 | 33.03 | O |
| ATOM | 4515 | N | THR | B | 1103 | 83.420 | 84.780 | 11.479 | 1.00 | 33.62 | N |
| ATOM | 4516 | CA | THR | B | 1103 | 84.121 | 83.630 | 12.068 | 1.00 | 33.91 | C |
| ATOM | 4517 | CB | THR | B | 1103 | 83.586 | 82.275 | 11.539 | 1.00 | 34.16 | C |
| ATOM | 4518 | OG1 | THR | B | 1103 | 83.593 | 82.273 | 10.107 | 1.00 | 35.57 | O |
| ATOM | 4519 | CG2 | THR | B | 1103 | 82.171 | 82.025 | 12.031 | 1.00 | 34.80 | C |
| ATOM | 4520 | C | THR | B | 1103 | 85.638 | 83.699 | 11.875 | 1.00 | 33.32 | C |
| ATOM | 4521 | O | THR | B | 1103 | 86.395 | 83.308 | 12.763 | 1.00 | 33.47 | O |
| ATOM | 4522 | N | GLU | B | 1104 | 86.068 | 84.205 | 10.720 | 1.00 | 32.64 | N |
| ATOM | 4523 | CA | GLU | B | 1104 | 87.489 | 84.420 | 10.441 | 1.00 | 32.36 | C |
| ATOM | 4524 | CB | GLU | B | 1104 | 87.700 | 84.813 | 8.980 | 1.00 | 32.49 | C |
| ATOM | 4525 | CG | GLU | B | 1104 | 87.699 | 83.642 | 8.023 | 1.00 | 35.61 | C |
| ATOM | 4526 | CD | GLU | B | 1104 | 87.989 | 84.059 | 6.598 | 1.00 | 39.16 | C |
| ATOM | 4527 | OE1 | GLU | B | 1104 | 89.041 | 84.698 | 6.360 | 1.00 | 39.15 | O |
| ATOM | 4528 | OE2 | GLU | B | 1104 | 87.164 | 83.744 | 5.715 | 1.00 | 42.13 | O |
| ATOM | 4529 | C | GLU | B | 1104 | 88.108 | 85.475 | 11.354 | 1.00 | 31.11 | C |
| ATOM | 4530 | O | GLU | B | 1104 | 89.255 | 85.336 | 11.781 | 1.00 | 30.76 | O |
| ATOM | 4531 | N | CYS | B | 1105 | 87.346 | 86.530 | 11.640 | 1.00 | 30.31 | N |
| ATOM | 4532 | CA | CYS | B | 1105 | 87.758 | 87.543 | 12.610 | 1.00 | 29.20 | C |
| ATOM | 4533 | CB | CYS | B | 1105 | 86.765 | 88.709 | 12.639 | 1.00 | 29.04 | C |
| ATOM | 4534 | SG | CYS | B | 1105 | 86.775 | 89.757 | 11.166 | 1.00 | 30.93 | S |
| ATOM | 4535 | C | CYS | B | 1105 | 87.890 | 86.937 | 14.006 | 1.00 | 29.13 | C |
| ATOM | 4536 | O | CYS | B | 1105 | 88.727 | 87.372 | 14.798 | 1.00 | 28.79 | O |
| ATOM | 4537 | N | TRP | B | 1106 | 87.064 | 85.931 | 14.293 | 1.00 | 29.33 | N |
| ATOM | 4538 | CA | TRP | B | 1106 | 87.049 | 85.287 | 15.606 | 1.00 | 29.57 | C |
| ATOM | 4539 | CB | TRP | B | 1106 | 85.628 | 84.899 | 16.022 | 1.00 | 29.41 | C |
| ATOM | 4540 | CG | TRP | B | 1106 | 84.655 | 86.028 | 16.061 | 1.00 | 28.94 | C |
| ATOM | 4541 | CD1 | TRP | B | 1106 | 84.908 | 87.326 | 16.401 | 1.00 | 28.90 | C |
| ATOM | 4542 | NE1 | TRP | B | 1106 | 83.753 | 88.069 | 16.327 | 1.00 | 28.81 | N |
| ATOM | 4543 | CE2 | TRP | B | 1106 | 82.723 | 87.249 | 15.949 | 1.00 | 28.34 | C |
| ATOM | 4544 | CD2 | TRP | B | 1106 | 83.256 | 85.951 | 15.775 | 1.00 | 29.32 | C |
| ATOM | 4545 | CE3 | TRP | B | 1106 | 82.400 | 84.911 | 15.383 | 1.00 | 29.70 | C |
| ATOM | 4546 | CZ3 | TRP | B | 1106 | 81.056 | 85.197 | 15.180 | 1.00 | 29.62 | C |
| ATOM | 4547 | CH2 | TRP | B | 1106 | 80.556 | 86.501 | 15.366 | 1.00 | 28.64 | C |
| ATOM | 4548 | CZ2 | TRP | B | 1106 | 81.371 | 87.536 | 15.746 | 1.00 | 28.09 | C |
| ATOM | 4549 | C | TRP | B | 1106 | 87.950 | 84.061 | 15.680 | 1.00 | 29.81 | C |
| ATOM | 4550 | O | TRP | B | 1106 | 87.570 | 83.035 | 16.247 | 1.00 | 29.95 | O |
| ATOM | 4551 | N | ASN | B | 1107 | 89.145 | 84.171 | 15.113 | 1.00 | 30.34 | N |
| ATOM | 4552 | CA | ASN | B | 1107 | 90.115 | 83.093 | 15.198 | 1.00 | 30.90 | C |
| ATOM | 4553 | CB | ASN | B | 1107 | 91.060 | 83.123 | 13.995 | 1.00 | 30.49 | C |
| ATOM | 4554 | CG | ASN | B | 1107 | 91.635 | 81.758 | 13.674 | 1.00 | 30.31 | C |
| ATOM | 4555 | OD1 | ASN | B | 1107 | 92.172 | 81.075 | 14.547 | 1.00 | 30.41 | O |
| ATOM | 4556 | ND2 | ASN | B | 1107 | 91.523 | 81.352 | 12.414 | 1.00 | 29.20 | N |
| ATOM | 4557 | C | ASN | B | 1107 | 90.904 | 83.175 | 16.501 | 1.00 | 31.25 | C |
| ATOM | 4558 | O | ASN | B | 1107 | 91.405 | 84.240 | 16.867 | 1.00 | 31.23 | O |
| ATOM | 4559 | N | ASN | B | 1108 | 90.998 | 82.047 | 17.203 | 1.00 | 32.26 | N |
| ATOM | 4560 | CA | ASN | B | 1108 | 91.827 | 81.952 | 18.402 | 1.00 | 33.55 | C |
| ATOM | 4561 | CB | ASN | B | 1108 | 91.704 | 80.566 | 19.038 | 1.00 | 34.24 | C |
| ATOM | 4562 | CG | ASN | B | 1108 | 90.389 | 80.376 | 19.771 | 1.00 | 36.27 | C |
| ATOM | 4563 | OD1 | ASN | B | 1108 | 89.798 | 81.335 | 20.274 | 1.00 | 37.36 | O |
| ATOM | 4564 | ND2 | ASN | B | 1108 | 89.926 | 79.132 | 19.841 | 1.00 | 38.18 | N |
| ATOM | 4565 | C | ASN | B | 1108 | 93.289 | 82.277 | 18.110 | 1.00 | 33.56 | C |
| ATOM | 4566 | O | ASN | B | 1108 | 93.994 | 82.824 | 18.959 | 1.00 | 33.71 | O |
| ATOM | 4567 | N | ASN | B | 1109 | 93.730 | 81.938 | 16.901 | 1.00 | 33.35 | N |
| ATOM | 4568 | CA | ASN | B | 1109 | 95.058 | 82.301 | 16.432 | 1.00 | 33.53 | C |
| ATOM | 4569 | CB | ASN | B | 1109 | 95.514 | 81.350 | 15.314 | 1.00 | 33.38 | C |
| ATOM | 4570 | CG | ASN | B | 1109 | 96.972 | 81.558 | 14.906 | 1.00 | 35.55 | C |

APPENDIX 1-continued

| ATOM | 4571 | OD1 | ASN | B | 1109 | 97.685 | 82.394 | 15.466 | 1.00 | 34.92 | O |
|---|---|---|---|---|---|---|---|---|---|---|---|
| ATOM | 4572 | ND2 | ASN | B | 1109 | 97.418 | 80.784 | 13.919 | 1.00 | 35.81 | N |
| ATOM | 4573 | C | ASN | B | 1109 | 95.064 | 83.751 | 15.960 | 1.00 | 33.06 | C |
| ATOM | 4574 | O | ASN | B | 1109 | 94.497 | 84.080 | 14.914 | 1.00 | 32.08 | O |
| ATOM | 4575 | N | VAL | B | 1110 | 95.703 | 84.606 | 16.754 | 1.00 | 33.21 | N |
| ATOM | 4576 | CA | VAL | B | 1110 | 95.867 | 86.030 | 16.452 | 1.00 | 33.63 | C |
| ATOM | 4577 | CB | VAL | B | 1110 | 96.814 | 86.701 | 17.493 | 1.00 | 34.57 | C |
| ATOM | 4578 | CG1 | VAL | B | 1110 | 97.295 | 88.065 | 17.025 | 1.00 | 36.89 | C |
| ATOM | 4579 | CG2 | VAL | B | 1110 | 96.122 | 86.823 | 18.843 | 1.00 | 35.25 | C |
| ATOM | 4580 | C | VAL | B | 1110 | 96.380 | 86.262 | 15.023 | 1.00 | 33.48 | C |
| ATOM | 4581 | O | VAL | B | 1110 | 95.874 | 87.130 | 14.306 | 1.00 | 33.19 | O |
| ATOM | 4582 | N | ASN | B | 1111 | 97.367 | 85.466 | 14.614 | 1.00 | 32.77 | N |
| ATOM | 4583 | CA | ASN | B | 1111 | 97.996 | 85.609 | 13.299 | 1.00 | 32.61 | C |
| ATOM | 4584 | CB | ASN | B | 1111 | 99.331 | 84.854 | 13.256 | 1.00 | 32.55 | C |
| ATOM | 4585 | CG | ASN | B | 1111 | 100.335 | 85.385 | 14.264 | 1.00 | 34.80 | C |
| ATOM | 4586 | OD1 | ASN | B | 1111 | 100.914 | 84.621 | 15.038 | 1.00 | 37.23 | O |
| ATOM | 4587 | ND2 | ASN | B | 1111 | 100.541 | 86.698 | 14.265 | 1.00 | 35.28 | N |
| ATOM | 4588 | C | ASN | B | 1111 | 97.113 | 85.204 | 12.119 | 1.00 | 31.91 | C |
| ATOM | 4589 | O | ASN | B | 1111 | 97.407 | 85.554 | 10.974 | 1.00 | 32.61 | O |
| ATOM | 4590 | N | GLN | B | 1112 | 96.039 | 84.467 | 12.400 | 1.00 | 31.58 | N |
| ATOM | 4591 | CA | GLN | B | 1112 | 95.094 | 84.047 | 11.361 | 1.00 | 31.70 | C |
| ATOM | 4592 | CB | GLN | B | 1112 | 94.614 | 82.621 | 11.599 | 1.00 | 31.74 | C |
| ATOM | 4593 | CG | GLN | B | 1112 | 95.241 | 81.628 | 10.652 | 1.00 | 32.92 | C |
| ATOM | 4594 | CD | GLN | B | 1112 | 94.743 | 80.220 | 10.869 | 1.00 | 32.94 | C |
| ATOM | 4595 | OE1 | GLN | B | 1112 | 94.960 | 79.628 | 11.926 | 1.00 | 31.51 | O |
| ATOM | 4596 | NE2 | GLN | B | 1112 | 94.077 | 79.669 | 9.860 | 1.00 | 35.33 | N |
| ATOM | 4597 | C | GLN | B | 1112 | 93.894 | 84.973 | 11.183 | 1.00 | 31.80 | C |
| ATOM | 4598 | O | GLN | B | 1112 | 93.046 | 84.733 | 10.323 | 1.00 | 31.73 | O |
| ATOM | 4599 | N | ARG | B | 1113 | 93.814 | 86.018 | 11.997 | 1.00 | 31.30 | N |
| ATOM | 4600 | CA | ARG | B | 1113 | 92.778 | 87.025 | 11.811 | 1.00 | 30.92 | C |
| ATOM | 4601 | CB | ARG | B | 1113 | 92.579 | 87.850 | 13.084 | 1.00 | 30.77 | C |
| ATOM | 4602 | CG | ARG | B | 1113 | 92.062 | 87.021 | 14.249 | 1.00 | 29.72 | C |
| ATOM | 4603 | CD | ARG | B | 1113 | 91.986 | 87.817 | 15.533 | 1.00 | 26.93 | C |
| ATOM | 4604 | NE | ARG | B | 1113 | 91.949 | 86.922 | 16.683 | 1.00 | 27.08 | N |
| ATOM | 4605 | CZ | ARG | B | 1113 | 92.258 | 87.267 | 17.929 | 1.00 | 25.88 | C |
| ATOM | 4606 | NH1 | ARG | B | 1113 | 92.627 | 88.509 | 18.217 | 1.00 | 24.27 | N |
| ATOM | 4607 | NH2 | ARG | B | 1113 | 92.201 | 86.355 | 18.890 | 1.00 | 24.69 | N |
| ATOM | 4608 | C | ARG | B | 1113 | 93.156 | 87.907 | 10.623 | 1.00 | 30.98 | C |
| ATOM | 4609 | O | ARG | B | 1113 | 94.318 | 88.302 | 10.491 | 1.00 | 31.01 | O |
| ATOM | 4610 | N | PRO | B | 1114 | 92.182 | 88.197 | 9.739 | 1.00 | 30.58 | N |
| ATOM | 4611 | CA | PRO | B | 1114 | 92.463 | 89.015 | 8.558 | 1.00 | 30.56 | C |
| ATOM | 4612 | CB | PRO | B | 1114 | 91.145 | 88.969 | 7.772 | 1.00 | 30.32 | C |
| ATOM | 4613 | CG | PRO | B | 1114 | 90.106 | 88.643 | 8.777 | 1.00 | 29.81 | C |
| ATOM | 4614 | CD | PRO | B | 1114 | 90.769 | 87.777 | 9.800 | 1.00 | 30.44 | C |
| ATOM | 4615 | C | PRO | B | 1114 | 92.821 | 90.456 | 8.915 | 1.00 | 30.61 | C |
| ATOM | 4616 | O | PRO | B | 1114 | 92.480 | 90.928 | 10.002 | 1.00 | 31.39 | O |
| ATOM | 4617 | N | SER | B | 1115 | 93.521 | 91.135 | 8.011 | 1.00 | 29.75 | N |
| ATOM | 4618 | CA | SER | B | 1115 | 93.829 | 92.552 | 8.177 | 1.00 | 29.37 | C |
| ATOM | 4619 | CB | SER | B | 1115 | 95.029 | 92.941 | 7.313 | 1.00 | 29.50 | C |
| ATOM | 4620 | OG | SER | B | 1115 | 94.687 | 92.920 | 5.937 | 1.00 | 31.06 | O |
| ATOM | 4621 | C | SER | B | 1115 | 92.610 | 93.390 | 7.794 | 1.00 | 29.29 | C |
| ATOM | 4622 | O | SER | B | 1115 | 91.706 | 92.899 | 7.116 | 1.00 | 28.92 | O |
| ATOM | 4623 | N | PHE | B | 1116 | 92.582 | 94.650 | 8.228 | 1.00 | 29.79 | N |
| ATOM | 4624 | CA | PHE | B | 1116 | 91.493 | 95.559 | 7.857 | 1.00 | 30.34 | C |
| ATOM | 4625 | CB | PHE | B | 1116 | 91.528 | 96.841 | 8.692 | 1.00 | 29.66 | C |
| ATOM | 4626 | CG | PHE | B | 1116 | 90.975 | 96.676 | 10.078 | 1.00 | 28.42 | C |
| ATOM | 4627 | CD1 | PHE | B | 1116 | 89.626 | 96.381 | 10.275 | 1.00 | 27.78 | C |
| ATOM | 4628 | CE1 | PHE | B | 1116 | 89.108 | 96.226 | 11.562 | 1.00 | 27.35 | C |
| ATOM | 4629 | CZ | PHE | B | 1116 | 89.944 | 96.375 | 12.667 | 1.00 | 27.56 | C |
| ATOM | 4630 | CE2 | PHE | B | 1116 | 91.289 | 96.677 | 12.481 | 1.00 | 28.17 | C |
| ATOM | 4631 | CD2 | PHE | B | 1116 | 91.798 | 96.822 | 11.188 | 1.00 | 27.77 | C |
| ATOM | 4632 | C | PHE | B | 1116 | 91.510 | 95.885 | 6.364 | 1.00 | 31.28 | C |
| ATOM | 4633 | O | PHE | B | 1116 | 90.457 | 96.085 | 5.757 | 1.00 | 31.77 | O |
| ATOM | 4634 | N | ARG | B | 1117 | 92.710 | 95.929 | 5.788 | 1.00 | 32.01 | N |
| ATOM | 4635 | CA | ARG | B | 1117 | 92.896 | 96.101 | 4.345 | 1.00 | 33.07 | C |
| ATOM | 4636 | CB | ARG | B | 1117 | 94.390 | 96.131 | 4.011 | 1.00 | 33.60 | C |
| ATOM | 4637 | CG | ARG | B | 1117 | 94.721 | 96.430 | 2.556 | 1.00 | 38.28 | C |
| ATOM | 4638 | CD | ARG | B | 1117 | 96.210 | 96.239 | 2.303 | 1.00 | 44.12 | C |
| ATOM | 4639 | NE | ARG | B | 1117 | 96.574 | 96.469 | .906 | 1.00 | 49.69 | N |
| ATOM | 4640 | CZ | ARG | B | 1117 | 97.788 | 96.268 | .398 | 1.00 | 51.87 | C |
| ATOM | 4641 | NH1 | ARG | B | 1117 | 98.776 | 95.827 | 1.170 | 1.00 | 53.04 | N |
| ATOM | 4642 | NH2 | ARG | B | 1117 | 98.016 | 96.506 | −.887 | 1.00 | 52.95 | N |
| ATOM | 4643 | C | ARG | B | 1117 | 92.204 | 94.979 | 3.569 | 1.00 | 32.69 | C |
| ATOM | 4644 | O | ARG | B | 1117 | 91.486 | 95.237 | 2.604 | 1.00 | 32.99 | O |
| ATOM | 4645 | N | ASP | B | 1118 | 92.421 | 93.742 | 4.008 | 1.00 | 32.34 | N |
| ATOM | 4646 | CA | ASP | B | 1118 | 91.804 | 92.572 | 3.387 | 1.00 | 33.02 | C |
| ATOM | 4647 | CB | ASP | B | 1118 | 92.454 | 91.287 | 3.899 | 1.00 | 33.67 | C |
| ATOM | 4648 | CG | ASP | B | 1118 | 93.829 | 91.053 | 3.302 | 1.00 | 38.68 | C |
| ATOM | 4649 | OD1 | ASP | B | 1118 | 93.939 | 90.983 | 2.055 | 1.00 | 42.29 | O |

APPENDIX 1-continued

| | | | | | | | | | | |
|---|---|---|---|---|---|---|---|---|---|---|
| ATOM | 4650 | OD2 | ASP | B | 1118 | 94.798 | 90.932 | 4.082 | 1.00 | 44.39 | O |
| ATOM | 4651 | C | ASP | B | 1118 | 90.298 | 92.536 | 3.616 | 1.00 | 32.20 | C |
| ATOM | 4652 | O | ASP | B | 1118 | 89.537 | 92.179 | 2.712 | 1.00 | 31.74 | O |
| ATOM | 4653 | N | LEU | B | 1119 | 89.878 | 92.913 | 4.824 | 1.00 | 31.07 | N |
| ATOM | 4654 | CA | LEU | B | 1119 | 88.459 | 92.993 | 5.169 | 1.00 | 30.77 | C |
| ATOM | 4655 | CB | LEU | B | 1119 | 88.275 | 93.344 | 6.649 | 1.00 | 29.99 | C |
| ATOM | 4656 | CG | LEU | B | 1119 | 88.532 | 92.217 | 7.650 | 1.00 | 30.58 | C |
| ATOM | 4657 | CD1 | LEU | B | 1119 | 88.627 | 92.764 | 9.068 | 1.00 | 28.35 | C |
| ATOM | 4658 | CD2 | LEU | B | 1119 | 87.453 | 91.143 | 7.546 | 1.00 | 28.48 | C |
| ATOM | 4659 | C | LEU | B | 1119 | 87.710 | 93.994 | 4.296 | 1.00 | 30.57 | C |
| ATOM | 4660 | O | LEU | B | 1119 | 86.611 | 93.705 | 3.822 | 1.00 | 30.12 | O |
| ATOM | 4661 | N | ALA | B | 1120 | 88.311 | 95.163 | 4.086 | 1.00 | 31.20 | N |
| ATOM | 4662 | CA | ALA | B | 1120 | 87.724 | 96.201 | 3.238 | 1.00 | 32.18 | C |
| ATOM | 4663 | CB | ALA | B | 1120 | 88.560 | 97.476 | 3.290 | 1.00 | 31.80 | C |
| ATOM | 4664 | C | ALA | B | 1120 | 87.564 | 95.717 | 1.799 | 1.00 | 32.75 | C |
| ATOM | 4665 | O | ALA | B | 1120 | 86.534 | 95.961 | 1.170 | 1.00 | 33.04 | O |
| ATOM | 4666 | N | LEU | B | 1121 | 88.578 | 95.017 | 1.295 | 1.00 | 33.65 | N |
| ATOM | 4667 | CA | LEU | B | 1121 | 88.546 | 94.468 | −.061 | 1.00 | 34.65 | C |
| ATOM | 4668 | CB | LEU | B | 1121 | 89.929 | 93.940 | −.472 | 1.00 | 34.95 | C |
| ATOM | 4669 | CG | LEU | B | 1121 | 91.020 | 94.976 | −.773 | 1.00 | 36.94 | C |
| ATOM | 4670 | CD1 | LEU | B | 1121 | 92.405 | 94.336 | −.730 | 1.00 | 39.22 | C |
| ATOM | 4671 | CD2 | LEU | B | 1121 | 90.787 | 95.666 | −2.117 | 1.00 | 38.96 | C |
| ATOM | 4672 | C | LEU | B | 1121 | 87.491 | 93.375 | −.210 | 1.00 | 34.79 | C |
| ATOM | 4673 | O | LEU | B | 1121 | 86.796 | 93.317 | −1.225 | 1.00 | 34.15 | O |
| ATOM | 4674 | N | ARG | B | 1122 | 87.373 | 92.519 | .805 | 1.00 | 34.81 | N |
| ATOM | 4675 | CA | ARG | B | 1122 | 86.390 | 91.436 | .797 | 1.00 | 35.70 | C |
| ATOM | 4676 | CB | ARG | B | 1122 | 86.628 | 90.465 | 1.960 | 1.00 | 35.73 | C |
| ATOM | 4677 | CG | ARG | B | 1122 | 87.769 | 89.476 | 1.735 | 1.00 | 38.34 | C |
| ATOM | 4678 | CD | ARG | B | 1122 | 88.086 | 88.688 | 3.003 | 1.00 | 37.57 | C |
| ATOM | 4679 | NE | ARG | B | 1122 | 87.058 | 87.694 | 3.315 | 1.00 | 44.09 | N |
| ATOM | 4680 | CZ | ARG | B | 1122 | 87.042 | 86.942 | 4.415 | 1.00 | 45.58 | C |
| ATOM | 4681 | NH1 | ARG | B | 1122 | 87.995 | 87.065 | 5.330 | 1.00 | 47.09 | N |
| ATOM | 4682 | NH2 | ARG | B | 1122 | 86.065 | 86.062 | 4.604 | 1.00 | 46.17 | N |
| ATOM | 4683 | C | ARG | B | 1122 | 84.964 | 91.975 | .844 | 1.00 | 35.09 | C |
| ATOM | 4684 | O | ARG | B | 1122 | 84.096 | 91.508 | .103 | 1.00 | 35.17 | O |
| ATOM | 4685 | N | VAL | B | 1123 | 84.735 | 92.963 | 1.710 | 1.00 | 34.46 | N |
| ATOM | 4686 | CA | VAL | B | 1123 | 83.418 | 93.582 | 1.865 | 1.00 | 33.49 | C |
| ATOM | 4687 | CB | VAL | B | 1123 | 83.365 | 94.524 | 3.103 | 1.00 | 33.28 | C |
| ATOM | 4688 | CG1 | VAL | B | 1123 | 82.091 | 95.360 | 3.106 | 1.00 | 32.70 | C |
| ATOM | 4689 | CG2 | VAL | B | 1123 | 83.465 | 93.710 | 4.393 | 1.00 | 32.20 | C |
| ATOM | 4690 | C | VAL | B | 1123 | 82.990 | 94.313 | .588 | 1.00 | 33.27 | C |
| ATOM | 4691 | O | VAL | B | 1123 | 81.867 | 94.134 | .117 | 1.00 | 32.62 | O |
| ATOM | 4692 | N | ASP | B | 1124 | 83.895 | 95.116 | .030 | 1.00 | 33.58 | N |
| ATOM | 4693 | CA | ASP | B | 1124 | 83.621 | 95.867 | −1.195 | 1.00 | 34.24 | C |
| ATOM | 4694 | CB | ASP | B | 1124 | 84.775 | 96.824 | −1.520 | 1.00 | 34.55 | C |
| ATOM | 4695 | CG | ASP | B | 1124 | 84.800 | 98.043 | −.609 | 1.00 | 35.52 | C |
| ATOM | 4696 | OD1 | ASP | B | 1124 | 83.790 | 98.305 | .077 | 1.00 | 37.28 | O |
| ATOM | 4697 | OD2 | ASP | B | 1124 | 85.830 | 98.747 | −.584 | 1.00 | 39.20 | O |
| ATOM | 4698 | C | ASP | B | 1124 | 83.327 | 94.959 | −2.385 | 1.00 | 34.34 | C |
| ATOM | 4699 | O | ASP | B | 1124 | 82.484 | 95.283 | −3.222 | 1.00 | 34.33 | O |
| ATOM | 4700 | N | GLN | B | 1125 | 84.017 | 93.820 | −2.443 | 1.00 | 34.55 | N |
| ATOM | 4701 | CA | GLN | B | 1125 | 83.804 | 92.823 | −3.490 | 1.00 | 34.87 | C |
| ATOM | 4702 | CB | GLN | B | 1125 | 84.888 | 91.746 | −3.425 | 1.00 | 35.49 | C |
| ATOM | 4703 | CG | GLN | B | 1125 | 84.781 | 90.674 | −4.493 | 1.00 | 39.77 | C |
| ATOM | 4704 | CD | GLN | B | 1125 | 85.793 | 89.570 | −4.289 | 1.00 | 44.15 | C |
| ATOM | 4705 | OE1 | GLN | B | 1125 | 86.948 | 89.689 | −4.694 | 1.00 | 47.73 | O |
| ATOM | 4706 | NE2 | GLN | B | 1125 | 85.363 | 88.485 | −3.656 | 1.00 | 46.34 | N |
| ATOM | 4707 | C | GLN | B | 1125 | 82.414 | 92.194 | −3.404 | 1.00 | 34.26 | C |
| ATOM | 4708 | O | GLN | B | 1125 | 81.743 | 92.033 | −4.423 | 1.00 | 33.82 | O |
| ATOM | 4709 | N | ILE | B | 1126 | 81.989 | 91.842 | −2.190 | 1.00 | 34.31 | N |
| ATOM | 4710 | CA | ILE | B | 1126 | 80.639 | 91.315 | −1.967 | 1.00 | 34.52 | C |
| ATOM | 4711 | CB | ILE | B | 1126 | 80.445 | 90.780 | −.522 | 1.00 | 34.51 | C |
| ATOM | 4712 | CG1 | ILE | B | 1126 | 81.468 | 89.680 | −.222 | 1.00 | 33.64 | C |
| ATOM | 4713 | CD1 | ILE | B | 1126 | 81.606 | 89.335 | 1.248 | 1.00 | 35.59 | C |
| ATOM | 4714 | CG2 | ILE | B | 1126 | 79.031 | 90.224 | −.331 | 1.00 | 35.04 | C |
| ATOM | 4715 | C | ILE | B | 1126 | 79.586 | 92.374 | −2.309 | 1.00 | 34.98 | C |
| ATOM | 4716 | O | ILE | B | 1126 | 78.560 | 92.053 | −2.910 | 1.00 | 35.18 | O |
| ATOM | 4717 | N | ARG | B | 1127 | 79.860 | 93.628 | −1.940 | 1.00 | 35.33 | N |
| ATOM | 4718 | CA | ARG | B | 1127 | 79.010 | 94.770 | −2.309 | 1.00 | 36.41 | C |
| ATOM | 4719 | CB | ARG | B | 1127 | 79.585 | 96.081 | −1.762 | 1.00 | 36.29 | C |
| ATOM | 4720 | CG | ARG | B | 1127 | 79.392 | 96.304 | −.268 | 1.00 | 36.00 | C |
| ATOM | 4721 | CD | ARG | B | 1127 | 80.188 | 97.512 | .214 | 1.00 | 36.48 | C |
| ATOM | 4722 | NE | ARG | B | 1127 | 79.581 | 98.778 | −.197 | 1.00 | 39.01 | N |
| ATOM | 4723 | CZ | ARG | B | 1127 | 80.246 | 99.918 | −.372 | 1.00 | 39.46 | C |
| ATOM | 4724 | NH1 | ARG | B | 1127 | 81.561 | 99.969 | −.194 | 1.00 | 40.30 | N |
| ATOM | 4725 | NH2 | ARG | B | 1127 | 79.595 | 101.013 | −.741 | 1.00 | 38.15 | N |
| ATOM | 4726 | C | ARG | B | 1127 | 78.844 | 94.884 | −3.825 | 1.00 | 37.14 | C |
| ATOM | 4727 | O | ARG | B | 1127 | 77.735 | 95.091 | −4.320 | 1.00 | 37.21 | O |
| ATOM | 4728 | N | ASP | B | 1128 | 79.955 | 94.750 | −4.549 | 1.00 | 38.25 | N |

APPENDIX 1-continued

| ATOM | 4729 | CA | ASP | B | 1128 | 79.955 | 94.791 | −6.012 | 1.00 | 39.92 | C |
|---|---|---|---|---|---|---|---|---|---|---|---|
| ATOM | 4730 | CB | ASP | B | 1128 | 81.390 | 94.765 | −6.552 | 1.00 | 40.52 | C |
| ATOM | 4731 | CG | ASP | B | 1128 | 82.166 | 96.034 | −6.232 | 1.00 | 43.07 | C |
| ATOM | 4732 | OD1 | ASP | B | 1128 | 81.566 | 97.008 | −5.725 | 1.00 | 46.52 | O |
| ATOM | 4733 | OD2 | ASP | B | 1128 | 83.387 | 96.056 | −6.493 | 1.00 | 45.96 | O |
| ATOM | 4734 | C | ASP | B | 1128 | 79.156 | 93.637 | −6.613 | 1.00 | 40.18 | C |
| ATOM | 4735 | O | ASP | B | 1128 | 78.431 | 93.823 | −7.591 | 1.00 | 40.22 | O |
| ATOM | 4736 | N | GLN | B | 1129 | 79.294 | 92.455 | −6.015 | 1.00 | 40.69 | N |
| ATOM | 4737 | CA | GLN | B | 1129 | 78.588 | 91.253 | −6.462 | 1.00 | 41.85 | C |
| ATOM | 4738 | CB | GLN | B | 1129 | 79.161 | 90.007 | −5.779 | 1.00 | 41.48 | C |
| ATOM | 4739 | CG | GLN | B | 1129 | 80.546 | 89.597 | −6.277 | 1.00 | 43.23 | C |
| ATOM | 4740 | CD | GLN | B | 1129 | 81.206 | 88.523 | −5.417 | 1.00 | 43.53 | C |
| ATOM | 4741 | OE1 | GLN | B | 1129 | 80.819 | 88.293 | −4.267 | 1.00 | 45.19 | O |
| ATOM | 4742 | NE2 | GLN | B | 1129 | 82.219 | 87.866 | −5.974 | 1.00 | 45.65 | N |
| ATOM | 4743 | C | GLN | B | 1129 | 77.083 | 91.346 | −6.210 | 1.00 | 41.75 | C |
| ATOM | 4744 | O | GLN | B | 1129 | 76.282 | 90.888 | −7.027 | 1.00 | 41.64 | O |
| ATOM | 4745 | N | MET | B | 1130 | 76.710 | 91.943 | −5.079 | 1.00 | 41.97 | N |
| ATOM | 4746 | CA | MET | B | 1130 | 75.305 | 92.109 | −4.708 | 1.00 | 42.42 | C |
| ATOM | 4747 | CB | MET | B | 1130 | 75.176 | 92.503 | −3.235 | 1.00 | 42.11 | C |
| ATOM | 4748 | CG | MET | B | 1130 | 75.429 | 91.364 | −2.260 | 1.00 | 41.59 | C |
| ATOM | 4749 | SD | MET | B | 1130 | 75.396 | 91.889 | −.534 | 1.00 | 43.28 | S |
| ATOM | 4750 | CE | MET | B | 1130 | 73.636 | 92.071 | −.256 | 1.00 | 42.65 | C |
| ATOM | 4751 | C | MET | B | 1130 | 74.587 | 93.127 | −5.592 | 1.00 | 42.42 | C |
| ATOM | 4752 | O | MET | B | 1130 | 73.391 | 92.993 | −5.850 | 1.00 | 42.56 | O |
| ATOM | 4753 | N | ALA | B | 1131 | 75.326 | 94.133 | −6.057 | 1.00 | 42.76 | N |
| ATOM | 4754 | CA | ALA | B | 1131 | 74.771 | 95.186 | −6.910 | 1.00 | 43.84 | C |
| ATOM | 4755 | CB | ALA | B | 1131 | 75.504 | 96.501 | −6.672 | 1.00 | 43.53 | C |
| ATOM | 4756 | C | ALA | B | 1131 | 74.794 | 94.819 | −8.396 | 1.00 | 44.67 | C |
| ATOM | 4757 | O | ALA | B | 1131 | 74.326 | 95.590 | −9.238 | 1.00 | 44.64 | O |
| ATOM | 4758 | N | GLY | B | 1132 | 75.337 | 93.644 | −8.711 | 1.00 | 45.94 | N |
| ATOM | 4759 | CA | GLY | B | 1132 | 75.433 | 93.171 | −10.093 | 1.00 | 47.34 | C |
| ATOM | 4760 | C | GLY | B | 1132 | 74.080 | 92.872 | −10.714 | 1.00 | 48.44 | C |
| ATOM | 4761 | O | GLY | B | 1132 | 73.892 | 93.008 | −11.925 | 1.00 | 49.07 | O |
| ATOM | 4762 | OXT | GLY | B | 1132 | 73.135 | 92.489 | −10.021 | 1.00 | 49.00 | O |
| ATOM | 4763 | O0 | INH | I | 1 | 117.708 | 67.477 | 10.894 | 1.00 | 27.17 | O |
| ATOM | 4764 | C11 | INH | I | 1 | 117.277 | 66.878 | 9.880 | 1.00 | 26.82 | C |
| ATOM | 4765 | N2 | INH | I | 1 | 118.091 | 66.743 | 8.798 | 1.00 | 28.57 | N |
| ATOM | 4766 | C12 | INH | I | 1 | 117.693 | 66.099 | 7.686 | 1.00 | 27.05 | C |
| ATOM | 4767 | C13 | INH | I | 1 | 116.416 | 65.546 | 7.594 | 1.00 | 27.77 | C |
| ATOM | 4768 | C9 | INH | I | 1 | 115.518 | 65.633 | 8.661 | 1.00 | 26.99 | C |
| ATOM | 4769 | C1 | INH | I | 1 | 114.242 | 65.075 | 8.571 | 1.00 | 26.25 | C |
| ATOM | 4770 | C10 | INH | I | 1 | 115.905 | 66.289 | 9.835 | 1.00 | 26.54 | C |
| ATOM | 4771 | C8 | INH | I | 1 | 114.925 | 66.379 | 10.970 | 1.00 | 26.63 | C |
| ATOM | 4772 | C7 | INH | I | 1 | 115.203 | 67.008 | 12.179 | 1.00 | 26.77 | C |
| ATOM | 4773 | C6 | INH | I | 1 | 114.205 | 67.016 | 13.146 | 1.00 | 26.50 | C |
| ATOM | 4774 | F | INH | I | 1 | 114.458 | 67.672 | 14.446 | 1.00 | 25.98 | C |
| ATOM | 4775 | C5 | INH | I | 1 | 112.971 | 66.403 | 12.892 | 1.00 | 27.33 | C |
| ATOM | 4776 | C4 | INH | I | 1 | 112.710 | 65.818 | 11.765 | 1.00 | 27.08 | C |
| ATOM | 4777 | C3 | INH | I | 1 | 113.577 | 65.764 | 10.808 | 1.00 | 26.23 | C |
| ATOM | 4778 | C0 | INH | I | 1 | 113.307 | 65.138 | 9.595 | 1.00 | 26.80 | C |
| ATOM | 4779 | N1 | INH | I | 1 | 112.172 | 64.512 | 9.210 | 1.00 | 26.50 | N |
| ATOM | 4780 | C2 | INH | I | 1 | 112.466 | 64.089 | 7.958 | 1.00 | 26.58 | C |
| ATOM | 4781 | N0 | INH | I | 1 | 113.704 | 64.415 | 7.522 | 1.00 | 26.25 | N |
| ATOM | 4782 | C14 | INH | I | 1 | 111.481 | 63.340 | 7.088 | 1.00 | 27.03 | C |
| ATOM | 4783 | C17 | INH | I | 1 | 110.351 | 62.754 | 7.925 | 1.00 | 26.81 | C |
| ATOM | 4784 | C16 | INH | I | 1 | 112.157 | 62.218 | 6.312 | 1.00 | 28.32 | C |
| ATOM | 4785 | C15 | INH | I | 1 | 110.887 | 64.332 | 6.096 | 1.00 | 28.23 | C |
| ATOM | 4786 | O0 | INH | J | 1 | 77.433 | 114.174 | 18.222 | 1.00 | 25.05 | O |
| ATOM | 4787 | C11 | INH | J | 1 | 78.314 | 113.532 | 18.832 | 1.00 | 24.61 | C |
| ATOM | 4788 | N2 | INH | J | 1 | 79.617 | 113.867 | 18.671 | 1.00 | 25.01 | N |
| ATOM | 4789 | C12 | INH | J | 1 | 80.602 | 113.213 | 19.307 | 1.00 | 24.87 | C |
| ATOM | 4790 | C13 | INH | J | 1 | 80.329 | 112.146 | 20.163 | 1.00 | 24.18 | C |
| ATOM | 4791 | C9 | INH | J | 1 | 79.012 | 111.737 | 20.380 | 1.00 | 25.71 | C |
| ATOM | 4792 | C1 | INH | J | 1 | 78.727 | 110.672 | 21.233 | 1.00 | 24.74 | C |
| ATOM | 4793 | C10 | INH | J | 1 | 77.963 | 112.399 | 19.734 | 1.00 | 24.96 | C |
| ATOM | 4794 | C8 | INH | J | 1 | 76.553 | 111.947 | 19.973 | 1.00 | 24.76 | C |
| ATOM | 4795 | C7 | INH | J | 1 | 75.444 | 112.535 | 19.381 | 1.00 | 24.38 | C |
| ATOM | 4796 | C6 | INH | J | 1 | 74.191 | 112.015 | 19.696 | 1.00 | 25.06 | C |
| ATOM | 4797 | F | INH | J | 1 | 72.985 | 112.612 | 19.088 | 1.00 | 24.10 | C |
| ATOM | 4798 | C5 | INH | J | 1 | 74.079 | 110.935 | 20.579 | 1.00 | 25.04 | C |
| ATOM | 4799 | C4 | INH | J | 1 | 75.114 | 110.382 | 21.131 | 1.00 | 24.94 | C |
| ATOM | 4800 | C3 | INH | J | 1 | 76.317 | 110.800 | 20.899 | 1.00 | 25.51 | C |
| ATOM | 4801 | C0 | INH | J | 1 | 77.441 | 110.217 | 21.481 | 1.00 | 25.55 | C |
| ATOM | 4802 | N1 | INH | J | 1 | 77.493 | 109.181 | 22.346 | 1.00 | 25.57 | N |
| ATOM | 4803 | C2 | INH | J | 1 | 78.817 | 109.051 | 22.586 | 1.00 | 24.84 | C |
| ATOM | 4804 | N0 | INH | J | 1 | 79.611 | 109.924 | 21.928 | 1.00 | 25.04 | N |
| ATOM | 4805 | C14 | INH | J | 1 | 79.379 | 107.988 | 23.496 | 1.00 | 24.62 | C |
| ATOM | 4806 | C17 | INH | J | 1 | 78.315 | 107.519 | 24.483 | 1.00 | 25.73 | C |
| ATOM | 4807 | C16 | INH | J | 1 | 80.578 | 108.519 | 24.276 | 1.00 | 22.32 | C |

APPENDIX 1-continued

| | | | | | | | | | | | |
|---|---|---|---|---|---|---|---|---|---|---|---|
| ATOM | 4808 | C15 | INH | J | 1 | 79.804 | 106.817 | 22.619 | 1.00 | 24.10 | C |
| ATOM | 4809 | OW0 | HOH | W | 1 | 70.917 | 93.358 | 20.298 | 1.00 | 41.89 | O |
| ATOM | 4810 | OW0 | HOH | W | 2 | 73.433 | 95.984 | 22.357 | 1.00 | 47.84 | O |
| ATOM | 4811 | OW0 | HOH | W | 3 | 103.118 | 85.369 | −12.316 | 1.00 | 44.29 | O |
| ATOM | 4812 | OW0 | HOH | W | 4 | 118.097 | 66.784 | −18.096 | 1.00 | 41.86 | O |
| ATOM | 4813 | OW0 | HOH | W | 5 | 93.992 | 133.337 | 17.324 | 1.00 | 66.78 | O |
| ATOM | 4814 | OW0 | HOH | W | 6 | 134.295 | 62.978 | 19.108 | 1.00 | 45.14 | O |
| ATOM | 4815 | OW0 | HOH | W | 7 | 69.685 | 87.062 | 14.840 | 1.00 | 51.70 | O |
| ATOM | 4816 | OW0 | HOH | W | 8 | 97.022 | 83.538 | 19.035 | 1.00 | 46.57 | O |
| ATOM | 4817 | OW0 | HOH | W | 9 | 99.205 | 56.988 | −14.930 | 1.00 | 54.46 | O |
| ATOM | 4818 | OW0 | HOH | W | 10 | 119.796 | 52.017 | 3.823 | 1.00 | 38.95 | O |
| ATOM | 4819 | OW0 | HOH | W | 11 | 75.006 | 106.711 | 25.978 | 1.00 | 46.58 | O |
| ATOM | 4820 | OW0 | HOH | W | 12 | 119.915 | 82.871 | 1.682 | 1.00 | 40.79 | O |
| ATOM | 4821 | OW0 | HOH | W | 13 | 92.070 | 88.024 | 4.610 | 1.00 | 63.86 | O |
| ATOM | 4822 | OW0 | HOH | W | 14 | 69.960 | 110.837 | 6.303 | 1.00 | 53.46 | O |
| ATOM | 4823 | OW0 | HOH | W | 15 | 77.732 | 78.159 | 34.672 | 1.00 | 55.55 | O |
| ATOM | 4824 | OW0 | HOH | W | 16 | 74.626 | 95.030 | 20.041 | 1.00 | 31.15 | O |
| ATOM | 4825 | OW0 | HOH | W | 17 | 87.672 | 80.036 | −.800 | 1.00 | 47.69 | O |
| ATOM | 4826 | OW0 | HOH | W | 18 | 132.244 | 66.608 | 26.694 | 1.00 | 50.26 | O |
| ATOM | 4827 | OW0 | HOH | W | 19 | 131.148 | 62.103 | .536 | 1.00 | 54.55 | O |
| ATOM | 4828 | OW0 | HOH | W | 20 | 93.027 | 105.072 | 27.351 | 1.00 | 62.44 | O |
| ATOM | 4829 | OW0 | HOH | W | 21 | 95.843 | 106.442 | 27.325 | 1.00 | 56.69 | O |
| ATOM | 4830 | OW0 | HOH | W | 22 | 114.332 | 84.311 | .335 | 1.00 | 57.67 | O |
| ATOM | 4831 | OW0 | HOH | W | 23 | 110.945 | 89.375 | 5.753 | 1.00 | 57.37 | O |
| ATOM | 4832 | OW0 | HOH | W | 24 | 100.305 | 110.868 | 15.109 | 1.00 | 55.45 | O |
| ATOM | 4833 | OW0 | HOH | W | 25 | 69.937 | 114.215 | 18.346 | 1.00 | 69.80 | O |
| ATOM | 4834 | OW0 | HOH | W | 26 | 138.486 | 61.567 | 14.458 | 1.00 | 60.37 | O |
| ATOM | 4835 | OW0 | HOH | W | 27 | 131.633 | 64.840 | 14.857 | 1.00 | 53.30 | O |
| ATOM | 4836 | OW0 | HOH | W | 28 | 110.563 | 96.545 | 25.922 | 1.00 | 56.84 | O |
| ATOM | 4837 | OW0 | HOH | W | 29 | 102.455 | 99.541 | 12.106 | 1.00 | 50.09 | O |
| ATOM | 4838 | OW0 | HOH | W | 30 | 84.602 | 88.581 | −.947 | 1.00 | 45.73 | O |
| ATOM | 4839 | OW0 | HOH | W | 31 | 101.469 | 60.636 | 1.692 | 1.00 | 59.09 | O |
| ATOM | 4840 | OW0 | HOH | W | 32 | 98.341 | 97.611 | 10.916 | 1.00 | 39.21 | O |
| ATOM | 4841 | OW0 | HOH | W | 33 | 124.810 | 63.933 | −10.113 | 1.00 | 53.45 | O |
| ATOM | 4842 | OW0 | HOH | W | 34 | 99.015 | 89.405 | 14.083 | 1.00 | 62.42 | O |
| ATOM | 4843 | OW0 | HOH | W | 35 | 71.902 | 116.304 | 9.937 | 1.00 | 55.49 | O |
| ATOM | 4844 | OW0 | HOH | W | 36 | 79.987 | 93.459 | 29.930 | 1.00 | 52.79 | O |
| ATOM | 4845 | OW0 | HOH | W | 37 | 137.177 | 53.923 | 12.884 | 1.00 | 74.18 | O |
| ATOM | 4846 | OW0 | HOH | W | 38 | 96.587 | 98.732 | 6.076 | 1.00 | 62.98 | O |
| ATOM | 4847 | OW0 | HOH | W | 39 | 81.741 | 80.295 | 8.988 | 1.00 | 55.73 | O |
| ATOM | 4848 | OW0 | HOH | W | 40 | 115.071 | 52.417 | 9.252 | 1.00 | 63.32 | O |
| ATOM | 4849 | OW0 | HOH | W | 41 | 105.531 | 73.095 | −18.140 | 1.00 | 64.23 | O |
| ATOM | 4850 | OW0 | HOH | W | 42 | 99.697 | 97.550 | 8.540 | 1.00 | 46.10 | O |
| ATOM | 4851 | OW0 | HOH | W | 43 | 102.343 | 93.980 | 8.305 | 1.00 | 66.21 | O |
| ATOM | 4852 | OW0 | HOH | W | 44 | 64.724 | 94.601 | 20.020 | 1.00 | 57.15 | O |
| ATOM | 4853 | OW0 | HOH | W | 45 | 73.133 | 137.373 | 12.796 | 1.00 | 46.60 | O |
| ATOM | 4854 | OW0 | HOH | W | 46 | 87.203 | 88.213 | −1.616 | 1.00 | 59.78 | O |
| ATOM | 4855 | OW0 | HOH | W | 47 | 96.447 | 88.955 | 8.910 | 1.00 | 58.27 | O |
| ATOM | 4856 | OW0 | HOH | W | 48 | 124.120 | 79.150 | 10.222 | 1.00 | 58.60 | O |
| ATOM | 4857 | OW0 | HOH | W | 49 | 78.815 | 102.141 | 28.484 | 1.00 | 64.86 | O |
| ATOM | 4858 | OW0 | HOH | W | 50 | 90.532 | 96.728 | 29.422 | 1.00 | 54.43 | O |
| ATOM | 4859 | OW0 | HOH | W | 51 | 77.408 | 133.348 | 18.737 | 1.00 | 38.22 | O |
| ATOM | 4860 | OW0 | HOH | W | 52 | 94.774 | 91.239 | 12.195 | 1.00 | 36.79 | O |
| ATOM | 4861 | OW0 | HOH | W | 53 | 115.541 | 57.517 | 21.993 | 1.00 | 34.95 | O |
| ATOM | 4862 | OW0 | HOH | W | 54 | 100.981 | 88.653 | −6.973 | 1.00 | 47.99 | O |
| ATOM | 4863 | OW0 | HOH | W | 55 | 105.647 | 82.989 | −14.901 | 1.00 | 35.77 | O |
| ATOM | 4864 | OW0 | HOH | W | 56 | 108.584 | 63.439 | 12.017 | 1.00 | 39.21 | O |
| ATOM | 4865 | OW0 | HOH | W | 57 | 68.281 | 89.373 | 14.553 | 1.00 | 45.77 | O |
| ATOM | 4866 | OW0 | HOH | W | 58 | 114.389 | 72.946 | −15.678 | 1.00 | 42.82 | O |
| ATOM | 4867 | OW0 | HOH | W | 59 | 117.727 | 82.079 | 3.133 | 1.00 | 35.82 | O |
| ATOM | 4868 | OW0 | HOH | W | 60 | 94.938 | 95.412 | 9.728 | 1.00 | 35.57 | O |
| ATOM | 4869 | OW0 | HOH | W | 61 | 103.875 | 65.541 | −4.864 | 1.00 | 42.99 | O |
| ATOM | 4870 | OW0 | HOH | W | 62 | 100.363 | 96.230 | 14.526 | 1.00 | 39.33 | O |
| ATOM | 4871 | OW0 | HOH | W | 63 | 115.901 | 58.355 | −5.932 | 1.00 | 35.42 | O |
| ATOM | 4872 | OW0 | HOH | W | 64 | 71.437 | 89.474 | 1.166 | 1.00 | 38.18 | O |
| ATOM | 4873 | OW0 | HOH | W | 65 | 92.988 | 77.444 | −9.196 | 1.00 | 36.93 | O |
| ATOM | 4874 | OW0 | HOH | W | 66 | 82.508 | 107.755 | 3.840 | 1.00 | 40.17 | O |
| ATOM | 4875 | OW0 | HOH | W | 67 | 69.792 | 84.830 | 23.011 | 1.00 | 48.53 | O |
| ATOM | 4876 | OW0 | HOH | W | 68 | 93.845 | 121.886 | 19.306 | 1.00 | 57.60 | O |
| ATOM | 4877 | OW0 | HOH | W | 69 | 113.465 | 57.703 | 19.542 | 1.00 | 36.89 | O |
| ATOM | 4878 | OW0 | HOH | W | 70 | 117.632 | 80.028 | −6.582 | 1.00 | 37.62 | O |
| ATOM | 4879 | OW0 | HOH | W | 71 | 89.867 | 92.572 | 22.566 | 1.00 | 39.34 | O |
| ATOM | 4880 | OW0 | HOH | W | 72 | 78.285 | 97.650 | 23.552 | 1.00 | 44.81 | O |
| ATOM | 4881 | OW0 | HOH | W | 73 | 102.321 | 66.577 | −9.038 | 1.00 | 32.06 | O |
| ATOM | 4882 | OW0 | HOH | W | 74 | 94.370 | 83.334 | 25.559 | 1.00 | 49.32 | O |
| ATOM | 4883 | OW0 | HOH | W | 75 | 83.472 | 102.711 | 1.696 | 1.00 | 44.31 | O |
| ATOM | 4884 | OW0 | HOH | W | 76 | 93.986 | 77.291 | 12.946 | 1.00 | 42.99 | O |
| ATOM | 4885 | OW0 | HOH | W | 77 | 76.972 | 99.266 | −1.109 | 1.00 | 55.11 | O |
| ATOM | 4886 | OW0 | HOH | W | 78 | 109.743 | 60.414 | −20.628 | 1.00 | 80.40 | O |

APPENDIX 1-continued

| ATOM | 4887 | OW0 | HOH | W | 79 | 68.859 | 90.209 | 7.819 | 1.00 | 47.41 | O |
|---|---|---|---|---|---|---|---|---|---|---|---|
| ATOM | 4888 | OW0 | HOH | W | 80 | 86.630 | 96.031 | 22.826 | 1.00 | 50.19 | O |
| ATOM | 4889 | OW0 | HOH | W | 81 | 121.799 | 54.093 | −8.248 | 1.00 | 43.46 | O |
| ATOM | 4890 | OW0 | HOH | W | 82 | 71.808 | 111.866 | 3.226 | 1.00 | 56.18 | O |
| ATOM | 4891 | OW0 | HOH | W | 83 | 121.288 | 60.976 | −9.413 | 1.00 | 51.98 | O |
| ATOM | 4892 | OW0 | HOH | W | 84 | 114.829 | 87.967 | .007 | 1.00 | 53.79 | O |
| ATOM | 4893 | OW0 | HOH | W | 85 | 98.284 | 89.927 | 20.635 | 1.00 | 47.37 | O |
| ATOM | 4894 | OW0 | HOH | W | 86 | 89.965 | 109.043 | 30.735 | 1.00 | 47.09 | O |
| ATOM | 4895 | OW0 | HOH | W | 87 | 83.055 | 87.289 | −2.792 | 1.00 | 48.97 | O |
| ATOM | 4896 | OW0 | HOH | W | 88 | 90.846 | 78.497 | 11.786 | 1.00 | 44.66 | O |
| ATOM | 4897 | OW0 | HOH | W | 89 | 91.823 | 66.452 | −13.286 | 1.00 | 47.69 | O |
| ATOM | 4898 | OW0 | HOH | W | 90 | 96.186 | 99.612 | 8.576 | 1.00 | 36.63 | O |
| ATOM | 4899 | OW0 | HOH | W | 91 | 96.284 | 106.391 | 24.744 | 1.00 | 52.91 | O |
| ATOM | 4900 | OW0 | HOH | W | 92 | 105.603 | 66.821 | 9.996 | 1.00 | 40.89 | O |
| ATOM | 4901 | OW0 | HOH | W | 93 | 78.775 | 117.342 | 12.106 | 1.00 | 43.01 | O |
| ATOM | 4902 | OW0 | HOH | W | 94 | 98.605 | 105.276 | 24.341 | 1.00 | 57.73 | O |
| ATOM | 4903 | OW0 | HOH | W | 95 | 116.536 | 60.059 | −9.087 | 1.00 | 42.94 | O |
| ATOM | 4904 | OW0 | HOH | W | 96 | 121.967 | 78.085 | 6.124 | 1.00 | 53.23 | O |
| ATOM | 4905 | OW0 | HOH | W | 97 | 71.803 | 86.240 | 16.580 | 1.00 | 54.25 | O |
| ATOM | 4906 | OW0 | HOH | W | 98 | 131.097 | 57.443 | −1.009 | 1.00 | 56.82 | O |
| ATOM | 4907 | OW0 | HOH | W | 99 | 124.297 | 77.535 | 3.090 | 1.00 | 45.65 | O |
| ATOM | 4908 | OW0 | HOH | W | 100 | 70.806 | 85.756 | 28.143 | 1.00 | 55.13 | O |
| ATOM | 4909 | OW0 | HOH | W | 101 | 91.919 | 106.381 | 38.145 | 1.00 | 53.91 | O |
| ATOM | 4910 | OW0 | HOH | W | 102 | 87.866 | 116.612 | 34.630 | 1.00 | 46.45 | O |
| ATOM | 4911 | OW0 | HOH | W | 103 | 109.106 | 58.520 | 12.759 | 1.00 | 58.95 | O |
| ATOM | 4912 | OW0 | HOH | W | 104 | 93.853 | 78.237 | 17.559 | 1.00 | 50.70 | O |
| ATOM | 4913 | OW0 | HOH | W | 105 | 93.349 | 80.258 | −20.252 | 1.00 | 55.35 | O |
| ATOM | 4914 | OW0 | HOH | W | 106 | 100.360 | 63.113 | 1.629 | 1.00 | 51.44 | O |
| ATOM | 4915 | OW0 | HOH | W | 107 | 123.345 | 75.161 | 7.955 | 1.00 | 46.48 | O |
| ATOM | 4916 | OW0 | HOH | W | 108 | 94.267 | 71.216 | 14.752 | 1.00 | 52.35 | O |
| ATOM | 4917 | OW0 | HOH | W | 109 | 78.093 | 122.843 | 11.997 | 1.00 | 57.23 | O |
| ATOM | 4918 | OW0 | HOH | W | 110 | 104.468 | 87.631 | 15.500 | 1.00 | 63.46 | O |
| ATOM | 4919 | OW0 | HOH | W | 111 | 71.077 | 111.221 | 22.706 | 1.00 | 43.02 | O |
| ATOM | 4920 | OW0 | HOH | W | 112 | 82.012 | 98.084 | −3.278 | 1.00 | 48.81 | O |
| ATOM | 4921 | OW0 | HOH | W | 113 | 128.566 | 59.812 | −1.693 | 1.00 | 50.26 | O |
| ATOM | 4922 | OW0 | HOH | W | 114 | 80.473 | 93.288 | 27.169 | 1.00 | 35.46 | O |
| ATOM | 4923 | OW0 | HOH | W | 115 | 105.649 | 70.408 | −18.499 | 1.00 | 53.39 | O |
| ATOM | 4924 | OW0 | HOH | W | 116 | 131.374 | 60.572 | 3.290 | 1.00 | 52.25 | O |
| ATOM | 4925 | OW0 | HOH | W | 117 | 129.307 | 75.866 | −4.542 | 1.00 | 57.07 | O |
| ATOM | 4926 | OW0 | HOH | W | 118 | 104.135 | 75.503 | 22.231 | 1.00 | 56.18 | O |
| ATOM | 4927 | OW0 | HOH | W | 119 | 97.278 | 68.311 | 9.722 | 1.00 | 50.25 | O |
| ATOM | 4928 | OW0 | HOH | W | 120 | 79.770 | 95.836 | 26.457 | 1.00 | 50.62 | O |
| ATOM | 4929 | OW0 | HOH | W | 121 | 91.985 | 65.439 | −15.798 | 1.00 | 49.59 | O |
| ATOM | 4930 | OW0 | HOH | W | 122 | 68.692 | 108.778 | 14.612 | 1.00 | 51.91 | O |
| ATOM | 4931 | OW0 | HOH | W | 123 | 87.999 | 76.024 | 12.378 | 1.00 | 48.29 | O |
| ATOM | 4932 | OW0 | HOH | W | 124 | 105.493 | 71.479 | 21.530 | 1.00 | 59.50 | O |
| ATOM | 4933 | OW0 | HOH | W | 125 | 96.599 | 116.121 | 33.589 | 1.00 | 58.48 | O |
| ATOM | 4934 | OW0 | HOH | W | 126 | 98.907 | 87.369 | 21.156 | 1.00 | 54.67 | O |
| ATOM | 4935 | OW0 | HOH | W | 127 | 69.525 | 116.165 | 11.099 | 1.00 | 51.95 | O |
| ATOM | 4936 | OW0 | HOH | W | 128 | 91.440 | 76.793 | 18.821 | 1.00 | 56.60 | O |
| ATOM | 4937 | OW0 | HOH | W | 129 | 85.042 | 131.102 | 30.335 | 1.00 | 48.33 | O |
| ATOM | 4938 | OW0 | HOH | W | 130 | 87.437 | 80.137 | 2.635 | 1.00 | 44.31 | O |
| ATOM | 4939 | OW0 | HOH | W | 131 | 96.022 | 82.694 | 7.382 | 1.00 | 38.19 | O |
| ATOM | 4940 | OW0 | HOH | W | 132 | 94.510 | 104.265 | 5.533 | 1.00 | 42.80 | O |
| ATOM | 4941 | OW0 | HOH | W | 133 | 95.804 | 116.765 | 25.160 | 1.00 | 49.87 | O |
| ATOM | 4942 | OW0 | HOH | W | 134 | 74.398 | 94.688 | 24.483 | 1.00 | 52.11 | O |
| ATOM | 4943 | OW0 | HOH | W | 135 | 76.348 | 116.464 | 10.588 | 1.00 | 54.66 | O |
| ATOM | 4944 | OW0 | HOH | W | 136 | 117.687 | 79.541 | 16.935 | 1.00 | 43.49 | O |
| ATOM | 4945 | OW0 | HOH | W | 137 | 94.695 | 90.908 | −.790 | 1.00 | 53.54 | O |
| ATOM | 4946 | OW0 | HOH | W | 138 | 90.692 | 106.459 | 31.487 | 1.00 | 50.01 | O |
| ATOM | 4947 | OW0 | HOH | W | 139 | 115.174 | 64.059 | 5.039 | 1.00 | 26.95 | O |
| ATOM | 4948 | OW0 | HOH | W | 140 | 105.977 | 67.308 | −9.211 | 1.00 | 20.03 | O |
| ATOM | 4949 | OW0 | HOH | W | 141 | 91.572 | 95.734 | 20.696 | 1.00 | 27.96 | O |
| ATOM | 4950 | OW0 | HOH | W | 142 | 111.726 | 71.415 | −10.274 | 1.00 | 24.44 | O |
| ATOM | 4951 | OW0 | HOH | W | 143 | 110.063 | 77.678 | −12.733 | 1.00 | 24.16 | O |
| ATOM | 4952 | OW0 | HOH | W | 144 | 106.494 | 68.467 | −5.715 | 1.00 | 24.95 | O |
| ATOM | 4953 | OW0 | HOH | W | 145 | 98.134 | 92.663 | 15.550 | 1.00 | 35.88 | O |
| ATOM | 4954 | OW0 | HOH | W | 146 | 95.612 | 66.740 | −6.057 | 1.00 | 30.19 | O |
| ATOM | 4955 | OW0 | HOH | W | 147 | 111.602 | 64.288 | −3.200 | 1.00 | 23.93 | O |
| ATOM | 4956 | OW0 | HOH | W | 148 | 95.454 | 71.602 | −5.183 | 1.00 | 28.35 | O |
| ATOM | 4957 | OW0 | HOH | W | 149 | 84.588 | 87.845 | 24.112 | 1.00 | 27.22 | O |
| ATOM | 4958 | OW0 | HOH | W | 150 | 122.468 | 75.135 | 3.144 | 1.00 | 30.68 | O |
| ATOM | 4959 | OW0 | HOH | W | 151 | 88.884 | 94.935 | 21.686 | 1.00 | 30.32 | O |
| ATOM | 4960 | OW0 | HOH | W | 152 | 88.510 | 103.747 | 22.240 | 1.00 | 25.34 | O |
| ATOM | 4961 | OW0 | HOH | W | 153 | 104.006 | 76.352 | −16.329 | 1.00 | 33.30 | O |
| ATOM | 4962 | OW0 | HOH | W | 154 | 117.100 | 63.462 | .906 | 1.00 | 28.58 | O |
| ATOM | 4963 | OW0 | HOH | W | 155 | 93.950 | 99.216 | 15.261 | 1.00 | 28.79 | O |
| ATOM | 4964 | OW0 | HOH | W | 156 | 109.555 | 67.391 | 12.508 | 1.00 | 33.01 | O |
| ATOM | 4965 | OW0 | HOH | W | 157 | 81.662 | 84.819 | 18.586 | 1.00 | 32.09 | O |

APPENDIX 1-continued

| | | | | | | | | | | | |
|---|---|---|---|---|---|---|---|---|---|---|---|
| ATOM | 4966 | OW0 | HOH | W | 158 | 74.314 | 112.891 | 12.440 | 1.00 | 41.20 | O |
| ATOM | 4967 | OW0 | HOH | W | 159 | 98.007 | 63.045 | −.197 | 1.00 | 27.27 | O |
| ATOM | 4968 | OW0 | HOH | W | 160 | 107.413 | 72.406 | −16.586 | 1.00 | 28.13 | O |
| ATOM | 4969 | OW0 | HOH | W | 161 | 105.468 | 76.492 | −13.953 | 1.00 | 32.67 | O |
| ATOM | 4970 | OW0 | HOH | W | 162 | 69.672 | 97.709 | −2.338 | 1.00 | 29.43 | O |
| ATOM | 4971 | OW0 | HOH | W | 163 | 95.657 | 97.751 | 10.748 | 1.00 | 32.09 | O |
| ATOM | 4972 | OW0 | HOH | W | 164 | 90.311 | 108.749 | 27.961 | 1.00 | 39.93 | O |
| ATOM | 4973 | OW0 | HOH | W | 165 | 96.414 | 69.185 | −4.994 | 1.00 | 30.65 | O |
| ATOM | 4974 | OW0 | HOH | W | 166 | 102.900 | 68.266 | 4.562 | 1.00 | 27.02 | O |
| ATOM | 4975 | OW0 | HOH | W | 167 | 70.375 | 105.688 | 1.130 | 1.00 | 37.09 | O |
| ATOM | 4976 | OW0 | HOH | W | 168 | 89.004 | 113.747 | 14.123 | 1.00 | 37.10 | O |
| ATOM | 4977 | OW0 | HOH | W | 169 | 95.791 | 91.043 | 20.913 | 1.00 | 36.59 | O |
| ATOM | 4978 | OW0 | HOH | W | 170 | 112.331 | 76.127 | −12.262 | 1.00 | 30.80 | O |
| ATOM | 4979 | OW0 | HOH | W | 171 | 124.631 | 68.678 | 11.902 | 1.00 | 27.18 | O |
| ATOM | 4980 | OW0 | HOH | W | 172 | 88.296 | 97.216 | 19.585 | 1.00 | 26.66 | O |
| ATOM | 4981 | OW0 | HOH | W | 173 | 93.287 | 77.064 | 9.356 | 1.00 | 30.61 | O |
| ATOM | 4982 | OW0 | HOH | W | 174 | 93.351 | 73.164 | −4.714 | 1.00 | 31.37 | O |
| ATOM | 4983 | OW0 | HOH | W | 175 | 83.589 | 88.477 | 21.664 | 1.00 | 30.32 | O |
| ATOM | 4984 | OW0 | HOH | W | 176 | 115.793 | 61.018 | −5.488 | 1.00 | 30.48 | O |
| ATOM | 4985 | OW0 | HOH | W | 177 | 92.617 | 107.270 | 24.263 | 1.00 | 31.04 | O |
| ATOM | 4986 | OW0 | HOH | W | 178 | 75.390 | 107.388 | 22.547 | 1.00 | 30.30 | O |
| ATOM | 4987 | OW0 | HOH | W | 179 | 109.595 | 70.790 | −16.532 | 1.00 | 30.40 | O |
| ATOM | 4988 | OW0 | HOH | W | 180 | 83.941 | 58.961 | −3.517 | 1.00 | 67.45 | O |
| ATOM | 4989 | OW0 | HOH | W | 181 | 77.401 | 98.133 | 20.880 | 1.00 | 24.22 | O |
| ATOM | 4990 | OW0 | HOH | W | 182 | 94.044 | 98.992 | 12.540 | 1.00 | 31.36 | O |
| ATOM | 4991 | OW0 | HOH | W | 183 | 86.874 | 110.399 | 21.683 | 1.00 | 36.25 | O |
| ATOM | 4992 | OW0 | HOH | W | 184 | 86.193 | 116.768 | 32.234 | 1.00 | 37.97 | O |
| ATOM | 4993 | OW0 | HOH | W | 185 | 85.770 | 104.064 | 22.958 | 1.00 | 37.76 | O |
| ATOM | 4994 | OW0 | HOH | W | 186 | 104.260 | 66.839 | −7.168 | 1.00 | 33.09 | O |
| ATOM | 4995 | OW0 | HOH | W | 187 | 90.341 | 81.111 | 22.906 | 1.00 | 33.23 | O |
| ATOM | 4996 | OW0 | HOH | W | 188 | 68.982 | 100.968 | 2.618 | 1.00 | 38.00 | O |
| ATOM | 4997 | OW0 | HOH | W | 189 | 111.789 | 72.130 | −17.304 | 1.00 | 37.41 | O |
| ATOM | 4998 | OW0 | HOH | W | 190 | 72.877 | 107.394 | 20.431 | 1.00 | 32.09 | O |
| ATOM | 4999 | OW0 | HOH | W | 191 | 115.686 | 80.943 | 15.761 | 1.00 | 43.19 | O |
| ATOM | 5000 | OW0 | HOH | W | 192 | 94.562 | 107.918 | 39.798 | 1.00 | 46.00 | O |
| ATOM | 5001 | OW0 | HOH | W | 193 | 90.845 | 83.527 | 10.683 | 1.00 | 36.18 | O |
| ATOM | 5002 | OW0 | HOH | W | 194 | 108.585 | 62.650 | 3.633 | 1.00 | 31.09 | O |
| ATOM | 5003 | OW0 | HOH | W | 195 | 95.349 | 96.528 | 7.244 | 1.00 | 42.42 | O |
| ATOM | 5004 | OW0 | HOH | W | 196 | 106.788 | 63.442 | 8.141 | 1.00 | 40.36 | O |
| ATOM | 5005 | OW0 | HOH | W | 197 | 123.250 | 69.617 | .178 | 1.00 | 33.17 | O |
| ATOM | 5006 | OW0 | HOH | W | 198 | 76.085 | 104.781 | 22.249 | 1.00 | 30.70 | O |
| ATOM | 5007 | OW0 | HOH | W | 199 | 107.829 | 65.821 | 8.641 | 1.00 | 28.48 | O |
| ATOM | 5008 | OW0 | HOH | W | 200 | 85.378 | 81.766 | 14.598 | 1.00 | 32.10 | O |
| ATOM | 5009 | OW0 | HOH | W | 201 | 83.740 | 97.120 | 22.812 | 1.00 | 40.47 | O |
| ATOM | 5010 | OW0 | HOH | W | 202 | 98.060 | 80.187 | −13.870 | 1.00 | 35.66 | O |
| ATOM | 5011 | OW0 | HOH | W | 203 | 70.038 | 99.984 | .339 | 1.00 | 30.42 | O |
| ATOM | 5012 | OW0 | HOH | W | 204 | 73.808 | 103.355 | 21.960 | 1.00 | 40.14 | O |
| ATOM | 5013 | OW0 | HOH | W | 205 | 81.277 | 104.283 | 24.948 | 1.00 | 38.79 | O |
| ATOM | 5014 | OW0 | HOH | W | 206 | 112.126 | 74.131 | −10.310 | 1.00 | 25.57 | O |
| ATOM | 5015 | OW0 | HOH | W | 207 | 108.041 | 77.020 | −14.682 | 1.00 | 37.20 | O |
| ATOM | 5016 | OW0 | HOH | W | 208 | 70.927 | 89.169 | 9.133 | 1.00 | 34.47 | O |
| ATOM | 5017 | OW0 | HOH | W | 209 | 98.608 | 87.851 | −6.249 | 1.00 | 37.05 | O |
| ATOM | 5018 | OW0 | HOH | W | 210 | 100.532 | 58.630 | −19.386 | 1.00 | 43.86 | O |
| ATOM | 5019 | OW0 | HOH | W | 211 | 89.828 | 81.758 | 25.473 | 1.00 | 43.05 | O |
| ATOM | 5020 | OW0 | HOH | W | 212 | 96.516 | 88.957 | 12.560 | 1.00 | 35.03 | O |
| ATOM | 5021 | OW0 | HOH | W | 213 | 88.283 | 113.021 | 11.492 | 1.00 | 31.14 | O |
| ATOM | 5022 | OW0 | HOH | W | 214 | 110.656 | 64.044 | −.576 | 1.00 | 33.32 | O |
| ATOM | 5023 | OW0 | HOH | W | 215 | 119.207 | 60.233 | −10.988 | 1.00 | 58.93 | O |
| ATOM | 5024 | OW0 | HOH | W | 216 | 88.945 | 79.238 | 13.812 | 1.00 | 44.84 | O |
| ATOM | 5025 | OW0 | HOH | W | 217 | 129.842 | 68.821 | 20.358 | 1.00 | 43.56 | O |
| ATOM | 5026 | OW0 | HOH | W | 218 | 79.349 | 120.509 | 15.148 | 1.00 | 37.35 | O |
| ATOM | 5027 | OW0 | HOH | W | 219 | 74.600 | 100.462 | −.267 | 1.00 | 36.66 | O |
| ATOM | 5028 | OW0 | HOH | W | 220 | 91.912 | 103.597 | 5.094 | 1.00 | 44.67 | O |
| ATOM | 5029 | OW0 | HOH | W | 221 | 111.811 | 79.875 | −12.714 | 1.00 | 33.86 | O |
| ATOM | 5030 | OW0 | HOH | W | 222 | 92.769 | 78.464 | 15.119 | 1.00 | 37.93 | O |
| ATOM | 5031 | OW0 | HOH | W | 223 | 100.556 | 93.769 | −.962 | 1.00 | 62.50 | O |
| ATOM | 5032 | OW0 | HOH | W | 224 | 91.339 | 76.054 | 4.899 | 1.00 | 35.87 | O |
| ATOM | 5033 | OW0 | HOH | W | 225 | 103.866 | 66.093 | −2.056 | 1.00 | 42.76 | O |
| ATOM | 5034 | OW0 | HOH | W | 226 | 96.756 | 69.216 | −16.088 | 1.00 | 41.82 | O |
| ATOM | 5035 | OW0 | HOH | W | 227 | 94.254 | 88.974 | 5.767 | 1.00 | 41.94 | O |
| ATOM | 5036 | OW0 | HOH | W | 228 | 96.060 | 93.104 | 10.769 | 1.00 | 38.14 | O |
| ATOM | 5037 | OW0 | HOH | W | 229 | 112.813 | 75.816 | −14.932 | 1.00 | 37.00 | O |
| ATOM | 5038 | OW0 | HOH | W | 230 | 126.326 | 69.356 | −1.254 | 1.00 | 52.07 | O |
| ATOM | 5039 | OW0 | HOH | W | 231 | 72.109 | 96.793 | −8.546 | 1.00 | 39.67 | O |
| ATOM | 5040 | OW0 | HOH | W | 232 | 109.758 | 65.029 | 10.344 | 1.00 | 33.92 | O |
| ATOM | 5041 | OW0 | HOH | W | 233 | 110.406 | 72.922 | 16.817 | 1.00 | 49.71 | O |
| ATOM | 5042 | OW0 | HOH | W | 234 | 122.888 | 72.710 | .585 | 1.00 | 28.97 | O |
| ATOM | 5043 | OW0 | HOH | W | 235 | 108.699 | 68.060 | −23.487 | 1.00 | 33.67 | O |
| ATOM | 5044 | OW0 | HOH | W | 236 | 83.099 | 86.754 | 19.485 | 1.00 | 28.13 | O |

APPENDIX 1-continued

| | | | | | | | | | | | |
|---|---|---|---|---|---|---|---|---|---|---|---|
| ATOM | 5045 | OW0 | HOH | W | 237 | 82.503 | 112.833 | 6.690 | 1.00 | 44.01 | O |
| ATOM | 5046 | OW0 | HOH | W | 238 | 116.514 | 60.486 | −11.919 | 1.00 | 45.97 | O |
| ATOM | 5047 | OW0 | HOH | W | 239 | 67.941 | 104.773 | 7.050 | 1.00 | 40.45 | O |
| ATOM | 5048 | OW0 | HOH | W | 240 | 91.918 | 77.752 | 7.181 | 1.00 | 32.08 | O |
| ATOM | 5049 | OW0 | HOH | W | 241 | 110.549 | 59.928 | −18.195 | 1.00 | 52.99 | O |
| ATOM | 5050 | OW0 | HOH | W | 242 | 121.524 | 72.009 | 16.696 | 1.00 | 41.42 | O |
| ATOM | 5051 | OW0 | HOH | W | 243 | 111.022 | 64.406 | 15.468 | 1.00 | 41.06 | O |
| ATOM | 5052 | OW0 | HOH | W | 244 | 82.435 | 110.272 | 21.889 | 1.00 | 32.58 | O |
| ATOM | 5053 | OW0 | HOH | W | 245 | 71.668 | 93.725 | −2.529 | 1.00 | 39.86 | O |
| ATOM | 5054 | OW0 | HOH | W | 246 | 108.451 | 89.715 | 24.160 | 1.00 | 53.15 | O |
| ATOM | 5055 | OW0 | HOH | W | 247 | 94.785 | 79.079 | −12.257 | 1.00 | 33.57 | O |
| ATOM | 5056 | OW0 | HOH | W | 248 | 103.630 | 67.635 | −15.084 | 1.00 | 26.72 | O |
| ATOM | 5057 | OW0 | HOH | W | 249 | 132.725 | 50.985 | 11.789 | 1.00 | 53.07 | O |
| ATOM | 5058 | OW0 | HOH | W | 250 | 75.133 | 79.616 | 13.771 | 1.00 | 51.74 | O |
| ATOM | 5059 | OW0 | HOH | W | 251 | 99.363 | 70.167 | 6.055 | 1.00 | 42.31 | O |
| ATOM | 5060 | OW0 | HOH | W | 252 | 93.926 | 84.285 | 21.276 | 1.00 | 40.96 | O |
| ATOM | 5061 | OW0 | HOH | W | 253 | 76.437 | 104.048 | 24.843 | 1.00 | 38.48 | O |
| ATOM | 5062 | OW0 | HOH | W | 254 | 97.057 | 72.019 | 6.459 | 1.00 | 38.58 | O |
| ATOM | 5063 | OW0 | HOH | W | 255 | 97.939 | 71.125 | −19.622 | 1.00 | 42.95 | O |
| ATOM | 5064 | OW0 | HOH | W | 256 | 74.047 | 111.057 | 1.539 | 1.00 | 42.06 | O |
| ATOM | 5065 | OW0 | HOH | W | 257 | 102.841 | 90.335 | −6.080 | 1.00 | 44.71 | O |
| ATOM | 5066 | OW0 | HOH | W | 258 | 89.664 | 79.557 | 16.489 | 1.00 | 36.55 | O |
| ATOM | 5067 | OW0 | HOH | W | 259 | 125.229 | 74.030 | 1.313 | 1.00 | 55.38 | O |
| ATOM | 5068 | OW0 | HOH | W | 260 | 108.362 | 74.964 | −16.447 | 1.00 | 40.28 | O |
| ATOM | 5069 | OW0 | HOH | W | 261 | 76.854 | 79.541 | 17.939 | 1.00 | 49.23 | O |
| ATOM | 5070 | OW0 | HOH | W | 262 | 89.178 | 110.220 | 4.497 | 1.00 | 39.11 | O |
| ATOM | 5071 | OW0 | HOH | W | 263 | 86.696 | 80.774 | 10.301 | 1.00 | 57.10 | O |
| ATOM | 5072 | OW0 | HOH | W | 264 | 65.659 | 109.504 | 2.040 | 1.00 | 84.74 | O |
| ATOM | 5073 | OW0 | HOH | W | 265 | 92.168 | 75.504 | −14.167 | 1.00 | 38.54 | O |
| ATOM | 5074 | OW0 | HOH | W | 266 | 73.103 | 93.029 | 18.731 | 1.00 | 35.19 | O |
| ATOM | 5075 | OW0 | HOH | W | 267 | 74.442 | 114.699 | 10.445 | 1.00 | 41.03 | O |
| ATOM | 5076 | OW0 | HOH | W | 268 | 70.192 | 112.744 | 20.614 | 1.00 | 43.13 | O |
| ATOM | 5077 | OW0 | HOH | W | 269 | 85.465 | 113.334 | 9.409 | 1.00 | 34.59 | O |
| ATOM | 5078 | OW0 | HOH | W | 270 | 99.852 | 99.001 | 12.658 | 1.00 | 44.70 | O |
| ATOM | 5079 | OW0 | HOH | W | 271 | 86.914 | 128.516 | 29.593 | 1.00 | 50.39 | O |
| ATOM | 5080 | OW0 | HOH | W | 272 | 110.683 | 50.733 | 13.023 | 1.00 | 49.18 | O |
| ATOM | 5081 | OW0 | HOH | W | 273 | 70.722 | 95.324 | 22.555 | 1.00 | 52.80 | O |
| ATOM | 5082 | OW0 | HOH | W | 274 | 111.395 | 55.621 | −8.166 | 1.00 | 53.26 | O |
| ATOM | 5083 | OW0 | HOH | W | 275 | 92.557 | 81.253 | 26.291 | 1.00 | 43.90 | O |
| ATOM | 5084 | OW0 | HOH | W | 276 | 122.499 | 79.826 | −1.479 | 1.00 | 46.72 | O |
| ATOM | 5085 | OW0 | HOH | W | 277 | 108.657 | 88.418 | 4.969 | 1.00 | 36.38 | O |
| ATOM | 5086 | OW0 | HOH | W | 278 | 115.500 | 57.569 | −2.833 | 1.00 | 40.33 | O |
| ATOM | 5087 | OW0 | HOH | W | 279 | 86.712 | 75.892 | −2.123 | 1.00 | 56.75 | O |
| ATOM | 5088 | OW0 | HOH | W | 280 | 71.105 | 125.282 | 15.633 | 1.00 | 62.07 | O |
| ATOM | 5089 | OW0 | HOH | W | 281 | 103.695 | 67.865 | −17.750 | 1.00 | 42.51 | O |
| ATOM | 5090 | OW0 | HOH | W | 282 | 107.208 | 62.146 | 5.822 | 1.00 | 40.43 | O |
| ATOM | 5091 | OW0 | HOH | W | 283 | 115.353 | 73.467 | −18.262 | 1.00 | 50.51 | O |
| ATOM | 5092 | OW0 | HOH | W | 284 | 88.763 | 79.990 | 32.160 | 1.00 | 42.88 | O |
| ATOM | 5093 | OW0 | HOH | W | 285 | 135.850 | 59.817 | 11.242 | 1.00 | 50.54 | O |
| ATOM | 5094 | OW0 | HOH | W | 286 | 92.886 | 79.771 | 28.566 | 1.00 | 46.38 | O |
| ATOM | 5095 | OW0 | HOH | W | 287 | 83.439 | 79.501 | 14.040 | 1.00 | 48.23 | O |
| ATOM | 5096 | OW0 | HOH | W | 288 | 78.571 | 124.277 | 29.320 | 1.00 | 50.95 | O |
| ATOM | 5097 | OW0 | HOH | W | 289 | 107.891 | 61.672 | 10.153 | 1.00 | 36.79 | O |
| ATOM | 5098 | OW0 | HOH | W | 290 | 113.998 | 79.456 | 19.853 | 1.00 | 50.02 | O |
| ATOM | 5099 | OW0 | HOH | W | 291 | 118.804 | 79.460 | −8.971 | 1.00 | 50.40 | O |
| ATOM | 5100 | OW0 | HOH | W | 292 | 81.364 | 115.880 | 9.194 | 1.00 | 50.70 | O |
| ATOM | 5101 | OW0 | HOH | W | 293 | 68.721 | 109.194 | 8.074 | 1.00 | 58.52 | O |
| ATOM | 5102 | OW0 | HOH | W | 294 | 120.768 | 79.007 | 13.034 | 1.00 | 61.33 | O |
| ATOM | 5103 | OW0 | HOH | W | 295 | 75.891 | 88.994 | .297 | 1.00 | 54.11 | O |
| ATOM | 5104 | OW0 | HOH | W | 296 | 94.588 | 67.737 | −16.583 | 1.00 | 58.97 | O |
| ATOM | 5105 | OW0 | HOH | W | 297 | 99.039 | 95.049 | 16.448 | 1.00 | 42.72 | O |
| ATOM | 5106 | OW0 | HOH | W | 298 | 115.474 | 57.648 | −8.512 | 1.00 | 48.77 | O |
| ATOM | 5107 | OW0 | HOH | W | 299 | 110.837 | 60.813 | 1.979 | 1.00 | 45.33 | O |
| ATOM | 5108 | OW0 | HOH | W | 300 | 101.882 | 63.758 | 7.062 | 1.00 | 49.28 | O |
| ATOM | 5109 | OW0 | HOH | W | 301 | 129.321 | 60.524 | −4.131 | 1.00 | 81.69 | O |
| ATOM | 5110 | OW0 | HOH | W | 302 | 89.398 | 102.624 | 34.870 | 1.00 | 54.86 | O |
| ATOM | 5111 | OW0 | HOH | W | 303 | 117.335 | 82.652 | .516 | 1.00 | 51.21 | O |
| ATOM | 5112 | OW0 | HOH | W | 304 | 107.766 | 59.670 | −22.058 | 1.00 | 60.61 | O |
| ATOM | 5113 | OW0 | HOH | W | 305 | 91.333 | 83.287 | −6.655 | 1.00 | 45.34 | O |
| ATOM | 5114 | OW0 | HOH | W | 306 | 70.806 | 94.171 | −.060 | 1.00 | 29.76 | O |
| ATOM | 5115 | OW0 | HOH | W | 307 | 80.862 | 97.349 | 24.024 | 1.00 | 40.63 | O |
| ATOM | 5116 | OW0 | HOH | W | 308 | 122.294 | 63.458 | −9.831 | 1.00 | 49.86 | O |
| ATOM | 5117 | OW0 | HOH | W | 309 | 105.097 | 60.746 | −.335 | 1.00 | 43.25 | O |
| ATOM | 5118 | OW0 | HOH | W | 310 | 77.872 | 133.218 | 16.159 | 1.00 | 43.95 | O |
| ATOM | 5119 | OW0 | HOH | W | 311 | 78.465 | 83.721 | 32.304 | 1.00 | 156.25 | O |
| ATOM | 5120 | OW0 | HOH | W | 312 | 106.423 | 62.667 | 1.983 | 1.00 | 49.39 | O |
| ATOM | 5121 | OW0 | HOH | W | 313 | 81.520 | 99.833 | 24.843 | 1.00 | 57.71 | O |
| ATOM | 5122 | OW0 | HOH | W | 314 | 92.840 | 104.472 | 36.480 | 1.00 | 62.76 | O |
| ATOM | 5123 | OW0 | HOH | W | 315 | 112.645 | 58.639 | 1.176 | 1.00 | 42.29 | O |

APPENDIX 1-continued

| | | | | | | | | | | | |
|---|---|---|---|---|---|---|---|---|---|---|---|
| ATOM | 5124 | OW0 | HOH | W | 316 | 116.231 | 54.884 | 10.794 | 1.00 | 63.78 | O |
| ATOM | 5125 | OW0 | HOH | W | 317 | 93.497 | 107.612 | 26.807 | 1.00 | 49.41 | O |
| ATOM | 5126 | OW0 | HOH | W | 318 | 91.655 | 80.630 | 32.623 | 1.00 | 46.46 | O |
| ATOM | 5127 | OW0 | HOH | W | 319 | 68.620 | 103.926 | 4.542 | 1.00 | 52.31 | O |
| ATOM | 5128 | OW0 | HOH | W | 320 | 100.302 | 82.905 | −13.439 | 1.00 | 63.00 | O |
| ATOM | 5129 | OW0 | HOH | W | 321 | 92.533 | 77.840 | −12.820 | 1.00 | 56.04 | O |
| ATOM | 5130 | OW0 | HOH | W | 322 | 96.113 | 125.485 | 19.031 | 1.00 | 63.79 | O |
| ATOM | 5131 | OW0 | HOH | W | 323 | 124.205 | 53.811 | 16.855 | 1.00 | 57.01 | O |
| ATOM | 5132 | OW0 | HOH | W | 324 | 99.937 | 87.553 | 10.667 | 1.00 | 41.77 | O |
| ATOM | 5133 | OW0 | HOH | W | 325 | 117.411 | 44.033 | −8.380 | 1.00 | 59.38 | O |
| ATOM | 5134 | OW0 | HOH | W | 326 | 70.407 | 113.807 | 6.661 | 1.00 | 55.06 | O |
| ATOM | 5135 | OW0 | HOH | W | 327 | 122.232 | 49.416 | −5.933 | 1.00 | 61.01 | O |
| ATOM | 5136 | OW0 | HOH | W | 328 | 75.914 | 119.200 | 13.201 | 1.00 | 45.69 | O |
| ATOM | 5137 | OW0 | HOH | W | 329 | 97.359 | 113.808 | 36.221 | 1.00 | 71.00 | O |
| ATOM | 5138 | OW0 | HOH | W | 330 | 86.966 | 105.740 | 33.144 | 1.00 | 83.46 | O |
| ATOM | 5139 | OW0 | HOH | W | 331 | 84.694 | 118.423 | 33.770 | 1.00 | 54.87 | O |
| ATOM | 5140 | OW0 | HOH | W | 332 | 75.041 | 137.652 | 14.556 | 1.00 | 54.16 | O |
| ATOM | 5141 | OW0 | HOH | W | 333 | 118.473 | 56.262 | 10.143 | 1.00 | 51.75 | O |
| ATOM | 5142 | OW0 | HOH | W | 334 | 69.844 | 115.369 | 20.679 | 1.00 | 68.33 | O |
| ATOM | 5143 | OW0 | HOH | W | 335 | 132.249 | 63.977 | 2.287 | 1.00 | 53.55 | O |
| ATOM | 5144 | OW0 | HOH | W | 336 | 65.931 | 95.727 | 15.720 | 1.00 | 46.12 | O |
| ATOM | 5145 | OW0 | HOH | W | 337 | 109.437 | 60.036 | 14.960 | 1.00 | 54.27 | O |
| ATOM | 5146 | OW0 | HOH | W | 338 | 70.157 | 111.060 | 18.344 | 1.00 | 48.36 | O |
| ATOM | 5147 | OW0 | HOH | W | 339 | 92.468 | 78.069 | 31.740 | 1.00 | 47.99 | O |
| ATOM | 5148 | OW0 | HOH | W | 340 | 87.508 | 64.848 | 5.461 | 1.00 | 63.21 | O |
| ATOM | 5149 | OW0 | HOH | W | 341 | 104.374 | 73.674 | −20.292 | 1.00 | 53.74 | O |
| ATOM | 5150 | OW0 | HOH | W | 342 | 95.984 | 115.521 | 37.803 | 1.00 | 60.49 | O |
| ATOM | 5151 | OW0 | HOH | W | 343 | 130.089 | 67.975 | 23.429 | 1.00 | 61.04 | O |
| ATOM | 5152 | OW0 | HOH | W | 344 | 125.417 | 71.247 | 11.596 | 1.00 | 48.12 | O |
| ATOM | 5153 | OW0 | HOH | W | 345 | 87.101 | 109.316 | 27.903 | 1.00 | 44.47 | O |
| ATOM | 5154 | OW0 | HOH | W | 346 | 122.737 | 71.288 | 14.312 | 1.00 | 28.47 | O |
| ATOM | 5155 | OW0 | HOH | W | 347 | 72.071 | 80.297 | 22.360 | 1.00 | 55.77 | O |
| ATOM | 5156 | OW0 | HOH | W | 348 | 109.514 | 62.652 | −20.374 | 1.00 | 130.62 | O |
| ATOM | 5157 | OW0 | HOH | W | 349 | 83.000 | 104.004 | 29.016 | 1.00 | 88.90 | O |
| ATOM | 5158 | OW0 | HOH | W | 350 | 73.530 | 82.271 | 2.640 | 1.00 | 51.33 | O |
| ATOM | 5159 | OW0 | HOH | W | 351 | 114.203 | 82.325 | −14.269 | 1.00 | 65.94 | O |
| ATOM | 5160 | OW0 | HOH | W | 352 | 97.702 | 115.321 | 18.510 | 1.00 | 44.81 | O |
| ATOM | 5161 | OW0 | HOH | W | 353 | 125.760 | 74.373 | −7.665 | 1.00 | 48.72 | O |
| ATOM | 5162 | OW0 | HOH | W | 354 | 113.193 | 69.388 | −23.556 | 1.00 | 47.29 | O |
| ATOM | 5163 | OW0 | HOH | W | 355 | 113.067 | 81.905 | −7.350 | 1.00 | 43.16 | O |
| ATOM | 5164 | OW0 | HOH | W | 356 | 102.549 | 86.934 | 27.057 | 1.00 | 71.97 | O |
| ATOM | 5165 | OW0 | HOH | W | 357 | 92.366 | 45.705 | −7.314 | 1.00 | 56.41 | O |
| ATOM | 5166 | OW0 | HOH | W | 358 | 91.155 | 75.091 | 29.904 | 1.00 | 47.34 | O |
| ATOM | 5167 | OW0 | HOH | W | 359 | 64.634 | 97.395 | 17.240 | 1.00 | 72.67 | O |
| ATOM | 5168 | OW0 | HOH | W | 360 | 129.805 | 45.061 | 4.002 | 1.00 | 52.65 | O |
| ATOM | 5169 | OW0 | HOH | W | 361 | 95.676 | 87.369 | −9.456 | 1.00 | 65.98 | O |
| ATOM | 5170 | OW0 | HOH | W | 362 | 109.470 | 54.055 | 6.367 | 1.00 | 57.50 | O |
| ATOM | 5171 | OW0 | HOH | W | 363 | 92.493 | 102.710 | 28.535 | 1.00 | 49.05 | O |
| ATOM | 5172 | OW0 | HOH | W | 364 | 115.690 | 50.561 | 11.023 | 1.00 | 84.17 | O |
| ATOM | 5173 | OW0 | HOH | W | 365 | 134.066 | 62.283 | 6.214 | 1.00 | 68.68 | O |
| ATOM | 5174 | OW0 | HOH | W | 366 | 75.031 | 116.109 | 30.832 | 1.00 | 56.68 | O |
| ATOM | 5175 | OW0 | HOH | W | 367 | 97.909 | 119.332 | 20.590 | 1.00 | 74.32 | O |
| ATOM | 5176 | OW0 | HOH | W | 368 | 109.279 | 71.011 | 14.097 | 1.00 | 43.41 | O |
| ATOM | 5177 | OW0 | HOH | W | 369 | 87.346 | 94.559 | −3.541 | 1.00 | 52.78 | O |
| ATOM | 5178 | OW0 | HOH | W | 370 | 91.527 | 102.222 | 32.591 | 1.00 | 60.65 | O |
| ATOM | 5179 | OW0 | HOH | W | 371 | 109.744 | 77.602 | 18.619 | 1.00 | 52.76 | O |
| ATOM | 5180 | OW0 | HOH | W | 372 | 111.425 | 80.275 | 17.032 | 1.00 | 63.07 | O |
| ATOM | 5181 | OW0 | HOH | W | 373 | 126.548 | 64.330 | −6.963 | 1.00 | 39.43 | O |
| ATOM | 5182 | OW0 | HOH | W | 374 | 103.683 | 64.751 | 8.737 | 1.00 | 65.43 | O |
| ATOM | 5183 | OW0 | HOH | W | 375 | 112.456 | 88.279 | −5.906 | 1.00 | 57.23 | O |
| ATOM | 5184 | OW0 | HOH | W | 376 | 116.589 | 83.516 | −14.656 | 1.00 | 73.15 | O |
| ATOM | 5185 | OW0 | HOH | W | 377 | 98.856 | 100.105 | 8.262 | 1.00 | 51.64 | O |
| ATOM | 5186 | OW0 | HOH | W | 378 | 77.782 | 133.705 | 25.841 | 1.00 | 64.24 | O |
| ATOM | 5187 | OW0 | HOH | W | 379 | 82.932 | 87.852 | 35.486 | 1.00 | 64.01 | O |
| ATOM | 5188 | OW0 | HOH | W | 380 | 106.078 | 82.165 | 22.558 | 1.00 | 58.31 | O |
| ATOM | 5189 | OW0 | HOH | W | 381 | 97.557 | 80.942 | 18.359 | 1.00 | 91.36 | O |
| ATOM | 5190 | OW0 | HOH | W | 382 | 114.756 | 66.918 | 17.638 | 1.00 | 50.36 | O |
| ATOM | 5191 | OW0 | HOH | W | 383 | 80.954 | 56.912 | 5.182 | 1.00 | 64.92 | O |
| ATOM | 5192 | OW0 | HOH | W | 384 | 124.014 | 57.209 | −8.373 | 1.00 | 61.29 | O |
| ATOM | 5193 | OW0 | HOH | W | 385 | 98.784 | 108.361 | 23.704 | 1.00 | 61.81 | O |
| ATOM | 5194 | OW0 | HOH | W | 386 | 86.110 | 74.369 | −5.011 | 1.00 | 39.77 | O |
| ATOM | 5195 | OW0 | HOH | W | 387 | 71.068 | 92.965 | −7.221 | 1.00 | 52.87 | O |
| ATOM | 5196 | OW0 | HOH | W | 388 | 85.614 | 107.203 | 34.965 | 1.00 | 68.28 | O |
| ATOM | 5197 | OW0 | HOH | W | 389 | 61.922 | 106.172 | 5.591 | 1.00 | 62.57 | O |
| ATOM | 5198 | OW0 | HOH | W | 390 | 80.788 | 95.999 | 30.535 | 1.00 | 64.76 | O |
| ATOM | 5199 | OW0 | HOH | W | 391 | 115.160 | 76.769 | −13.018 | 1.00 | 62.62 | O |

APPENDIX 1-continued

| ATOM | 5200 | OW0 | HOH | W | 392 | 90.444 | 73.324 | −17.047 | 1.00 | 43.73 | O |
| --- | --- | --- | --- | --- | --- | --- | --- | --- | --- | --- | --- |
| ATOM | 5201 | OW0 | HOH | W | 393 | 74.341 | 126.822 | 29.543 | 1.00 | 53.77 | O |
| ATOM | 5202 | OW0 | HOH | W | 394 | 104.216 | 102.960 | 17.673 | 1.00 | 57.08 | O |
| ATOM | 5203 | OW0 | HOH | W | 395 | 68.611 | 107.135 | 16.686 | 1.00 | 79.51 | O |

REFERENCES

Beddell, C. R. (1984). Designing drugs to a fit a macromolecular receptor. *Chem. Soc. Rev.* 13, 279-314.

Bohm, H. J. & Stahl, M. (1999). Rapid empirical scoring functions in virtual screening applications. *Med. Chem. Res.* 9, 445-462.

Booz G W, Day J N, Speth R, Baker K M. Cytokine G-protein signaling crosstalk in cardiomyocytes: attenuation of Jak-STAT activation by endothelin-1. Mol Cell Biochem. 2002 November; 240(1-2):39-46.

Connolly, M. L. (1983). Solvent-accessible surfaces of proteins and nucleic acids. *Science* 221, 709-713.

El-Adawi H, Deng L, Tramontano A, Smith S, Mascareno E, Ganguly K, Castillo R, El-Sherif N. The functional role of the JAK-STAT pathway in post-infarction remodeling. Cardiovasc Res. 2003 January; 57(1):129-38.

Ewing, T. J., Makino, S., Skillman, A. G. & Kuntz, I. D. (2001). DOCK 4.0: search strategies for automated molecular docking of flexible molecule databases. *J. Comput. Aided Mol. Des.* 15, 411-428.

Ferrara P, Gohlke H, Price D J, Klebe G, and Brooks III C L, Assessing scoring functions for protein-ligand interactions, J. Med. Chem., vol. 47, 3032-3047(2004).

Flowers L O, Johnson H M, Mujtaba M G, Ellis M R, Haider S M, Subramaniam P S. Characterization of a peptide inhibitor of Janus kinase 2 that mimics suppressor of cytokine signaling 1 function. J. Immunol. 2004; 172(12):7510-8.

Gane, P. J. & Dean, P. M. (2000). Recent advances in structure-based rational drug design. *Curr. Opin. Struct. Biol.* 10, 401-404.

Giordanetto F, Kroemer R T. Prediction of the structure of human Janus kinase 2 (JAK2) comprising JAK homology domains 1 through 7. Protein Eng. 2002; 15(9):727-37

Good, A. (2001). Structure-based virtual screening protocols. *Curr. Opin. Drug Discov. Devel.* 4, 301-307.

Goodford, P. J. (1984). Drug design by the method of receptor fit. *J. Med. Chem.* 27, 558-564.

Hanks S K, Hunter T. Protein kinases 6. The eukaryotic protein kinase superfamily: kinase (catalytic) domain structure and classification. FASEB J. 1995 May; 9(8):576-96.

Harpur A G, Andres A C, Ziemiecki A, Aston R R, Wilks A F. JAK2, a third member of the JAK family of protein tyrosine kinases. Oncogene. 1992; 7:1347-53

Hol, W. G. J. (1986). Protein crystallography and computer graphics—on the path to systematic drug design. *Angewandte Chemie* 98, 765-777.

Hubbard S R, Till J H. Protein tyrosine kinase structure and function. Annu Rev Biochem. 2000; 69:373-98

Huse M, Kuriyan J., The conformational plasticity of protein kinases. Cell. 2002; 109:275-82

James C, Ugo V, Le Couedic J P, Staerk J, Delhommeau F, Lacout C, Garcon L, Raslova H, Berger R, Bennaceur-Griscelli A, Villeval J L, Constantinescu S N, Casadevall N, Vainchenker W. A unique clonal JAK2 mutation leading to constitutive signalling causes polycythaemia vera. Nature. 2005 Apr. 28; 434(7037):1144-8.

Kisseleva T, Bhattacharya S, Braunstein J, Schindler C W. (2002). Signaling through the JAK/STAT pathway, recent advances and future challenges. Gene 285(1-2):1-24

Kozma S C, Redmond S M, Fu X C, Saurer S M, Groner B, Hynes N E. Activation of the receptor kinase domain of the trk oncogene by recombination with two different cellular sequences. EMBO J. 1988 January; 7(1):147-54.

Kuntz, I. D., Blaney, J. M., Oatley, S. J., Langridge, R. & Ferrin, T. E. (1982). A geometric approach to macromolecule-ligand interactions. *J. Mol. Biol.* 161, 269-288.

Langer, T. & Hoffmann, R. D. (2001). Virtual Screening: An Effective Tool for Lead Structure Discovery? *Current Pharmaceutical Design* 7, 509-527.

Lattman, E. (1985). Diffraction methods for biological macromolecules. Use of the rotation and translation functions. *Methods Enzymol.* 115, 55-77.

Myers M P, Andersen J N, Cheng A, Tremblay M L, Horvath C M, Parisien J P, Salmeen A, Barford D, Tonks N K. TYK2 and JAK2 are substrates of protein-tyrosine phosphatase 1B. J Biol. Chem. 2001; 276:47771-4

Rarey, M., Kramer, B., Lengauer, T. & Klebe, G. (1996). A fast flexible docking method using an incremental construction algorithm. *J. Mol. Biol.* 261, 470-489.

Rawlings J S, Rosler K M, Harrison D A. The JAK/STAT signaling pathway. J Cell Sci. 2004; 117:1281-3.

Rossmann, M. G. (1990). The molecular replacement method. *Acta Crystallogr. A* 46, 73-82.

Sadowski I, Stone J C, Pawson T. A noncatalytic domain conserved among cytoplasmic protein-tyrosine kinases modifies the kinase function and transforming activity of Fujinami sarcoma virus P130gag-fps. Mol Cell Biol. 1986 December; 6(12):4396-408.

Sali, A. & Blundell, T. L. (1993). Comparative protein modelling by satisfaction of spatial restraints. *J. Mol. Biol.* 234, 779-815.

Sheridan, R. P. & Venkataraghavan, R. (1987). New methods in computer-aided drug design. *Acc. Chem. Res.* 20, 322-329.

Spiotto M T, and Chung T D. (2000) STAT3 mediates IL-6-induced growth inhibition in the human prostate cancer cell line LNCaP. Prostate 42, 88-98

Takemoto, S. et al. Proliferation of adult T cell leukemia/lymphoma cells is associated with the constitutive activation of JAK/STAT proteins. *Proc Natl Acad Sci USA* 94, 13897-902 (1997

Thompson J E, Cubbon R M, Cummings R T, Wicker L S, Frankshun R, Cunningham B R, Cameron P M, Meinke P T, Liverton N, Weng Y, DeMartino J A. Photochemical preparation of a pyridone containing tetracycle: a Jak protein kinase inhibitor. Bioorg Med Chem Lett. 2002; 12(8):1219-23.

Verlinde, C. L. & Hol, W. G. (1994). Structure-based drug design: progress, results and challenges. *Structure* 2, 577-57.

Walters, W. P., Stahl, M. T. & Murcko, M. A. (1998). Virtual screening—an overview. *Drug Discovery Today* 3, 160-178.

Wang R, Lai L, Wang S, Further development and validation of empirical scoring functions for structure-based binding affinity prediction, J. Comput.-Aided Mol. Des., vol. 16, 11-26(2002)

Wilks A F, Harpur A G, Kurban R R, Ralph S J, Zurcher G, Ziemiecki A. Two novel protein-tyrosine kinases, each with a second phosphotransferase-related catalytic domain, define a new class of protein kinase. Mol Cell Biol. 1991; 11:2057-65.

Wilks A F, Kurban R R. Isolation and structural analysis of murine c-fes cDNA clones. Oncogene. 1988 September; 3(3):289-94.

Yoshikawa H, Matsubara K, Qian G S, Jackson P, Groopman J D, Manning J E, Harris C C, Herman J G. SOCS-1, a negative regulator of the JAK/STAT pathway, is silenced by methylation in human hepatocellular carcinoma and shows growth-suppression activity. Nat. Genet. 2001; 28:29-35

The invention claimed is:

1. A method of selecting or designing a candidate compound or compounds that interact with human Janus Kinase 2 (JAK2) and modulate human JAK2 kinase activity, the method comprising the steps of:
   (a) generating a three-dimensional model of the kinase domain of said human JAK2 defined by the three-dimensional structural coordinates according to Appendix I, wherein said kinase domain consists of SEQ ID NO: 7 and/or SEQ ID NO: 8;
   (b) selecting the region that form the ATP binding pocket and sugar binding pocket from the three-dimensional model in (a) which comprise amino acid acids Glu930, Leu932, Asp939, Ser936, Leu855, Arg980, Gly993, Asp994, Ala880, Val911, Leu983, Gly935, Met929 and Tyr931, Gln853, Gly856, Lys857, Gly858, Asn859, Phe860, Gly861, Ser862, Val863, Met865, Val878, Lys882, Glu898, Leu902, Tyr913, Leu927, Pro933, Tyr934, Asn981, 11e982, Phe995, Gly996, including the sugar binding pocket amino acids Arg938, Ala978, Thr979 to generate a three-dimensional target; wherein the numbering of human JAK 2 is shown in either sequence A (SEQ ID NO: 7) or sequence B (SEQ ID NO: 8) of Appendix 1,
   (c) assessing the stereochemical complementarity between the candidate compound(s) and said region; and
   (d) testing the compound in vitro or in vivo for its capacity to modulate the kinase activity of human JAK2;
   wherein the structural coordinates of the amino acids and water molecules in (a) and/or (b) have a root mean square deviation of no more than 1.0 Å from the backbone atoms in the amino acids shown in Appendix 1.

2. The method according to claim 1 wherein the root mean square deviation is not more than 0.7 Å.

3. The method according to claim 1 comprising selecting a compound which forms hydrogen bonds or water-mediated hydrogen bonds with at least one amino acid selected from the group consisting of Glu930, Leu932, Asp939, Ser936, Leu855, Arg980, Gly993 and Asp994 wherein the positions set forth are defined by either sequence A or sequence B of Appendix 1.

4. The method according to claim 1 or claim 3 comprising selecting a compound which forms hydrophobic contacts with the side chains of at least one amino acid residue selected from the group consisting of Leu855, Ala880, Val911, Leu983, Gly935, Met929, Tyr 931, Pro933, Asn981, Ala993, Asp994, Gly856, Lys857 and Val863 wherein the positions set forth are defined by either sequence A or sequence B of Appendix 1.

5. The method according to claim 1 wherein the compound is of formula I:

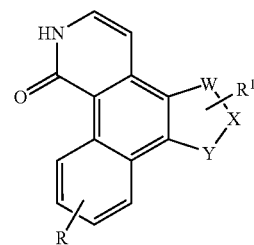

where:
R is one to three groups selected from H, halogen, OH, $OR^2$, $NR^2R^3$, CN, $NO_2$, $CO_2R^2$, $CONR^2R^3$, $NR^4CONR^2R^3$, $OCONR^2R^3$, $NR^2COOR^3$, $NR^2COR^3$, $NR^2SO_2R^3$, $SO_2R^2$, $OC_{2-6}$alkylOH, $OC_{2-6}$alkyl$NR^2R^3$, $OC_{1-6}$alkylCN, $C_{1-6}$alkylOH, $C_{1-6}$alkyl$NR^2R^3$, $C_{1-6}$alkylCN;

where $R^2$ and $R^3$ are independently H, $C_{1-6}$alkyl, $C_{2-6}$alkenyl, $C_{2-6}$alkynyl, aryl, hetaryl, $C_{1-6}$alkylCN, $C_{2-6}$alkyl$NR^5R^6$, or may be joined to form a 4-7-membered ring which may contain a heteroatom selected from O, S, $SO_2$ or $NR^7$;

where $R^4$ is H, $C_{1-6}$alkyl;

where $R^5$ and $R^6$ are independently H, $C_{1-6}$alkyl, or may be joined to form a 4-7-membered ring which may contain a heteroatom selected from O, S, $SO_2$ or $NR^7$;

where $R^7$ is H, $C_{1-6}$alkyl, $C_{1-6}$alkylOH;

W, X, Y form a 5- or 6-membered aromatic ring, selected from furan, pyrrole, imidazole, oxazole, thiazole, pyrazine, pyridazine, pyridine; and $R^1$ is selected from H, halogen, OH, $OC_{1-6}$alkyl, $C_{1-6}$alkyl, $C_{1-6}$alkylCN, $NR^2R^3$, $C_{2-6}$alkyl$NR^2COR^3$, aryl, and hetaryl.

* * * * *